US011254731B2

(12) United States Patent
Falkner et al.

(10) Patent No.: US 11,254,731 B2
(45) Date of Patent: Feb. 22, 2022

(54) VIRAL VECTORS ENCODING RECOMBINANT FVIII VARIANTS WITH INCREASED EXPRESSION FOR GENE THERAPY OF HEMOPHILIA A

(71) Applicant: TAKEDA PHARMACEUTICAL COMPANY LIMITED, Osaka (JP)

(72) Inventors: Falko-Günter Falkner, Orth/Donau (AT); Franziska Horling, Gaenserndorf (AT); Johannes Lengler, Vienna (AT); Hanspeter Rottensteiner, Vienna (AT); Friedrich Scheiflinger, Vienna (AT)

(73) Assignee: Takeda Pharmaceutical Company Limited, Osaka (JP)

(*) Notice: Subject to any disclaimer, the term of this patent is extended or adjusted under 35 U.S.C. 154(b) by 675 days.

(21) Appl. No.: 16/211,202

(22) Filed: Dec. 5, 2018

(65) Prior Publication Data

US 2019/0194295 A1 Jun. 27, 2019

Related U.S. Application Data

(63) Continuation of application No. 15/349,930, filed on Nov. 11, 2016, now Pat. No. 10,189,888.

(60) Provisional application No. 62/255,317, filed on Nov. 13, 2015.

(51) Int. Cl.

| | |
|---|---|
| ***C07K 14/755*** | (2006.01) |
| ***A61K 48/00*** | (2006.01) |
| ***C12N 15/86*** | (2006.01) |

(52) U.S. Cl.

CPC ........ *C07K 14/755* (2013.01); *A61K 48/0008* (2013.01); *A61K 48/0058* (2013.01); *A61K 48/0066* (2013.01); *C12N 15/86* (2013.01); *C12N 2750/14143* (2013.01); *C12N 2800/22* (2013.01); *C12N 2840/007* (2013.01)

(58) Field of Classification Search

None

See application file for complete search history.

(56) References Cited

U.S. PATENT DOCUMENTS

| | | | |
|---|---|---|---|
| 4,797,368 | A | 1/1989 | Carter et al. |
| 4,868,112 | A | 9/1989 | Toole, Jr. |
| 5,112,950 | A | 5/1992 | Meulien et al. |
| 5,139,941 | A | 8/1992 | Muzyczka et al. |
| 5,171,844 | A | 12/1992 | Van Ooyen et al. |
| 5,543,502 | A | 8/1996 | Nordfang et al. |
| 5,595,886 | A | 1/1997 | Chapman et al. |
| 5,610,278 | A | 3/1997 | Nordfang et al. |
| 5,789,203 | A | 4/1998 | Chapman et al. |
| 5,935,935 | A | 8/1999 | Connelly et al. |
| 5,972,885 | A | 10/1999 | Spira et al. |
| 5,994,136 | A | 11/1999 | Naldini et al. |
| 6,013,516 | A | 1/2000 | Verma et al. |
| 6,048,720 | A | 4/2000 | Dalborg et al. |
| 6,060,447 | A | 5/2000 | Chapman et al. |
| 6,114,148 | A | 9/2000 | Seed et al. |
| 6,200,560 | B1 | 3/2001 | Couto et al. |
| 6,228,620 | B1 | 5/2001 | Chapman et al. |
| 6,316,226 | B1 | 11/2001 | Van Ooyen et al. |
| 6,346,513 | B1 | 2/2002 | Van Ooyen et al. |
| 6,458,563 | B1 | 10/2002 | Lollar |
| 6,649,375 | B2 | 11/2003 | Connelly et al. |
| 6,818,439 | B1 | 11/2004 | Jolly et al. |
| 6,924,365 | B1 | 8/2005 | Miller et al. |
| 7,041,635 | B2 | 5/2006 | Kim et al. |
| 7,635,763 | B2 | 12/2009 | Lollar |
| 7,943,374 | B2 | 5/2011 | Hildinger |
| 7,973,374 | B2 | 7/2011 | Jeong |
| 8,188,246 | B2 | 5/2012 | Lollar |
| 8,519,111 | B2 | 8/2013 | Lollar |
| 8,986,991 | B2 | 3/2015 | Denning et al. |
| 9,393,323 | B2 | 7/2016 | Nathwani et al. |
| 9,447,168 | B2 | 9/2016 | Nathwani et al. |
| 9,504,762 | B2 | 11/2016 | Colosi et al. |
| 10,421,798 | B2 | 9/2019 | Schellenberger et al. |
| 2005/0003482 | A1 | 1/2005 | Fang et al. |
| 2006/0099685 | A1 | 5/2006 | Yallop et al. |
| 2011/0184049 | A1 | 7/2011 | Chuah et al. |
| 2012/0178691 | A1 | 7/2012 | Schellenberger et al. |
| 2013/0017997 | A1 | 1/2013 | Schellenberger et al. |
| 2013/0024960 | A1 | 1/2013 | Nathwani et al. |
| 2013/0202596 | A1 | 8/2013 | Salas et al. |
| 2014/0370035 | A1 | 12/2014 | Jiang et al. |
| 2015/0023959 | A1 | 1/2015 | Chhabra et al. |
| 2015/0038421 | A1 | 2/2015 | Schellenberger et al. |
| 2015/0071883 | A1 | 3/2015 | Colosi et al. |

(Continued)

FOREIGN PATENT DOCUMENTS

| | | | |
|---|---|---|---|
| WO | WO 2003/052051 | A2 | 6/2003 |
| WO | WO 2007/149852 | A2 | 12/2007 |

(Continued)

OTHER PUBLICATIONS

Asokan et al. "The AAV Vector Toolkit: Poised at the Clinical Crossroads" Molecular Therapy, vol. 20, No. 4, pp. 699-708 (2012).

Bancel. S. et al., EBII Accession No. GSN:BAW43417.

Blomer et al. "Highly Efficient and Sustained Gene Transfer in Adult Neurons with a Lentivirus Vector" Journal of Virology, vol. 71, No. 9, pp. 6641-6649 (1997).

Cao et al. "ASGCT abstract #460; details of mutations disclosed in oral presentation—A Novel Factor VII Variant with Enhanced Secretion for Gene Therapy of Hemophilia A," Molecular Therapy (2014).

(Continued)

*Primary Examiner* — James D Schultz

(74) *Attorney, Agent, or Firm* — Morgan, Lewis & Bockius LLP

(57) ABSTRACT

The present disclosure provides, among other aspects, codon-altered polynucleotides encoding Factor VIII variants for expression in mammalian cells. In some embodiments, the disclosure also provides mammalian gene therapy vectors and methods for treating hemophilia A.

10 Claims, 89 Drawing Sheets

Specification includes a Sequence Listing.

(56) References Cited

U.S. PATENT DOCUMENTS

2015/0158929 A1 6/2015 Schellenberger et al.
2015/0158930 A1 6/2015 Nathwani et al.
2015/0283267 A1 10/2015 Vandendriessche et al.
2015/0361158 A1 12/2015 Tan et al.
2016/0030524 A1 2/2016 Wang et al.
2016/0102133 A1 4/2016 Xiao et al.
2016/0229904 A1 8/2016 Xiao
2016/0251409 A1 9/2016 Oestergaard et al.
2017/0049859 A1 2/2017 Nathwani et al.
2017/0095538 A1 4/2017 Colosi et al.
2017/0233455 A1 8/2017 Falkner et al.
2019/0194295 A1 6/2019 Falkner et al.

FOREIGN PATENT DOCUMENTS

WO WO 2008/077616 A1 7/2008
WO WO 2013/016454 A1 1/2013
WO WO 2013/123503 A1 8/2013
WO WO 2013/151666 A2 10/2013
WO WO 2013/186563 A2 12/2013
WO WO 2014/064277 A1 5/2014
WO WO 2014/127215 A1 8/2014
WO WO 2016/025764 A2 2/2016
WO WO 2016/146757 A1 9/2016

OTHER PUBLICATIONS

Cotten et al. "High-efficiency receptor-mediated delivery of small and large (48 kilobase gene constructs using the endosome-disruption activity of defective or chemically inactivated adenovirus particles" Proc. Natl. Acad. Sci. USA, vol. 89, pp. 6094-6098 (1992).
Curiel "High-efficiency gene transfer employing adenovirus-polylysine-DNA complexes." Natural Immunity, vol. 13, pp. 141-164 (1994).
Daya and Berns "Gene Therapy Using Adeno-Associated Virus Vectors" Clinical Microbiology Reviews, vol. 21, No. 4, pp. 583-593 (2008).
Donath et al. "Characterization of des-(741-1668)-factor VIII, a single-chain factor VIII variant with a fusion site susceptible to proteolysis by thrombin and factor Xa" Biochem Journal, vol. 312, pp. 49-55 (1995).
Fath et al. "Multiparameter RNA and Codon Optimization: A Standardized Tool to Assess and Enhance Autologous Mammalian Gene Expression" PLoS ONE, vol. 6, Issue 3, pp. 1-14 (2011).
Gardinier-Garden et al. "CpG Islands in vertebrate genomes" Journal of Molecular Biology, vol. 196, Issue 2, pp. 261-282 (1987).
Gray et al. "Optimizing Promoters for Recombinant Adeno-Associated Virus-Mediated Gene Expression in the Peripheral and Central Nervous System Using Self-Complementary Vectors" Human Gene Therapy, vol. 22, pp. 1143-1153 (2011).
Grieger et al. "Production of Recombinant Adeno-associated Virus Vectors Using Suspension HEK293 Cells and Continuous Harvest of Vector From the Culture Media for GMP FIX and FLT1 Clinical Vector" Molecular Therapy, vol. 24, No. 2, pp. 287-297 (2015).
Grote et al. "JCat: a novel tool to adapt codon usage of a target gene to its potential expression host" Nucleic Acid Research, vol. 33, pp. W526-W531 (2005).
Gupta, R. et al., "NetNGlyc 1.0 Server," located at: http://www.cbs.dtu.dk/services/NetNGlyc/, 2004, last accessed, May 30, 2018.
Haas et al. "Codon usage limitation in the expression of HIV-1 envelope glycoprotein" Current Biology, vol. 6, No. 3, pp. 315-324 (1996).
International Search Report for International Application No. PCT/US2016/061684, dated Feb. 15, 2017, 16 pages.
International Search Report for International Application No. PCT/US2016/061688, dated Feb. 6, 2017, 16 pages.
Kelleher and Vos, "Long-term episomal gene delivery in human lymphoid cells using human and avian adenoviral-assisted transfection" Biotechniques, vol. 17, pp. 1110-1117 (1994).
Kriegler "Gene Transfer and Expression, A Laboratory Manual" (1990).
Krinner et al. "CpG domains downstream of TSSs promote high levels of gene expression" Nucleic Acid Research, vol. 42, No. 6, pp. 3551-3564 (2014).
Kudla et al. "High Guanine and Cytosine Content Increases mRNA Levels in Mammalian Cells" PLoS Biology, vol. 4, Issue 6, pp. 0933-0942 (2006).
Mann et al. "Construction of a retrovirus packaging mutant and its use to produce helper-free defective retrovirus" Cell, vol. 33, Issue 1, pp. 153-159 (1983).
Manno et al. "Successful transduction of liver in hemophilia by AAV-Factor IX and limitations imposed by the host immune response." Nature Medicine, vol. 12 pp. 342-347 (2006).
McIntosh et al. "Therapeutic levels of FVIII following a single peripheral vein administration of rAAV vector encoding a novel human factor VIII variant" Blood Journal, vol. 121, No. 17, pp. 3335-3344 (2013).
Miao et al. "Bioengineering of coagulation factor VIII for improved secretion" Blood Journal, vol. 103, No. 9, pp. 3412-3419 (2004).
Mirsafian et al. "A Comparative Analysis of Synonymous Codon Usage Bias Pattern in Human Albumin Superfamily" Scientific World Journal, vol. 2014, Article 639682, pp. 1-7 (2014).
Murray, E.J., "Gene Transfer and Expression Protocols" Methods in Molecular Biology, vol. 7, Humana Press, Inc. (1991).
Muzyczka "Use of adeno-associated virus as a general transduction vector for mammalian cells." Current Topics Microbiology and Immunology, vol. 158, pp. 97-129 (1992).
Naldini et al. "In Vivo Gene Delivery and Stable Transduction of Nondividing Cells by a Lentiviral Vector" Science, vol. 272, Issue 5259, pp. 263-267 (1996).
Nicolas and Rubenstein, "Retroviral vectors," In: Vectors. A survey of molecular cloning vectors and their uses, Rodriguez and Denhardt (eds.), Stoneham: Butterworth, pp. 494-513 (1988).
Oh et al. "Purification of Recombinant Human B-Domain-Deleted Factor VIII Using Anti-Factor VIII Monoclonal Antibody Selected by the Surface Plasmon Resonance Biosensor" Biotechnol. Prog., vol. 17, pp. 1119-1127 (2001).
Radcliff et al. "Analysis of factor VIII mediated suppression of lentiviral vector titres" Gene Therapy, vol. 15, pp. 289-297 (2008).
Sandberg et al. "Structural and functional characteristics of the B-domain-deleted recombinant factor VIII, r-VIII SQ", Journal of Thrombosis and Haemostasis, vol. 85, pp. 93-100 (2001).
Selvaraj et al. "Bioengineering of coagulation factor VIII for efficient expression through elimination of a dispensable disulfide loop" Journal of Thrombosis and Haemostasis, vol. 10, pp. 107-115 (2012).
Swaaroop et al. "Mutagenesis of a Potential Immunoglobulin-binding Protein-binding Site Enhances Secretion of Coagulation Factor VIII" Journal of Biological Chemistry, vol. 272, No. 39, pp. 24121-24124 (1997).
Tats et al. "Preferred and avoided codon pairs in three domains of life" BMC Genomics, vol. 9, Issue 463, pp. 1-15 (2008).
Temin, H.M. "Retrovirus Vectors for Gene Transfer: Efficient Integration into and Expression of Exogenous DNA in Vertebrate Cell Genomes" In: Kucherlapati R. (eds) Gene Transfer (1986).
Thim et al., "Purification and characterization of a new recombinant factor VIII (N8)" Haemophilia, vol. 16, Issue 2, pp. 349-359 (2010).
Toschi et al. OBI-1, porcine recombinant Factor VIII for the potential treatment of patients with congenital hemophilia A and alloantibodies against human Factor VIII, Current Opinion in Molecular Therapy, vol. 12, No. 5, pp. 617-625 (2010).
Varfaj et al. "Residues Surrounding Arg336 and Arg562 Contribute to the Disparate Rates of Proteolysis of Factor VIIIa Catalyzed by Activated Protein C" Journal of Biological Chemistry, vol. 282, No. 28, pp. 20264-20272 (2007).
Wakabayashi et al. "A Glu113Ala mutation within a factor VIII Ca2+ binding site enhances cofactor interactions in factor Xase" Biochemistry, vol. 44, pp. 10298-10304 (2005).
Wakabayashi et al. "Ca(2+) binding to both the heavy and light chains of factor VIII is required for cofactor activity" Biochemistry, vol. 41, pp. 8485-8492 (2002).

(56) References Cited

OTHER PUBLICATIONS

Wakabayashi et al. "Combining mutations of charged residues at the A2 domain interface enhances factor VIII stability over single point mutations" Journal of Thrombosis and Haemostasis, vol. 7, pp. 438-444 (2009).
Wakabayashi et al. "Enhancing factor VIII and VIIIa stability by combining mutations at the A2 domain interface and A1-C2 domain interface" Journal of Thrombosis and Haemostasis., vol. 10, pp. 492-495 (2012).
Wakabayashi et al. "Generation of enhanced stability factor VIII variants by replacement of charged residues at the A2 domain interface" Blood, vol. 12, No. 7, pp. 2761-2769 (2008).
Wakabayashi et al. "Increasing Hydrophobicity or Disulfide Bridging at the Factor VIII A1 and C2 Domain Interface Enhances Procofactor Stability" Journal of Biological Chemistry, vol. 286, No. 29 pp. 25748-25755 (2011).
Wakabayashi et al. "Residues 110-126 in the A1 Domain of Factor VIII Contain a Ca2+ Binding Site Required for Cofactor Activity" Journal of Biochemistry, vol. 279, No. 13, pp. 12677-12684 (2004).
Ward et al. "Codon optimization of human factor VIII cDNAs leads to high-level expression" Blood Journal, vol. 117, No. 3, pp. 798-807 (2011).
Zollner et al. "Non-clinical pharmacokinetics and pharmacodynamics of rVIII-SingleChain, a novel recombinant single-chain factor VIII", Thrombosis Research, vol. 134, pp. 125-131 (2014).
Zufferey et al. "Multiply attenuated lentiviral vector achieves efficient gene delivery in vivo" Nature Biotechnology, vol. 15, pp. 871-875 (1997).
Altschul et al. (1996) "Local alignment statistics," Methods in enzymology. 266(2):460-480.
Altschul et al. (1990) "Basic local alignment search tool," Journal of molecular biology. 215(3):403-410.
Altschul et al. (1997) "Gapped BLAST and PSI-BLAST: a new generation of protein database search programs," Nucleic acids research. 25(17):3389-3402.
Aponte-Ubillus et al. (2018) "Molecular design for recombinant adeno-associated virus (rAAV) vector production," Applied microbiology and biotechnology. 102(3):1045-1054.
Bolivar (1979) "Molecular cloning vectors derived from the CoLEI type plasmid pMBI," Life sciences. 25(10):807-817.
Chuah et al. (2012) "Platelet-directed gene therapy overcomes inhibitory antibodies to factor VIII," Journal of Thrombosis and Haemostasis. 10(8):1566-1569.
Chuah et al. (2013) "Gene therapy for hemophilia," Journal of thrombosis and haemostasis. 11:99-110.
Chuah et al. (2014) "Liver-specific transcriptional modules identified by genome-wide in silico analysis enable efficient gene therapy in mice and non-human primates," Molecular Therapy. 22(9):1605-1613.
Chuah et al. (2012) "Recent progress in gene therapy for hemophilia," Human gene therapy. 23(6):557-565.
Desmet et al. (2005) "Anchor profiles of HLA-specific peptides: analysis by a novel affinity scoring method and experimental validation," Proteins: Structure, Function, and Bioinformatics. 58(1):53-69.
Fagone et al. (2012) "Systemic errors in quantitative polymerase chain reaction titration of self-complementary adeno-associated viral vectors and improved alternative methods," Human Gene Therapy, Part B: Methods. 23(1):1-7.
Feng et al. (1987) "Progressive sequence alignment as a prerequisitetto correct phylogenetic trees," Journal of molecular evolution. 25(4):351-360.
Graw et al. (2005) "Haemophilia A: from mutation analysis to new therapies," Nature Reviews Genetics. 6(6):488-501.
Higgins et al. (1989) "Fast and sensitive multiple sequence alignments on a microcomputer," Bioinformatics. 5(2):151-153.
High (2012) "The gene therapy journey for hemophilia: are we there yet?" Blood, The Journal of the American Society of Hematology. 120(23):4482-4487.
Hsieh et al. (2009) "Transthyretin-driven oncolytic adenovirus suppresses tumor growth in orthotopic and ascites models of hepatocellular carcinoma," Cancer science. 100(3):537-545.
Karlin et al. (1993) "Applications and statistics for multiple high-scoring segments in molecular sequences," Proceedings of the National Academy of Sciences. 90(12):5873-5877.
Kotin (2011) "Large-scale recombinant adeno-associated virus production," Human molecular genetics. 20(R1):R2-R6.
Laupeze et al. (1999) "Differential expression of major histocompatibility complex class Ia, Ib and II molecules on monocytes and monocyte-derived dendritic and macrophagic cells," Human immunology. 60(7):591-597.
Lenting et al. (1998) "The life cycle of coagulation factor VIII in view of its structure and function," Blood, The Journal of the American Society of Hematology. 92(11):3983-3996.
Mannucci (2003) "Hemophilia: treatment options in the twenty-first century," Journal of Thrombosis and Haemostasis. 1(7):1349-1355.
Mátrai et al. (2010) "Preclinical and clinical progress in hemophilia gene therapy," Current opinion in hematology. 17(5):387-392.
Mátrai et al. (2010) "Recent advances in lentiviral vector development and applications," Molecular therapy. 18(3):477-490.
Nair et al. (2014) "Computationally designed liver-specific transcriptional modules and hyperactive factor IX improve hepatic gene therapy," Blood, The Journal of the American Society of Hematology. 123(20):3195-3199.
Needleman et al. (1970) "A general method applicable to the search for similarities in the amino acid sequence of two proteins," Journal of molecular biology. 48(3):443-453.
Pearson et al. (1988) "Improved tools for biological sequence comparison," Proceedings of the National Academy of Sciences. 85(8):2444-2448.
Penaud-Budloo et al. (2018) "Pharmacology of recombinant adeno-associated virus production," Molecular Therapy—Methods & Clinical Development. 8:166-180.
Reipert et al. (2010) "Animal models of inhibitors," Haemophilia. 16:47-53.
Saenko et al. (1999) "Role of activation of the coagulation factor VIII in interaction with vWf, phospholipid, and functioning within the factor Xase complex," Trends in cardiovascular medicine. 9(7):185-192.
Smith et al. (1981) "Comparison of biosequences," Advances in applied mathematics. 2(4):482-489.
Steentoft et al. (2013) "Precision mapping of the human O-GalNAc glycoproteome through SimpleCell technology," The EMBO journal. 32(10):1478-1488.
Sutcliffe (1978) "Nucleotide sequence of the ampicillin resistance gene of *Escherichia coli* plasmid pBR322," Proceedings of the National Academy of Sciences. 75(8):3737-3741.
Van Helden et al. (2011) "Maintenance and break of immune tolerance against human factor VIII in a new transgenic hemophilic mouse model," Blood, The Journal of the American Society of Hematology. 118(13):3698-3707.
Vandendriessche et al. (2012) "Clinical progress in gene therapy: sustained partial correction of the bleeding disorder in patients suffering from severe hemophilia B," Human gene therapy. 23(1):4-6.
Verreck et al. (1996) "The generation of SDS-stable HLA DR dimers is independent of efficient peptide binding," International immunology. 8(3):397-404.
Yan et al. (1990) "Distinct positive and negative elements control the limited hepatocyte and choroid plexus expression of transthyretin in transgenic mice," The EMBO journal. 9(3):869-878.
Zhang et al. (2009) "Factor VIII inhibitors: risk factors and methods for prevention and immune modulation," Clinical reviews in allergy & immunology. 37(2):114-124.
Database GenBank (Jun. 7, 1993) "coagulation factor VIII [*Mus musculus domesticus*]," NCBI Reference Sequence: AAA37385.1, 2 pages.
Database GenBank (Apr. 6, 2016) "coagulation factor VIII [*Homo sapiens*]," NCBI Reference Sequence: AAA52420.1, 3 pages.
Database GenBank (Nov. 8, 1994) "factor VIII [*Homo sapiens*]," NCBI Reference Sequence: AAA52484.1, 3 pages.

(56) References Cited

OTHER PUBLICATIONS

Database GenBank (Nov. 8, 1994) "preprocoagulation factor VIII:C [*Homo sapiens*]," NCBI Reference Sequence: AAA52485.1, 4 pages.
Database GenBank (Dec. 31, 1994) "coagulation factor VIII associated protein B [*Homo sapiens*]," NCBI Reference Sequence: AAA58466.1, 1 page.
Database GenBank (Jun. 15, 1997) "clotting factor VIII, partial [*Homo sapiens*]," NCBI Reference Sequence: AAB61261.1, 1 page.
Database GenBank (Aug. 4, 2008) "Coagulation factor VIII, procoagulant component [*Homo sapiens*]," NCBI Reference Sequence: AAH22513.1, 2 pages.
Database GenBank (Aug. 4, 2008) "Coagulation factor VIII, procoagulant component [*Homo sapiens*]," NCBI Reference Sequence: AAH64380.1, 2 pages.
Database GenBank (Aug. 4, 2008) "Coagulation factor VIII, procoagulant component [*Homo sapiens*]," NCBI Reference Sequence: AAH98389.1, 2 pages.
Database GenBank (Aug. 4, 2008) "Coagulation factor VIII, procoagulant component [*Homo sapiens*]," NCBI Reference Sequence: AAI11968.1, 2 pages.
Database GenBank (Aug. 4, 2008) "Coagulation factor VIII, procoagulant component [*Homo sapiens*]," NCBI Reference Sequence: AAI11970.1, 2 pages.
Database GenBank (Aug. 13, 2003) "factor VIII [Rattus norvegicus]," NCBI Reference Sequence: AAQ21580.1, 2 pages.
Database GenBank (Dec. 11, 2004) "coagulation factor VIII, procoagulant component (hemophilia A) [*Homo sapiens*]," NCBI Reference Sequence: AAV85964.1, 3 pages.
Database GenBank (Jan. 9, 2008) "unnamed protein product [*Homo sapiens*]," NCBI Reference Sequence: BAF82636.1, 2 pages.
Database GenBank (May 24, 2008) "unnamed protein product [*Homo sapiens*]," NCBI Reference Sequence: BAG36452.1, 2 pages.
Database GenBank (Jan. 29, 2011) "HS14F12r HS *Hordeum vulgare* subsp. *vulgare* cDNA clone HS14F12 5-PRIME, mRNA sequence," NCBI Reference Sequence: CA003404.1, 1 page.
Database GenBank (Oct. 7, 2008) "unnamed protein product [*Homo sapiens*]," NCBI Reference Sequence: CAA25619.1, 4 pages.
Database GenBank (Jan. 15, 2009) "coagulation factor VIII, procoagulant component [*Homo sapiens*]," NCBI Reference Sequence: CAI41660.1, 3 pages.
Database GenBank (Jan. 15, 2009) "coagulation factor VIII, procoagulant component [*Homo sapiens*]," NCBI Reference Sequence: CAI41666.1, 3 pages.
Database GenBank (Jan. 15, 2009) "coagulation factor VIII, procoagulant component [*Homo sapiens*]," NCBI Reference Sequence: CAI41672.1, 3 pages.
Database GenBank (Jan. 15, 2009) "coagulation factor VIII, procoagulant component [*Homo sapiens*]," NCBI Reference Sequence: CAI43241.1, 3 pages.
Database GenBank (May 3, 2008) "coagulation factor VIII [Mus musculus]," NCBI Reference Sequence: CAM15581.1, 2 pages.
Database GenBank (Jan. 15, 2009) "coagulation factor VIII [Mus musculus]," NCBI Reference Sequence: CAM26492.1, 3 pages.
Database GenBank (Mar. 23, 2015) "coagulation factor VIII, procoagulant component (hemophilia A), isoform CRA_a [*Homo sapiens*]," NCBI Reference Sequence: EAW72645.1, 2 pages.
Database GenBank (Jul. 26, 2016) "coagulation factor VIII [Mus musculus]," NCBI Reference Sequence: EDL29229.1, 3 pages.
Database GenBank (Nov. 8, 1994) "Human coagulation factor VIII:C mRNA, complete cds," NCBI Reference Sequence: M14113.1, 4 pages.
Database GenBank (Apr. 23, 2019) "*Homo sapiens* serpin family A member 1 (SERPINA1), transcript variant 1, mRNA," NCBI Reference Sequence: NM_000295.4, 5 pages.
Database UniProt (May 3, 2011) "ull=Coagulation factor VIII {ECO:0000313|Ensembl:ENSSSCP00000013628}" NCBI Reference Sequence: F1RZ36, 2 pages.
Database UniProt (Jan. 9, 2013) "Full=Coagulation factor VIII {ECO:0000313|Ensembl:ENSSSCP00000031036}" NCBI Reference Sequence: F1RZ36, 1 page.
Database UniProt (Nov. 13, 2019) "RecName: Full=Coagulation factor VIII; AltName: Full=Antihemophilic factor; Short=AHF; AltName: Full=Procoagulant component; Contains: RecName: Full=Factor VIIIa heavy chain, 200 kDa isoform; Contains: RecName: Full=Factor VIIIa heavy chain, 92 kDa isoform; Co . . . ," NCBI Reference Sequence: P00451.1, 61 pages.
Database UniProt (Oct. 16, 2019) "RecName: Full=Coagulation factor IX; AltName: Full=Christmas factor; AltName: Full=Plasma thromboplastin component; Short=PTC; Contains: RecName: Full=Coagulation factor IXa light chain; Contains: RecName: Full=Coagulation factor IXa heavy chain; Flags: Precursor" NCBI Reference Sequence: P00740.2, 36 pages.

CS04-FL-NA atgcagattgagctgagcacctgcttcttcctgtgcctgctgaggttctgcttctctgccaccagga
gatactacctggggctgtggagctttcttgggactacatgcagtctgacctgggggagctgcctgt
ggatgccaggttcccacccagagtgcccaaatccttcccattcaacacctctgtggtctacaagaag
accctctttgtggagttcactgaccacctgttcaacattgccaaacccaggccaccctggatgggac
tcctgggacccaccattcaggctgaggtgtatgacactgtggtcatcaccctcaagaacatggcctc
ccaccctgtgagcctgcatgctgtgggggtcagctactggaaggcctctgagggggctgagtatgat
gaccagacctcccagagggagaaggaggatgacaaagtgttccctggggggcagccacacctatgtgt
ggcaggtcctcaaggagaatggccccatggcctctgacccactctgcctgacctactcctacctttc
tcatgtggacctggtcaaggacctcaactctggactgattggggccctgctggtgtgcagggagggc
tccctggccaaagagaagacccagaccctgcacaagttcattctcctgtttgctgtctttgatgagg
gcaagagctggcactctgaaaccaagaactccctgatgcaggacagggatgctgcctctgccagggc
ctggcccaagatgcacactgtgaatggctatgtgaacaggagcctgcctggactcattggctgccac
aggaaatctgtctactggcatgtgattggcatggggacaacccctgaggtgcactccattttcctgg
agggccacaccttcctggtcaggaaccacagacaggccagcctggagatcagccccatcaccttcct
cactgcccagaccctgctgatggacctcggacagttcctgctgttctgccacatcagctcccaccag
catgatggcatggaggcctatgtcaaggtggacagctgccctgaggagccacagctcaggatgaaga
acaatgaggaggctgaggactatgatgatgacctgactgactctgagatggatgtggtccgctttga
tgatgacaacagcccatccttcattcagatcaggtctgtggccaagaaacaccccaagacctgggtg
cactacattgctgctgaggaggaggactgggactatgccccactggtcctggcccctgatgacagga
gctacaagagccagtacctcaacaatggcccacagaggattggacgcaagtacaagaaagtcaggtt
catggcctacactgatgaaaccttcaagaccagggaggccattcagcatgagtctggcatcctgggc
ccactcctgtatggggaggtgggggacaccctgctcatcatcttcaagaaccaggcctccaggccct
acaacatctacccacatggcatcactgatgtcaggcccctgtacagccgcaggctgccaaaggggt
gaaacacctcaaggacttccccattctgcctggggagatcttcaagtacaagtggactgtcactgtg
gaggatggaccaaccaaatctgaccccaggtgcctcaccagatactactccagctttgtgaacatgg
agagggacctggcctctggcctgattggcccactgctcatctgctacaaggagtctgtggaccagag
gggaaaccagatcatgtctgacaagaggaatgtgattctgttctctgtctttgatgagaacaggagc
tggtacctgactgagaacattcagcgcttcctgcccaaccctgctggggtgcagctggaggaccctg
agttccaggccagcaacatcatgcactccatcaatggctatgtgtttgacagcctccagctttctgt
ctgcctgcatgaggtggcctactggtacattctttctattggggcccagactgacttcctttctgtc
ttcttctctggctacaccttcaaacacaagatggtgtatgaggacaccctgaccctcttcccattct
ctggggagactgtgttcatgagcatggagaaccctggcctgtggattctgggatgccacaactctga
cttccgcaacaggggcatgactgccctgctcaaagtctcctcctgtgacaagaacactggggactac
tatgaggacagctatgaggacatctctgcctacctgctcagcaagaacaatgccattgagcccagga
gcttcagccagaatccacctgtcctgaaacgccaccagagggagatcaccaggaccaccctccagtc
tgaccaggaggagattgactatgatgacaccatttctgtggagatgaagaaagaggactttgacatc
tatgacgaggacgagaaccagagcccaaggagcttccagaagaagaccaggcactacttcattgctg
ctgtggagcgcctgtgggactatggcatgagctccagccccatgtcctcaggaacagggcccagtc
tggctctgtgccacagttcaagaaagtggtcttccaagagttcactgatggcagcttcacccagccc
ctgtacagaggggagctgaatgagcacctgggactcctgggcccatacatcagggctgaggtggagg
acaacatcatggtgaccttccgcaaccaggcctccaggccctacagcttctacagctccctcatcag
ctatgagGaggaccagaggcagggggctgagccacgcaagaactttgtgaaacccaatgaaaccaag
acctacttctggaaagtccagcaccacatggcccccaccaaggatgagtttgactgcaaggcctggg (Continued)

Figure 2A cctacttctctgatgtggacctggagaaggatgtgcactctggcctgattggcccactcctggtctg
ccacaccaacaccctgaaccctgcccatggaaggcaagtgactgtgcaggagtttgccctcttcttc
accatctttgatgaaaccaagagctggtacttcactgagaacatggagcgcaactgcagggccccat
gcaacattcagatggaggaccccaccttcaaagagaactaccgcttccatgccatcaatggctacat
catggacaccctgcctgggcttgtcatggcccaggaccagaggatcaggtggtacctgctttctatg
ggctccaatgagaacattcactccatccacttctctgggcatgtcttcactgtgcgcaagaaggagg
agtacaagatggccctgtacaacctctaccctggggtctttgagactgtggagatgctgccctccaa
agctggcatctggagggtggagtgcctcattggggagcacctgcatgctggcatgagcaccctgttc
ctggtctacagcaacaagtgccagacccccctgggaatggcctctggccacatcagggacttccaga
tcactgcctctggccagtatggccagtgggcccccaagctggccaggctccactactctggatccat
caatgcctggagcaccaaggagccattcagctggatcaaagtggacctgctggcccccatgatcatc
catggcatcaagacccaggggccaggcagaagttctccagcctgtacatcagccagttcatcatca
tgtacagcctggatggcaagaaatggcagacctacagaggcaactccactggaacactcatggtctt
ctttggcaatgtggacagctctggcatcaagcacaacatcttcaaccccccaatcatcgccagatac
atcaggctgcaccccacccactacagcatccgcagcaccctcaggatggagctgatgggctgtgacc
tgaactcctgcagcatgcccctgggcatggagagcaaggccatttctgatgcccagatcactgcctc
cagctacttcaccaacatgtttgccacctggagcccaagcaaggccaggctgcacctccagggaagg
agcaatgcctggaggccccaggtcaacaacccaaaggagtggctgcaggtggacttccagaagacca
tgaaggtcactggggtgaccacccaggggtcaagagcctgctcaccagcatgtatgtgaaggagtt
cctgatcagctccagccaggatggccaccagtggaccctcttcttccagaatggcaaggtcaaggtg
ttccagggcaaccaggacagcttcacCcctgtggtgaacagcctggacccccccctcctgaccagat
acctgaggattcacccccagagctgggtccaccagattgccctgaggatggaggtcctgggatgtga
ggcccaggacctgtactga (SEQ ID NO:1)

MQIELSTCFFLCLLRFCFSATRRYYLGAVELSWDYMQSDLGELPVDAR'FPPRVPKSFPFNTSVVYK
KTLFVEFTDHLFNIAKPRPPWMGLLGPTIQAEVYDTVVITLKNMASHPVSLHAVGVSYWKASEGAEY
DDQTSQREKEDDKVFPGGSHTYVWQVLKENGPMASDPLCLTYSYLSHVDLVKDLNSGLIGALLVCRE
GSLAKEKTQTLHKFILLFAVFDEGKSWHSETKNSLMQDRDAASARAWPKMHTVNGYVNRSLPGLIGC
HRKSVYWHVIGMGTTPEVHSIFLEGHTFLVRNHRQASLEISPITFLTAQTLLMDLGQFLLFCHISSH
QHDGMEAYVKVDSCPEEPQLRMKNNEEAEDYDDDLTDSEMDVVRFDDDNSPSFIQIRSVAKKHPKTW
VHYIAAEEEDWDYAPLVLAPDDRSYKSQYLNNGPQRIGRKYKKVRFMAYTDETFKTREAIQHESGIL
GPLLYGEVGDTLLIIFKNQASRPYNIYPHGITDVRPLYSRRLPKGVKHLKDFPILPGEIFKYKWTVT
VEDGPTKSDPRCLTRYYSSFVNMERDLASGLIGPLLICYKESVDQRGNQIMSDKRNVILFSVFDENR
SWYLTENIQRFLPNPAGVQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNRGMTALLKVSSCDKNTGD
YYEDSYEDISAYLLSKNNAIEPRSFSQNPPVLKRHQREITRTTLQSDQEEIDYDDTISVEMKKEDFD
IYDEDENQSPRSFQKKTRHYFIAAVERLWDYGMSSSPHVLRNRAQSGSVPQFKKVVFQEFTDGSFTQ
PLYRGELNEHLGLLGPYIRAEVEDNIMVTFRNQASRPYSFYSSLISYEEDQRQGAEPRKNFVKPNET
KTYFWKVQHHMAPTKDEFDCKAWAYFSDVDLEKDVHSGLIGPLLVCHTNTLNPAHGRQVTVQEFALF
FTIFDETKSWYFTENMERNCRAPCNIQMEDPTFKENYRFHAINGYIMDTLPGLVMAQDQRIRWYLLS
MGSNENIHSIHFSGHVFTVRKKEEYKMALYNLYPGVFETVEMLPSKAGIWRVECLIGEHLHAGMSTL
FLVYSNKCQTPLGMASGHIRDFQITASGQYGQWAPKLARLHYSGSINAWSTKEPFSWIKVDLLAPMI
IHGIKTQGARQKFSSLYISQFIIMYSLDGKKWQTYRGNSTGTLMVFFGNVDSSGIKHNIFNPPIIAR
YIRLHPTHYSIRSTLRMELMGCDLNSCSMPLGMESKAISDAQITASSYFTNMFATWSPSKARLHLQG
RSNAWRPQVNNPKEWLQVDFQKTMKVTGVTTQGVKSLLTSMYVKEFLISSSQDGHQWTLFFQNGKVK
VFQGNQDSFTPVVNSLDPPLLTRYLRIHPQSWVHQIALRMEVLGCEAQDLY (SEQ ID NO:2)

Figure 3

CS04-HC-NA gcc
accaggagat actacctggg ggctgtggag ctttcttggg actacatgca gtctgacctg
ggggagctgc ctgtggatgc caggttccca cccagagtgc ccaaatcctt cccattcaac
acctctgtgg tctacaagaa gaccctcttt gtggagttca ctgaccacct gttcaacatt
gccaaaccca ggccaccctg gatgggactc ctgggaccca ccattcaggc tgaggtgtat
gacactgtgg tcatcaccct caagaacatg gcctcccacc ctgtgagcct gcatgctgtg
ggggtcagct actggaaggc ctctgagggg gctgagtatg atgaccagac ctcccagagg
gagaaggagg atgacaaagt gttccctggg ggcagccaca cctatgtgtg gcaggtcctc
aaggagaatg gccccatggc ctctgaccca ctctgcctga cctactccta cctttctcat
gtggacctgg tcaaggacct caactctgga ctgattgggg ccctgctggt gtgcagggag
ggctccctgg ccaaagagaa gacccagacc ctgcacaagt tcattctcct gtttgctgtc
tttgatgagg gcaagagctg gcactctgaa accaagaact ccctgatgca ggacagggat
gctgcctctg ccagggcctg gcccaagatg cacactgtga atggctatgt gaacaggagc
ctgcctggac tcattggctg ccacaggaaa tctgtctact ggcatgtgat tggcatgggg
acaaccccctg aggtgcactc cattttcctg gagggccaca ccttcctggt caggaaccac
agacaggcca gcctggagat cagccccatc accttcctca ctgcccagac cctgctgatg
gacctcggac agttcctgct gttctgccac atcagctccc accagcatga tggcatggag
gcctatgtca aggtggacag ctgccctgag gagccacagc tcaggatgaa gaacaatgag
gaggctgagg actatgatga tgacctgact gactctgaga tggatgtggt ccgctttgat
gatgacaaca gcccatcctt cattcagatc aggtctgtgg ccaagaaaca ccccaagacc
tgggtgcact acattgctgc tgaggaggag gactgggact atgccccact ggtcctggcc
cctgatgaca ggagctacaa gagccagtac ctcaacaatg gcccacagag gattggacgc
aagtacaaga aagtcaggtt catggcctac actgatgaaa ccttcaagac cagggaggcc
attcagcatg agtctggcat cctgggccca ctcctgtatg gggaggtggg ggacaccctg
ctcatcatct tcaagaacca ggcctccagg ccctacaaca tctacccaca tggcatcact
gatgtcaggc ccctgtacag ccgcaggctg ccaaaggggg tgaaacacct caaggacttc
cccattctgc ctggggagat cttcaagtac aagtggactg tcactgtgga ggatggacca
accaaatctg accccaggtg cctcaccaga tactactcca gctttgtgaa catggagagg
gacctggcct ctggcctgat tggcccactg ctcatctgct acaaggagtc tgtggaccag
aggggaaacc agatcatgtc tgacaagagg aatgtgattc tgttctctgt ctttgatgag
aacaggagct ggtacctgac tgagaacatt cagcgcttcc tgcccaaccc tgctggggtg
cagctggagg accctgagtt ccaggccagc aacatcatgc actccatcaa tggctatgtg
tttgacagcc tccagctttc tgtctgcctg catgaggtgg cctactggta cattctttct
attggggccc agactgactt cctttctgtc ttcttctctg gctacacctt caaacacaag
atggtgtatg aggacaccct gaccctcttc ccattctctg ggagactgt gttcatgagc
atggagaacc ctggcctgtg gattctggga tgccacaact ctgacttccg caacaggggc
atgactgccc tgctcaaagt ctcctcctgt gacaagaaca ctggggacta ctatgaggac
agctatgagg acatctctgc ctacctgctc agcaagaaca atgccattga gcccagg
(SEQ ID NO:3)

```
                                                       g agatcaccag gaccaccctc
cagtctgacc aggaggagat tgactatgat gacaccattt ctgtggagat gaagaaagag
gactttgaca tctatgacga ggacgagaac cagagcccaa ggagcttcca gaagaagacc
aggcactact tcattgctgc tgtggagcgc ctgtgggact atggcatgag ctccagcccc
catgtcctca ggaacagggc ccagtctggc tctgtgccac agttcaagaa agtggtcttc
caagagttca ctgatggcag cttcacccag cccctgtaca gaggggagct gaatgagcac
ctgggactcc tgggcccata catcagggct gaggtggagg acaacatcat ggtgaccttc
cgcaaccagg cctccaggcc ctacagcttc tacagctccc tcatcagcta tgaggaggac
cagaggcagg gggctgagcc acgcaagaac tttgtgaaac ccaatgaaac caagacctac
ttctggaaag tccagcacca catggccccc accaaggatg agtttgactg caaggcctgg
gcctacttct ctgatgtgga cctggagaag gatgtgcact ctggcctgat tggcccactc
ctggtctgcc acaccaacac cctgaaccct gcccatggaa ggcaagtgac tgtgcaggag
tttgccctct tcttcaccat ctttgatgaa accaagagct ggtacttcac tgagaacatg
gagcgcaact gcagggcccc atgcaacatt cagatggagg accccacctt caaagagaac
taccgcttcc atgccatcaa tggctacatc atggacaccc tgcctgggct tgtcatggcc
caggaccaga ggatcaggtg gtacctgctt tctatgggct ccaatgagaa cattcactcc
atccacttct ctgggcatgt cttcactgtg cgcaagaagg aggagtacaa gatggccctg
tacaacctct accctggggt ctttgagact gtggagatgc tgccctccaa agctggcatc
tggagggtgg agtgcctcat tggggagcac ctgcatgctg gcatgagcac cctgttcctg
gtctacagca acaagtgcca gaccccccctg ggaatggcct ctggccacat cagggacttc
cagatcactg cctctggcca gtatggccag tgggccccca agctggccag gctccactac
tctggatcca tcaatgcctg gagcaccaag gagccattca gctggatcaa agtggacctg
ctggccccca tgatcatcca tggcatcaag acccaggggg ccaggcagaa gttctccagc
ctgtacatca gccagttcat catcatgtac agcctggatg gcaagaaatg gcagacctac
agaggcaact ccactggaac actcatggtc ttctttggca atgtggacag ctctggcatc
aagcacaaca tcttcaaccc cccaatcatc gccagataca tcaggctgca ccccacccac
tacagcatcc gcagcaccct caggatggag ctgatgggct gtgacctgaa ctcctgcagc
atgcccctgg gcatggagag caaggccatt tctgatgccc agatcactgc ctccagctac
ttcaccaaca tgtttgccac ctggagccca agcaaggcca ggctgcacct ccagggaagg
agcaatgcct ggaggcccca ggtcaacaac ccaaaggagt ggctgcaggt ggacttccag
aagaccatga aggtcactgg ggtgaccacc cagggggtca agagcctgct caccagcatg
tatgtgaagg agttcctgat cagctccagc caggatggcc accagtggac cctcttcttc
cagaatggca aggtcaaggt gttccagggc aaccaggaca gcttcacccc tgtggtgaac
agcctggacc cccccctcct gaccagatac ctgaggattc acccccagag ctgggtccac
cagattgccc tgaggatgga ggtcctggga tgtgaggccc aggacctgta c
(SEQ ID NO:4)
```

Figure 5

BDLO01 - agc ttctctcaga atccacctgt cctgaagaga caccagaga (SEQ ID NO:5)

BDLO04 - agc ttcagccaga atccacctgt cctgaaacgc caccagagg (SEQ ID NO:6)

BDLO23 - agc ttcagccaga accccccgt gctgaagagg caccagagg (SEQ ID NO:7)

BDLNG1 - agcttcagccagaatGTGAGCAACAATGTGAGCAACAATGCCACCAATAATGCTACCAACccacctgtcctgaaacgccaccagagg (SEQ ID NO:36)

BDLNG4 - agcttcagccagaatGTGAGCAACAATGCCACCAACAATGTGAGCAACccacctgtcctgaaacgccaccagagg (SEQ ID NO:37)

BDLNG5 - agcttcagccagaatGTGAGCAATAATGCCACCAACccacctgtcctgaaacgccaccagagg (SEQ ID NO:38)

BDLNG6 - agcttcagccagaatGTGAGCAATAATccacctgtcctgaaacgccaccagagg (SEQ ID NO:39)

BDLNG9 - agcttcagccagaatAGGAGCCTGccacctgtcctgaaacgccaccagagg (SEQ ID NO:40)

BDLNG10 - agcttcagccagaatGCCACTAATGTGTCTAACAACTCTGCTACCTCTGCTGACTCTGCTGTGAGCccacctgtcctgaaacgccaccagagg (SEQ ID NO:41)

BDLNG16 - agcttcagccagaatGCCACCAACTATGTGAACAGGAGCCTGccacctgtcctgaaacgccaccagagg (SEQ ID NO:42)

BDLNG17 - agcttcagccagaatGCCACCAACTATGTGAACAGGAGCCTGTCTGCCACCTCTGCTGACTCTGCTGTGAGCCAGAATccacctgtcctgaaacgccaccag agg(SEQ ID NO:43)

BDLNG18 - agcttcagccagaatGTGAGCAACAATGTGAGCAATGCTGTGTCTGCTGTGTCTGCTccacctgtcctgaaacgccaccagagg (SEQ ID NO:44)

BDLNG19 - agcttcagccagaatATCACTGTGGCCTCTGCCACCTCTAACATCACTGTGGCCTCTGCTGACccacctgtcctgaaacgccaccagagg (SEQ ID NO:45)

BDLNG20 - agcttcagccagaatATCACTGTGACCAACATCACTGTGACTGCCccacctgtcctgaaacgccaccagagg (SEQ ID NO:46)

BDLNG21 - agcttcagccagaatCAGACTGTGACCAACATCACTGTGACTGCCccacctgtcctgaaacgccaccagagg (SEQ ID NO:47)

BDLNGV - agcttcagccagaatGCCACTAATGTGTCTAACAACAGCAACACCAGCAATGACAGCAATGTGTCTccacctgtcctgaaacgccaccagagg (SEQ ID NO:48)

```
1    tcgcgcgttt cggtgatgac ggtgaaaacc tctgacacat gcagctcccg gagacggtca
61   cagcttgtct gtaagcggat gccgggagca gacaagcccg tcagggcgcg tcagcgggtg
121  ttggcgggtg tcggggctgg cttaactatg cggcatcaga gcagattgta ctgagagtgc
181  accatatgcg gtgtgaaata ccgcacagat gcgtaaggag aaaataccgc atcaggcgcc
241  attcgccatt caggctgcgc aactgttggg aagggcgatc ggtgcgggcc tcttcgctat
301  tacgccagct ggcgaaaggg ggatgtgctg caaggcgatt aagttgggta acgccagggt
361  tttcccagtc acgacgttgt aaaacgacgg ccagtgaatt cctcgagatt taaatgacgt
421  tggccactcc ctctctgcgc gctcgctcgc tcactgaggc cgggcgacca aaggtcgccc
481  gacgcccggg ctttgcccgg gcggcctcag tgagcgagcg agcgcgcaga gagggagtgg
541  ccaactccat cactaggggt tcctgagttt aaacttcgtc gacgattcga gcttgggctg
601  caggtcgagg gcactgggag gatgttgagt aagatggaaa actactgatg acccttgcag
661  agacagagta ttaggacatg tttgaacagg ggccgggcga tcagcaggta gctctagagg
721  atccccgtct gtctgcacat ttcgtagagc gagtgttccg atactctaat ctccctaggc
781  aaggttcata tttgtgtagg ttacttattc tccttttgtt gactaagtca ataatcagaa
841  tcagcaggtt tggagtcagc ttggcaggga tcagcagcct gggttggaag gagggggtat
901  aaaagcccct tcaccaggag aagccgtcac acagactagg cgcgccaccg ccaccatgca
961  gattgagctg agcacctgct tcttcctgtg cctgctgagg ttctgcttct ctgccaccag
1021 gagatactac ctgggggctg tggagctttc ttgggactac atgcagtctg acctggggga
1081 gctgcctgtg gatgccaggt tcccacccag agtgcccaaa tccttcccat tcaacacctc
1141 tgtggtctac aagaagaccc tctttgtgga gttcactgac cacctgttca acattgccaa
1201 acccaggcca ccctggatgg gactcctggg acccaccatt caggctgagg tgtatgacac
1261 tgtggtcatc accctcaaga acatggcctc ccaccctgtg agcctgcatg ctgtgggggt
1321 cagctactgg aaggcctctg agggggctga gtatgatgac cagacctccc agagggagaa
1381 ggaggatgac aaagtgttcc ctgggggcag ccacacctat gtgtggcagg tcctcaagga
1441 gaatggcccc atggcctctg acccactctg cctgacctac tcctaccttt ctcatgtgga
1501 cctggtcaag gacctcaact ctggactgat tggggccctg ctggtgtgca gggagggctc
1561 cctggccaaa gagaagaccc agaccctgca caagttcatt ctcctgtttg ctgtctttga
1621 tgagggcaag agctggcact ctgaaaccaa gaactccctg atgcaggaca gggatgctgc
1681 ctctgccagg gcctggccca agatgcacac tgtgaatggc tatgtgaaca ggagcctgcc
1741 tggactcatt ggctgccaca ggaaatctgt ctactggcat gtgattggca tggggacaac
1801 ccctgaggtg cactccattt tcctggaggg ccacaccttc ctggtcagga accacagaca
1861 ggccagcctg gagatcagcc ccatcacctt cctcactgcc cagaccctgc tgatggacct
1921 cggacagttc ctgctgttct gccacatcag ctcccaccag catgatggca tggaggccta
1981 tgtcaaggtg gacagctgcc ctgaggagcc acagctcagg atgaagaaca atgaggaggc
2041 tgaggactat gatgatgacc tgactgactc tgagatggat gtggtccgct ttgatgatga
2101 caacagccca tccttcattc agatcaggtc tgtggccaag aaacacccca agacctgggt
2161 gcactacatt gctgctgagg aggaggactg ggactatgcc ccactggtcc tggcccctga
2221 tgacaggagc tacaagagcc agtacctcaa caatggccca cagaggattg gacgcaagta
2281 caagaaagtc aggttcatgg cctacactga tgaaaccttc aagaccaggg aggccattca
2341 gcatgagtct ggcatcctgg gcccactcct gtatggggag gtgggggaca ccctgctcat
2401 catcttcaag aaccaggcct ccaggcccta caacatctac ccacatggca tcactgatgt
2461 caggcccctg tacagccgca ggctgccaaa gggggtgaaa cacctcaagg acttccccat
```

Figure 7A

```
2521 tctgcctggg gagatcttca agtacaagtg gactgtcact gtggaggatg gaccaaccaa
2581 atctgacccc aggtgcctca ccagatacta ctccagcttt gtgaacatgg agagggacct
2641 ggcctctggc ctgattggcc cactgctcat ctgctacaag gagtctgtgg accagagggg
2701 aaaccagatc atgtctgaca agaggaatgt gattctgttc tctgtctttg atgagaacag
2761 gagctggtac ctgactgaga acattcagcg cttcctgccc aaccctgctg ggtgcagct
2821 ggaggaccct gagttccagg ccagcaacat catgcactcc atcaatggct atgtgtttga
2881 cagcctccag ctttctgtct gcctgcatga ggtggcctac tggtacattc tttctattgg
2941 ggcccagact gacttccttt ctgtcttctt ctctggctac accttcaaac acaagatggt
3001 gtatgaggac accctgaccc tcttcccatt ctctggggag actgtgttca tgagcatgga
3061 gaaccctggc ctgtggattc tgggatgcca caactctgac ttccgcaaca ggggcatgac
3121 tgccctgctc aaagtctcct cctgtgacaa gaacactggg gactactatg aggacagcta
3181 tgaggacatc tctgcctacc tgctcagcaa gaacaatgcc attgagccca ggagcttcag
3241 ccagaatcca cctgtcctga aacgccacca gagggagatc accaggacca ccctccagtc
3301 tgaccaggag gagattgact atgatgacac catttctgtg gagatgaaga aagaggactt
3361 tgacatctat gacgaggacg agaaccagag cccaaggagc ttccagaaga agaccaggca
3421 ctacttcatt gctgctgtgg agcgcctgtg ggactatggc atgagctcca gcccccatgt
3481 cctcaggaac agggcccagt ctggctctgt gccacagttc aagaaagtgg tcttccaaga
3541 gttcactgat ggcagcttca cccagcccct gtacagaggg gagctgaatg agcacctggg
3601 actcctgggc ccatacatca gggctgaggt ggaggacaac atcatggtga ccttccgcaa
3661 ccaggcctcc aggccctaca gcttctacag ctccctcatc agctatgagg aggaccagag
3721 gcaggggggct gagccacgca agaactttgt gaaacccaat gaaaccaaga cctacttctg
3781 gaaagtccag caccacatgg cccccaccaa ggatgagttt gactgcaagg cctgggccta
3841 cttctctgat gtggacctgg agaaggatgt gcactctggc ctgattggcc cactcctggt
3901 ctgccacacc aacaccctga accctgccca tggaaggcaa gtgactgtgc aggagtttgc
3961 cctcttcttc accatctttg atgaaaccaa gagctggtac ttcactgaga acatggagcg
4021 caactgcagg gccccatgca acattcagat ggaggacccc accttcaaag agaactaccg
4081 cttccatgcc atcaatggct acatcatgga caccctgcct gggcttgtca tggcccagga
4141 ccagaggatc aggtggtacc tgctttctat gggctccaat gagaacattc actccatcca
4201 cttctctggg catgtcttca ctgtgcgcaa gaaggaggag tacaagatgg ccctgtacaa
4261 cctctaccct ggggtctttg agactgtgga gatgctgccc tccaaagctg gcatctggag
4321 ggtggagtgc ctcattgggg agcacctgca tgctggcatg agcaccctgt tcctggtcta
4381 cagcaacaag tgccagaccc ccctgggaat ggcctctggc cacatcaggg acttccagat
4441 cactgcctct ggccagtatg gccagtgggc cccaagctg gccaggctcc actactctgg
4501 atccatcaat gcctggagca ccaaggagcc attcagctgg atcaaagtgg acctgctggc
4561 ccccatgatc atccatggca tcaagaccca gggggccagg cagaagttct ccagcctgta
4621 catcagccag ttcatcatca tgtacagcct ggatggcaag aaatggcaga cctacagagg
4681 caactccact ggaacactca tggtcttctt tggcaatgtg gacagctctg gcatcaagca
4741 caacatcttc aacccccaa tcatcgccag atacatcagg ctgcacccca cccactacag
4801 catccgcagc accctcagga tggagctgat gggctgtgac ctgaactcct gcagcatgcc
4861 cctgggcatg gagagcaagg ccatttctga tgcccagatc actgcctcca gctacttcac
4921 caacatgttt gccacctgga gcccaagcaa ggccaggctg cacctccagg gaaggagcaa
4981 tgcctggagg ccccaggtca acaacccaaa ggagtggctg caggtggact tccagaagac
```

Figure 7B

```
5041 catgaaggtc actggggtga ccacccaggg ggtcaagagc ctgctcacca gcatgtatgt
5101 gaaggagttc ctgatcagct ccagccagga tggccaccag tggaccctct tcttccagaa
5161 tggcaaggtc aaggtgttcc agggcaacca ggacagcttc acccctgtgg tgaacagcct
5221 ggaccccccc ctcctgacca gatacctgag gattcacccc cagagctggg tccaccagat
5281 tgccctgagg atggaggtcc tgggatgtga ggcccaggac ctgtactgat gacgagcggc
5341 cgctcttagt agcagtatcg ataataaaag atctttattt tcattagatc tgtgtgttgg
5401 ttttttgtgt gttaattaag ctcgcgaagg aacccctagt gatggagttg gccactccct
5461 ctctgcgcgc tcgctcgctc actgaggccg ggcgaccaaa ggtcgcccga cgcccgggct
5521 ttgcccgggc ggcctcagtg agcgagcgag cgcgcagaga gggagtggcc aagacgattt
5581 aaatgacaag cttggcgtaa tcatggtcat agctgtttcc tgtgtgaaat tgttatccgc
5641 tcacaattcc acacaacata cgagccggaa gcataaagtg taaagcctgg ggtgcctaat
5701 gagtgagcta actcacatta attgcgttgc gctcactgcc cgctttccag tcgggaaacc
5761 tgtcgtgcca gctgcattaa tgaatcggcc aacgcgcggg gagaggcggt ttgcgtattg
5821 ggcgctcttc cgcttcctcg ctcactgact cgctgcgctc ggtcgttcgg ctgcggcgag
5881 cggtatcagc tcactcaaag gcggtaatac ggttatccac agaatcaggg gataacgcag
5941 gaaagaacat gtgagcaaaa ggccagcaaa aggccaggaa ccgtaaaaag gccgcgttgc
6001 tggcgttttt ccataggctc cgcccccctg acgagcatca caaaaatcga cgctcaagtc
6061 agaggtggcg aaacccgaca ggactataaa gataccaggc gtttccccct ggaagctccc
6121 tcgtgcgctc tcctgttccg accctgccgc ttaccggata cctgtccgcc tttctccctt
6181 cgggaagcgt ggcgctttct catagctcac gctgtaggta tctcagttcg gtgtaggtcg
6241 ttcgctccaa gctgggctgt gtgcacgaac cccccgttca gcccgaccgc tgcgccttat
6301 ccggtaacta tcgtcttgag tccaacccgg taagacacga cttatcgcca ctggcagcag
6361 ccactggtaa caggattagc agagcgaggt atgtaggcgg tgctacagag ttcttgaagt
6421 ggtggcctaa ctacggctac actagaagaa cagtatttgg tatctgcgct ctgctgaagc
6481 cagttacctt cggaaaaaga gttggtagct cttgatccgg caaacaaacc accgctggta
6541 gcggtggttt ttttgtttgc aagcagcaga ttacgcgcag aaaaaaagga tctcaagaag
6601 atcctttgat cttttctacg gggtctgacg ctcagtggaa cgaaaactca cgttaaggga
6661 ttttggtcat gagattatca aaaaggatct tcacctagat ccttttaaat taaaaatgaa
6721 gttttaaatc aatctaaagt atatatgagt aaacttggtc tgacagttac caatgcttaa
6781 tcagtgaggc acctatctca gcgatctgtc tatttcgttc atccatagtt gcctgactcc
6841 ccgtcgtgta gataactacg atacgggagg gcttaccatc tggccccagt gctgcaatga
6901 taccgcgaga cccacgctca ccggctccag atttatcagc aataaaccag ccagccggaa
6961 gggccgagcg cagaagtggt cctgcaactt tatccgcctc catccagtct attaattgtt
7021 gccgggaagc tagagtaagt agttcgccag ttaatagttt gcgcaacgtt gttgccattg
7081 ctacaggcat cgtggtgtca cgctcgtcgt ttggtatggc ttcattcagc tccggttccc
7141 aacgatcaag gcgagttaca tgatccccca tgttgtgcaa aaaagcggtt agctccttcg
7201 gtcctccgat cgttgtcaga agtaagttgg ccgcagtgtt atcactcatg gttatggcag
7261 cactgcataa ttctcttact gtcatgccat ccgtaagatg cttttctgtg actggtgagt
7321 actcaaccaa gtcattctga gaatagtgta tgcggcgacc gagttgctct tgcccggcgt
7381 caatacggga taataccgcg ccacatagca gaactttaaa agtgctcatc attggaaaac
7441 gttcttcggg gcgaaaactc tcaaggatct taccgctgtt gagatccagt tcgatgtaac
7501 ccactcgtgc acccaactga tcttcagcat cttttacttt caccagcgtt tctgggtgag
7561 caaaaacagg aaggcaaaat gccgcaaaaa agggaataag ggcgacacgg aaatgttgaa
7621 tactcatact cttccttttt caatattatt gaagcattta tcagggttat tgtctcatga
7681 gcggatacat atttgaatgt atttagaaaa ataaacaaat aggggttccg cgcacatttc
7741 cccgaaaagt gccacctgac gtctaagaaa ccattattat catgacatta acctataaaa
7801 ataggcgtat cacgaggccc tttcgtc  (SEQ ID NO:8)
```

ATGCAGATTGAGCTGTCCACCTGCTTCTTTCTGTGCCTGCTGAGATTCTGCTTCTCTGCCACCAGGA
GATACTACCTGGGGGCTGTGGAACTTTCTTGGGACTACATGCAGTCTGACCTGGGAGAGCTGCCTGT
GGATGCCAGGTTCCCACCCAGAGTGCCCAAGTCCTTCCCATTCAACACCTCTGTGGTCTACAAGAAG
ACACTCTTTGTGGAATTCACTGACCACCTGTTCAACATTGCAAAACCCAGACCACCCTGGATGGGAC
TCCTGGGACCCACCATTCAGGCTGAGGTGTATGACACTGTGGTCATCACCCTCAAGAACATGGCATC
CCACCCTGTGTCTCTGCATGCTGTGGGAGTCTCATACTGGAAAGCCTCTGAAGGGGCTGAGTATGAT
GACCAGACATCCCAGAGAGAGAAAGAGGATGACAAGGTGTTCCCTGGGGGATCTCACACCTATGTGT
GGCAAGTCCTCAAGGAGAATGGACCCATGGCATCTGACCCACTCTGCCTGACATACTCCTACCTTTC
TCATGTGGACCTGGTCAAGGACCTCAACTCTGGACTGATTGGGGCACTGCTGGTGTGCAGGGAAGGA
TCCCTGGCCAAGGAGAAAACCCAGACACTGCACAAGTTCATTCTCCTGTTTGCTGTCTTTGATGAGG
GCAAGTCTTGGCACTCTGAAACAAAGAACTCCCTGATGCAAGACAGGGATGCTGCCTCTGCCAGGGC
ATGGCCCAAGATGCACACTGTGAATGGCTATGTGAACAGATCACTGCCTGGACTCATTGGCTGCCAC
AGGAAATCTGTCTACTGGCATGTGATTGGCATGGGGACAACCCCTGAAGTGCACTCCATTTTCCTGG
AGGGACACACCTTCCTGGTCAGGAACCACAGACAAGCCTCTCTGGAGATCTCTCCCATCACCTTCCT
CACTGCACAGACACTGCTGATGGACCTTGGACAGTTCCTGCTGTCCTGCCACATCTCTTCCCACCAG
CATGATGGCATGGAAGCCTATGTCAAGGTGGACTCATGCCCTGAGGAACCACAGCTCAGGATGAAGA
ACAATGAGGAGGCTGAGGACTATGATGATGACCTGACTGACTCTGAGATGGATGTGGTCAGATTTGA
TGATGACAACTCTCCATCCTTCATTCAGATCAGGTCTGTGGCAAAGAAACACCCCAAGACATGGGTG
CACTACATTGCTGCTGAGGAAGAGGACTGGGACTATGCACCACTGGTCCTGGCCCCTGATGACAGGA
GCTACAAGTCTCAGTACCTCAACAATGGCCCACAAAGAATTGGAAGAAAGTACAAGAAAGTCAGATT
CATGGCCTACACTGATGAAACCTTCAAGACAAGAGAAGCCATTCAGCATGAGTCTGGCATTCTGGGA
CCACTCCTGTATGGGGAAGTGGGAGACACCCTGCTCATCATCTTCAAGAACCAGGCCTCCAGGCCCT
ACAACATCTACCCACATGGCATCACTGATGTCAGGCCCCTGTACAGCAGGAGACTGCCAAAGGGGT
GAAACACCTCAAGGACTTCCCCATTCTGCCTGGAGAGATCTTCAAGTACAAGTGGACTGTCACTGTG
GAGGATGGACCAACAAAGTCTGACCCCAGGTGCCTCACCAGATACTACTCCTCTTTTGTGAACATGG
AGAGAGACCTGGCATCTGGACTGATTGGACCACTGCTCATCTGCTACAAGGAGTCTGTGGACCAGAG
AGGCAACCAGATCATGTCTGACAAGAGAAATGTGATTCTGTTCTCTGTCTTTGATGAGAACAGATCA
TGGTACCTGACTGAGAACATTCAGAGATTCCTGCCCAACCCTGCTGGGGTGCAACTGGAAGACCCTG
AGTTCCAGGCAAGCAACATCATGCACTCCATCAATGGCTATGTGTTTGACTCTCTCCAGCTTTCTGT
CTGCCTGCATGAGGTGGCCTACTGGTACATTCTTTCTATTGGGGCACAAACTGACTTCCTTTCTGTC
TTCTTCTCTGGATACACCTTCAAGCACAAGATGGTGTATGAGGACACCCTGACACTCTTCCCATTCT
CTGGGGAAACTGTGTTCATGAGCATGGAGAACCCTGGACTGTGGATTCTGGGATGCCACAACTCTGA
CTTCAGAAACAGGGGAATGACTGCACTGCTCAAAGTCTCCTCCTGTGACAAGAACACTGGGGACTAC
TATGAGGACTCTTATGAGGACATCTCTGCCTACCTGCTCAGCAAGAACAATGCCATTGAGCCCAGAA
GCTTCTCTCAGAATCCACCTGTCCTGAAGAGACACCAGAGAGAGATCACCAGGACAACCCTCCAGTC
TGACCAGGAAGAGATTGACTATGATGACACCATTTCTGTGGAGATGAAGAAGGAGGACTTTGACATC
TATGATGAGGACGAGAACCAGTCTCCAAGATCATTCCAGAAGAAGACAAGACACTACTTCATTGCTG
CTGTGGAAAGACTGTGGGACTATGGCATGTCTTCCTCTCCCCATGTCCTCAGGAACAGGGCACAGTC
TGGCTCTGTGCCACAGTTCAAGAAAGTGGTCTTCCAGGAGTTCACTGATGGCTCATTCACCCAGCCC
CTGTACAGAGGGGAACTGAATGAGCACCTGGGACTCCTGGGACCATACATCAGGGCTGAGGTGGAAG
ACAACATCATGGTGACATTCAGAAACCAGGCCTCCAGGCCCTACAGCTTCTACTCTTCCCTCATCAG
CTATGAGGAAGACCAGAGACAAGGGGCTGAGCCAAGAAAGAACTTTGTGAAACCCAATGAAACCAAG
ACCTACTTCTGGAAAGTCCAGCACCACATGGCACCCACCAAGGATGAGTTTGACTGCAAGGCCTGGG (Continued)

Figure 8A

CATACTTCTCTGATGTGGACCTGGAGAAAGATGTGCACTCTGGCCTGATTGGCCCACTCCTGGTCTG
CCACACCAACACCCTGAACCCTGCACATGGAAGGCAAGTGACTGTGCAGGAGTTTGCCCTCTTCTTC
ACCATCTTTGATGAAACCAAGTCATGGTACTTCACTGAGAACATGGAGAGAAACTGCAGAGCACCAT
GCAACATTCAGATGGAAGACCCCACCTTCAAGGAGAACTACAGGTTCCATGCCATCAATGGCTACAT
CATGGACACCCTGCCTGGGCTTGTCATGGCACAGGACCAGAGAATCAGATGGTACCTGCTTTCTATG
GGATCCAATGAGAACATTCACTCCATCCACTTCTCTGGGCATGTCTTCACTGTGAGAAAGAAGGAGG
AATACAAGATGGCCCTGTACAACCTCTACCCTGGGGTCTTTGAGACTGTGGAGATGCTGCCCTCCAA
AGCTGGCATCTGGAGGGTGGAATGCCTCATTGGGGAGCACCTGCATGCTGGCATGTCAACCCTGTTC
CTGGTCTACAGCAACAAGTGCCAGACACCCCTGGGAATGGCCTCTGGCCACATCAGGGACTTCCAGA
TCACTGCCTCTGGCCAGTATGGCCAGTGGGCACCCAAACTGGCCAGGCTCCACTACTCTGGCTCCAT
CAATGCATGGTCAACCAAGGAGCCATTCTCTTGGATCAAGGTGGACCTGCTGGCACCCATGATCATT
CATGGCATCAAGACACAGGGGGCAAGACAGAAATTCTCCTCTCTGTACATCTCACAGTTCATCATCA
TGTACTCTCTGGATGGCAAGAAGTGGCAGACATACAGAGGCAACTCCACTGGCACCCTCATGGTCTT
CTTTGGCAATGTGGACAGCTCTGGCATCAAGCACAACATCTTCAACCCTCCCATCATTGCCAGATAC
ATCAGGCTGCACCCCACCCACTACTCAATCAGATCAACCCTCAGGATGGAACTGATGGGATGTGACC
TGAACTCCTGCTCAATGCCCCTGGGAATGGAGAGCAAGGCCATTTCTGATGCCCAGATCACTGCATC
CTCTTACTTCACCAACATGTTTGCCACCTGGTCACCATCAAAAGCCAGGCTGCACCTCCAGGGAAGA
AGCAATGCCTGGAGACCCCAGGTCAACAACCCAAAGGAATGGCTGCAAGTGGACTTCCAGAAGACAA
TGAAAGTCACTGGGGTGACAACCCAGGGGGTCAAGTCTCTGCTCACCTCAATGTATGTGAAGGAGTT
CCTGATCTCTTCCTCACAGGATGGCCACCAGTGGACACTCTTCTTCCAGAATGGCAAAGTCAAGGTG
TTCCAGGGCAACCAGGACTCTTTCACACCTGTGGTGAACTCACTGGACCCCCCCCTCCTGACAAGAT
ACCTGAGAATTCACCCCCAGTCTTGGGTCCACCAGATTGCCCTGAGAATGGAAGTCCTGGGATGTGA
GGCACAAGACCTGTACTGA (SEQ ID NO:49)

ATGCAGATTGAGCTGAGCACCTGCTTCTTCCTGTGCCTGCTGAGGTTCTGCTTCTCTGCCACCAGGAGATAC
TACCTGGGGGCTGTGGAGCTTTCTTGGGACTACATGCAGTCTGACCTGGGGGAGCTGCCTGTGGATGCCAGG
TTCCCACCCAGAGTGCCCAAATCCTTCCCATTCAACACCTCTGTGGTCTACAAGAAGACCCTCTTTGTGGAG
TTCACTGACCACCTGTTCAACATTGCCAAACCCAGGCCACCCTGGATGGGACTCCTGGGACCCACCATTCAG
GCTGAGGTGTATGACACTGTGGTCATCACCCTCAAGAACATGGCCTCCCACCCTGTGAGCCTGCATGCTGTG
GGGGTCAGCTACTGGAAGGCCTCTGAGGGGGCTGAGTATGATGACCAGACCTCCCAGAGGGAGAAGGAGGAT
GACAAAGTGTTCCCTGGGGGCAGCCACACCTATGTGTGGCAGGTCCTCAAGGAGAATGGCCCCATGGCCTCT
GACCCACTCTGCCTGACCTACTCCTACCTTTCTCATGTGGACCTGGTCAAGGACCTCAACTCTGGACTGATT
GGGGCCCTGCTGGTGTGCAGGGAGGGCTCCCTGGCCAAAGAGAAGACCCAGACCCTGCACAAGTTCATTCTC
CTGTTTGCTGTCTTTGATGAGGGCAAGAGCTGGCACTCTGAAACCAAGAACTCCCTGATGCAGGACAGGGAT
GCTGCCTCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGGACAACCCCTGAGGTGCACTCCATT
TTCCTGGAGGGCCACACCTTCCTGGTCAGGAACCACAGACAGGCCAGCCTGGAGATCAGCCCCATCACCTTC
CTCACTGCCCAGACCCTGCTGATGGACCTCGGACAGTTCCTGCTGTTCTGCCACATCAGCTCCCACCAGCAT
GATGGCATGGAGGCCTATGTCAAGGTGGACAGCTGCCCTGAGGAGCCACAGCTCAGGATGAAGAACAATGAG
GAGGCTGAGGACTATGATGATGACCTGACTGACTCTGAGATGGATGTGGTCCGCTTTGATGATGACAACAGC
CCATCCTTCATTCAGATCAGGTCTGTGGCCAAGAAACACCCCAAGACCTGGGTGCACTACATTGCTGCTGAG
GAGGAGGACTGGGACTATGCCCCACTGGTCCTGGCCCCTGATGACAGGAGCTACAAGAGCCAGTACCTCAAC
AATGGCCCACAGAGGATTGGACGCAAGTACAAGAAAGTCAGGTTCATGGCCTACACTGATGAAACCTTCAAG
ACCAGGGAGGCCATTCAGCATGAGTCTGGCATCCTGGGCCCACTCCTGTATGGGGAGGTGGGGGACACCCTG
CTCATCATCTTCAAGAACCAGGCCTCCAGGCCCTACAACATCTACCCACATGGCATCACTGATGTCAGGCCC
CTGTACAGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGATACTAC
TCCAGCTTTGTGAACATGGAGAGGGACCTGGCCTCTGGCCTGATTGGCCCACTGCTCATCTGCTACAAGGAG
TCTGTGGACCAGAGGGGAAACCAGATCATGTCTGACAAGAGGAATGTGATTCTGTTCTCTGTCTTTGATGAG
AACAGGAGCTGGTACCTGACTGAGAACATTCAGCGCTTCCTGCCCAACCCTGCTGGGGTGCAGCTGGAGGAC
CCTGAGTTCCAGGCCAGCAACATCATGCACTCCATCAATGGCTATGTGTTTGACAGCCTCCAGCTTTCTGTC
TGCCTGCATGAGGTGGCCTACTGGTACATTCTTTCTATTGGGGCCCAGACTGACTTCCTTTCTGTCTTCTTC
TCTGGCTACACCTTCAAACACAAGATGGTGTATGAGGACACCCTGACCCTCTTCCCATTCTCTGGGGAGACT
GTGTTCATGAGCATGGAGAACCCTGGCCTGTGGATTCTGGGATGCCACAACTCTGACTTCCGCAACAGGGGC
ATGACTGCCCTGCTCAAAGTCTCCTCCTGTGACAAGAACACTGGGGACTACTATGAGGACAGCTATGAGGAC
ATCTCTGCCTACCTGCTCAGCAAGAACAATGCCATTGAGCCCAGGGAGATCACCAGGACCACCCTCCAGTCT
GACCAGGAGGAGATTGACTATGATGACACCATTTCTGTGGAGATGAAGAAAGAGGACTTTGACATCTATGAC
GAGGACGAGAACCAGAGCCCAAGGAGCTTCCAGAAGAAGACCAGGCACTACTTCATTGCTGCTGTGGAGCGC
CTGTGGGACTATGGCATGAGCTCCAGCCCCCATGTCCTCAGGAACAGGGCCCAGTCTGGCTCTGTGCCACAG
TTCAAGAAAGTGGTCTTCCAAGAGTTCACTGATGGCAGCTTCACCCAGCCCCTGTACAGAGGGGAGCTGAAT
GAGCACCTGGGACTCCTGGGCCCATACATCAGGGCTGAGGTGGAGGACAACATCATGGTGACCTTCCGCAAC
CAGGCCTCCAGGCCCTACAGCTTCTACAGCTCCCTCATCAGCTATGAGGAGGACCAGAGGCAGGGGGCTGAG
CCACGCAAGAACTTTGTGAAACCCAATGAAACCAAGACCTACTTCTGGAAAGTCCAGCACCACATGGCCCCC (Continued)

Figure 9A

ACCAAGGATGAGTTTGACTGCAAGGCCTGGGCCTACTTCTCTGATGTGGACCTGGAGAAGGATGTGCACTCT
GGCCTGATTGGCCCACTCCTGGTCTGCCACACCAACACCCTGAACCCTGCCCATGGAAGGCAAGTGACTGTG
CAGGAGTTTGCCCTCTTCTTCACCATCTTTGATGAAACCAAGAGCTGGTACTTCACTGAGAACATGGAGCGC
AACTGCAGGGCCCCATGCAACATTCAGATGGAGGACCCCACCTTCAAAGAGAACTACCGCTTCCATGCCATC
AATGGCTACATCATGGACACCCTGCCTGGGCTTGTCATGGCCCAGGACCAGAGGATCAGGTGGTACCTGCTT
TCTATGGGCTCCAATGAGAACATTCACTCCATCCACTTCTCTGGGCATGTCTTCACTGTGCGCAAGAAGGAG
GAGTACAAGATGGCCCTGTACAACCTCTACCCTGGGGTCTTTGAGACTGTGGAGATGCTGCCCTCCAAAGCT
GGCATCTGGAGGGTGGAGTGCCTCATTGGGGAGCACCTGCATGCTGGCATGAGCACCCTGTTCCTGGTCTAC
AGCAACAAGTGCCAGACCCCCCTGGGAATGGCCTCTGGCCACATCAGGGACTTCCAGATCACTGCCTCTGGC
CAGTATGGCCAGTGGGCCCCCAAGCTGGCCAGGCTCCACTACTCTGGATCCATCAATGCCTGGAGCACCAAG
GAGCCATTCAGCTGGATCAAAGTGGACCTGCTGGCCCCCATGATCATCCATGGCATCAAGACCCAGGGGGCC
AGGCAGAAGTTCTCCAGCCTGTACATCAGCCAGTTCATCATCATGTACAGCCTGGATGGCAAGAAATGGCAG
ACCTACAGAGGCAACTCCACTGGAACACTCATGGTCTTCTTTGGCAATGTGGACAGCTCTGGCATCAAGCAC
AACATCTTCAACCCCCCAATCATCGCCAGATACATCAGGCTGCACCCCACCCACTACAGCATCCGCAGCACC
CTCAGGATGGAGCTGATGGGCTGTGACCTGAACTCCTGCAGCATGCCCCTGGGCATGGAGAGCAAGGCCATT
TCTGATGCCCAGATCACTGCCTCCAGCTACTTCACCAACATGTTTGCCACCTGGAGCCCAAGCAAGGCCAGG
CTGCACCTCCAGGGAAGGAGCAATGCCTGGAGGCCCCAGGTCAACAACCCAAAGGAGTGGCTGCAGGTGGAC
TTCCAGAAGACCATGAAGGTCACTGGGGTGACCACCCAGGGGGTCAAGAGCCTGCTCACCAGCATGTATGTG
AAGGAGTTCCTGATCAGCTCCAGCCAGGATGGCCACCAGTGGACCCTCTTCTTCCAGAATGGCAAGGTCAAG
GTGTTCCAGGGCAACCAGGACAGCTTCACCCCTGTGGTGAACAGCCTGGACCCCCCCCTCCTGACCAGATAC
CTGAGGATTCACCCCCAGAGCTGGGTCCACCAGATTGCCCTGAGGATGGAGGTCCTGGGATGTGAGGCCCAG
GACCTGTACTGA (SEQ ID NO:9)

MQIELSTCFFLCLLRFCFSATRRYYLGAVELSWDYMQSDLGELPVDARFPPRVPKSFPFNTSVVYKK
TLFVEFTDHLFNIAKPRPPWMGLLGPTIQAEVYDTVVITLKNMASHPVSLHAVGVSYWKASEGAEYD
DQTSQREKEDDKVFPGGSHTYVWQVLKENGPMASDPLCLTYSYLSHVDLVKDLNSGLIGALLVCREG
SLAKEKTQTLHKFILLFAVFDEGKSWHSETKNSLMQDRDAASARAWPKMHTVNGYVNRSLPGLIGCH
RKSVYWHVIGMGTTPEVHSIFLEGHTFLVRNHRQASLEISPITFLTAQTLLMDLGQFLLFCHISSHQ
HDGMEAYVKVDSCPEEPQLRMKNNEEAEDYDDDLTDSEMDVVRFDDDNSPSFIQIRSVAKKHPKTWV
HYIAAEEEDWDYAPLVLAPDDRSYKSQYLNNGPQRIGRKYKKVRFMAYTDETFKTREAIQHESGILG
PLLYGEVGDTLLIIFKNQASRPYNIYPHGITDVRPLYSRRLPKGVKHLKDFPILPGEIFKYKWTVTV
EDGPTKSDPRCLTRYYSSFVNMERDLASGLIGPLLICYKESVDQRGNQIMSDKRNVILFSVFDENRS
WYLTENIQRFLPNPAGVQLEDPEFQASNIMHSINGYVFDSLQLSVCLHEVAYWYILSIGAQTDFLSV
FFSGYTFKHKMVYEDTLTLFPFSGETVFMSMENPGLWILGCHNSDFRNRGMTALLKVSSCDKNTGDY
YEDSYEDISAYLLSKNNAIEPREITRTTLQSDQEEIDYDDTISVEMKKEDFDIYDEDENQSPRSFQK
KTRHYFIAAVERLWDYGMSSSPHVLRNRAQSGSVPQFKKVVFQEFTDGSFTQPLYRGELNEHLGLLG
PYIRAEVEDNIMVTFRNQASRPYSFYSSLISYEEDQRQGAEPRKNFVKPNETKTYFWKVQHHMAPTK
DEFDCKAWAYFSDVDLEKDVHSGLIGPLLVCHTNTLNPAHGRQVTVQEFALFFTIFDETKSWYFTEN
MERNCRAPCNIQMEDPTFKENYRFHAINGYIMDTLPGLVMAQDQRIRWYLLSMGSNENIHSIHFSGH
VFTVRKKEEYKMALYNLYPGVFETVEMLPSKAGIWRVECLIGEHLHAGMSTLFLVYSNKCQTPLGMA
SGHIRDFQITASGQYGQWAPKLARLHYSGSINAWSTKEPFSWIKVDLLAPMIIHGIKTQGARQKFSS
LYISQFIIMYSLDGKKWQTYRGNSTGTLMVFFGNVDSSGIKHNIFNPPIIARYIRLHPTHYSIRSTL
RMELMGCDLNSCSMPLGMESKAISDAQITASSYFTNMFATWSPSKARLHLQGRSNAWRPQVNNPKEW
LQVDFQKTMKVTGVTTQGVKSLLTSMYVKEFLISSSQDGHQWTLFFQNGKVKVFQGNQDSFTPVVNS
LDPPLLTRYLRIHPQSWVHQIALRMEVLGCEAQDLY (SEQ ID NO:10)

ATGCAGATTGAGCTGAGCACCTGCTTCTTCCTGTGCCTGCTGAGGTTCTGCTTCTCTGCCACCAGG
AGATACTACCTGGGGGCTGTGGAGCTTTCTTGGGACTACATGCAGTCTGACCTGGGGGAGCTGCCT
GTGGATGCCAGGTTCCCACCCAGAGTGCCCAAATCCTTCCCATTCAACACCTCTGTGGTCTACAAG
AAGACCCTCTTTGTGGAGTTCACTGACCACCTGTTCAACATTGCCAAACCCAGGCCACCCTGGATG
GGACTCCTGGGACCCACCATTCAGGCTGAGGTGTATGACACTGTGGTCATCACCCTCAAGAACATG
GCCTCCCACCCTGTGAGCCTGCATGCTGTGGGGGTCAGCTACTGGAAGGCCTCTGAGGGGGCTGAG
TATGATGACCAGACCTCCCAGAGGGAGAAGGAGGATGACAAAGTGTTCCCTGGGGGCAGCCACACC
TATGTGTGGCAGGTCCTCAAGGAGAATGGCCCCATGGCCTCTGACCCACTCTGCCTGACCTACTCC
TACCTTTCTCATGTGGACCTGGTCAAGGACCTCAACTCTGGACTGATTGGGGCCCTGCTGGTGTGC
AGGGAGGGCTCCCTGGCCAAAGAGAAGACCCAGACCCTGCACAAGTTCATTCTCCTGTTTGCTGTC
TTTGATGAGGGCAAGAGCTGGCACTCTGAAACCAAGAACTCCCTGATGCAGGACAGGGATGCTGCC
TCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGGACAACCCCTGAGGTGCAC
TCCATTTTCCTGGAGGGCCACACCTTCCTGGTCAGGAACCACAGACAGGCCAGCCTGGAGATCAGC
CCCATCACCTTCCTCACTGCCCAGACCCTGCTGATGGACCTCGGACAGTTCCTGCTGTTCTGCCAC
ATCAGCTCCCACCAGCATGATGGCATGGAGGCCTATGTCAAGGTGGACAGCTGCCCTGAGGAGCCA
CAGCTCAGGATGAAGAACAATGAGGAGGCTGAGGACTATGATGATGACCTGACTGACTCTGAGATG
GATGTGGTCCGCTTTGATGATGACAACAGCCCATCCTTCATTCAGATCAGGTCTGTGGCCAAGAAA
CACCCCAAGACCTGGGTGCACTACATTGCTGCTGAGGAGGAGGACTGGGACTATGCCCCACTGGTC
CTGGCCCCTGATGACAGGAGCTACAAGAGCCAGTACCTCAACAATGGCCCACAGAGGATTGGACGC
AAGTACAAGAAAGTCAGGTTCATGGCCTACACTGATGAAACCTTCAAGACCAGGGAGGCCATTCAG
CATGAGTCTGGCATCCTGGGCCCACTCCTGTATGGGGAGGTGGGGGACACCCTGCTCATCATCTTC
AAGAACCAGGCCTCCAGGCCCTACAACATCTACCCACATGGCATCACTGATGTCAGGCCCCTGTAC
AGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGA
TACTACTCCAGCTTTGTGAACATGGAGAGGGACCTGGCCTCTGGCCTGATTGGCCCACTGCTCATC
TGCTACAAGGAGTCTGTGGACCAGAGGGGAAACCAGATCATGTCTGACAAGAGGAATGTGATTCTG
TTCTCTGTCTTTGATGAGAACAGGAGCTGGTACCTGACTGAGAACATTCAGCGCTTCCTGCCCAAC
CCTGCTGGGGTGCAGCTGGAGGACCCTGAGTTCCAGGCCAGCAACATCATGCACTCCATCAATGGC
TATGTGTTTGACAGCCTCCAGCTTTCTGTCTGCCTGCATGAGGTGGCCTACTGGTACATTCTTTCT
ATTGGGGCCCAGACTGACTTCCTTTCTGTCTTCTTCTCTGGCTACACCTTCAAACACAAGATGGTG
TATGAGGACACCCTGACCCTCTTCCCATTCTCTGGGGAGACTGTGTTCATGAGCATGGAGAACCCT
GGCCTGTGGATTCTGGGATGCCACAACTCTGACTTCCGCAACAGGGGCATGACTGCCCTGCTCAAA
GTCTCCTCCTGTGACAAGAACACTGGGGACTACTATGAGGACAGCTATGAGGACATCTCTGCCTAC
CTGCTCAGCAAGAACAATGCCATTGAGCCCAGGAGCTTCAGCCAGAATTCCAGACACCCCAGCACC
AGGGAGATCACCAGGACCACCCTCCAGTCTGACCAGGAGGAGATTGACTATGATGACACCATTTCT
GTGGAGATGAAGAAAGAGGACTTTGACATCTATGACGAGGACGAGAACCAGAGCCCAAGGAGCTTC (Continued)

Figure 11A

CAGAAGAAGACCAGGCACTACTTCATTGCTGCTGTGGAGCGCCTGTGGGACTATGGCATGAGCTCC
AGCCCCCATGTCCTCAGGAACAGGGCCCAGTCTGGCTCTGTGCCACAGTTCAAGAAAGTGGTCTTC
CAAGAGTTCACTGATGGCAGCTTCACCCAGCCCCTGTACAGAGGGGAGCTGAATGAGCACCTGGGA
CTCCTGGGCCCATACATCAGGGCTGAGGTGGAGGACAACATCATGGTGACCTTCCGCAACCAGGCC
TCCAGGCCCTACAGCTTCTACAGCTCCCTCATCAGCTATGAGGAGGACCAGAGGCAGGGGGCTGAG
CCACGCAAGAACTTTGTGAAACCCAATGAAACCAAGACCTACTTCTGGAAAGTCCAGCACCACATG
GCCCCCACCAAGGATGAGTTTGACTGCAAGGCCTGGGCCTACTTCTCTGATGTGGACCTGGAGAAG
GATGTGCACTCTGGCCTGATTGGCCCACTCCTGGTCTGCCACACCAACACCCTGAACCCTGCCCAT
GGAAGGCAAGTGACTGTGCAGGAGTTTGCCCTCTTCTTCACCATCTTTGATGAAACCAAGAGCTGG
TACTTCACTGAGAACATGGAGCGCAACTGCAGGGCCCCATGCAACATTCAGATGGAGGACCCCACC
TTCAAAGAGAACTACCGCTTCCATGCCATCAATGGCTACATCATGGACACCCTGCCTGGGCTTGTC
ATGGCCCAGGACCAGAGGATCAGGTGGTACCTGCTTTCTATGGGCTCCAATGAGAACATTCACTCC
ATCCACTTCTCTGGGCATGTCTTCACTGTGCGCAAGAAGGAGGAGTACAAGATGGCCCTGTACAAC
CTCTACCCTGGGGTCTTTGAGACTGTGGAGATGCTGCCCTCCAAAGCTGGCATCTGGAGGGTGGAG
TGCCTCATTGGGGAGCACCTGCATGCTGGCATGAGCACCCTGTTCCTGGTCTACAGCAACAAGTGC
CAGACCCCCCTGGGAATGGCCTCTGGCCACATCAGGGACTTCCAGATCACTGCCTCTGGCCAGTAT
GGCCAGTGGGCCCCCAAGCTGGCCAGGCTCCACTACTCTGGATCCATCAATGCCTGGAGCACCAAG
GAGCCATTCAGCTGGATCAAAGTGGACCTGCTGGCCCCCATGATCATCCATGGCATCAAGACCCAG
GGGGCCAGGCAGAAGTTCTCCAGCCTGTACATCAGCCAGTTCATCATCATGTACAGCCTGGATGGC
AAGAAATGGCAGACCTACAGAGGCAACTCCACTGGAACACTCATGGTCTTCTTTGGCAATGTGGAC
AGCTCTGGCATCAAGCACAACATCTTCAACCCCCCAATCATCGCCAGATACATCAGGCTGCACCCC
ACCCACTACAGCATCCGCAGCACCCTCAGGATGGAGCTGATGGGCTGTGACCTGAACTCCTGCAGC
ATGCCCCTGGGCATGGAGAGCAAGGCCATTTCTGATGCCCAGATCACTGCCTCCAGCTACTTCACC
AACATGTTTGCCACCTGGAGCCCAAGCAAGGCCAGGCTGCACCTCCAGGGAAGGAGCAATGCCTGG
AGGCCCCAGGTCAACAACCCAAAGGAGTGGCTGCAGGTGGACTTCCAGAAGACCATGAAGGTCACT
GGGGTGACCACCCAGGGGGTCAAGAGCCTGCTCACCAGCATGTATGTGAAGGAGTTCCTGATCAGC
TCCAGCCAGGATGGCCACCAGTGGACCCTCTTCTTCCAGAATGGCAAGGTCAAGGTGTTCCAGGGC
AACCAGGACAGCTTCACCCCTGTGGTGAACAGCCTGGACCCCCCCCTCCTGACCAGATACCTGAGG
ATTCACCCCCAGAGCTGGGTCCACCAGATTGCCCTGAGGATGGAGGTCCTGGGATGTGAGGCCCAG
GACCTGTACTGA (SEQ ID NO:11)

MQIELSTCFFLCLLRFCFSATRRYYLGAVELSWDYMQSDLGELPVDARFPPRVPKSFPFNTSVVYKKTLFVEF
TDHLFNIAKPRPPWMGLLGPTIQAEVYDTVVITLKNMASHPVSLHAVGVSYWKASEGAEYDDQTSQREKEDDK
VFPGGSHTYVWQVLKENGPMASDPLCLTYSYLSHVDLVKDLNSGLIGALLVCREGSLAKEKTQTLHKFILLFA
VFDEGKSWHSETKNSLMQDRDAASARAWPKMHTVNGYVNRSLPGLIGCHRKSVYWHVIGMGTTPEVHSIFLEG
HTFLVRNHRQASLEISPITFLTAQTLLMDLGQFLLFCHISSHQHDGMEAYVKVDSCPEEPQLRMKNNEEAEDY
DDDLTDSEMDVVRFDDDNSPSFIQIRSVAKKHPKTWVHYIAAEEEDWDYAPLVLAPDDRSYKSQYLNNGPQRI
GRKYKKVRFMAYTDETFKTREAIQHESGILGPLLYGEVGDTLLIIFKNQASRPYNIYPHGITDVRPLYSRRLP
KGVKHLKDFPILPGEIFKYKWTVTVEDGPTKSDPRCLTRYYSSFVNMERDLASGLIGPLLICYKESVDQRGNQ
IMSDKRNVILFSVFDENRSWYLTENIQRFLPNPAGVQLEDPEFQASNIMHSINGYVFDSLQLSVCLHEVAYWY
ILSIGAQTDFLSVFFSGYTFKHKMVYEDTLTLFPFSGETVFMSMENPGLWILGCHNSDFRNRGMTALLKVSSC
DKNTGDYYEDSYEDISAYLLSKNNAIEPRSFSQNSRHPSTREITRTTLQSDQEEIDYDDTISVEMKKEDFDIY
DEDENQSPRSFQKKTRHYFIAAVERLWDYGMSSSPHVLRNRAQSGSVPQFKKVVFQEFTDGSFTQPLYRGELN
EHLGLLGPYIRAEVEDNIMVTFRNQASRPYSFYSSLISYEEDQRQGAEPRKNFVKPNETKTYFWKVQHHMAPT
KDEFDCKAWAYFSDVDLEKDVHSGLIGPLLVCHTNTLNPAHGRQVTVQEFALFFTIFDETKSWYFTENMERNC
RAPCNIQMEDPTFKENYRFHAINGYIMDTLPGLVMAQDQRIRWYLLSMGSNENIHSIHFSGHVFTVRKKEEYK
MALYNLYPGVFETVEMLPSKAGIWRVECLIGEHLHAGMSTLFLVYSNKCQTPLGMASGHIRDFQITASGQYGQ
WAPKLARLHYSGSINAWSTKEPFSWIKVDLLAPMIIHGIKTQGARQKFSSLYISQFIIMYSLDGKKWQTYRGN
STGTLMVFFGNVDSSGIKHNIFNPPIIARYIRLHPTHYSIRSTLRMELMGCDLNSCSMPLGMESKAISDAQIT
ASSYFTNMFATWSPSKARLHLQGRSNAWRPQVNNPKEWLQVDFQKTMKVTGVTTQGVKSLLTSMYVKEFLISS
SQDGHQWTLFFQNGKVKVFQGNQDSFTPVVNSLDPPLLTRYLRIHPQSWVHQIALRMEVLGCEAQDLY
(SEQ ID NO:12)

Figure 12

```
NG1:  V   S   N   N   V   S   N   N   A   T   N   N   A   T   N   (SEQ ID NO:51)
      GTG AGC AAC AAT GTG AGC AAC AAT GCC ACC AAT AAT GCT ACC AAC (SEQ ID NO:50)

NG4:  V   S   N   N   A   T   N   N   V   S   N   (SEQ ID NO:53)
      GTG AGC AAC AAT GCC ACC AAC AAT GTG AGC AAC (SEQ ID NO:52)

NG5:  V   S   N   N   A   T   N   (SEQ ID NO:55)
      GTG AGC AAT AAT GCC ACC AAC (SEQ ID NO:54)

NG6:  V   S   N   N   (SEQ ID NO:57)
      GTG AGC AAT AAT (SEQ ID NO:56)

NG9:  R   S   L   (SEQ ID NO:59)
      AGG AGC CTG (SEQ ID NO:58)

NG10: A   T   N   V   S   N   N   S   A   T   S   A   D   S   A   V   S   (SEQ ID NO:61)
      GCC ACT AAT GTG TCT AAC AAC TCT GCT ACC TCT GCT GAC TCT GCT GTG AGC (SEQ ID NO:60)

NG16: A   T   N   Y   V   N   R   S   L   (SEQ ID NO:63)
      GCC ACC AAC TAT GTG AAC AGG AGC CTG (SEQ ID NO:62)
```

Figure 13A

NG17: A T N Y V N R S L S A T S A D S A V S Q N (SEQ ID NO:65)
GCC ACC AAC TAT GTG AAC AGG AGC CTG TCT GCC ACC TCT GCT GAC TCT GCT GTG AGC CAG AAT (SEQ ID NO:64)

NG18: V S N N V S N A V S A V S A (SEQ ID NO:67)
GTG AGC AAC AAT GTG AGC AAT GCT GTG TCT GCT GTG TCT GCT (SEQ ID NO:66)

NG19: I T V A S A T S N I T V A S A D (SEQ ID NO:69)
ATC ACT GTG GCC TCT GCC ACC TCT AAC ATC ACT GTG GCC TCT GCT GAC (SEQ ID NO:68)

NG20: I T V T N I T V T A (SEQ ID NO:71)
ATC ACT GTG ACC AAC ATC ACT GTG ACT GCC (SEQ ID NO:70)

NG21: Q T V T N I T V T A (SEQ ID NO:73)
CAG ACT GTG ACC AAC ATC ACT GTG ACT GCC (SEQ ID NO:72)

NGV: A T N V S N N S N T S N D S N V S (SEQ ID NO:75)
GCC ACT AAT GTG TCT AAC AAC AGC AAC ACC AGC AAT GAC AGC AAT GTG TCT (SEQ ID NO:74)

Figure 13B

```
# Predictions for N-Glycosylation sites in 1 sequence


Name:  CBG_HUMAN        Length:  405

(Sequence)
Asn-Xaa-Ser/Thr sequons (including Asn-Pro-Ser/Thr) are shown in blue.
Asparagines predicted to be N-glycosylated are shown in red.
Note that not all sequons are predicted glycosylated.

MPLLLYTCLLWLPTSGLWTVQAMDPNAAYVNMSNHHRGLASANVDFAFSLYKHLVALSPKKNIFISPVSISMALAMLSLG      80
TCGHTRAQLLQGLGFNLTERSETEIHQGFQHLHQLFAKSDTSLEMTMGNALFLDGSLELLESFSADIKHYYESEVLAMNF     160
QDWATASRQINSYVKNKTQGKIVDLFSGLDSPAILVLVNYIFFKGTWTQPFDLASTREENFYVDETTVVKVPMMLQSSTI     240
SYLHDSELPCQLVQMNYVGNGTVFFILPDKGKMNTVIAALSRDTINRWSAGLTSSQVDLYIPKVTISGVYDLGDVLEEMG     320
IADLFTNQANFSRITQDAQLKSSKVVHKAVLQLNEEGVDTAGSTGVTLNLTSKPIILRFNQPFIIMIFDHFTWSSLFLAR     400
VMNPV

(Annotation line)
`N' represents a predicted N-glycosylation site.
`n' represents an Asn with a positive score,
but not occuring within an Asn-Xaa-Ser/Thr sequon

..............................N.................................................      80
...............N................................................................     160
................................................................................     240
...................N............................................................     320
................................................N...............................     400
.....


(Threshold=0.5)
----------------------------------------------------------------------
SeqName      Position  Potential   Jury    NGlyc
                                agreement result
----------------------------------------------------------------------
CBG_HUMAN     31 NMSN   0.7166     (9/9)   ++  <-- Predicted as N-glycosylated (++)
CBG_HUMAN     96 NLTE   0.6356     (8/9)   +   <-- Predicted as N-glycosylated (+)
CBG_HUMAN    176 NKTQ   0.3941     (7/9)   -   <-- A negative site
CBG_HUMAN    260 NGTV   0.7400     (9/9)   ++
CBG_HUMAN    330 NFSR   0.4222     (7/9)   -      see below for
CBG_HUMAN    369 NLTS   0.6684     (9/9)   ++    more information
----------------------------------------------------------------------
```

Figure 14

```
Name:  Sequence         Length:  41
LSKNNAIEPRSFSQNATNVSNNSNTSNDSNVSPFVLKRHQR
..............N..N.......................

(Threshold=0.5)
----------------------------------------------------------------------
SeqName      Position  Potential   Jury    N-Glyc
                                agreement result
----------------------------------------------------------------------
Sequence      15 NATN   0.6224     (8/9)   +
Sequence      18 NVSN   0.6453     (9/9)   ++
Sequence      21 NNSN   0.4158     (8/9)   -
Sequence      24 NTSN   0.4158     (8/9)   -
Sequence      27 NDSN   0.3619     (8/9)   -
Sequence      30 NVSP   0.1149     (9/9)   ---
----------------------------------------------------------------------
```

ATGCAGATTGAGCTGTCCACCTGCTTCTTTCTGTGCCTGCTGAGATTCTGCTTCTCTGCCACCAGG
AGATACTACCTGGGGGCTGTGGAACTTTCTTGGGACTACATGCAGTCTGACCTGGGAGAGCTGCCT
GTGGATGCCAGGTTCCCACCCAGAGTGCCCAAGTCCTTCCCATTCAACACCTCTGTGGTCTACAAG
AAGACACTCTTTGTGGAATTCACTGACCACCTGTTCAACATTGCAAAACCCAGACCACCCTGGATG
GGACTCCTGGGACCCACCATTCAGGCTGAGGTGTATGACACTGTGGTCATCACCCTCAAGAACATG
GCATCCCACCCTGTGTCTCTGCATGCTGTGGGAGTCTCATACTGGAAAGCCTCTGAAGGGGCTGAG
TATGATGACCAGACATCCCAGAGAGAGAAAGAGGATGACAAGGTGTTCCCTGGGGGATCTCACACC
TATGTGTGGCAAGTCCTCAAGGAGAATGGACCCATGGCATCTGACCCACTCTGCCTGACATACTCC
TACCTTTCTCATGTGGACCTGGTCAAGGACCTCAACTCTGGACTGATTGGGGCACTGCTGGTGTGC
AGGGAAGGATCCCTGGCCAAGGAGAAAACCCAGACACTGCACAAGTTCATTCTCCTGTTTGCTGTC
TTTGATGAGGGCAAGTCTTGGCACTCTGAAACAAAGAACTCCCTGATGCAAGACAGGGATGCTGCC
TCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGGACAACCCCTGAAGTGCAC
TCCATTTTCCTGGAGGGACACACCTTCCTGGTCAGGAACCACAGACAAGCCTCTCTGGAGATCTCT
CCCATCACCTTCCTCACTGCACAGACACTGCTGATGGACCTTGGACAGTTCCTGCTGTTCTGCCAC
ATCTCTTCCCACCAGCATGATGGCATGGAAGCCTATGTCAAGGTGGACTCATGCCCTGAGGAACCA
CAGCTCAGGATGAAGAACAATGAGGAGGCTGAGGACTATGATGATGACCTGACTGACTCTGAGATG
GATGTGGTCAGATTTGATGATGACAACTCTCCATCCTTCATTCAGATCAGGTCTGTGGCAAAGAAA
CACCCCAAGACATGGGTGCACTACATTGCTGCTGAGGAAGAGGACTGGGACTATGCACCACTGGTC
CTGGCCCCTGATGACAGGAGCTACAAGTCTCAGTACCTCAACAATGGCCCACAAAGAATTGGAAGA
AAGTACAAGAAAGTCAGATTCATGGCCTACACTGATGAAACCTTCAAGACAAGAGAAGCCATTCAG
CATGAGTCTGGCATTCTGGGACCACTCCTGTATGGGGAAGTGGGAGACACCCTGCTCATCATCTTC
AAGAACCAGGCCTCCAGGCCCTACAACATCTACCCACATGGCATCACTGATGTCAGGCCCCTGTAC
AGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGA
TACTACTCCTCTTTTGTGAACATGGAGAGAGACCTGGCATCTGGACTGATTGGACCACTGCTCATC
TGCTACAAGGAGTCTGTGGACCAGAGAGGCAACCAGATCATGTCTGACAAGAGAAATGTGATTCTG
TTCTCTGTCTTTGATGAGAACAGATCATGGTACCTGACTGAGAACATTCAGAGATTCCTGCCCAAC
CCTGCTGGGGTGCAACTGGAAGACCCTGAGTTCCAGGCAAGCAACATCATGCACTCCATCAATGGC
TATGTGTTTGACTCTCTCCAGCTTTCTGTCTGCCTGCATGAGGTGGCCTACTGGTACATTCTTTCT
ATTGGGGCACAAACTGACTTCCTTTCTGTCTTCTTCTCTGGATACACCTTCAAGCACAAGATGGTG
TATGAGGACACCCTGACACTCTTCCCATTCTCTGGGGAAACTGTGTTCATGAGCATGGAGAACCCT
GGACTGTGGATTCTGGGATGCCACAACTCTGACTTCAGAAACAGGGGAATGACTGCACTGCTCAAA
GTCTCCTCCTGTGACAAGAACACTGGGGACTACTATGAGGACTCTTATGAGGACATCTCTGCCTAC
CTGCTCAGCAAGAACAATGCCATTGAGCCCAGAAGCTTCTCTCAGAATCCACCTGTCCTGAAGAGA
CACCAGAGAGAGATCACCAGGACAACCCTCCAGTCTGACCAGGAAGAGATTGACTATGATGACACC
ATTTCTGTGGAGATGAAGAAGGAGGACTTTGACATCTATGATGAGGACGAGAACCAGTCTCCAAGA
TCATTCCAGAAGAAGACAAGACACTACTTCATTGCTGCTGTGGAAAGACTGTGGGACTATGGCATG
TCTTCCTCTCCCCATGTCCTCAGGAACAGGGCACAGTCTGGCTCTGTGCCACAGTTCAAGAAAGTG
GTCTTCCAGGAGTTCACTGATGGCTCATTCACCCAGCCCCTGTACAGAGGGGAACTGAATGAGCAC (Continued)

Figure 16A

CTGGGACTCCTGGGACCATACATCAGGGCTGAGGTGGAAGACAACATCATGGTGACATTCAGAAAC
CAGGCCTCCAGGCCCTACAGCTTCTACTCTTCCCTCATCAGCTATGAGGAAGACCAGAGACAAGGG
GCTGAGCCAAGAAAGAACTTTGTGAAACCCAATGAAACCAAGACCTACTTCTGGAAAGTCCAGCAC
CACATGGCACCCACCAAGGATGAGTTTGACTGCAAGGCCTGGGCATACTTCTCTGATGTGGACCTG
GAGAAAGATGTGCACTCTGGCCTGATTGGCCCACTCCTGGTCTGCCACACCAACACCCTGAACCCT
GCACATGGAAGGCAAGTGACTGTGCAGGAGTTTGCCCTCTTCTTCACCATCTTTGATGAAACCAAG
TCATGGTACTTCACTGAGAACATGGAGAGAAACTGCAGAGCACCATGCAACATTCAGATGGAAGAC
CCCACCTTCAAGGAGAACTACAGGTTCCATGCCATCAATGGCTACATCATGGACACCCTGCCTGGG
CTTGTCATGGCACAGGACCAGAGAATCAGATGGTACCTGCTTTCTATGGGATCCAATGAGAACATT
CACTCCATCCACTTCTCTGGGCATGTCTTCACTGTGAGAAAGAAGGAGGAATACAAGATGGCCCTG
TACAACCTCTACCCTGGGGTCTTTGAGACTGTGGAGATGCTGCCCTCCAAAGCTGGCATCTGGAGG
GTGGAATGCCTCATTGGGGAGCACCTGCATGCTGGCATGTCAACCCTGTTCCTGGTCTACAGCAAC
AAGTGCCAGACACCCCTGGGAATGGCCTCTGGCCACATCAGGGACTTCCAGATCACTGCCTCTGGC
CAGTATGGCCAGTGGGCACCCAAACTGGCCAGGCTCCACTACTCTGGCTCCATCAATGCATGGTCA
ACCAAGGAGCCATTCTCTTGGATCAAGGTGGACCTGCTGGCACCCATGATCATTCATGGCATCAAG
ACACAGGGGGCAAGACAGAAATTCTCCTCTCTGTACATCTCACAGTTCATCATCATGTACTCTCTG
GATGGCAAGAAGTGGCAGACATACAGAGGCAACTCCACTGGCACCCTCATGGTCTTCTTTGGCAAT
GTGGACAGCTCTGGCATCAAGCACAACATCTTCAACCCTCCCATCATTGCCAGATACATCAGGCTG
CACCCCACCCACTACTCAATCAGATCAACCCTCAGGATGGAACTGATGGGATGTGACCTGAACTCC
TGCTCAATGCCCCTGGGAATGGAGAGCAAGGCCATTTCTGATGCCCAGATCACTGCATCCTCTTAC
TTCACCAACATGTTTGCCACCTGGTCACCATCAAAAGCCAGGCTGCACCTCCAGGGAAGAAGCAAT
GCCTGGAGACCCCAGGTCAACAACCCAAAGGAATGGCTGCAAGTGGACTTCCAGAAGACAATGAAA
GTCACTGGGGTGACAACCCAGGGGGTCAAGTCTCTGCTCACCTCAATGTATGTGAAGGAGTTCCTG
ATCTCTTCCTCACAGGATGGCCACCAGTGGACACTCTTCTTCCAGAATGGCAAAGTCAAGGTGTTC
CAGGGCAACCAGGACTCTTTCACACCTGTGGTGAACTCACTGGACCCCCCCCTCCTGACAAGATAC
CTGAGAATTCACCCCCAGTCTTGGGTCCACCAGATTGCCCTGAGAATGGAAGTCCTGGGATGTGAG
GCACAAGACCTGTACTGA (SEQ ID NO:13)

ATGCAGATCGAACTGAGCACTTGCTTCTTCCTGTGTCTCCTGCGCTTTTGCTTCTCCGCCACAAGG
AGATACTATCTCGGTGCCGTGGAGCTCAGCTGGGACTACATGCAGAGCGACTTGGGTGAACTGCCT
GTGGACGCCAGGTTTCCACCCCGCGTGCCCAAGAGTTTCCCGTTCAACACCAGTGTCGTGTACAAG
AAAACCCTCTTCGTGGAATTCACCGACCACCTGTTCAACATCGCCAAACCGCGCCCTCCCTGGATG
GGGCTGCTCGGCCCGACGATCCAGGCTGAGGTCTATGACACGGTGGTGATTACCCTCAAGAACATG
GCTAGCCACCCGGTGAGCCTGCACGCCGTGGGCGTGTCCTATTGGAAAGCGTCCGAGGGTGCGGAG
TACGATGACCAGACTTCACAGCGGGAGAAGGAAGACGACAAAGTGTTCCCCGGGGGTTCCCACACC
TATGTCTGGCAGGTCCTGAAGGAGAATGGTCCTATGGCCTCCGACCCATTGTGCCTCACCTACTCT
TACCTAAGCCATGTGGATCTCGTCAAGGACCTGAACTCGGGGCTGATCGGCGCCCTGCTCGTGTGC
CGGGAGGGCTCACTGGCCAAGGAGAAGACCCAAACTCTGCACAAGTTCATCCTGCTGTTCGCGGTA
TTCGACGAGGGGAAGTCCTGGCACTCCGAGACCAAGAACAGCCTGATGCAGGACCGCGACGCAGCC
TCGGCCCGTGCGTGGCCAAAGATGCACACCGTGAACGGCTACGTTAACAGGAGCCTACCCGGCCTG
ATCGGCTGCCACCGCAAATCGGTCTACTGGCATGTGATCGGAATGGGCACAACGCCCGAGGTCCAC
AGTATCTTCCTCGAGGGCCACACTTTCCTGGTCCGGAATCACCGCCAGGCCAGCCTGGAGATCAGC
CCCATAACCTTTCTGACGGCGCAGACCTTACTCATGGATCTCGGCCAGTTCCTCCTGTTCTGCCAC
ATTTCGTCCCACCAGCACGATGGGATGGAAGCATATGTGAAAGTGGACTCCTGCCCCGAGGAACCC
CAGCTTAGGATGAAGAACAATGAGGAGGCCGAGGACTACGACGATGACCTTACCGATTCAGAAATG
GACGTAGTACGCTTTGACGACGACAACTCTCCATCCTTCATACAGATTCGCTCCGTCGCCAAGAAG
CACCCTAAGACTTGGGTGCACTACATCGCGGCCGAGGAGGAGGACTGGGATTATGCTCCCCTGGTG
CTGGCCCCCGACGACCGCAGCTACAAGAGCCAGTACCTGAATAACGGGCCCCAGCGCATCGGCCGG
AAGTACAAGAAAGTGCGGTTCATGGCTTACACGGACGAGACCTTCAAGACCCGGGAGGCTATCCAG
CATGAGAGCGGCATCTTGGGGCCCCTCCTGTACGGCGAAGTTGGAGACACACTGCTGATCATCTTC
AAGAACCAGGCGAGCAGGCCCTACAACATCTACCCCCACGGCATTACCGATGTCCGGCCGTTGTAC
AGCCGACGGCTGCCCAAGGGCGTGAAGCACCTGAAGGACTTTCCGATCCTGCCGGGCGAGATCTTC
AAGTACAAGTGGACTGTGACCGTGGAGGATGGGCCGACCAAGAGCGATCCGCGCTGCCTGACCCGT
TACTACTCCAGCTTTGTCAATATGGAGCGCGACCTCGCTAGCGGCTTGATTGGCCCTCTGCTGATC
TGCTACAAGGAGTCCGTGGACCAGAGGGGGAATCAGATCATGAGTGACAAGAGGAACGTGATCCTG
TTCTCCGTGTTCGACGAAAACCGCAGCTGGTATCTCACCGAGAATATCCAGCGCTTCCTGCCCAAC
CCGGCCGGTGTGCAGCTGGAGGACCCCGAGTTTCAGGCCAGCAACATCATGCATTCTATCAACGGA
TATGTGTTTGATTCCCTGCAGCTCTCAGTGTGTCTGCACGAGGTCGCCTACTGGTATATCCTCAGC
ATTGGGGCACAGACCGACTTCCTGAGCGTGTTCTTCTCCGGGTATACCTTCAAGCACAAGATGGTG
TACGAGGATACCCTGACCCTGTTCCCCTTTAGCGGCGAAACCGTGTTTATGTCTATGGAGAACCCC
GGGCTCTGGATCCTTGGCTGCCATAACTCCGACTTCCGCAACCGCGGAATGACCGCGCTCCTGAAA
GTGTCGAGTTGTGACAAGAACACCGGCGACTATTACGAGGACAGTTACGAGGACATCTCTGCGTAC
CTCCTTAGCAAGAATAACGCCATCGAGCCAAGATCCTTCAGCCAGAACCCCCCAGTGCTGAAGAGG
CATCAGCGGGAGATCACCCGCACGACCCTGCAGTCGGATCAGGAGGAGATTGATTACGACGACACG
ATCAGTGTGGAGATGAAGAAGGAGGACTTCGACATCTACGACGAAGATGAAAACCAGTCCCCTCGG
TCCTTCCAAAAGAAGACCCGGCACTACTTCATCGCCGCTGTGGAACGCCTGTGGGACTATGGAATG (Continued)

Figure 17A

TCTTCTAGCCCTCACGTTTTGAGGAACCGCGCCCAGTCGGGCAGCGTGCCCCAGTTCAAGAAAGTG
GTGTTCCAGGAGTTCACCGACGGCTCCTTCACCCAGCCACTTTACCGGGGCGAGCTCAATGAACAT
CTGGGCCTGCTGGGACCCTACATCAGGGCTGAGGTGGAGGACAACATCATGGTGACATTCCGGAAT
CAGGCCAGCAGACCATACAGTTTCTACAGTTCACTCATCTCCTACGAGGAGGACCAGCGCCAGGGG
GCTGAACCCCGTAAGAACTTCGTGAAGCCAAACGAAACAAAGACCTACTTCTGGAAGGTCCAGCAC
CACATGGCACCTACCAAGGACGAGTTCGATTGCAAGGCCTGGGCCTACTTCTCCGACGTGGACCTG
GAGAAAGATGTGCACAGCGGCCTGATTGGCCCTCTGCTGGTGTGTCACACGAACACACTCAACCCT
GCACACGGGCGGCAGGTCACTGTGCAGGAATTCGCCCTGTTCTTTACCATCTTTGATGAGACGAAG
TCCTGGTATTTCACCGAAAACATGGAGAGGAACTGCCGCGCACCCTGCAACATCCAGATGGAAGAT
CCGACATTCAAGGAGAACTACCGGTTCCATGCCATCAATGGCTACATCATGGACACCCTGCCTGGC
CTCGTGATGGCCCAAGACCAGCGTATCCGCTGGTATCTGCTGTCGATGGGCTCCAACGAGAACATC
CATAGTATCCACTTCAGCGGGCATGTCTTCACGGTGAGGAAAAAGGAGGAGTACAAGATGGCACTG
TACAACCTCTATCCCGGCGTGTTCGAGACCGTGGAGATGCTGCCCTCCAAGGCCGGCATCTGGAGA
GTGGAATGCCTGATCGGCGAGCACCTCCACGCTGGGATGTCCACGCTGTTCCTCGTTTACAGCAAT
AAGTGCCAGACCCCTCTGGGCATGGCGAGCGGCCACATCCGCGACTTCCAGATTACAGCCAGCGGC
CAGTACGGTCAGTGGGCTCCAAAGCTGGCCCGTCTGCACTACTCCGGATCCATCAACGCCTGGTCC
ACCAAGGAACCGTTCTCCTGGATCAAAGTAGACCTGCTAGCCCCCATGATCATTCACGGCATCAAG
ACACAAGGCGCCCGACAGAAGTTCTCGAGCCTCTATATCTCCCAGTTCATCATCATGTATAGCCTG
GACGGAAAGAAGTGGCAGACTTACCGCGGAAACTCGACAGGGACCCTGATGGTATTCTTCGGTAAC
GTGGACAGCTCCGGAATCAAGCACAACATCTTCAACCCACCCATTATCGCCCGCTACATCCGCCTG
CACCCCACTCACTATAGCATTAGGTCCACCCTGCGAATGGAGCTCATGGGCTGTGACCTGAACAGC
TGTAGCATGCCCCTCGGCATGGAGTCTAAGGCGATCTCCGACGCACAGATAACGGCATCATCCTAC
TTTACCAACATGTTCGCTACCTGGTCCCCCTCCAAGGCCCGACTCCACCTGCAAGGGAGATCCAAC
GCCTGGCGGCCACAGGTCAACAATCCCAAGGAGTGGCTGCAAGTGGACTTTCAGAAAACTATGAAA
GTCACCGGAGTGACCACACAGGGAGTGAAGTCTCTGCTGACCAGCATGTACGTGAAGGAGTTCCTC
ATCTCCAGTTCGCAGGATGGCCACCAGTGGACGTTGTTCTTCCAAAACGGTAAAGTCAAAGTCTTC
CAAGGGAACCAGGACAGCTTTACACCCGTCGTGAACTCCCTGGACCCCCCGCTTCTCACTAGATAC
CTCCGCATCCACCCTCAGAGCTGGGTGCACCAGATTGCCCTGCGCATGGAGGTTCTGGGGTGTGAA
GCCCAGGACCTGTACTAA (SEQ ID NO:14)

ATGCAGATTGAGCTCTCCACCTGCTTCTTTCTCTGCCTTCTTCGCTTCTGCTTTTCTGCCACACGC
AGGTACTATTTGGGAGCAGTGGAACTGAGCTGGGATTACATGCAGAGTGACCTTGGTGAACTTCCT
GTGGACGCTCGTTTTCCACCTAGAGTTCCCAAGTCCTTCCCCTTCAACACCTCAGTGGTCTACAAG
AAAACGCTGTTTGTGGAGTTCACTGACCACCTCTTCAACATTGCCAAACCAAGACCCCCTTGGATG
GGATTGCTGGGACCCACAATACAAGCAGAAGTCTACGACACGGTGGTGATTACCCTGAAGAACATG
GCGTCACACCCTGTTTCACTTCACGCTGTTGGGGTCAGTTATTGGAAAGCCTCAGAGGGTGCGGAA
TACGATGATCAAACCAGCCAGAGGGAGAAGGAAGATGACAAGGTCTTTCCTGGGGGTAGCCATACC
TATGTTTGGCAGGTGCTGAAAGAGAATGGGCCTATGGCCTCTGATCCCTTGTGCCTCACATACTCT
TACCTGAGTCACGTCGACCTGGTGAAAGACCTGAATAGCGGTCTGATTGGTGCACTGCTTGTTTGT
AGAGAGGGGAGTTTGGCCAAGGAGAAAACTCAGACTCTCCACAAGTTTATCCTCCTGTTTGCTGTG
TTCGACGAGGGCAAGTCTTGGCACTCTGAAACAAAGAACTCCCTGATGCAGGACAGAGATGCTGCA
TCTGCAAGGGCTTGGCCAAAAATGCACACAGTGAACGGCTATGTGAATCGATCACTGCCAGGACTG
ATAGGCTGTCATCGCAAGTCAGTGTATTGGCACGTTATCGGGATGGGAACAACTCCAGAAGTGCAC
AGCATCTTCCTTGAGGGCCACACTTTCCTGGTTCGGAATCATAGACAGGCCAGCCTTGAGATCAGC
CCAATCACCTTTCTGACTGCCCAAACCTTGCTGATGGATCTGGGACAGTTCCTCCTGTTTTGTCAC
ATCTCCTCCCACCAACATGACGGGATGGAGGCTTATGTGAAGGTCGATAGCTGTCCGGAGGAACCA
CAACTGAGGATGAAGAACAACGAAGAGGCAGAGGACTATGACGACGATCTGACTGACAGTGAAATG
GACGTGGTTCGGTTCGACGATGACAATTCTCCTTCATTTATCCAGATCCGTTCCGTGGCCAAGAAG
CACCCCAAGACTTGGGTTCATTACATCGCTGCTGAGGAGGAGGATTGGGACTACGCGCCCTTGGTG
TTGGCCCCAGACGATCGCTCATACAAGAGCCAGTACCTTAACAATGGTCCACAAAGGATCGGCCGG
AAGTACAAGAAGGTTAGATTTATGGCTTATACCGACGAGACTTTTAAAACTAGGGAAGCAATTCAG
CATGAAAGTGGCATTCTTGGACCCCTGCTGTATGGCGAGGTTGGCGACACCCTGCTGATTATCTTT
AAGAACCAGGCAAGCCGGCCCTACAACATCTACCCGCACGGCATAACCGATGTACGACCCCTGTAC
AGTCGCAGACTTCCTAAAGGGGTGAAACACCTGAAGGACTTCCCAATTCTGCCCGGGGAGATCTTC
AAGTATAAATGGACCGTGACGGTTGAGGATGGTCCCACAAAGTCCGATCCGAGATGCCTTACCCGA
TATTATTCCAGCTTCGTGAACATGGAAAGGGACCTGGCCAGCGGGCTGATTGGCCCACTGCTGATT
TGTTACAAGGAGTCTGTCGATCAAAGAGGAAACCAAATAATGAGCGACAAACGTAACGTCATCCTG
TTCAGCGTCTTTGATGAGAATAGAAGCTGGTACCTCACAGAAAATATTCAGCGGTTTCTGCCTAAC
CCCGCAGGCGTCCAGCTGGAAGATCCCGAGTTCCAAGCCTCAAACATCATGCATAGCATCAACGGA
TACGTATTCGATAGCCTGCAGCTGTCCGTCTGTCTCCATGAAGTGGCATATTGGTACATCCTGAGT
ATCGGGGCGCAGACCGACTTCCTGAGCGTGTTCTTTTCTGGATACACGTTCAAACACAAAATGGTC
TATGAAGATACCCTGACTCTGTTTCCATTCTCAGGAGAGACAGTCTTTATGAGTATGGAAAATCCT
GGACTGTGGATCCTGGGCTGTCACAATTCTGATTTTCGGAACAGAGGCATGACAGCCCTGCTTAAA
GTGAGCTCATGCGACAAGAACACCGGTGATTACTACGAAGATAGCTATGAGGACATCAGTGCGTAT
TTGCTCTCCAAGAACAACGCTATCGAGCCACGGTCTTTCAGTCAGAATCCTCCCGTTCTGAAGCGG
CATCAGCGCGAAATAACACGCACAACCCTTCAGTCAGACCAAGAGGAAATCGACTACGATGATACT
ATCTCTGTGGAGATGAAGAAGGAGGATTTCGACATTTACGACGAGGACGAGAATCAGTCCCCAAGG
AGCTTTCAGAAGAAAACAAGACACTATTTCATTGCCGCCGTGGAGCGACTGTGGGACTACGGCATG (Continued)

Figure 18A

TCTAGCTCTCCGCATGTACTTAGAAATAGGGCACAAAGCGGATCCGTGCCTCAGTTTAAGAAAGTT
GTCTTTCAGGAGTTTACAGATGGCTCCTTCACCCAGCCCTTGTATCGCGGGGAACTCAATGAACAC
CTGGGCCTCCTGGGTCCTTATATTAGGGCCGAAGTCGAGGACAATATCATGGTGACCTTTAGGAAC
CAGGCATCTAGACCTTACTCTTTCTACTCCTCCCTGATATCCTATGAGGAGGACCAGCGGCAAGGC
GCTGAGCCTCGGAAGAACTTTGTGAAGCCAAATGAAACCAAAACATACTTTTGGAAAGTTCAGCAC
CACATGGCTCCCACGAAGGACGAATTTGACTGTAAAGCCTGGGCCTACTTCTCAGATGTAGATCTC
GAGAAAGACGTGCACTCAGGGCTCATTGGTCCCCTCCTGGTCTGTCATACTAATACCCTCAATCCA
GCACACGGACGTCAGGTAACCGTCCAGGAATTTGCCCTGTTCTTTACCATTTTCGATGAGACTAAA
TCCTGGTACTTTACCGAAAACATGGAGAGGAATTGCAGAGCCCCATGCAACATCCAGATGGAGGAC
CCTACCTTCAAAGAGAACTATCGCTTCCATGCCATTAACGGTTACATTATGGATACTCTCCCAGGA
CTTGTGATGGCACAGGATCAGCGGATAAGATGGTATCTGTTGAGCATGGGCTCCAACGAGAATATT
CACAGCATCCATTTCTCCGGTCACGTGTTTACAGTGAGAAAGAAAGAAGAGTACAAGATGGCTCTG
TATAATCTCTATCCAGGCGTATTCGAAACGGTGGAGATGTTGCCTAGCAAGGCCGGCATTTGGCGA
GTAGAATGCCTTATCGGGGAACATCTGCATGCCGGAATGAGCACGCTCTTCCTGGTGTATAGTAAC
AAGTGCCAGACTCCGCTGGGCATGGCATCTGGCCATATACGGGACTTTCAGATTACGGCTAGCGGG
CAGTATGGGCAGTGGGCACCCAAACTTGCGCGACTGCACTATTCAGGCTCTATCAATGCATGGTCC
ACCAAGGAACCCTTCTCTTGGATTAAGGTGGACCTTTTGGCGCCCATGATAATCCATGGGATCAAA
ACCCAGGGCGCTCGTCAGAAATTCTCATCACTCTACATCTCTCAGTTCATAATAATGTATTCACTG
GATGGGAAGAAATGGCAGACTTACAGAGGAAACAGCACCGGGACGCTGATGGTGTTCTTTGGCAAC
GTGGACAGCAGCGGCATCAAACACAACATCTTCAATCCTCCCATTATTGCCCGTTATATTAGACTG
CATCCCACTCACTACTCTATACGCAGCACACTTAGGATGGAGCTCATGGGATGCGACCTGAACAGT
TGTAGTATGCCCTTGGGGATGGAGTCCAAAGCTATAAGCGACGCACAAATTACAGCTAGCTCTTAC
TTTACGAATATGTTCGCCACGTGGAGCCCAAGCAAAGCCCGGCTGCATTTGCAGGGTCGGAGTAAT
GCTTGGCGCCCACAGGTGAATAACCCTAAGGAATGGTTGCAAGTAGATTTCCAGAAAACTATGAAG
GTAACCGGCGTCACTACACAGGGAGTCAAGTCCCTCTTGACCTCTATGTACGTCAAGGAGTTCCTG
ATTAGCAGCAGTCAGGATGGGCACCAATGGACACTGTTCTTCCAGAATGGGAAAGTTAAAGTATTT
CAGGGTAACCAGGACTCCTTTACACCTGTGGTGAATAGCCTCGACCCACCCCTGCTGACACGATAC
CTCCGCATCCACCCTCAGTCTTGGGTGCATCAAATTGCCCTGCGAATGGAGGTGTTGGGATGCGAA
GCTCAGGACCTCTACTGA (SEQ ID NO:15)

ATGCAGATCGAACTCTCTACTTGCTTCTTCCTGTGCCTTCTGAGGTTCTGCTTCTCTGCCACTCGC
CGATATTACCTCGGGGCCGTGGAGTTGAGTTGGGACTACATGCAATCAGATCTGGGCGAACTCCCT
GTGGATGCCCGATTCCCACCGCGCGTGCCCAAGTCTTTCCCATTTAATACTTCTGTGGTGTACAAG
AAGACATTGTTTGTGGAGTTTACCGATCACCTGTTCAACATCGCCAAACCGCGGCCCCCATGGATG
GGTCTGCTTGGGCCCACCATTCAAGCGGAGGTCTATGATACAGTGGTGATAACGCTTAAGAACATG
GCGAGCCACCCAGTGTCTCTGCATGCCGTTGGTGTATCATATTGGAAGGCCAGCGAAGGAGCGGAG
TACGATGACCAGACCTCTCAGAGAGAGAAGGAAGACGATAAGGTTTTTCCTGGCGGAAGTCATACA
TATGTATGGCAGGTCCTGAAAGAGAATGGGCCGATGGCTTCTGACCCCCTTTGTCTTACCTATAGT
TATCTGAGCCACGTGGACCTGGTCAAGGACCTCAACAGTGGTCTGATTGGGGCTCTGCTTGTTTGT
AGAGAGGGTAGCTTGGCTAAGGAGAAAACCCAAACACTCCATAAGTTCATTTTGCTGTTCGCGGTG
TTCGACGAGGGAAAGAGTTGGCACAGCGAAACAAAGAATTCACTGATGCAAGACAGGGACGCCGCT
TCCGCAAGGGCTTGGCCTAAGATGCATACGGTGAATGGGTATGTGAACCGGAGCCTCCCGGGGCTG
ATCGGGTGCCATCGCAAGTCTGTTTACTGGCACGTCATTGGAATGGGGACAACGCCAGAGGTACAT
AGTATATTTCTTGAAGGCCACACGTTCCTCGTACGGAACCACCGACAGGCTTCCCTGGAGATAAGC
CCCATTACCTTTCTGACCGCTCAGACTCTGCTGATGGACCTTGGCCAGTTTCTCCTGTTCTGCCAT
ATTAGCAGCCACCAGCACGACGGTATGGAAGCATACGTGAAAGTCGATAGCTGTCCTGAGGAGCCT
CAGCTCAGAATGAAGAACAACGAGGAGGCCGAAGACTATGACGATGACCTTACAGATTCCGAGATG
GACGTGGTGCGCTTTGACGACGATAACAGTCCTAGTTTCATTCAAATCAGATCCGTAGCCAAAAAG
CATCCAAAGACATGGGTGCATTACATTGCAGCCGAAGAGGAGGATTGGGATTATGCGCCCCTTGTT
CTGGCTCCAGATGACAGGAGCTATAAGTCCCAGTACTTGAACAACGGGCCACAGCGAATCGGTAGA
AAATATAAGAAGGTAAGATTCATGGCCTACACTGACGAAACATTTAAAACCAGGGAAGCTATCCAA
CACGAATCTGGAATTCTCGGCCCTCTGCTCTACGGTGAGGTGGGGGACACCTTGCTGATCATTTTC
AAAAATCAGGCATCCAGGCCTTACAACATATACCCCCATGGCATCACCGATGTCCGCCCGCTGTAT
TCCAGAAGACTCCCCAAGGGAGTGAAACATCTGAAAGATTTTCCCATCCTGCCGGGCGAGATCTTT
AAATACAAATGGACTGTGACTGTAGAGGACGGGCCTACAAAATCAGACCCACGGTGCCTGACAAGG
TATTACAGTAGCTTCGTCAACATGGAACGCGACCTCGCCAGCGGACTCATTGGCCCACTGTTGATC
TGTTACAAAGAGTCAGTGGATCAGAGGGGAAATCAGATCATGAGCGATAAGAGAAACGTTATCCTG
TTTAGTGTCTTCGACGAGAACCGGTCTTGGTACCTTACTGAGAACATCCAGAGGTTCCTGCCGAAT
CCGGCTGGCGTTCAGCTCGAGGACCCAGAGTTCCAGGCCAGTAATATAATGCACTCAATCAACGGT
TATGTGTTCGATAGCCTGCAGCTGAGCGTCTGCCTCCACGAGGTAGCCTATTGGTACATATTGTCC
ATCGGGGCTCAGACCGATTTTCTGTCCGTGTTCTTTAGCGGGTATACCTTTAAACATAAAATGGTC
TATGAAGACACCCTGACCCTGTTCCCATTCTCCGGTGAGACTGTGTTCATGTCCATGGAGAACCCA
GGGCTGTGGATCCTGGGGTGTCACAATAGTGACTTTAGGAATCGGGGAATGACGGCACTGCTGAAG
GTGAGTTCTTGCGATAAAAATACAGGAGATTACTATGAGGATAGTTACGAGGATATCAGTGCCTAT
CTGCTTTCAAAAAACAACGCAATTGAGCCCCGGTCTTTCTCACAAAACCCCCCGGTGCTGAAGCGC
CACCAGCGCGAAATTACCCGGACAACCTTGCAGTCCGACCAGGAGGAAATCGATTATGACGATACT
ATCAGTGTAGAAATGAAAAAGGAGGATTTTGATATTTACGACGAAGACGAGAACCAGTCTCCGCGA (Continued)

Figure 19A

AGTTTTCAGAAGAAAACGCGACACTACTTTATAGCTGCCGTGGAACGACTCTGGGATTATGGCATG
TCCTCCAGCCCTCATGTCCTTAGGAATCGAGCGCAGAGTGGCTCTGTGCCTCAGTTCAAAAAGGTT
GTGTTCCAGGAATTCACCGACGGCTCATTTACCCAGCCGCTGTACAGAGGCGAACTCAACGAACAC
CTTGGGCTGCTTGGGCCATATATTCGAGCAGAGGTGGAAGATAATATCATGGTAACCTTTAGAAAC
CAGGCGTCAAGACCCTATTCCTTCTACAGTTCTCTGATCAGCTACGAGGAGGACCAAAGACAGGGA
GCTGAACCCAGGAAGAACTTTGTGAAACCTAATGAGACCAAGACCTACTTCTGGAAGGTCCAGCAC
CATATGGCCCCAACTAAAGATGAATTCGATTGCAAGGCCTGGGCTTATTTCAGCGACGTGGATCTC
GAAAAGGATGTGCACAGCGGGTTGATCGGACCGCTTTTGGTGTGCCACACAAATACCCTCAATCCT
GCCCACGGGCGGCAGGTCACAGTTCAAGAGTTTGCACTCTTCTTTACAATATTTGACGAGACAAAG
TCATGGTATTTTACAGAGAATATGGAGAGAAATTGTCGCGCACCTTGCAACATTCAGATGGAGGAC
CCCACATTTAAGGAGAATTACAGATTTCATGCTATCAATGGGTACATTATGGATACTCTGCCTGGT
CTGGTCATGGCCCAGGATCAGCGCATAAGGTGGTACTTGCTGAGCATGGGATCTAATGAGAATATA
CACAGCATTCACTTCAGTGGCCACGTTTTTACTGTTAGAAAGAAGGAGGAGTACAAAATGGCGCTC
TACAACCTTTACCCGGGTGTGTTTGAGACAGTGGAGATGCTGCCAAGCAAGGCAGGCATCTGGAGG
GTTGAGTGTCTTATTGGGGAGCATCTGCATGCTGGAATGTCCACCCTCTTTCTTGTGTACAGCAAT
AAGTGCCAGACACCGCTTGGCATGGCCAGCGGCCACATTAGGGACTTTCAGATAACTGCCAGTGGA
CAGTACGGCCAGTGGGCTCCCAAGCTTGCAAGACTCCACTACTCCGGAAGCATAAACGCATGGAGC
ACCAAGGAACCCTTCTCTTGGATTAAGGTGGACCTGCTGGCGCCAATGATCATTCACGGCATAAAA
ACCCAAGGGGCACGACAGAAATTTTCATCTTTGTATATTAGTCAGTTTATCATCATGTACAGCTTG
GATGGAAAGAAGTGGCAGACGTACAGGGGCAATTCTACAGGAACACTTATGGTGTTTTTTGGGAAT
GTCGATTCCAGCGGGATCAAACATAACATCTTCAATCCTCCTATTATCGCCCGATATATCCGCCTG
CACCCTACGCATTACTCCATCAGGTCCACATTGAGAATGGAACTGATGGGGTGCGACCTGAATAGT
TGTAGTATGCCACTGGGCATGGAGTCTAAAGCCATCAGCGATGCACAGATCACTGCCAGCTCTTAC
TTCACCAACATGTTTGCAACTTGGTCCCCCTCTAAAGCTCGCCTGCATCTGCAGGGACGCTCAAAT
GCATGGCGACCACAGGTGAACAATCCAAAAGAGTGGCTCCAGGTCGACTTTCAGAAGACAATGAAG
GTAACAGGAGTGACAACCCAGGGTGTAAAAAGCCTCCTTACGAGTATGTACGTTAAGGAGTTTCTG
ATTTCTAGCTCCCAGGACGGACACCAGTGGACTCTGTTCTTCCAGAACGGCAAAGTGAAGGTATTT
CAGGGAAACCAGGATTCTTTTACCCCGGTAGTGAATAGCCTGGATCCACCGTTGCTGACCCGCTAT
CTGAGAATTCATCCACAATCCTGGGTGCATCAGATTGCCCTCCGGATGGAAGTGCTCGGCTGTGAA
GCTCAGGATCTGTATTAG (SEQ ID NO:16)

ATGCAAATAGAGCTCTCCACCTGCTTCTTTCTGTGCCTTTTGCGATTCTGCTTTAGTGCCACCAGA
AGATACTACCTGGGTGCAGTGGAACTGTCATGGGACTATATGCAAAGTGATCTCGGTGAGCTGCCT
GTGGACGCAAGATTTCCTCCTAGAGTGCCAAAATCTTTTCCATTCAACACCTCAGTCGTGTACAAA
AAGACTCTGTTTGTAGAATTCACGGATCACCTTTTCAACATCGCTAAGCCAAGGCCACCCTGGATG
GGTCTGCTAGGTCCTACCATCCAGGCTGAGGTTTATGATACAGTGGTCATTACACTTAAGAACATG
GCTTCCCATCCTGTCAGTCTTCATGCTGTTGGTGTATCCTACTGGAAAGCTTCTGAGGGAGCTGAA
TATGATGATCAGACCAGTCAAAGGGAGAAAGAAGATGATAAAGTCTTCCCTGGTGGAAGCCATACA
TATGTCTGGCAGGTCCTGAAAGAGAATGGTCCAATGGCCTCTGACCCACTGTGCCTTACCTACTCA
TATCTTTCTCATGTGGACCTGGTAAAAGACTTGAATTCAGGCCTCATTGGAGCCCTACTAGTATGT
AGAGAAGGGAGTCTGGCCAAGGAAAAGACACAGACCTTGCACAAATTTATACTACTTTTTGCTGTA
TTTGATGAAGGGAAAAGTTGGCACTCAGAAACAAAGAACTCCTTGATGCAGGATAGGGATGCTGCA
TCTGCTCGGGCCTGGCCTAAAATGCACACAGTCAATGGTTATGTAAACAGGTCTCTGCCAGGTCTG
ATTGGATGCCACAGGAAATCAGTCTATTGGCATGTGATTGGAATGGGCACCACTCCTGAAGTGCAC
TCAATATTCCTCGAAGGTCACACATTTCTTGTGAGGAACCATCGCCAGGCGTCCTTGGAAATCTCG
CCAATAACTTTCCTTACTGCTCAAACACTCTTGATGGACCTTGGACAGTTTCTACTGTTTTGTCAT
ATCTCTTCCCACCAACATGATGGCATGGAAGCTTATGTCAAAGTAGACAGCTGTCCAGAGGAACCC
CAACTACGAATGAAAAATAATGAAGAAGCGGAAGACTATGATGATGATCTTACTGATTCTGAAATG
GATGTGGTCAGGTTTGATGATGACAACTCTCCTTCCTTTATCCAAATTCGCTCAGTTGCCAAGAAG
CATCCTAAAACTTGGGTACATTACATTGCTGCTGAAGAGGAGGACTGGGACTATGCTCCCTTAGTC
CTCGCCCCCGATGACAGAAGTTATAAAAGTCAATATTTGAACAATGGCCCTCAGCGGATTGGTAGG
AAGTACAAAAAAGTCCGATTTATGGCATACACAGATGAAACCTTTAAGACTCGTGAAGCTATTCAG
CATGAATCAGGAATCTTGGGACCTTTACTTTATGGGGAAGTTGGAGACACACTGTTGATTATATTT
AAGAATCAAGCAAGCAGACCATATAACATCTACCCTCACGGAATCACTGATGTCCGTCCTTTGTAT
TCAAGGAGATTACCAAAAGGTGTAAAACATTTGAAGGATTTTCCAATTCTGCCAGGAGAAATATTC
AAATATAAATGGACAGTGACTGTAGAAGATGGGCCAACTAAATCAGATCCTCGGTGCCTGACCCGC
TATTACTCTAGTTTCGTTAATATGGAGAGAGATCTAGCTTCAGGACTCATTGGCCCTCTCCTCATC
TGCTACAAAGAATCTGTAGATCAAAGAGGAAACCAGATAATGTCAGACAAGAGGAATGTCATCCTG
TTTTCTGTATTTGATGAGAACCGAAGCTGGTACCTCACAGAGAATATACAACGCTTTCTCCCCAAT
CCAGCTGGAGTGCAGCTTGAGGATCCAGAGTTCCAAGCCTCCAACATCATGCACAGCATCAATGGC
TATGTTTTTGATAGTTTGCAGTTGTCAGTTTGTTTGCATGAGGTGGCATACTGGTACATTCTAAGC
ATTGGAGCACAGACTGACTTCCTTTCTGTCTTCTTCTCTGGATATACCTTCAAACACAAAATGGTC
TATGAAGACACACTCACCCTATTCCCATTCTCAGGAGAAACTGTCTTCATGTCGATGGAAAACCCA
GGTCTATGGATTCTGGGGTGCCACAACTCAGACTTTCGGAACAGAGGCATGACCGCCTTACTGAAG
GTTTCTAGTTGTGACAAGAACACTGGTGATTATTACGAGGACAGTTATGAAGATATTTCAGCATAC
TTGCTGAGTAAAAACAATGCCATTGAACCAAGAAGCTTCTCCCAGAATCCACCAGTCTTGAAACGC
CATCAACGGGAAATAACTCGTACTACTCTTCAGTCAGATCAAGAGGAAATTGACTATGATGATACC
ATATCAGTTGAAATGAAGAAGGAAGATTTTGACATTTATGATGAGGATGAAAATCAGAGCCCCCGC
AGCTTTCAAAAGAAAACACGACACTATTTTATTGCTGCAGTGGAGAGGCTCTGGGATTATGGGATG (Continued)

Figure 20A

AGTAGCTCCCCACATGTTCTAAGAAACAGGGCTCAGAGTGGCAGTGTCCCTCAGTTCAAGAAAGTT
GTTTTCCAGGAATTTACTGATGGCTCCTTTACTCAGCCCTTATACCGTGGAGAACTAAATGAACAT
TTGGGACTCCTGGGGCCATATATAAGAGCAGAAGTTGAAGATAATATCATGGTAACTTTCAGAAAT
CAGGCCTCTCGTCCCTATTCCTTCTATTCTAGCCTTATTTCTTATGAGGAAGATCAGAGGCAAGGA
GCAGAACCTAGAAAAAACTTTGTCAAGCCTAATGAAACCAAAACTTACTTTTGGAAAGTGCAACAT
CATATGGCACCCACTAAAGATGAGTTTGACTGCAAAGCCTGGGCTTATTTCTCTGATGTTGACCTG
GAAAAAGATGTGCACTCAGGCCTGATTGGACCCCTTCTGGTCTGCCACACTAACACACTGAACCCT
GCTCATGGGAGACAAGTGACAGTACAGGAATTTGCTCTGTTTTTCACCATCTTTGATGAGACCAAA
AGCTGGTACTTCACTGAAAATATGGAAAGAAACTGCAGGGCTCCCTGCAATATCCAGATGGAAGAT
CCCACTTTTAAAGAGAATTATCGCTTCCATGCAATCAATGGCTACATAATGGATACACTACCTGGC
TTAGTAATGGCTCAGGATCAAAGGATTCGATGGTATCTGCTCAGCATGGGCAGCAATGAAAACATC
CATTCTATTCATTTCAGTGGACATGTGTTCACTGTACGAAAAAAAGAGGAGTATAAAATGGCACTG
TACAATCTCTATCCAGGTGTTTTTGAGACAGTGGAAATGTTACCATCCAAAGCTGGAATTTGGCGG
GTGGAATGCCTTATTGGCGAGCATCTACATGCTGGGATGAGCACACTTTTTCTGGTGTACAGCAAT
AAGTGTCAGACTCCCCTGGGAATGGCTTCTGGACACATTAGAGATTTTCAGATTACAGCTTCAGGA
CAATATGGACAGTGGGCCCCAAAGCTGGCCAGACTTCATTATTCCGGATCAATCAATGCCTGGAGC
ACCAAGGAGCCCTTTTCTTGGATCAAGGTGGATCTGTTGGCACCAATGATTATTCACGGCATCAAG
ACCCAGGGTGCCCGTCAGAAGTTCTCCAGCCTCTACATCTCTCAGTTTATCATCATGTATAGTCTT
GATGGGAAGAAGTGGCAGACTTATCGAGGAAATTCCACTGGAACCTTAATGGTCTTCTTTGGCAAT
GTGGATTCATCTGGGATAAAACACAATATTTTTAACCCTCCAATTATTGCTCGATACATCCGTTTG
CACCCAACTCATTATAGCATTCGCAGCACTCTTCGCATGGAGTTGATGGGCTGTGATTTAAATAGT
TGCAGCATGCCATTGGGAATGGAGAGTAAAGCAATATCAGATGCACAGATTACTGCTTCATCCTAC
TTTACCAATATGTTTGCCACCTGGTCTCCTTCAAAAGCTCGACTTCACCTCCAAGGGAGGAGTAAT
GCCTGGAGACCTCAGGTGAATAATCCAAAAGAGTGGCTGCAAGTGGACTTCCAGAAGACAATGAAA
GTCACAGGAGTAACTACTCAGGGAGTAAAATCTCTGCTTACCAGCATGTATGTGAAGGAGTTCCTC
ATCTCCAGCAGTCAAGATGGCCATCAGTGGACTCTCTTTTTTCAGAATGGCAAAGTAAAGGTTTTT
CAGGGAAATCAAGACTCCTTCACACCTGTGGTGAACTCTCTAGACCCACCGTTACTGACTCGCTAC
CTTCGAATTCACCCCCAGAGTTGGGTGCACCAGATTGCCCTGAGGATGGAGGTTCTGGGCTGCGAG
GCACAGGACCTCTACTGA (SEQ ID NO:17)

ATGCAGATCGAGCTGTCCACATGCTTTTTTCTGTGCCTGCTGCGGTTCTGCTTCAGCGCCACCCGG
CGGTACTACCTGGGCGCCGTGGAGCTGTCCTGGGACTACATGCAGAGCGACCTGGGCGAGCTGCCC
GTGGACGCCCGGTTCCCCCCCAGAGTGCCCAAGAGCTTCCCCTTCAACACCAGCGTGGTGTACAAG
AAAACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGATCACCCTGAAGAACATG
GCCAGCCACCCCGTGAGCCTGCACGCCGTGGGCGTGAGCTACTGGAAGGCCTCCGAGGGCGCCGAG
TACGACGACCAGACCAGCCAGCGGGAGAAAGAGGACGACAAAGTCTTTCCTGGCGGCAGCCACACC
TACGTGTGGCAGGTCCTGAAAGAAAACGGCCCCATGGCCTCCGACCCCCTGTGCCTGACCTACAGC
TACCTGAGCCACGTGGACCTGGTGAAGGACCTGAACAGCGGGCTGATTGGGGCCCTGCTGGTCTGC
CGGGAGGGCAGCCTGGCCAAAGAGAAAACCCAGACCCTGCACAAGTTCATCCTGCTGTTCGCCGTG
TTCGACGAGGGCAAGAGCTGGCACAGCGAGACCAAGAACAGCCTGATGCAGGACCGGGACGCCGCC
TCTGCCAGAGCCTGGCCCAAGATGCACACCGTGAACGGCTACGTGAACAGAAGCCTGCCCGGCCTG
ATTGGCTGCCACCGGAAGAGCGTGTACTGGCACGTGATCGGCATGGGCACCACACCCGAGGTGCAC
AGCATCTTTCTGGAAGGGCACACCTTTCTGGTGCGGAACCACCGGCAGGCCAGCCTGGAAATCAGC
CCTATCACCTTCCTGACCGCCCAGACACTGCTGATGGACCTGGGCCAGTTCCTGCTGTTTTGCCAC
ATCAGCTCTCACCAGCACGACGGCATGGAAGCCTACGTGAAGGTGGACTCCTGCCCCGAGGAACCC
CAGCTGCGGATGAAGAACAACGAGGAAGCCGAGGACTACGACGACGACCTGACCGACAGCGAGATG
GACGTGGTGCGGTTCGACGACGACAACAGCCCCAGCTTCATCCAGATCAGAAGCGTGGCCAAGAAG
CACCCCAAGACCTGGGTGCACTACATCGCCGCCGAGGAAGAGGACTGGGACTACGCCCCCCTGGTG
CTGGCCCCCGACGACAGAAGCTACAAGAGCCAGTACCTGAACAATGGCCCCCAGCGGATCGGCCGG
AAGTACAAGAAAGTGCGGTTCATGGCCTACACCGACGAGACCTTCAAGACCCGGGAGGCCATCCAG
CACGAGAGCGGCATCCTGGGCCCCCTGCTGTACGGCGAAGTGGGCGACACACTGCTGATCATCTTC
AAGAACCAGGCCAGCCGGCCCTACAACATCTACCCCCACGGCATCACCGACGTGCGGCCCCTGTAC
AGCAGGCGGCTGCCCAAGGGCGTGAAGCACCTGAAGGACTTCCCCATCCTGCCCGGCGAGATCTTC
AAGTACAAGTGGACCGTGACCGTGGAGGACGGCCCCACCAAGAGCGACCCCAGATGCCTGACCCGG
TACTACAGCAGCTTCGTGAACATGGAACGGGACCTGGCCTCCGGGCTGATCGGACCTCTGCTGATC
TGCTACAAAGAAAGCGTGGACCAGCGGGGCAACCAGATCATGAGCGACAAGCGGAACGTGATCCTG
TTCAGCGTGTTCGATGAGAACCGGTCCTGGTATCTGACCGAGAACATCCAGCGGTTTCTGCCCAAC
CCTGCCGGGGTGCAGCTGGAAGATCCCGAGTTCCAGGCCAGCAACATCATGCACTCCATCAATGGC
TACGTGTTCGACAGCCTGCAGCTGTCCGTGTGTCTGCACGAGGTGGCCTACTGGTACATCCTGAGC
ATCGGCGCCCAGACCGACTTCCTGAGCGTGTTCTTCAGCGGCTACACCTTCAAGCACAAGATGGTG
TACGAGGACACCCTGACCCTGTTCCCTTTCAGCGGCGAGACCGTGTTCATGAGCATGGAAAACCCC
GGCCTGTGGATCCTGGGCTGCCACAACAGCGACTTCCGGAACCGGGGCATGACCGCCCTGCTGAAG
GTGTCCAGCTGCGACAAGAACACCGGCGACTACTACGAGGACAGCTACGAGGATATCAGCGCCTAC
CTGCTGTCCAAGAACAACGCCATCGAGCCCAGAAGCTTCAGCCAGAACCCCCCTGTGCTGAAGCGG
CACCAGAGAGAGATCACCCGGACCACCCTGCAGTCCGACCAGGAAGAGATCGATTACGACGACACC (Continued)

Figure 21A

ATCAGCGTGGAGATGAAAAAAGAAGATTTCGACATCTACGACGAGGACGAGAACCAGAGCCCCCGG
TCCTTCCAGAAGAAAACCCGGCACTACTTTATCGCCGCCGTGGAGCGGCTGTGGGACTACGGCATG
AGCAGCAGCCCCCACGTGCTGCGGAACCGGGCCCAGAGCGGCAGCGTGCCCCAGTTCAAGAAAGTG
GTGTTCCAGGAATTCACCGACGGCAGCTTCACCCAGCCCCTGTACCGGGGCGAGCTGAACGAGCAC
CTGGGGCTGCTGGGGCCCTACATCAGGGCCGAAGTGGAGGACAACATCATGGTGACCTTCCGGAAT
CAGGCCAGCAGACCCTACTCCTTCTACAGCAGCCTGATCAGCTACGAAGAGGACCAGCGGCAGGGC
GCTGAACCCCGGAAGAACTTCGTGAAGCCCAATGAGACCAAGACCTACTTCTGGAAAGTGCAGCAC
CACATGGCCCCCACCAAGGACGAGTTCGACTGCAAGGCCTGGGCCTACTTCAGCGACGTGGATCTG
GAAAAGGACGTGCACTCTGGACTGATTGGCCCTCTGCTGGTGTGCCACACCAACACCCTGAACCCC
GCCCACGGCCGGCAGGTGACCGTGCAGGAATTCGCCCTGTTCTTCACCATCTTCGACGAGACCAAG
TCCTGGTACTTCACCGAGAATATGGAACGGAACTGCAGAGCCCCCTGCAACATCCAGATGGAAGAT
CCTACCTTCAAAGAGAACTACCGGTTCCACGCCATCAACGGCTACATCATGGACACCCTGCCTGGC
CTGGTGATGGCCCAGGACCAGAGGATCCGGTGGTATCTGCTGTCCATGGGCAGCAACGAGAATATC
CACAGCATCCACTTCAGCGGCCACGTGTTCACCGTGAGGAAGAAAGAAGAGTACAAGATGGCCCTG
TACAACCTGTACCCCGGCGTGTTCGAGACCGTGGAGATGCTGCCCAGCAAGGCCGGCATCTGGCGG
GTGGAGTGTCTGATCGGCGAGCACCTGCATGCCGGGATGAGCACCCTGTTTCTGGTGTACAGCAAC
AAGTGCCAGACCCCCCTGGGCATGGCCAGCGGCCACATCCGGGACTTCCAGATCACCGCCTCCGGC
CAGTACGGCCAGTGGGCCCCCAAGCTGGCCCGGCTGCACTACAGCGGCAGCATCAACGCCTGGTCC
ACCAAAGAGCCCTTCAGCTGGATCAAGGTGGACCTGCTGGCCCCTATGATCATCCACGGCATTAAG
ACCCAGGGCGCCAGGCAGAAGTTCAGCAGCCTGTACATCAGCCAGTTCATCATCATGTACAGCCTG
GACGGCAAGAAGTGGCAGACCTACCGGGGCAACAGCACCGGCACCCTGATGGTGTTCTTCGGCAAC
GTGGACAGCAGCGGCATCAAGCACAACATCTTCAACCCCCCCATCATCGCCCGGTACATCCGGCTG
CACCCCACCCACTACAGCATCAGATCCACCCTGCGGATGGAACTGATGGGCTGCGACCTGAACTCC
TGCAGCATGCCTCTGGGCATGGAAAGCAAGGCCATCAGCGACGCCCAGATCACAGCCAGCAGCTAC
TTCACCAACATGTTCGCCACCTGGTCCCCCTCCAAGGCCAGGCTGCACCTGCAGGGCCGGTCCAAC
GCCTGGCGGCCTCAGGTGAACAACCCCAAAGAATGGCTGCAGGTGGACTTTCAGAAAACCATGAAG
GTGACCGGCGTGACCACCCAGGGCGTGAAAAGCCTGCTGACCAGCATGTACGTGAAAGAGTTTCTG
ATCAGCAGCAGCCAGGACGGCCACCAGTGGACCCTGTTCTTTCAGAACGGCAAGGTGAAAGTGTTC
CAGGGCAACCAGGACTCCTTCACCCCCGTGGTGAACTCCCTGGACCCCCCCCTGCTGACCCGCTAC
CTGCGGATCCACCCCCAGTCTTGGGTGCACCAGATCGCCCTGAGGATGGAAGTGCTGGGATGTGAG
GCCCAGGATCTGTACTGA (SEQ ID NO:18)

Figure 21B

FVIII-FL-AA mqielstcff lcllrfcfsa trryylgave lswdymqsdl gelpvdarfp prvpksfpfn
tsvvykktlf veftdhlfni akprppwmgl lgptiqaevy dtvvitlknm ashpvslhav
gvsywkaseg aeyddqtsqr ekeddkvfpg gshtyvwqvl kengpmasdp lcltysylsh
vdlvkdlnsg ligallvcre gslakektqt lhkfillfav fdegkswhse tknslmqdrd
aasarawpkm htvngyvnrs lpgligchrk svywhvigmg ttpevhsifl eghtflvrnh
rqasleispi tfltaqtllm dlgqfllfch isshqhdgme ayvkvdscpe epqlrmknne
eaedydddlt dsemdvvrfd ddnspsfiqi rsvakkhpkt wvhyiaaeee dwdyaplvla
pddrsyksqy lnngpqrigr kykkvrfmay tdetfktrea iqhesgilgp llygevgdtl
liifknqasr pyniyphgit dvrplysrrl pkgvkhlkdf pilpgeifky kwtvtvedgp
tksdprcltr yyssfvnmer dlasgligpl licykesvdq rgnqimsdkr nvilfsvfde
nrswylteni qrflpnpagv qledpefqas nimhsingyv fdslqlsvcl hevaywyils
igaqtdflsv ffsgytfkhk mvyedtltlf pfsgetvfms menpglwilg chnsdfrnrg
mtallkvssc dkntgdyyed syedisayll sknnaieprs fsqnsrhpst rqkqfnatti
pendiektdp wfahrtpmpk iqnvsssdll mllrqsptph glslsdlqea kyetfsddps
pgaidsnnsl semthfrpql hhsgdmvftp esglqlrlne klgttaatel kkldfkvsst
snnlistips dnlaagtdnt sslgppsmpv hydsqldttl fgkkssplte sggplslsee
nndskllesg lmnsqesswg knvsstesgr lfkgkrahgp alltkdnalf kvsisllktn
ktsnnsatnr kthidgpsll ienspsvwqn ilesdtefkk vtplihdrml mdknatalrl
nhmsnkttss knmemvqqkk egpippdaqn pdmsffkmlf lpesarwiqr thgknslnsg
qgpspkqlvs lgpeksvegq nflseknkvv vgkgeftkdv glkemvfpss rnlfltnldn
lhennthnqe kkiqeeiekk etliqenvvl pqihtvtgtk nfmknlflls trqnvegsyd
gayapvlqdf rslndstnrt kkhtahfskk geeenleglg nqtkqiveky acttrispnt
sqqnfvtqrs kralkqfrlp leetelekri ivddtstqws knmkhltpst ltqidyneke
kgaitqspls dcltrshsip qanrsplpia kvssfpsirp iyltrvlfqd nsshlpaasy
rkkdsgvqes shflqgakkn nlslailtle mtgdqrevgs lgtsatnsvt ykkventvlp
kpdlpktsgk vellpkvhiy qkdlfptets ngspghldlv egsllqgteg aikwneanrp
gkvpflrvat essaktpskl ldplawdnhy gtqipkeewk sqekspekta fkkkdtilsl
nacesnhaia ainegqnkpe ievtwakqgr terlcsqnpp vlkrhqreit rttlqsdqee
idyddtisve mkkedfdiyd edenqsprsf qkktrhyfia averlwdygm sssphvlrnr
aqsgsvpqfk kvvfqeftdg sftqplyrge lnehlgllgp yiraevedni mvtfrnqasr
pysfysslis yeedqrqgae prknfvkpne tktyfwkvqh hmaptkdefd ckawayfsdv
dlekdvhsgl igpllvchtn tlnpahgrqv tvqefalfft ifdetkswyf tenmerncra
pcniqmedpt fkenyrfhai ngyimdtlpg lvmaqdqrir wyllsmgsne nihsihfsgh
vftvrkkeey kmalynlypg vfetvemlps kagiwrvecl igehlhagms tlflvysnkc
qtplgmasgh irdfqitasg qygqwapkla rlhysgsina wstkepfswi kvdllapmii
hgiktqgarq kfsslyisqf iimysldgkk wqtyrgnstg tlmvffgnvd ssgikhnifn
ppiiaryirl hpthysirst lrmelmgcdl nscsmplgme skaisdaqit assyftnmfa
twspskarlh lqgrsnawrp qvnnpkewlq vdfqktmkvt gvttqgvksl ltsmyvkefl
isssqdghqw tlffqngkvk vfqgnqdsft pvvnsldppl ltrylrihpq swvhqialrm
evlgceaqdl y (SEQ ID NO:19)

Figure 22

CS23-FL-NA atgcagattgagctgagcacctgcttcttcctgtgcctgctgaggttctgcttctctgccaccagg
agatactacctgggcgccgtggagctgagctgggactacatgcagtctgacctgggcgagctgcct
gtggacgccaggttcccccccagagtgcccaagagcttccccttcaacacctcagtggtgtacaag
aagaccctgttcgtggagttcaccgaccacctgttcaacatcgccaagcccaggcccccctggatg
ggcctgctgggccccaccatccaggccgaggtgtacgacaccgtggtgatcaccctgaagaacatg
gccagccaccccgtgagcctgcacgccgtgggcgtgagctactggaaggcctctgagggcgccgag
tatgacgaccagaccagccagagggagaaggaggacgacaaggtgttccccggcggcagccacacc
tacgtgtggcaggtgctgaaggagaacggccccatggccagcgacccccctgtgcctgacctacagc
tacctgagccacgtggacctggtgaaggacctgaactctggcctgatcggcgccctgctggtgtgc
agggagggcagcctggccaaggagaagacccagaccctgcacaagttcatcctgctgttcgccgtg
ttcgatgagggcaagagctggcacagcgagaccaagaacagcctgatgcaggacagggatgccgcc
tctgccagggcctggcccaagatgcacaccgtgaacggctacgtgaacaggagcctgcccggcctg
atcggctgccacaggaagtctgtgtactggcacgtgatcggcatgggcaccacccccgaggtgcac
agcatcttcctggagggccacaccttcctggtgaggaaccacaggcaggccagcctggagatcagc
cccatcaccttcctgaccgcccagaccctgctgatggacctgggccagttcctgctgttctgccac
atcagcagccaccagcacgacggcatggaggcctacgtgaaggtggacagctgccccgaggagccc
cagctgaggatgaagaacaacgaggaggccgaggactatgatgatgacctgaccgactctgagatg
gacgtggtgaggtttgatgatgacaacagccccagcttcatccagatcaggtctgtggccaagaag
caccccaagacctgggtgcactacatcgccgccgaggaggaggactgggactacgcccccctggtg
ctggcccccgacgacaggagctacaagagccagtacctgaacaacggcccccagaggatcggcagg
aagtacaagaaggtcagattcatggcctacaccgacgagaccttcaagaccagggaggccatccag
cacgagtctggcatcctgggccccctgctgtacggcgaggtgggcgacaccctgctgatcatcttc
aagaaccaggccagcaggccctacaacatctacccccacggcatcaccgatgtgaggcccctgtac
agcaggaggctgcccaagggcgtgaagcacctgaaggacttccccatcctgcccggcgagatcttc
aagtacaagtggaccgtgaccgtggaggatggccccaccaagtctgacccccaggtgcctgaccagg
tactacagcagcttcgtgaacatggagagggacctggcctctggcctgatcggccccctgctgatc
tgctacaaggagagcgtggaccagaggggcaaccagatcatgtctgacaagaggaacgtgatcctg
ttctctgtgttcgatgagaacaggagctggtatctgaccgagaacatccagaggttcctgcccaac
cccgccggcgtgcagctggaggaccccgagttccaggccagcaacatcatgcacagcatcaacggc
tacgtgttcgacagcctgcagctgtctgtgtgcctgcacgaggtggcctactggtacatcctgagc
atcggcgcccagaccgacttcctgtctgtgttcttctctggctacaccttcaagcacaagatggtg
tacgaggacaccctgaccctgttccccttcagcggcgagaccgtgttcatgagcatggagaacccc
ggcctgtggatcctgggctgccacaacagcgacttcaggaacaggggcatgaccgccctgctgaaa
gtcagcagctgcgacaagaacaccggcgactactacgaggacagctacgaggacatcagcgcctac
ctgctgagcaagaacaacgccatcgagcccaggagcttcagccagaacccccccgtgctgaagagg
caccagagggagatcaccaggaccaccctgcagagcgaccaggaggagatcgactatgatgacacc (Continued)

Figure 26A atcagcgtggagatgaagaaggaggacttcgacatctacgacgaggacgagaaccagagccccagg
agcttccagaagaagaccaggcactacttcatcgccgccgtggagaggctgtgggactatggcatg
agcagcagcccccacgtgctgaggaacagggcccagagcggcagcgtgccccagttcaagaaggtg
gtgttccaggagttcaccgacggcagcttcacccagcccctgtacagaggcgagctgaacgagcac
ctgggcctgctgggcccctacatcagggccgaggtggaggacaacatcatggtgaccttcaggaac
caggccagcaggccctacagcttctacagcagcctgatcagctacgaggaggaccagaggcagggc
gccgagcccaggaagaacttcgtgaagcccaacgagaccaagacctacttctggaaggtgcagcac
cacatggcccccaccaaggacgagttcgactgcaaggcctgggcctacttctctgatgtggacctg
gagaaggacgtgcacagcggcctgatcggccccctgctggtgtgccacaccaacaccctgaacccc
gcccacggcaggcaggtgaccgtgcaggagttcgccctgttcttcaccatcttcgacgagaccaag
agctggtacttcaccgagaacatggagaggaactgcagggccccctgcaacatccagatggaggac
cccaccttcaaggagaactacaggttccacgccatcaacggctacatcatggacaccctgcccggc
ctggtgatggcccaggaccagaggatcaggtggtatctgctgagcatgggcagcaacgagaacatc
cacagcatccacttcagcggccacgtgttcaccgtgaggaagaaggaggagtacaagatggccctg
tacaacctgtaccccggcgtgttcgagaccgtggagatgctgcccagcaaggccggcatctggagg
gtggagtgcctgatcggcgagcacctgcacgccggcatgagcaccctgttcctggtgtacagcaac
aagtgccagacccccctgggcatggccagcggccacatcagggacttccagatcaccgcctctggc
cagtacggccagtgggcccccaagctggccaggctgcactacagcggcagcatcaacgcctggagc
accaaggagcccttcagctggatcaaggtggacctgctggcccccatgatcatccacggcatcaag
acccagggcgccaggcagaagttcagcagcctgtacatcagccagttcatcatcatgtacagcctg
gacggcaagaagtggcagacctacaggggcaacagcaccggcaccctgatggtgttcttcggcaac
gtggacagcagcggcatcaagcacaacatcttcaacccccccatcatcgccaggtacatcaggctg
cacccccacccactacagcatcaggagcaccctgcggatggaactgatgggctgcgacctgaacagc
tgcagcatgcccctgggcatggagagcaaggccatctctgacgcccagatcaccgccagcagctac
ttcaccaacatgttcgccacctggagccccagcaaggccaggctgcacctgcagggcaggagcaac
gcctggaggccccaggtgaacaaccccaaggagtggctgcaggtggacttccagaagaccatgaag
gtgaccggcgtgaccacccagggcgtgaagagcctgctgaccagcatgtacgtgaaggagttcctg
atcagcagcagccaggacggccaccagtggaccctgttcttccagaacggcaaagtgaaggtgttc
cagggcaaccaggacagcttcacCcccgtggtgaacagcctggaccccccctgctgaccaggtat
ctgaggatccacccccagagctgggtgcaccagatcgccctgagaatggaagtgctgggatgcgag
gcccaggacctgtactga (SEQ ID NO:20)

MQIELSTCFFLCLLRFCFSATRRYYLGAVELSWDYMQSDLGELPVDAR′FPPRVPKSFPFNTSVVYK
KTLFVEFTDHLFNIAKPRPPWMGLLGPTIQAEVYDTVVITLKNMASHPVSLHAVGVSYWKASEGAEY
DDQTSQREKEDDKVFPGGSHTYVWQVLKENGPMASDPLCLTYSYLSHVDLVKDLNSGLIGALLVCRE
GSLAKEKTQTLHKFILLFAVFDEGKSWHSETKNSLMQDRDAASARAWPKMHTVNGYVNRSLPGLIGC
HRKSVYWHVIGMGTTPEVHSIFLEGHTFLVRNHRQASLEISPITFLTAQTLLMDLGQFLLFCHISSH
QHDGMEAYVKVDSCPEEPQLRMKNNEEAEDYDDDLTDSEMDVVRFDDDNSPSFIQIRSVAKKHPKTW
VHYIAAEEEDWDYAPLVLAPDDRSYKSQYLNNGPQRIGRKYKKVRFMAYTDETFKTREAIQHESGIL
GPLLYGEVGDTLLIIFKNQASRPYNIYPHGITDVRPLYSRRLPKGVKHLKDFPILPGEIFKYKWTVT
VEDGPTKSDPRCLTRYYSSFVNMERDLASGLIGPLLICYKESVDQRGNQIMSDKRNVILFSVFDENR
SWYLTENIQRFLPNPAGVQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNRGMTALLKVSSCDKNTGD
YYEDSYEDISAYLLSKNNAIEPRSFSQNPPVLKRHQREITRTTLQSDQEEIDYDDTISVEMKKEDFD
IYDEDENQSPRSFQKKTRHYFIAAVERLWDYGMSSSPHVLRNRAQSGSVPQFKKVVFQEFTDGSFTQ
PLYRGELNEHLGLLGPYIRAEVEDNIMVTFRNQASRPYSFYSSLISYEEDQRQGAEPRKNFVKPNET
KTYFWKVQHHMAPTKDEFDCKAWAYFSDVDLEKDVHSGLIGPLLVCHTNTLNPAHGRQVTVQEFALF
FTIFDETKSWYFTENMERNCRAPCNIQMEDPTFKENYRFHAINGYIMDTLPGLVMAQDQRIRWYLLS
MGSNENIHSIHFSGHVFTVRKKEEYKMALYNLYPGVFETVEMLPSKAGIWRVECLIGEHLHAGMSTL
FLVYSNKCQTPLGMASGHIRDFQITASGQYGQWAPKLARLHYSGSINAWSTKEPFSWIKVDLLAPMI
IHGIKTQGARQKFSSLYISQFIIMYSLDGKKWQTYRGNSTGTLMVFFGNVDSSGIKHNIFNPPIIAR
YIRLHPTHYSIRSTLRMELMGCDLNSCSMPLGMESKAISDAQITASSYFTNMFATWSPSKARLHLQG
RSNAWRPQVNNPKEWLQVDFQKTMKVTGVTTQGVKSLLTSMYVKEFLISSSQDGHQWTLFFQNGKVK
VFQGNQDSFTPVVNSLDPPLLTRYLRIHPQSWVHQIALRMEVLGCEAQDLY (SEQ ID NO:21)

Figure 27

CS23-HC-NA gcc
accaggagat actacctggg cgccgtggag ctgagctggg actacatgca gtctgacctg
ggcgagctgc ctgtggacgc caggttcccc cccagagtgc ccaagagctt ccccttcaac
acctcagtgg tgtacaagaa gaccctgttc gtggagttca ccgaccacct gttcaacatc
gccaagccca ggccccctg gatgggcctg ctgggcccca ccatccaggc cgaggtgtac
gacaccgtgg tgatcaccct gaagaacatg gccagccacc ccgtgagcct gcacgccgtg
ggcgtgagct actggaaggc ctctgagggc gccgagtatg acgaccagac cagccagagg
gagaaggagg acgacaaggt gttccccggc ggcagccaca cctacgtgtg gcaggtgctg
aaggagaacg gccccatggc cagcgacccc ctgtgcctga cctacagcta cctgagccac
gtggacctgg tgaaggacct gaactctggc ctgatcggcg ccctgctggt gtgcagggag
ggcagcctgg ccaaggagaa gacccagacc ctgcacaagt tcatcctgct gttcgccgtg
ttcgatgagg gcaagagctg gcacagcgag accaagaaca gcctgatgca ggacagggat
gccgcctctg ccagggcctg gcccaagatg cacaccgtga acggctacgt gaacaggagc
ctgcccggcc tgatcggctg ccacaggaag tctgtgtact ggcacgtgat cggcatgggc
accacccccg aggtgcacag catcttcctg gagggccaca ccttcctggt gaggaaccac
aggcaggcca gcctggagat cagccccatc accttcctga ccgcccagac cctgctgatg
gacctgggcc agttcctgct gttctgccac atcagcagcc accagcacga cggcatggag
gcctacgtga aggtggacag ctgccccgag gagccccagc tgaggatgaa gaacaacgag
gaggccgagg actatgatga tgacctgacc gactctgaga tggacgtggt gaggtttgat
gatgacaaca gccccagctt catccagatc aggtctgtgg ccaagaagca ccccaagacc
tgggtgcact acatcgccgc cgaggaggag gactgggact acgcccccct ggtgctggcc
cccgacgaca ggagctacaa gagccagtac ctgaacaacg gcccccagag gatcggcagg
aagtacaaga aggtcagatt catggcctac accgacgaga ccttcaagac cagggaggcc
atccagcacg agtctggcat cctgggcccc ctgctgtacg gcgaggtggg cgacaccctg
ctgatcatct tcaagaacca ggccagcagg ccctacaaca tctaccccca cggcatcacc
gatgtgaggc ccctgtacag caggaggctg cccaagggcg tgaagcacct gaaggacttc
cccatcctgc ccggcgagat cttcaagtac aagtggaccg tgaccgtgga ggatggcccc
accaagtctg accccaggtg cctgaccagg tactacagca gcttcgtgaa catggagagg
gacctggcct ctggcctgat cggccccctg ctgatctgct acaaggagag cgtggaccag
aggggcaacc agatcatgtc tgacaagagg aacgtgatcc tgttctctgt gttcgatgag
aacaggagct ggtatctgac cgagaacatc cagaggttcc tgcccaaccc cgccggcgtg
cagctggagg accccgagtt ccaggccagc aacatcatgc acagcatcaa cggctacgtg
ttcgacagcc tgcagctgtc tgtgtgcctg cacgaggtgg cctactggta catcctgagc
atcggcgccc agaccgactt cctgtctgtg ttcttctctg gctacacctt caagcacaag
atggtgtacg aggacaccct gaccctgttc cccttcagcg gcgagaccgt gttcatgagc
atggagaacc ccggcctgtg gatcctgggc tgccacaaca gcgacttcag gaacaggggc
atgaccgccc tgctgaaagt cagcagctgc gacaagaaca ccggcgacta ctacgaggac
agctacgagg acatcagcgc ctacctgctg agcaagaaca acgccatcga gcccagg
(SEQ ID NO:22)

```
                                                  g agatcaccag gaccaccctg
cagagcgacc aggaggagat cgactatgat gacaccatca gcgtggagat gaagaaggag
gacttcgaca tctacgacga ggacgagaac cagagcccca ggagcttcca gaagaagacc
aggcactact tcatcgccgc cgtggagagg ctgtgggact atggcatgag cagcagcccc
cacgtgctga ggaacagggc ccagagcggc agcgtgcccc agttcaagaa ggtggtgttc
caggagttca ccgacggcag cttcacccag cccctgtaca gaggcgagct gaacgagcac
ctgggcctgc tgggccccta catcagggcc gaggtggagg acaacatcat ggtgaccttc
aggaaccagg ccagcaggcc ctacagcttc tacagcagcc tgatcagcta cgaggaggac
cagaggcagg gcgccgagcc caggaagaac ttcgtgaagc ccaacgagac caagacctac
ttctggaagg tgcagcacca catggccccc accaaggacg agttcgactg caaggcctgg
gcctacttct ctgatgtgga cctggagaag gacgtgcaca gcggcctgat cggccccctg
ctggtgtgcc acaccaacac cctgaacccc gcccacggca ggcaggtgac cgtgcaggag
ttcgccctgt tcttcaccat cttcgacgag accaagagct ggtacttcac cgagaacatg
gagaggaact gcagggcccc ctgcaacatc cagatggagg accccacctt caaggagaac
tacaggttcc acgccatcaa cggctacatc atggacaccc tgcccggcct ggtgatggcc
caggaccaga ggatcaggtg gtatctgctg agcatgggca gcaacgagaa catccacagc
atccacttca gcggccacgt gttcaccgtg aggaagaagg aggagtacaa gatggccctg
tacaacctgt accccggcgt gttcgagacc gtggagatgc tgcccagcaa ggccggcatc
tggagggtgg agtgcctgat cggcgagcac ctgcacgccg gcatgagcac cctgttcctg
gtgtacagca acaagtgcca gacccccctg ggcatggcca gcggccacat cagggacttc
cagatcaccg cctctggcca gtacggccag tgggccccca agctggccag gctgcactac
agcggcagca tcaacgcctg gagcaccaag gagcccttca gctggatcaa ggtggacctg
ctggccccca tgatcatcca cggcatcaag acccagggcg ccaggcagaa gttcagcagc
ctgtacatca gccagttcat catcatgtac agcctggacg gcaagaagtg gcagacctac
aggggcaaca gcaccggcac cctgatggtg ttcttcggca acgtggacag cagcggcatc
aagcacaaca tcttcaaccc ccccatcatc gccaggtaca tcaggctgca ccccacccac
tacagcatca ggagcaccct gcggatggaa ctgatgggct gcgacctgaa cagctgcagc
atgcccctgg gcatggagag caaggccatc tctgacgccc agatcaccgc cagcagctac
ttcaccaaca tgttcgccac ctggagcccc agcaaggcca ggctgcacct gcagggcagg
agcaacgcct ggaggcccca ggtgaacaac cccaaggagt ggctgcaggt ggacttccag
aagaccatga aggtgaccgg cgtgaccacc cagggcgtga agagcctgct gaccagcatg
tacgtgaagg agttcctgat cagcagcagc caggacggcc accagtggac cctgttcttc
cagaacggca aagtgaaggt gttccagggc aaccaggaca gcttcacccc cgtggtgaac
agcctggacc ccccccctgct gaccaggtat ctgaggatcc acccccagag ctgggtgcac
cagatcgccc tgagaatgga agtgctggga tgcgaggccc aggacctgta c
(SEQ ID NO:23)
```

ATGCAGATTGAGCTGTCCACCTGCTTCTTTCTGTGCCTGCTGAGATTCTGCTTCTCTGCCACCAGG
AGATACTACCTGGGGGCTGTGGAACTTTCTTGGGACTACATGCAGTCTGACCTGGGAGAGCTGCCT
GTGGATGCCAGGTTCCCACCCAGAGTGCCCAAGTCCTTCCCATTCAACACCTCTGTGGTCTACAAG
AAGACACTCTTTGTGGAATTCACTGACCACCTGTTCAACATTGCAAAACCCAGACCACCCTGGATG
GGACTCCTGGGACCCACCATTCAGGCTGAGGTGTATGACACTGTGGTCATCACCCTCAAGAACATG
GCATCCCACCCTGTGTCTCTGCATGCTGTGGGAGTCTCATACTGGAAAGCCTCTGAAGGGGCTGAG
TATGATGACCAGACATCCCAGAGAGAGAAAGAGGATGACAAGGTGTTCCCTGGGGGATCTCACACC
TATGTGTGGCAAGTCCTCAAGGAGAATGGACCCATGGCATCTGACCCACTCTGCCTGACATACTCC
TACCTTTCTCATGTGGACCTGGTCAAGGACCTCAACTCTGGACTGATTGGGGCACTGCTGGTGTGC
AGGGAAGGATCCCTGGCCAAGGAGAAAACCCAGACACTGCACAAGTTCATTCTCCTGTTTGCTGTC
TTTGATGAGGGCAAGTCTTGGCACTCTGAAACAAAGAACTCCCTGATGCAAGACAGGGATGCTGCC
TCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGGACAACCCCTGAAGTGCAC
TCCATTTTCCTGGAGGGACACACCTTCCTGGTCAGGAACCACAGACAAGCCTCTCTGGAGATCTCT
CCCATCACCTTCCTCACTGCACAGACACTGCTGATGGACCTTGGACAGTTCCTGCTGTCCTGCCAC
ATCTCTTCCCACCAGCATGATGGCATGGAAGCCTATGTCAAGGTGGACTCATGCCCTGAGGAACCA
CAGCTCAGGATGAAGAACAATGAGGAGGCTGAGGACTATGATGATGACCTGACTGACTCTGAGATG
GATGTGGTCAGATTTGATGATGACAACTCTCCATCCTTCATTCAGATCAGGTCTGTGGCAAAGAAA
CACCCCAAGACATGGGTGCACTACATTGCTGCTGAGGAAGAGGACTGGGACTATGCACCACTGGTC
CTGGCCCCTGATGACAGGAGCTACAAGTCTCAGTACCTCAACAATGGCCCACAAAGAATTGGAAGA
AAGTACAAGAAAGTCAGATTCATGGCCTACACTGATGAAACCTTCAAGACAAGAGAAGCCATTCAG
CATGAGTCTGGCATTCTGGGACCACTCCTGTATGGGGAAGTGGGAGACACCCTGCTCATCATCTTC
AAGAACCAGGCCTCCAGGCCCTACAACATCTACCCACATGGCATCACTGATGTCAGGCCCCTGTAC
AGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGA
TACTACTCCTCTTTTGTGAACATGGAGAGAGACCTGGCATCTGGACTGATTGGACCACTGCTCATC
TGCTACAAGGAGTCTGTGGACCAGAGAGGCAACCAGATCATGTCTGACAAGAGAAATGTGATTCTG
TTCTCTGTCTTTGATGAGAACAGATCATGGTACCTGACTGAGAACATTCAGAGATTCCTGCCCAAC
CCTGCTGGGGTGCAACTGGAAGACCCTGAGTTCCAGGCAAGCAACATCATGCACTCCATCAATGGC
TATGTGTTTGACTCTCTCCAGCTTTCTGTCTGCCTGCATGAGGTGGCCTACTGGTACATTCTTTCT
ATTGGGGCACAAACTGACTTCCTTTCTGTCTTCTTCTCTGGATACACCTTCAAGCACAAGATGGTG
TATGAGGACACCCTGACACTCTTCCCATTCTCTGGGGAAACTGTGTTCATGAGCATGGAGAACCCT
GGACTGTGGATTCTGGGATGCCACAACTCTGACTTCAGAAACAGGGGAATGACTGCACTGCTCAAA
GTCTCCTCCTGTGACAAGAACACTGGGGACTACTATGAGGACTCTTATGAGGACATCTCTGCCTAC
CTGCTCAGCAAGAACAATACCACCTACGTGAACCGCTCCCTGTCTCAGAATCCACCTGTCCTGAAG
AGACACCAGAGAGAGATCACCAGGACAACCCTCCAGTCTGACCAGGAAGAGATTGACTATGATGAC
ACCATTTCTGTGGAGATGAAGAAGGAGGACTTTGACATCTATGATGAGGACGAGAACCAGTCTCCA
AGATCATTCCAGAAGAAGACAAGACACTACTTCATTGCTGCTGTGGAAAGACTGTGGGACTATGGC
ATGTCTTCCTCTCCCCATGTCCTCAGGAACAGGGCACAGTCTGGCTCTGTGCCACAGTTCAAGAAA (Continued)

Figure 30A

GTGGTCTTCCAGGAGTTCACTGATGGCTCATTCACCCAGCCCCTGTACAGAGGGGAACTGAATGAG
CACCTGGGACTCCTGGGACCATACATCAGGGCTGAGGTGGAAGACAACATCATGGTGACATTCAGA
AACCAGGCCTCCAGGCCCTACAGCTTCTACTCTTCCCTCATCAGCTATGAGGAAGACCAGAGACAA
GGGGCTGAGCCAAGAAAGAACTTTGTGAAACCCAATGAAACCAAGACCTACTTCTGGAAAGTCCAG
CACCACATGGCACCCACCAAGGATGAGTTTGACTGCAAGGCCTGGGCATACTTCTCTGATGTGGAC
CTGGAGAAAGATGTGCACTCTGGCCTGATTGGCCCACTCCTGGTCTGCCACACCAACACCCTGAAC
CCTGCACATGGAAGGCAAGTGACTGTGCAGGAGTTTGCCCTCTTCTTCACCATCTTTGATGAAACC
AAGTCATGGTACTTCACTGAGAACATGGAGAGAAACTGCAGAGCACCATGCAACATTCAGATGGAA
GACCCCACCTTCAAGGAGAACTACAGGTTCCATGCCATCAATGGCTACATCATGGACACCCTGCCT
GGGCTTGTCATGGCACAGGACCAGAGAATCAGATGGTACCTGCTTTCTATGGGATCCAATGAGAAC
ATTCACTCCATCCACTTCTCTGGGCATGTCTTCACTGTGAGAAAGAAGGAGGAATACAAGATGGCC
CTGTACAACCTCTACCCTGGGGTCTTTGAGACTGTGGAGATGCTGCCCTCCAAAGCTGGCATCTGG
AGGGTGGAATGCCTCATTGGGGAGCACCTGCATGCTGGCATGTCAACCCTGTTCCTGGTCTACAGC
AACAAGTGCCAGACACCCCTGGGAATGGCCTCTGGCCACATCAGGGACTTCCAGATCACTGCCTCT
GGCCAGTATGGCCAGTGGGCACCCAAACTGGCCAGGCTCCACTACTCTGGCTCCATCAATGCATGG
TCAACCAAGGAGCCATTCTCTTGGATCAAGGTGGACCTGCTGGCACCCATGATCATTCATGGCATC
AAGACACAGGGGGCAAGACAGAAATTCTCCTCTCTGTACATCTCACAGTTCATCATCATGTACTCT
CTGGATGGCAAGAAGTGGCAGACATACAGAGGCAACTCCACTGGCACCCTCATGGTCTTCTTTGGC
AATGTGGACAGCTCTGGCATCAAGCACAACATCTTCAACCCTCCCATCATTGCCAGATACATCAGG
CTGCACCCCACCCACTACTCAATCAGATCAACCCTCAGGATGGAACTGATGGGATGTGACCTGAAC
TCCTGCTCAATGCCCCTGGGAATGGAGAGCAAGGCCATTTCTGATGCCCAGATCACTGCATCCTCT
TACTTCACCAACATGTTTGCCACCTGGTCACCATCAAAAGCCAGGCTGCACCTCCAGGGAAGAAGC
AATGCCTGGAGACCCCAGGTCAACAACCCAAAGGAATGGCTGCAAGTGGACTTCCAGAAGACAATG
AAAGTCACTGGGGTGACAACCCAGGGGGTCAAGTCTCTGCTCACCTCAATGTATGTGAAGGAGTTC
CTGATCTCTTCCTCACAGGATGGCCACCAGTGGACACTCTTCTTCCAGAATGGCAAAGTCAAGGTG
TTCCAGGGCAACCAGGACTCTTTCACACCTGTGGTGAACTCACTGGACCCCCCCCTCCTGACAAGA
TACCTGAGAATTCACCCCCAGTCTTGGGTCCACCAGATTGCCCTGAGAATGGAAGTCCTGGGATGT
GAGGCACAAGACCTGTACTGA (SEQ ID NO:90)

ATGCAGATTGAGCTGTCCACCTGCTTCTTTCTGTGCCTGCTGAGATTCTGCTTCTCTGCCACCAGG
AGATACTACCTGGGGGCTGTGGAACTTTCTTGGGACTACATGCAGTCTGACCTGGGAGAGCTGCCT
GTGGATGCCAGGTTCCCACCCAGAGTGCCCAAGTCCTTCCCATTCAACACCTCTGTGGTCTACAAG
AAGACACTCTTTGTGGAATTCACTGACCACCTGTTCAACATTGCAAAACCCAGACCACCCTGGATG
GGACTCCTGGGACCCACCATTCAGGCTGAGGTGTATGACACTGTGGTCGTCACCCTCAAGAACATG
GCATCCCACCCTGTGTCTCTGCATGCTGTGGGAGTCTCATACTGGAAATCCTCTGAAGGGGCTGAG
TATGATGACCAGACATCCCAGAGAGAGAAAGAGGATGACAAGGTGTTCCCTGGGAAGTCTCACACC
TATGTGTGGCAAGTCCTCAAGGAGAATGGACCCACTGCATCTGACCCACCCTGCCTGACATACTCC
TACCTTTCTCATGTGGACCTGGTCAAGGACCTCAACTCTGGACTGATTGGGGCACTGCTGGTGTGC
AGGGAAGGATCCCTGGCCAAGGAGAAAACCCAGACACTGCACAAGTTCATTCTCCTGTTTGCTGTC
TTTGATGAGGGCAAGTCTTGGCACTCTGAAACAAAGAACTCCCTGATGCAAGACAGGGATGCTGCC
TCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGGACAACCCCTGAAGTGCAC
TCCATTTTCCTGGAGGGACACACCTTCCTGGTCAGGAACCACAGACAAGCCTCTCTGGAGATCTCT
CCCATCACCTTCCTCACTGCACAGACACTGCTGATGGACCTTGGACAGTTCCTGCTGTTCTGCCAC
ATCTCTTCCCACCAGCATGATGGCATGGAAGCCTATGTCAAGGTGGACTCATGCCCTGAGGAACCA
CAGCTCAGGATGAAGAACAATGAGGAGGCTGAGGACTATGATGATGACCTGACTGACTCTGAGATG
GATGTGGTCAGATTTGATGATGACAACTCTCCATCCTTCATTCAGATCAGGTCTGTGGCAAAGAAA
CACCCCAAGACATGGGTGCACTACATTGCTGCTGAGGAAGAGGACTGGGACTATGCACCACTGGTC
CTGGCCCCTGATGACAGGAGCTACAAGTCTCAGTACCTCAACAATGGCCCACAAAGAATTGGAAGA
AAGTACAAGAAAGTCAGATTCATGGCCTACACTGATGAAACCTTCAAGACAAGAGAAGCCATTCAG
CATGAGTCTGGCATTCTGGGACCACTCCTGTATGGGGAAGTGGGAGACACCCTGCTCATCATCTTC
AAGAACCAGGCCTCCAGGCCCTACAACATCTACCCACATGGCATCACTGATGTCAGGCCCCTGTAC
AGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGA
TACTACTCCTCTTTTGTGAACATGGAGAGAGACCTGGCATCTGGACTGATTGGACCACTGCTCATC
TGCTACAAGGAGTCTGTGGACCAGAGAGGCAACCAGATCATGTCTGACAAGAGAAATGTGATTCTG
TTCTCTGTCTTTGATGAGAACAGATCATGGTACCTGACTGAGAACATTCAGAGATTCCTGCCCAAC
CCTGCTGGGGTGCAACTGGAAGACCCTGAGTTCCAGGCAAGCAACATCATGCACTCCATCAATGGC
TATGTGTTTGACTCTCTCCAGCTTTCTGTCTGCCTGCATGAGGTGGCCTACTGGTACATTCTTTCT
ATTGGGGCACAAACTGACTTCCTTTCTGTCTTCTTCTCTGGATACACCTTCAAGCACAAGATGGTG
TATGAGGACACCCTGACACTCTTCCCATTCTCTGGGGAAACTGTGTTCATGAGCATGGAGAACCCT
GGACTGTGGATTCTGGGATGCCACAACTCTGACTTCAGAAACAGGGGAATGACTGCACTGCTCAAA
GTCTCCTCCTGTGACAAGAACACTGGGGACTACTATGAGGACTCTTATGAGGACATCTCTGCCTAC
CTGCTCAGCAAGAACAATACCACCTACGTGAACCGCTCCCTGTCTCAGAATCCACCTGTCCTGAAG
AGACACCAGAGAGAGATCACCAGGACAACCCTCCAGTCTGACCAGGAAGAGATTGACTATGATGAC
ACCATTTCTGTGGAGATGAAGAAGGAGGACTTTGACATCTATGATGAGGACGAGAACCAGTCTCCA
AGATCATTCCAGAAGAAGACAAGACACTACTTCATTGCTGCTGTGGAAAGACTGTGGGACTATGGC
ATGTCTTCCTCTCCCCATGTCCTCAGGAACAGGGCACAGTCTGGCTCTGTGCCACAGTTCAAGAAA (Continued)

Figure 31A

GTGGTCTTCCAGGAGTTCACTGATGGCTCATTCACCCAGCCCCTGTACAGAGGGGAACTGAATGAG
CACCTGGGACTCCTGGGACCATACATCAGGGCTGAGGTGGAAGACAACATCATGGTGACATTCAGA
AACCAGGCCTCCAGGCCCTACAGCTTCTACTCTTCCCTCATCAGCTATGAGGAAGACCAGAGACAA
GGGGCTGAGCCAAGAAAGAACTTTGTGAAACCCAATGAAACCAAGACCTACTTCTGGAAAGTCCAG
CACCACATGGCACCCACCAAGGATGAGTTTGACTGCAAGGCCTGGGCATACTTCTCTGATGTGGAC
CTGGAGAAAGATGTGCACTCTGGCCTGATTGGCCCACTCCTGGTCTGCCACACCAACACCCTGAAC
CCTGCACATGGAAGGCAAGTGACTGTGCAGGAGTTTGCCCTCTTCTTCACCATCTTTGATGAAACC
AAGTCATGGTACTTCACTGAGAACATGGAGAGAAACTGCAGAGCACCATGCAACATTCAGATGGAA
GACCCCACCTTCAAGGAGAACTACAGGTTCCATGCCATCAATGGCTACATCATGGACACCCTGCCT
GGGCTTGTCATGGCACAGGACCAGAGAATCAGATGGTACCTGCTTTCTATGGGATCCAATGAGAAC
ATTCACTCCATCCACTTCTCTGGGCATGTCTTCACTGTGAGAAAGAAGGAGGAATACAAGATGGCC
CTGTACAACCTCTACCCTGGGGTCTTTGAGACTGTGGAGATGCTGCCCTCCAAAGCTGGCATCTGG
AGGGTGGAATGCCTCATTGGGGAGCACCTGCATGCTGGCATGTCAACCCTGTTCCTGGTCTACAGC
AACAAGTGCCAGACACCCCTGGGAATGGCCTCTGGCCACATCAGGGACTTCCAGATCACTGCCTCT
GGCCAGTATGGCCAGTGGGCACCCAAACTGGCCAGGCTCCACTACTCTGGCTCCATCAATGCATGG
TCAACCAAGGAGCCATTCTCTTGGATCAAGGTGGACCTGCTGGCACCCATGATCATTCATGGCATC
AAGACACAGGGGGCAAGACAGAAATTCTCCTCTCTGTACATCTCACAGTTCATCATCATGTACTCT
CTGGATGGCAAGAAGTGGCAGACATACAGAGGCAACTCCACTGGCACCCTCATGGTCTTCTTTGGC
AATGTGGACAGCTCTGGCATCAAGCACAACATCTTCAACCCTCCCATCATTGCCAGATACATCAGG
CTGCACCCCACCCACTACTCAATCAGATCAACCCTCAGGATGGAACTGATGGGATGTGACCTGAAC
TCCTGCTCAATGCCCCTGGGAATGGAGAGCAAGGCCATTTCTGATGCCCAGATCACTGCATCCTCT
TACTTCACCAACATGTTTGCCACCTGGTCACCATCAAAAGCCAGGCTGCACCTCCAGGGAAGAAGC
AATGCCTGGAGACCCCAGGTCAACAACCCAAAGGAATGGCTGCAAGTGGACTTCCAGAAGACAATG
AAAGTCACTGGGGTGACAACCCAGGGGGTCAAGTCTCTGCTCACCTCAATGTATGTGAAGGAGTTC
CTGATCTCTTCCTCACAGGATGGCCACCAGTGGACACTCTTCTTCCAGAATGGCAAAGTCAAGGTG
TTCCAGGGCAACCAGGACTCTTTCACACCTGTGGTGAACTCACTGGACCCCCCCCTCCTGACAAGA
TACCTGAGAATTCACCCCCAGTCTTGGGTCCACCAGATTGCCCTGAGAATGGAAGTCCTGGGATGT
GAGGCACAAGACCTGTACTGA (SEQ ID NO:91)

ATGCAGATTGAGCTGTCCACCTGCTTCTTTCTGTGCCTGCTGAGATTCTGCTTCTCTGCCACCAGG
AGATACTACCTGGGGGCTGTGGAACTTTCTTGGGACTACATGCAGTCTGACCTGGGAGAGCTGCCT
GTGGATGCCAGGTTCCCACCCAGAGTGCCCAAGTCCTTCCCATTCAACACCTCTGTGGTCTACAAG
AAGACACTCTTTGTGGAATTCACTGACCACCTGTTCAACATTGCAAAACCCAGACCACCCTGGATG
GGACTCCTGGGACCCACCATTCAGGCTGAGGTGTATGACACTGTGGTCATCACCCTCAAGAACATG
GCATCCCACCCTGTGTCTCTGCATGCTGTGGGAGTCTCATACTGGAAAGCCTCTGAAGGGGCTGAG
TATGATGACCAGACATCCCAGAGAGAGAAAGAGGATGACAAGGTGTTCCCTGGGGGATCTCACACC
TATGTGTGGCAAGTCCTCAAGGAGAATGGACCCATGGCATCTGACCCACTCTGCCTGACATACTCC
TACCTTTCTCATGTGGACCTGGTCAAGGACCTCAACTCTGGACTGATTGGGGCACTGCTGGTGTGC
AGGGAAGGATCCCTGGCCAAGGAGAAAACCCAGACACTGCACAAGTTCATTCTCCTGTTTGCTGTC
TTTGATGAGGGCAAGTCTTGGCACTCTGAAACAAAGAACTCCCTGATGCAAGACAGGGATGCTGCC
TCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGGACAACCCCTGAAGTGCAC
TCCATTTTCCTGGAGGGACACACCTTCCTGGTCAGGAACCACAGACAAGCCTCTCTGGAGATCTCT
CCCATCACCTTCCTCACTGCACAGACACTGCTGATGGACCTTGGACAGTTCCTGCTGTTCTGCCAC
ATCTCTTCCCACCAGCATGATGGCATGGAAGCCTATGTCAAGGTGGACTCATGCCCTGAGGAACCA
CAGCTCAGGATGAAGAACAATGAGGAGGCTGAGGACTATGATGATGACCTGACTGACTCTGAGATG
GATGTGGTCAGATTTGATGATGACAACTCTCCATCCTTCATTCAGATCAGGTCTGTGGCAAAGAAA
CACCCCAAGACATGGGTGCACTACATTGCTGCTGAGGAAGAGGACTGGGACTATGCACCACTGGTC
CTGGCCCCTGATGACAGGAGCTACAAGTCTCAGTACCTCAACAATGGCCCACAAAGAATTGGAAGA
AAGTACAAGAAAGTCAGATTCATGGCCTACACTGATGAAACCTTCAAGACAAGAGAAGCCATTCAG
CATGAGTCTGGCATTCTGGGACCACTCCTGTATGGGGAAGTGGGAGACACCCTGCTCATCATCTTC
AAGAACCAGGCCTCCAGGCCCTACAACATCTACCCACATGGCATCACTGATGTCAGGCCCCTGTAC
AGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGA
TACTACTCCTCTTTTGTGAACATGGAGAGAGACCTGGCATCTGGACTGATTGGACCACTGCTCATC
TGCTACAAGGAGTCTGTGGACCAGAGAGGCAACCAGATCATGTCTGACAAGAGAAATGTGATTCTG
TTCTCTGTCTTTGATGAGAACAGATCATGGTACCTGACTGAGAACATTCAGAGATTCCTGCCCAAC
CCTGCTGGGGTGCAACTGGAAGACCCTGAGTTCCAGGCAAGCAACATCATGCACTCCATCAATGGC
TATGTGTTTGACTCTCTCCAGCTTTCTGTCTGCCTGCATGAGGTGGCCTACTGGTACATTCTTTCT
ATTGGGGCACAAACTGACTTCCTTTCTGTCTTCTTCTCTGGATACACCTTCAAGCACAAGATGGTG
TATGAGGACACCCTGACACTCTTCCCATTCTCTGGGGAAACTGTGTTCATGAGCATGGAGAACCCT
GGACTGTGGATTCTGGGATGCCACAACTCTGACTTCAGAAACAGGGGAATGACTGCACTGCTCAAA
GTCTCCTCCTGTGACAAGAACACTGGGGACTACTATGAGGACTCTTATGAGGACATCTCTGCCTAC
CTGCTCAGCAAGAACAATACCACCTACGTGAACCGCTCCCTGTCTCAGAATCCACCTGTCCTGAAG
AGACACCAGAGAGAGATCACCAGGACAACCCTCCAGTCTGACCAGGAAGAGATTGACTATGATGAC
ACCATTTCTGTGGAGATGAAGAAGGAGGACTTTGACATCTATGATGAGGACGAGAACCAGTCTCCA
AGATCATTCCAGAAGAAGACAAGACACTACTTCATTGCTGCTGTGGAAAGACTGTGGGACTATGGC
ATGTCTTCCTCTCCCCATGTCCTCAGGAACAGGGCACAGTCTGGCTCTGTGCCACAGTTCAAGAAA (Continued)

Figure 32A

GTGGTCTTCCAGGAGTTCACTGATGGCTCATTCACCCAGCCCCTGTACAGAGGGGAACTGAATGAG
CACCTGGGACTCCTGGGACCATACATCAGGGCTGAGGTGGAAGACAACATCATGGTGACATTCAGA
AACCAGGCCTCCAGGCCCTACAGCTTCTACTCTTCCCTCATCAGCTATGAGGAAGACCAGAGACAA
GGGGCTGAGCCAAGAAAGAACTTTGTGAAACCCAATGAAACCAAGACCTACTTCTGGAAAGTCCAG
CACCACATGGCACCCACCAAGGATGAGTTTGACTGCAAGGCCTGGGCATACTTCTCTGATGTGGAC
CTGGAGAAAGATGTGCACTCTGGCCTGATTGGCCCACTCCTGGTCTGCCACACCAACACCCTGAAC
CCTGCACATGGAAGGCAAGTGACTGTGCAGGAGTTTGCCCTCTTCTTCACCATCTTTGATGAAACC
AAGTCATGGTACTTCACTGAGAACATGGAGAGAAACTGCAGAGCACCATGCAACATTCAGATGGAA
GACCCCACCTTCAAGGAGAACTACAGGTTCCATGCCATCAATGGCTACATCATGGACACCCTGCCT
GGGCTTGTCATGGCACAGGACCAGAGAATCAGATGGTACCTGCTTTCTATGGGATCCAATGAGAAC
ATTCACTCCATCCACTTCTCTGGGCATGTCTTCACTGTGAGAAAGAAGGAGGAATACAAGATGGCC
CTGTACAACCTCTACCCTGGGGTCTTTGAGACTGTGGAGATGCTGCCCTCCAAAGCTGGCATCTGG
AGGGTGGAATGCCTCATTGGGGAGCACCTGCATGCTGGCATGTCAACCCTGTTCCTGGTCTACAGC
AACAAGTGCCAGACACCCCTGGGAATGGCCTCTGGCCACATCAGGGACTTCCAGATCACTGCCTCT
GGCCAGTATGGCCAGTGGGCACCCAAACTGGCCAGGCTCCACTACTCTGGCTCCATCAATGCATGG
TCAACCAAGGAGCCATTCTCTTGGATCAAGGTGGACCTGCTGGCACCCATGATCATTCATGGCATC
AAGACACAGGGGGCAAGACAGAAATTCTCCTCTCTGTACATCTCACAGTTCATCATCATGTACTCT
CTGGATGGCAAGAAGTGGCAGACATACAGAGGCAACTCCACTGGCACCCTCATGGTCTTCTTTGGC
AATGTGGACAGCTCTGGCATCAAGCACAACATCTTCAACCCTCCCATCATTGCCAGATACATCAGG
CTGCACCCCACCCACTACTCAATCAGATCAACCCTCAGGATGGAACTGATGGGATGTGACCTGAAC
TCCTGCTCAATGCCCCTGGGAATGGAGAGCAAGGCCATTTCTGATGCCCAGATCACTGCATCCTCT
TACTTCACCAACATGTTTGCCACCTGGTCACCATCAAAAGCCAGGCTGCACCTCCAGGGAAGAAGC
AATGCCTGGAGACCCCAGGTCAACAACCCAAAGGAATGGCTGCAAGTGGACTTCCAGAAGACAATG
AAAGTCACTGGGGTGACAACCCAGGGGGTCAAGTCTCTGCTCACCTCAATGTATGTGAAGGAGTTC
CTGATCTCTTCCTCACAGGATGGCCACCAGTGGACACTCTTCTTCCAGAATGGCAAAGTCAAGGTG
TTCCAGGGCAACCAGGACTCTTTCACACCTGTGGTGAACTCACTGGACCCCCCCCTCCTGACAAGA
TACCTGAGAATTCACCCCCAGTCTTGGGTCCACCAGATTGCCCTGAGAATGGAAGTCCTGGGATGT
GAGGCACAAGACCTGTACTGA (SEQ ID NO:92)

ATGCAGATTGAGCTGTCCACCTGCTTCTTTCTGTGCCTGCTGAGATTCTGCTTCTCTGCCACCAGG
AGATACTACCTGGGGGCTGTGGAACTTTCTTGGGACTACATGCAGTCTGACCTGGGAGAGCTGCCT
GTGGATGCCAGGTTCCCACCCAGAGTGCCCAAGTCCTTCCCATTCAACACCTCTGTGGTCTACAAG
AAGACACTCTTTGTGGAATTCACTGACCACCTGTTCAACATTGCAAAACCCAGACCACCCTGGATG
GGACTCCTGGGACCCACCATTCAGGCTGAGGTGTATGACACTGTGGTCGTCACCCTCAAGAACATG
GCATCCCACCCTGTGTCTCTGCATGCTGTGGGAGTCTCATACTGGAAATCCTCTGAAGGGGCTGAG
TATGATGACCAGACATCCCAGAGAGAGAAAGAGGATGACAAGGTGTTCCCTGGGAAGTCTCACACC
TATGTGTGGCAAGTCCTCAAGGAGAATGGACCCACTGCATCTGACCCACCCTGCCTGACATACTCC
TACCTTTCTCATGTGGACCTGGTCAAGGACCTCAACTCTGGACTGATTGGGGCACTGCTGGTGTGC
AGGGAAGGATCCCTGGCCAAGGAGAAAACCCAGACACTGCACAAGTTCATTCTCCTGTTTGCTGTC
TTTGATGAGGGCAAGTCTTGGCACTCTGAAACAAAGAACTCCCTGATGCAAGACAGGGATGCTGCC
TCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGGACAACCCCTGAAGTGCAC
TCCATTTTCCTGGAGGGACACACCTTCCTGGTCAGGAACCACAGACAAGCCTCTCTGGAGATCTCT
CCCATCACCTTCCTCACTGCACAGACACTGCTGATGGACCTTGGACAGTTCCTGCTGTTCTGCCAC
ATCTCTTCCCACCAGCATGATGGCATGGAAGCCTATGTCAAGGTGGACTCATGCCCTGAGGAACCA
CAGCTCAGGATGAAGAACAATGAGGAGGCTGAGGACTATGATGATGACCTGACTGACTCTGAGATG
GATGTGGTCAGATTTGATGATGACAACTCTCCATCCTTCATTCAGATCAGGTCTGTGGCAAAGAAA
CACCCCAAGACATGGGTGCACTACATTGCTGCTGAGGAAGAGGACTGGGACTATGCACCACTGGTC
CTGGCCCCTGATGACAGGAGCTACAAGTCTCAGTACCTCAACAATGGCCCACAAAGAATTGGAAGA
AAGTACAAGAAAGTCAGATTCATGGCCTACACTGATGAAACCTTCAAGACAAGAGAAGCCATTCAG
CATGAGTCTGGCATTCTGGGACCACTCCTGTATGGGGAAGTGGGAGACACCCTGCTCATCATCTTC
AAGAACCAGGCCTCCAGGCCCTACAACATCTACCCACATGGCATCACTGATGTCAGGCCCCTGTAC
AGCAGGAGACTGCCAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGA
TACTACTCCTCTTTTGTGAACATGGAGAGAGACCTGGCATCTGGACTGATTGGACCACTGCTCATC
TGCTACAAGGAGTCTGTGGACCAGAGAGGCAACCAGATCATGTCTGACAAGAGAAATGTGATTCTG
TTCTCTGTCTTTGATGAGAACAGATCATGGTACCTGACTGAGAACATTCAGAGATTCCTGCCCAAC
CCTGCTGGGGTGCAACTGGAAGACCCTGAGTTCCAGGCAAGCAACATCATGCACTCCATCAATGGC
TATGTGTTTGACTCTCTCCAGCTTTCTGTCTGCCTGCATGAGGTGGCCTACTGGTACATTCTTTCT
ATTGGGGCACAAACTGACTTCCTTTCTGTCTTCTTCTCTGGATACACCTTCAAGCACAAGATGGTG
TATGAGGACACCCTGACACTCTTCCCATTCTCTGGGGAAACTGTGTTCATGAGCATGGAGAACCCT
GGACTGTGGATTCTGGGATGCCACAACTCTGACTTCAGAAACAGGGGAATGACTGCACTGCTCAAA
GTCTCCTCCTGTGACAAGAACACTGGGGACTACTATGAGGACTCTTATGAGGACATCTCTGCCTAC
CTGCTCAGCAAGAACAATGCCATTGAGCCCAGAAGCTTCTCTCAGAATCCACCTGTCCTGAAGAGA
CACCAGAGAGAGATCACCAGGACAACCCTCCAGTCTGACCAGGAAGAGATTGACTATGATGACACC
ATTTCTGTGGAGATGAAGAAGGAGGACTTTGACATCTATGATGAGGACGAGAACCAGTCTCCAAGA
TCATTCCAGAAGAAGACAAGACACTACTTCATTGCTGCTGTGGAAAGACTGTGGGACTATGGCATG
TCTTCCTCTCCCCATGTCCTCAGGAACAGGGCACAGTCTGGCTCTGTGCCACAGTTCAAGAAAGTG (Continued)

Figure 33A

GTCTTCCAGGAGTTCACTGATGGCTCATTCACCCAGCCCCTGTACAGAGGGGAACTGAATGAGCAC
CTGGGACTCCTGGGACCATACATCAGGGCTGAGGTGGAAGACAACATCATGGTGACATTCAGAAAC
CAGGCCTCCAGGCCCTACAGCTTCTACTCTTCCCTCATCAGCTATGAGGAAGACCAGAGACAAGGG
GCTGAGCCAAGAAAGAACTTTGTGAAACCCAATGAAACCAAGACCTACTTCTGGAAAGTCCAGCAC
CACATGGCACCCACCAAGGATGAGTTTGACTGCAAGGCCTGGGCATACTTCTCTGATGTGGACCTG
GAGAAAGATGTGCACTCTGGCCTGATTGGCCCACTCCTGGTCTGCCACACCAACACCCTGAACCCT
GCACATGGAAGGCAAGTGACTGTGCAGGAGTTTGCCCTCTTCTTCACCATCTTTGATGAAACCAAG
TCATGGTACTTCACTGAGAACATGGAGAGAAACTGCAGAGCACCATGCAACATTCAGATGGAAGAC
CCCACCTTCAAGGAGAACTACAGGTTCCATGCCATCAATGGCTACATCATGGACACCCTGCCTGGG
CTTGTCATGGCACAGGACCAGAGAATCAGATGGTACCTGCTTTCTATGGGATCCAATGAGAACATT
CACTCCATCCACTTCTCTGGGCATGTCTTCACTGTGAGAAAGAAGGAGGAATACAAGATGGCCCTG
TACAACCTCTACCCTGGGGTCTTTGAGACTGTGGAGATGCTGCCCTCCAAAGCTGGCATCTGGAGG
GTGGAATGCCTCATTGGGGAGCACCTGCATGCTGGCATGTCAACCCTGTTCCTGGTCTACAGCAAC
AAGTGCCAGACACCCCTGGGAATGGCCTCTGGCCACATCAGGGACTTCCAGATCACTGCCTCTGGC
CAGTATGGCCAGTGGGCACCCAAACTGGCCAGGCTCCACTACTCTGGCTCCATCAATGCATGGTCA
ACCAAGGAGCCATTCTCTTGGATCAAGGTGGACCTGCTGGCACCCATGATCATTCATGGCATCAAG
ACACAGGGGGCAAGACAGAAATTCTCCTCTCTGTACATCTCACAGTTCATCATCATGTACTCTCTG
GATGGCAAGAAGTGGCAGACATACAGAGGCAACTCCACTGGCACCCTCATGGTCTTCTTTGGCAAT
GTGGACAGCTCTGGCATCAAGCACAACATCTTCAACCCTCCCATCATTGCCAGATACATCAGGCTG
CACCCCACCCACTACTCAATCAGATCAACCCTCAGGATGGAACTGATGGGATGTGACCTGAACTCC
TGCTCAATGCCCCTGGGAATGGAGAGCAAGGCCATTTCTGATGCCCAGATCACTGCATCCTCTTAC
TTCACCAACATGTTTGCCACCTGGTCACCATCAAAAGCCAGGCTGCACCTCCAGGGAAGAAGCAAT
GCCTGGAGACCCCAGGTCAACAACCCAAAGGAATGGCTGCAAGTGGACTTCCAGAAGACAATGAAA
GTCACTGGGGTGACAACCCAGGGGGTCAAGTCTCTGCTCACCTCAATGTATGTGAAGGAGTTCCTG
ATCTCTTCCTCACAGGATGGCCACCAGTGGACACTCTTCTTCCAGAATGGCAAAGTCAAGGTGTTC
CAGGGCAACCAGGACTCTTTCACACCTGTGGTGAACTCACTGGACCCCCCCCTCCTGACAAGATAC
CTGAGAATTCACCCCCAGTCTTGGGTCCACCAGATTGCCCTGAGAATGGAAGTCCTGGGATGTGAG
GCACAAGACCTGTACTGA (SEQ ID NO:93)

ATGCAGATTGAGCTGAGCACCTGCTTCTTCCTGTGCCTGCTGAGGTTCTGCTTCTCTGCCACCAGG
AGATACTACCTGGGGGCTGTGGAGCTTTCTTGGGACTACATGCAGTCTGACCTGGGGGAGCTGCCT
GTGGATGCCAGGTTCCCACCCAGAGTGCCCAAATCCTTCCCATTCAACACCTCTGTGGTCTACAAG
AAGACCCTCTTTGTGGAGTTCACTGACCACCTGTTCAACATTGCCAAACCCAGGCCACCCTGGATG
GGACTCCTGGGACCCACCATTCAGGCTGAGGTGTATGACACTGTGGTCGTCACCCTCAAGAACATG
GCCTCCCACCCTGTGAGCCTGCATGCTGTGGGGGTCAGCTACTGGAAGTCCTCTGAGGGGGCTGAG
TATGATGACCAGACCTCCCAGAGGGAGAAGGAGGATGACAAAGTGTTCCCTGGGAAGAGCCACACC
TATGTGTGGCAGGTCCTCAAGGAGAATGGCCCCACTGCCTCTGACCCACCCTGCCTGACCTACTCC
TACCTTTCTCATGTGGACCTGGTCAAGGACCTCAACTCTGGACTGATTGGGGCCCTGCTGGTGTGC
AGGGAGGGCTCCCTGGCCAAAGAGAAGACCCAGACCCTGCACAAGTTCATTCTCCTGTTTGCTGTC
TTTGATGAGGGCAAGAGCTGGCACTCTGAAACCAAGAACTCCCTGATGCAGGACAGGGATGCTGCC
TCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGGACAACCCCTGAGGTGCAC
TCCATTTTCCTGGAGGGCCACACCTTCCTGGTCAGGAACCACAGACAGGCCAGCCTGGAGATCAGC
CCCATCACCTTCCTCACTGCCCAGACCCTGCTGATGGACCTCGGACAGTTCCTGCTGTTCTGCCAC
ATCAGCTCCCACCAGCATGATGGCATGGAGGCCTATGTCAAGGTGGACAGCTGCCCTGAGGAGCCA
CAGCTCAGGATGAAGAACAATGAGGAGGCTGAGGACTATGATGATGACCTGACTGACTCTGAGATG
GATGTGGTCCGCTTTGATGATGACAACAGCCCATCCTTCATTCAGATCAGGTCTGTGGCCAAGAAA
CACCCCAAGACCTGGGTGCACTACATTGCTGCTGAGGAGGAGGACTGGGACTATGCCCCACTGGTC
CTGGCCCCTGATGACAGGAGCTACAAGAGCCAGTACCTCAACAATGGCCCACAGAGGATTGGACGC
AAGTACAAGAAAGTCAGGTTCATGGCCTACACTGATGAAACCTTCAAGACCAGGGAGGCCATTCAG
CATGAGTCTGGCATCCTGGGCCCACTCCTGTATGGGGAGGTGGGGGACACCCTGCTCATCATCTTC
AAGAACCAGGCCTCCAGGCCCTACAACATCTACCCACATGGCATCACTGATGTCAGGCCCCTGTAC
AGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGA
TACTACTCCAGCTTTGTGAACATGGAGAGGGACCTGGCCTCTGGCCTGATTGGCCCACTGCTCATC
TGCTACAAGGAGTCTGTGGACCAGAGGGGAAACCAGATCATGTCTGACAAGAGGAATGTGATTCTG
TTCTCTGTCTTTGATGAGAACAGGAGCTGGTACCTGACTGAGAACATTCAGCGCTTCCTGCCCAAC
CCTGCTGGGGTGCAGCTGGAGGACCCTGAGTTCCAGGCCAGCAACATCATGCACTCCATCAATGGC
TATGTGTTTGACAGCCTCCAGCTTTCTGTCTGCCTGCATGAGGTGGCCTACTGGTACATTCTTTCT
ATTGGGGCCCAGACTGACTTCCTTTCTGTCTTCTTCTCTGGCTACACCTTCAAACACAAGATGGTG
TATGAGGACACCCTGACCCTCTTCCCATTCTCTGGGGAGACTGTGTTCATGAGCATGGAGAACCCT
GGCCTGTGGATTCTGGGATGCCACAACTCTGACTTCCGCAACAGGGGCATGACTGCCCTGCTCAAA
GTCTCCTCCTGTGACAAGAACACTGGGGACTACTATGAGGACAGCTATGAGGACATCTCTGCCTAC
CTGCTCAGCAAGAACAATGCCATTGAGCCCAGGAGCTTCAGCCAGAATCCACCTGTCCTGAAACGC
CACCAGAGGGAGATCACCAGGACCACCCTCCAGTCTGACCAGGAGGAGATTGACTATGATGACACC
ATTTCTGTGGAGATGAAGAAAGAGGACTTTGACATCTATGACGAGGACGAGAACCAGAGCCCAAGG
AGCTTCCAGAAGAAGACCAGGCACTACTTCATTGCTGCTGTGGAGCGCCTGTGGGACTATGGCATG
AGCTCCAGCCCCCATGTCCTCAGGAACAGGGCCCAGTCTGGCTCTGTGCCACAGTTCAAGAAAGTG (Continued)

Figure 34A

GTCTTCCAAGAGTTCACTGATGGCAGCTTCACCCAGCCCCTGTACAGAGGGGAGCTGAATGAGCAC
CTGGGACTCCTGGGCCCATACATCAGGGCTGAGGTGGAGGACAACATCATGGTGACCTTCCGCAAC
CAGGCCTCCAGGCCCTACAGCTTCTACAGCTCCCTCATCAGCTATGAGGAGGACCAGAGGCAGGGG
GCTGAGCCACGCAAGAACTTTGTGAAACCCAATGAAACCAAGACCTACTTCTGGAAAGTCCAGCAC
CACATGGCCCCCACCAAGGATGAGTTTGACTGCAAGGCCTGGGCCTACTTCTCTGATGTGGACCTG
GAGAAGGATGTGCACTCTGGCCTGATTGGCCCACTCCTGGTCTGCCACACCAACACCCTGAACCCT
GCCCATGGAAGGCAAGTGACTGTGCAGGAGTTTGCCCTCTTCTTCACCATCTTTGATGAAACCAAG
AGCTGGTACTTCACTGAGAACATGGAGCGCAACTGCAGGGCCCCATGCAACATTCAGATGGAGGAC
CCCACCTTCAAAGAGAACTACCGCTTCCATGCCATCAATGGCTACATCATGGACACCCTGCCTGGG
CTTGTCATGGCCCAGGACCAGAGGATCAGGTGGTACCTGCTTTCTATGGGCTCCAATGAGAACATT
CACTCCATCCACTTCTCTGGGCATGTCTTCACTGTGCGCAAGAAGGAGGAGTACAAGATGGCCCTG
TACAACCTCTACCCTGGGGTCTTTGAGACTGTGGAGATGCTGCCCTCCAAAGCTGGCATCTGGAGG
GTGGAGTGCCTCATTGGGGAGCACCTGCATGCTGGCATGAGCACCCTGTTCCTGGTCTACAGCAAC
AAGTGCCAGACCCCCCTGGGAATGGCCTCTGGCCACATCAGGGACTTCCAGATCACTGCCTCTGGC
CAGTATGGCCAGTGGGCCCCCAAGCTGGCCAGGCTCCACTACTCTGGATCCATCAATGCCTGGAGC
ACCAAGGAGCCATTCAGCTGGATCAAAGTGGACCTGCTGGCCCCCATGATCATCCATGGCATCAAG
ACCCAGGGGGCCAGGCAGAAGTTCTCCAGCCTGTACATCAGCCAGTTCATCATCATGTACAGCCTG
GATGGCAAGAAATGGCAGACCTACAGAGGCAACTCCACTGGAACACTCATGGTCTTCTTTGGCAAT
GTGGACAGCTCTGGCATCAAGCACAACATCTTCAACCCCCCAATCATCGCCAGATACATCAGGCTG
CACCCCACCCACTACAGCATCCGCAGCACCCTCAGGATGGAGCTGATGGGCTGTGACCTGAACTCC
TGCAGCATGCCCCTGGGCATGGAGAGCAAGGCCATTTCTGATGCCCAGATCACTGCCTCCAGCTAC
TTCACCAACATGTTTGCCACCTGGAGCCCAAGCAAGGCCAGGCTGCACCTCCAGGGAAGGAGCAAT
GCCTGGAGGCCCCAGGTCAACAACCCAAAGGAGTGGCTGCAGGTGGACTTCCAGAAGACCATGAAG
GTCACTGGGGTGACCACCCAGGGGGTCAAGAGCCTGCTCACCAGCATGTATGTGAAGGAGTTCCTG
ATCAGCTCCAGCCAGGATGGCCACCAGTGGACCCTCTTCTTCCAGAATGGCAAGGTCAAGGTGTTC
CAGGGCAACCAGGACAGCTTCACCCCTGTGGTGAACAGCCTGGACCCCCCCCTCCTGACCAGATAC
CTGAGGATTCACCCCCAGAGCTGGGTCCACCAGATTGCCCTGAGGATGGAGGTCCTGGGATGTGAG
GCCCAGGACCTGTACTGA (SEQ ID NO:94)

ATGCAGATTGAGCTGAGCACCTGCTTCTTCCTGTGCCTGCTGAGGTTCTGCTTCTCTGCCACCAGG
AGATACTACCTGGGGGCTGTGGAGCTTTCTTGGGACTACATGCAGTCTGACCTGGGGGAGCTGCCT
GTGGATGCCAGGTTCCCACCCAGAGTGCCCAAATCCTTCCCATTCAACACCTCTGTGGTCTACAAG
AAGACCCTCTTTGTGGAGTTCACTGACCACCTGTTCAACATTGCCAAACCCAGGCCACCCTGGATG
GGACTCCTGGGACCCACCATTCAGGCTGAGGTGTATGACACTGTGGTCATCACCCTCAAGAACATG
GCCTCCCACCCTGTGAGCCTGCATGCTGTGGGGGTCAGCTACTGGAAGGCCTCTGAGGGGGCTGAG
TATGATGACCAGACCTCCCAGAGGGAGAAGGAGGATGACAAAGTGTTCCCTGGGGGCAGCCACACC
TATGTGTGGCAGGTCCTCAAGGAGAATGGCCCCATGGCCTCTGACCCACTCTGCCTGACCTACTCC
TACCTTTCTCATGTGGACCTGGTCAAGGACCTCAACTCTGGACTGATTGGGGCCCTGCTGGTGTGC
AGGGAGGGCTCCCTGGCCAAAGAGAAGACCCAGACCCTGCACAAGTTCATTCTCCTGTTTGCTGTC
TTTGATGAGGGCAAGAGCTGGCACTCTGAAACCAAGAACTCCCTGATGCAGGACAGGGATGCTGCC
TCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGGACAACCCCTGAGGTGCAC
TCCATTTTCCTGGAGGGCCACACCTTCCTGGTCAGGAACCACAGACAGGCCAGCCTGGAGATCAGC
CCCATCACCTTCCTCACTGCCCAGACCCTGCTGATGGACCTCGGACAGTTCCTGCTGTTCTGCCAC
ATCAGCTCCCACCAGCATGATGGCATGGAGGCCTATGTCAAGGTGGACAGCTGCCCTGAGGAGCCA
CAGCTCAGGATGAAGAACAATGAGGAGGCTGAGGACTATGATGATGACCTGACTGACTCTGAGATG
GATGTGGTCCGCTTTGATGATGACAACAGCCCATCCTTCATTCAGATCAGGTCTGTGGCCAAGAAA
CACCCCAAGACCTGGGTGCACTACATTGCTGCTGAGGAGGAGGACTGGGACTATGCCCCACTGGTC
CTGGCCCCTGATGACAGGAGCTACAAGAGCCAGTACCTCAACAATGGCCCACAGAGGATTGGACGC
AAGTACAAGAAAGTCAGGTTCATGGCCTACACTGATGAAACCTTCAAGACCAGGGAGGCCATTCAG
CATGAGTCTGGCATCCTGGGCCCACTCCTGTATGGGGAGGTGGGGGACACCCTGCTCATCATCTTC
AAGAACCAGGCCTCCAGGCCCTACAACATCTACCCACATGGCATCACTGATGTCAGGCCCCTGTAC
AGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGA
TACTACTCCAGCTTTGTGAACATGGAGAGGGACCTGGCCTCTGGCCTGATTGGCCCACTGCTCATC
TGCTACAAGGAGTCTGTGGACCAGAGGGGAAACCAGATCATGTCTGACAAGAGGAATGTGATTCTG
TTCTCTGTCTTTGATGAGAACAGGAGCTGGTACCTGACTGAGAACATTCAGCGCTTCCTGCCCAAC
CCTGCTGGGGTGCAGCTGGAGGACCCTGAGTTCCAGGCCAGCAACATCATGCACTCCATCAATGGC
TATGTGTTTGACAGCCTCCAGCTTTCTGTCTGCCTGCATGAGGTGGCCTACTGGTACATTCTTTCT
ATTGGGGCCCAGACTGACTTCCTTTCTGTCTTCTTCTCTGGCTACACCTTCAAACACAAGATGGTG
TATGAGGACACCCTGACCCTCTTCCCATTCTCTGGGGAGACTGTGTTCATGAGCATGGAGAACCCT
GGCCTGTGGATTCTGGGATGCCACAACTCTGACTTCCGCAACAGGGGCATGACTGCCCTGCTCAAA
GTCTCCTCCTGTGACAAGAACACTGGGGACTACTATGAGGACAGCTATGAGGACATCTCTGCCTAC
CTGCTCAGCAAGAACAATACCACCTACGTGAACCGCTCCCTGAGCCAGAATCCACCTGTCCTGAAA
CGCCACCAGAGGGAGATCACCAGGACCACCCTCCAGTCTGACCAGGAGGAGATTGACTATGATGAC
ACCATTTCTGTGGAGATGAAGAAAGAGGACTTTGACATCTATGACGAGGACGAGAACCAGAGCCCA
AGGAGCTTCCAGAAGAAGACCAGGCACTACTTCATTGCTGCTGTGGAGCGCCTGTGGGACTATGGC
ATGAGCTCCAGCCCCCATGTCCTCAGGAACAGGGCCCAGTCTGGCTCTGTGCCACAGTTCAAGAAA (Continued)

Figure 35A

GTGGTCTTCCAAGAGTTCACTGATGGCAGCTTCACCCAGCCCCTGTACAGAGGGGAGCTGAATGAG
CACCTGGGACTCCTGGGCCCATACATCAGGGCTGAGGTGGAGGACAACATCATGGTGACCTTCCGC
AACCAGGCCTCCAGGCCCTACAGCTTCTACAGCTCCCTCATCAGCTATGAGGAGGACCAGAGGCAG
GGGGCTGAGCCACGCAAGAACTTTGTGAAACCCAATGAAACCAAGACCTACTTCTGGAAAGTCCAG
CACCACATGGCCCCCACCAAGGATGAGTTTGACTGCAAGGCCTGGGCCTACTTCTCTGATGTGGAC
CTGGAGAAGGATGTGCACTCTGGCCTGATTGGCCCACTCCTGGTCTGCCACACCAACACCCTGAAC
CCTGCCCATGGAAGGCAAGTGACTGTGCAGGAGTTTGCCCTCTTCTTCACCATCTTTGATGAAACC
AAGAGCTGGTACTTCACTGAGAACATGGAGCGCAACTGCAGGGCCCCATGCAACATTCAGATGGAG
GACCCCACCTTCAAAGAGAACTACCGCTTCCATGCCATCAATGGCTACATCATGGACACCCTGCCT
GGGCTTGTCATGGCCCAGGACCAGAGGATCAGGTGGTACCTGCTTTCTATGGGCTCCAATGAGAAC
ATTCACTCCATCCACTTCTCTGGGCATGTCTTCACTGTGCGCAAGAAGGAGGAGTACAAGATGGCC
CTGTACAACCTCTACCCTGGGGTCTTTGAGACTGTGGAGATGCTGCCCTCCAAAGCTGGCATCTGG
AGGGTGGAGTGCCTCATTGGGGAGCACCTGCATGCTGGCATGAGCACCCTGTTCCTGGTCTACAGC
AACAAGTGCCAGACCCCCCTGGGAATGGCCTCTGGCCACATCAGGGACTTCCAGATCACTGCCTCT
GGCCAGTATGGCCAGTGGGCCCCCAAGCTGGCCAGGCTCCACTACTCTGGATCCATCAATGCCTGG
AGCACCAAGGAGCCATTCAGCTGGATCAAAGTGGACCTGCTGGCCCCCATGATCATCCATGGCATC
AAGACCCAGGGGGCCAGGCAGAAGTTCTCCAGCCTGTACATCAGCCAGTTCATCATCATGTACAGC
CTGGATGGCAAGAAATGGCAGACCTACAGAGGCAACTCCACTGGAACACTCATGGTCTTCTTTGGC
AATGTGGACAGCTCTGGCATCAAGCACAACATCTTCAACCCCCCAATCATCGCCAGATACATCAGG
CTGCACCCCACCCACTACAGCATCCGCAGCACCCTCAGGATGGAGCTGATGGGCTGTGACCTGAAC
TCCTGCAGCATGCCCCTGGGCATGGAGAGCAAGGCCATTTCTGATGCCCAGATCACTGCCTCCAGC
TACTTCACCAACATGTTTGCCACCTGGAGCCCAAGCAAGGCCAGGCTGCACCTCCAGGGAAGGAGC
AATGCCTGGAGGCCCCAGGTCAACAACCCAAAGGAGTGGCTGCAGGTGGACTTCCAGAAGACCATG
AAGGTCACTGGGGTGACCACCCAGGGGGTCAAGAGCCTGCTCACCAGCATGTATGTGAAGGAGTTC
CTGATCAGCTCCAGCCAGGATGGCCACCAGTGGACCCTCTTCTTCCAGAATGGCAAGGTCAAGGTG
TTCCAGGGCAACCAGGACAGCTTCACCCCTGTGGTGAACAGCCTGGACCCCCCCCTCCTGACCAGA
TACCTGAGGATTCACCCCCAGAGCTGGGTCCACCAGATTGCCCTGAGGATGGAGGTCCTGGGATGT
GAGGCCCAGGACCTGTACTGA (SEQ ID NO:95)

ATGCAGATTGAGCTGAGCACCTGCTTCTTCCTGTGCCTGCTGAGGTTCTGCTTCTCTGCCACCAGG
AGATACTACCTGGGGGCTGTGGAGCTTTCTTGGGACTACATGCAGTCTGACCTGGGGGAGCTGCCT
GTGGATGCCAGGTTCCCACCCAGAGTGCCCAAATCCTTCCCATTCAACACCTCTGTGGTCTACAAG
AAGACCCTCTTTGTGGAGTTCACTGACCACCTGTTCAACATTGCCAAACCCAGGCCACCCTGGATG
GGACTCCTGGGACCCACCATTCAGGCTGAGGTGTATGACACTGTGGTCGTCACCCTCAAGAACATG
GCCTCCCACCCTGTGAGCCTGCATGCTGTGGGGGTCAGCTACTGGAAGTCCTCTGAGGGGGCTGAG
TATGATGACCAGACCTCCCAGAGGGAGAAGGAGGATGACAAAGTGTTCCCTGGGAAGAGCCACACC
TATGTGTGGCAGGTCCTCAAGGAGAATGGCCCCACTGCCTCTGACCCACCCTGCCTGACCTACTCC
TACCTTTCTCATGTGGACCTGGTCAAGGACCTCAACTCTGGACTGATTGGGGCCCTGCTGGTGTGC
AGGGAGGGCTCCCTGGCCAAAGAGAAGACCCAGACCCTGCACAAGTTCATTCTCCTGTTTGCTGTC
TTTGATGAGGGCAAGAGCTGGCACTCTGAAACCAAGAACTCCCTGATGCAGGACAGGGATGCTGCC
TCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGGACAACCCCTGAGGTGCAC
TCCATTTTCCTGGAGGGCCACACCTTCCTGGTCAGGAACCACAGACAGGCCAGCCTGGAGATCAGC
CCCATCACCTTCCTCACTGCCCAGACCCTGCTGATGGACCTCGGACAGTTCCTGCTGTTCTGCCAC
ATCAGCTCCCACCAGCATGATGGCATGGAGGCCTATGTCAAGGTGGACAGCTGCCCTGAGGAGCCA
CAGCTCAGGATGAAGAACAATGAGGAGGCTGAGGACTATGATGATGACCTGACTGACTCTGAGATG
GATGTGGTCCGCTTTGATGATGACAACAGCCCATCCTTCATTCAGATCAGGTCTGTGGCCAAGAAA
CACCCCAAGACCTGGGTGCACTACATTGCTGCTGAGGAGGAGGACTGGGACTATGCCCCACTGGTC
CTGGCCCCTGATGACAGGAGCTACAAGAGCCAGTACCTCAACAATGGCCCACAGAGGATTGGACGC
AAGTACAAGAAAGTCAGGTTCATGGCCTACACTGATGAAACCTTCAAGACCAGGGAGGCCATTCAG
CATGAGTCTGGCATCCTGGGCCCACTCCTGTATGGGGAGGTGGGGGACACCCTGCTCATCATCTTC
AAGAACCAGGCCTCCAGGCCCTACAACATCTACCCACATGGCATCACTGATGTCAGGCCCCTGTAC
AGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGA
TACTACTCCAGCTTTGTGAACATGGAGAGGGACCTGGCCTCTGGCCTGATTGGCCCACTGCTCATC
TGCTACAAGGAGTCTGTGGACCAGAGGGGAAACCAGATCATGTCTGACAAGAGGAATGTGATTCTG
TTCTCTGTCTTTGATGAGAACAGGAGCTGGTACCTGACTGAGAACATTCAGCGCTTCCTGCCCAAC
CCTGCTGGGGTGCAGCTGGAGGACCCTGAGTTCCAGGCCAGCAACATCATGCACTCCATCAATGGC
TATGTGTTTGACAGCCTCCAGCTTTCTGTCTGCCTGCATGAGGTGGCCTACTGGTACATTCTTTCT
ATTGGGGCCCAGACTGACTTCCTTTCTGTCTTCTTCTCTGGCTACACCTTCAAACACAAGATGGTG
TATGAGGACACCCTGACCCTCTTCCCATTCTCTGGGGAGACTGTGTTCATGAGCATGGAGAACCCT
GGCCTGTGGATTCTGGGATGCCACAACTCTGACTTCCGCAACAGGGGCATGACTGCCCTGCTCAAA
GTCTCCTCCTGTGACAAGAACACTGGGGACTACTATGAGGACAGCTATGAGGACATCTCTGCCTAC
CTGCTCAGCAAGAACAATACCACCTACGTGAACCGCTCCCTGAGCCAGAATCCACCTGTCCTGAAA
CGCCACCAGAGGGAGATCACCAGGACCACCCTCCAGTCTGACCAGGAGGAGATTGACTATGATGAC
ACCATTTCTGTGGAGATGAAGAAAGAGGACTTTGACATCTATGACGAGGACGAGAACCAGAGCCCA
AGGAGCTTCCAGAAGAAGACCAGGCACTACTTCATTGCTGCTGTGGAGCGCCTGTGGGACTATGGC
ATGAGCTCCAGCCCCCATGTCCTCAGGAACAGGGCCCAGTCTGGCTCTGTGCCACAGTTCAAGAAA (Continued)

Figure 36A

GTGGTCTTCCAAGAGTTCACTGATGGCAGCTTCACCCAGCCCCTGTACAGAGGGGAGCTGAATGAG
CACCTGGGACTCCTGGGCCCATACATCAGGGCTGAGGTGGAGGACAACATCATGGTGACCTTCCGC
AACCAGGCCTCCAGGCCCTACAGCTTCTACAGCTCCCTCATCAGCTATGAGGAGGACCAGAGGCAG
GGGGCTGAGCCACGCAAGAACTTTGTGAAACCCAATGAAACCAAGACCTACTTCTGGAAAGTCCAG
CACCACATGGCCCCCACCAAGGATGAGTTTGACTGCAAGGCCTGGGCCTACTTCTCTGATGTGGAC
CTGGAGAAGGATGTGCACTCTGGCCTGATTGGCCCACTCCTGGTCTGCCACACCAACACCCTGAAC
CCTGCCCATGGAAGGCAAGTGACTGTGCAGGAGTTTGCCCTCTTCTTCACCATCTTTGATGAAACC
AAGAGCTGGTACTTCACTGAGAACATGGAGCGCAACTGCAGGGCCCCATGCAACATTCAGATGGAG
GACCCCACCTTCAAAGAGAACTACCGCTTCCATGCCATCAATGGCTACATCATGGACACCCTGCCT
GGGCTTGTCATGGCCCAGGACCAGAGGATCAGGTGGTACCTGCTTTCTATGGGCTCCAATGAGAAC
ATTCACTCCATCCACTTCTCTGGGCATGTCTTCACTGTGCGCAAGAAGGAGGAGTACAAGATGGCC
CTGTACAACCTCTACCCTGGGGTCTTTGAGACTGTGGAGATGCTGCCCTCCAAAGCTGGCATCTGG
AGGGTGGAGTGCCTCATTGGGGAGCACCTGCATGCTGGCATGAGCACCCTGTTCCTGGTCTACAGC
AACAAGTGCCAGACCCCCCTGGGAATGGCCTCTGGCCACATCAGGGACTTCCAGATCACTGCCTCT
GGCCAGTATGGCCAGTGGGCCCCCAAGCTGGCCAGGCTCCACTACTCTGGATCCATCAATGCCTGG
AGCACCAAGGAGCCATTCAGCTGGATCAAAGTGGACCTGCTGGCCCCCATGATCATCCATGGCATC
AAGACCCAGGGGGCCAGGCAGAAGTTCTCCAGCCTGTACATCAGCCAGTTCATCATCATGTACAGC
CTGGATGGCAAGAAATGGCAGACCTACAGAGGCAACTCCACTGGAACACTCATGGTCTTCTTTGGC
AATGTGGACAGCTCTGGCATCAAGCACAACATCTTCAACCCCCCAATCATCGCCAGATACATCAGG
CTGCACCCCACCCACTACAGCATCCGCAGCACCCTCAGGATGGAGCTGATGGGCTGTGACCTGAAC
TCCTGCAGCATGCCCCTGGGCATGGAGAGCAAGGCCATTTCTGATGCCCAGATCACTGCCTCCAGC
TACTTCACCAACATGTTTGCCACCTGGAGCCCAAGCAAGGCCAGGCTGCACCTCCAGGGAAGGAGC
AATGCCTGGAGGCCCCAGGTCAACAACCCAAAGGAGTGGCTGCAGGTGGACTTCCAGAAGACCATG
AAGGTCACTGGGGTGACCACCCAGGGGGTCAAGAGCCTGCTCACCAGCATGTATGTGAAGGAGTTC
CTGATCAGCTCCAGCCAGGATGGCCACCAGTGGACCCTCTTCTTCCAGAATGGCAAGGTCAAGGTG
TTCCAGGGCAACCAGGACAGCTTCACCCCTGTGGTGAACAGCCTGGACCCCCCCCTCCTGACCAGA
TACCTGAGGATTCACCCCCAGAGCTGGGTCCACCAGATTGCCCTGAGGATGGAGGTCCTGGGATGT
GAGGCCCAGGACCTGTACTGA (SEQ ID NO:96)

ATGCAGATTGAGCTGAGCACCTGCTTCTTCCTGTGCCTGCTGAGGTTCTGCTTCTCTGCCACCAGG
AGATACTACCTGGGGGCTGTGGAGCTTTCTTGGGACTACATGCAGTCTGACCTGGGGGAGCTGCCT
GTGGATGCCAGGTTCCCACCCAGAGTGCCCAAATCCTTCCCATTCAACACCTCTGTGGTCTACAAG
AAGACCCTCTTTGTGGAGTTCACTGACCACCTGTTCAACATTGCCAAACCCAGGCCACCCTGGATG
GGACTCCTGGGACCCACCATTCAGGCTGAGGTGTATGACACTGTGGTCATCACCCTCAAGAACATG
GCCTCCCACCCTGTGAGCCTGCATGCTGTGGGGGTCAGCTACTGGAAGGCCTCTGAGGGGGCTGAG
TATGATGACCAGACCTCCCAGAGGGAGAAGGAGGATGACAAAGTGTTCCCTGGGGGCAGCCACACC
TATGTGTGGCAGGTCCTCAAGGAGAATGGCCCCATGGCCTCTGACCCACTCTGCCTGACCTACTCC
TACCTTTCTCATGTGGACCTGGTCAAGGACCTCAACTCTGGACTGATTGGGGCCCTGCTGGTGTGC
AGGGAGGGCTCCCTGGCCAAAGAGAAGACCCAGACCCTGCACAAGTTCATTCTCCTGTTTGCTGTC
TTTGATGAGGGCAAGAGCTGGCACTCTGAAACCAAGAACTCCCTGATGCAGGACAGGGATGCTGCC
TCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGGACAACCCCTGAGGTGCAC
TCCATTTTCCTGGAGGGCCACACCTTCCTGGTCAGGAACCACAGACAGGCCAGCCTGGAGATCAGC
CCCATCACCTTCCTCACTGCCCAGACCCTGCTGATGGACCTCGGACAGTTCCTGCTGTCCTGCCAC
ATCAGCTCCCACCAGCATGATGGCATGGAGGCCTATGTCAAGGTGGACAGCTGCCCTGAGGAGCCA
CAGCTCAGGATGAAGAACAATGAGGAGGCTGAGGACTATGATGATGACCTGACTGACTCTGAGATG
GATGTGGTCCGCTTTGATGATGACAACAGCCCATCCTTCATTCAGATCAGGTCTGTGGCCAAGAAA
CACCCCAAGACCTGGGTGCACTACATTGCTGCTGAGGAGGAGGACTGGGACTATGCCCCACTGGTC
CTGGCCCCTGATGACAGGAGCTACAAGAGCCAGTACCTCAACAATGGCCCACAGAGGATTGGACGC
AAGTACAAGAAAGTCAGGTTCATGGCCTACACTGATGAAACCTTCAAGACCAGGGAGGCCATTCAG
CATGAGTCTGGCATCCTGGGCCCACTCCTGTATGGGGAGGTGGGGGACACCCTGCTCATCATCTTC
AAGAACCAGGCCTCCAGGCCCTACAACATCTACCCACATGGCATCACTGATGTCAGGCCCCTGTAC
AGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGA
TACTACTCCAGCTTTGTGAACATGGAGAGGGACCTGGCCTCTGGCCTGATTGGCCCACTGCTCATC
TGCTACAAGGAGTCTGTGGACCAGAGGGGAAACCAGATCATGTCTGACAAGAGGAATGTGATTCTG
TTCTCTGTCTTTGATGAGAACAGGAGCTGGTACCTGACTGAGAACATTCAGCGCTTCCTGCCCAAC
CCTGCTGGGGTGCAGCTGGAGGACCCTGAGTTCCAGGCCAGCAACATCATGCACTCCATCAATGGC
TATGTGTTTGACAGCCTCCAGCTTTCTGTCTGCCTGCATGAGGTGGCCTACTGGTACATTCTTTCT
ATTGGGGCCCAGACTGACTTCCTTTCTGTCTTCTTCTCTGGCTACACCTTCAAACACAAGATGGTG
TATGAGGACACCCTGACCCTCTTCCCATTCTCTGGGGAGACTGTGTTCATGAGCATGGAGAACCCT
GGCCTGTGGATTCTGGGATGCCACAACTCTGACTTCCGCAACAGGGGCATGACTGCCCTGCTCAAA
GTCTCCTCCTGTGACAAGAACACTGGGGACTACTATGAGGACAGCTATGAGGACATCTCTGCCTAC
CTGCTCAGCAAGAACAATGCCATTGAGCCCAGGAGCTTCAGCCAGAATCCACCTGTCCTGAAACGC
CACCAGAGGGAGATCACCAGGACCACCCTCCAGTCTGACCAGGAGGAGATTGACTATGATGACACC
ATTTCTGTGGAGATGAAGAAAGAGGACTTTGACATCTATGACGAGGACGAGAACCAGAGCCCAAGG
AGCTTCCAGAAGAAGACCAGGCACTACTTCATTGCTGCTGTGGAGCGCCTGTGGGACTATGGCATG
AGCTCCAGCCCCCATGTCCTCAGGAACAGGGCCCAGTCTGGCTCTGTGCCACAGTTCAAGAAAGTG (Continued)

Figure 37A

GTCTTCCAAGAGTTCACTGATGGCAGCTTCACCCAGCCCCTGTACAGAGGGGAGCTGAATGAGCAC
CTGGGACTCCTGGGCCCATACATCAGGGCTGAGGTGGAGGACAACATCATGGTGACCTTCCGCAAC
CAGGCCTCCAGGCCCTACAGCTTCTACAGCTCCCTCATCAGCTATGAGGAGGACCAGAGGCAGGGG
GCTGAGCCACGCAAGAACTTTGTGAAACCCAATGAAACCAAGACCTACTTCTGGAAAGTCCAGCAC
CACATGGCCCCCACCAAGGATGAGTTTGACTGCAAGGCCTGGGCCTACTTCTCTGATGTGGACCTG
GAGAAGGATGTGCACTCTGGCCTGATTGGCCCACTCCTGGTCTGCCACACCAACACCCTGAACCCT
GCCCATGGAAGGCAAGTGACTGTGCAGGAGTTTGCCCTCTTCTTCACCATCTTTGATGAAACCAAG
AGCTGGTACTTCACTGAGAACATGGAGCGCAACTGCAGGGCCCCATGCAACATTCAGATGGAGGAC
CCCACCTTCAAAGAGAACTACCGCTTCCATGCCATCAATGGCTACATCATGGACACCCTGCCTGGG
CTTGTCATGGCCCAGGACCAGAGGATCAGGTGGTACCTGCTTTCTATGGGCTCCAATGAGAACATT
CACTCCATCCACTTCTCTGGGCATGTCTTCACTGTGCGCAAGAAGGAGGAGTACAAGATGGCCCTG
TACAACCTCTACCCTGGGGTCTTTGAGACTGTGGAGATGCTGCCCTCCAAAGCTGGCATCTGGAGG
GTGGAGTGCCTCATTGGGGAGCACCTGCATGCTGGCATGAGCACCCTGTTCCTGGTCTACAGCAAC
AAGTGCCAGACCCCCCTGGGAATGGCCTCTGGCCACATCAGGGACTTCCAGATCACTGCCTCTGGC
CAGTATGGCCAGTGGGCCCCCAAGCTGGCCAGGCTCCACTACTCTGGATCCATCAATGCCTGGAGC
ACCAAGGAGCCATTCAGCTGGATCAAAGTGGACCTGCTGGCCCCCATGATCATCCATGGCATCAAG
ACCCAGGGGGCCAGGCAGAAGTTCTCCAGCCTGTACATCAGCCAGTTCATCATCATGTACAGCCTG
GATGGCAAGAAATGGCAGACCTACAGAGGCAACTCCACTGGAACACTCATGGTCTTCTTTGGCAAT
GTGGACAGCTCTGGCATCAAGCACAACATCTTCAACCCCCCAATCATCGCCAGATACATCAGGCTG
CACCCCACCCACTACAGCATCCGCAGCACCCTCAGGATGGAGCTGATGGGCTGTGACCTGAACTCC
TGCAGCATGCCCCTGGGCATGGAGAGCAAGGCCATTTCTGATGCCCAGATCACTGCCTCCAGCTAC
TTCACCAACATGTTTGCCACCTGGAGCCCAAGCAAGGCCAGGCTGCACCTCCAGGGAAGGAGCAAT
GCCTGGAGGCCCCAGGTCAACAACCCAAAGGAGTGGCTGCAGGTGGACTTCCAGAAGACCATGAAG
GTCACTGGGGTGACCACCCAGGGGGTCAAGAGCCTGCTCACCAGCATGTATGTGAAGGAGTTCCTG
ATCAGCTCCAGCCAGGATGGCCACCAGTGGACCCTCTTCTTCCAGAATGGCAAGGTCAAGGTGTTC
CAGGGCAACCAGGACAGCTTCACCCCTGTGGTGAACAGCCTGGACCCCCCCCTCCTGACCAGATAC
CTGAGGATTCACCCCCAGAGCTGGGTCCACCAGATTGCCCTGAGGATGGAGGTCCTGGGATGTGAG
GCCCAGGACCTGTACTGA (SEQ ID NO:97)

ATGCAGATTGAGCTGAGCACCTGCTTCTTCCTGTGCCTGCTGAGGTTCTGCTTCTCTGCCACCAGG
AGATACTACCTGGGGGCTGTGGAGCTTTCTTGGGACTACATGCAGTCTGACCTGGGGGAGCTGCCT
GTGGATGCCAGGTTCCCACCCAGAGTGCCCAAATCCTTCCCATTCAACACCTCTGTGGTCTACAAG
AAGACCCTCTTTGTGGAGTTCACTGACCACCTGTTCAACATTGCCAAACCCAGGCCACCCTGGATG
GGACTCCTGGGACCCACCATTCAGGCTGAGGTGTATGACACTGTGGTCATCACCCTCAAGAACATG
GCCTCCCACCCTGTGAGCCTGCATGCTGTGGGGGTCAGCTACTGGAAGGCCTCTGAGGGGGCTGAG
TATGATGACCAGACCTCCCAGAGGGAGAAGGAGGATGACAAAGTGTTCCCTGGGGGCAGCCACACC
TATGTGTGGCAGGTCCTCAAGGAGAATGGCCCCATGGCCTCTGACCCACTCTGCCTGACCTACTCC
TACCTTTCTCATGTGGACCTGGTCAAGGACCTCAACTCTGGACTGATTGGGGCCCTGCTGGTGTGC
AGGGAGGGCTCCCTGGCCAAAGAGAAGACCCAGACCCTGCACAAGTTCATTCTCCTGTTTGCTGTC
TTTGATGAGGGCAAGAGCTGGCACTCTGAAACCAAGAACTCCCTGATGCAGGACAGGGATGCTGCC
TCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGGACAACCCCTGAGGTGCAC
TCCATTTTCCTGGAGGGCCACACCTTCCTGGTCAGGAACCACAGACAGGCCAGCCTGGAGATCAGC
CCCATCACCTTCCTCACTGCCCAGACCCTGCTGATGGACCTCGGACAGTTCCTGCTGTCCTGCCAC
ATCAGCTCCCACCAGCATGATGGCATGGAGGCCTATGTCAAGGTGGACAGCTGCCCTGAGGAGCCA
CAGCTCAGGATGAAGAACAATGAGGAGGCTGAGGACTATGATGATGACCTGACTGACTCTGAGATG
GATGTGGTCCGCTTTGATGATGACAACAGCCCATCCTTCATTCAGATCAGGTCTGTGGCCAAGAAA
CACCCCAAGACCTGGGTGCACTACATTGCTGCTGAGGAGGAGGACTGGGACTATGCCCCACTGGTC
CTGGCCCCTGATGACAGGAGCTACAAGAGCCAGTACCTCAACAATGGCCCACAGAGGATTGGACGC
AAGTACAAGAAAGTCAGGTTCATGGCCTACACTGATGAAACCTTCAAGACCAGGGAGGCCATTCAG
CATGAGTCTGGCATCCTGGGCCCACTCCTGTATGGGGAGGTGGGGGACACCCTGCTCATCATCTTC
AAGAACCAGGCCTCCAGGCCCTACAACATCTACCCACATGGCATCACTGATGTCAGGCCCCTGTAC
AGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGA
TACTACTCCAGCTTTGTGAACATGGAGAGGGACCTGGCCTCTGGCCTGATTGGCCCACTGCTCATC
TGCTACAAGGAGTCTGTGGACCAGAGGGGAAACCAGATCATGTCTGACAAGAGGAATGTGATTCTG
TTCTCTGTCTTTGATGAGAACAGGAGCTGGTACCTGACTGAGAACATTCAGCGCTTCCTGCCCAAC
CCTGCTGGGGTGCAGCTGGAGGACCCTGAGTTCCAGGCCAGCAACATCATGCACTCCATCAATGGC
TATGTGTTTGACAGCCTCCAGCTTTCTGTCTGCCTGCATGAGGTGGCCTACTGGTACATTCTTTCT
ATTGGGGCCCAGACTGACTTCCTTTCTGTCTTCTTCTCTGGCTACACCTTCAAACACAAGATGGTG
TATGAGGACACCCTGACCCTCTTCCCATTCTCTGGGGAGACTGTGTTCATGAGCATGGAGAACCCT
GGCCTGTGGATTCTGGGATGCCACAACTCTGACTTCCGCAACAGGGGCATGACTGCCCTGCTCAAA
GTCTCCTCCTGTGACAAGAACACTGGGGACTACTATGAGGACAGCTATGAGGACATCTCTGCCTAC
CTGCTCAGCAAGAACAATACCACCTACGTGAACCGCTCCCTGAGCCAGAATCCACCTGTCCTGAAA
CGCCACCAGAGGGAGATCACCAGGACCACCCTCCAGTCTGACCAGGAGGAGATTGACTATGATGAC
ACCATTTCTGTGGAGATGAAGAAAGAGGACTTTGACATCTATGACGAGGACGAGAACCAGAGCCCA
AGGAGCTTCCAGAAGAAGACCAGGCACTACTTCATTGCTGCTGTGGAGCGCCTGTGGGACTATGGC
ATGAGCTCCAGCCCCCATGTCCTCAGGAACAGGGCCCAGTCTGGCTCTGTGCCACAGTTCAAGAAA (Continued)

Figure 38A

GTGGTCTTCCAAGAGTTCACTGATGGCAGCTTCACCCAGCCCCTGTACAGAGGGGAGCTGAATGAG
CACCTGGGACTCCTGGGCCCATACATCAGGGCTGAGGTGGAGGACAACATCATGGTGACCTTCCGC
AACCAGGCCTCCAGGCCCTACAGCTTCTACAGCTCCCTCATCAGCTATGAGGAGGACCAGAGGCAG
GGGGCTGAGCCACGCAAGAACTTTGTGAAACCCAATGAAACCAAGACCTACTTCTGGAAAGTCCAG
CACCACATGGCCCCCACCAAGGATGAGTTTGACTGCAAGGCCTGGGCCTACTTCTCTGATGTGGAC
CTGGAGAAGGATGTGCACTCTGGCCTGATTGGCCCACTCCTGGTCTGCCACACCAACACCCTGAAC
CCTGCCCATGGAAGGCAAGTGACTGTGCAGGAGTTTGCCCTCTTCTTCACCATCTTTGATGAAACC
AAGAGCTGGTACTTCACTGAGAACATGGAGCGCAACTGCAGGGCCCCATGCAACATTCAGATGGAG
GACCCCACCTTCAAAGAGAACTACCGCTTCCATGCCATCAATGGCTACATCATGGACACCCTGCCT
GGGCTTGTCATGGCCCAGGACCAGAGGATCAGGTGGTACCTGCTTTCTATGGGCTCCAATGAGAAC
ATTCACTCCATCCACTTCTCTGGGCATGTCTTCACTGTGCGCAAGAAGGAGGAGTACAAGATGGCC
CTGTACAACCTCTACCCTGGGGTCTTTGAGACTGTGGAGATGCTGCCCTCCAAAGCTGGCATCTGG
AGGGTGGAGTGCCTCATTGGGGAGCACCTGCATGCTGGCATGAGCACCCTGTTCCTGGTCTACAGC
AACAAGTGCCAGACCCCCCTGGGAATGGCCTCTGGCCACATCAGGGACTTCCAGATCACTGCCTCT
GGCCAGTATGGCCAGTGGGCCCCCAAGCTGGCCAGGCTCCACTACTCTGGATCCATCAATGCCTGG
AGCACCAAGGAGCCATTCAGCTGGATCAAAGTGGACCTGCTGGCCCCCATGATCATCCATGGCATC
AAGACCCAGGGGGCCAGGCAGAAGTTCTCCAGCCTGTACATCAGCCAGTTCATCATCATGTACAGC
CTGGATGGCAAGAAATGGCAGACCTACAGAGGCAACTCCACTGGAACACTCATGGTCTTCTTTGGC
AATGTGGACAGCTCTGGCATCAAGCACAACATCTTCAACCCCCCAATCATCGCCAGATACATCAGG
CTGCACCCCACCCACTACAGCATCCGCAGCACCCTCAGGATGGAGCTGATGGGCTGTGACCTGAAC
TCCTGCAGCATGCCCCTGGGCATGGAGAGCAAGGCCATTTCTGATGCCCAGATCACTGCCTCCAGC
TACTTCACCAACATGTTTGCCACCTGGAGCCCAAGCAAGGCCAGGCTGCACCTCCAGGGAAGGAGC
AATGCCTGGAGGCCCCAGGTCAACAACCCAAAGGAGTGGCTGCAGGTGGACTTCCAGAAGACCATG
AAGGTCACTGGGGTGACCACCCAGGGGGTCAAGAGCCTGCTCACCAGCATGTATGTGAAGGAGTTC
CTGATCAGCTCCAGCCAGGATGGCCACCAGTGGACCCTCTTCTTCCAGAATGGCAAGGTCAAGGTG
TTCCAGGGCAACCAGGACAGCTTCACCCCTGTGGTGAACAGCCTGGACCCCCCCCTCCTGACCAGA
TACCTGAGGATTCACCCCCAGAGCTGGGTCCACCAGATTGCCCTGAGGATGGAGGTCCTGGGATGT
GAGGCCCAGGACCTGTACTGA (SEQ ID NO:98)

ATGCAGATTGAGCTGAGCACCTGCTTCTTCCTGTGCCTGCTGAGGTTCTGCTTCTCTGCCACCAGG
AGATACTACCTGGGCGCCGTGGAGCTGAGCTGGGACTACATGCAGTCTGACCTGGGCGAGCTGCCT
GTGGACGCCAGGTTCCCCCCCAGAGTGCCCAAGAGCTTCCCCTTCAACACCTCAGTGGTGTACAAG
AAGACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGATCACCCTGAAGAACATG
GCCAGCCACCCCGTGAGCCTGCACGCCGTGGGCGTGAGCTACTGGAAGGCCTCTGAGGGCGCCGAG
TATGACGACCAGACCAGCCAGAGGGAGAAGGAGGACGACAAGGTGTTCCCCGGCGGCAGCCACACC
TACGTGTGGCAGGTGCTGAAGGAGAACGGCCCCATGGCCAGCGACCCCCTGTGCCTGACCTACAGC
TACCTGAGCCACGTGGACCTGGTGAAGGACCTGAACTCTGGCCTGATCGGCGCCCTGCTGGTGTGC
AGGGAGGGCAGCCTGGCCAAGGAGAAGACCCAGACCCTGCACAAGTTCATCCTGCTGTTCGCCGTG
TTCGATGAGGGCAAGAGCTGGCACAGCGAGACCAAGAACAGCCTGATGCAGGACAGGGATGCCGCC
TCTGCCAGGGCCTGGCCCAAGATGCACACCGTGAACGGCTACGTGAACAGGAGCCTGCCCGGCCTG
ATCGGCTGCCACAGGAAGTCTGTGTACTGGCACGTGATCGGCATGGGCACCACCCCCGAGGTGCAC
AGCATCTTCCTGGAGGGCCACACCTTCCTGGTGAGGAACCACAGGCAGGCCAGCCTGGAGATCAGC
CCCATCACCTTCCTGACCGCCCAGACCCTGCTGATGGACCTGGGCCAGTTCCTGCTGTCCTGCCAC
ATCAGCAGCCACCAGCACGACGGCATGGAGGCCTACGTGAAGGTGGACAGCTGCCCCGAGGAGCCC
CAGCTGAGGATGAAGAACAACGAGGAGGCCGAGGACTATGATGATGACCTGACCGACTCTGAGATG
GACGTGGTGAGGTTTGATGATGACAACAGCCCCAGCTTCATCCAGATCAGGTCTGTGGCCAAGAAG
CACCCCAAGACCTGGGTGCACTACATCGCCGCCGAGGAGGAGGACTGGGACTACGCCCCCCTGGTG
CTGGCCCCCGACGACAGGAGCTACAAGAGCCAGTACCTGAACAACGGCCCCCAGAGGATCGGCAGG
AAGTACAAGAAGGTCAGATTCATGGCCTACACCGACGAGACCTTCAAGACCAGGGAGGCCATCCAG
CACGAGTCTGGCATCCTGGGCCCCCTGCTGTACGGCGAGGTGGGCGACACCCTGCTGATCATCTTC
AAGAACCAGGCCAGCAGGCCCTACAACATCTACCCCCACGGCATCACCGATGTGAGGCCCCTGTAC
AGCAGGAGGCTGCCCAAGGGCGTGAAGCACCTGAAGGACTTCCCCATCCTGCCCGGCGAGATCTTC
AAGTACAAGTGGACCGTGACCGTGGAGGATGGCCCCACCAAGTCTGACCCCAGGTGCCTGACCAGG
TACTACAGCAGCTTCGTGAACATGGAGAGGGACCTGGCCTCTGGCCTGATCGGCCCCCTGCTGATC
TGCTACAAGGAGAGCGTGGACCAGAGGGGCAACCAGATCATGTCTGACAAGAGGAACGTGATCCTG
TTCTCTGTGTTCGATGAGAACAGGAGCTGGTATCTGACCGAGAACATCCAGAGGTTCCTGCCCAAC
CCCGCCGGCGTGCAGCTGGAGGACCCCGAGTTCCAGGCCAGCAACATCATGCACAGCATCAACGGC
TACGTGTTCGACAGCCTGCAGCTGTCTGTGTGCCTGCACGAGGTGGCCTACTGGTACATCCTGAGC
ATCGGCGCCCAGACCGACTTCCTGTCTGTGTTCTTCTCTGGCTACACCTTCAAGCACAAGATGGTG
TACGAGGACACCCTGACCCTGTTCCCCTTCAGCGGCGAGACCGTGTTCATGAGCATGGAGAACCCC
GGCCTGTGGATCCTGGGCTGCCACAACAGCGACTTCAGGAACAGGGGCATGACCGCCCTGCTGAAA
GTCAGCAGCTGCGACAAGAACACCGGCGACTACTACGAGGACAGCTACGAGGACATCAGCGCCTAC
CTGCTGAGCAAGAACAACACCACCTACGTGAACCGCTCCCTGAGCCAGAACCCCCCGTGCTGAAG
AGGCACCAGAGGGAGATCACCAGGACCACCCTGCAGAGCGACCAGGAGGAGATCGACTATGATGAC
ACCATCAGCGTGGAGATGAAGAAGGAGGACTTCGACATCTACGACGAGGACGAGAACCAGAGCCCC
AGGAGCTTCCAGAAGAAGACCAGGCACTACTTCATCGCCGCCGTGGAGAGGCTGTGGGACTATGGC
ATGAGCAGCAGCCCCCACGTGCTGAGGAACAGGGCCCAGAGCGGCAGCGTGCCCCAGTTCAAGAAG (Continued)

Figure 39A

GTGGTGTTCCAGGAGTTCACCGACGGCAGCTTCACCCAGCCCCTGTACAGAGGCGAGCTGAACGAG
CACCTGGGCCTGCTGGGCCCCTACATCAGGGCCGAGGTGGAGGACAACATCATGGTGACCTTCAGG
AACCAGGCCAGCAGGCCCTACAGCTTCTACAGCAGCCTGATCAGCTACGAGGAGGACCAGAGGCAG
GGCGCCGAGCCCAGGAAGAACTTCGTGAAGCCCAACGAGACCAAGACCTACTTCTGGAAGGTGCAG
CACCACATGGCCCCCACCAAGGACGAGTTCGACTGCAAGGCCTGGGCCTACTTCTCTGATGTGGAC
CTGGAGAAGGACGTGCACAGCGGCCTGATCGGCCCCCTGCTGGTGTGCCACACCAACACCCTGAAC
CCCGCCCACGGCAGGCAGGTGACCGTGCAGGAGTTCGCCCTGTTCTTCACCATCTTCGACGAGACC
AAGAGCTGGTACTTCACCGAGAACATGGAGAGGAACTGCAGGGCCCCCTGCAACATCCAGATGGAG
GACCCCACCTTCAAGGAGAACTACAGGTTCCACGCCATCAACGGCTACATCATGGACACCCTGCCC
GGCCTGGTGATGGCCCAGGACCAGAGGATCAGGTGGTATCTGCTGAGCATGGGCAGCAACGAGAAC
ATCCACAGCATCCACTTCAGCGGCCACGTGTTCACCGTGAGGAAGAAGGAGGAGTACAAGATGGCC
CTGTACAACCTGTACCCCGGCGTGTTCGAGACCGTGGAGATGCTGCCCAGCAAGGCCGGCATCTGG
AGGGTGGAGTGCCTGATCGGCGAGCACCTGCACGCCGGCATGAGCACCCTGTTCCTGGTGTACAGC
AACAAGTGCCAGACCCCCCTGGGCATGGCCAGCGGCCACATCAGGGACTTCCAGATCACCGCCTCT
GGCCAGTACGGCCAGTGGGCCCCCAAGCTGGCCAGGCTGCACTACAGCGGCAGCATCAACGCCTGG
AGCACCAAGGAGCCCTTCAGCTGGATCAAGGTGGACCTGCTGGCCCCCATGATCATCCACGGCATC
AAGACCCAGGGCGCCAGGCAGAAGTTCAGCAGCCTGTACATCAGCCAGTTCATCATCATGTACAGC
CTGGACGGCAAGAAGTGGCAGACCTACAGGGGCAACAGCACCGGCACCCTGATGGTGTTCTTCGGC
AACGTGGACAGCAGCGGCATCAAGCACAACATCTTCAACCCCCCCATCATCGCCAGGTACATCAGG
CTGCACCCCACCCACTACAGCATCAGGAGCACCCTGCGGATGGAACTGATGGGCTGCGACCTGAAC
AGCTGCAGCATGCCCCTGGGCATGGAGAGCAAGGCCATCTCTGACGCCCAGATCACCGCCAGCAGC
TACTTCACCAACATGTTCGCCACCTGGAGCCCCAGCAAGGCCAGGCTGCACCTGCAGGGCAGGAGC
AACGCCTGGAGGCCCCAGGTGAACAACCCCAAGGAGTGGCTGCAGGTGGACTTCCAGAAGACCATG
AAGGTGACCGGCGTGACCACCCAGGGCGTGAAGAGCCTGCTGACCAGCATGTACGTGAAGGAGTTC
CTGATCAGCAGCAGCCAGGACGGCCACCAGTGGACCCTGTTCTTCCAGAACGGCAAAGTGAAGGTG
TTCCAGGGCAACCAGGACAGCTTCACCCCCGTGGTGAACAGCCTGGACCCCCCCCTGCTGACCAGG
TATCTGAGGATCCACCCCCAGAGCTGGGTGCACCAGATCGCCCTGAGAATGGAAGTGCTGGGATGC
GAGGCCCAGGACCTGTACTGA (SEQ ID NO:99)

ATGCAGATTGAGCTGAGCACCTGCTTCTTCCTGTGCCTGCTGAGGTTCTGCTTCTCTGCCACCAGG
AGATACTACCTGGGCGCCGTGGAGCTGAGCTGGGACTACATGCAGTCTGACCTGGGCGAGCTGCCT
GTGGACGCCAGGTTCCCCCCCAGAGTGCCCAAGAGCTTCCCCTTCAACACCTCAGTGGTGTACAAG
AAGACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGATCACCCTGAAGAACATG
GCCAGCCACCCCGTGAGCCTGCACGCCGTGGGCGTGAGCTACTGGAAGGCCTCTGAGGGCGCCGAG
TATGACGACCAGACCAGCCAGAGGGAGAAGGAGGACGACAAGGTGTTCCCCGGCGGCAGCCACACC
TACGTGTGGCAGGTGCTGAAGGAGAACGGCCCCATGGCCAGCGACCCCCTGTGCCTGACCTACAGC
TACCTGAGCCACGTGGACCTGGTGAAGGACCTGAACTCTGGCCTGATCGGCGCCCTGCTGGTGTGC
AGGGAGGGCAGCCTGGCCAAGGAGAAGACCCAGACCCTGCACAAGTTCATCCTGCTGTTCGCCGTG
TTCGATGAGGGCAAGAGCTGGCACAGCGAGACCAAGAACAGCCTGATGCAGGACAGGGATGCCGCC
TCTGCCAGGGCCTGGCCCAAGATGCACACCGTGAACGGCTACGTGAACAGGAGCCTGCCCGGCCTG
ATCGGCTGCCACAGGAAGTCTGTGTACTGGCACGTGATCGGCATGGGCACCACCCCCGAGGTGCAC
AGCATCTTCCTGGAGGGCCACACCTTCCTGGTGAGGAACCACAGGCAGGCCAGCCTGGAGATCAGC
CCCATCACCTTCCTGACCGCCCAGACCCTGCTGATGGACCTGGGCCAGTTCCTGCTGTTCTGCCAC
ATCAGCAGCCACCAGCACGACGGCATGGAGGCCTACGTGAAGGTGGACAGCTGCCCCGAGGAGCCC
CAGCTGAGGATGAAGAACAACGAGGAGGCCGAGGACTATGATGATGACCTGACCGACTCTGAGATG
GACGTGGTGAGGTTTGATGATGACAACAGCCCCAGCTTCATCCAGATCAGGTCTGTGGCCAAGAAG
CACCCCAAGACCTGGGTGCACTACATCGCCGCCGAGGAGGAGGACTGGGACTACGCCCCCCTGGTG
CTGGCCCCCGACGACAGGAGCTACAAGAGCCAGTACCTGAACAACGGCCCCCAGAGGATCGGCAGG
AAGTACAAGAAGGTCAGATTCATGGCCTACACCGACGAGACCTTCAAGACCAGGGAGGCCATCCAG
CACGAGTCTGGCATCCTGGGCCCCCTGCTGTACGGCGAGGTGGGCGACACCCTGCTGATCATCTTC
AAGAACCAGGCCAGCAGGCCCTACAACATCTACCCCCACGGCATCACCGATGTGAGGCCCCTGTAC
AGCAGGAGGCTGCCCAAGGGCGTGAAGCACCTGAAGGACTTCCCCATCCTGCCCGGCGAGATCTTC
AAGTACAAGTGGACCGTGACCGTGGAGGATGGCCCCACCAAGTCTGACCCCAGGTGCCTGACCAGG
TACTACAGCAGCTTCGTGAACATGGAGAGGGACCTGGCCTCTGGCCTGATCGGCCCCCTGCTGATC
TGCTACAAGGAGAGCGTGGACCAGAGGGGCAACCAGATCATGTCTGACAAGAGGAACGTGATCCTG
TTCTCTGTGTTCGATGAGAACAGGAGCTGGTATCTGACCGAGAACATCCAGAGGTTCCTGCCCAAC
CCCGCCGGCGTGCAGCTGGAGGACCCCGAGTTCCAGGCCAGCAACATCATGCACAGCATCAACGGC
TACGTGTTCGACAGCCTGCAGCTGTCTGTGTGCCTGCACGAGGTGGCCTACTGGTACATCCTGAGC
ATCGGCGCCCAGACCGACTTCCTGTCTGTGTTCTTCTCTGGCTACACCTTCAAGCACAAGATGGTG
TACGAGGACACCCTGACCCTGTTCCCCTTCAGCGGCGAGACCGTGTTCATGAGCATGGAGAACCCC
GGCCTGTGGATCCTGGGCTGCCACAACAGCGACTTCAGGAACAGGGGCATGACCGCCCTGCTGAAA
GTCAGCAGCTGCGACAAGAACACCGGCGACTACTACGAGGACAGCTACGAGGACATCAGCGCCTAC
CTGCTGAGCAAGAACAACACCACCTACGTGAACCGCTCCCTGAGCCAGAACCCCCCCGTGCTGAAG
AGGCACCAGAGGGAGATCACCAGGACCACCCTGCAGAGCGACCAGGAGGAGATCGACTATGATGAC
ACCATCAGCGTGGAGATGAAGAAGGAGGACTTCGACATCTACGACGAGGACGAGAACCAGAGCCCC
AGGAGCTTCCAGAAGAAGACCAGGCACTACTTCATCGCCGCCGTGGAGAGGCTGTGGGACTATGGC
ATGAGCAGCAGCCCCCACGTGCTGAGGAACAGGGCCCAGAGCGGCAGCGTGCCCCAGTTCAAGAAG (Continued)

Figure 40A

GTGGTGTTCCAGGAGTTCACCGACGGCAGCTTCACCCAGCCCCTGTACAGAGGCGAGCTGAACGAG
CACCTGGGCCTGCTGGGCCCCTACATCAGGGCCGAGGTGGAGGACAACATCATGGTGACCTTCAGG
AACCAGGCCAGCAGGCCCTACAGCTTCTACAGCAGCCTGATCAGCTACGAGGAGGACCAGAGGCAG
GGCGCCGAGCCCAGGAAGAACTTCGTGAAGCCCAACGAGACCAAGACCTACTTCTGGAAGGTGCAG
CACCACATGGCCCCCACCAAGGACGAGTTCGACTGCAAGGCCTGGGCCTACTTCTCTGATGTGGAC
CTGGAGAAGGACGTGCACAGCGGCCTGATCGGCCCCCTGCTGGTGTGCCACACCAACACCCTGAAC
CCCGCCCACGGCAGGCAGGTGACCGTGCAGGAGTTCGCCCTGTTCTTCACCATCTTCGACGAGACC
AAGAGCTGGTACTTCACCGAGAACATGGAGAGGAACTGCAGGGCCCCCTGCAACATCCAGATGGAG
GACCCCACCTTCAAGGAGAACTACAGGTTCCACGCCATCAACGGCTACATCATGGACACCCTGCCC
GGCCTGGTGATGGCCCAGGACCAGAGGATCAGGTGGTATCTGCTGAGCATGGGCAGCAACGAGAAC
ATCCACAGCATCCACTTCAGCGGCCACGTGTTCACCGTGAGGAAGAAGGAGGAGTACAAGATGGCC
CTGTACAACCTGTACCCCGGCGTGTTCGAGACCGTGGAGATGCTGCCCAGCAAGGCCGGCATCTGG
AGGGTGGAGTGCCTGATCGGCGAGCACCTGCACGCCGGCATGAGCACCCTGTTCCTGGTGTACAGC
AACAAGTGCCAGACCCCCCTGGGCATGGCCAGCGGCCACATCAGGGACTTCCAGATCACCGCCTCT
GGCCAGTACGGCCAGTGGGCCCCCAAGCTGGCCAGGCTGCACTACAGCGGCAGCATCAACGCCTGG
AGCACCAAGGAGCCCTTCAGCTGGATCAAGGTGGACCTGCTGGCCCCCATGATCATCCACGGCATC
AAGACCCAGGGCGCCAGGCAGAAGTTCAGCAGCCTGTACATCAGCCAGTTCATCATCATGTACAGC
CTGGACGGCAAGAAGTGGCAGACCTACAGGGGCAACAGCACCGGCACCCTGATGGTGTTCTTCGGC
AACGTGGACAGCAGCGGCATCAAGCACAACATCTTCAACCCCCCCATCATCGCCAGGTACATCAGG
CTGCACCCCACCCACTACAGCATCAGGAGCACCCTGCGGATGGAACTGATGGGCTGCGACCTGAAC
AGCTGCAGCATGCCCCTGGGCATGGAGAGCAAGGCCATCTCTGACGCCCAGATCACCGCCAGCAGC
TACTTCACCAACATGTTCGCCACCTGGAGCCCCAGCAAGGCCAGGCTGCACCTGCAGGGCAGGAGC
AACGCCTGGAGGCCCCAGGTGAACAACCCCAAGGAGTGGCTGCAGGTGGACTTCCAGAAGACCATG
AAGGTGACCGGCGTGACCACCCAGGGCGTGAAGAGCCTGCTGACCAGCATGTACGTGAAGGAGTTC
CTGATCAGCAGCAGCCAGGACGGCCACCAGTGGACCCTGTTCTTCCAGAACGGCAAAGTGAAGGTG
TTCCAGGGCAACCAGGACAGCTTCACCCCCGTGGTGAACAGCCTGGACCCCCCCCTGCTGACCAGG
TATCTGAGGATCCACCCCCAGAGCTGGGTGCACCAGATCGCCCTGAGAATGGAAGTGCTGGGATGC
GAGGCCCAGGACCTGTACTGA (SEQ ID NO:100)

ATGCAGATTGAGCTGAGCACCTGCTTCTTCCTGTGCCTGCTGAGGTTCTGCTTCTCTGCCACCAGG
AGATACTACCTGGGCGCCGTGGAGCTGAGCTGGGACTACATGCAGTCTGACCTGGGCGAGCTGCCT
GTGGACGCCAGGTTCCCCCCCAGAGTGCCCAAGAGCTTCCCCTTCAACACCTCAGTGGTGTACAAG
AAGACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGGTCACCCTGAAGAACATG
GCCAGCCACCCCGTGAGCCTGCACGCCGTGGGCGTGAGCTACTGGAAGTCCTCTGAGGGCGCCGAG
TATGACGACCAGACCAGCCAGAGGGAGAAGGAGGACGACAAGGTGTTCCCCGGCAAGAGCCACACC
TACGTGTGGCAGGTGCTGAAGGAGAACGGCCCCACTGCCAGCGACCCCCCCTGCCTGACCTACAGC
TACCTGAGCCACGTGGACCTGGTGAAGGACCTGAACTCTGGCCTGATCGGCGCCCTGCTGGTGTGC
AGGGAGGGCAGCCTGGCCAAGGAGAAGACCCAGACCCTGCACAAGTTCATCCTGCTGTTCGCCGTG
TTCGATGAGGGCAAGAGCTGGCACAGCGAGACCAAGAACAGCCTGATGCAGGACAGGGATGCCGCC
TCTGCCAGGGCCTGGCCCAAGATGCACACCGTGAACGGCTACGTGAACAGGAGCCTGCCCGGCCTG
ATCGGCTGCCACAGGAAGTCTGTGTACTGGCACGTGATCGGCATGGGCACCACCCCCGAGGTGCAC
AGCATCTTCCTGGAGGGCCACACCTTCCTGGTGAGGAACCACAGGCAGGCCAGCCTGGAGATCAGC
CCCATCACCTTCCTGACCGCCCAGACCCTGCTGATGGACCTGGGCCAGTTCCTGCTGTTCTGCCAC
ATCAGCAGCCACCAGCACGACGGCATGGAGGCCTACGTGAAGGTGGACAGCTGCCCCGAGGAGCCC
CAGCTGAGGATGAAGAACAACGAGGAGGCCGAGGACTATGATGATGACCTGACCGACTCTGAGATG
GACGTGGTGAGGTTTGATGATGACAACAGCCCCAGCTTCATCCAGATCAGGTCTGTGGCCAAGAAG
CACCCCAAGACCTGGGTGCACTACATCGCCGCCGAGGAGGAGGACTGGGACTACGCCCCCCTGGTG
CTGGCCCCCGACGACAGGAGCTACAAGAGCCAGTACCTGAACAACGGCCCCCAGAGGATCGGCAGG
AAGTACAAGAAGGTCAGATTCATGGCCTACACCGACGAGACCTTCAAGACCAGGGAGGCCATCCAG
CACGAGTCTGGCATCCTGGGCCCCCTGCTGTACGGCGAGGTGGGCGACACCCTGCTGATCATCTTC
AAGAACCAGGCCAGCAGGCCCTACAACATCTACCCCCACGGCATCACCGATGTGAGGCCCCTGTAC
AGCAGGAGGCTGCCCAAGGGCGTGAAGCACCTGAAGGACTTCCCCATCCTGCCCGGCGAGATCTTC
AAGTACAAGTGGACCGTGACCGTGGAGGATGGCCCCACCAAGTCTGACCCCAGGTGCCTGACCAGG
TACTACAGCAGCTTCGTGAACATGGAGAGGGACCTGGCCTCTGGCCTGATCGGCCCCCTGCTGATC
TGCTACAAGGAGAGCGTGGACCAGAGGGGCAACCAGATCATGTCTGACAAGAGGAACGTGATCCTG
TTCTCTGTGTTCGATGAGAACAGGAGCTGGTATCTGACCGAGAACATCCAGAGGTTCCTGCCCAAC
CCCGCCGGCGTGCAGCTGGAGGACCCCGAGTTCCAGGCCAGCAACATCATGCACAGCATCAACGGC
TACGTGTTCGACAGCCTGCAGCTGTCTGTGTGCCTGCACGAGGTGGCCTACTGGTACATCCTGAGC
ATCGGCGCCCAGACCGACTTCCTGTCTGTGTTCTTCTCTGGCTACACCTTCAAGCACAAGATGGTG
TACGAGGACACCCTGACCCTGTTCCCCTTCAGCGGCGAGACCGTGTTCATGAGCATGGAGAACCCC
GGCCTGTGGATCCTGGGCTGCCACAACAGCGACTTCAGGAACAGGGGCATGACCGCCCTGCTGAAA
GTCAGCAGCTGCGACAAGAACACCGGCGACTACTACGAGGACAGCTACGAGGACATCAGCGCCTAC
CTGCTGAGCAAGAACAACGCCATCGAGCCCAGGAGCTTCAGCCAGAACCCCCCCGTGCTGAAGAGG
CACCAGAGGGAGATCACCAGGACCACCCTGCAGAGCGACCAGGAGGAGATCGACTATGATGACACC
ATCAGCGTGGAGATGAAGAAGGAGGACTTCGACATCTACGACGAGGACGAGAACCAGAGCCCCAGG
AGCTTCCAGAAGAAGACCAGGCACTACTTCATCGCCGCCGTGGAGAGGCTGTGGGACTATGGCATG
AGCAGCAGCCCCCACGTGCTGAGGAACAGGGCCCAGAGCGGCAGCGTGCCCCAGTTCAAGAAGGTG (Continued)

Figure 41A

GTGTTCCAGGAGTTCACCGACGGCAGCTTCACCCAGCCCCTGTACAGAGGCGAGCTGAACGAGCAC
CTGGGCCTGCTGGGCCCCTACATCAGGGCCGAGGTGGAGGACAACATCATGGTGACCTTCAGGAAC
CAGGCCAGCAGGCCCTACAGCTTCTACAGCAGCCTGATCAGCTACGAGGAGGACCAGAGGCAGGGC
GCCGAGCCCAGGAAGAACTTCGTGAAGCCCAACGAGACCAAGACCTACTTCTGGAAGGTGCAGCAC
CACATGGCCCCCACCAAGGACGAGTTCGACTGCAAGGCCTGGGCCTACTTCTCTGATGTGGACCTG
GAGAAGGACGTGCACAGCGGCCTGATCGGCCCCCTGCTGGTGTGCCACACCAACACCCTGAACCCC
GCCCACGGCAGGCAGGTGACCGTGCAGGAGTTCGCCCTGTTCTTCACCATCTTCGACGAGACCAAG
AGCTGGTACTTCACCGAGAACATGGAGAGGAACTGCAGGGCCCCCTGCAACATCCAGATGGAGGAC
CCCACCTTCAAGGAGAACTACAGGTTCCACGCCATCAACGGCTACATCATGGACACCCTGCCCGGC
CTGGTGATGGCCCAGGACCAGAGGATCAGGTGGTATCTGCTGAGCATGGGCAGCAACGAGAACATC
CACAGCATCCACTTCAGCGGCCACGTGTTCACCGTGAGGAAGAAGGAGGAGTACAAGATGGCCCTG
TACAACCTGTACCCCGGCGTGTTCGAGACCGTGGAGATGCTGCCCAGCAAGGCCGGCATCTGGAGG
GTGGAGTGCCTGATCGGCGAGCACCTGCACGCCGGCATGAGCACCCTGTTCCTGGTGTACAGCAAC
AAGTGCCAGACCCCCCTGGGCATGGCCAGCGGCCACATCAGGGACTTCCAGATCACCGCCTCTGGC
CAGTACGGCCAGTGGGCCCCCAAGCTGGCCAGGCTGCACTACAGCGGCAGCATCAACGCCTGGAGC
ACCAAGGAGCCCTTCAGCTGGATCAAGGTGGACCTGCTGGCCCCCATGATCATCCACGGCATCAAG
ACCCAGGGCGCCAGGCAGAAGTTCAGCAGCCTGTACATCAGCCAGTTCATCATCATGTACAGCCTG
GACGGCAAGAAGTGGCAGACCTACAGGGGCAACAGCACCGGCACCCTGATGGTGTTCTTCGGCAAC
GTGGACAGCAGCGGCATCAAGCACAACATCTTCAACCCCCCCATCATCGCCAGGTACATCAGGCTG
CACCCCACCCACTACAGCATCAGGAGCACCCTGCGGATGGAACTGATGGGCTGCGACCTGAACAGC
TGCAGCATGCCCCTGGGCATGGAGAGCAAGGCCATCTCTGACGCCCAGATCACCGCCAGCAGCTAC
TTCACCAACATGTTCGCCACCTGGAGCCCCAGCAAGGCCAGGCTGCACCTGCAGGGCAGGAGCAAC
GCCTGGAGGCCCCAGGTGAACAACCCCAAGGAGTGGCTGCAGGTGGACTTCCAGAAGACCATGAAG
GTGACCGGCGTGACCACCCAGGGCGTGAAGAGCCTGCTGACCAGCATGTACGTGAAGGAGTTCCTG
ATCAGCAGCAGCCAGGACGGCCACCAGTGGACCCTGTTCTTCCAGAACGGCAAAGTGAAGGTGTTC
CAGGGCAACCAGGACAGCTTCACCCCCGTGGTGAACAGCCTGGACCCCCCCCTGCTGACCAGGTAT
CTGAGGATCCACCCCCAGAGCTGGGTGCACCAGATCGCCCTGAGAATGGAAGTGCTGGGATGCGAG
GCCCAGGACCTGTACTGA (SEQ ID NO:101)

ATGCAGATTGAGCTGAGCACCTGCTTCTTCCTGTGCCTGCTGAGGTTCTGCTTCTCTGCCACCAGG
AGATACTACCTGGGCGCCGTGGAGCTGAGCTGGGACTACATGCAGTCTGACCTGGGCGAGCTGCCT
GTGGACGCCAGGTTCCCCCCCAGAGTGCCCAAGAGCTTCCCCTTCAACACCTCAGTGGTGTACAAG
AAGACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGATCACCCTGAAGAACATG
GCCAGCCACCCCGTGAGCCTGCACGCCGTGGGCGTGAGCTACTGGAAGGCCTCTGAGGGCGCCGAG
TATGACGACCAGACCAGCCAGAGGGAGAAGGAGGACGACAAGGTGTTCCCCGGCGGCAGCCACACC
TACGTGTGGCAGGTGCTGAAGGAGAACGGCCCCATGGCCAGCGACCCCCTGTGCCTGACCTACAGC
TACCTGAGCCACGTGGACCTGGTGAAGGACCTGAACTCTGGCCTGATCGGCGCCCTGCTGGTGTGC
AGGGAGGGCAGCCTGGCCAAGGAGAAGACCCAGACCCTGCACAAGTTCATCCTGCTGTTCGCCGTG
TTCGATGAGGGCAAGAGCTGGCACAGCGAGACCAAGAACAGCCTGATGCAGGACAGGGATGCCGCC
TCTGCCAGGGCCTGGCCCAAGATGCACACCGTGAACGGCTACGTGAACAGGAGCCTGCCCGGCCTG
ATCGGCTGCCACAGGAAGTCTGTGTACTGGCACGTGATCGGCATGGGCACCACCCCCGAGGTGCAC
AGCATCTTCCTGGAGGGCCACACCTTCCTGGTGAGGAACCACAGGCAGGCCAGCCTGGAGATCAGC
CCCATCACCTTCCTGACCGCCCAGACCCTGCTGATGGACCTGGGCCAGTTCCTGCTGTCCTGCCAC
ATCAGCAGCCACCAGCACGACGGCATGGAGGCCTACGTGAAGGTGGACAGCTGCCCCGAGGAGCCC
CAGCTGAGGATGAAGAACAACGAGGAGGCCGAGGACTATGATGATGACCTGACCGACTCTGAGATG
GACGTGGTGAGGTTTGATGATGACAACAGCCCCAGCTTCATCCAGATCAGGTCTGTGGCCAAGAAG
CACCCCAAGACCTGGGTGCACTACATCGCCGCCGAGGAGGAGGACTGGGACTACGCCCCCCTGGTG
CTGGCCCCCGACGACAGGAGCTACAAGAGCCAGTACCTGAACAACGGCCCCCAGAGGATCGGCAGG
AAGTACAAGAAGGTCAGATTCATGGCCTACACCGACGAGACCTTCAAGACCAGGGAGGCCATCCAG
CACGAGTCTGGCATCCTGGGCCCCCTGCTGTACGGCGAGGTGGGCGACACCCTGCTGATCATCTTC
AAGAACCAGGCCAGCAGGCCCTACAACATCTACCCCCACGGCATCACCGATGTGAGGCCCCTGTAC
AGCAGGAGGCTGCCCAAGGGCGTGAAGCACCTGAAGGACTTCCCCATCCTGCCCGGCGAGATCTTC
AAGTACAAGTGGACCGTGACCGTGGAGGATGGCCCCACCAAGTCTGACCCCAGGTGCCTGACCAGG
TACTACAGCAGCTTCGTGAACATGGAGAGGGACCTGGCCTCTGGCCTGATCGGCCCCCTGCTGATC
TGCTACAAGGAGAGCGTGGACCAGAGGGGCAACCAGATCATGTCTGACAAGAGGAACGTGATCCTG
TTCTCTGTGTTCGATGAGAACAGGAGCTGGTATCTGACCGAGAACATCCAGAGGTTCCTGCCCAAC
CCCGCCGGCGTGCAGCTGGAGGACCCCGAGTTCCAGGCCAGCAACATCATGCACAGCATCAACGGC
TACGTGTTCGACAGCCTGCAGCTGTCTGTGTGCCTGCACGAGGTGGCCTACTGGTACATCCTGAGC
ATCGGCGCCCAGACCGACTTCCTGTCTGTGTTCTTCTCTGGCTACACCTTCAAGCACAAGATGGTG
TACGAGGACACCCTGACCCTGTTCCCCTTCAGCGGCGAGACCGTGTTCATGAGCATGGAGAACCCC
GGCCTGTGGATCCTGGGCTGCCACAACAGCGACTTCAGGAACAGGGGCATGACCGCCCTGCTGAAA
GTCAGCAGCTGCGACAAGAACACCGGCGACTACTACGAGGACAGCTACGAGGACATCAGCGCCTAC
CTGCTGAGCAAGAACAACGCCATCGAGCCCAGGAGCTTCAGCCAGAACCCCCCCGTGCTGAAGAGG
CACCAGAGGGAGATCACCAGGACCACCCTGCAGAGCGACCAGGAGGAGATCGACTATGATGACACC
ATCAGCGTGGAGATGAAGAAGGAGGACTTCGACATCTACGACGAGGACGAGAACCAGAGCCCCAGG
AGCTTCCAGAAGAAGACCAGGCACTACTTCATCGCCGCCGTGGAGAGGCTGTGGGACTATGGCATG
AGCAGCAGCCCCCACGTGCTGAGGAACAGGGCCCAGAGCGGCAGCGTGCCCCAGTTCAAGAAGGTG (Continued)

Figure 42A

GTGTTCCAGGAGTTCACCGACGGCAGCTTCACCCAGCCCCTGTACAGAGGCGAGCTGAACGAGCAC
CTGGGCCTGCTGGGCCCCTACATCAGGGCCGAGGTGGAGGACAACATCATGGTGACCTTCAGGAAC
CAGGCCAGCAGGCCCTACAGCTTCTACAGCAGCCTGATCAGCTACGAGGAGGACCAGAGGCAGGGC
GCCGAGCCCAGGAAGAACTTCGTGAAGCCCAACGAGACCAAGACCTACTTCTGGAAGGTGCAGCAC
CACATGGCCCCCACCAAGGACGAGTTCGACTGCAAGGCCTGGGCCTACTTCTCTGATGTGGACCTG
GAGAAGGACGTGCACAGCGGCCTGATCGGCCCCCTGCTGGTGTGCCACACCAACACCCTGAACCCC
GCCCACGGCAGGCAGGTGACCGTGCAGGAGTTCGCCCTGTTCTTCACCATCTTCGACGAGACCAAG
AGCTGGTACTTCACCGAGAACATGGAGAGGAACTGCAGGGCCCCCTGCAACATCCAGATGGAGGAC
CCCACCTTCAAGGAGAACTACAGGTTCCACGCCATCAACGGCTACATCATGGACACCCTGCCCGGC
CTGGTGATGGCCCAGGACCAGAGGATCAGGTGGTATCTGCTGAGCATGGGCAGCAACGAGAACATC
CACAGCATCCACTTCAGCGGCCACGTGTTCACCGTGAGGAAGAAGGAGGAGTACAAGATGGCCCTG
TACAACCTGTACCCCGGCGTGTTCGAGACCGTGGAGATGCTGCCCAGCAAGGCCGGCATCTGGAGG
GTGGAGTGCCTGATCGGCGAGCACCTGCACGCCGGCATGAGCACCCTGTTCCTGGTGTACAGCAAC
AAGTGCCAGACCCCCCTGGGCATGGCCAGCGGCCACATCAGGGACTTCCAGATCACCGCCTCTGGC
CAGTACGGCCAGTGGGCCCCCAAGCTGGCCAGGCTGCACTACAGCGGCAGCATCAACGCCTGGAGC
ACCAAGGAGCCCTTCAGCTGGATCAAGGTGGACCTGCTGGCCCCCATGATCATCCACGGCATCAAG
ACCCAGGGCGCCAGGCAGAAGTTCAGCAGCCTGTACATCAGCCAGTTCATCATCATGTACAGCCTG
GACGGCAAGAAGTGGCAGACCTACAGGGGCAACAGCACCGGCACCCTGATGGTGTTCTTCGGCAAC
GTGGACAGCAGCGGCATCAAGCACAACATCTTCAACCCCCCCATCATCGCCAGGTACATCAGGCTG
CACCCCACCCACTACAGCATCAGGAGCACCCTGCGGATGGAACTGATGGGCTGCGACCTGAACAGC
TGCAGCATGCCCCTGGGCATGGAGAGCAAGGCCATCTCTGACGCCCAGATCACCGCCAGCAGCTAC
TTCACCAACATGTTCGCCACCTGGAGCCCCAGCAAGGCCAGGCTGCACCTGCAGGGCAGGAGCAAC
GCCTGGAGGCCCCAGGTGAACAACCCCAAGGAGTGGCTGCAGGTGGACTTCCAGAAGACCATGAAG
GTGACCGGCGTGACCACCCAGGGCGTGAAGAGCCTGCTGACCAGCATGTACGTGAAGGAGTTCCTG
ATCAGCAGCAGCCAGGACGGCCACCAGTGGACCCTGTTCTTCCAGAACGGCAAAGTGAAGGTGTTC
CAGGGCAACCAGGACAGCTTCACCCCCGTGGTGAACAGCCTGGACCCCCCCCTGCTGACCAGGTAT
CTGAGGATCCACCCCCAGAGCTGGGTGCACCAGATCGCCCTGAGAATGGAAGTGCTGGGATGCGAG
GCCCAGGACCTGTACTGA (SEQ ID NO:102)

ATGCAGATTGAGCTGAGCACCTGCTTCTTCCTGTGCCTGCTGAGGTTCTGCTTCTCTGCCACCAGG
AGATACTACCTGGGCGCCGTGGAGCTGAGCTGGGACTACATGCAGTCTGACCTGGGCGAGCTGCCT
GTGGACGCCAGGTTCCCCCCCAGAGTGCCCAAGAGCTTCCCCTTCAACACCTCAGTGGTGTACAAG
AAGACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGGTCACCCTGAAGAACATG
GCCAGCCACCCCGTGAGCCTGCACGCCGTGGGCGTGAGCTACTGGAAGTCCTCTGAGGGCGCCGAG
TATGACGACCAGACCAGCCAGAGGGAGAAGGAGGACGACAAGGTGTTCCCCGGCAAGAGCCACACC
TACGTGTGGCAGGTGCTGAAGGAGAACGGCCCCACTGCCAGCGACCCCCCCTGCCTGACCTACAGC
TACCTGAGCCACGTGGACCTGGTGAAGGACCTGAACTCTGGCCTGATCGGCGCCCTGCTGGTGTGC
AGGGAGGGCAGCCTGGCCAAGGAGAAGACCCAGACCCTGCACAAGTTCATCCTGCTGTTCGCCGTG
TTCGATGAGGGCAAGAGCTGGCACAGCGAGACCAAGAACAGCCTGATGCAGGACAGGGATGCCGCC
TCTGCCAGGGCCTGGCCCAAGATGCACACCGTGAACGGCTACGTGAACAGGAGCCTGCCCGGCCTG
ATCGGCTGCCACAGGAAGTCTGTGTACTGGCACGTGATCGGCATGGGCACCACCCCCGAGGTGCAC
AGCATCTTCCTGGAGGGCCACACCTTCCTGGTGAGGAACCACAGGCAGGCCAGCCTGGAGATCAGC
CCCATCACCTTCCTGACCGCCCAGACCCTGCTGATGGACCTGGGCCAGTTCCTGCTGTTCTGCCAC
ATCAGCAGCCACCAGCACGACGGCATGGAGGCCTACGTGAAGGTGGACAGCTGCCCCGAGGAGCCC
CAGCTGAGGATGAAGAACAACGAGGAGGCCGAGGACTATGATGATGACCTGACCGACTCTGAGATG
GACGTGGTGAGGTTTGATGATGACAACAGCCCCAGCTTCATCCAGATCAGGTCTGTGGCCAAGAAG
CACCCCAAGACCTGGGTGCACTACATCGCCGCCGAGGAGGAGGACTGGGACTACGCCCCCCTGGTG
CTGGCCCCCGACGACAGGAGCTACAAGAGCCAGTACCTGAACAACGGCCCCCAGAGGATCGGCAGG
AAGTACAAGAAGGTCAGATTCATGGCCTACACCGACGAGACCTTCAAGACCAGGGAGGCCATCCAG
CACGAGTCTGGCATCCTGGGCCCCCTGCTGTACGGCGAGGTGGGCGACACCCTGCTGATCATCTTC
AAGAACCAGGCCAGCAGGCCCTACAACATCTACCCCCACGGCATCACCGATGTGAGGCCCCTGTAC
AGCAGGAGGCTGCCCAAGGGCGTGAAGCACCTGAAGGACTTCCCCATCCTGCCCGGCGAGATCTTC
AAGTACAAGTGGACCGTGACCGTGGAGGATGGCCCCACCAAGTCTGACCCCAGGTGCCTGACCAGG
TACTACAGCAGCTTCGTGAACATGGAGAGGGACCTGGCCTCTGGCCTGATCGGCCCCCTGCTGATC
TGCTACAAGGAGAGCGTGGACCAGAGGGGCAACCAGATCATGTCTGACAAGAGGAACGTGATCCTG
TTCTCTGTGTTCGATGAGAACAGGAGCTGGTATCTGACCGAGAACATCCAGAGGTTCCTGCCCAAC
CCCGCCGGCGTGCAGCTGGAGGACCCCGAGTTCCAGGCCAGCAACATCATGCACAGCATCAACGGC
TACGTGTTCGACAGCCTGCAGCTGTCTGTGTGCCTGCACGAGGTGGCCTACTGGTACATCCTGAGC
ATCGGCGCCCAGACCGACTTCCTGTCTGTGTTCTTCTCTGGCTACACCTTCAAGCACAAGATGGTG
TACGAGGACACCCTGACCCTGTTCCCCTTCAGCGGCGAGACCGTGTTCATGAGCATGGAGAACCCC
GGCCTGTGGATCCTGGGCTGCCACAACAGCGACTTCAGGAACAGGGGCATGACCGCCCTGCTGAAA
GTCAGCAGCTGCGACAAGAACACCGGCGACTACTACGAGGACAGCTACGAGGACATCAGCGCCTAC
CTGCTGAGCAAGAACAACACCACCTACGTGAACCGCTCCCTGAGCCAGAACCCCCCCGTGCTGAAG
AGGCACCAGAGGGAGATCACCAGGACCACCCTGCAGAGCGACCAGGAGGAGATCGACTATGATGAC
ACCATCAGCGTGGAGATGAAGAAGGAGGACTTCGACATCTACGACGAGGACGAGAACCAGAGCCCC
AGGAGCTTCCAGAAGAAGACCAGGCACTACTTCATCGCCGCCGTGGAGAGGCTGTGGGACTATGGC
ATGAGCAGCAGCCCCCACGTGCTGAGGAACAGGGCCCAGAGCGGCAGCGTGCCCCAGTTCAAGAAG (Continued)

Figure 43A

GTGGTGTTCCAGGAGTTCACCGACGGCAGCTTCACCCAGCCCCTGTACAGAGGCGAGCTGAACGAG
CACCTGGGCCTGCTGGGCCCCTACATCAGGGCCGAGGTGGAGGACAACATCATGGTGACCTTCAGG
AACCAGGCCAGCAGGCCCTACAGCTTCTACAGCAGCCTGATCAGCTACGAGGAGGACCAGAGGCAG
GGCGCCGAGCCCAGGAAGAACTTCGTGAAGCCCAACGAGACCAAGACCTACTTCTGGAAGGTGCAG
CACCACATGGCCCCCACCAAGGACGAGTTCGACTGCAAGGCCTGGGCCTACTTCTCTGATGTGGAC
CTGGAGAAGGACGTGCACAGCGGCCTGATCGGCCCCCTGCTGGTGTGCCACACCAACACCCTGAAC
CCCGCCCACGGCAGGCAGGTGACCGTGCAGGAGTTCGCCCTGTTCTTCACCATCTTCGACGAGACC
AAGAGCTGGTACTTCACCGAGAACATGGAGAGGAACTGCAGGGCCCCCTGCAACATCCAGATGGAG
GACCCCACCTTCAAGGAGAACTACAGGTTCCACGCCATCAACGGCTACATCATGGACACCCTGCCC
GGCCTGGTGATGGCCCAGGACCAGAGGATCAGGTGGTATCTGCTGAGCATGGGCAGCAACGAGAAC
ATCCACAGCATCCACTTCAGCGGCCACGTGTTCACCGTGAGGAAGAAGGAGGAGTACAAGATGGCC
CTGTACAACCTGTACCCCGGCGTGTTCGAGACCGTGGAGATGCTGCCCAGCAAGGCCGGCATCTGG
AGGGTGGAGTGCCTGATCGGCGAGCACCTGCACGCCGGCATGAGCACCCTGTTCCTGGTGTACAGC
AACAAGTGCCAGACCCCCCTGGGCATGGCCAGCGGCCACATCAGGGACTTCCAGATCACCGCCTCT
GGCCAGTACGGCCAGTGGGCCCCCAAGCTGGCCAGGCTGCACTACAGCGGCAGCATCAACGCCTGG
AGCACCAAGGAGCCCTTCAGCTGGATCAAGGTGGACCTGCTGGCCCCCATGATCATCCACGGCATC
AAGACCCAGGGCGCCAGGCAGAAGTTCAGCAGCCTGTACATCAGCCAGTTCATCATCATGTACAGC
CTGGACGGCAAGAAGTGGCAGACCTACAGGGGCAACAGCACCGGCACCCTGATGGTGTTCTTCGGC
AACGTGGACAGCAGCGGCATCAAGCACAACATCTTCAACCCCCCCATCATCGCCAGGTACATCAGG
CTGCACCCCACCCACTACAGCATCAGGAGCACCCTGCGGATGGAACTGATGGGCTGCGACCTGAAC
AGCTGCAGCATGCCCCTGGGCATGGAGAGCAAGGCCATCTCTGACGCCCAGATCACCGCCAGCAGC
TACTTCACCAACATGTTCGCCACCTGGAGCCCCAGCAAGGCCAGGCTGCACCTGCAGGGCAGGAGC
AACGCCTGGAGGCCCCAGGTGAACAACCCCAAGGAGTGGCTGCAGGTGGACTTCCAGAAGACCATG
AAGGTGACCGGCGTGACCACCCAGGGCGTGAAGAGCCTGCTGACCAGCATGTACGTGAAGGAGTTC
CTGATCAGCAGCAGCCAGGACGGCCACCAGTGGACCCTGTTCTTCCAGAACGGCAAAGTGAAGGTG
TTCCAGGGCAACCAGGACAGCTTCACCCCCGTGGTGAACAGCCTGGACCCCCCCCTGCTGACCAGG
TATCTGAGGATCCACCCCCAGAGCTGGGTGCACCAGATCGCCCTGAGAATGGAAGTGCTGGGATGC
GAGGCCCAGGACCTGTACTGA (SEQ ID NO:103)

Figure 43B

| | | Algorithm | | |
|---|---|---|---|---|
| | | CS01 | CS04 | CS23 |
| Mutation(s) | X1, F328S | pCS01m13 | pCS04m13 | pCS23m13 |
| | X1 | pCS01m3 | pCS04m3 | pCS23m3 |
| | X5 | pCS01m2 | pCS04m2 | pCS23m2 |
| | F328S | pCS01m1 | pCS04m1 | pCS23m1 |
| | X1, X5 | pCS01m23 | pCS04m23 | pCS23m23 |

CS01-HC-NA

```
                                                                        gcc
accaggagat actacctggg ggctgtggaa ctttcttggg actacatgca gtctgacctg
ggagagctgc ctgtggatgc caggttccca cccagagtgc ccaagtcctt cccattcaac
acctctgtgg tctacaagaa gacactcttt gtggaattca ctgaccacct gttcaacatt
gcaaaaccca gaccaccctg gatgggactc ctgggaccca ccattcaggc tgaggtgtat
gacactgtgg tcatcaccct caagaacatg gcatcccacc ctgtgtctct gcatgctgtg
ggagtctcat actggaaagc ctctgaaggg gctgagtatg atgaccagac atcccagaga
gagaaagagg atgacaaggt gttccctggg ggatctcaca cctatgtgtg gcaagtcctc
aaggagaatg gacccatggc atctgaccca ctctgcctga catactccta cctttctcat
gtggacctgg tcaaggacct caactctgga ctgattgggg cactgctggt gtgcagggaa
ggatccctgg ccaaggagaa aacccagaca ctgcacaagt tcattctcct gtttgctgtc
tttgatgagg gcaagtcttg gcactctgaa acaaagaact ccctgatgca agacagggat
gctgcctctg ccagggcatg gcccaagatg cacactgtga atggctatgt gaacagatca
ctgcctggac tcattggctg ccacaggaaa tctgtctact ggcatgtgat tggcatgggg
acaacccctg aagtgcactc cattttcctg gagggacaca ccttcctggt caggaaccac
agacaagcct ctctggagat ctctcccatc accttcctca ctgcacagac actgctgatg
gaccttggac agttcctgct gttctgccac atctcttccc accagcatga tggcatggaa
gcctatgtca aggtggactc atgccctgag gaaccacagc tcaggatgaa gaacaatgag
gaggctgagg actatgatga tgacctgact gactctgaga tggatgtggt cagatttgat
gatgacaact ctccatcctt cattcagatc aggtctgtgg caaagaaaca ccccaagaca
tgggtgcact acattgctgc tgaggaagag gactgggact atgcaccact ggtcctggcc
cctgatgaca ggagctacaa gtctcagtac ctcaacaatg gcccacaaag aattggaaga
aagtacaaga aagtcagatt catggcctac actgatgaaa ccttcaagac aagagaagcc
attcagcatg agtctggcat tctgggacca ctcctgtatg gggaagtggg agacaccctg
ctcatcatct tcaagaacca ggcctccagg ccctacaaca tctacccaca tggcatcact
gatgtcaggc ccctgtacag caggagactg ccaaaagggg tgaaacacct caaggacttc
cccattctgc ctggagagat cttcaagtac aagtggactg tcactgtgga ggatggacca
acaaagtctg accccaggtg cctcaccaga tactactcct cttttgtgaa catggagaga
gacctggcat ctggactgat tggaccactg ctcatctgct acaaggagtc tgtggaccag
agaggcaacc agatcatgtc tgacaagaga aatgtgattc tgttctctgt ctttgatgag
aacagatcat ggtacctgac tgagaacatt cagagattcc tgcccaaccc tgctggggtg
caactggaag accctgagtt ccaggcaagc aacatcatgc actccatcaa tggctatgtg
tttgactctc tccagctttc tgtctgcctg catgaggtgg cctactggta cattctttct
attggggcac aaactgactt cctttctgtc ttcttctctg gatacacctt caagcacaag
atggtgtatg aggacaccct gacactcttc ccattctctg ggaaactgt gttcatgagc
atggagaacc ctggactgtg gattctggga tgccacaact ctgacttcag aaacagggga
atgactgcac tgctcaaagt ctcctcctgt gacaagaaca ctggggacta ctatgaggac
tcttatgagg acatctctgc ctacctgctc agcaagaaca atgccattga gcccaga
(SEQ ID NO:24X)
```

```
                                                  g agatcaccag gacaaccctc
cagtctgacc aggaagagat tgactatgat gacaccattt ctgtggagat gaagaaggag
gactttgaca tctatgatga ggacgagaac cagtctccaa gatcattcca gaagaagaca
agacactact tcattgctgc tgtggaaaga ctgtgggact atggcatgtc ttcctctccc
catgtcctca ggaacagggc acagtctggc tctgtgccac agttcaagaa agtggtcttc
caggagttca ctgatggctc attcacccag cccctgtaca gaggggaact gaatgagcac
ctgggactcc tgggaccata catcagggct gaggtggaag acaacatcat ggtgacattc
agaaaccagg cctccaggcc ctacagcttc tactcttccc tcatcagcta tgaggaagac
cagagacaag gggctgagcc aagaaagaac tttgtgaaac ccaatgaaac caagacctac
ttctggaaag tccagcacca catggcaccc accaaggatg agtttgactg caaggcctgg
gcatacttct ctgatgtgga cctggagaaa gatgtgcact ctggcctgat tggcccactc
ctggtctgcc acaccaacac cctgaaccct gcacatggaa ggcaagtgac tgtgcaggag
tttgccctct tcttcaccat ctttgatgaa accaagtcat ggtacttcac tgagaacatg
gagagaaact gcagagcacc atgcaacatt cagatggaag accccacctt caaggagaac
tacaggttcc atgccatcaa tggctacatc atggacaccc tgcctgggct tgtcatggca
caggaccaga gaatcagatg gtacctgctt tctatgggat ccaatgagaa cattcactcc
atccacttct ctgggcatgt cttcactgtg agaaagaagg aggaatacaa gatggccctg
tacaacctct accctggggt ctttgagact gtggagatgc tgccctccaa agctggcatc
tggagggtgg aatgcctcat tggggagcac ctgcatgctg gcatgtcaac cctgttcctg
gtctacagca acaagtgcca gacacccctg ggaatggcct ctggccacat cagggacttc
cagatcactg cctctggcca gtatggccag tgggcaccca aactggccag gctccactac
tctggctcca tcaatgcatg gtcaacccag gagccattct cttggatcaa ggtggacctg
ctggcaccca tgatcattca tggcatcaag acacaggggg caagacagaa attctcctct
ctgtacatct cacagttcat catcatgtac tctctggatg gcaagaagtg gcagacatac
agaggcaact ccactggcac cctcatggtc ttctttggca atgtggacag ctctggcatc
aagcacaaca tcttcaaccc tcccatcatt gccagataca tcaggctgca ccccacccac
tactcaatca gatcaaccct caggatggaa ctgatgggat gtgacctgaa ctcctgctca
atgcccctgg gaatggagag caaggccatt tctgatgccc agatcactgc atcctcttac
ttcaccaaca tgtttgccac ctggtcacca tcaaaagcca ggctgcacct ccagggaaga
agcaatgcct ggagacccca ggtcaacaac ccaaaggaat ggctgcaagt ggacttccag
aagacaatga aagtcactgg ggtgacaacc caggggtca agtctctgct cacctcaatg
tatgtgaagg agttcctgat ctcttcctca caggatggcc accagtggac actcttcttc
cagaatggca aagtcaaggt gttccagggc aaccaggact ctttcacacc tgtggtgaac
tcactggacc cccccctcct gacaagatac ctgagaattc acccccagtc ttgggtccac
cagattgccc tgagaatgga agtcctggga tgtgaggcac aagacctgta c
(SEQ ID NO:25)
```

ATGCAGATTGAGCTGTCCACCTGCTTCTTTCTGTGCCTGCTGAGATTCTGCTTCTCTGCCACCAGGAGATAC
TACCTGGGGGCTGTGGAACTTTCTTGGGACTACATGCAGTCTGACCTGGGAGAGCTGCCTGTGGATGCCAGG
TTCCCACCCAGAGTGCCCAAGTCCTTCCCATTCAACACCTCTGTGGTCTACAAGAAGACACTCTTTGTGGAA
TTCACTGACCACCTGTTCAACATTGCAAAACCCAGACCACCCTGGATGGGACTCCTGGGACCCACCATTCAG
GCTGAGGTGTATGACACTGTGGTCATCACCCTCAAGAACATGGCATCCCACCCTGTGTCTCTGCATGCTGTG
GGAGTCTCATACTGGAAAGCCTCTGAAGGGGCTGAGTATGATGACCAGACATCCCAGAGAGAGAAAGAGGAT
GACAAGGTGTTCCCTGGGGGATCTCACACCTATGTGTGGCAAGTCCTCAAGGAGAATGGACCCATGGCATCT
GACCCACTCTGCCTGACATACTCCTACCTTTCTCATGTGGACCTGGTCAAGGACCTCAACTCTGGACTGATT
GGGGCACTGCTGGTGTGCAGGGAAGGATCCCTGGCCAAGGAGAAAACCCAGACACTGCACAAGTTCATTCTC
CTGTTTGCTGTCTTTGATGAGGGCAAGTCTTGGCACTCTGAAACAAAGAACTCCCTGATGCAAGACAGGGAT
GCTGCCTCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGGACAACCCCTGAAGTGCACTCCATT
TTCCTGGAGGGACACACCTTCCTGGTCAGGAACCACAGACAAGCCTCTCTGGAGATCTCTCCCATCACCTTC
CTCACTGCACAGACACTGCTGATGGACCTTGGACAGTTCCTGCTGTTCTGCCACATCTCTTCCCACCAGCAT
GATGGCATGGAAGCCTATGTCAAGGTGGACTCATGCCCTGAGGAACCACAGCTCAGGATGAAGAACAATGAG
GAGGCTGAGGACTATGATGATGACCTGACTGACTCTGAGATGGATGTGGTCAGATTTGATGATGACAACTCT
CCATCCTTCATTCAGATCAGGTCTGTGGCAAAGAAACACCCCAAGACATGGGTGCACTACATTGCTGCTGAG
GAAGAGGACTGGGACTATGCACCACTGGTCCTGGCCCCTGATGACAGGAGCTACAAGTCTCAGTACCTCAAC
AATGGCCCACAAAGAATTGGAAGAAAGTACAAGAAAGTCAGATTCATGGCCTACACTGATGAAACCTTCAAG
ACAAGAGAAGCCATTCAGCATGAGTCTGGCATTCTGGGACCACTCCTGTATGGGGAAGTGGGAGACACCCTG
CTCATCATCTTCAAGAACCAGGCCTCCAGGCCCTACAACATCTACCCACATGGCATCACTGATGTCAGGCCC
CTGTACAGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGATACTAC
TCCTCTTTTGTGAACATGGAGAGAGACCTGGCATCTGGACTGATTGGACCACTGCTCATCTGCTACAAGGAG
TCTGTGGACCAGAGAGGCAACCAGATCATGTCTGACAAGAGAAATGTGATTCTGTTCTCTGTCTTTGATGAG
AACAGATCATGGTACCTGACTGAGAACATTCAGAGATTCCTGCCCAACCCTGCTGGGGTGCAACTGGAAGAC
CCTGAGTTCCAGGCAAGCAACATCATGCACTCCATCAATGGCTATGTGTTTGACTCTCTCCAGCTTTCTGTC
TGCCTGCATGAGGTGGCCTACTGGTACATTCTTTCTATTGGGGCACAAACTGACTTCCTTTCTGTCTTCTTC
TCTGGATACACCTTCAAGCACAAGATGGTGTATGAGGACACCCTGACACTCTTCCCATTCTCTGGGGAAACT
GTGTTCATGAGCATGGAGAACCCTGGACTGTGGATTCTGGGATGCCACAACTCTGACTTCAGAAACAGGGGA
ATGACTGCACTGCTCAAAGTCTCCTCCTGTGACAAGAACACTGGGGACTACTATGAGGACTCTTATGAGGAC
ATCTCTGCCTACCTGCTCAGCAAGAACAATGCCATTGAGCCCAGAGAGATCACCAGGACAACCCTCCAGTCT
GACCAGGAAGAGATTGACTATGATGACACCATTTCTGTGGAGATGAAGAAGGAGGACTTTGACATCTATGAT
GAGGACGAGAACCAGTCTCCAAGATCATTCCAGAAGAAGACAAGACACTACTTCATTGCTGCTGTGGAAAGA
CTGTGGGACTATGGCATGTCTTCCTCTCCCCATGTCCTCAGGAACAGGGCACAGTCTGGCTCTGTGCCACAG
TTCAAGAAAGTGGTCTTCCAGGAGTTCACTGATGGCTCATTCACCCAGCCCCTGTACAGAGGGGAACTGAAT
GAGCACCTGGGACTCCTGGGACCATACATCAGGGCTGAGGTGGAAGACAACATCATGGTGACATTCAGAAAC
CAGGCCTCCAGGCCCTACAGCTTCTACTCTTCCCTCATCAGCTATGAGGAAGACCAGAGACAAGGGGCTGAG
CCAAGAAAGAACTTTGTGAAACCCAATGAAACCAAGACCTACTTCTGGAAAGTCCAGCACCACATGGCACCC (Continued)

Figure 49A

ACCAAGGATGAGTTTGACTGCAAGGCCTGGGCATACTTCTCTGATGTGGACCTGGAGAAAGATGTGCACTCT
GGCCTGATTGGCCCACTCCTGGTCTGCCACACCAACACCCTGAACCCTGCACATGGAAGGCAAGTGACTGTG
CAGGAGTTTGCCCTCTTCTTCACCATCTTTGATGAAACCAAGTCATGGTACTTCACTGAGAACATGGAGAGA
AACTGCAGAGCACCATGCAACATTCAGATGGAAGACCCCACCTTCAAGGAGAACTACAGGTTCCATGCCATC
AATGGCTACATCATGGACACCCTGCCTGGGCTTGTCATGGCACAGGACCAGAGAATCAGATGGTACCTGCTT
TCTATGGGATCCAATGAGAACATTCACTCCATCCACTTCTCTGGGCATGTCTTCACTGTGAGAAAGAAGGAG
GAATACAAGATGGCCCTGTACAACCTCTACCCTGGGGTCTTTGAGACTGTGGAGATGCTGCCCTCCAAAGCT
GGCATCTGGAGGGTGGAATGCCTCATTGGGGAGCACCTGCATGCTGGCATGTCAACCCTGTTCCTGGTCTAC
AGCAACAAGTGCCAGACACCCCTGGGAATGGCCTCTGGCCACATCAGGGACTTCCAGATCACTGCCTCTGGC
CAGTATGGCCAGTGGGCACCCAAACTGGCCAGGCTCCACTACTCTGGCTCCATCAATGCATGGTCAACCAAG
GAGCCATTCTCTTGGATCAAGGTGGACCTGCTGGCACCCATGATCATTCATGGCATCAAGACACAGGGGGCA
AGACAGAAATTCTCCTCTCTGTACATCTCACAGTTCATCATCATGTACTCTCTGGATGGCAAGAAGTGGCAG
ACATACAGAGGCAACTCCACTGGCACCCTCATGGTCTTCTTTGGCAATGTGGACAGCTCTGGCATCAAGCAC
AACATCTTCAACCCTCCCATCATTGCCAGATACATCAGGCTGCACCCCACCCACTACTCAATCAGATCAACC
CTCAGGATGGAACTGATGGGATGTGACCTGAACTCCTGCTCAATGCCCCTGGGAATGGAGAGCAAGGCCATT
TCTGATGCCCAGATCACTGCATCCTCTTACTTCACCAACATGTTTGCCACCTGGTCACCATCAAAAGCCAGG
CTGCACCTCCAGGGAAGAAGCAATGCCTGGAGACCCCAGGTCAACAACCCAAAGGAATGGCTGCAAGTGGAC
TTCCAGAAGACAATGAAAGTCACTGGGGTGACAACCCAGGGGGTCAAGTCTCTGCTCACCTCAATGTATGTG
AAGGAGTTCCTGATCTCTTCCTCACAGGATGGCCACCAGTGGACACTCTTCTTCCAGAATGGCAAAGTCAAG
GTGTTCCAGGGCAACCAGGACTCTTTCACACCTGTGGTGAACTCACTGGACCCCCCCCTCCTGACAAGATAC
CTGAGAATTCACCCCCAGTCTTGGGTCCACCAGATTGCCCTGAGAATGGAAGTCCTGGGATGTGAGGCACAA
GACCTGTACTGA (SEQ ID NO:26)

ATGCAGATTGAGCTGTCCACCTGCTTCTTTCTGTGCCTGCTGAGATTCTGCTTCTCTGCCACCAGG
AGATACTACCTGGGGGCTGTGGAACTTTCTTGGGACTACATGCAGTCTGACCTGGGAGAGCTGCCT
GTGGATGCCAGGTTCCCACCCAGAGTGCCCAAGTCCTTCCCATTCAACACCTCTGTGGTCTACAAG
AAGACACTCTTTGTGGAATTCACTGACCACCTGTTCAACATTGCAAAACCCAGACCACCCTGGATG
GGACTCCTGGGACCCACCATTCAGGCTGAGGTGTATGACACTGTGGTCATCACCCTCAAGAACATG
GCATCCCACCCTGTGTCTCTGCATGCTGTGGGAGTCTCATACTGGAAAGCCTCTGAAGGGGCTGAG
TATGATGACCAGACATCCCAGAGAGAGAAAGAGGATGACAAGGTGTTCCCTGGGGGATCTCACACC
TATGTGTGGCAAGTCCTCAAGGAGAATGGACCCATGGCATCTGACCCACTCTGCCTGACATACTCC
TACCTTTCTCATGTGGACCTGGTCAAGGACCTCAACTCTGGACTGATTGGGGCACTGCTGGTGTGC
AGGGAAGGATCCCTGGCCAAGGAGAAAACCCAGACACTGCACAAGTTCATTCTCCTGTTTGCTGTC
TTTGATGAGGGCAAGTCTTGGCACTCTGAAACAAAGAACTCCCTGATGCAAGACAGGGATGCTGCC
TCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGGACAACCCCTGAAGTGCAC
TCCATTTTCCTGGAGGGACACACCTTCCTGGTCAGGAACCACAGACAAGCCTCTCTGGAGATCTCT
CCCATCACCTTCCTCACTGCACAGACACTGCTGATGGACCTTGGACAGTTCCTGCTGTTCTGCCAC
ATCTCTTCCCACCAGCATGATGGCATGGAAGCCTATGTCAAGGTGGACTCATGCCCTGAGGAACCA
CAGCTCAGGATGAAGAACAATGAGGAGGCTGAGGACTATGATGATGACCTGACTGACTCTGAGATG
GATGTGGTCAGATTTGATGATGACAACTCTCCATCCTTCATTCAGATCAGGTCTGTGGCAAAGAAA
CACCCCAAGACATGGGTGCACTACATTGCTGCTGAGGAAGAGGACTGGGACTATGCACCACTGGTC
CTGGCCCCTGATGACAGGAGCTACAAGTCTCAGTACCTCAACAATGGCCCACAAAGAATTGGAAGA
AAGTACAAGAAAGTCAGATTCATGGCCTACACTGATGAAACCTTCAAGACAAGAGAAGCCATTCAG
CATGAGTCTGGCATTCTGGGACCACTCCTGTATGGGGAAGTGGGAGACACCCTGCTCATCATCTTC
AAGAACCAGGCCTCCAGGCCCTACAACATCTACCCACATGGCATCACTGATGTCAGGCCCCTGTAC
AGCAGGAGACTGCCAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGA
TACTACTCCTCTTTTGTGAACATGGAGAGAGACCTGGCATCTGGACTGATTGGACCACTGCTCATC
TGCTACAAGGAGTCTGTGGACCAGAGAGGCAACCAGATCATGTCTGACAAGAGAAATGTGATTCTG
TTCTCTGTCTTTGATGAGAACAGATCATGGTACCTGACTGAGAACATTCAGAGATTCCTGCCCAAC
CCTGCTGGGGTGCAACTGGAAGACCCTGAGTTCCAGGCAAGCAACATCATGCACTCCATCAATGGC
TATGTGTTTGACTCTCTCCAGCTTTCTGTCTGCCTGCATGAGGTGGCCTACTGGTACATTCTTTCT
ATTGGGGCACAAACTGACTTCCTTTCTGTCTTCTTCTCTGGATACACCTTCAAGCACAAGATGGTG
TATGAGGACACCCTGACACTCTTCCCATTCTCTGGGGAAACTGTGTTCATGAGCATGGAGAACCCT
GGACTGTGGATTCTGGGATGCCACAACTCTGACTTCAGAAACAGGGGAATGACTGCACTGCTCAAA
GTCTCCTCCTGTGACAAGAACACTGGGGACTACTATGAGGACTCTTATGAGGACATCTCTGCCTAC
CTGCTCAGCAAGAACAATGCCATTGAGCCCAGAAGCTTCTCTCAGAATTCCAGACACCCCAGCACC
AGGGAGATCACCAGGACAACCCTCCAGTCTGACCAGGAAGAGATTGACTATGATGACACCATTTCT
GTGGAGATGAAGAAGGAGGACTTTGACATCTATGATGAGGACGAGAACCAGTCTCCAAGATCATTC (Continued)

Figure 50A

CAGAAGAAGACAAGACACTACTTCATTGCTGCTGTGGAAAGACTGTGGGACTATGGCATGTCTTCC
TCTCCCCATGTCCTCAGGAACAGGGCACAGTCTGGCTCTGTGCCACAGTTCAAGAAAGTGGTCTTC
CAGGAGTTCACTGATGGCTCATTCACCCAGCCCCTGTACAGAGGGGAACTGAATGAGCACCTGGGA
CTCCTGGGACCATACATCAGGGCTGAGGTGGAAGACAACATCATGGTGACATTCAGAAACCAGGCC
TCCAGGCCCTACAGCTTCTACTCTTCCCTCATCAGCTATGAGGAAGACCAGAGACAAGGGGCTGAG
CCAAGAAAGAACTTTGTGAAACCCAATGAAACCAAGACCTACTTCTGGAAAGTCCAGCACCACATG
GCACCCACCAAGGATGAGTTTGACTGCAAGGCCTGGGCATACTTCTCTGATGTGGACCTGGAGAAA
GATGTGCACTCTGGCCTGATTGGCCCACTCCTGGTCTGCCACACCAACACCCTGAACCCTGCACAT
GGAAGGCAAGTGACTGTGCAGGAGTTTGCCCTCTTCTTCACCATCTTTGATGAAACCAAGTCATGG
TACTTCACTGAGAACATGGAGAGAAACTGCAGAGCACCATGCAACATTCAGATGGAAGACCCCACC
TTCAAGGAGAACTACAGGTTCCATGCCATCAATGGCTACATCATGGACACCCTGCCTGGGCTTGTC
ATGGCACAGGACCAGAGAATCAGATGGTACCTGCTTTCTATGGGATCCAATGAGAACATTCACTCC
ATCCACTTCTCTGGGCATGTCTTCACTGTGAGAAAGAAGGAGGAATACAAGATGGCCCTGTACAAC
CTCTACCCTGGGGTCTTTGAGACTGTGGAGATGCTGCCCTCCAAAGCTGGCATCTGGAGGGTGGAA
TGCCTCATTGGGGAGCACCTGCATGCTGGCATGTCAACCCTGTTCCTGGTCTACAGCAACAAGTGC
CAGACACCCCTGGGAATGGCCTCTGGCCACATCAGGGACTTCCAGATCACTGCCTCTGGCCAGTAT
GGCCAGTGGGCACCCAAACTGGCCAGGCTCCACTACTCTGGCTCCATCAATGCATGGTCAACCAAG
GAGCCATTCTCTTGGATCAAGGTGGACCTGCTGGCACCCATGATCATTCATGGCATCAAGACACAG
GGGGCAAGACAGAAATTCTCCTCTCTGTACATCTCACAGTTCATCATCATGTACTCTCTGGATGGC
AAGAAGTGGCAGACATACAGAGGCAACTCCACTGGCACCCTCATGGTCTTCTTTGGCAATGTGGAC
AGCTCTGGCATCAAGCACAACATCTTCAACCCTCCCATCATTGCCAGATACATCAGGCTGCACCCC
ACCCACTACTCAATCAGATCAACCCTCAGGATGGAACTGATGGGATGTGACCTGAACTCCTGCTCA
ATGCCCCTGGGAATGGAGAGCAAGGCCATTTCTGATGCCCAGATCACTGCATCCTCTTACTTCACC
AACATGTTTGCCACCTGGTCACCATCAAAAGCCAGGCTGCACCTCCAGGGAAGAAGCAATGCCTGG
AGACCCCAGGTCAACAACCCAAAGGAATGGCTGCAAGTGGACTTCCAGAAGACAATGAAAGTCACT
GGGGTGACAACCCAGGGGGTCAAGTCTCTGCTCACCTCAATGTATGTGAAGGAGTTCCTGATCTCT
TCCTCACAGGATGGCCACCAGTGGACACTCTTCTTCCAGAATGGCAAAGTCAAGGTGTTCCAGGGC
AACCAGGACTCTTTCACACCTGTGGTGAACTCACTGGACCCCCCCCTCCTGACAAGATACCTGAGA
ATTCACCCCCAGTCTTGGGTCCACCAGATTGCCCTGAGAATGGAAGTCCTGGGATGTGAGGCACAA
GACCTGTACTGA (SEQ ID NO:27)

ATGCAGATTGAGCTGAGCACCTGCTTCTTCCTGTGCCTGCTGAGGTTCTGCTTCTCTGCCACCAGGAGATAC
TACCTGGGCGCCGTGGAGCTGAGCTGGGACTACATGCAGTCTGACCTGGGCGAGCTGCCTGTGGACGCCAGG
TTCCCCCCCAGAGTGCCCAAGAGCTTCCCCTTCAACACCTCAGTGGTGTACAAGAAGACCCTGTTCGTGGAG
TTCACCGACCACCTGTTCAACATCGCCAAGCCCAGGCCCCCCTGGATGGGCCTGCTGGGCCCCACCATCCAG
GCCGAGGTGTACGACACCGTGGTGATCACCCTGAAGAACATGGCCAGCCACCCCGTGAGCCTGCACGCCGTG
GGCGTGAGCTACTGGAAGGCCTCTGAGGGCGCCGAGTATGACGACCAGACCAGCCAGAGGGAGAAGGAGGAC
GACAAGGTGTTCCCCGGCGGCAGCCACACCTACGTGTGGCAGGTGCTGAAGGAGAACGGCCCCATGGCCAGC
GACCCCCTGTGCCTGACCTACAGCTACCTGAGCCACGTGGACCTGGTGAAGGACCTGAACTCTGGCCTGATC
GGCGCCCTGCTGGTGTGCAGGGAGGGCAGCCTGGCCAAGGAGAAGACCCAGACCCTGCACAAGTTCATCCTG
CTGTTCGCCGTGTTCGATGAGGGCAAGAGCTGGCACAGCGAGACCAAGAACAGCCTGATGCAGGACAGGGAT
GCCGCCTCTGCCAGGGCCTGGCCCAAGATGCACACCGTGAACGGCTACGTGAACAGGAGCCTGCCCGGCCTG
ATCGGCTGCCACAGGAAGTCTGTGTACTGGCACGTGATCGGCATGGGCACCACCCCCGAGGTGCACAGCATC
TTCCTGGAGGGCCACACCTTCCTGGTGAGGAACCACAGGCAGGCCAGCCTGGAGATCAGCCCCATCACCTTC
CTGACCGCCCAGACCCTGCTGATGGACCTGGGCCAGTTCCTGCTGTTCTGCCACATCAGCAGCCACCAGCAC
GACGGCATGGAGGCCTACGTGAAGGTGGACAGCTGCCCCGAGGAGCCCCAGCTGAGGATGAAGAACAACGAG
GAGGCCGAGGACTATGATGATGACCTGACCGACTCTGAGATGGACGTGGTGAGGTTTGATGATGACAACAGC
CCCAGCTTCATCCAGATCAGGTCTGTGGCCAAGAAGCACCCCAAGACCTGGGTGCACTACATCGCCGCCGAG
GAGGAGGACTGGGACTACGCCCCCCTGGTGCTGGCCCCCGACGACAGGAGCTACAAGAGCCAGTACCTGAAC
AACGGCCCCCAGAGGATCGGCAGGAAGTACAAGAAGGTCAGATTCATGGCCTACACCGACGAGACCTTCAAG
ACCAGGGAGGCCATCCAGCACGAGTCTGGCATCCTGGGCCCCCTGCTGTACGGCGAGGTGGGCGACACCCTG
CTGATCATCTTCAAGAACCAGGCCAGCAGGCCCTACAACATCTACCCCCACGGCATCACCGATGTGAGGCCC
CTGTACAGCAGGAGGCTGCCCAAGGGCGTGAAGCACCTGAAGGACTTCCCCATCCTGCCCGGCGAGATCTTC
AAGTACAAGTGGACCGTGACCGTGGAGGATGGCCCCACCAAGTCTGACCCCAGGTGCCTGACCAGGTACTAC
AGCAGCTTCGTGAACATGGAGAGGGACCTGGCCTCTGGCCTGATCGGCCCCCTGCTGATCTGCTACAAGGAG
AGCGTGGACCAGAGGGGCAACCAGATCATGTCTGACAAGAGGAACGTGATCCTGTTCTCTGTGTTCGATGAG
AACAGGAGCTGGTATCTGACCGAGAACATCCAGAGGTTCCTGCCCAACCCCGCCGGCGTGCAGCTGGAGGAC
CCCGAGTTCCAGGCCAGCAACATCATGCACAGCATCAACGGCTACGTGTTCGACAGCCTGCAGCTGTCTGTG
TGCCTGCACGAGGTGGCCTACTGGTACATCCTGAGCATCGGCGCCCAGACCGACTTCCTGTCTGTGTTCTTC
TCTGGCTACACCTTCAAGCACAAGATGGTGTACGAGGACACCCTGACCCTGTTCCCCTTCAGCGGCGAGACC
GTGTTCATGAGCATGGAGAACCCCGGCCTGTGGATCCTGGGCTGCCACAACAGCGACTTCAGGAACAGGGGC
ATGACCGCCCTGCTGAAAGTCAGCAGCTGCGACAAGAACACCGGCGACTACTACGAGGACAGCTACGAGGAC
ATCAGCGCCTACCTGCTGAGCAAGAACAACGCCATCGAGCCCAGGGAGATCACCAGGACCACCCTGCAGAGC
GACCAGGAGGAGATCGACTATGATGACACCATCAGCGTGGAGATGAAGAAGGAGGACTTCGACATCTACGAC
GAGGACGAGAACCAGAGCCCCAGGAGCTTCCAGAAGAAGACCAGGCACTACTTCATCGCCGCCGTGGAGAGG
CTGTGGGACTATGGCATGAGCAGCAGCCCCCACGTGCTGAGGAACAGGGCCCAGAGCGGCAGCGTGCCCCAG
TTCAAGAAGGTGGTGTTCCAGGAGTTCACCGACGGCAGCTTCACCCAGCCCCTGTACAGAGGCGAGCTGAAC
GAGCACCTGGGCCTGCTGGGCCCCTACATCAGGGCCGAGGTGGAGGACAACATCATGGTGACCTTCAGGAAC
CAGGCCAGCAGGCCCTACAGCTTCTACAGCAGCCTGATCAGCTACGAGGAGGACCAGAGGCAGGGCGCCGAG (Continued)

Figure 51A

CCCAGGAAGAACTTCGTGAAGCCCAACGAGACCAAGACCTACTTCTGGAAGGTGCAGCACCACATGGCCCCC
ACCAAGGACGAGTTCGACTGCAAGGCCTGGGCCTACTTCTCTGATGTGGACCTGGAGAAGGACGTGCACAGC
GGCCTGATCGGCCCCCTGCTGGTGTGCCACACCAACACCCTGAACCCCGCCCACGGCAGGCAGGTGACCGTG
CAGGAGTTCGCCCTGTTCTTCACCATCTTCGACGAGACCAAGAGCTGGTACTTCACCGAGAACATGGAGAGG
AACTGCAGGGCCCCCTGCAACATCCAGATGGAGGACCCCACCTTCAAGGAGAACTACAGGTTCCACGCCATC
AACGGCTACATCATGGACACCCTGCCCGGCCTGGTGATGGCCCAGGACCAGAGGATCAGGTGGTATCTGCTG
AGCATGGGCAGCAACGAGAACATCCACAGCATCCACTTCAGCGGCCACGTGTTCACCGTGAGGAAGAAGGAG
GAGTACAAGATGGCCCTGTACAACCTGTACCCCGGCGTGTTCGAGACCGTGGAGATGCTGCCCAGCAAGGCC
GGCATCTGGAGGGTGGAGTGCCTGATCGGCGAGCACCTGCACGCCGGCATGAGCACCCTGTTCCTGGTGTAC
AGCAACAAGTGCCAGACCCCCCTGGGCATGGCCAGCGGCCACATCAGGGACTTCCAGATCACCGCCTCTGGC
CAGTACGGCCAGTGGGCCCCCAAGCTGGCCAGGCTGCACTACAGCGGCAGCATCAACGCCTGGAGCACCAAG
GAGCCCTTCAGCTGGATCAAGGTGGACCTGCTGGCCCCCATGATCATCCACGGCATCAAGACCCAGGGCGCC
AGGCAGAAGTTCAGCAGCCTGTACATCAGCCAGTTCATCATCATGTACAGCCTGGACGGCAAGAAGTGGCAG
ACCTACAGGGGCAACAGCACCGGCACCCTGATGGTGTTCTTCGGCAACGTGGACAGCAGCGGCATCAAGCAC
AACATCTTCAACCCCCCCATCATCGCCAGGTACATCAGGCTGCACCCCACCCACTACAGCATCAGGAGCACC
CTGCGGATGGAACTGATGGGCTGCGACCTGAACAGCTGCAGCATGCCCCTGGGCATGGAGAGCAAGGCCATC
TCTGACGCCCAGATCACCGCCAGCAGCTACTTCACCAACATGTTCGCCACCTGGAGCCCCAGCAAGGCCAGG
CTGCACCTGCAGGGCAGGAGCAACGCCTGGAGGCCCCAGGTGAACAACCCCAAGGAGTGGCTGCAGGTGGAC
TTCCAGAAGACCATGAAGGTGACCGGCGTGACCACCCAGGGCGTGAAGAGCCTGCTGACCAGCATGTACGTG
AAGGAGTTCCTGATCAGCAGCAGCCAGGACGGCCACCAGTGGACCCTGTTCTTCCAGAACGGCAAAGTGAAG
GTGTTCCAGGGCAACCAGGACAGCTTCACCCCCGTGGTGAACAGCCTGGACCCCCCCCTGCTGACCAGGTAT
CTGAGGATCCACCCCCAGAGCTGGGTGCACCAGATCGCCCTGAGAATGGAAGTGCTGGGATGCGAGGCCCAG
GACCTGTACTGA (SEQ ID NO:28)

ATGCAGATTGAGCTGAGCACCTGCTTCTTCCTGTGCCTGCTGAGGTTCTGCTTCTCTGCCACCAGG
AGATACTACCTGGGCGCCGTGGAGCTGAGCTGGGACTACATGCAGTCTGACCTGGGCGAGCTGCCT
GTGGACGCCAGGTTCCCCCCCAGAGTGCCCAAGAGCTTCCCCTTCAACACCTCAGTGGTGTACAAG
AAGACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGATCACCCTGAAGAACATG
GCCAGCCACCCCGTGAGCCTGCACGCCGTGGGCGTGAGCTACTGGAAGGCCTCTGAGGGCGCCGAG
TATGACGACCAGACCAGCCAGAGGGAGAAGGAGGACGACAAGGTGTTCCCCGGCGGCAGCCACACC
TACGTGTGGCAGGTGCTGAAGGAGAACGGCCCCATGGCCAGCGACCCCCTGTGCCTGACCTACAGC
TACCTGAGCCACGTGGACCTGGTGAAGGACCTGAACTCTGGCCTGATCGGCGCCCTGCTGGTGTGC
AGGGAGGGCAGCCTGGCCAAGGAGAAGACCCAGACCCTGCACAAGTTCATCCTGCTGTTCGCCGTG
TTCGATGAGGGCAAGAGCTGGCACAGCGAGACCAAGAACAGCCTGATGCAGGACAGGGATGCCGCC
TCTGCCAGGGCCTGGCCCAAGATGCACACCGTGAACGGCTACGTGAACAGGAGCCTGCCCGGCCTG
ATCGGCTGCCACAGGAAGTCTGTGTACTGGCACGTGATCGGCATGGGCACCACCCCCGAGGTGCAC
AGCATCTTCCTGGAGGGCCACACCTTCCTGGTGAGGAACCACAGGCAGGCCAGCCTGGAGATCAGC
CCCATCACCTTCCTGACCGCCCAGACCCTGCTGATGGACCTGGGCCAGTTCCTGCTGTTCTGCCAC
ATCAGCAGCCACCAGCACGACGGCATGGAGGCCTACGTGAAGGTGGACAGCTGCCCCGAGGAGCCC
CAGCTGAGGATGAAGAACAACGAGGAGGCCGAGGACTATGATGATGACCTGACCGACTCTGAGATG
GACGTGGTGAGGTTTGATGATGACAACAGCCCCAGCTTCATCCAGATCAGGTCTGTGGCCAAGAAG
CACCCCAAGACCTGGGTGCACTACATCGCCGCCGAGGAGGAGGACTGGGACTACGCCCCCCTGGTG
CTGGCCCCCGACGACAGGAGCTACAAGAGCCAGTACCTGAACAACGGCCCCCAGAGGATCGGCAGG
AAGTACAAGAAGGTCAGATTCATGGCCTACACCGACGAGACCTTCAAGACCAGGGAGGCCATCCAG
CACGAGTCTGGCATCCTGGGCCCCCTGCTGTACGGCGAGGTGGGCGACACCCTGCTGATCATCTTC
AAGAACCAGGCCAGCAGGCCCTACAACATCTACCCCCACGGCATCACCGATGTGAGGCCCCTGTAC
AGCAGGAGGCTGCCCAAGGGCGTGAAGCACCTGAAGGACTTCCCCATCCTGCCCGGCGAGATCTTC
AAGTACAAGTGGACCGTGACCGTGGAGGATGGCCCCACCAAGTCTGACCCCAGGTGCCTGACCAGG
TACTACAGCAGCTTCGTGAACATGGAGAGGGACCTGGCCTCTGGCCTGATCGGCCCCCTGCTGATC
TGCTACAAGGAGAGCGTGGACCAGAGGGGCAACCAGATCATGTCTGACAAGAGGAACGTGATCCTG
TTCTCTGTGTTCGATGAGAACAGGAGCTGGTATCTGACCGAGAACATCCAGAGGTTCCTGCCCAAC
CCCGCCGGCGTGCAGCTGGAGGACCCCGAGTTCCAGGCCAGCAACATCATGCACAGCATCAACGGC
TACGTGTTCGACAGCCTGCAGCTGTCTGTGTGCCTGCACGAGGTGGCCTACTGGTACATCCTGAGC
ATCGGCGCCCAGACCGACTTCCTGTCTGTGTTCTTCTCTGGCTACACCTTCAAGCACAAGATGGTG
TACGAGGACACCCTGACCCTGTTCCCCTTCAGCGGCGAGACCGTGTTCATGAGCATGGAGAACCCC
GGCCTGTGGATCCTGGGCTGCCACAACAGCGACTTCAGGAACAGGGGCATGACCGCCCTGCTGAAA
GTCAGCAGCTGCGACAAGAACACCGGCGACTACTACGAGGACAGCTACGAGGACATCAGCGCCTAC
CTGCTGAGCAAGAACAACGCCATCGAGCCCAGGAGCTTCAGCCAGAACTCCAGACACCCCAGCACC (Continued)

Figure 52A

AGGGAGATCACCAGGACCACCCTGCAGAGCGACCAGGAGGAGATCGACTATGATGACACCATCAGC
GTGGAGATGAAGAAGGAGGACTTCGACATCTACGACGAGGACGAGAACCAGAGCCCCAGGAGCTTC
CAGAAGAAGACCAGGCACTACTTCATCGCCGCCGTGGAGAGGCTGTGGGACTATGGCATGAGCAGC
AGCCCCCACGTGCTGAGGAACAGGGCCCAGAGCGGCAGCGTGCCCCAGTTCAAGAAGGTGGTGTTC
CAGGAGTTCACCGACGGCAGCTTCACCCAGCCCCTGTACAGAGGCGAGCTGAACGAGCACCTGGGC
CTGCTGGGCCCCTACATCAGGGCCGAGGTGGAGGACAACATCATGGTGACCTTCAGGAACCAGGCC
AGCAGGCCCTACAGCTTCTACAGCAGCCTGATCAGCTACGAGGAGGACCAGAGGCAGGGCGCCGAG
CCCAGGAAGAACTTCGTGAAGCCCAACGAGACCAAGACCTACTTCTGGAAGGTGCAGCACCACATG
GCCCCCACCAAGGACGAGTTCGACTGCAAGGCCTGGGCCTACTTCTCTGATGTGGACCTGGAGAAG
GACGTGCACAGCGGCCTGATCGGCCCCCTGCTGGTGTGCCACACCAACACCCTGAACCCCGCCCAC
GGCAGGCAGGTGACCGTGCAGGAGTTCGCCCTGTTCTTCACCATCTTCGACGAGACCAAGAGCTGG
TACTTCACCGAGAACATGGAGAGGAACTGCAGGGCCCCCTGCAACATCCAGATGGAGGACCCCACC
TTCAAGGAGAACTACAGGTTCCACGCCATCAACGGCTACATCATGGACACCCTGCCCGGCCTGGTG
ATGGCCCAGGACCAGAGGATCAGGTGGTATCTGCTGAGCATGGGCAGCAACGAGAACATCCACAGC
ATCCACTTCAGCGGCCACGTGTTCACCGTGAGGAAGAAGGAGGAGTACAAGATGGCCCTGTACAAC
CTGTACCCCGGCGTGTTCGAGACCGTGGAGATGCTGCCCAGCAAGGCCGGCATCTGGAGGGTGGAG
TGCCTGATCGGCGAGCACCTGCACGCCGGCATGAGCACCCTGTTCCTGGTGTACAGCAACAAGTGC
CAGACCCCCCTGGGCATGGCCAGCGGCCACATCAGGGACTTCCAGATCACCGCCTCTGGCCAGTAC
GGCCAGTGGGCCCCCAAGCTGGCCAGGCTGCACTACAGCGGCAGCATCAACGCCTGGAGCACCAAG
GAGCCCTTCAGCTGGATCAAGGTGGACCTGCTGGCCCCCATGATCATCCACGGCATCAAGACCCAG
GGCGCCAGGCAGAAGTTCAGCAGCCTGTACATCAGCCAGTTCATCATCATGTACAGCCTGGACGGC
AAGAAGTGGCAGACCTACAGGGGCAACAGCACCGGCACCCTGATGGTGTTCTTCGGCAACGTGGAC
AGCAGCGGCATCAAGCACAACATCTTCAACCCCCCCATCATCGCCAGGTACATCAGGCTGCACCCC
ACCCACTACAGCATCAGGAGCACCCTGCGGATGGAACTGATGGGCTGCGACCTGAACAGCTGCAGC
ATGCCCCTGGGCATGGAGAGCAAGGCCATCTCTGACGCCCAGATCACCGCCAGCAGCTACTTCACC
AACATGTTCGCCACCTGGAGCCCCAGCAAGGCCAGGCTGCACCTGCAGGGCAGGAGCAACGCCTGG
AGGCCCCAGGTGAACAACCCCAAGGAGTGGCTGCAGGTGGACTTCCAGAAGACCATGAAGGTGACC
GGCGTGACCACCCAGGGCGTGAAGAGCCTGCTGACCAGCATGTACGTGAAGGAGTTCCTGATCAGC
AGCAGCCAGGACGGCCACCAGTGGACCCTGTTCTTCCAGAACGGCAAAGTGAAGGTGTTCCAGGGC
AACCAGGACAGCTTCACCCCCGTGGTGAACAGCCTGGACCCCCCCCTGCTGACCAGGTATCTGAGG
ATCCACCCCCAGAGCTGGGTGCACCAGATCGCCCTGAGAATGGAAGTGCTGGGATGCGAGGCCCAG
GACCTGTACTGA (SEQ ID NO:29)

Figure 52B

CS01m23-FL-AA (SEQ ID NO: 104)

MQIELSTCFFLCLLRFCFSATRRYYLGAVELSWDYMQSDLGELPVDARFPPRVPKSFPFN
TSVVYKKTLFVEFTDHLFNIAKPRPPWMGLLGPTIQAEVYDTVVVTLKNMASHPVSLHAV
GVSYWKSSEGAEYDDQTSQREKEDDKVFPGKSHTYVWQVLKENGPTASDPPCLTYSYLSH
VDLVKDLNSGLIGALLVCREGSLAKEKTQTLHKFILLFAVFDEGKSWHSETKNSLMQDRD
AASARAWPKMHTVNGYVNRSLPGLIGCHRKSVYWHVIGMGTTPEVHSIFLEGHTFLVRNH
RQASLEISPITFLTAQTLLMDLGQFLLFCHISSHQHDGMEAYVKVDSCPEEPQLRMKNNE
EAEDYDDDLTDSEMDVVRFDDDNSPSFIQIRSVAKKHPKTWVHYIAAEEEDWDYAPLVLA
PDDRSYKSQYLNNGPQRIGRKYKKVRFMAYTDETFKTREAIQHESGILGPLLYGEVGDTL
LIIFKNQASRPYNIYPHGITDVRPLYSRRLPKGVKHLKDFPILPGEIFKYKWTVTVEDGP
TKSDPRCLTRYYSSFVNMERDLASGLIGPLLICYKESVDQRGNQIMSDKRNVILFSVFDE
NRSWYLTENIQRFLPNPAGVQLEDPEFQASNIMHSINGYVFDSLQLSVCLHEVAYWYILS
IGAQTDFLSVFFSGYTFKHKMVYEDTLTLFPFSGETVFMSMENPGLWILGCHNSDFRNRG
MTALLKVSSCDKNTGDYYEDSYEDISAYLLSKNNTTYVNRSLSQNPPVLKRHQREITRTT
LQSDQEEIDYDDTISVEMKKEDFDIYDEDENQSPRSFQKKTRHYFIAAVERLWDYGMSSS
PHVLRNRAQSGSVPQFKKVVFQEFTDGSFTQPLYRGELNEHLGLLGPYIRAEVEDNIMVT
FRNQASRPYSFYSSLISYEEDQRQGAEPRKNFVKPNETKTYFWKVQHHMAPTKDEFDCKA
WAYFSDVDLEKDVHSGLIGPLLVCHTNTLNPAHGRQVTVQEFALFFTIFDETKSWYFTEN
MERNCRAPCNIQMEDPTFKENYRFHAINGYIMDTLPGLVMAQDQRIRWYLLSMGSNENIH
SIHFSGHVFTVRKKEEYKMALYNLYPGVFETVEMLPSKAGIWRVECLIGEHLHAGMSTLF
LVYSNKCQTPLGMASGHIRDFQITASGQYGQWAPKLARLHYSGSINAWSTKEPFSWIKVD
LLAPMIIHGIKTQGARQKFSSLYISQFIIMYSLDGKKWQTYRGNSTGTLMVFFGNVDSSG
IKHNIFNPPIIARYIRLHPTHYSIRSTLRMELMGCDLNSCSMPLGMESKAISDAQITASS
YFTNMFATWSPSKARLHLQGRSNAWRPQVNNPKEWLQVDFQKTMKVTGVTTQGVKSLLTS
MYVKEFLISSSQDGHQWTLFFQNGKVKVFQGNQDSFTPVVNSLDPPLLTRYLRIHPQSWV
HQIALRMEVLGCEAQDLY

Figure 53

CS04m3-FL-AA (SEQ ID NO: 105)

MQIELSTCFFLCLLRFCFSATRRYYLGAVELSWDYMQSDLGELPVDARFPPRVPKSFPFN
TSVVYKKTLFVEFTDHLFNIAKPRPPWMGLLGPTIQAEVYDTVVITLKNMASHPVSLHAV
GVSYWKASEGAEYDDQTSQREKEDDKVFPGGSHTYVWQVLKENGPMASDPLCLTYSYLSH
VDLVKDLNSGLIGALLVCREGSLAKEKTQTLHKFILLFAVFDEGKSWHSETKNSLMQDRD
AASARAWPKMHTVNGYVNRSLPGLIGCHRKSVYWHVIGMGTTPEVHSIFLEGHTFLVRNH
RQASLEISPITFLTAQTLLMDLGQFLLFCHISSHQHDGMEAYVKVDSCPEEPQLRMKNNE
EAEDYDDDLTDSEMDVVRFDDDNSPSFIQIRSVAKKHPKTWVHYIAAEEEDWDYAPLVLA
PDDRSYKSQYLNNGPQRIGRKYKKVRFMAYTDETFKTREAIQHESGILGPLLYGEVGDTL
LIIFKNQASRPYNIYPHGITDVRPLYSRRLPKGVKHLKDFPILPGEIFKYKWTVTVEDGP
TKSDPRCLTRYYSSFVNMERDLASGLIGPLLICYKESVDQRGNQIMSDKRNVILFSVFDE
NRSWYLTENIQRFLPNPAGVQLEDPEFQASNIMHSINGYVFDSLQLSVCLHEVAYWYILS
IGAQTDFLSVFFSGYTFKHKMVYEDTLTLFPFSGETVFMSMENPGLWILGCHNSDFRNRG
MTALLKVSSCDKNTGDYYEDSYEDISAYLLSKNNTTYVNRSLSQNPPVLKRHQREITRTT
LQSDQEEIDYDDTISVEMKKEDFDIYDEDENQSPRSFQKKTRHYFIAAVERLWDYGMSSS
PHVLRNRAQSGSVPQFKKVVFQEFTDGSFTQPLYRGELNEHLGLLGPYIRAEVEDNIMVT
FRNQASRPYSFYSSLISYEEDQRQGAEPRKNFVKPNETKTYFWKVQHHMAPTKDEFDCKA
WAYFSDVDLEKDVHSGLIGPLLVCHTNTLNPAHGRQVTVQEFALFFTIFDETKSWYFTEN
MERNCRAPCNIQMEDPTFKENYRFHAINGYIMDTLPGLVMAQDQRIRWYLLSMGSNENIH
SIHFSGHVFTVRKKEEYKMALYNLYPGVFETVEMLPSKAGIWRVECLIGEHLHAGMSTLF
LVYSNKCQTPLGMASGHIRDFQITASGQYGQWAPKLARLHYSGSINAWSTKEPFSWIKVD
LLAPMIIHGIKTQGARQKFSSLYISQFIIMYSLDGKKWQTYRGNSTGTLMVFFGNVDSSG
IKHNIFNPPIIARYIRLHPTHYSIRSTLRMELMGCDLNSCSMPLGMESKAISDAQITASS
YFTNMFATWSPSKARLHLQGRSNAWRPQVNNPKEWLQVDFQKTMKVTGVTTQGVKSLLTS
MYVKEFLISSSQDGHQWTLFFQNGKVKVFQGNQDSFTPVVNSLDPPLLTRYLRIHPQSWV
HQIALRMEVLGCEAQDLY

Figure 54

CS01-FL-AAm12 (SEQ ID NO: 106)

MQIELSTCFFLCLLRFCFSATRRYYLGAVELSWDYMQSDLGELPVDARFPPRVPKSFPFNTSVVYK
KTLFVEFTDHLFNIAKPRPPWMGLLGPTIQAEVYDTVVVTLKNMASHPVSLHAVGVSYWKSSEGAE
YDDQTSQREKEDDKVFPGKSHTYVWQVLKENGPTASDPPCLTYSYLSHVDLVKDLNSGLIGALLVC
REGSLAKEKTQTLHKFILLFAVFDEGKSWHSETKNSLMQDRDAASARAWPKMHTVNGYVNRSLPGL
IGCHRKSVYWHVIGMGTTPEVHSIFLEGHTFLVRNHRQASLEISPITFLTAQTLLMDLGQFLLSCH
ISSHQHDGMEAYVKVDSCPEEPQLRMKNNEEAEDYDDDLTDSEMDVVRFDDDNSPSFIQIRSVAKK
HPKTWVHYIAAEEEDWDYAPLVLAPDDRSYKSQYLNNGPQRIGRKYKKVRFMAYTDETFKTREAIQ
HESGILGPLLYGEVGDTLLIIFKNQASRPYNIYPHGITDVRPLYSRRLPKGVKHLKDFPILPGEIF
KYKWTVTVEDGPTKSDPRCLTRYYSSFVNMERDLASGLIGPLLICYKESVDQRGNQIMSDKRNVIL
FSVFDENRSWYLTENIQRFLPNPAGVQLEDPEFQASNIMHSINGYVFDSLQLSVCLHEVAYWYILS
IGAQTDFLSVFFSGYTFKHKMVYEDTLTLFPFSGETVFMSMENPGLWILGCHNSDFRNRGMTALLK
VSSCDKNTGDYYEDSYEDISAYLLSKNNAIEPRSFSQNPPVLKRHQREITRTTLQSDQEEIDYDDT
ISVEMKKEDFDIYDEDENQSPRSFQKKTRHYFIAAVERLWDYGMSSSPHVLRNRAQSGSVPQFKKV
VFQEFTDGSFTQPLYRGELNEHLGLLGPYIRAEVEDNIMVTFRNQASRPYSFYSSLISYEEDQRQG
AEPRKNFVKPNETKTYFWKVQHHMAPTKDEFDCKAWAYFSDVDLEKDVHSGLIGPLLVCHTNTLNP
AHGRQVTVQEFALFFTIFDETKSWYFTENMERNCRAPCNIQMEDPTFKENYRFHAINGYIMDTLPG
LVMAQDQRIRWYLLSMGSNENIHSIHFSGHVFTVRKKEEYKMALYNLYPGVFETVEMLPSKAGIWR
VECLIGEHLHAGMSTLFLVYSNKCQTPLGMASGHIRDFQITASGQYGQWAPKLARLHYSGSINAWS
TKEPFSWIKVDLLAPMIIHGIKTQGARQKFSSLYISQFIIMYSLDGKKWQTYRGNSTGTLMVFFGN
VDSSGIKHNIFNPPIIARYIRLHPTHYSIRSTLRMELMGCDLNSCSMPLGMESKAISDAQITASSY
FTNMFATWSPSKARLHLQGRSNAWRPQVNNPKEWLQVDFQKTMKVTGVTTQGVKSLLTSMYVKEFL
ISSSQDGHQWTLFFQNGKVKVFQGNQDSFTPVVNSLDPPLLTRYLRIHPQSWVHQIALRMEVLGCE
AQDLY

Figure 55

CS04-FL-AAm12 (SEQ ID NO: 107)

MQIELSTCFFLCLLRFCFSATRRYYLGAVELSWDYMQSDLGELPVDARFPPRVPKSFPFNTSVVYK
KTLFVEFTDHLFNIAKPRPPWMGLLGPTIQAEVYDTVVVTLKNMASHPVSLHAVGVSYWKSSEGAE
YDDQTSQREKEDDKVFPGKSHTYVWQVLKENGPTASDPPCLTYSYLSHVDLVKDLNSGLIGALLVC
REGSLAKEKTQTLHKFILLFAVFDEGKSWHSETKNSLMQDRDAASARAWPKMHTVNGYVNRSLPGL
IGCHRKSVYWHVIGMGTTPEVHSIFLEGHTFLVRNHRQASLEISPITFLTAQTLLMDLGQFLLSCH
ISSHQHDGMEAYVKVDSCPEEPQLRMKNNEEAEDYDDDLTDSEMDVVRFDDDNSPSFIQIRSVAKK
HPKTWVHYIAAEEEDWDYAPLVLAPDDRSYKSQYLNNGPQRIGRKYKKVRFMAYTDETFKTREAIQ
HESGILGPLLYGEVGDTLLIIFKNQASRPYNIYPHGITDVRPLYSRRLPKGVKHLKDFPILPGEIF
KYKWTVTVEDGPTKSDPRCLTRYYSSFVNMERDLASGLIGPLLICYKESVDQRGNQIMSDKRNVIL
FSVFDENRSWYLTENIQRFLPNPAGVQLEDPEFQASNIMHSINGYVFDSLQLSVCLHEVAYWYILS
IGAQTDFLSVFFSGYTFKHKMVYEDTLTLFPFSGETVFMSMENPGLWILGCHNSDFRNRGMTALLK
VSSCDKNTGDYYEDSYEDISAYLLSKNNAIEPRSFSQNPPVLKRHQREITRTTLQSDQEEIDYDDT
ISVEMKKEDFDIYDEDENQSPRSFQKKTRHYFIAAVERLWDYGMSSSPHVLRNRAQSGSVPQFKKV
VFQEFTDGSFTQPLYRGELNEHLGLLGPYIRAEVEDNIMVTFRNQASRPYSFYSSLISYEEDQRQG
AEPRKNFVKPNETKTYFWKVQHHMAPTKDEFDCKAWAYFSDVDLEKDVHSGLIGPLLVCHTNTLNP
AHGRQVTVQEFALFFTIFDETKSWYFTENMERNCRAPCNIQMEDPTFKENYRFHAINGYIMDTLPG
LVMAQDQRIRWYLLSMGSNENIHSIHFSGHVFTVRKKEEYKMALYNLYPGVFETVEMLPSKAGIWR
VECLIGEHLHAGMSTLFLVYSNKCQTPLGMASGHIRDFQITASGQYGQWAPKLARLHYSGSINAWS
TKEPFSWIKVDLLAPMIIHGIKTQGARQKFSSLYISQFIIMYSLDGKKWQTYRGNSTGTLMVFFGN
VDSSGIKHNIFNPPIIARYIRLHPTHYSIRSTLRMELMGCDLNSCSMPLGMESKAISDAQITASSY
FTNMFATWSPSKARLHLQGRSNAWRPQVNNPKEWLQVDFQKTMKVTGVTTQGVKSLLTSMYVKEFL
ISSSQDGHQWTLFFQNGKVKVFQGNQDSFTPVVNSLDPPLLTRYLRIHPQSWVHQIALRMEVLGCE
AQDLY

Figure 56

CS01-FL-NAm12 (SEQ ID NO: 108)

ATGCAGATTGAGCTGTCCACCTGCTTCTTTCTGTGCCTGCTGAGATTCTGCTTCTCTGCCACCAGG
AGATACTACCTGGGGGCTGTGGAACTTTCTTGGGACTACATGCAGTCTGACCTGGGAGAGCTGCCT
GTGGATGCCAGGTTCCCACCCAGAGTGCCCAAGTCCTTCCCATTCAACACCTCTGTGGTCTACAAG
AAGACACTCTTTGTGGAATTCACTGACCACCTGTTCAACATTGCAAAACCCAGACCACCCTGGATG
GGACTCCTGGGACCCACCATTCAGGCTGAGGTGTATGACACTGTGGTCGTCACCCTCAAGAACATG
GCATCCCACCCTGTGTCTCTGCATGCTGTGGGAGTCTCATACTGGAAATCCTCTGAAGGGGCTGAG
TATGATGACCAGACATCCCAGAGAGAGAAAGAGGATGACAAGGTGTTCCCTGGGAAGTCTCACACC
TATGTGTGGCAAGTCCTCAAGGAGAATGGACCCACTGCATCTGACCCACCCTGCCTGACATACTCC
TACCTTTCTCATGTGGACCTGGTCAAGGACCTCAACTCTGGACTGATTGGGGCACTGCTGGTGTGC
AGGGAAGGATCCCTGGCCAAGGAGAAAACCCAGACACTGCACAAGTTCATTCTCCTGTTTGCTGTC
TTTGATGAGGGCAAGTCTTGGCACTCTGAAACAAAGAACTCCCTGATGCAAGACAGGGATGCTGCC
TCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGGACAACCCCTGAAGTGCAC
TCCATTTTCCTGGAGGGACACACCTTCCTGGTCAGGAACCACAGACAAGCCTCTCTGGAGATCTCT
CCCATCACCTTCCTCACTGCACAGACACTGCTGATGGACCTTGGACAGTTCCTGCTGTCCTGCCAC
ATCTCTTCCCACCAGCATGATGGCATGGAAGCCTATGTCAAGGTGGACTCATGCCCTGAGGAACCA
CAGCTCAGGATGAAGAACAATGAGGAGGCTGAGGACTATGATGATGACCTGACTGACTCTGAGATG
GATGTGGTCAGATTTGATGATGACAACTCTCCATCCTTCATTCAGATCAGGTCTGTGGCAAAGAAA
CACCCCAAGACATGGGTGCACTACATTGCTGCTGAGGAAGAGGACTGGGACTATGCACCACTGGTC
CTGGCCCCTGATGACAGGAGCTACAAGTCTCAGTACCTCAACAATGGCCCACAAAGAATTGGAAGA
AAGTACAAGAAAGTCAGATTCATGGCCTACACTGATGAAACCTTCAAGACAAGAGAAGCCATTCAG
CATGAGTCTGGCATTCTGGGACCACTCCTGTATGGGGAAGTGGGAGACACCCTGCTCATCATCTTC
AAGAACCAGGCCTCCAGGCCCTACAACATCTACCCACATGGCATCACTGATGTCAGGCCCCTGTAC
AGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGA
TACTACTCCTCTTTTGTGAACATGGAGAGAGACCTGGCATCTGGACTGATTGGACCACTGCTCATC
TGCTACAAGGAGTCTGTGGACCAGAGAGGCAACCAGATCATGTCTGACAAGAGAAATGTGATTCTG
TTCTCTGTCTTTGATGAGAACAGATCATGGTACCTGACTGAGAACATTCAGAGATTCCTGCCCAAC
CCTGCTGGGGTGCAACTGGAAGACCCTGAGTTCCAGGCAAGCAACATCATGCACTCCATCAATGGC
TATGTGTTTGACTCTCTCCAGCTTTCTGTCTGCCTGCATGAGGTGGCCTACTGGTACATTCTTTCT
ATTGGGGCACAAACTGACTTCCTTTCTGTCTTCTTCTCTGGATACACCTTCAAGCACAAGATGGTG
TATGAGGACACCCTGACACTCTTCCCATTCTCTGGGGAAACTGTGTTCATGAGCATGGAGAACCCT
GGACTGTGGATTCTGGGATGCCACAACTCTGACTTCAGAAACAGGGGAATGACTGCACTGCTCAAA
GTCTCCTCCTGTGACAAGAACACTGGGGACTACTATGAGGACTCTTATGAGGACATCTCTGCCTAC
CTGCTCAGCAAGAACAATGCCATTGAGCCCAGAAGCTTCTCTCAGAATCCACCTGTCCTGAAGAGA
CACCAGAGAGAGATCACCAGGACAACCCTCCAGTCTGACCAGGAAGAGATTGACTATGATGACACC
ATTTCTGTGGAGATGAAGAAGGAGGACTTTGACATCTATGATGAGGACGAGAACCAGTCTCCAAGA
TCATTCCAGAAGAAGACAAGACACTACTTCATTGCTGCTGTGGAAAGACTGTGGGACTATGGCATG
TCTTCCTCTCCCCATGTCCTCAGGAACAGGGCACAGTCTGGCTCTGTGCCACAGTTCAAGAAAGTG (Continued)

Figure 57A

GTCTTCCAGGAGTTCACTGATGGCTCATTCACCCAGCCCCTGTACAGAGGGGAACTGAATGAGCAC
CTGGGACTCCTGGGACCATACATCAGGGCTGAGGTGGAAGACAACATCATGGTGACATTCAGAAAC
CAGGCCTCCAGGCCCTACAGCTTCTACTCTTCCCTCATCAGCTATGAGGAAGACCAGAGACAAGGG
GCTGAGCCAAGAAAGAACTTTGTGAAACCCAATGAAACCAAGACCTACTTCTGGAAAGTCCAGCAC
CACATGGCACCCACCAAGGATGAGTTTGACTGCAAGGCCTGGGCATACTTCTCTGATGTGGACCTG
GAGAAAGATGTGCACTCTGGCCTGATTGGCCCACTCCTGGTCTGCCACACCAACACCCTGAACCCT
GCACATGGAAGGCAAGTGACTGTGCAGGAGTTTGCCCTCTTCTTCACCATCTTTGATGAAACCAAG
TCATGGTACTTCACTGAGAACATGGAGAGAAACTGCAGAGCACCATGCAACATTCAGATGGAAGAC
CCCACCTTCAAGGAGAACTACAGGTTCCATGCCATCAATGGCTACATCATGGACACCCTGCCTGGG
CTTGTCATGGCACAGGACCAGAGAATCAGATGGTACCTGCTTTCTATGGGATCCAATGAGAACATT
CACTCCATCCACTTCTCTGGGCATGTCTTCACTGTGAGAAAGAAGGAGGAATACAAGATGGCCCTG
TACAACCTCTACCCTGGGGTCTTTGAGACTGTGGAGATGCTGCCCTCCAAAGCTGGCATCTGGAGG
GTGGAATGCCTCATTGGGGAGCACCTGCATGCTGGCATGTCAACCCTGTTCCTGGTCTACAGCAAC
AAGTGCCAGACACCCCTGGGAATGGCCTCTGGCCACATCAGGGACTTCCAGATCACTGCCTCTGGC
CAGTATGGCCAGTGGGCACCCAAACTGGCCAGGCTCCACTACTCTGGCTCCATCAATGCATGGTCA
ACCAAGGAGCCATTCTCTTGGATCAAGGTGGACCTGCTGGCACCCATGATCATTCATGGCATCAAG
ACACAGGGGGCAAGACAGAAATTCTCCTCTCTGTACATCTCACAGTTCATCATCATGTACTCTCTG
GATGGCAAGAAGTGGCAGACATACAGAGGCAACTCCACTGGCACCCTCATGGTCTTCTTTGGCAAT
GTGGACAGCTCTGGCATCAAGCACAACATCTTCAACCCTCCCATCATTGCCAGATACATCAGGCTG
CACCCCACCCACTACTCAATCAGATCAACCCTCAGGATGGAACTGATGGGATGTGACCTGAACTCC
TGCTCAATGCCCCTGGGAATGGAGAGCAAGGCCATTTCTGATGCCCAGATCACTGCATCCTCTTAC
TTCACCAACATGTTTGCCACCTGGTCACCATCAAAAGCCAGGCTGCACCTCCAGGGAAGAAGCAAT
GCCTGGAGACCCCAGGTCAACAACCCAAAGGAATGGCTGCAAGTGGACTTCCAGAAGACAATGAAA
GTCACTGGGGTGACAACCCAGGGGGTCAAGTCTCTGCTCACCTCAATGTATGTGAAGGAGTTCCTG
ATCTCTTCCTCACAGGATGGCCACCAGTGGACACTCTTCTTCCAGAATGGCAAAGTCAAGGTGTTC
CAGGGCAACCAGGACTCTTTCACACCTGTGGTGAACTCACTGGACCCCCCCCTCCTGACAAGATAC
CTGAGAATTCACCCCCAGTCTTGGGTCCACCAGATTGCCCTGAGAATGGAAGTCCTGGGATGTGAG
GCACAAGACCTGTACTGA

Figure 57B

CS04-FL-NAm12 (SEQ ID NO: 109)

ATGCAGATTGAGCTGAGCACCTGCTTCTTCCTGTGCCTGCTGAGGTTCTGCTTCTCTGCCACCAGG
AGATACTACCTGGGGGCTGTGGAGCTTTCTTGGGACTACATGCAGTCTGACCTGGGGGAGCTGCCT
GTGGATGCCAGGTTCCCACCCAGAGTGCCCAAATCCTTCCCATTCAACACCTCTGTGGTCTACAAG
AAGACCCTCTTTGTGGAGTTCACTGACCACCTGTTCAACATTGCCAAACCCAGGCCACCCTGGATG
GGACTCCTGGGACCCACCATTCAGGCTGAGGTGTATGACACTGTGGTCGTCACCCTCAAGAACATG
GCCTCCCACCCTGTGAGCCTGCATGCTGTGGGGGTCAGCTACTGGAAGTCCTCTGAGGGGGCTGAG
TATGATGACCAGACCTCCCAGAGGGAGAAGGAGGATGACAAAGTGTTCCCTGGGAAGAGCCACACC
TATGTGTGGCAGGTCCTCAAGGAGAATGGCCCCACTGCCTCTGACCCACCCTGCCTGACCTACTCC
TACCTTTCTCATGTGGACCTGGTCAAGGACCTCAACTCTGGACTGATTGGGGCCCTGCTGGTGTGC
AGGGAGGGCTCCCTGGCCAAAGAGAAGACCCAGACCCTGCACAAGTTCATTCTCCTGTTTGCTGTC
TTTGATGAGGGCAAGAGCTGGCACTCTGAAACCAAGAACTCCCTGATGCAGGACAGGGATGCTGCC
TCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGGACAACCCCTGAGGTGCAC
TCCATTTTCCTGGAGGGCCACACCTTCCTGGTCAGGAACCACAGACAGGCCAGCCTGGAGATCAGC
CCCATCACCTTCCTCACTGCCCAGACCCTGCTGATGGACCTCGGACAGTTCCTGCTGTCCTGCCAC
ATCAGCTCCCACCAGCATGATGGCATGGAGGCCTATGTCAAGGTGGACAGCTGCCCTGAGGAGCCA
CAGCTCAGGATGAAGAACAATGAGGAGGCTGAGGACTATGATGATGACCTGACTGACTCTGAGATG
GATGTGGTCCGCTTTGATGATGACAACAGCCCATCCTTCATTCAGATCAGGTCTGTGGCCAAGAAA
CACCCCAAGACCTGGGTGCACTACATTGCTGCTGAGGAGGAGGACTGGGACTATGCCCCACTGGTC
CTGGCCCCTGATGACAGGAGCTACAAGAGCCAGTACCTCAACAATGGCCCACAGAGGATTGGACGC
AAGTACAAGAAAGTCAGGTTCATGGCCTACACTGATGAAACCTTCAAGACCAGGGAGGCCATTCAG
CATGAGTCTGGCATCCTGGGCCCACTCCTGTATGGGGAGGTGGGGGACACCCTGCTCATCATCTTC
AAGAACCAGGCCTCCAGGCCCTACAACATCTACCCACATGGCATCACTGATGTCAGGCCCCTGTAC
AGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGA
TACTACTCCAGCTTTGTGAACATGGAGAGGGACCTGGCCTCTGGCCTGATTGGCCCACTGCTCATC
TGCTACAAGGAGTCTGTGGACCAGAGGGGAAACCAGATCATGTCTGACAAGAGGAATGTGATTCTG
TTCTCTGTCTTTGATGAGAACAGGAGCTGGTACCTGACTGAGAACATTCAGCGCTTCCTGCCCAAC
CCTGCTGGGGTGCAGCTGGAGGACCCTGAGTTCCAGGCCAGCAACATCATGCACTCCATCAATGGC
TATGTGTTTGACAGCCTCCAGCTTTCTGTCTGCCTGCATGAGGTGGCCTACTGGTACATTCTTTCT
ATTGGGGCCCAGACTGACTTCCTTTCTGTCTTCTTCTCTGGCTACACCTTCAAACACAAGATGGTG
TATGAGGACACCCTGACCCTCTTCCCATTCTCTGGGGAGACTGTGTTCATGAGCATGGAGAACCCT
GGCCTGTGGATTCTGGGATGCCACAACTCTGACTTCCGCAACAGGGGCATGACTGCCCTGCTCAAA
GTCTCCTCCTGTGACAAGAACACTGGGGACTACTATGAGGACAGCTATGAGGACATCTCTGCCTAC
CTGCTCAGCAAGAACAATGCCATTGAGCCCAGGAGCTTCAGCCAGAATCCACCTGTCCTGAAACGC
CACCAGAGGGAGATCACCAGGACCACCCTCCAGTCTGACCAGGAGGAGATTGACTATGATGACACC
ATTTCTGTGGAGATGAAGAAAGAGGACTTTGACATCTATGACGAGGACGAGAACCAGAGCCCAAGG
AGCTTCCAGAAGAAGACCAGGCACTACTTCATTGCTGCTGTGGAGCGCCTGTGGGACTATGGCATG
AGCTCCAGCCCCCATGTCCTCAGGAACAGGGCCCAGTCTGGCTCTGTGCCACAGTTCAAGAAAGTG
GTCTTCCAAGAGTTCACTGATGGCAGCTTCACCCAGCCCCTGTACAGAGGGGAGCTGAATGAGCAC
CTGGGACTCCTGGGCCCATACATCAGGGCTGAGGTGGAGGACAACATCATGGTGACCTTCCGCAAC (Continued)

Figure 58A

CAGGCCTCCAGGCCCTACAGCTTCTACAGCTCCCTCATCAGCTATGAGGAGGACCAGAGGCAGGGG
GCTGAGCCACGCAAGAACTTTGTGAAACCCAATGAAACCAAGACCTACTTCTGGAAAGTCCAGCAC
CACATGGCCCCCACCAAGGATGAGTTTGACTGCAAGGCCTGGGCCTACTTCTCTGATGTGGACCTG
GAGAAGGATGTGCACTCTGGCCTGATTGGCCCACTCCTGGTCTGCCACACCAACACCCTGAACCCT
GCCCATGGAAGGCAAGTGACTGTGCAGGAGTTTGCCCTCTTCTTCACCATCTTTGATGAAACCAAG
AGCTGGTACTTCACTGAGAACATGGAGCGCAACTGCAGGGCCCCATGCAACATTCAGATGGAGGAC
CCCACCTTCAAAGAGAACTACCGCTTCCATGCCATCAATGGCTACATCATGGACACCCTGCCTGGG
CTTGTCATGGCCCAGGACCAGAGGATCAGGTGGTACCTGCTTTCTATGGGCTCCAATGAGAACATT
CACTCCATCCACTTCTCTGGGCATGTCTTCACTGTGCGCAAGAAGGAGGAGTACAAGATGGCCCTG
TACAACCTCTACCCTGGGGTCTTTGAGACTGTGGAGATGCTGCCCTCCAAAGCTGGCATCTGGAGG
GTGGAGTGCCTCATTGGGGAGCACCTGCATGCTGGCATGAGCACCCTGTTCCTGGTCTACAGCAAC
AAGTGCCAGACCCCCCTGGGAATGGCCTCTGGCCACATCAGGGACTTCCAGATCACTGCCTCTGGC
CAGTATGGCCAGTGGGCCCCCAAGCTGGCCAGGCTCCACTACTCTGGATCCATCAATGCCTGGAGC
ACCAAGGAGCCATTCAGCTGGATCAAAGTGGACCTGCTGGCCCCCATGATCATCCATGGCATCAAG
ACCCAGGGGGCCAGGCAGAAGTTCTCCAGCCTGTACATCAGCCAGTTCATCATCATGTACAGCCTG
GATGGCAAGAAATGGCAGACCTACAGAGGCAACTCCACTGGAACACTCATGGTCTTCTTTGGCAAT
GTGGACAGCTCTGGCATCAAGCACAACATCTTCAACCCCCCAATCATCGCCAGATACATCAGGCTG
CACCCCACCCACTACAGCATCCGCAGCACCCTCAGGATGGAGCTGATGGGCTGTGACCTGAACTCC
TGCAGCATGCCCCTGGGCATGGAGAGCAAGGCCATTTCTGATGCCCAGATCACTGCCTCCAGCTAC
TTCACCAACATGTTTGCCACCTGGAGCCCAAGCAAGGCCAGGCTGCACCTCCAGGGAAGGAGCAAT
GCCTGGAGGCCCCAGGTCAACAACCCAAAGGAGTGGCTGCAGGTGGACTTCCAGAAGACCATGAAG
GTCACTGGGGTGACCACCCAGGGGGTCAAGAGCCTGCTCACCAGCATGTATGTGAAGGAGTTCCTG
ATCAGCTCCAGCCAGGATGGCCACCAGTGGACCCTCTTCTTCCAGAATGGCAAGGTCAAGGTGTTC
CAGGGCAACCAGGACAGCTTCACCCCTGTGGTGAACAGCCTGGACCCCCCCCTCCTGACCAGATAC
CTGAGGATTCACCCCCAGAGCTGGGTCCACCAGATTGCCCTGAGGATGGAGGTCCTGGGATGTGAG
GCCCAGGACCTGTACTGA

Figure 58B

SEQUENCE LISTING

<160> NUMBER OF SEQ ID NOS: 109

<210> SEQ ID NO 1
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1
atgcagattg agctgagcac ctgcttcttc ctgtgcctgc tgaggttctg cttctctgcc 60
accaggagat actacctggg ggctgtggag ctttcttggg actacatgca gtctgacctg 120
ggggagctgc ctgtggatgc caggttccca cccagagtgc ccaaatcctt cccattcaac 180
acctctgtgg tctacaagaa gaccctcttt gtggagttca ctgaccacct gttcaacatt 240
gccaaaccca ggccaccctg gatgggactc ctgggaccca ccattcaggc tgaggtgtat 300
gacactgtgg tcatcaccct caagaacatg gcctcccacc ctgtgagcct gcatgctgtg 360
ggggtcagct actggaaggc ctctgagggg gctgagtatg atgaccagac ctcccagagg 420
gagaaggagg atgacaaagt gttccctggg ggcagccaca cctatgtgtg gcaggtcctc 480
aaggagaatg gccccatggc ctctgaccca ctctgcctga cctactccta cctttctcat 540
gtggacctgg tcaaggacct caactctgga ctgattgggg ccctgctggt gtgcagggag 600
ggctccctgg ccaaagagaa gacccagacc ctgcacaagt tcattctcct gtttgctgtc 660
tttgatgagg gcaagagctg gcactctgaa accaagaact ccctgatgca ggacagggat 720
gctgcctctg ccagggcctg gcccaagatg cacactgtga atggctatgt gaacaggagc 780
ctgcctggac tcattggctg ccacaggaaa tctgtctact ggcatgtgat tggcatgggg 840
acaacccctg aggtgcactc cattttcctg gagggccaca ccttcctggt caggaaccac 900
agacaggcca gcctggagat cagccccatc accttcctca ctgcccagac cctgctgatg 960
gacctcggac agttcctgct gttctgccac atcagctccc accagcatga tggcatggag 1020
gcctatgtca aggtggacag ctgccctgag gagccacagc tcaggatgaa gaacaatgag 1080
gaggctgagg actatgatga tgacctgact gactctgaga tggatgtggt ccgctttgat 1140
gatgacaaca gcccatcctt cattcagatc aggtctgtgg ccaagaaaca ccccaagacc 1200
tgggtgcact acattgctgc tgaggaggag gactgggact atgccccact ggtcctggcc 1260
cctgatgaca ggagctacaa gagccagtac ctcaacaatg gcccacagag gattggacgc 1320
aagtacaaga aagtcaggtt catggcctac actgatgaaa ccttcaagac cagggaggcc 1380
attcagcatg agtctggcat cctgggccca ctcctgtatg gggaggtggg ggacaccctg 1440
ctcatcatct tcaagaacca ggcctccagg ccctacaaca tctacccaca tggcatcact 1500
gatgtcaggc ccctgtacag ccgcaggctg ccaaaggggg tgaaacacct caaggacttc 1560
cccattctgc ctggggagat cttcaagtac aagtggactg tcactgtgga ggatggacca 1620
accaaatctg accccaggtg cctcaccaga tactactcca gctttgtgaa catggagagg 1680
gacctggcct ctggcctgat tggcccactg ctcatctgct acaaggagtc tgtggaccag 1740
aggggaaacc agatcatgtc tgacaagagg aatgtgattc tgttctctgt ctttgatgag 1800
aacaggagct ggtacctgac tgagaacatt cagcgcttcc tgcccaaccc tgctggggtg 1860
cagctggagg accctgagtt ccaggccagc aacatcatgc actccatcaa tggctatgtg 1920
tttgacagcc tccagctttc tgtctgcctg catgaggtgg cctactggta cattctttct 1980

-continued

```
attggggccc agactgactt cctttctgtc ttcttctctg gctacacctt caaacacaag   2040
atggtgtatg aggacaccct gaccctcttc ccattctctg ggagagactgt gttcatgagc   2100
atggagaacc ctggcctgtg gattctggga tgccacaact ctgacttccg caacaggggc   2160
atgactgccc tgctcaaagt ctcctcctgt gacaagaaca ctggggacta ctatgaggac   2220
agctatgagg acatctctgc ctacctgctc agcaagaaca atgccattga gcccaggagc   2280
ttcagccaga atccacctgt cctgaaacgc caccagaggg agatcaccag gaccaccctc   2340
cagtctgacc aggaggagat tgactatgat gacaccattt ctgtggagat gaagaaagag   2400
gactttgaca tctatgacga ggacgagaac cagagcccaa ggagcttcca gaagaagacc   2460
aggcactact tcattgctgc tgtggagcgc ctgtgggact atggcatgag ctccagcccc   2520
catgtcctca ggaacagggc ccagtctggc tctgtgccac agttcaagaa agtggtcttc   2580
caagagttca ctgatggcag cttcacccag cccctgtaca gaggggagct gaatgagcac   2640
ctgggactcc tgggcccata catcagggct gaggtggagg acaacatcat ggtgaccttc   2700
cgcaaccagg cctccaggcc ctacagcttc tacagctccc tcatcagcta tgaggaggac   2760
cagaggcagg gggctgagcc acgcaagaac tttgtgaaac ccaatgaaac caagacctac   2820
ttctggaaag tccagcacca catggccccc accaaggatg agtttgactg caaggcctgg   2880
gcctacttct ctgatgtgga cctggagaag gatgtgcact ctggcctgat tggcccactc   2940
ctggtctgcc acaccaacac cctgaaccct gcccatggaa ggcaagtgac tgtgcaggag   3000
tttgccctct tcttcaccat ctttgatgaa accaagagct ggtacttcac tgagaacatg   3060
gagcgcaact gcagggcccc atgcaacatt cagatggagg accccacctt caaagagaac   3120
taccgcttcc atgccatcaa tggctacatc atggacaccc tgcctgggct tgtcatggcc   3180
caggaccaga ggatcaggtg gtacctgctt tctatgggct ccaatgagaa cattcactcc   3240
atccacttct ctgggcatgt cttcactgtg cgcaagaagg aggagtacaa gatggccctg   3300
tacaacctct accctggggt ctttgagact gtggagatgc tgccctccaa agctggcatc   3360
tggagggtgg agtgcctcat tggggagcac ctgcatgctg gcatgagcac cctgttcctg   3420
gtctacagca acaagtgcca gaccccccctg ggaatggcct ctggccacat cagggacttc   3480
cagatcactg cctctggcca gtatggccag tgggccccca agctggccag gctccactac   3540
tctggatcca tcaatgcctg gagcaccaag gagccattca gctggatcaa agtggacctg   3600
ctggccccca tgatcatcca tggcatcaag acccaggggg ccaggcagaa gttctccagc   3660
ctgtacatca gccagttcat catcatgtac agcctggatg gcaagaaatg gcagacctac   3720
agaggcaact ccactggaac actcatggtc ttctttggca atgtggacag ctctggcatc   3780
aagcacaaca tcttcaaccc cccaatcatc gccagataca tcaggctgca ccccacccac   3840
tacagcatcc gcagcaccct caggatggag ctgatgggct gtgacctgaa ctcctgcagc   3900
atgcccctgg gcatggagag caaggccatt tctgatgccc agatcactgc ctccagctac   3960
ttcaccaaca tgtttgccac ctggagccca agcaaggcca ggctgcacct ccagggaagg   4020
agcaatgcct ggaggcccca ggtcaacaac ccaaaggagt ggctgcaggt ggacttccag   4080
aagaccatga aggtcactgg ggtgaccacc caggggggtca agagcctgct caccagcatg   4140
tatgtgaagg agttcctgat cagctccagc caggatggcc accagtggac cctcttcttc   4200
cagaatggca aggtcaaggt gttccagggc aaccaggaca gcttcacccc tgtggtgaac   4260
agcctggacc ccccccctcct gaccagatac ctgaggattc acccccagag ctgggtccac   4320
cagattgccc tgaggatgga ggtcctggga tgtgaggccc aggacctgta ctga         4374
```

<210> SEQ ID NO 2
<211> LENGTH: 1457
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
```

-continued

```
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780
```

-continued

```
Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
    1145                1150                1155

Asp Phe  Gln Ile Thr Ala Ser  Gly Gln Tyr Gly Gln  Trp Ala Pro
    1160                1165                1170

Lys Leu  Ala Arg Leu His Tyr  Ser Gly Ser Ile Asn  Ala Trp Ser
    1175                1180                1185
```

```
Thr Lys  Glu Pro Phe Ser Trp  Ile Lys Val Asp Leu  Leu Ala Pro
    1190                 1195                 1200

Met Ile  Ile His Gly Ile Lys  Thr Gln Gly Ala Arg  Gln Lys Phe
    1205                 1210                 1215

Ser Ser  Leu Tyr Ile Ser Gln  Phe Ile Ile Met Tyr  Ser Leu Asp
    1220                 1225                 1230

Gly Lys  Lys Trp Gln Thr Tyr  Arg Gly Asn Ser Thr  Gly Thr Leu
    1235                 1240                 1245

Met Val  Phe Phe Gly Asn Val  Asp Ser Ser Gly Ile  Lys His Asn
    1250                 1255                 1260

Ile Phe  Asn Pro Pro Ile Ile  Ala Arg Tyr Ile Arg  Leu His Pro
    1265                 1270                 1275

Thr His  Tyr Ser Ile Arg Ser  Thr Leu Arg Met Glu  Leu Met Gly
    1280                 1285                 1290

Cys Asp  Leu Asn Ser Cys Ser  Met Pro Leu Gly Met  Glu Ser Lys
    1295                 1300                 1305

Ala Ile  Ser Asp Ala Gln Ile  Thr Ala Ser Ser Tyr  Phe Thr Asn
    1310                 1315                 1320

Met Phe  Ala Thr Trp Ser Pro  Ser Lys Ala Arg Leu  His Leu Gln
    1325                 1330                 1335

Gly Arg  Ser Asn Ala Trp Arg  Pro Gln Val Asn Asn  Pro Lys Glu
    1340                 1345                 1350

Trp Leu  Gln Val Asp Phe Gln  Lys Thr Met Lys Val  Thr Gly Val
    1355                 1360                 1365

Thr Thr  Gln Gly Val Lys Ser  Leu Leu Thr Ser Met  Tyr Val Lys
    1370                 1375                 1380

Glu Phe  Leu Ile Ser Ser Ser  Gln Asp Gly His Gln  Trp Thr Leu
    1385                 1390                 1395

Phe Phe  Gln Asn Gly Lys Val  Lys Val Phe Gln Gly  Asn Gln Asp
    1400                 1405                 1410

Ser Phe  Thr Pro Val Val Asn  Ser Leu Asp Pro Pro  Leu Leu Thr
    1415                 1420                 1425

Arg Tyr  Leu Arg Ile His Pro  Gln Ser Trp Val His  Gln Ile Ala
    1430                 1435                 1440

Leu Arg  Met Glu Val Leu Gly  Cys Glu Ala Gln Asp  Leu Tyr
    1445                 1450                 1455
```

```
<210> SEQ ID NO 3
<211> LENGTH: 2220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

gccaccagga gatactacct gggggctgtg gagctttctt gggactacat gcagtctgac      60

ctgggggagc tgcctgtgga tgccaggttc ccacccagag tgcccaaatc cttcccattc     120

aacacctctg tggtctacaa gaagaccctc tttgtggagt tcactgacca cctgttcaac     180

attgccaaac ccaggccacc ctggatggga ctcctgggac ccaccattca ggctgaggtg     240

tatgacactg tggtcatcac cctcaagaac atggcctccc accctgtgag cctgcatgct     300

gtgggggtca gctactggaa ggcctctgag ggggctgagt atgatgacca gacctcccag     360

agggagaagg aggatgacaa agtgttccct gggggcagcc acacctatgt gtggcaggtc     420
```

-continued ctcaaggaga atggccccat ggcctctgac ccactctgcc tgacctactc ctacctttct 480
catgtggacc tggtcaagga cctcaactct ggactgattg gggccctgct ggtgtgcagg 540
gagggctccc tggccaaaga gaagacccag accctgcaca agttcattct cctgtttgct 600
gtctttgatg agggcaagag ctggcactct gaaaccaaga actccctgat gcaggacagg 660
gatgctgcct ctgccagggc ctggcccaag atgcacactg tgaatggcta tgtgaacagg 720
agcctgcctg gactcattgg ctgccacagg aaatctgtct actggcatgt gattggcatg 780
gggacaaccc ctgaggtgca ctccattttc ctggagggcc acaccttcct ggtcaggaac 840
cacagacagg ccagcctgga gatcagcccc atcaccttcc tcactgccca gaccctgctg 900
atggacctcg gacagttcct gctgttctgc cacatcagct cccaccagca tgatggcatg 960
gaggcctatg tcaaggtgga cagctgccct gaggagccac agctcaggat gaagaacaat 1020
gaggaggctg aggactatga tgatgacctg actgactctg agatggatgt ggtccgcttt 1080
gatgatgaca acagcccatc cttcattcag atcaggtctg tggccaagaa acaccccaag 1140
acctgggtgc actacattgc tgctgaggag gaggactggg actatgcccc actggtcctg 1200
gcccctgatg acaggagcta caagagccag tacctcaaca atggcccaca gaggattgga 1260
cgcaagtaca agaaagtcag gttcatggcc tacactgatg aaaccttcaa gaccagggag 1320
gccattcagc atgagtctgg catcctgggc ccactcctgt atggggaggt gggggacacc 1380
ctgctcatca tcttcaagaa ccaggcctcc aggccctaca acatctaccc acatggcatc 1440
actgatgtca ggcccctgta cagccgcagg ctgccaaagg gggtgaaaca cctcaaggac 1500
ttccccattc tgcctgggga gatcttcaag tacaagtgga ctgtcactgt ggaggatgga 1560
ccaaccaaat ctgaccccag gtgcctcacc agatactact ccagctttgt gaacatggag 1620
agggacctgg cctctggcct gattggccca ctgctcatct gctacaagga gtctgtggac 1680
cagaggggaa accagatcat gtctgacaag aggaatgtga ttctgttctc tgtctttgat 1740
gagaacagga gctggtacct gactgagaac attcagcgct tcctgcccaa ccctgctggg 1800
gtgcagctgg aggaccctga gttccaggcc agcaacatca tgcactccat caatggctat 1860
gtgtttgaca gcctccagct ttctgtctgc ctgcatgagg tggcctactg gtacattctt 1920
tctattgggg cccagactga cttcctttct gtcttcttct ctggctacac cttcaaacac 1980
aagatggtgt atgaggacac cctgaccctc ttcccattct ctggggagac tgtgttcatg 2040
agcatggaga accctggcct gtggattctg ggatgccaca actctgactt ccgcaacagg 2100
ggcatgactg ccctgctcaa agtctcctcc tgtgacaaga acactgggga ctactatgag 2160
gacagctatg aggacatctc tgcctacctg ctcagcaaga acaatgccat tgagcccagg 2220

<210> SEQ ID NO 4
<211> LENGTH: 2052
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4
gagatcacca ggaccaccct ccagtctgac caggaggaga ttgactatga tgacaccatt 60
tctgtggaga tgaagaaaga ggactttgac atctatgacg aggacgagaa ccagagccca 120
aggagcttcc agaagaagac caggcactac ttcattgctg ctgtggagcg cctgtgggac 180
tatggcatga gctccagccc ccatgtcctc aggaacaggg cccagtctgg ctctgtgcca 240

-continued

```
cagttcaaga aagtggtctt ccaagagttc actgatggca gcttcaccca gcccctgtac    300

agaggggagc tgaatgagca cctgggactc ctgggcccat acatcagggc tgaggtggag    360

gacaacatca tggtgacctt ccgcaaccag gcctccaggc cctacagctt ctacagctcc    420

ctcatcagct atgaggagga ccagaggcag gggctgagc cacgcaagaa ctttgtgaaa    480

cccaatgaaa ccaagaccta cttctggaaa gtccagcacc acatggcccc caccaaggat    540

gagtttgact gcaaggcctg ggcctacttc tctgatgtgg acctggagaa ggatgtgcac    600

tctggcctga ttggcccact cctggtctgc cacaccaaca ccctgaaccc tgcccatgga    660

aggcaagtga ctgtgcagga gtttgccctc ttcttcacca tctttgatga aaccaagagc    720

tggtacttca ctgagaacat ggagcgcaac tgcagggccc catgcaacat tcagatggag    780

gaccccacct tcaaagagaa ctaccgcttc catgccatca atggctacat catggacacc    840

ctgcctgggc ttgtcatggc ccaggaccag aggatcaggt ggtacctgct ttctatgggc    900

tccaatgaga acattcactc catccacttc tctgggcatg tcttcactgt gcgcaagaag    960

gaggagtaca agatggccct gtacaacctc taccctgggg tctttgagac tgtggagatg   1020

ctgccctcca aagctggcat ctggagggtg gagtgcctca ttggggagca cctgcatgct   1080

ggcatgagca ccctgttcct ggtctacagc aacaagtgcc agaccccct gggaatggcc   1140

tctggccaca tcagggactt ccagatcact gcctctggcc agtatggcca gtgggccccc   1200

aagctggcca ggctccacta ctctggatcc atcaatgcct ggagcaccaa ggagccattc   1260

agctggatca aagtggacct gctggccccc atgatcatcc atggcatcaa gacccagggg   1320

gccaggcaga agttctccag cctgtacatc agccagttca tcatcatgta cagcctggat   1380

ggcaagaaat ggcagaccta cagaggcaac tccactggaa cactcatggt cttctttggc   1440

aatgtggaca gctctggcat caagcacaac atcttcaacc ccccaatcat cgccagatac   1500

atcaggctgc accccaccca ctacagcatc cgcagcaccc tcaggatgga gctgatgggc   1560

tgtgacctga actcctgcag catgcccctg ggcatggaga gcaaggccat ttctgatgcc   1620

cagatcactg cctccagcta cttcaccaac atgtttgcca cctggagccc aagcaaggcc   1680

aggctgcacc tccagggaag gagcaatgcc tggaggcccc aggtcaacaa cccaaaggag   1740

tggctgcagg tggacttcca gaagaccatg aaggtcactg gggtgaccac ccagggggtc   1800

aagagcctgc tcaccagcat gtatgtgaag gagttcctga tcagctccag ccaggatggc   1860

caccagtgga ccctcttctt ccagaatggc aaggtcaagg tgttccaggg caaccaggac   1920

agcttcaccc ctgtggtgaa cagcctggac ccccccctcc tgaccagata cctgaggatt   1980

cacccccaga gctgggtcca ccagattgcc ctgaggatgg aggtcctggg atgtgaggcc   2040

caggacctgt ac                                                       2052
```

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5

```
agcttctctc agaatccacc tgtcctgaag agacaccaga ga                        42
```

<210> SEQ ID NO 6
<211> LENGTH: 42
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 6
agcttcagcc agaatccacc tgtcctgaaa cgccaccaga gg 42

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
agcttcagcc agaacccccc cgtgctgaag aggcaccaga gg 42

<210> SEQ ID NO 8
<211> LENGTH: 7827
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cctcgagatt taaatgacgt 420
tggccactcc ctctctgcgc gctcgctcgc tcactgaggc cgggcgacca aaggtcgccc 480
gacgcccggg ctttgcccgg gcggcctcag tgagcgagcg agcgcgcaga gagggagtgg 540
ccaactccat cactaggggt tcctgagttt aaacttcgtc gacgattcga gcttgggctg 600
caggtcgagg gcactgggag gatgttgagt aagatggaaa actactgatg acccttgcag 660
agacagagta ttaggacatg tttgaacagg ggccgggcga tcagcaggta gctctagagg 720
atccccgtct gtctgcacat ttcgtagagc gagtgttccg atactctaat ctccctaggc 780
aaggttcata tttgtgtagg ttacttattc tccttttgtt gactaagtca ataatcagaa 840
tcagcaggtt tggagtcagc ttggcaggga tcagcagcct gggttggaag gagggggtat 900
aaaagcccct tcaccaggag aagccgtcac acagactagg cgcgccaccg ccaccatgca 960
gattgagctg agcacctgct tcttcctgtg cctgctgagg ttctgcttct ctgccaccag 1020
gagatactac ctgggggctg tggagctttc ttgggactac atgcagtctg acctgggggga 1080 gctgcctgtg gatgccaggt tcccacccag agtgcccaaa tccttcccat tcaacacctc 1140
tgtggtctac aagaagaccc tctttgtgga gttcactgac cacctgttca acattgccaa 1200
acccaggcca ccctggatgg gactcctggg acccaccatt caggctgagg tgtatgacac 1260
tgtggtcatc accctcaaga acatggcctc ccaccctgtg agcctgcatg ctgtgggggt 1320
cagctactgg aaggcctctg agggggctga gtatgatgac cagacctccc agagggagaa 1380

-continued

```
ggaggatgac aaagtgttcc ctgggggcag ccacacctat gtgtggcagg tcctcaagga   1440
gaatggcccc atggcctctg acccactctg cctgacctac tcctaccttt ctcatgtgga   1500
cctggtcaag gacctcaact ctggactgat tggggccctg ctggtgtgca gggagggctc   1560
cctggccaaa gagaagaccc agaccctgca caagttcatt ctcctgtttg ctgtctttga   1620
tgagggcaag agctggcact ctgaaaccaa gaactccctg atgcaggaca gggatgctgc   1680
ctctgccagg gcctggccca agatgcacac tgtgaatggc tatgtgaaca ggagcctgcc   1740
tggactcatt ggctgccaca ggaaatctgt ctactggcat gtgattggca tggggacaac   1800
ccctgaggtg cactccattt tcctggaggg ccacaccttc ctggtcagga accacagaca   1860
ggccagcctg gagatcagcc ccatcacctt cctcactgcc cagaccctgc tgatggacct   1920
cggacagttc ctgctgttct gccacatcag ctcccaccag catgatggca tggaggccta   1980
tgtcaaggtg gacagctgcc ctgaggagcc acagctcagg atgaagaaca atgaggaggc   2040
tgaggactat gatgatgacc tgactgactc tgagatggat gtggtccgct ttgatgatga   2100
caacagccca tccttcattc agatcaggtc tgtggccaag aaacacccca agacctgggt   2160
gcactacatt gctgctgagg aggaggactg ggactatgcc ccactggtcc tggcccctga   2220
tgacaggagc tacaagagcc agtacctcaa caatggccca cagaggattg gacgcaagta   2280
caagaaagtc aggttcatgg cctacactga tgaaaccttc aagaccaggg aggccattca   2340
gcatgagtct ggcatcctgg gcccactcct gtatggggag gtgggggaca ccctgctcat   2400
catcttcaag aaccaggcct ccaggcccta caacatctac ccacatggca tcactgatgt   2460
caggcccctg tacagccgca ggctgccaaa gggggtgaaa cacctcaagg acttccccat   2520
tctgcctggg gagatcttca agtacaagtg gactgtcact gtggaggatg gaccaaccaa   2580
atctgacccc aggtgcctca ccagatacta ctccagcttt gtgaacatgg agagggacct   2640
ggcctctggc ctgattggcc cactgctcat ctgctacaag gagtctgtgg accagagggg   2700
aaaccagatc atgtctgaca agaggaatgt gattctgttc tctgtctttg atgagaacag   2760
gagctggtac ctgactgaga acattcagcg cttcctgccc aaccctgctg ggggtgcagct   2820
ggaggaccct gagttccagg ccagcaacat catgcactcc atcaatggct atgtgtttga   2880
cagcctccag ctttctgtct gcctgcatga ggtggcctac tggtacattc tttctattgg   2940
ggcccagact gacttccttt ctgtcttctt ctctggctac accttcaaac acaagatggt   3000
gtatgaggac accctgaccc tcttcccatt ctctggggag actgtgttca tgagcatgga   3060
gaaccctggc ctgtggattc tgggatgcca caactctgac ttccgcaaca ggggcatgac   3120
tgccctgctc aaagtctcct cctgtgacaa gaacactggg gactactatg aggacagcta   3180
tgaggacatc tctgcctacc tgctcagcaa gaacaatgcc attgagccca ggagcttcag   3240
ccagaatcca cctgtcctga aacgccacca gagggagatc accaggacca ccctccagtc   3300
tgaccaggag gagattgact atgatgacac catttctgtg gagatgaaga aagaggactt   3360
tgacatctat gacgaggacg agaaccagag cccaaggagc ttccagaaga agaccaggca   3420
ctacttcatt gctgctgtgg agcgcctgtg ggactatggc atgagctcca gcccccatgt   3480
cctcaggaac agggcccagt ctggctctgt gccacagttc aagaaagtgg tcttccaaga   3540
gttcactgat ggcagcttca cccagcccct gtacagaggg gagctgaatg agcacctggg   3600
actcctgggc ccatacatca gggctgaggt ggaggacaac atcatggtga ccttccgcaa   3660
ccaggcctcc aggccctaca gcttctacag ctccctcatc agctatgagg aggaccagag   3720
gcagggggct gagccacgca agaactttgt gaaacccaat gaaaccaaga cctacttctg   3780
```

-continued

```
gaaagtccag caccacatgg cccccaccaa ggatgagttt gactgcaagg cctgggccta   3840
cttctctgat gtggacctgg agaaggatgt gcactctggc ctgattggcc cactcctggt   3900
ctgccacacc aacaccctga accctgccca tggaaggcaa gtgactgtgc aggagtttgc   3960
cctcttcttc accatctttg atgaaaccaa gagctggtac ttcactgaga acatggagcg   4020
caactgcagg gccccatgca acattcagat ggaggacccc accttcaaag agaactaccg   4080
cttccatgcc atcaatggct acatcatgga caccctgcct gggcttgtca tggcccagga   4140
ccagaggatc aggtggtacc tgctttctat gggctccaat gagaacattc actccatcca   4200
cttctctggg catgtcttca ctgtgcgcaa gaaggaggag tacaagatgg ccctgtacaa   4260
cctctaccct ggggtctttg agactgtgga gatgctgccc tccaaagctg gcatctggag   4320
ggtggagtgc ctcattgggg agcacctgca tgctggcatg agcaccctgt tcctggtcta   4380
cagcaacaag tgccagaccc ccctgggaat ggcctctggc cacatcaggg acttccagat   4440
cactgcctct ggccagtatg gccagtgggc ccccaagctg gccaggctcc actactctgg   4500
atccatcaat gcctggagca ccaaggagcc attcagctgg atcaaagtgg acctgctggc   4560
ccccatgatc atccatggca tcaagaccca gggggccagg cagaagttct ccagcctgta   4620
catcagccag ttcatcatca tgtacagcct ggatggcaag aaatggcaga cctacagagg   4680
caactccact ggaacactca tggtcttctt tggcaatgtg gacagctctg gcatcaagca   4740
caacatcttc aacccccca a tcatcgccag atacatcagg ctgcacccca cccactacag   4800
catccgcagc accctcagga tggagctgat gggctgtgac ctgaactcct gcagcatgcc   4860
cctgggcatg gagagcaagg ccatttctga tgcccagatc actgcctcca gctacttcac   4920
caacatgttt gccacctgga gcccaagcaa ggccaggctg cacctccagg gaaggagcaa   4980
tgcctggagg ccccaggtca acaacccaaa ggagtggctg caggtggact tccagaagac   5040
catgaaggtc actggggtga ccacccaggg ggtcaagagc ctgctcacca gcatgtatgt   5100
gaaggagttc ctgatcagct ccagccagga tggccaccag tggaccctct tcttccagaa   5160
tggcaaggtc aaggtgttcc agggcaacca ggacagcttc acccctgtgg tgaacagcct   5220
ggaccccccc ctcctgacca gatacctgag gattcacccc cagagctggg tccaccagat   5280
tgccctgagg atggaggtcc tgggatgtga ggcccaggac ctgtactgat gacgagcggc   5340
cgctcttagt agcagtatcg ataataaaag atctttattt tcattagatc tgtgtgttgg   5400
tttttgtgt gttaattaag ctcgcgaagg aacccctagt gatggagttg gccactccct   5460
ctctgcgcgc tcgctcgctc actgaggccg ggcgaccaaa ggtcgcccga cgcccgggct   5520
ttgcccgggc ggcctcagtg agcgagcgag cgcgcagaga gggagtggcc aagacgattt   5580
aaatgacaag cttggcgtaa tcatggtcat agctgtttcc tgtgtgaaat tgttatccgc   5640
tcacaattcc acacaacata cgagccggaa gcataaagtg taaagcctgg ggtgcctaat   5700
gagtgagcta actcacatta attgcgttgc gctcactgcc cgctttccag tcgggaaacc   5760
tgtcgtgcca gctgcattaa tgaatcggcc aacgcgcggg gagaggcggt ttgcgtattg   5820
ggcgctcttc cgcttcctcg ctcactgact cgctgcgctc ggtcgttcgg ctgcggcgag   5880
cggtatcagc tcactcaaag gcggtaatac ggttatccac agaatcaggg gataacgcag   5940
gaaagaacat gtgagcaaaa ggccagcaaa aggccaggaa ccgtaaaaag gccgcgttgc   6000
tggcgttttt ccataggctc cgcccccctg acgagcatca caaaaatcga cgctcaagtc   6060
agaggtggcg aaacccgaca ggactataaa gataccaggc gtttccccct ggaagctccc   6120
```

-continued

```
tcgtgcgctc tcctgttccg accctgccgc ttaccggata cctgtccgcc tttctccctt   6180
cgggaagcgt ggcgctttct catagctcac gctgtaggta tctcagttcg gtgtaggtcg   6240
ttcgctccaa gctgggctgt gtgcacgaac cccccgttca gcccgaccgc tgcgccttat   6300
ccggtaacta tcgtcttgag tccaacccgg taagacacga cttatcgcca ctggcagcag   6360
ccactggtaa caggattagc agagcgaggt atgtaggcgg tgctacagag ttcttgaagt   6420
ggtggcctaa ctacggctac actagaagaa cagtatttgg tatctgcgct ctgctgaagc   6480
cagttacctt cggaaaaaga gttggtagct cttgatccgg caaacaaacc accgctggta   6540
gcggtggttt ttttgtttgc aagcagcaga ttacgcgcag aaaaaaagga tctcaagaag   6600
atcctttgat cttttctacg gggtctgacg ctcagtggaa cgaaaactca cgttaaggga   6660
ttttggtcat gagattatca aaaaggatct tcacctagat ccttttaaat taaaaatgaa   6720
gttttaaatc aatctaaagt atatatgagt aaacttggtc tgacagttac caatgcttaa   6780
tcagtgaggc acctatctca gcgatctgtc tatttcgttc atccatagtt gcctgactcc   6840
ccgtcgtgta gataactacg atacgggagg gcttaccatc tggccccagt gctgcaatga   6900
taccgcgaga cccacgctca ccggctccag atttatcagc aataaaccag ccagccggaa   6960
gggccgagcg cagaagtggt cctgcaactt tatccgcctc catccagtct attaattgtt   7020
gccgggaagc tagagtaagt agttcgccag ttaatagttt gcgcaacgtt gttgccattg   7080
ctacaggcat cgtggtgtca cgctcgtcgt ttggtatggc ttcattcagc tccggttccc   7140
aacgatcaag gcgagttaca tgatccccca tgttgtgcaa aaaagcggtt agctccttcg   7200
gtcctccgat cgttgtcaga agtaagttgg ccgcagtgtt atcactcatg gttatggcag   7260
cactgcataa ttctcttact gtcatgccat ccgtaagatg cttttctgtg actggtgagt   7320
actcaaccaa gtcattctga gaatagtgta tgcggcgacc gagttgctct tgcccggcgt   7380
caatacggga taataccgcg ccacatagca gaactttaaa agtgctcatc attggaaaac   7440
gttcttcggg gcgaaaactc tcaaggatct taccgctgtt gagatccagt tcgatgtaac   7500
ccactcgtgc acccaactga tcttcagcat cttttacttt caccagcgtt tctgggtgag   7560
caaaaacagg aaggcaaaat gccgcaaaaa agggaataag ggcgacacgg aaatgttgaa   7620
tactcatact cttccttttt caatattatt gaagcattta tcagggttat tgtctcatga   7680
gcggatacat atttgaatgt atttagaaaa ataaacaaat aggggttccg cgcacatttc   7740
cccgaaaagt gccacctgac gtctaagaaa ccattattat catgacatta acctataaaa   7800
ataggcgtat cacgaggccc tttcgtc                                       7827
```

<210> SEQ ID NO 9
<211> LENGTH: 4332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
atgcagattg agctgagcac ctgcttcttc ctgtgcctgc tgaggttctg cttctctgcc     60
accaggagat actacctggg ggctgtggag ctttcttggg actacatgca gtctgacctg    120
ggggagctgc ctgtggatgc caggttccca cccagagtgc ccaaatcctt cccattcaac    180
acctctgtgg tctacaagaa gaccctcttt gtggagttca ctgaccacct gttcaacatt    240
gccaaaccca ggccaccctg gatgggactc ctgggaccca ccattcaggc tgaggtgtat    300
```

-continued

```
gacactgtgg tcatcaccct caagaacatg gcctcccacc ctgtgagcct gcatgctgtg    360
ggggtcagct actggaaggc ctctgagggg gctgagtatg atgaccagac ctcccagagg    420
gagaaggagg atgacaaagt gttccctggg ggcagccaca cctatgtgtg gcaggtcctc    480
aaggagaatg gccccatggc ctctgaccca ctctgcctga cctactccta cctttctcat    540
gtggacctgg tcaaggacct caactctgga ctgattgggg ccctgctggt gtgcagggag    600
ggctccctgg ccaaagagaa gacccagacc ctgcacaagt tcattctcct gtttgctgtc    660
tttgatgagg gcaagagctg gcactctgaa accaagaact ccctgatgca ggacagggat    720
gctgcctctg ccagggcctg gcccaagatg cacactgtga atggctatgt gaacaggagc    780
ctgcctggac tcattggctg ccacaggaaa tctgtctact ggcatgtgat tggcatgggg    840
acaacccctg aggtgcactc cattttcctg gagggccaca ccttcctggt caggaaccac    900
agacaggcca gcctggagat cagccccatc accttcctca ctgcccagac cctgctgatg    960
gacctcggac agttcctgct gttctgccac atcagctccc accagcatga tggcatggag   1020
gcctatgtca aggtggacag ctgccctgag gagccacagc tcaggatgaa gaacaatgag   1080
gaggctgagg actatgatga tgacctgact gactctgaga tggatgtggt ccgctttgat   1140
gatgacaaca gcccatcctt cattcagatc aggtctgtgg ccaagaaaca ccccaagacc   1200
tgggtgcact acattgctgc tgaggaggag gactgggact atgcccact ggtcctggcc   1260
cctgatgaca ggagctacaa gagccagtac ctcaacaatg gcccacagag gattggacgc   1320
aagtacaaga aagtcaggtt catggcctac actgatgaaa ccttcaagac cagggaggcc   1380
attcagcatg agtctggcat cctgggccca ctcctgtatg ggggaggtggg ggacaccctg   1440
ctcatcatct tcaagaacca ggcctccagg ccctacaaca tctacccaca tggcatcact   1500
gatgtcaggc ccctgtacag ccgcaggctg ccaaaggggg tgaaacacct caaggacttc   1560
cccattctgc ctggggagat cttcaagtac aagtggactg tcactgtgga ggatggacca   1620
accaaatctg accccaggtg cctcaccaga tactactcca gctttgtgaa catggagagg   1680
gacctggcct ctggcctgat tggcccactg ctcatctgct acaaggagtc tgtggaccag   1740
aggggaaacc agatcatgtc tgacaagagg aatgtgattc tgttctctgt ctttgatgag   1800
aacaggagct ggtacctgac tgagaacatt cagcgcttcc tgcccaaccc tgctggggtg   1860
cagctggagg accctgagtt ccaggccagc aacatcatgc actccatcaa tggctatgtg   1920
tttgacagcc tccagctttc tgtctgcctg catgaggtgg cctactggta cattctttct   1980
attggggccc agactgactt cctttctgtc ttcttctctg gctacacctt caaacacaag   2040
atggtgtatg aggacaccct gaccctcttc ccattctctg gggagactgt gttcatgagc   2100
atggagaacc ctggcctgtg gattctggga tgccacaact ctgacttccg caacaggggc   2160
atgactgccc tgctcaaagt ctcctcctgt gacaagaaca ctggggacta ctatgaggac   2220
agctatgagg acatctctgc ctacctgctc agcaagaaca atgccattga gcccagggag   2280
atcaccagga ccaccctcca gtctgaccag gaggagattg actatgatga caccatttct   2340
gtggagatga agaaagagga ctttgacatc tatgacgagg acgagaacca gagcccaagg   2400
agcttccaga agaagaccag gcactacttc attgctgctg tggagcgcct gtgggactat   2460
ggcatgagct ccagccccca tgtcctcagg aacagggccc agtctggctc tgtgccacag   2520
ttcaagaaag tggtcttcca agagttcact gatggcagct tcacccagcc cctgtacaga   2580
ggggagctga atgagcacct gggactcctg ggcccataca tcagggctga ggtggaggac   2640
aacatcatgg tgaccttccg caaccaggcc tccaggccct acagcttcta cagctccctc   2700
```

```
atcagctatg aggaggacca gaggcagggg gctgagccac gcaagaactt tgtgaaaccc   2760

aatgaaacca agacctactt ctggaaagtc cagcaccaca tggcccccac caaggatgag   2820

tttgactgca aggcctgggc ctacttctct gatgtggacc tggagaagga tgtgcactct   2880

ggcctgattg gcccactcct ggtctgccac accaacaccc tgaaccctgc ccatggaagg   2940

caagtgactg tgcaggagtt tgccctcttc ttcaccatct ttgatgaaac caagagctgg   3000

tacttcactg agaacatgga gcgcaactgc agggccccat gcaacattca gatggaggac   3060

cccaccttca aagagaacta ccgcttccat gccatcaatg gctacatcat ggacaccctg   3120

cctgggcttg tcatggccca ggaccagagg atcaggtggt acctgctttc tatgggctcc   3180

aatgagaaca ttcactccat ccacttctct gggcatgtct tcactgtgcg caagaaggag   3240

gagtacaaga tggccctgta caacctctac cctggggtct ttgagactgt ggagatgctg   3300

ccctccaaag ctggcatctg gagggtggag tgcctcattg gggagcacct gcatgctggc   3360

atgagcaccc tgttcctggt ctacagcaac aagtgccaga ccccccctggg aatggcctct   3420

ggccacatca gggacttcca gatcactgcc tctggccagt atggccagtg ggcccccaag   3480

ctggccaggc tccactactc tggatccatc aatgcctgga gcaccaagga gccattcagc   3540

tggatcaaag tggacctgct ggcccccatg atcatccatg gcatcaagac ccaggggggcc   3600

aggcagaagt tctccagcct gtacatcagc cagttcatca tcatgtacag cctggatggc   3660

aagaaatggc agacctacag aggcaactcc actggaacac tcatggtctt ctttggcaat   3720

gtggacagct ctggcatcaa gcacaacatc ttcaaccccc caatcatcgc cagatacatc   3780

aggctgcacc ccacccacta cagcatccgc agcaccctca ggatggagct gatgggctgt   3840

gacctgaact cctgcagcat gcccctgggc atggagagca aggccatttc tgatgcccag   3900

atcactgcct ccagctactt caccaacatg tttgccacct ggagcccaag caaggccagg   3960

ctgcacctcc agggaaggag caatgcctgg aggccccagg tcaacaaccc aaaggagtgg   4020

ctgcaggtgg acttccagaa gaccatgaag gtcactgggg tgaccaccca gggggtcaag   4080

agcctgctca ccagcatgta tgtgaaggag ttcctgatca gctccagcca ggatggccac   4140

cagtggaccc tcttcttcca gaatggcaag gtcaaggtgt tccagggcaa ccaggacagc   4200

ttcacccctg tggtgaacag cctggacccc cccctcctga ccagatacct gaggattcac   4260

ccccagagct gggtccacca gattgccctg aggatggagg tcctgggatg tgaggcccag   4320

gacctgtact ga                                                       4332
```

<210> SEQ ID NO 10
<211> LENGTH: 1443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60
```

Tyr Lys Lys Thr Leu Phe Val Glu Phe Thr Asp His Leu Phe Asn Ile
65 70 75 80

Ala Lys Pro Arg Pro Pro Trp Met Gly Leu Leu Gly Pro Thr Ile Gln
85 90 95

Ala Glu Val Tyr Asp Thr Val Val Ile Thr Leu Lys Asn Met Ala Ser
100 105 110

His Pro Val Ser Leu His Ala Val Gly Val Ser Tyr Trp Lys Ala Ser
115 120 125

Glu Gly Ala Glu Tyr Asp Asp Gln Thr Ser Gln Arg Glu Lys Glu Asp
130 135 140

Asp Lys Val Phe Pro Gly Gly Ser His Thr Tyr Val Trp Gln Val Leu
145 150 155 160

Lys Glu Asn Gly Pro Met Ala Ser Asp Pro Leu Cys Leu Thr Tyr Ser
165 170 175

Tyr Leu Ser His Val Asp Leu Val Lys Asp Leu Asn Ser Gly Leu Ile
180 185 190

Gly Ala Leu Leu Val Cys Arg Glu Gly Ser Leu Ala Lys Glu Lys Thr
195 200 205

Gln Thr Leu His Lys Phe Ile Leu Leu Phe Ala Val Phe Asp Glu Gly
210 215 220

Lys Ser Trp His Ser Glu Thr Lys Asn Ser Leu Met Gln Asp Arg Asp
225 230 235 240

Ala Ala Ser Ala Arg Ala Trp Pro Lys Met His Thr Val Asn Gly Tyr
245 250 255

Val Asn Arg Ser Leu Pro Gly Leu Ile Gly Cys His Arg Lys Ser Val
260 265 270

Tyr Trp His Val Ile Gly Met Gly Thr Thr Pro Glu Val His Ser Ile
275 280 285

Phe Leu Glu Gly His Thr Phe Leu Val Arg Asn His Arg Gln Ala Ser
290 295 300

Leu Glu Ile Ser Pro Ile Thr Phe Leu Thr Ala Gln Thr Leu Leu Met
305 310 315 320

Asp Leu Gly Gln Phe Leu Leu Phe Cys His Ile Ser Ser His Gln His
325 330 335

Asp Gly Met Glu Ala Tyr Val Lys Val Asp Ser Cys Pro Glu Glu Pro
340 345 350

Gln Leu Arg Met Lys Asn Asn Glu Glu Ala Glu Asp Tyr Asp Asp Asp
355 360 365

Leu Thr Asp Ser Glu Met Asp Val Val Arg Phe Asp Asp Asp Asn Ser
370 375 380

Pro Ser Phe Ile Gln Ile Arg Ser Val Ala Lys Lys His Pro Lys Thr
385 390 395 400

Trp Val His Tyr Ile Ala Ala Glu Glu Glu Asp Trp Asp Tyr Ala Pro
405 410 415

Leu Val Leu Ala Pro Asp Asp Arg Ser Tyr Lys Ser Gln Tyr Leu Asn
420 425 430

Asn Gly Pro Gln Arg Ile Gly Arg Lys Tyr Lys Lys Val Arg Phe Met
435 440 445

Ala Tyr Thr Asp Glu Thr Phe Lys Thr Arg Glu Ala Ile Gln His Glu
450 455 460

Ser Gly Ile Leu Gly Pro Leu Leu Tyr Gly Glu Val Gly Asp Thr Leu
465 470 475 480

-continued

```
Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Glu Ile Thr Arg Thr Thr Leu Gln Ser
        755                 760                 765

Asp Gln Glu Glu Ile Asp Tyr Asp Asp Thr Ile Ser Val Glu Met Lys
    770                 775                 780

Lys Glu Asp Phe Asp Ile Tyr Asp Glu Asp Glu Asn Gln Ser Pro Arg
785                 790                 795                 800

Ser Phe Gln Lys Lys Thr Arg His Tyr Phe Ile Ala Ala Val Glu Arg
                805                 810                 815

Leu Trp Asp Tyr Gly Met Ser Ser Ser Pro His Val Leu Arg Asn Arg
            820                 825                 830

Ala Gln Ser Gly Ser Val Pro Gln Phe Lys Lys Val Val Phe Gln Glu
        835                 840                 845

Phe Thr Asp Gly Ser Phe Thr Gln Pro Leu Tyr Arg Gly Glu Leu Asn
    850                 855                 860

Glu His Leu Gly Leu Leu Gly Pro Tyr Ile Arg Ala Glu Val Glu Asp
865                 870                 875                 880

Asn Ile Met Val Thr Phe Arg Asn Gln Ala Ser Arg Pro Tyr Ser Phe
                885                 890                 895

Tyr Ser Ser Leu Ile Ser Tyr Glu Glu Asp Gln Arg Gln Gly Ala Glu
```

```
            900                 905                 910

Pro Arg Lys Asn Phe Val Lys Pro Asn Glu Thr Lys Thr Tyr Phe Trp
        915                 920                 925

Lys Val Gln His His Met Ala Pro Thr Lys Asp Glu Phe Asp Cys Lys
    930                 935                 940

Ala Trp Ala Tyr Phe Ser Asp Val Asp Leu Glu Lys Asp Val His Ser
945                 950                 955                 960

Gly Leu Ile Gly Pro Leu Leu Val Cys His Thr Asn Thr Leu Asn Pro
                965                 970                 975

Ala His Gly Arg Gln Val Thr Val Gln Glu Phe Ala Leu Phe Phe Thr
            980                 985                 990

Ile Phe Asp Glu Thr Lys Ser Trp  Tyr Phe Thr Glu Asn  Met Glu Arg
        995                 1000                1005

Asn Cys  Arg Ala Pro Cys Asn  Ile Gln Met Glu Asp  Pro Thr Phe
    1010                 1015                 1020

Lys Glu  Asn Tyr Arg Phe His  Ala Ile Asn Gly Tyr  Ile Met Asp
    1025                 1030                 1035

Thr Leu  Pro Gly Leu Val Met  Ala Gln Asp Gln Arg  Ile Arg Trp
    1040                 1045                 1050

Tyr Leu  Leu Ser Met Gly Ser  Asn Glu Asn Ile His  Ser Ile His
    1055                 1060                 1065

Phe Ser  Gly His Val Phe Thr  Val Arg Lys Lys Glu  Glu Tyr Lys
    1070                 1075                 1080

Met Ala  Leu Tyr Asn Leu Tyr  Pro Gly Val Phe Glu  Thr Val Glu
    1085                 1090                 1095

Met Leu  Pro Ser Lys Ala Gly  Ile Trp Arg Val Glu  Cys Leu Ile
    1100                 1105                 1110

Gly Glu  His Leu His Ala Gly  Met Ser Thr Leu Phe  Leu Val Tyr
    1115                 1120                 1125

Ser Asn  Lys Cys Gln Thr Pro  Leu Gly Met Ala Ser  Gly His Ile
    1130                 1135                 1140

Arg Asp  Phe Gln Ile Thr Ala  Ser Gly Gln Tyr Gly  Gln Trp Ala
    1145                 1150                 1155

Pro Lys  Leu Ala Arg Leu His  Tyr Ser Gly Ser Ile  Asn Ala Trp
    1160                 1165                 1170

Ser Thr  Lys Glu Pro Phe Ser  Trp Ile Lys Val Asp  Leu Leu Ala
    1175                 1180                 1185

Pro Met  Ile Ile His Gly Ile  Lys Thr Gln Gly Ala  Arg Gln Lys
    1190                 1195                 1200

Phe Ser  Ser Leu Tyr Ile Ser  Gln Phe Ile Ile Met  Tyr Ser Leu
    1205                 1210                 1215

Asp Gly  Lys Lys Trp Gln Thr  Tyr Arg Gly Asn Ser  Thr Gly Thr
    1220                 1225                 1230

Leu Met  Val Phe Phe Gly Asn  Val Asp Ser Ser Gly  Ile Lys His
    1235                 1240                 1245

Asn Ile  Phe Asn Pro Pro Ile  Ile Ala Arg Tyr Ile  Arg Leu His
    1250                 1255                 1260

Pro Thr  His Tyr Ser Ile Arg  Ser Thr Leu Arg Met  Glu Leu Met
    1265                 1270                 1275

Gly Cys  Asp Leu Asn Ser Cys  Ser Met Pro Leu Gly  Met Glu Ser
    1280                 1285                 1290

Lys Ala  Ile Ser Asp Ala Gln  Ile Thr Ala Ser Ser  Tyr Phe Thr
    1295                 1300                 1305
```

```
Asn Met  Phe Ala Thr Trp Ser  Pro Ser Lys Ala Arg  Leu His Leu
    1310                 1315                 1320

Gln Gly  Arg Ser Asn Ala Trp  Arg Pro Gln Val Asn  Asn Pro Lys
    1325                 1330                 1335

Glu Trp  Leu Gln Val Asp Phe  Gln Lys Thr Met Lys  Val Thr Gly
    1340                 1345                 1350

Val Thr  Thr Gln Gly Val Lys  Ser Leu Leu Thr Ser  Met Tyr Val
    1355                 1360                 1365

Lys Glu  Phe Leu Ile Ser Ser  Ser Gln Asp Gly His  Gln Trp Thr
    1370                 1375                 1380

Leu Phe  Phe Gln Asn Gly Lys  Val Lys Val Phe Gln  Gly Asn Gln
    1385                 1390                 1395

Asp Ser  Phe Thr Pro Val Val  Asn Ser Leu Asp Pro  Pro Leu Leu
    1400                 1405                 1410

Thr Arg  Tyr Leu Arg Ile His  Pro Gln Ser Trp Val  His Gln Ile
    1415                 1420                 1425

Ala Leu  Arg Met Glu Val Leu  Gly Cys Glu Ala Gln  Asp Leu Tyr
    1430                 1435                 1440
```

<210> SEQ ID NO 11
<211> LENGTH: 4368
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
atgcagattg agctgagcac ctgcttcttc ctgtgcctgc tgaggttctg cttctctgcc     60

accaggagat actacctggg ggctgtggag ctttcttggg actacatgca gtctgacctg    120

ggggagctgc ctgtggatgc caggttccca cccagagtgc ccaaatcctt cccattcaac    180

acctctgtgg tctacaagaa gaccctcttt gtggagttca ctgaccacct gttcaacatt    240

gccaaaccca ggccaccctg gatgggactc ctgggaccca ccattcaggc tgaggtgtat    300

gacactgtgg tcatcaccct caagaacatg gcctcccacc ctgtgagcct gcatgctgtg    360

ggggtcagct actggaaggc ctctgagggg gctgagtatg atgaccagac ctcccagagg    420

gagaaggagg atgacaaagt gttccctggg ggcagccaca cctatgtgtg gcaggtcctc    480

aaggagaatg gccccatggc ctctgaccca ctctgcctga cctactccta cctttctcat    540

gtggacctgg tcaaggacct caactctgga ctgattgggg ccctgctggt gtgcagggag    600

ggctccctgg ccaaagagaa gacccagacc ctgcacaagt tcattctcct gtttgctgtc    660

tttgatgagg gcaagagctg gcactctgaa accaagaact ccctgatgca ggacagggat    720

gctgcctctg ccagggcctg gcccaagatg cacactgtga atggctatgt gaacaggagc    780

ctgcctggac tcattggctg ccacaggaaa tctgtctact ggcatgtgat tggcatgggg    840

acaacccctg aggtgcactc cattttcctg gagggccaca ccttcctggt caggaaccac    900

agacaggcca gcctggagat cagccccatc accttcctca ctgcccagac cctgctgatg    960

gacctcggac agttcctgct gttctgccac atcagctccc accagcatga tggcatggag   1020

gcctatgtca aggtggacag ctgccctgag gagccacagc tcaggatgaa gaacaatgag   1080

gaggctgagg actatgatga tgacctgact gactctgaga tggatgtggt ccgctttgat   1140

gatgacaaca gcccatcctt cattcagatc aggtctgtgg ccaagaaaca ccccaagacc   1200
```

```
tgggtgcact acattgctgc tgaggaggag gactgggact atgccccact ggtcctggcc   1260
cctgatgaca ggagctacaa gagccagtac ctcaacaatg gcccacagag gattggacgc   1320
aagtacaaga aagtcaggtt catggcctac actgatgaaa ccttcaagac cagggaggcc   1380
attcagcatg agtctggcat cctgggccca ctcctgtatg gggaggtggg ggacaccctg   1440
ctcatcatct tcaagaacca ggcctccagg ccctacaaca tctacccaca tggcatcact   1500
gatgtcaggc ccctgtacag ccgcaggctg ccaaaggggg tgaaacacct caaggacttc   1560
cccattctgc ctggggagat cttcaagtac aagtggactg tcactgtgga ggatggacca   1620
accaaatctg accccaggtg cctcaccaga tactactcca gctttgtgaa catggagagg   1680
gacctggcct ctggcctgat tggcccactg ctcatctgct acaaggagtc tgtggaccag   1740
aggggaaacc agatcatgtc tgacaagagg aatgtgattc tgttctctgt ctttgatgag   1800
aacaggagct ggtacctgac tgagaacatt cagcgcttcc tgcccaaccc tgctggggtg   1860
cagctggagg accctgagtt ccaggccagc aacatcatgc actccatcaa tggctatgtg   1920
tttgacagcc tccagctttc tgtctgcctg catgaggtgg cctactggta cattctttct   1980
attggggccc agactgactt cctttctgtc ttcttctctg gctacacctt caaacacaag   2040
atggtgtatg aggacaccct gaccctcttc ccattctctg ggagagactgt gttcatgagc   2100
atggagaacc ctggcctgtg gattctggga tgccacaact ctgacttccg caacaggggc   2160
atgactgccc tgctcaaagt ctcctcctgt gacaagaaca ctggggacta ctatgaggac   2220
agctatgagg acatctctgc ctacctgctc agcaagaaca atgccattga gcccaggagc   2280
ttcagccaga attccagaca ccccagcacc agggagatca ccaggaccac cctccagtct   2340
gaccaggagg agattgacta tgatgacacc atttctgtgg agatgaagaa agaggacttt   2400
gacatctatg acgaggacga gaaccagagc ccaaggagct tccagaagaa gaccaggcac   2460
tacttcattg ctgctgtgga gcgcctgtgg gactatggca tgagctccag cccccatgtc   2520
ctcaggaaca gggcccagtc tggctctgtg ccacagttca agaaagtggt cttccaagag   2580
ttcactgatg gcagcttcac ccagcccctg tacagagggg agctgaatga gcacctggga   2640
ctcctgggcc catacatcag ggctgaggtg gaggacaaca tcatggtgac cttccgcaac   2700
caggcctcca ggccctacag cttctacagc tccctcatca gctatgagga ggaccagagg   2760
cagggggctg agccacgcaa gaactttgtg aaacccaatg aaaccaagac ctacttctgg   2820
aaagtccagc accacatggc ccccaccaag gatgagtttg actgcaaggc ctgggcctac   2880
ttctctgatg tggacctgga gaaggatgtg cactctggcc tgattggccc actcctggtc   2940
tgccacacca acaccctgaa ccctgcccat ggaaggcaag tgactgtgca ggagtttgcc   3000
ctcttcttca ccatctttga tgaaaccaag agctggtact tcactgagaa catggagcgc   3060
aactgcaggg ccccatgcaa cattcagatg gaggacccca ccttcaaaga gaactaccgc   3120
ttccatgcca tcaatggcta catcatggac accctgcctg ggcttgtcat ggcccaggac   3180
cagaggatca ggtggtacct gctttctatg ggctccaatg agaacattca ctccatccac   3240
ttctctgggc atgtcttcac tgtgcgcaag aaggaggagt acaagatggc cctgtacaac   3300
ctctaccctg ggtctttga gactgtggag atgctgccct ccaaagctgg catctggagg   3360
gtggagtgcc tcattgggga gcacctgcat gctggcatga gcaccctgtt cctggtctac   3420
agcaacaagt gccagacccc cctgggaatg gcctctggcc acatcaggga cttccagatc   3480
actgcctctg gccagtatgg ccagtgggcc cccaagctgg ccaggctcca ctactctgga   3540
tccatcaatg cctggagcac caaggagcca ttcagctgga tcaaagtgga cctgctggcc   3600
```

```
cccatgatca tccatggcat caagacccag ggggccaggc agaagttctc cagcctgtac   3660

atcagccagt tcatcatcat gtacagcctg gatggcaaga aatggcagac ctacagaggc   3720

aactccactg gaacactcat ggtcttcttt ggcaatgtgg acagctctgg catcaagcac   3780

aacatcttca accccccaat catcgccaga tacatcaggc tgcaccccac ccactacagc   3840

atccgcagca ccctcaggat ggagctgatg ggctgtgacc tgaactcctg cagcatgccc   3900

ctgggcatgg agagcaaggc catttctgat gcccagatca ctgcctccag ctacttcacc   3960

aacatgtttg ccacctggag cccaagcaag gccaggctgc acctccaggg aaggagcaat   4020

gcctggaggc cccaggtcaa caacccaaag gagtggctgc aggtggactt ccagaagacc   4080

atgaaggtca ctggggtgac cacccagggg gtcaagagcc tgctcaccag catgtatgtg   4140

aaggagttcc tgatcagctc cagccaggat ggccaccagt ggaccctctt cttccagaat   4200

ggcaaggtca aggtgttcca gggcaaccag gacagcttca cccctgtggt gaacagcctg   4260

gacccccccc tcctgaccag atacctgagg attcaccccc agagctgggt ccaccagatt   4320

gccctgagga tggaggtcct gggatgtgag gcccaggacc tgtactga                4368
```

<210> SEQ ID NO 12
<211> LENGTH: 1455
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220
```

-continued

```
Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640
```

-continued

```
Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Glu Ile Thr Arg Thr Thr Leu Gln Ser Asp Gln Glu Glu
    770                 775                 780

Ile Asp Tyr Asp Asp Thr Ile Ser Val Glu Met Lys Lys Glu Asp Phe
785                 790                 795                 800

Asp Ile Tyr Asp Glu Asp Glu Asn Gln Ser Pro Arg Ser Phe Gln Lys
                805                 810                 815

Lys Thr Arg His Tyr Phe Ile Ala Ala Val Glu Arg Leu Trp Asp Tyr
            820                 825                 830

Gly Met Ser Ser Ser Pro His Val Leu Arg Asn Arg Ala Gln Ser Gly
        835                 840                 845

Ser Val Pro Gln Phe Lys Lys Val Val Phe Gln Glu Phe Thr Asp Gly
    850                 855                 860

Ser Phe Thr Gln Pro Leu Tyr Arg Gly Glu Leu Asn Glu His Leu Gly
865                 870                 875                 880

Leu Leu Gly Pro Tyr Ile Arg Ala Glu Val Glu Asp Asn Ile Met Val
                885                 890                 895

Thr Phe Arg Asn Gln Ala Ser Arg Pro Tyr Ser Phe Tyr Ser Ser Leu
            900                 905                 910

Ile Ser Tyr Glu Glu Asp Gln Arg Gln Gly Ala Glu Pro Arg Lys Asn
        915                 920                 925

Phe Val Lys Pro Asn Glu Thr Lys Thr Tyr Phe Trp Lys Val Gln His
    930                 935                 940

His Met Ala Pro Thr Lys Asp Glu Phe Asp Cys Lys Ala Trp Ala Tyr
945                 950                 955                 960

Phe Ser Asp Val Asp Leu Glu Lys Asp Val His Ser Gly Leu Ile Gly
                965                 970                 975

Pro Leu Leu Val Cys His Thr Asn Thr Leu Asn Pro Ala His Gly Arg
            980                 985                 990

Gln Val Thr Val Gln Glu Phe Ala  Leu Phe Phe Thr Ile  Phe Asp Glu
        995                 1000                1005

Thr Lys  Ser Trp Tyr Phe Thr  Glu Asn Met Glu Arg  Asn Cys Arg
    1010                1015                1020

Ala Pro  Cys Asn Ile Gln Met  Glu Asp Pro Thr Phe  Lys Glu Asn
    1025                1030                1035

Tyr Arg  Phe His Ala Ile Asn  Gly Tyr Ile Met Asp  Thr Leu Pro
    1040                1045                1050

Gly Leu  Val Met Ala Gln Asp  Gln Arg Ile Arg Trp  Tyr Leu Leu
```

-continued

```
    1055                1060                1065

Ser Met  Gly Ser Asn Glu Asn  Ile His Ser Ile His  Phe Ser Gly
    1070                1075                1080

His Val  Phe Thr Val Arg Lys  Lys Glu Glu Tyr Lys  Met Ala Leu
    1085                1090                1095

Tyr Asn  Leu Tyr Pro Gly Val  Phe Glu Thr Val Glu  Met Leu Pro
    1100                1105                1110

Ser Lys  Ala Gly Ile Trp Arg  Val Glu Cys Leu Ile  Gly Glu His
    1115                1120                1125

Leu His  Ala Gly Met Ser Thr  Leu Phe Leu Val Tyr  Ser Asn Lys
    1130                1135                1140

Cys Gln  Thr Pro Leu Gly Met  Ala Ser Gly His Ile  Arg Asp Phe
    1145                1150                1155

Gln Ile  Thr Ala Ser Gly Gln  Tyr Gly Gln Trp Ala  Pro Lys Leu
    1160                1165                1170

Ala Arg  Leu His Tyr Ser Gly  Ser Ile Asn Ala Trp  Ser Thr Lys
    1175                1180                1185

Glu Pro  Phe Ser Trp Ile Lys  Val Asp Leu Leu Ala  Pro Met Ile
    1190                1195                1200

Ile His  Gly Ile Lys Thr Gln  Gly Ala Arg Gln Lys  Phe Ser Ser
    1205                1210                1215

Leu Tyr  Ile Ser Gln Phe Ile  Ile Met Tyr Ser Leu  Asp Gly Lys
    1220                1225                1230

Lys Trp  Gln Thr Tyr Arg Gly  Asn Ser Thr Gly Thr  Leu Met Val
    1235                1240                1245

Phe Phe  Gly Asn Val Asp Ser  Ser Gly Ile Lys His  Asn Ile Phe
    1250                1255                1260

Asn Pro  Pro Ile Ile Ala Arg  Tyr Ile Arg Leu His  Pro Thr His
    1265                1270                1275

Tyr Ser  Ile Arg Ser Thr Leu  Arg Met Glu Leu Met  Gly Cys Asp
    1280                1285                1290

Leu Asn  Ser Cys Ser Met Pro  Leu Gly Met Glu Ser  Lys Ala Ile
    1295                1300                1305

Ser Asp  Ala Gln Ile Thr Ala  Ser Ser Tyr Phe Thr  Asn Met Phe
    1310                1315                1320

Ala Thr  Trp Ser Pro Ser Lys  Ala Arg Leu His Leu  Gln Gly Arg
    1325                1330                1335

Ser Asn  Ala Trp Arg Pro Gln  Val Asn Asn Pro Lys  Glu Trp Leu
    1340                1345                1350

Gln Val  Asp Phe Gln Lys Thr  Met Lys Val Thr Gly  Val Thr Thr
    1355                1360                1365

Gln Gly  Val Lys Ser Leu Leu  Thr Ser Met Tyr Val  Lys Glu Phe
    1370                1375                1380

Leu Ile  Ser Ser Ser Gln Asp  Gly His Gln Trp Thr  Leu Phe Phe
    1385                1390                1395

Gln Asn  Gly Lys Val Lys Val  Phe Gln Gly Asn Gln  Asp Ser Phe
    1400                1405                1410

Thr Pro  Val Val Asn Ser Leu  Asp Pro Pro Leu Leu  Thr Arg Tyr
    1415                1420                1425

Leu Arg  Ile His Pro Gln Ser  Trp Val His Gln Ile  Ala Leu Arg
    1430                1435                1440

Met Glu  Val Leu Gly Cys Glu  Ala Gln Asp Leu Tyr
    1445                1450                1455
```

<210> SEQ ID NO 13
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
atgcagattg agctgtccac ctgcttcttt ctgtgcctgc tgagattctg cttctctgcc 60
accaggagat actacctggg ggctgtggaa ctttcttggg actacatgca gtctgacctg 120
ggagagctgc ctgtggatgc caggttccca cccagagtgc ccaagtcctt cccattcaac 180
acctctgtgg tctacaagaa gacactcttt gtggaattca ctgaccacct gttcaacatt 240
gcaaaaccca gaccaccctg gatgggactc ctgggaccca ccattcaggc tgaggtgtat 300
gacactgtgg tcatcaccct caagaacatg gcatcccacc ctgtgtctct gcatgctgtg 360
ggagtctcat actggaaagc ctctgaaggg gctgagtatg atgaccagac atcccagaga 420
gagaaagagg atgacaaggt gttccctggg ggatctcaca cctatgtgtg gcaagtcctc 480
aaggagaatg gacccatggc atctgaccca ctctgcctga catactccta cctttctcat 540
gtggacctgg tcaaggacct caactctgga ctgattgggg cactgctggt gtgcagggaa 600
ggatccctgg ccaaggagaa aacccagaca ctgcacaagt tcattctcct gtttgctgtc 660
tttgatgagg gcaagtcttg gcactctgaa acaaagaact ccctgatgca agacagggat 720
gctgcctctg ccagggcatg gcccaagatg cacactgtga atggctatgt gaacagatca 780
ctgcctggac tcattggctg ccacaggaaa tctgtctact ggcatgtgat tggcatgggg 840
acaacccctg aagtgcactc cattttcctg gagggacaca ccttcctggt caggaaccac 900
agacaagcct ctctggagat ctctcccatc accttcctca ctgcacagac actgctgatg 960
gaccttggac agttcctgct gttctgccac atctcttccc accagcatga tggcatggaa 1020
gcctatgtca aggtggactc atgccctgag gaaccacagc tcaggatgaa gaacaatgag 1080
gaggctgagg actatgatga tgacctgact gactctgaga tggatgtggt cagatttgat 1140
gatgacaact ctccatcctt cattcagatc aggtctgtgg caaagaaaca ccccaagaca 1200
tgggtgcact acattgctgc tgaggaagag gactgggact atgcaccact ggtcctggcc 1260
cctgatgaca ggagctacaa gtctcagtac ctcaacaatg gcccacaaag aattggaaga 1320
aagtacaaga aagtcagatt catggcctac actgatgaaa ccttcaagac aagagaagcc 1380
attcagcatg agtctggcat tctgggacca ctcctgtatg gggaagtggg agacaccctg 1440
ctcatcatct tcaagaacca ggcctccagg ccctacaaca tctacccaca tggcatcact 1500
gatgtcaggc ccctgtacag caggagactg ccaaaagggg tgaaacacct caaggacttc 1560
cccattctgc ctggagagat cttcaagtac aagtggactg tcactgtgga ggatggacca 1620
acaaagtctg accccaggtg cctcaccaga tactactcct cttttgtgaa catggagaga 1680
gacctggcat ctggactgat tggaccactg ctcatctgct acaaggagtc tgtggaccag 1740
agaggcaacc agatcatgtc tgacaagaga aatgtgattc tgttctctgt ctttgatgag 1800
aacagatcat ggtacctgac tgagaacatt cagagattcc tgcccaaccc tgctggggtg 1860
caactggaag accctgagtt ccaggcaagc aacatcatgc actccatcaa tggctatgtg 1920
tttgactctc tccagctttc tgtctgcctg catgaggtgg cctactggta cattctttct 1980
attggggcac aaactgactt cctttctgtc ttcttctctg gatacacctt caagcacaag 2040
atggtgtatg aggacaccct gacactcttc ccattctctg gggaaactgt gttcatgagc 2100
atggagaacc ctggactgtg gattctggga tgccacaact ctgacttcag aaacagggga 2160
atgactgcac tgctcaaagt ctcctcctgt gacaagaaca ctggggacta ctatgaggac 2220
tcttatgagg acatctctgc ctacctgctc agcaagaaca atgccattga gcccagaagc 2280
ttctctcaga atccacctgt cctgaagaga caccagagag agatcaccag gacaaccctc 2340
cagtctgacc aggaagagat tgactatgat gacaccattt ctgtggagat gaagaaggag 2400
gactttgaca tctatgatga ggacgagaac cagtctccaa gatcattcca gaagaagaca 2460
agacactact tcattgctgc tgtggaaaga ctgtgggact atggcatgtc ttcctctccc 2520
catgtcctca ggaacagggc acagtctggc tctgtgccac agttcaagaa agtggtcttc 2580
caggagttca ctgatggctc attcacccag cccctgtaca gaggggaact gaatgagcac 2640
ctgggactcc tgggaccata catcagggct gaggtggaag acaacatcat ggtgacattc 2700
agaaaccagg cctccaggcc ctacagcttc tactcttccc tcatcagcta tgaggaagac 2760
cagagacaag ggctgagcc aagaaagaac tttgtgaaac ccaatgaaac caagacctac 2820
ttctggaaag tccagcacca catggcaccc accaaggatg agtttgactg caaggcctgg 2880
gcatacttct ctgatgtgga cctggagaaa gatgtgcact ctggcctgat tggcccactc 2940
ctggtctgcc acaccaacac cctgaaccct gcacatggaa ggcaagtgac tgtgcaggag 3000
tttgccctct tcttcaccat ctttgatgaa accaagtcat ggtacttcac tgagaacatg 3060
gagagaaact gcagagcacc atgcaacatt cagatggaag accccacctt caaggagaac 3120
tacaggttcc atgccatcaa tggctacatc atggacaccc tgcctgggct tgtcatggca 3180
caggaccaga gaatcagatg gtacctgctt tctatgggat ccaatgagaa cattcactcc 3240
atccacttct ctgggcatgt cttcactgtg agaaagaagg aggaatacaa gatggccctg 3300
tacaacctct accctggggt ctttgagact gtggagatgc tgccctccaa agctggcatc 3360
tggagggtgg aatgcctcat tggggagcac ctgcatgctg gcatgtcaac cctgttcctg 3420
gtctacagca acaagtgcca gacacccctg ggaatggcct ctggccacat cagggacttc 3480
cagatcactg cctctggcca gtatggccag tgggcaccca aactggccag gctccactac 3540
tctggctcca tcaatgcatg gtcaaccaag gagccattct cttggatcaa ggtggacctg 3600
ctggcaccca tgatcattca tggcatcaag acacaggggg caagacagaa attctcctct 3660
ctgtacatct cacagttcat catcatgtac tctctggatg gcaagaagtg gcagacatac 3720
agaggcaact ccactggcac cctcatggtc ttctttggca atgtggacag ctctggcatc 3780
aagcacaaca tcttcaaccc tcccatcatt gccagataca tcaggctgca ccccacccac 3840
tactcaatca gatcaaccct caggatggaa ctgatgggat gtgacctgaa ctcctgctca 3900
atgcccctgg gaatggagag caaggccatt tctgatgccc agatcactgc atcctcttac 3960
ttcaccaaca tgtttgccac ctggtcacca tcaaaagcca ggctgcacct ccagggaaga 4020
agcaatgcct ggagacccca ggtcaacaac ccaaaggaat ggctgcaagt ggacttccag 4080
aagacaatga aagtcactgg ggtgacaacc caggggtca agtctctgct cacctcaatg 4140
tatgtgaagg agttcctgat ctcttcctca caggatggcc accagtggac actcttcttc 4200
cagaatggca aagtcaaggt gttccagggc aaccaggact ctttcacacc tgtggtgaac 4260
tcactggacc cccccctcct gacaagatac ctgagaattc acccccagtc ttgggtccac 4320
cagattgccc tgagaatgga agtcctggga tgtgaggcac aagacctgta ctga 4374

<210> SEQ ID NO 14
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14
atgcagatcg aactgagcac ttgcttcttc ctgtgtctcc tgcgcttttg cttctccgcc 60
acaaggagat actatctcgg tgccgtggag ctcagctggg actacatgca gagcgacttg 120
ggtgaactgc ctgtggacgc caggtttcca ccccgcgtgc ccaagagttt cccgttcaac 180
accagtgtcg tgtacaagaa aaccctcttc gtggaattca ccgaccacct gttcaacatc 240
gccaaaccgc gccctccctg gatggggctg ctcggcccga cgatccaggc tgaggtctat 300
gacacggtgg tgattaccct caagaacatg gctagccacc cggtgagcct gcacgccgtg 360
ggcgtgtcct attggaaagc gtccgagggt gcggagtacg atgaccagac ttcacagcgg 420
gagaaggaag acgacaaagt gttccccggg ggttcccaca cctatgtctg gcaggtcctg 480
aaggagaatg gtcctatggc ctccgaccca ttgtgcctca cctactctta cctaagccat 540
gtggatctcg tcaaggacct gaactcgggg ctgatcggcg ccctgctcgt gtgccgggag 600
ggctcactgg ccaaggagaa gacccaaact ctgcacaagt tcatcctgct gttcgcggta 660
ttcgacgagg ggaagtcctg gcactccgag accaagaaca gcctgatgca ggaccgcgac 720
gcagcctcgg cccgtgcgtg gccaaagatg cacaccgtga acggctacgt taacaggagc 780
ctacccggcc tgatcggctg ccaccgcaaa tcggtctact ggcatgtgat cggaatgggc 840
acaacgcccg aggtccacag tatcttcctc gagggccaca ctttcctggt ccggaatcac 900
cgccaggcca gcctggagat cagccccata acctttctga cggcgcagac cttactcatg 960
gatctcggcc agttcctcct gttctgccac atttcgtccc accagcacga tgggatggaa 1020
gcatatgtga aagtggactc ctgccccgag gaaccccagc ttaggatgaa gaacaatgag 1080
gaggccgagg actacgacga tgaccttacc gattcagaaa tggacgtagt acgctttgac 1140
gacgacaact ctccatcctt catacagatt cgctccgtcg ccaagaagca ccctaagact 1200
tgggtgcact acatcgcggc cgaggaggag gactgggatt atgctcccct ggtgctggcc 1260
cccgacgacc gcagctacaa gagccagtac ctgaataacg ggccccagcg catcggccgg 1320
aagtacaaga aagtgcggtt catggcttac acggacgaga ccttcaagac ccgggaggct 1380
atccagcatg agagcggcat cttggggccc ctcctgtacg gcgaagttgg agacacactg 1440
ctgatcatct tcaagaacca ggcgagcagg ccctacaaca tctacccccca cggcattacc 1500 gatgtccggc cgttgtacag ccgacggctg cccaagggcg tgaagcacct gaaggacttt 1560
ccgatcctgc cgggcgagat cttcaagtac aagtggactg tgaccgtgga ggatgggccg 1620
accaagagcg atccgcgctg cctgacccgt tactactcca gctttgtcaa tatggagcgc 1680
gacctcgcta gcggcttgat tggccctctg ctgatctgct acaaggagtc cgtggaccag 1740
agggggaatc agatcatgag tgacaagagg aacgtgatcc tgttctccgt gttcgacgaa 1800
aaccgcagct ggtatctcac cgagaatatc cagcgcttcc tgcccaaccc ggccggtgtg 1860
cagctggagg accccgagtt tcaggccagc aacatcatgc attctatcaa cggatatgtg 1920
tttgattccc tgcagctctc agtgtgtctg cacgaggtcg cctactggta tatcctcagc 1980
attggggcac agaccgactt cctgagcgtg ttcttctccg ggtatacctt caagcacaag 2040

-continued atggtgtacg aggataccct gaccctgttc ccctttagcg gcgaaaccgt gtttatgtct 2100
atggagaacc ccgggctctg gatccttggc tgccataact ccgacttccg caaccgcgga 2160
atgaccgcgc tcctgaaagt gtcgagttgt gacaagaaca ccggcgacta ttacgaggac 2220
agttacgagg acatctctgc gtacctcctt agcaagaata acgccatcga gccaagatcc 2280
ttcagccaga accccccagt gctgaagagg catcagcggg agatcacccg cacgaccctg 2340
cagtcggatc aggaggagat tgattacgac gacacgatca gtgtggagat gaagaaggag 2400
gacttcgaca tctacgacga agatgaaaac cagtcccctc ggtccttcca aaagaagacc 2460
cggcactact tcatcgccgc tgtggaacgc ctgtgggact atggaatgtc ttctagccct 2520
cacgttttga ggaaccgcgc ccagtcgggc agcgtgcccc agttcaagaa agtggtgttc 2580
caggagttca ccgacggctc cttcacccag ccactttacc ggggcgagct caatgaacat 2640
ctgggcctgc tgggacccta catcagggct gaggtggagg acaacatcat ggtgacattc 2700
cggaatcagg ccagcagacc atacagtttc tacagttcac tcatctccta cgaggaggac 2760
cagcgccagg gggctgaacc ccgtaagaac ttcgtgaagc caaacgaaac aaagacctac 2820
ttctggaagg tccagcacca catggcacct accaaggacg agttcgattg caaggcctgg 2880
gcctacttct ccgacgtgga cctggagaaa gatgtgcaca gcggcctgat tggccctctg 2940
ctggtgtgtc acacgaacac actcaaccct gcacacgggc ggcaggtcac tgtgcaggaa 3000
ttcgccctgt tctttaccat ctttgatgag acgaagtcct ggtatttcac cgaaaacatg 3060
gagaggaact gccgcgcacc ctgcaacatc cagatggaag atccgacatt caaggagaac 3120
taccggttcc atgccatcaa tggctacatc atggacaccc tgcctggcct cgtgatggcc 3180
caagaccagc gtatccgctg gtatctgctg tcgatgggct ccaacgagaa catccatagt 3240
atccacttca gcgggcatgt cttcacggtg aggaaaaagg aggagtacaa gatggcactg 3300
tacaacctct atcccggcgt gttcgagacc gtggagatgc tgccctccaa ggccggcatc 3360
tggagagtgg aatgcctgat cggcgagcac ctccacgctg ggatgtccac gctgttcctc 3420
gtttacagca ataagtgcca gacccctctg ggcatggcga gcggccacat ccgcgacttc 3480
cagattacag ccagcggcca gtacggtcag tgggctccaa agctggcccg tctgcactac 3540
tccggatcca tcaacgcctg gtccaccaag gaaccgttct cctggatcaa agtagacctg 3600
ctagccccca tgatcattca cggcatcaag acacaaggcg cccgacagaa gttctcgagc 3660
ctctatatct cccagttcat catcatgtat agcctggacg gaaagaagtg gcagacttac 3720
cgcggaaact cgacagggac cctgatggta ttcttcggta acgtggacag ctccggaatc 3780
aagcacaaca tcttcaaccc acccattatc gcccgctaca tccgcctgca ccccactcac 3840
tatagcatta ggtccaccct gcgaatggag ctcatgggct gtgacctgaa cagctgtagc 3900
atgcccctcg gcatggagtc taaggcgatc tccgacgcac agataacggc atcatcctac 3960
tttaccaaca tgttcgctac ctggtccccc tccaaggccc gactccacct gcaagggaga 4020
tccaacgcct ggcggccaca ggtcaacaat cccaaggagt ggctgcaagt ggactttcag 4080
aaaactatga aagtcaccgg agtgaccaca cagggagtga agtctctgct gaccagcatg 4140
tacgtgaagg agttcctcat ctccagttcg caggatggcc accagtggac gttgttcttc 4200
caaaacggta aagtcaaagt cttccaaggg aaccaggaca gctttacacc cgtcgtgaac 4260
tccctggacc ccccgcttct cactagatac ctccgcatcc accctcagag ctgggtgcac 4320
cagattgccc tgcgcatgga ggttctgggg tgtgaagccc aggacctgta ctaa 4374

<210> SEQ ID NO 15
<211> LENGTH: 4374
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15
atgcagattg agctctccac ctgcttcttt ctctgccttc ttcgcttctg cttttctgcc 60
acacgcaggt actatttggg agcagtggaa ctgagctggg attacatgca gagtgacctt 120
ggtgaacttc ctgtggacgc tcgttttcca cctagagttc ccaagtcctt ccccttcaac 180
acctcagtgg tctacaagaa aacgctgttt gtggagttca ctgaccacct cttcaacatt 240
gccaaaccaa gacccccttg gatgggattg ctgggaccca caatacaagc agaagtctac 300
gacacggtgg tgattaccct gaagaacatg gcgtcacacc ctgtttcact tcacgctgtt 360
ggggtcagtt attggaaagc ctcagagggt gcggaatacg atgatcaaac cagccagagg 420
gagaaggaag atgacaaggt ctttcctggg ggtagccata cctatgtttg gcaggtgctg 480
aaagagaatg ggcctatggc ctctgatccc ttgtgcctca catactctta cctgagtcac 540
gtcgacctgg tgaaagacct gaatagcggt ctgattggtg cactgcttgt ttgtagagag 600
gggagtttgg ccaaggagaa aactcagact ctccacaagt ttatcctcct gtttgctgtg 660
ttcgacgagg gcaagtcttg gcactctgaa acaaagaact ccctgatgca ggacagagat 720
gctgcatctg caagggcttg gccaaaaatg cacacagtga acggctatgt gaatcgatca 780
ctgccaggac tgataggctg tcatcgcaag tcagtgtatt ggcacgttat cgggatggga 840
acaactccag aagtgcacag catcttcctt gagggccaca ctttcctggt tcggaatcat 900
agacaggcca gccttgagat cagcccaatc acctttctga ctgcccaaac cttgctgatg 960
gatctgggac agttcctcct gttttgtcac atctcctccc accaacatga cgggatggag 1020
gcttatgtga aggtcgatag ctgtccggag gaaccacaac tgaggatgaa gaacaacgaa 1080
gaggcagagg actatgacga cgatctgact gacagtgaaa tggacgtggt tcggttcgac 1140
gatgacaatt ctccttcatt tatccagatc cgttccgtgg ccaagaagca ccccaagact 1200
tgggttcatt acatcgctgc tgaggaggag gattgggact acgcgccctt ggtgttggcc 1260
ccagacgatc gctcatacaa gagccagtac cttaacaatg gtccacaaag gatcggccgg 1320
aagtacaaga aggttagatt tatggcttat accgacgaga cttttaaaac tagggaagca 1380
attcagcatg aaagtggcat tcttggaccc ctgctgtatg gcgaggttgg cgacaccctg 1440
ctgattatct ttaagaacca ggcaagccgg ccctacaaca tctacccgca cggcataacc 1500
gatgtacgac ccctgtacag tcgcagactt cctaaagggg tgaaacacct gaaggacttc 1560
ccaattctgc ccggggagat cttcaagtat aaatggaccg tgacggttga ggatggtccc 1620
acaaagtccg atccgagatg ccttacccga tattattcca gcttcgtgaa catggaaagg 1680
gacctggcca gcgggctgat tggcccactg ctgatttgtt acaaggagtc tgtcgatcaa 1740
agaggaaacc aaataatgag cgacaaacgt aacgtcatcc tgttcagcgt ctttgatgag 1800
aatagaagct ggtacctcac agaaaatatt cagcggtttc tgcctaaccc cgcaggcgtc 1860
cagctggaag atcccgagtt ccaagcctca aacatcatgc atagcatcaa cggatacgta 1920
ttcgatagcc tgcagctgtc cgtctgtctc catgaagtgg catattggta catcctgagt 1980
atcggggcgc agaccgactt cctgagcgtg ttcttttctg gatacacgtt caaacacaaa 2040
atggtctatg aagataccct gactctgttt ccattctcag gagagacagt ctttatgagt 2100

```
atggaaaatc ctggactgtg gatcctgggc tgtcacaatt ctgattttcg gaacagaggc   2160
atgacagccc tgcttaaagt gagctcatgc gacaagaaca ccggtgatta ctacgaagat   2220
agctatgagg acatcagtgc gtatttgctc tccaagaaca acgctatcga gccacggtct   2280
ttcagtcaga atcctcccgt tctgaagcgg catcagcgcg aaataacacg cacaaccctt   2340
cagtcagacc aagaggaaat cgactacgat gatactatct ctgtggagat gaagaaggag   2400
gatttcgaca tttacgacga ggacgagaat cagtccccaa ggagctttca gaagaaaaca   2460
agacactatt tcattgccgc cgtggagcga ctgtgggact acggcatgtc tagctctccg   2520
catgtactta gaaatagggc acaaagcgga tccgtgcctc agtttaagaa agttgtcttt   2580
caggagttta cagatggctc cttcacccag cccttgtatc gcggggaact caatgaacac   2640
ctgggcctcc tgggtcctta tattagggcc gaagtcgagg acaatatcat ggtgaccttt   2700
aggaaccagg catctagacc ttactctttc tactcctccc tgatatccta tgaggaggac   2760
cagcggcaag gcgctgagcc tcggaagaac tttgtgaagc caaatgaaac caaaacatac   2820
ttttggaaag ttcagcacca catggctccc acgaaggacg aatttgactg taaagcctgg   2880
gcctacttct cagatgtaga tctcgagaaa gacgtgcact cagggctcat tggtcccctc   2940
ctggtctgtc atactaatac cctcaatcca gcacacggac gtcaggtaac cgtccaggaa   3000
tttgccctgt tctttaccat tttcgatgag actaaatcct ggtactttac cgaaaacatg   3060
gagaggaatt gcagagcccc atgcaacatc cagatggagg accctacctt caaagagaac   3120
tatcgcttcc atgccattaa cggttacatt atggatactc tcccaggact tgtgatggca   3180
caggatcagc ggataagatg gtatctgttg agcatgggct ccaacgagaa tattcacagc   3240
atccatttct ccggtcacgt gtttacagtg agaaagaaag aagagtacaa gatggctctg   3300
tataatctct atccaggcgt attcgaaacg gtggagatgt tgcctagcaa ggccggcatt   3360
tggcgagtag aatgccttat cggggaacat ctgcatgccg gaatgagcac gctcttcctg   3420
gtgtatagta acaagtgcca gactccgctg ggcatggcat ctggccatat acgggacttt   3480
cagattacgg ctagcgggca gtatgggcag tgggcaccca aacttgcgcg actgcactat   3540
tcaggctcta tcaatgcatg gtccaccaag gaacccttct cttggattaa ggtggacctt   3600
ttggcgccca tgataatcca tggatcaaa acccagggcg ctcgtcagaa attctcatca   3660
ctctacatct ctcagttcat aataatgtat tcactggatg ggaagaaatg gcagacttac   3720
agaggaaaca gcaccgggac gctgatggtg ttctttggca acgtggacag cagcggcatc   3780
aaacacaaca tcttcaatcc tcccattatt gcccgttata ttagactgca tcccactcac   3840
tactctatac gcagcacact taggatggag ctcatgggat gcgacctgaa cagttgtagt   3900
atgcccttgg ggatggagtc caaagctata agcgacgcac aaattacagc tagctcttac   3960
tttacgaata tgttcgccac gtggagccca agcaaagccc ggctgcattt gcagggtcgg   4020
agtaatgctt ggcgcccaca ggtgaataac cctaaggaat ggttgcaagt agatttccag   4080
aaaactatga aggtaaccgg cgtcactaca cagggagtca agtccctctt gacctctatg   4140
tacgtcaagg agttcctgat tagcagcagt caggatgggc accaatggac actgttcttc   4200
cagaatggga aagttaaagt atttcagggt aaccaggact cctttacacc tgtggtgaat   4260
agcctcgacc cacccctgct gacacgatac ctccgcatcc accctcagtc ttgggtgcat   4320
caaattgccc tgcgaatgga ggtgttggga tgcgaagctc aggacctcta ctga         4374
```

<210> SEQ ID NO 16

<211> LENGTH: 4374
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 16
atgcagatcg aactctctac ttgcttcttc ctgtgccttc tgaggttctg cttctctgcc 60
actcgccgat attacctcgg ggccgtggag ttgagttggg actacatgca atcagatctg 120
ggcgaactcc ctgtggatgc ccgattccca ccgcgcgtgc ccaagtcttt cccatttaat 180
acttctgtgg tgtacaagaa gacattgttt gtggagttta ccgatcacct gttcaacatc 240
gccaaaccgc ggcccccatg gatgggtctg cttgggccca ccattcaagc ggaggtctat 300
gatacagtgg tgataacgct taagaacatg gcgagccacc cagtgtctct gcatgccgtt 360
ggtgtatcat attggaaggc cagcgaagga gcggagtacg atgaccagac ctctcagaga 420
gagaaggaag acgataaggt tttcctggc ggaagtcata catatgtatg gcaggtcctg 480
aaagagaatg ggccgatggc ttctgacccc ctttgtctta cctatagtta tctgagccac 540
gtggacctgg tcaaggacct caacagtggt ctgattgggg ctctgcttgt ttgtagagag 600
ggtagcttgg ctaaggagaa aacccaaaca ctccataagt tcattttgct gttcgcggtg 660
ttcgacgagg gaaagagttg gcacagcgaa acaaagaatt cactgatgca agacagggac 720
gccgcttccg caagggcttg gcctaagatg catacggtga atgggtatgt gaaccggagc 780
ctcccggggc tgatcgggtg ccatcgcaag tctgtttact ggcacgtcat tggaatgggg 840
acaacgccag aggtacatag tatatttctt gaaggccaca cgttcctcgt acggaaccac 900
cgacaggctt ccctggagat aagccccatt acctttctga ccgctcagac tctgctgatg 960
gaccttggcc agtttctcct gttctgccat attagcagcc accagcacga cggtatggaa 1020
gcatacgtga aagtcgatag ctgtcctgag gagcctcagc tcagaatgaa gaacaacgag 1080
gaggccgaag actatgacga tgaccttaca gattccgaga tggacgtggt gcgctttgac 1140
gacgataaca gtcctagttt cattcaaatc agatccgtag ccaaaaagca tccaaagaca 1200
tgggtgcatt acattgcagc cgaagaggag gattgggatt atgcgcccct tgttctggct 1260
ccagatgaca ggagctataa gtcccagtac ttgaacaacg ggccacagcg aatcggtaga 1320
aaatataaga aggtaagatt catggcctac actgacgaaa catttaaaac cagggaagct 1380
atccaacacg aatctggaat tctcggccct ctgctctacg gtgaggtggg ggacaccttg 1440
ctgatcattt tcaaaaatca ggcatccagg ccttacaaca tatacccccca tggcatcacc 1500 gatgtccgcc cgctgtattc cagaagactc cccaagggag tgaaacatct gaaagatttt 1560
cccatcctgc cgggcgagat ctttaaatac aaatggactg tgactgtaga ggacgggcct 1620
acaaaatcag acccacggtg cctgacaagg tattacagta gcttcgtcaa catggaacgc 1680
gacctcgcca gcggactcat tggcccactg ttgatctgtt acaaagagtc agtggatcag 1740
aggggaaatc agatcatgag cgataagaga aacgttatcc tgtttagtgt cttcgacgag 1800
aaccggtctt ggtaccttac tgagaacatc cagaggttcc tgccgaatcc ggctggcgtt 1860
cagctcgagg acccagagtt ccaggccagt aatataatgc actcaatcaa cggttatgtg 1920
ttcgatagcc tgcagctgag cgtctgcctc cacgaggtag cctattggta catattgtcc 1980
atcggggctc agaccgattt tctgtccgtg ttctttagcg ggtatacctt taaacataaa 2040
atggtctatg aagacaccct gaccctgttc ccattctccg gtgagactgt gttcatgtcc 2100

-continued atggagaacc cagggctgtg gatcctgggg tgtcacaata gtgactttag gaatcgggga 2160
atgacggcac tgctgaaggt gagttcttgc gataaaaata caggagatta ctatgaggat 2220
agttacgagg atatcagtgc ctatctgctt tcaaaaaaca acgcaattga gccccggtct 2280
ttctcacaaa accccccggt gctgaagcgc caccagcgcg aaattacccg gacaaccttg 2340
cagtccgacc aggaggaaat cgattatgac gatactatca gtgtagaaat gaaaaaggag 2400
gattttgata tttacgacga agacgagaac cagtctccgc gaagttttca gaagaaaacg 2460
cgacactact ttatagctgc cgtggaacga ctctgggatt atggcatgtc ctccagccct 2520
catgtcctta ggaatcgagc gcagagtggc tctgtgcctc agttcaaaaa ggttgtgttc 2580
caggaattca ccgacggctc atttacccag ccgctgtaca gaggcgaact caacgaacac 2640
cttgggctgc ttgggccata tattcgagca gaggtggaag ataatatcat ggtaaccttt 2700
agaaaccagg cgtcaagacc ctattccttc tacagttctc tgatcagcta cgaggaggac 2760
caaagacagg gagctgaacc caggaagaac tttgtgaaac ctaatgagac caagacctac 2820
ttctggaagg tccagcacca tatggcccca actaaagatg aattcgattg caaggcctgg 2880
gcttatttca gcgacgtgga tctcgaaaag gatgtgcaca gcgggttgat cggaccgctt 2940
ttggtgtgcc acacaaatac cctcaatcct gcccacgggc ggcaggtcac agttcaagag 3000
tttgcactct tctttacaat atttgacgag acaaagtcat ggtattttac agagaatatg 3060
gagagaaatt gtcgcgcacc ttgcaacatt cagatggagg accccacatt taaggagaat 3120
tacagatttc atgctatcaa tgggtacatt atggatactc tgcctggtct ggtcatggcc 3180
caggatcagc gcataaggtg gtacttgctg agcatgggat ctaatgagaa tatacacagc 3240
attcacttca gtggccacgt ttttactgtt agaaagaagg aggagtacaa aatggcgctc 3300
tacaaccttt acccgggtgt gtttgagaca gtggagatgc tgccaagcaa ggcaggcatc 3360
tggagggttg agtgtcttat tggggagcat ctgcatgctg gaatgtccac cctctttctt 3420
gtgtacagca ataagtgcca gacaccgctt ggcatggcca gcggccacat tagggacttt 3480
cagataactg ccagtggaca gtacggccag tgggctccca agcttgcaag actccactac 3540
tccggaagca taaacgcatg gagcaccaag gaacccttct cttggattaa ggtggacctg 3600
ctggcgccaa tgatcattca cggcataaaa acccaagggg cacgacagaa attttcatct 3660
ttgtatatta gtcagtttat catcatgtac agcttggatg gaaagaagtg gcagacgtac 3720
aggggcaatt ctacaggaac acttatggtg tttttgggga atgtcgattc cagcgggatc 3780
aaacataaca tcttcaatcc tcctattatc gcccgatata tccgcctgca ccctacgcat 3840
tactccatca ggtccacatt gagaatggaa ctgatggggt gcgacctgaa tagttgtagt 3900
atgccactgg gcatggagtc taaagccatc agcgatgcac agatcactgc cagctcttac 3960
ttcaccaaca tgtttgcaac ttggtccccc tctaaagctc gcctgcatct gcagggacgc 4020
tcaaatgcat ggcgaccaca ggtgaacaat ccaaaagagt ggctccaggt cgactttcag 4080
aagacaatga aggtaacagg agtgacaacc cagggtgtaa aaagcctcct tacgagtatg 4140
tacgttaagg agtttctgat ttctagctcc caggacggac accagtggac tctgttcttc 4200
cagaacggca aagtgaaggt atttcaggga aaccaggatt cttttacccc ggtagtgaat 4260
agcctggatc caccgttgct gacccgctat ctgagaattc atccacaatc ctgggtgcat 4320
cagattgccc tccggatgga agtgctcggc tgtgaagctc aggatctgta ttag 4374

<210> SEQ ID NO 17
<211> LENGTH: 4374

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 17
atgcaaatag agctctccac ctgcttcttt ctgtgccttt tgcgattctg ctttagtgcc 60
accagaagat actacctggg tgcagtggaa ctgtcatggg actatatgca aagtgatctc 120
ggtgagctgc ctgtggacgc aagatttcct cctagagtgc caaaatcttt tccattcaac 180
acctcagtcg tgtacaaaaa gactctgttt gtagaattca cggatcacct tttcaacatc 240
gctaagccaa ggccaccctg gatgggtctg ctaggtccta ccatccaggc tgaggtttat 300
gatacagtgg tcattacact taagaacatg gcttcccatc ctgtcagtct tcatgctgtt 360
ggtgtatcct actggaaagc ttctgaggga gctgaatatg atgatcagac cagtcaaagg 420
gagaaagaag atgataaagt cttccctggt ggaagccata catatgtctg gcaggtcctg 480
aaagagaatg gtccaatggc ctctgaccca ctgtgcctta cctactcata tctttctcat 540
gtggacctgg taaaagactt gaattcaggc ctcattggag ccctactagt atgtagagaa 600
gggagtctgg ccaaggaaaa gacacagacc ttgcacaaat ttatactact tttgctgta 660 tttgatgaag ggaaaagttg gcactcagaa acaaagaact ccttgatgca ggatagggat 720
gctgcatctg ctcgggcctg gcctaaaatg cacacagtca atggttatgt aaacaggtct 780
ctgccaggtc tgattggatg ccacaggaaa tcagtctatt ggcatgtgat tggaatgggc 840
accactcctg aagtgcactc aatattcctc gaaggtcaca catttcttgt gaggaaccat 900
cgccaggcgt ccttggaaat ctcgccaata actttcctta ctgctcaaac actcttgatg 960
gaccttggac agtttctact gttttgtcat atctcttccc accaacatga tggcatggaa 1020
gcttatgtca aagtagacag ctgtccagag gaaccccaac tacgaatgaa aaataatgaa 1080
gaagcggaag actatgatga tgatcttact gattctgaaa tggatgtggt caggtttgat 1140
gatgacaact ctccttcctt tatccaaatt cgctcagttg ccaagaagca tcctaaaact 1200
tgggtacatt acattgctgc tgaagaggag gactgggact atgctccctt agtcctcgcc 1260
cccgatgaca gaagttataa aagtcaatat ttgaacaatg gccctcagcg gattggtagg 1320
aagtacaaaa aagtccgatt tatggcatac acagatgaaa cctttaagac tcgtgaagct 1380
attcagcatg aatcaggaat cttgggacct ttactttatg gggaagttgg agacacactg 1440
ttgattatat ttaagaatca agcaagcaga ccatataaca tctaccctca cggaatcact 1500
gatgtccgtc ctttgtattc aaggagatta ccaaaaggtg taaaacattt gaaggatttt 1560
ccaattctgc caggagaaat attcaaatat aaatggacag tgactgtaga agatgggcca 1620
actaaatcag atcctcggtg cctgacccgc tattactcta gtttcgttaa tatggagaga 1680
gatctagctt caggactcat tggccctctc ctcatctgct acaaagaatc tgtagatcaa 1740
agaggaaacc agataatgtc agacaagagg aatgtcatcc tgttttctgt atttgatgag 1800
aaccgaagct ggtacctcac agagaatata caacgctttc tccccaatcc agctggagtg 1860
cagcttgagg atccagagtt ccaagcctcc aacatcatgc acagcatcaa tggctatgtt 1920
tttgatagtt tgcagttgtc agtttgtttg catgaggtgg catactggta cattctaagc 1980
attggagcac agactgactt cctttctgtc ttcttctctg gatatacctt caaacacaaa 2040
atggtctatg aagacacact caccctattc ccattctcag gagaaactgt cttcatgtcg 2100
atggaaaacc caggtctatg gattctgggg tgccacaact cagactttcg gaacagaggc 2160
atgaccgcct tactgaaggt ttctagttgt gacaagaaca ctggtgatta ttacgaggac 2220
agttatgaag atatttcagc atacttgctg agtaaaaaca atgccattga accaagaagc 2280
ttctcccaga atccaccagt cttgaaacgc catcaacggg aaataactcg tactactctt 2340
cagtcagatc aagaggaaat tgactatgat gataccatat cagttgaaat gaagaaggaa 2400
gattttgaca tttatgatga ggatgaaaat cagagccccc gcagctttca aaagaaaaca 2460
cgacactatt ttattgctgc agtggagagg ctctgggatt atgggatgag tagctcccca 2520
catgttctaa gaaacagggc tcagagtggc agtgtccctc agttcaagaa agttgttttc 2580
caggaattta ctgatggctc ctttactcag cccttatacc gtggagaact aaatgaacat 2640
ttgggactcc tggggccata tataagagca gaagttgaag ataatatcat ggtaactttc 2700
agaaatcagg cctctcgtcc ctattccttc tattctagcc ttatttctta tgaggaagat 2760
cagaggcaag gagcagaacc tagaaaaaac tttgtcaagc ctaatgaaac caaaacttac 2820
ttttggaaag tgcaacatca tatggcaccc actaaagatg agtttgactg caaagcctgg 2880
gcttatttct ctgatgttga cctggaaaaa gatgtgcact caggcctgat tggacccctt 2940
ctggtctgcc acactaacac actgaaccct gctcatggga gacaagtgac agtacaggaa 3000
tttgctctgt ttttcaccat ctttgatgag accaaaagct ggtacttcac tgaaaatatg 3060
gaaagaaact gcagggctcc ctgcaatatc cagatggaag atcccacttt taaagagaat 3120
tatcgcttcc atgcaatcaa tggctacata atggatacac tacctggctt agtaatggct 3180
caggatcaaa ggattcgatg gtatctgctc agcatgggca gcaatgaaaa catccattct 3240
attcatttca gtggacatgt gttcactgta cgaaaaaaag aggagtataa aatggcactg 3300
tacaatctct atccaggtgt ttttgagaca gtggaaatgt taccatccaa agctggaatt 3360
tggcgggtgg aatgccttat tggcgagcat ctacatgctg ggatgagcac actttttctg 3420
gtgtacagca ataagtgtca gactcccctg ggaatggctt ctggacacat tagagatttt 3480
cagattacag cttcaggaca atatggacag tgggccccaa agctggccag acttcattat 3540
tccggatcaa tcaatgcctg gagcaccaag gagccctttt cttggatcaa ggtggatctg 3600
ttggcaccaa tgattattca cggcatcaag acccagggtg cccgtcagaa gttctccagc 3660
ctctacatct ctcagtttat catcatgtat agtcttgatg ggaagaagtg gcagacttat 3720
cgaggaaatt ccactggaac cttaatggtc ttctttggca atgtggattc atctgggata 3780
aaacacaata tttttaaccc tccaattatt gctcgataca tccgtttgca cccaactcat 3840
tatagcattc gcagcactct tcgcatggag ttgatgggct gtgatttaaa tagttgcagc 3900
atgccattgg gaatggagag taaagcaata tcagatgcac agattactgc ttcatcctac 3960
tttaccaata tgtttgccac ctggtctcct tcaaaagctc gacttcacct ccaagggagg 4020
agtaatgcct ggagacctca ggtgaataat ccaaaagagt ggctgcaagt ggacttccag 4080
aagacaatga aagtcacagg agtaactact cagggagtaa aatctctgct taccagcatg 4140
tatgtgaagg agttcctcat ctccagcagt caagatggcc atcagtggac tctctttttt 4200
cagaatggca aagtaaaggt ttttcaggga aatcaagact ccttcacacc tgtggtgaac 4260
tctctagacc caccgttact gactcgctac cttcgaattc acccccagag ttgggtgcac 4320
cagattgccc tgaggatgga ggttctgggc tgcgaggcac aggacctcta ctga 4374

<210> SEQ ID NO 18
<211> LENGTH: 4374
<212> TYPE: DNA

-continued

<213> ORGANISM: Artificial Sequence
<220> FEATURE:
<223> OTHER INFORMATION: Description of Artificial Sequence: Synthetic
polynucleotide

<400> SEQUENCE: 18
atgcagatcg agctgtccac atgctttttt ctgtgcctgc tgcggttctg cttcagcgcc 60
acccggcggt actacctggg cgccgtggag ctgtcctggg actacatgca gagcgacctg 120
ggcgagctgc ccgtggacgc ccggttcccc cccagagtgc ccaagagctt ccccttcaac 180
accagcgtgg tgtacaagaa aaccctgttc gtggagttca ccgaccacct gttcaacatc 240
gccaagccca ggcccccctg gatgggcctg ctgggcccca ccatccaggc cgaggtgtac 300
gacaccgtgg tgatcaccct gaagaacatg gccagccacc ccgtgagcct gcacgccgtg 360
ggcgtgagct actggaaggc ctccgagggc gccgagtacg acgaccagac cagccagcgg 420
gagaaagagg acgacaaagt ctttcctggc ggcagccaca cctacgtgtg gcaggtcctg 480
aaagaaaacg gccccatggc ctccgacccc ctgtgcctga cctacagcta cctgagccac 540
gtggacctgg tgaaggacct gaacagcggg ctgattgggg ccctgctggt ctgccgggag 600
ggcagcctgg ccaaagagaa aacccagacc ctgcacaagt tcatcctgct gttcgccgtg 660
ttcgacgagg gcaagagctg gcacagcgag accaagaaca gcctgatgca ggaccgggac 720
gccgcctctg ccagagcctg gcccaagatg cacaccgtga acggctacgt gaacagaagc 780
ctgcccggcc tgattggctg ccaccggaag agcgtgtact ggcacgtgat cggcatgggc 840
accacacccg aggtgcacag catctttctg gaagggcaca cctttctggt gcggaaccac 900
cggcaggcca gcctggaaat cagccctatc accttcctga ccgcccagac actgctgatg 960
gacctgggcc agttcctgct gttttgccac atcagctctc accagcacga cggcatggaa 1020
gcctacgtga aggtggactc ctgccccgag gaaccccagc tgcggatgaa gaacaacgag 1080
gaagccgagg actacgacga cgacctgacc gacagcgaga tggacgtggt gcggttcgac 1140
gacgacaaca gccccagctt catccagatc agaagcgtgg ccaagaagca ccccaagacc 1200
tgggtgcact acatcgccgc cgaggaagag gactgggact acgccccccct ggtgctggcc 1260 cccgacgaca gaagctacaa gagccagtac ctgaacaatg gcccccagcg gatcggccgg 1320
aagtacaaga aagtgcggtt catggcctac accgacgaga ccttcaagac ccgggaggcc 1380
atccagcacg agagcggcat cctgggcccc ctgctgtacg gcgaagtggg cgacacactg 1440
ctgatcatct tcaagaacca ggccagccgg ccctacaaca tctaccccca cggcatcacc 1500
gacgtgcggc ccctgtacag caggcggctg cccaagggcg tgaagcacct gaaggacttc 1560
cccatcctgc ccggcgagat cttcaagtac aagtggaccg tgaccgtgga ggacggcccc 1620
accaagagcg accccagatg cctgacccgg tactacagca gcttcgtgaa catggaacgg 1680
gacctggcct ccgggctgat cggacctctg ctgatctgct acaaagaaag cgtggaccag 1740
cggggcaacc agatcatgag cgacaagcgg aacgtgatcc tgttcagcgt gttcgatgag 1800
aaccggtcct ggtatctgac cgagaacatc cagcggtttc tgcccaaccc tgccggggtg 1860
cagctggaag atcccgagtt ccaggccagc aacatcatgc actccatcaa tggctacgtg 1920
ttcgacagcc tgcagctgtc cgtgtgtctg cacgaggtgg cctactggta catcctgagc 1980
atcggcgccc agaccgactt cctgagcgtg ttcttcagcg gctacacctt caagcacaag 2040
atggtgtacg aggacaccct gaccctgttc cctttcagcg gcgagaccgt gttcatgagc 2100
atggaaaacc ccggcctgtg gatcctgggc tgccacaaca gcgacttccg gaaccggggc 2160

-continued

```
atgaccgccc tgctgaaggt gtccagctgc gacaagaaca ccggcgacta ctacgaggac   2220
agctacgagg atatcagcgc ctacctgctg tccaagaaca acgccatcga gcccagaagc   2280
ttcagccaga accccccctgt gctgaagcgg caccagagag agatcacccg gaccaccctg   2340
cagtccgacc aggaagagat cgattacgac gacaccatca gcgtggagat gaaaaaagaa   2400
gatttcgaca tctacgacga ggacgagaac cagagccccc ggtccttcca gaagaaaacc   2460
cggcactact ttatcgccgc cgtggagcgg ctgtgggact acggcatgag cagcagcccc   2520
cacgtgctgc ggaaccgggc ccagagcggc agcgtgcccc agttcaagaa agtggtgttc   2580
caggaattca ccgacggcag cttcacccag cccctgtacc ggggcgagct gaacgagcac   2640
ctggggctgc tggggcccta catcagggcc gaagtggagg acaacatcat ggtgaccttc   2700
cggaatcagg ccagcagacc ctactccttc tacagcagcc tgatcagcta cgaagaggac   2760
cagcggcagg gcgctgaacc ccggaagaac ttcgtgaagc ccaatgagac caagacctac   2820
ttctggaaag tgcagcacca catggccccc accaaggacg agttcgactg caaggcctgg   2880
gcctacttca gcgacgtgga tctggaaaag gacgtgcact ctggactgat tggccctctg   2940
ctggtgtgcc acaccaacac cctgaacccc gcccacggcc ggcaggtgac cgtgcaggaa   3000
ttcgccctgt tcttcaccat cttcgacgag accaagtcct ggtacttcac cgagaatatg   3060
gaacggaact gcagagcccc ctgcaacatc cagatggaag atcctacctt caaagagaac   3120
taccggttcc acgccatcaa cggctacatc atggacaccc tgcctggcct ggtgatggcc   3180
caggaccaga ggatccggtg gtatctgctg tccatgggca gcaacgagaa tatccacagc   3240
atccacttca gcggccacgt gttcaccgtg aggaagaaag aagagtacaa gatggccctg   3300
tacaacctgt accccggcgt gttcgagacc gtggagatgc tgcccagcaa ggccggcatc   3360
tggcgggtgg agtgtctgat cggcgagcac ctgcatgccg ggatgagcac cctgtttctg   3420
gtgtacagca acaagtgcca gaccccccctg ggcatggcca gcggccacat ccgggacttc   3480
cagatcaccg cctccggcca gtacggccag tgggccccca agctggcccg gctgcactac   3540
agcggcagca tcaacgcctg gtccaccaaa gagcccttca gctggatcaa ggtggacctg   3600
ctggccccta tgatcatcca cggcattaag acccagggcg ccaggcagaa gttcagcagc   3660
ctgtacatca gccagttcat catcatgtac agcctggacg gcaagaagtg gcagacctac   3720
cggggcaaca gcaccggcac cctgatggtg ttcttcggca acgtggacag cagcggcatc   3780
aagcacaaca tcttcaaccc ccccatcatc gcccggtaca tccggctgca ccccacccac   3840
tacagcatca gatccaccct gcggatggaa ctgatgggct gcgacctgaa ctcctgcagc   3900
atgcctctgg gcatggaaag caaggccatc agcgacgccc agatcacagc cagcagctac   3960
ttcaccaaca tgttcgccac ctggtccccc tccaaggcca ggctgcacct gcagggccgg   4020
tccaacgcct ggcggcctca ggtgaacaac cccaaagaat ggctgcaggt ggactttcag   4080
aaaaccatga aggtgaccgg cgtgaccacc cagggcgtga aaagcctgct gaccagcatg   4140
tacgtgaaag agtttctgat cagcagcagc caggacggcc accagtggac cctgttcttt   4200
cagaacggca aggtgaaagt gttccagggc aaccaggact ccttcacccc cgtggtgaac   4260
tccctggacc ccccccctgct gacccgctac ctgcggatcc acccccagtc ttgggtgcac   4320
cagatcgccc tgaggatgga agtgctggga tgtgaggccc aggatctgta ctga         4374
```

<210> SEQ ID NO 19
<211> LENGTH: 2351
<212> TYPE: PRT
<213> ORGANISM: Homo sapiens

<400> SEQUENCE: 19

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro

-continued

```
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830
```

-continued

```
Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro  Ala Leu Leu Thr Lys  Asp Asn Ala
        995                 1000                1005

Leu Phe  Lys Val Ser Ile Ser  Leu Leu Lys Thr Asn  Lys Thr Ser
    1010                1015                1020

Asn Asn  Ser Ala Thr Asn Arg  Lys Thr His Ile Asp  Gly Pro Ser
    1025                1030                1035

Leu Leu  Ile Glu Asn Ser Pro  Ser Val Trp Gln Asn  Ile Leu Glu
    1040                1045                1050

Ser Asp  Thr Glu Phe Lys Lys  Val Thr Pro Leu Ile  His Asp Arg
    1055                1060                1065

Met Leu  Met Asp Lys Asn Ala  Thr Ala Leu Arg Leu  Asn His Met
    1070                1075                1080

Ser Asn  Lys Thr Thr Ser Ser  Lys Asn Met Glu Met  Val Gln Gln
    1085                1090                1095

Lys Lys  Glu Gly Pro Ile Pro  Pro Asp Ala Gln Asn  Pro Asp Met
    1100                1105                1110

Ser Phe  Phe Lys Met Leu Phe  Leu Pro Glu Ser Ala  Arg Trp Ile
    1115                1120                1125

Gln Arg  Thr His Gly Lys Asn  Ser Leu Asn Ser Gly  Gln Gly Pro
    1130                1135                1140

Ser Pro  Lys Gln Leu Val Ser  Leu Gly Pro Glu Lys  Ser Val Glu
    1145                1150                1155

Gly Gln  Asn Phe Leu Ser Glu  Lys Asn Lys Val Val  Val Gly Lys
    1160                1165                1170

Gly Glu  Phe Thr Lys Asp Val  Gly Leu Lys Glu Met  Val Phe Pro
    1175                1180                1185

Ser Ser  Arg Asn Leu Phe Leu  Thr Asn Leu Asp Asn  Leu His Glu
    1190                1195                1200

Asn Asn  Thr His Asn Gln Glu  Lys Lys Ile Gln Glu  Glu Ile Glu
    1205                1210                1215

Lys Lys  Glu Thr Leu Ile Gln  Glu Asn Val Val Leu  Pro Gln Ile
    1220                1225                1230
```

-continued

```
His Thr  Val Thr Gly Thr Lys  Asn Phe Met Lys Asn  Leu Phe Leu
    1235                 1240                 1245

Leu Ser  Thr Arg Gln Asn Val  Glu Gly Ser Tyr Asp  Gly Ala Tyr
    1250                 1255                 1260

Ala Pro  Val Leu Gln Asp Phe  Arg Ser Leu Asn Asp  Ser Thr Asn
    1265                 1270                 1275

Arg Thr  Lys Lys His Thr Ala  His Phe Ser Lys Lys  Gly Glu Glu
    1280                 1285                 1290

Glu Asn  Leu Glu Gly Leu Gly  Asn Gln Thr Lys Gln  Ile Val Glu
    1295                 1300                 1305

Lys Tyr  Ala Cys Thr Thr Arg  Ile Ser Pro Asn Thr  Ser Gln Gln
    1310                 1315                 1320

Asn Phe  Val Thr Gln Arg Ser  Lys Arg Ala Leu Lys  Gln Phe Arg
    1325                 1330                 1335

Leu Pro  Leu Glu Glu Thr Glu  Leu Glu Lys Arg Ile  Ile Val Asp
    1340                 1345                 1350

Asp Thr  Ser Thr Gln Trp Ser  Lys Asn Met Lys His  Leu Thr Pro
    1355                 1360                 1365

Ser Thr  Leu Thr Gln Ile Asp  Tyr Asn Glu Lys Glu  Lys Gly Ala
    1370                 1375                 1380

Ile Thr  Gln Ser Pro Leu Ser  Asp Cys Leu Thr Arg  Ser His Ser
    1385                 1390                 1395

Ile Pro  Gln Ala Asn Arg Ser  Pro Leu Pro Ile Ala  Lys Val Ser
    1400                 1405                 1410

Ser Phe  Pro Ser Ile Arg Pro  Ile Tyr Leu Thr Arg  Val Leu Phe
    1415                 1420                 1425

Gln Asp  Asn Ser Ser His Leu  Pro Ala Ala Ser Tyr  Arg Lys Lys
    1430                 1435                 1440

Asp Ser  Gly Val Gln Glu Ser  Ser His Phe Leu Gln  Gly Ala Lys
    1445                 1450                 1455

Lys Asn  Asn Leu Ser Leu Ala  Ile Leu Thr Leu Glu  Met Thr Gly
    1460                 1465                 1470

Asp Gln  Arg Glu Val Gly Ser  Leu Gly Thr Ser Ala  Thr Asn Ser
    1475                 1480                 1485

Val Thr  Tyr Lys Lys Val Glu  Asn Thr Val Leu Pro  Lys Pro Asp
    1490                 1495                 1500

Leu Pro  Lys Thr Ser Gly Lys  Val Glu Leu Leu Pro  Lys Val His
    1505                 1510                 1515

Ile Tyr  Gln Lys Asp Leu Phe  Pro Thr Glu Thr Ser  Asn Gly Ser
    1520                 1525                 1530

Pro Gly  His Leu Asp Leu Val  Glu Gly Ser Leu Leu  Gln Gly Thr
    1535                 1540                 1545

Glu Gly  Ala Ile Lys Trp Asn  Glu Ala Asn Arg Pro  Gly Lys Val
    1550                 1555                 1560

Pro Phe  Leu Arg Val Ala Thr  Glu Ser Ser Ala Lys  Thr Pro Ser
    1565                 1570                 1575

Lys Leu  Leu Asp Pro Leu Ala  Trp Asp Asn His Tyr  Gly Thr Gln
    1580                 1585                 1590

Ile Pro  Lys Glu Glu Trp Lys  Ser Gln Glu Lys Ser  Pro Glu Lys
    1595                 1600                 1605

Thr Ala  Phe Lys Lys Lys Asp  Thr Ile Leu Ser Leu  Asn Ala Cys
    1610                 1615                 1620

Glu Ser  Asn His Ala Ile Ala  Ala Ile Asn Glu Gly  Gln Asn Lys
```

1625 1630 1635

Pro Glu Ile Glu Val Thr Trp Ala Lys Gln Gly Arg Thr Glu Arg
1640 1645 1650

Leu Cys Ser Gln Asn Pro Pro Val Leu Lys Arg His Gln Arg Glu
1655 1660 1665

Ile Thr Arg Thr Thr Leu Gln Ser Asp Gln Glu Glu Ile Asp Tyr
1670 1675 1680

Asp Asp Thr Ile Ser Val Glu Met Lys Lys Glu Asp Phe Asp Ile
1685 1690 1695

Tyr Asp Glu Asp Glu Asn Gln Ser Pro Arg Ser Phe Gln Lys Lys
1700 1705 1710

Thr Arg His Tyr Phe Ile Ala Ala Val Glu Arg Leu Trp Asp Tyr
1715 1720 1725

Gly Met Ser Ser Ser Pro His Val Leu Arg Asn Arg Ala Gln Ser
1730 1735 1740

Gly Ser Val Pro Gln Phe Lys Lys Val Val Phe Gln Glu Phe Thr
1745 1750 1755

Asp Gly Ser Phe Thr Gln Pro Leu Tyr Arg Gly Glu Leu Asn Glu
1760 1765 1770

His Leu Gly Leu Leu Gly Pro Tyr Ile Arg Ala Glu Val Glu Asp
1775 1780 1785

Asn Ile Met Val Thr Phe Arg Asn Gln Ala Ser Arg Pro Tyr Ser
1790 1795 1800

Phe Tyr Ser Ser Leu Ile Ser Tyr Glu Glu Asp Gln Arg Gln Gly
1805 1810 1815

Ala Glu Pro Arg Lys Asn Phe Val Lys Pro Asn Glu Thr Lys Thr
1820 1825 1830

Tyr Phe Trp Lys Val Gln His His Met Ala Pro Thr Lys Asp Glu
1835 1840 1845

Phe Asp Cys Lys Ala Trp Ala Tyr Phe Ser Asp Val Asp Leu Glu
1850 1855 1860

Lys Asp Val His Ser Gly Leu Ile Gly Pro Leu Leu Val Cys His
1865 1870 1875

Thr Asn Thr Leu Asn Pro Ala His Gly Arg Gln Val Thr Val Gln
1880 1885 1890

Glu Phe Ala Leu Phe Phe Thr Ile Phe Asp Glu Thr Lys Ser Trp
1895 1900 1905

Tyr Phe Thr Glu Asn Met Glu Arg Asn Cys Arg Ala Pro Cys Asn
1910 1915 1920

Ile Gln Met Glu Asp Pro Thr Phe Lys Glu Asn Tyr Arg Phe His
1925 1930 1935

Ala Ile Asn Gly Tyr Ile Met Asp Thr Leu Pro Gly Leu Val Met
1940 1945 1950

Ala Gln Asp Gln Arg Ile Arg Trp Tyr Leu Leu Ser Met Gly Ser
1955 1960 1965

Asn Glu Asn Ile His Ser Ile His Phe Ser Gly His Val Phe Thr
1970 1975 1980

Val Arg Lys Lys Glu Glu Tyr Lys Met Ala Leu Tyr Asn Leu Tyr
1985 1990 1995

Pro Gly Val Phe Glu Thr Val Glu Met Leu Pro Ser Lys Ala Gly
2000 2005 2010

Ile Trp Arg Val Glu Cys Leu Ile Gly Glu His Leu His Ala Gly
2015 2020 2025

```
Met Ser  Thr Leu Phe Leu Val  Tyr Ser Asn Lys Cys  Gln Thr Pro
    2030                 2035                 2040

Leu Gly  Met Ala Ser Gly His  Ile Arg Asp Phe Gln  Ile Thr Ala
    2045                 2050                 2055

Ser Gly  Gln Tyr Gly Gln Trp  Ala Pro Lys Leu Ala  Arg Leu His
    2060                 2065                 2070

Tyr Ser  Gly Ser Ile Asn Ala  Trp Ser Thr Lys Glu  Pro Phe Ser
    2075                 2080                 2085

Trp Ile  Lys Val Asp Leu Leu  Ala Pro Met Ile Ile  His Gly Ile
    2090                 2095                 2100

Lys Thr  Gln Gly Ala Arg Gln  Lys Phe Ser Ser Leu  Tyr Ile Ser
    2105                 2110                 2115

Gln Phe  Ile Ile Met Tyr Ser  Leu Asp Gly Lys Lys  Trp Gln Thr
    2120                 2125                 2130

Tyr Arg  Gly Asn Ser Thr Gly  Thr Leu Met Val Phe  Phe Gly Asn
    2135                 2140                 2145

Val Asp  Ser Ser Gly Ile Lys  His Asn Ile Phe Asn  Pro Pro Ile
    2150                 2155                 2160

Ile Ala  Arg Tyr Ile Arg Leu  His Pro Thr His Tyr  Ser Ile Arg
    2165                 2170                 2175

Ser Thr  Leu Arg Met Glu Leu  Met Gly Cys Asp Leu  Asn Ser Cys
    2180                 2185                 2190

Ser Met  Pro Leu Gly Met Glu  Ser Lys Ala Ile Ser  Asp Ala Gln
    2195                 2200                 2205

Ile Thr  Ala Ser Ser Tyr Phe  Thr Asn Met Phe Ala  Thr Trp Ser
    2210                 2215                 2220

Pro Ser  Lys Ala Arg Leu His  Leu Gln Gly Arg Ser  Asn Ala Trp
    2225                 2230                 2235

Arg Pro  Gln Val Asn Asn Pro  Lys Glu Trp Leu Gln  Val Asp Phe
    2240                 2245                 2250

Gln Lys  Thr Met Lys Val Thr  Gly Val Thr Thr Gln  Gly Val Lys
    2255                 2260                 2265

Ser Leu  Leu Thr Ser Met Tyr  Val Lys Glu Phe Leu  Ile Ser Ser
    2270                 2275                 2280

Ser Gln  Asp Gly His Gln Trp  Thr Leu Phe Phe Gln  Asn Gly Lys
    2285                 2290                 2295

Val Lys  Val Phe Gln Gly Asn  Gln Asp Ser Phe Thr  Pro Val Val
    2300                 2305                 2310

Asn Ser  Leu Asp Pro Pro Leu  Leu Thr Arg Tyr Leu  Arg Ile His
    2315                 2320                 2325

Pro Gln  Ser Trp Val His Gln  Ile Ala Leu Arg Met  Glu Val Leu
    2330                 2335                 2340

Gly Cys  Glu Ala Gln Asp Leu  Tyr
    2345                 2350
```

<210> SEQ ID NO 20
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
atgcagattg agctgagcac ctgcttcttc ctgtgcctgc tgaggttctg cttctctgcc     60
```

-continued

```
accaggagat actacctggg cgccgtggag ctgagctggg actacatgca gtctgacctg    120
ggcgagctgc ctgtggacgc caggttcccc cccagagtgc ccaagagctt cccctcaac     180
acctcagtgg tgtacaagaa gaccctgttc gtggagttca ccgaccacct gttcaacatc    240
gccaagccca ggccccctg gatgggcctg ctgggcccca ccatccaggc cgaggtgtac     300
gacaccgtgg tgatcaccct gaagaacatg gccagccacc ccgtgagcct gcacgccgtg    360
ggcgtgagct actggaaggc ctctgagggc gccgagtatg acgaccagac cagccagagg    420
gagaaggagg acgacaaggt gttccccggc ggcagccaca cctacgtgtg gcaggtgctg    480
aaggagaacg gccccatggc cagcgacccc ctgtgcctga cctacagcta cctgagccac    540
gtggacctgg tgaaggacct gaactctggc ctgatcggcg ccctgctggt gtgcagggag    600
ggcagcctgg ccaaggagaa gacccagacc ctgcacaagt tcatcctgct gttcgccgtg    660
ttcgatgagg gcaagagctg gcacagcgag accaagaaca gcctgatgca ggacagggat    720
gccgcctctg ccagggcctg gcccaagatg cacaccgtga acggctacgt gaacaggagc    780
ctgcccggcc tgatcggctg ccacaggaag tctgtgtact ggcacgtgat cggcatgggc    840
accacccccg aggtgcacag catcttcctg gagggccaca ccttcctggt gaggaaccac    900
aggcaggcca gcctggagat cagccccatc accttcctga ccgcccagac cctgctgatg    960
gacctgggcc agttcctgct gttctgccac atcagcagcc accagcacga cggcatggag   1020
gcctacgtga aggtggacag ctgccccgag gagccccagc tgaggatgaa gaacaacgag   1080
gaggccgagg actatgatga tgacctgacc gactctgaga tggacgtggt gaggtttgat   1140
gatgacaaca gccccagctt catccagatc aggtctgtgg ccaagaagca ccccaagacc   1200
tgggtgcact acatcgccgc cgaggaggag gactgggact acgccccct ggtgctggcc    1260
cccgacgaca ggagctacaa gagccagtac ctgaacaacg gcccccagag gatcggcagg   1320
aagtacaaga aggtcagatt catggcctac accgacgaga ccttcaagac cagggaggcc   1380
atccagcacg agtctggcat cctgggcccc ctgctgtacg gcgaggtggg cgacaccctg   1440
ctgatcatct tcaagaacca ggccagcagg ccctacaaca tctaccccca cggcatcacc   1500
gatgtgaggc ccctgtacag caggaggctg cccaagggcg tgaagcacct gaaggacttc   1560
cccatcctgc ccggcgagat cttcaagtac aagtggaccg tgaccgtgga ggatggcccc   1620
accaagtctg accccaggtg cctgaccagg tactacagca gcttcgtgaa catggagagg   1680
gacctggcct ctggcctgat cggcccctg ctgatctgct acaaggagag cgtggaccag    1740
aggggcaacc agatcatgtc tgacaagagg aacgtgatcc tgttctctgt gttcgatgag   1800
aacaggagct ggtatctgac cgagaacatc cagaggttcc tgcccaaccc cgccggcgtg   1860
cagctggagg accccgagtt ccaggccagc aacatcatgc acagcatcaa cggctacgtg   1920
ttcgacagcc tgcagctgtc tgtgtgcctg cacgaggtgg cctactggta catcctgagc   1980
atcggcgccc agaccgactt cctgtctgtg ttcttctctg gctacacctt caagcacaag   2040
atggtgtacg aggacaccct gaccctgttc cccttcagcg gcgagaccgt gttcatgagc   2100
atggagaacc ccggcctgtg gatcctgggc tgccacaaca gcgacttcag gaacaggggc   2160
atgaccgccc tgctgaaagt cagcagctgc gacaagaaca ccggcgacta ctacgaggac   2220
agctacgagg acatcagcgc ctacctgctg agcaagaaca acgccatcga gcccaggagc   2280
ttcagccaga acccccccgt gctgaagagg caccagaggg agatcaccag gaccaccctg   2340
cagagcgacc aggaggagat cgactatgat gacaccatca gcgtggagat gaagaaggag   2400
```

gacttcgaca tctacgacga ggacgagaac cagagcccca ggagcttcca gaagaagacc 2460
aggcactact tcatcgccgc cgtggagagg ctgtgggact atggcatgag cagcagcccc 2520
cacgtgctga ggaacagggc ccagagcggc agcgtgcccc agttcaagaa ggtggtgttc 2580
caggagttca ccgacggcag cttcacccag cccctgtaca gaggcgagct gaacgagcac 2640
ctgggcctgc tgggccccta catcagggcc gaggtggagg acaacatcat ggtgaccttc 2700
aggaaccagg ccagcaggcc ctacagcttc tacagcagcc tgatcagcta cgaggaggac 2760
cagaggcagg gcgccgagcc caggaagaac ttcgtgaagc ccaacgagac caagacctac 2820
ttctggaagg tgcagcacca catggccccc accaaggacg agttcgactg caaggcctgg 2880
gcctacttct ctgatgtgga cctggagaag gacgtgcaca gcggcctgat cggcccccctg 2940 ctggtgtgcc acaccaacac cctgaacccc gcccacggca ggcaggtgac cgtgcaggag 3000
ttcgccctgt tcttcaccat cttcgacgag accaagagct ggtacttcac cgagaacatg 3060
gagaggaact gcagggcccc ctgcaacatc cagatggagg accccacctt caaggagaac 3120
tacaggttcc acgccatcaa cggctacatc atggacaccc tgcccggcct ggtgatggcc 3180
caggaccaga ggatcaggtg gtatctgctg agcatgggca gcaacgagaa catccacagc 3240
atccacttca gcggccacgt gttcaccgtg aggaagaagg aggagtacaa gatggccctg 3300
tacaacctgt accccggcgt gttcgagacc gtggagatgc tgcccagcaa ggccggcatc 3360
tggagggtgg agtgcctgat cggcgagcac ctgcacgccg gcatgagcac cctgttcctg 3420
gtgtacagca acaagtgcca gacccccctg ggcatggcca gcggccacat cagggacttc 3480
cagatcaccg cctctggcca gtacggccag tgggccccca agctggccag gctgcactac 3540
agcggcagca tcaacgcctg gagcaccaag gagcccttca gctggatcaa ggtggacctg 3600
ctggccccca tgatcatcca cggcatcaag acccagggcg ccaggcagaa gttcagcagc 3660
ctgtacatca gccagttcat catcatgtac agcctggacg gcaagaagtg gcagacctac 3720
aggggcaaca gcaccggcac cctgatggtg ttcttcggca acgtggacag cagcggcatc 3780
aagcacaaca tcttcaaccc ccccatcatc gccaggtaca tcaggctgca ccccacccac 3840
tacagcatca ggagcaccct gcggatggaa ctgatgggct gcgacctgaa cagctgcagc 3900
atgcccctgg gcatggagag caaggccatc tctgacgccc agatcaccgc cagcagctac 3960
ttcaccaaca tgttcgccac ctggagcccc agcaaggcca ggctgcacct gcagggcagg 4020
agcaacgcct ggaggcccca ggtgaacaac cccaaggagt ggctgcaggt ggacttccag 4080
aagaccatga aggtgaccgg cgtgaccacc cagggcgtga agagcctgct gaccagcatg 4140
tacgtgaagg agttcctgat cagcagcagc caggacggcc accagtggac cctgttcttc 4200
cagaacggca aagtgaaggt gttccagggc aaccaggaca gcttcacccc cgtggtgaac 4260
agcctggacc cccccctgct gaccaggtat ctgaggatcc acccccagag ctgggtgcac 4320
cagatcgccc tgagaatgga agtgctggga tgcgaggccc aggacctgta ctga 4374

<210> SEQ ID NO 21
<211> LENGTH: 1457
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 21

Met Gln Ile Glu Leu Ser Thr Cys Phe Phe Leu Cys Leu Leu Arg Phe
1 5 10 15

-continued

```
Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430
```

```
Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
```

```
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
    1145                1150                1155

Asp Phe  Gln Ile Thr Ala Ser  Gly Gln Tyr Gly Gln  Trp Ala Pro
    1160                1165                1170

Lys Leu  Ala Arg Leu His Tyr  Ser Gly Ser Ile Asn  Ala Trp Ser
    1175                1180                1185

Thr Lys  Glu Pro Phe Ser Trp  Ile Lys Val Asp Leu  Leu Ala Pro
    1190                1195                1200

Met Ile  Ile His Gly Ile Lys  Thr Gln Gly Ala Arg  Gln Lys Phe
    1205                1210                1215

Ser Ser  Leu Tyr Ile Ser Gln  Phe Ile Ile Met Tyr  Ser Leu Asp
    1220                1225                1230

Gly Lys  Lys Trp Gln Thr Tyr  Arg Gly Asn Ser Thr  Gly Thr Leu
    1235                1240                1245

Met Val  Phe Phe Gly Asn Val  Asp Ser Ser Gly Ile  Lys His Asn
    1250                1255                1260
```

```
Ile Phe  Asn Pro Pro Ile Ile  Ala Arg Tyr Ile Arg  Leu His Pro
    1265                 1270                 1275

Thr His  Tyr Ser Ile Arg Ser  Thr Leu Arg Met Glu  Leu Met Gly
    1280                 1285                 1290

Cys Asp  Leu Asn Ser Cys Ser  Met Pro Leu Gly Met  Glu Ser Lys
    1295                 1300                 1305

Ala Ile  Ser Asp Ala Gln Ile  Thr Ala Ser Ser Tyr  Phe Thr Asn
    1310                 1315                 1320

Met Phe  Ala Thr Trp Ser Pro  Ser Lys Ala Arg Leu  His Leu Gln
    1325                 1330                 1335

Gly Arg  Ser Asn Ala Trp Arg  Pro Gln Val Asn Asn  Pro Lys Glu
    1340                 1345                 1350

Trp Leu  Gln Val Asp Phe Gln  Lys Thr Met Lys Val  Thr Gly Val
    1355                 1360                 1365

Thr Thr  Gln Gly Val Lys Ser  Leu Leu Thr Ser Met  Tyr Val Lys
    1370                 1375                 1380

Glu Phe  Leu Ile Ser Ser Ser  Gln Asp Gly His Gln  Trp Thr Leu
    1385                 1390                 1395

Phe Phe  Gln Asn Gly Lys Val  Lys Val Phe Gln Gly  Asn Gln Asp
    1400                 1405                 1410

Ser Phe  Thr Pro Val Val Asn  Ser Leu Asp Pro Pro  Leu Leu Thr
    1415                 1420                 1425

Arg Tyr  Leu Arg Ile His Pro  Gln Ser Trp Val His  Gln Ile Ala
    1430                 1435                 1440

Leu Arg  Met Glu Val Leu Gly  Cys Glu Ala Gln Asp  Leu Tyr
    1445                 1450                 1455
```

<210> SEQ ID NO 22
<211> LENGTH: 2220
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
gccaccagga gatactacct gggcgccgtg gagctgagct gggactacat gcagtctgac     60

ctgggcgagc tgcctgtgga cgccaggttc ccccccagag tgcccaagag cttccccttc    120

aacacctcag tggtgtacaa gaagaccctg ttcgtggagt tcaccgacca cctgttcaac    180

atcgccaagc ccaggccccc ctggatgggc ctgctgggcc ccaccatcca ggccgaggtg    240

tacgacaccg tggtgatcac cctgaagaac atggccagcc accccgtgag cctgcacgcc    300

gtgggcgtga gctactggaa ggcctctgag ggcgccgagt atgacgacca gaccagccag    360

agggagaagg aggacgacaa ggtgttcccc ggcggcagcc acacctacgt gtggcaggtg    420

ctgaaggaga acggccccat ggccagcgac cccctgtgcc tgacctacag ctacctgagc    480

cacgtggacc tggtgaagga cctgaactct ggcctgatcg gcgccctgct ggtgtgcagg    540

gagggcagcc tggccaagga gaagacccag accctgcaca agttcatcct gctgttcgcc    600

gtgttcgatg agggcaagag ctggcacagc gagaccaaga acagcctgat gcaggacagg    660

gatgccgcct ctgccagggc ctggcccaag atgcacaccg tgaacggcta cgtgaacagg    720

agcctgcccg gcctgatcgg ctgccacagg aagtctgtgt actggcacgt gatcggcatg    780

ggcaccaccc ccgaggtgca cagcatcttc ctggagggcc acaccttcct ggtgaggaac    840
```

```
cacaggcagg ccagcctgga gatcagcccc atcaccttcc tgaccgccca gaccctgctg    900

atggacctgg gccagttcct gctgttctgc cacatcagca gccaccagca cgacggcatg    960

gaggcctacg tgaaggtgga cagctgcccc gaggagcccc agctgaggat gaagaacaac   1020

gaggaggccg aggactatga tgatgacctg accgactctg agatggacgt ggtgaggttt   1080

gatgatgaca acagccccag cttcatccag atcaggtctg tggccaagaa gcaccccaag   1140

acctgggtgc actacatcgc cgccgaggag gaggactggg actacgcccc cctggtgctg   1200

gcccccgacg acaggagcta caagagccag tacctgaaca acggccccca gaggatcggc   1260

aggaagtaca agaaggtcag attcatggcc tacaccgacg agaccttcaa gaccagggag   1320

gccatccagc acgagtctgg catcctgggc cccctgctgt acggcgaggt gggcgacacc   1380

ctgctgatca tcttcaagaa ccaggccagc aggccctaca acatctaccc ccacggcatc   1440

accgatgtga ggcccctgta cagcaggagg ctgcccaagg gcgtgaagca cctgaaggac   1500

ttccccatcc tgcccggcga gatcttcaag tacaagtgga ccgtgaccgt ggaggatggc   1560

cccaccaagt ctgaccccag gtgcctgacc aggtactaca gcagcttcgt gaacatggag   1620

agggacctgg cctctggcct gatcggcccc ctgctgatct gctacaagga gagcgtggac   1680

cagaggggca accagatcat gtctgacaag aggaacgtga tcctgttctc tgtgttcgat   1740

gagaacagga gctggtatct gaccgagaac atccagaggt tcctgcccaa ccccgccggc   1800

gtgcagctgg aggaccccga gttccaggcc agcaacatca tgcacagcat caacggctac   1860

gtgttcgaca gcctgcagct gtctgtgtgc ctgcacgagg tggcctactg gtacatcctg   1920

agcatcggcg cccagaccga cttcctgtct gtgttcttct ctggctacac cttcaagcac   1980

aagatggtgt acgaggacac cctgaccctg ttccccttca gcggcgagac cgtgttcatg   2040

agcatggaga accccggcct gtggatcctg ggctgccaca acagcgactt caggaacagg   2100

ggcatgaccg ccctgctgaa agtcagcagc tgcgacaaga acaccggcga ctactacgag   2160

gacagctacg aggacatcag cgcctacctg ctgagcaaga acaacgccat cgagcccagg   2220
```

<210> SEQ ID NO 23
<211> LENGTH: 2052
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
gagatcacca ggaccaccct gcagagcgac caggaggaga tcgactatga tgacaccatc     60

agcgtggaga tgaagaagga ggacttcgac atctacgacg aggacgagaa ccagagcccc    120

aggagcttcc agaagaagac caggcactac ttcatcgccg ccgtggagag gctgtgggac    180

tatggcatga gcagcagccc ccacgtgctg aggaacaggg cccagagcgg cagcgtgccc    240

cagttcaaga aggtggtgtt ccaggagttc accgacggca gcttcaccca gcccctgtac    300

agaggcgagc tgaacgagca cctgggcctg ctgggcccct acatcagggc cgaggtggag    360

gacaacatca tggtgacctt caggaaccag gccagcaggc cctacagctt ctacagcagc    420

ctgatcagct acgaggagga ccagaggcag ggcgccgagc ccaggaagaa cttcgtgaag    480

cccaacgaga ccaagaccta cttctggaag gtgcagcacc acatggcccc caccaaggac    540

gagttcgact gcaaggcctg ggcctacttc tctgatgtgg acctggagaa ggacgtgcac    600

agcggcctga tcggcccct gctggtgtgc cacaccaaca ccctgaaccc cgcccacggc    660
```

```
aggcaggtga ccgtgcagga gttcgccctg ttcttcacca tcttcgacga gaccaagagc    720

tggtacttca ccgagaacat ggagaggaac tgcagggccc cctgcaacat ccagatggag    780

gaccccacct tcaaggagaa ctacaggttc cacgccatca acggctacat catggacacc    840

ctgcccggcc tggtgatggc ccaggaccag aggatcaggt ggtatctgct gagcatgggc    900

agcaacgaga acatccacag catccacttc agcggccacg tgttcaccgt gaggaagaag    960

gaggagtaca agatggccct gtacaacctg taccccggcg tgttcgagac cgtggagatg   1020

ctgcccagca aggccggcat ctggagggtg gagtgcctga tcggcgagca cctgcacgcc   1080

ggcatgagca ccctgttcct ggtgtacagc aacaagtgcc agaccccct gggcatggcc   1140

agcggccaca tcagggactt ccagatcacc gcctctggcc agtacggcca gtgggccccc   1200

aagctggcca ggctgcacta cagcggcagc atcaacgcct ggagcaccaa ggagcccttc   1260

agctggatca aggtggacct gctggccccc atgatcatcc acggcatcaa gacccagggc   1320

gccaggcaga agttcagcag cctgtacatc agccagttca tcatcatgta cagcctggac   1380

ggcaagaagt ggcagaccta caggggcaac agcaccggca ccctgatggt gttcttcggc   1440

aacgtggaca gcagcggcat caagcacaac atcttcaacc cccccatcat cgccaggtac   1500

atcaggctgc accccaccca ctacagcatc aggagcaccc tgcggatgga actgatgggc   1560

tgcgacctga acagctgcag catgcccctg ggcatggaga gcaaggccat ctctgacgcc   1620

cagatcaccg ccagcagcta cttcaccaac atgttcgcca cctggagccc cagcaaggcc   1680

aggctgcacc tgcagggcag gagcaacgcc tggaggcccc aggtgaacaa ccccaaggag   1740

tggctgcagg tggacttcca gaagaccatg aaggtgaccg gcgtgaccac ccagggcgtg   1800

aagagcctgc tgaccagcat gtacgtgaag gagttcctga tcagcagcag ccaggacggc   1860

caccagtgga ccctgttctt ccagaacggc aaagtgaagg tgttccaggg caaccaggac   1920

agcttcaccc ccgtggtgaa cagcctggac ccccccctgc tgaccaggta tctgaggatc   1980

cacccccaga gctgggtgca ccagatcgcc ctgagaatgg aagtgctggg atgcgaggcc   2040

caggacctgt ac                                                       2052
```

```
<210> SEQ ID NO 24
<211> LENGTH: 2220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

gccaccagga gatactacct gggggctgtg gaactttctt gggactacat gcagtctgac     60

ctgggagagc tgcctgtgga tgccaggttc ccacccagag tgcccaagtc cttcccattc    120

aacacctctg tggtctacaa gaagacactc tttgtggaat tcactgacca cctgttcaac    180

attgcaaaac ccagaccacc ctggatggga ctcctgggac ccaccattca ggctgaggtg    240

tatgacactg tggtcatcac cctcaagaac atggcatccc accctgtgtc tctgcatgct    300

gtgggagtct catactggaa agcctctgaa ggggctgagt atgatgacca gacatcccag    360

agagagaaag aggatgacaa ggtgttccct gggggatctc acacctatgt gtggcaagtc    420

ctcaaggaga atggacccat ggcatctgac ccactctgcc tgacatactc ctacctttct    480

catgtggacc tggtcaagga cctcaactct ggactgattg gggcactgct ggtgtgcagg    540

gaaggatccc tggccaagga gaaaacccag acactgcaca agttcattct cctgtttgct    600
```

-continued

```
gtctttgatg agggcaagtc ttggcactct gaaacaaaga actccctgat gcaagacagg    660

gatgctgcct ctgccagggc atggcccaag atgcacactg tgaatggcta tgtgaacaga    720

tcactgcctg gactcattgg ctgccacagg aaatctgtct actggcatgt gattggcatg    780

gggacaaccc ctgaagtgca ctccattttc ctggagggac acaccttcct ggtcaggaac    840

cacagacaag cctctctgga gatctctccc atcaccttcc tcactgcaca gacactgctg    900

atggaccttg gacagttcct gctgttctgc cacatctctt cccaccagca tgatggcatg    960

gaagcctatg tcaaggtgga ctcatgccct gaggaaccac agctcaggat gaagaacaat   1020

gaggaggctg aggactatga tgatgacctg actgactctg agatggatgt ggtcagattt   1080

gatgatgaca actctccatc cttcattcag atcaggtctg tggcaaagaa acaccccaag   1140

acatgggtgc actacattgc tgctgaggaa gaggactggg actatgcacc actggtcctg   1200

gcccctgatg acaggagcta caagtctcag tacctcaaca atggcccaca aagaattgga   1260

agaaagtaca agaaagtcag attcatggcc tacactgatg aaaccttcaa gacaagagaa   1320

gccattcagc atgagtctgg cattctggga ccactcctgt atggggaagt gggagacacc   1380

ctgctcatca tcttcaagaa ccaggcctcc aggccctaca acatctaccc acatggcatc   1440

actgatgtca ggcccctgta cagcaggaga ctgccaaaag ggtgaaaca cctcaaggac   1500

ttccccattc tgcctggaga gatcttcaag tacaagtgga ctgtcactgt ggaggatgga   1560

ccaacaaagt ctgaccccag gtgcctcacc agatactact cctcttttgt gaacatggag   1620

agagacctgg catctggact gattggacca ctgctcatct gctacaagga gtctgtggac   1680

cagagaggca accagatcat gtctgacaag agaaatgtga ttctgttctc tgtctttgat   1740

gagaacagat catggtacct gactgagaac attcagagat tcctgcccaa ccctgctggg   1800

gtgcaactgg aagaccctga gttccaggca agcaacatca tgcactccat caatggctat   1860

gtgtttgact ctctccagct ttctgtctgc ctgcatgagg tggcctactg gtacattctt   1920

tctattgggg cacaaactga cttcctttct gtcttcttct ctggatacac cttcaagcac   1980

aagatggtgt atgaggacac cctgacactc ttcccattct ctggggaaac tgtgttcatg   2040

agcatggaga accctggact gtggattctg ggatgccaca actctgactt cagaaacagg   2100

ggaatgactg cactgctcaa agtctcctcc tgtgacaaga acactgggga ctactatgag   2160

gactcttatg aggacatctc tgcctacctg ctcagcaaga acaatgccat tgagcccaga   2220
```

```
<210> SEQ ID NO 25
<211> LENGTH: 2052
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

gagatcacca ggacaaccct ccagtctgac caggaagaga ttgactatga tgacaccatt     60

tctgtggaga tgaagaagga ggactttgac atctatgatg aggacgagaa ccagtctcca    120

agatcattcc agaagaagac aagacactac ttcattgctg ctgtggaaag actgtgggac    180

tatggcatgt cttcctctcc ccatgtcctc aggaacaggg cacagtctgg ctctgtgcca    240

cagttcaaga aagtggtctt ccaggagttc actgatggct cattcaccca gcccctgtac    300

agaggggaac tgaatgagca cctgggactc ctgggaccat acatcagggc tgaggtggaa    360

gacaacatca tggtgacatt cagaaaccag gcctccaggc cctacagctt ctactcttcc    420
```

```
ctcatcagct atgaggaaga ccagagacaa ggggctgagc caagaaagaa ctttgtgaaa     480

cccaatgaaa ccaagaccta cttctggaaa gtccagcacc acatggcacc caccaaggat     540

gagtttgact gcaaggcctg ggcatacttc tctgatgtgg acctggagaa agatgtgcac     600

tctggcctga ttggcccact cctggtctgc cacaccaaca ccctgaaccc tgcacatgga     660

aggcaagtga ctgtgcagga gtttgccctc ttcttcacca tctttgatga aaccaagtca     720

tggtacttca ctgagaacat ggagagaaac tgcagagcac catgcaacat tcagatggaa     780

gaccccacct tcaaggagaa ctacaggttc catgccatca atggctacat catggacacc     840

ctgcctgggc ttgtcatggc acaggaccag agaatcagat ggtacctgct ttctatggga     900

tccaatgaga acattcactc catccacttc tctgggcatg tcttcactgt gagaaagaag     960

gaggaataca agatggccct gtacaacctc taccctgggg tctttgagac tgtggagatg    1020

ctgccctcca aagctggcat ctggagggtg gaatgcctca ttggggagca cctgcatgct    1080

ggcatgtcaa ccctgttcct ggtctacagc aacaagtgcc agacacccct gggaatggcc    1140

tctggccaca tcagggactt ccagatcact gcctctggcc agtatggcca gtgggcaccc    1200

aaactggcca ggctccacta ctctggctcc atcaatgcat ggtcaaccaa ggagccattc    1260

tcttggatca aggtggacct gctggcaccc atgatcattc atggcatcaa gacacagggg    1320

gcaagacaga aattctcctc tctgtacatc tcacagttca tcatcatgta ctctctggat    1380

ggcaagaagt ggcagacata cagaggcaac tccactggca ccctcatggt cttctttggc    1440

aatgtggaca gctctggcat caagcacaac atcttcaacc ctcccatcat tgccagatac    1500

atcaggctgc accccaccca ctactcaatc agatcaaccc tcaggatgga actgatggga    1560

tgtgacctga actcctgctc aatgcccctg ggaatggaga gcaaggccat ttctgatgcc    1620

cagatcactg catcctctta cttcaccaac atgtttgcca cctggtcacc atcaaaagcc    1680

aggctgcacc tccagggaag aagcaatgcc tggagacccc aggtcaacaa cccaaaggaa    1740

tggctgcaag tggacttcca gaagacaatg aaagtcactg gggtgacaac ccagggggtc    1800

aagtctctgc tcacctcaat gtatgtgaag gagttcctga tctcttcctc acaggatggc    1860

caccagtgga cactcttctt ccagaatggc aaagtcaagg tgttccaggg caaccaggac    1920

tctttcacac ctgtggtgaa ctcactggac ccccccctcc tgacaagata cctgagaatt    1980

cacccccagt cttgggtcca ccagattgcc ctgagaatgg aagtcctggg atgtgaggca    2040

caagacctgt ac                                                        2052
```

<210> SEQ ID NO 26
<211> LENGTH: 4332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
atgcagattg agctgtccac ctgcttcttt ctgtgcctgc tgagattctg cttctctgcc      60

accaggagat actacctggg ggctgtggaa ctttcttggg actacatgca gtctgacctg     120

ggagagctgc ctgtggatgc caggttccca cccagagtgc ccaagtcctt cccattcaac     180

acctctgtgg tctacaagaa gacactcttt gtggaattca ctgaccacct gttcaacatt     240

gcaaaaccca gaccaccctg gatgggactc ctgggaccca ccattcaggc tgaggtgtat     300

gacactgtgg tcatcaccct caagaacatg gcatcccacc ctgtgtctct gcatgctgtg     360
```

-continued

```
ggagtctcat actggaaagc ctctgaaggg gctgagtatg atgaccagac atcccagaga    420
gagaaagagg atgacaaggt gttccctggg ggatctcaca cctatgtgtg gcaagtcctc    480
aaggagaatg gacccatggc atctgaccca ctctgcctga catactccta cctttctcat    540
gtggacctgg tcaaggacct caactctgga ctgattgggg cactgctggt gtgcagggaa    600
ggatccctgg ccaaggagaa aacccagaca ctgcacaagt tcattctcct gtttgctgtc    660
tttgatgagg gcaagtcttg gcactctgaa acaaagaact ccctgatgca agacagggat    720
gctgcctctg ccagggcatg gcccaagatg cacactgtga atggctatgt gaacagatca    780
ctgcctggac tcattggctg ccacaggaaa tctgtctact ggcatgtgat tggcatgggg    840
acaacccctg aagtgcactc cattttcctg gagggacaca ccttcctggt caggaaccac    900
agacaagcct ctctggagat ctctcccatc accttcctca ctgcacagac actgctgatg    960
gaccttggac agttcctgct gttctgccac atctcttccc accagcatga tggcatggaa   1020
gcctatgtca aggtggactc atgccctgag gaaccacagc tcaggatgaa gaacaatgag   1080
gaggctgagg actatgatga tgacctgact gactctgaga tggatgtggt cagatttgat   1140
gatgacaact ctccatcctt cattcagatc aggtctgtgg caaagaaaca ccccaagaca   1200
tgggtgcact acattgctgc tgaggaagag gactgggact atgcaccact ggtcctggcc   1260
cctgatgaca ggagctacaa gtctcagtac ctcaacaatg gcccacaaag aattggaaga   1320
aagtacaaga aagtcagatt catggcctac actgatgaaa ccttcaagac aagagaagcc   1380
attcagcatg agtctggcat tctgggacca ctcctgtatg gggaagtggg agacaccctg   1440
ctcatcatct tcaagaacca ggcctccagg ccctacaaca tctacccaca tggcatcact   1500
gatgtcaggc ccctgtacag caggagactg ccaaaagggg tgaaacacct caaggacttc   1560
cccattctgc ctggagagat cttcaagtac aagtggactg tcactgtgga ggatggacca   1620
acaaagtctg accccaggtg cctcaccaga tactactcct cttttgtgaa catggagaga   1680
gacctggcat ctggactgat tggaccactg ctcatctgct acaaggagtc tgtggaccag   1740
agaggcaacc agatcatgtc tgacaagaga aatgtgattc tgttctctgt ctttgatgag   1800
aacagatcat ggtacctgac tgagaacatt cagagattcc tgcccaaccc tgctggggtg   1860
caactggaag accctgagtt ccaggcaagc aacatcatgc actccatcaa tggctatgtg   1920
tttgactctc tccagctttc tgtctgcctg catgaggtgg cctactggta cattctttct   1980
attggggcac aaactgactt cctttctgtc ttcttctctg gatacacctt caagcacaag   2040
atggtgtatg aggacaccct gacactcttc ccattctctg ggaaactgt gttcatgagc   2100
atggagaacc ctggactgtg gattctggga tgccacaact ctgacttcag aaacagggga   2160
atgactgcac tgctcaaagt ctcctcctgt gacaagaaca ctggggacta ctatgaggac   2220
tcttatgagg acatctctgc ctacctgctc agcaagaaca atgccattga gcccagagag   2280
atcaccagga caaccctcca gtctgaccag gaagagattg actatgatga caccatttct   2340
gtggagatga agaaggagga ctttgacatc tatgatgagg acgagaacca gtctccaaga   2400
tcattccaga agaagacaag acactacttc attgctgctg tggaaagact gtgggactat   2460
ggcatgtctt cctctcccca tgtcctcagg aacagggcac agtctggctc tgtgccacag   2520
ttcaagaaag tggtcttcca ggagttcact gatggctcat tcacccagcc cctgtacaga   2580
ggggaactga atgagcacct gggactcctg ggaccataca tcagggctga ggtggaagac   2640
aacatcatgg tgacattcag aaaccaggcc tccaggccct acagcttcta ctcttccctc   2700
atcagctatg aggaagacca gagacaaggg gctgagccaa gaaagaactt tgtgaaaccc   2760
```

```
aatgaaacca agacctactt ctggaaagtc cagcaccaca tggcacccac caaggatgag   2820
tttgactgca aggcctgggc atacttctct gatgtggacc tggagaaaga tgtgcactct   2880
ggcctgattg gcccactcct ggtctgccac accaacaccc tgaaccctgc acatggaagg   2940
caagtgactg tgcaggagtt tgccctcttc ttcaccatct ttgatgaaac caagtcatgg   3000
tacttcactg agaacatgga gagaaactgc agagcaccat gcaacattca gatggaagac   3060
cccaccttca aggagaacta caggttccat gccatcaatg gctacatcat ggacaccctg   3120
cctgggcttg tcatggcaca ggaccagaga atcagatggt acctgctttc tatgggatcc   3180
aatgagaaca ttcactccat ccacttctct gggcatgtct tcactgtgag aaagaaggag   3240
gaatacaaga tggccctgta caacctctac cctggggtct ttgagactgt ggagatgctg   3300
ccctccaaag ctggcatctg gagggtggaa tgcctcattg gggagcacct gcatgctggc   3360
atgtcaaccc tgttcctggt ctacagcaac aagtgccaga caccccctggg aatggcctct   3420
ggccacatca gggacttcca gatcactgcc tctggccagt atggccagtg ggcacccaaa   3480
ctggccaggc tccactactc tggctccatc aatgcatggt caaccaagga gccattctct   3540
tggatcaagg tggacctgct ggcacccatg atcattcatg gcatcaagac acagggggca   3600
agacagaaat tctcctctct gtacatctca cagttcatca tcatgtactc tctggatggc   3660
aagaagtggc agacatacag aggcaactcc actggcaccc tcatggtctt ctttggcaat   3720
gtggacagct ctggcatcaa gcacaacatc ttcaaccctc ccatcattgc cagatacatc   3780
aggctgcacc ccacccacta ctcaatcaga tcaaccctca ggatggaact gatgggatgt   3840
gacctgaact cctgctcaat gcccctggga atggagagca aggccatttc tgatgcccag   3900
atcactgcat cctcttactt caccaacatg tttgccacct ggtcaccatc aaaagccagg   3960
ctgcacctcc agggaagaag caatgcctgg agaccccagg tcaacaaccc aaaggaatgg   4020
ctgcaagtgg acttccagaa gacaatgaaa gtcactgggg tgacaaccca gggggtcaag   4080
tctctgctca cctcaatgta tgtgaaggag ttcctgatct cttcctcaca ggatggccac   4140
cagtggacac tcttcttcca gaatggcaaa gtcaaggtgt tccagggcaa ccaggactct   4200
ttcacacctg tggtgaactc actggacccc cccctcctga caagatacct gagaattcac   4260
ccccagtctt gggtccacca gattgccctg agaatggaag tcctgggatg tgaggcacaa   4320
gacctgtact ga                                                       4332
```

<210> SEQ ID NO 27
<211> LENGTH: 4368
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
atgcagattg agctgtccac ctgcttcttt ctgtgcctgc tgagattctg cttctctgcc     60
accaggagat actacctggg ggctgtggaa ctttcttggg actacatgca gtctgacctg    120
ggagagctgc ctgtggatgc caggttccca cccagagtgc ccaagtcctt cccattcaac    180
acctctgtgg tctacaagaa gacactcttt gtggaattca ctgaccacct gttcaacatt    240
gcaaaaccca gaccaccctg gatgggactc ctgggaccca ccattcaggc tgaggtgtat    300
gacactgtgg tcatcaccct caagaacatg gcatcccacc ctgtgtctct gcatgctgtg    360
ggagtctcat actggaaagc ctctgaaggg gctgagtatg atgaccagac atcccagaga    420
```

```
gagaaagagg atgacaaggt gttccctggg ggatctcaca cctatgtgtg gcaagtcctc    480
aaggagaatg gacccatggc atctgaccca ctctgcctga catactccta cctttctcat    540
gtggacctgg tcaaggacct caactctgga ctgattgggg cactgctggt gtgcagggaa    600
ggatccctgg ccaaggagaa aacccagaca ctgcacaagt tcattctcct gtttgctgtc    660
tttgatgagg gcaagtcttg gcactctgaa acaaagaact ccctgatgca agacagggat    720
gctgcctctg ccagggcatg gcccaagatg cacactgtga atggctatgt gaacagatca    780
ctgcctggac tcattggctg ccacaggaaa tctgtctact ggcatgtgat tggcatgggg    840
acaacccctg aagtgcactc cattttcctg gagggacaca ccttcctggt caggaaccac    900
agacaagcct ctctggagat ctctcccatc accttcctca ctgcacagac actgctgatg    960
gaccttggac agttcctgct gttctgccac atctcttccc accagcatga tggcatggaa   1020
gcctatgtca aggtggactc atgccctgag gaaccacagc tcaggatgaa gaacaatgag   1080
gaggctgagg actatgatga tgacctgact gactctgaga tggatgtggt cagatttgat   1140
gatgacaact ctccatcctt cattcagatc aggtctgtgg caaagaaaca ccccaagaca   1200
tgggtgcact acattgctgc tgaggaagag gactgggact atgcaccact ggtcctggcc   1260
cctgatgaca ggagctacaa gtctcagtac ctcaacaatg gcccacaaag aattggaaga   1320
aagtacaaga aagtcagatt catggcctac actgatgaaa ccttcaagac aagagaagcc   1380
attcagcatg agtctggcat tctgggacca ctcctgtatg gggaagtggg agacaccctg   1440
ctcatcatct tcaagaacca ggcctccagg ccctacaaca tctacccaca tggcatcact   1500
gatgtcaggc ccctgtacag caggagactg ccaaaagggg tgaaacacct caaggacttc   1560
cccattctgc ctggagagat cttcaagtac aagtggactg tcactgtgga ggatggacca   1620
acaaagtctg accccaggtg cctcaccaga tactactcct cttttgtgaa catggagaga   1680
gacctggcat ctggactgat tggaccactg ctcatctgct acaaggagtc tgtggaccag   1740
agaggcaacc agatcatgtc tgacaagaga aatgtgattc tgttctctgt ctttgatgag   1800
aacagatcat ggtacctgac tgagaacatt cagagattcc tgcccaaccc tgctggggtg   1860
caactggaag accctgagtt ccaggcaagc aacatcatgc actccatcaa tggctatgtg   1920
tttgactctc tccagctttc tgtctgcctg catgaggtgg cctactggta cattctttct   1980
attggggcac aaactgactt cctttctgtc ttcttctctg gatacacctt caagcacaag   2040
atggtgtatg aggacaccct gacactcttc ccattctctg ggaaaactgt gttcatgagc   2100
atggagaacc ctggactgtg gattctggga tgccacaact ctgacttcag aaacagggga   2160
atgactgcac tgctcaaagt ctcctcctgt gacaagaaca ctggggacta ctatgaggac   2220
tcttatgagg acatctctgc ctacctgctc agcaagaaca atgccattga gcccagaagc   2280
ttctctcaga attccagaca ccccagcacc agggagatca ccaggacaac cctccagtct   2340
gaccaggaag agattgacta tgatgacacc atttctgtgg agatgaagaa ggaggacttt   2400
gacatctatg atgaggacga gaaccagtct ccaagatcat tccagaagaa gacaagacac   2460
tacttcattg ctgctgtgga aagactgtgg gactatggca tgtcttcctc tccccatgtc   2520
ctcaggaaca gggcacagtc tggctctgtg ccacagttca agaaagtggt cttccaggag   2580
ttcactgatg gctcattcac ccagcccctg tacagagggg aactgaatga gcacctggga   2640
ctcctgggac catacatcag ggctgaggtg gaagacaaca tcatggtgac attcagaaac   2700
caggcctcca ggccctacag cttctactct tccctcatca gctatgagga agaccagaga   2760
```

-continued

```
caaggggctg agccaagaaa gaactttgtg aaacccaatg aaaccaagac ctacttctgg   2820

aaagtccagc accacatggc acccaccaag gatgagtttg actgcaaggc ctgggcatac   2880

ttctctgatg tggacctgga gaaagatgtg cactctggcc tgattggccc actcctggtc   2940

tgccacacca acaccctgaa ccctgcacat ggaaggcaag tgactgtgca ggagtttgcc   3000

ctcttcttca ccatctttga tgaaaccaag tcatggtact tcactgagaa catggagaga   3060

aactgcagag caccatgcaa cattcagatg gaagacccca ccttcaagga gaactacagg   3120

ttccatgcca tcaatggcta catcatggac accctgcctg ggcttgtcat ggcacaggac   3180

cagagaatca gatggtacct gctttctatg ggatccaatg agaacattca ctccatccac   3240

ttctctgggc atgtcttcac tgtgagaaag aaggaggaat acaagatggc cctgtacaac   3300

ctctaccctg ggtctttga gactgtggag atgctgccct ccaaagctgg catctggagg   3360

gtggaatgcc tcattgggga gcacctgcat gctggcatgt caaccctgtt cctggtctac   3420

agcaacaagt gccagacacc cctgggaatg gcctctggcc acatcaggga cttccagatc   3480

actgcctctg gccagtatgg ccagtgggca cccaaactgg ccaggctcca ctactctggc   3540

tccatcaatg catggtcaac caaggagcca ttctcttgga tcaaggtgga cctgctggca   3600

cccatgatca ttcatggcat caagacacag gggcaagac agaaattctc ctctctgtac   3660

atctcacagt tcatcatcat gtactctctg gatggcaaga agtggcagac atacagaggc   3720

aactccactg gcaccctcat ggtcttcttt ggcaatgtgg acagctctgg catcaagcac   3780

aacatcttca accctcccat cattgccaga tacatcaggc tgcaccccac ccactactca   3840

atcagatcaa ccctcaggat ggaactgatg ggatgtgacc tgaactcctg ctcaatgccc   3900

ctgggaatgg agagcaaggc catttctgat gcccagatca ctgcatcctc ttacttcacc   3960

aacatgtttg ccacctggtc accatcaaaa gccaggctgc acctccaggg aagaagcaat   4020

gcctggagac cccaggtcaa caacccaaag gaatggctgc aagtggactt ccagaagaca   4080

atgaaagtca ctggggtgac aacccagggg gtcaagtctc tgctcacctc aatgtatgtg   4140

aaggagttcc tgatctcttc ctcacaggat ggccaccagt ggacactctt cttccagaat   4200

ggcaaagtca aggtgttcca gggcaaccag gactctttca cacctgtggt gaactcactg   4260

gacccccccc tcctgacaag atacctgaga attcaccccc agtcttgggt ccaccagatt   4320

gccctgagaa tggaagtcct gggatgtgag gcacaagacc tgtactga                 4368
```

<210> SEQ ID NO 28
<211> LENGTH: 4332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
atgcagattg agctgagcac ctgcttcttc ctgtgcctgc tgaggttctg cttctctgcc     60

accaggagat actacctggg cgccgtggag ctgagctggg actacatgca gtctgacctg    120

ggcgagctgc ctgtggacgc caggttcccc cccagagtgc ccaagagctt ccccttcaac    180

acctcagtgg tgtacaagaa gaccctgttc gtggagttca ccgaccacct gttcaacatc    240

gccaagccca ggccccccctg gatgggcctg ctgggcccca ccatccaggc cgaggtgtac    300

gacaccgtgg tgatcaccct gaagaacatg gccagccacc ccgtgagcct gcacgccgtg    360

ggcgtgagct actggaaggc ctctgagggc gccgagtatg acgaccagac cagccagagg    420
```

-continued

```
gagaaggagg acgacaaggt gttccccggc ggcagccaca cctacgtgtg gcaggtgctg    480
aaggagaacg gccccatggc cagcgacccc ctgtgcctga cctacagcta cctgagccac    540
gtggacctgg tgaaggacct gaactctggc ctgatcggcg ccctgctggt gtgcagggag    600
ggcagcctgg ccaaggagaa gacccagacc ctgcacaagt tcatcctgct gttcgccgtg    660
ttcgatgagg gcaagagctg gcacagcgag accaagaaca gcctgatgca ggacagggat    720
gccgcctctg ccagggcctg gcccaagatg cacaccgtga acggctacgt gaacaggagc    780
ctgcccggcc tgatcggctg ccacaggaag tctgtgtact ggcacgtgat cggcatgggc    840
accacccccg aggtgcacag catcttcctg gagggccaca ccttcctggt gaggaaccac    900
aggcaggcca gcctggagat cagccccatc accttcctga ccgcccagac cctgctgatg    960
gacctgggcc agttcctgct gttctgccac atcagcagcc accagcacga cggcatggag   1020
gcctacgtga aggtggacag ctgccccgag gagccccagc tgaggatgaa gaacaacgag   1080
gaggccgagg actatgatga tgacctgacc gactctgaga tggacgtggt gaggtttgat   1140
gatgacaaca gccccagctt catccagatc aggtctgtgg ccaagaagca ccccaagacc   1200
tgggtgcact acatcgccgc cgaggaggag gactgggact acgccccccct ggtgctggcc   1260
cccgacgaca ggagctacaa gagccagtac ctgaacaacg gcccccagag gatcggcagg   1320
aagtacaaga aggtcagatt catggcctac accgacgaga ccttcaagac cagggaggcc   1380
atccagcacg agtctggcat cctgggcccc ctgctgtacg gcgaggtggg cgacaccctg   1440
ctgatcatct tcaagaacca ggccagcagg ccctacaaca tctaccccca cggcatcacc   1500
gatgtgaggc ccctgtacag caggaggctg cccaagggcg tgaagcacct gaaggacttc   1560
cccatcctgc ccggcgagat cttcaagtac aagtggaccg tgaccgtgga ggatggcccc   1620
accaagtctg accccaggtg cctgaccagg tactacagca gcttcgtgaa catggagagg   1680
gacctggcct ctggcctgat cggcccccctg ctgatctgct acaaggagag cgtggaccag   1740
aggggcaacc agatcatgtc tgacaagagg aacgtgatcc tgttctctgt gttcgatgag   1800
aacaggagct ggtatctgac cgagaacatc cagaggttcc tgcccaaccc cgccggcgtg   1860
cagctggagg accccgagtt ccaggccagc aacatcatgc acagcatcaa cggctacgtg   1920
ttcgacagcc tgcagctgtc tgtgtgcctg cacgaggtgg cctactggta catcctgagc   1980
atcggcgccc agaccgactt cctgtctgtg ttcttctctg gctacacctt caagcacaag   2040
atggtgtacg aggacaccct gaccctgttc cccttcagcg gcgagaccgt gttcatgagc   2100
atggagaacc ccggcctgtg gatcctgggc tgccacaaca gcgacttcag gaacaggggc   2160
atgaccgccc tgctgaaagt cagcagctgc gacaagaaca ccggcgacta ctacgaggac   2220
agctacgagg acatcagcgc ctacctgctg agcaagaaca acgccatcga gcccagggag   2280
atcaccagga ccaccctgca gagcgaccag gaggagatcg actatgatga caccatcagc   2340
gtggagatga agaaggagga cttcgacatc tacgacgagg acgagaacca gagccccagg   2400
agcttccaga agaagaccag gcactacttc atcgccgccg tggagaggct gtgggactat   2460
ggcatgagca gcagccccca cgtgctgagg aacagggccc agagcggcag cgtgccccag   2520
ttcaagaagg tggtgttcca ggagttcacc gacggcagct tcacccagcc cctgtacaga   2580
ggcgagctga acgagcacct gggcctgctg ggcccctaca tcagggccga ggtggaggac   2640
aacatcatgg tgaccttcag gaaccaggcc agcaggccct acagcttcta cagcagcctg   2700
atcagctacg aggaggacca gaggcagggc gccgagccca ggaagaactt cgtgaagccc   2760
aacgagacca agacctactt ctggaaggtg cagcaccaca tggcccccac caaggacgag   2820
```

ttcgactgca aggcctgggc ctacttctct gatgtggacc tggagaagga cgtgcacagc 2880
ggcctgatcg gcccccctgct ggtgtgccac accaacaccc tgaaccccgc ccacggcagg 2940
caggtgaccg tgcaggagtt cgccctgttc ttcaccatct tcgacgagac caagagctgg 3000
tacttcaccg agaacatgga gaggaactgc agggcccccct gcaacatcca gatggaggac 3060
cccaccttca aggagaacta caggttccac gccatcaacg gctacatcat ggacaccctg 3120
cccggcctgg tgatggccca ggaccagagg atcaggtggt atctgctgag catgggcagc 3180
aacgagaaca tccacagcat ccacttcagc ggccacgtgt tcaccgtgag gaagaaggag 3240
gagtacaaga tggccctgta caacctgtac cccggcgtgt tcgagaccgt ggagatgctg 3300
cccagcaagg ccggcatctg gagggtggag tgcctgatcg gcgagcacct gcacgccggc 3360
atgagcaccc tgttcctggt gtacagcaac aagtgccaga cccccctggg catggccagc 3420
ggccacatca gggacttcca gatcaccgcc tctggccagt acggccagtg ggcccccaag 3480
ctggccaggc tgcactacag cggcagcatc aacgcctgga gcaccaagga gcccttcagc 3540
tggatcaagg tggacctgct ggcccccatg atcatccacg gcatcaagac ccagggcgcc 3600
aggcagaagt tcagcagcct gtacatcagc cagttcatca tcatgtacag cctggacggc 3660
aagaagtggc agacctacag gggcaacagc accggcaccc tgatggtgtt cttcggcaac 3720
gtggacagca gcggcatcaa gcacaacatc ttcaaccccc ccatcatcgc caggtacatc 3780
aggctgcacc ccacccacta cagcatcagg agcaccctgc ggatggaact gatgggctgc 3840
gacctgaaca gctgcagcat gcccctgggc atggagagca aggccatctc tgacgcccag 3900
atcaccgcca gcagctactt caccaacatg ttcgccacct ggagccccag caaggccagg 3960
ctgcacctgc agggcaggag caacgcctgg aggccccagg tgaacaaccc caaggagtgg 4020
ctgcaggtgg acttccagaa gaccatgaag gtgaccggcg tgaccaccca gggcgtgaag 4080
agcctgctga ccagcatgta cgtgaaggag ttcctgatca gcagcagcca ggacggccac 4140
cagtggaccc tgttcttcca gaacggcaaa gtgaaggtgt tccagggcaa ccaggacagc 4200
ttcacccccg tggtgaacag cctggacccc cccctgctga ccaggtatct gaggatccac 4260
ccccagagct gggtgcacca gatcgccctg agaatggaag tgctgggatg cgaggcccag 4320
gacctgtact ga 4332

<210> SEQ ID NO 29
<211> LENGTH: 4368
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 29
atgcagattg agctgagcac ctgcttcttc ctgtgcctgc tgaggttctg cttctctgcc 60
accaggagat actacctggg cgccgtggag ctgagctggg actacatgca gtctgacctg 120
ggcgagctgc ctgtggacgc caggttcccc cccagagtgc ccaagagctt ccccttcaac 180
acctcagtgg tgtacaagaa gaccctgttc gtggagttca ccgaccacct gttcaacatc 240
gccaagccca ggccccccctg gatgggcctg ctgggcccca ccatccaggc cgaggtgtac 300
gacaccgtgg tgatcaccct gaagaacatg gccagccacc ccgtgagcct gcacgccgtg 360
ggcgtgagct actggaaggc ctctgagggc gccgagtatg acgaccagac cagccagagg 420
gagaaggagg acgacaaggt gttccccggc ggcagccaca cctacgtgtg gcaggtgctg 480

-continued

```
aaggagaacg gccccatggc cagcgacccc ctgtgcctga cctacagcta cctgagccac    540
gtggacctgg tgaaggacct gaactctggc ctgatcggcg ccctgctggt gtgcagggag    600
ggcagcctgg ccaaggagaa gacccagacc ctgcacaagt tcatcctgct gttcgccgtg    660
ttcgatgagg gcaagagctg gcacagcgag accaagaaca gcctgatgca ggacagggat    720
gccgcctctg ccagggcctg gcccaagatg cacaccgtga acggctacgt gaacaggagc    780
ctgcccggcc tgatcggctg ccacaggaag tctgtgtact ggcacgtgat cggcatgggc    840
accacccccg aggtgcacag catcttcctg gagggccaca ccttcctggt gaggaaccac    900
aggcaggcca gcctggagat cagccccatc accttcctga ccgcccagac cctgctgatg    960
gacctgggcc agttcctgct gttctgccac atcagcagcc accagcacga cggcatggag   1020
gcctacgtga aggtggacag ctgccccgag gagccccagc tgaggatgaa gaacaacgag   1080
gaggccgagg actatgatga tgacctgacc gactctgaga tggacgtggt gaggtttgat   1140
gatgacaaca gccccagctt catccagatc aggtctgtgg ccaagaagca ccccaagacc   1200
tgggtgcact acatcgccgc cgaggaggag gactgggact acgcccccct ggtgctggcc   1260
cccgacgaca ggagctacaa gagccagtac ctgaacaacg gcccccagag gatcggcagg   1320
aagtacaaga aggtcagatt catggcctac accgacgaga ccttcaagac cagggaggcc   1380
atccagcacg agtctggcat cctgggcccc ctgctgtacg gcgaggtggg cgacaccctg   1440
ctgatcatct tcaagaacca ggccagcagg ccctacaaca tctaccccca cggcatcacc   1500
gatgtgaggc ccctgtacag caggaggctg cccaagggcg tgaagcacct gaaggacttc   1560
cccatcctgc ccggcgagat cttcaagtac aagtggaccg tgaccgtgga ggatggcccc   1620
accaagtctg accccaggtg cctgaccagg tactacagca gcttcgtgaa catggagagg   1680
gacctggcct ctggcctgat cggcccccctg ctgatctgct acaaggagag cgtggaccag   1740
aggggcaacc agatcatgtc tgacaagagg aacgtgatcc tgttctctgt gttcgatgag   1800
aacaggagct ggtatctgac cgagaacatc cagaggttcc tgcccaaccc cgccggcgtg   1860
cagctggagg accccgagtt ccaggccagc aacatcatgc acagcatcaa cggctacgtg   1920
ttcgacagcc tgcagctgtc tgtgtgcctg cacgaggtgg cctactggta catcctgagc   1980
atcggcgccc agaccgactt cctgtctgtg ttcttctctg gctacacctt caagcacaag   2040
atggtgtacg aggacaccct gaccctgttc cccttcagcg gcgagaccgt gttcatgagc   2100
atggagaacc ccggcctgtg gatcctgggc tgccacaaca gcgacttcag gaacaggggc   2160
atgaccgccc tgctgaaagt cagcagctgc gacaagaaca ccggcgacta ctacgaggac   2220
agctacgagg acatcagcgc ctacctgctg agcaagaaca acgccatcga gcccaggagc   2280
ttcagccaga actccagaca ccccagcacc agggagatca ccaggaccac cctgcagagc   2340
gaccaggagg agatcgacta tgatgacacc atcagcgtgg agatgaagaa ggaggacttc   2400
gacatctacg acgaggacga gaaccagagc cccaggagct tccagaagaa gaccaggcac   2460
tacttcatcg ccgccgtgga gaggctgtgg gactatggca tgagcagcag cccccacgtg   2520
ctgaggaaca gggcccagag cggcagcgtg ccccagttca agaaggtggt gttccaggag   2580
ttcaccgacg gcagcttcac ccagcccctg tacagaggcg agctgaacga gcacctgggc   2640
ctgctgggcc cctacatcag ggccgaggtg gaggacaaca tcatggtgac cttcaggaac   2700
caggccagca ggccctacag cttctacagc agcctgatca gctacgagga ggaccagagg   2760
cagggcgccg agcccaggaa gaacttcgtg aagcccaacg agaccaagac ctacttctgg   2820
```

```
aaggtgcagc accacatggc ccccaccaag gacgagttcg actgcaaggc ctgggcctac   2880

ttctctgatg tggacctgga gaaggacgtg cacagcggcc tgatcggccc cctgctggtg   2940

tgccacacca acaccctgaa ccccgcccac ggcaggcagg tgaccgtgca ggagttcgcc   3000

ctgttcttca ccatcttcga cgagaccaag agctggtact tcaccgagaa catggagagg   3060

aactgcaggg ccccctgcaa catccagatg gaggacccca ccttcaagga gaactacagg   3120

ttccacgcca tcaacggcta catcatggac accctgcccg gcctggtgat ggcccaggac   3180

cagaggatca ggtggtatct gctgagcatg ggcagcaacg agaacatcca cagcatccac   3240

ttcagcggcc acgtgttcac cgtgaggaag aaggaggagt acaagatggc cctgtacaac   3300

ctgtaccccg gcgtgttcga gaccgtggag atgctgccca gcaaggccgg catctggagg   3360

gtggagtgcc tgatcggcga gcacctgcac gccggcatga gcaccctgtt cctggtgtac   3420

agcaacaagt gccagacccc cctgggcatg gccagcggcc acatcaggga cttccagatc   3480

accgcctctg gccagtacgg ccagtgggcc cccaagctgg ccaggctgca ctacagcggc   3540

agcatcaacg cctggagcac caaggagccc ttcagctgga tcaaggtgga cctgctggcc   3600

cccatgatca tccacggcat caagacccag ggcgccaggc agaagttcag cagcctgtac   3660

atcagccagt tcatcatcat gtacagcctg gacggcaaga agtggcagac ctacaggggc   3720

aacagcaccg gcaccctgat ggtgttcttc ggcaacgtgg acagcagcgg catcaagcac   3780

aacatcttca acccccccat catcgccagg tacatcaggc tgcaccccac ccactacagc   3840

atcaggagca ccctgcggat ggaactgatg ggctgcgacc tgaacagctg cagcatgccc   3900

ctgggcatgg agagcaaggc catctctgac gcccagatca ccgccagcag ctacttcacc   3960

aacatgttcg ccacctggag ccccagcaag gccaggctgc acctgcaggg caggagcaac   4020

gcctggaggc cccaggtgaa caaccccaag gagtggctgc aggtggactt ccagaagacc   4080

atgaaggtga ccggcgtgac cacccagggc gtgaagagcc tgctgaccag catgtacgtg   4140

aaggagttcc tgatcagcag cagccaggac ggccaccagt ggaccctgtt cttccagaac   4200

ggcaaagtga aggtgttcca gggcaaccag gacagcttca cccccgtggt gaacagcctg   4260

gacccccccc tgctgaccag gtatctgagg atccaccccc agagctgggt gcaccagatc   4320

gccctgagaa tggaagtgct gggatgcgag gcccaggacc tgtactga              4368
```

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

```
Ser Phe Ser Gln Asn Pro Pro Val Leu Lys Arg His Gln Arg
1               5                   10
```

<210> SEQ ID NO 31
<211> LENGTH: 24
<212> TYPE: PRT
<213> ORGANISM: Sus sp.

<400> SEQUENCE: 31

```
Ser Phe Ala Gln Asn Ser Arg Pro Pro Ser Ala Ser Ala Pro Lys Pro
1               5                   10                  15

Pro Val Leu Arg Arg His Gln Arg
            20
```

<210> SEQ ID NO 32
<211> LENGTH: 16
<212> TYPE: PRT
<213> ORGANISM: Sus sp.

<400> SEQUENCE: 32

```
Ser Phe Ser Gln Asn Ser Arg His Gln Ala Tyr Arg Tyr Arg Arg Gly
1               5                   10                  15
```

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

```
Thr Thr Tyr Val Asn Arg Ser Leu
1               5
```

<210> SEQ ID NO 34
<211> LENGTH: 7
<212> TYPE: PRT
<213> ORGANISM: Homo sapiens

<400> SEQUENCE: 34

```
Pro Gln Leu Arg Met Lys Asn
1               5
```

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

```
Val Asp Gln Arg Gly Asn Gln
1               5
```

<210> SEQ ID NO 36
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36

```
agcttcagcc agaatgtgag caacaatgtg agcaacaatg ccaccaataa tgctaccaac     60

ccacctgtcc tgaaacgcca ccagagg                                         87
```

<210> SEQ ID NO 37
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37

```
agcttcagcc agaatgtgag caacaatgcc accaacaatg tgagcaaccc acctgtcctg     60
```

aaacgccacc agagg 75

<210> SEQ ID NO 38
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
agcttcagcc agaatgtgag caataatgcc accaacccac ctgtcctgaa acgccaccag 60
agg 63

<210> SEQ ID NO 39
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
agcttcagcc agaatgtgag caataatcca cctgtcctga aacgccacca gagg 54

<210> SEQ ID NO 40
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
agcttcagcc agaataggag cctgccacct gtcctgaaac gccaccagag g 51

<210> SEQ ID NO 41
<211> LENGTH: 93
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
agcttcagcc agaatgccac taatgtgtct aacaactctg ctacctctgc tgactctgct 60
gtgagcccac ctgtcctgaa acgccaccag agg 93

<210> SEQ ID NO 42
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
agcttcagcc agaatgccac caactatgtg aacaggagcc tgccacctgt cctgaaacgc 60
caccagagg 69

<210> SEQ ID NO 43
<211> LENGTH: 105
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 43
agcttcagcc agaatgccac caactatgtg aacaggagcc tgtctgccac ctctgctgac     60
tctgctgtga gccagaatcc acctgtcctg aaacgccacc agagg                   105

<210> SEQ ID NO 44
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
agcttcagcc agaatgtgag caacaatgtg agcaatgctg tgtctgctgt gtctgctcca     60
cctgtcctga aacgccacca gagg                                            84

<210> SEQ ID NO 45
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
agcttcagcc agaatatcac tgtggcctct gccacctcta acatcactgt ggcctctgct     60
gacccacctg tcctgaaacg ccaccagagg                                      90

<210> SEQ ID NO 46
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
agcttcagcc agaatatcac tgtgaccaac atcactgtga ctgccccacc tgtcctgaaa     60
cgccaccaga gg                                                         72

<210> SEQ ID NO 47
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
agcttcagcc agaatcagac tgtgaccaac atcactgtga ctgccccacc tgtcctgaaa     60
cgccaccaga gg                                                         72

<210> SEQ ID NO 48
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48

-continued agcttcagcc agaatgccac taatgtgtct aacaacagca acaccagcaa tgacagcaat 60
gtgtctccac ctgtcctgaa acgccaccag agg 93

<210> SEQ ID NO 49
<211> LENGTH: 4374
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 49
atgcagattg agctgtccac ctgcttcttt ctgtgcctgc tgagattctg cttctctgcc 60
accaggagat actacctggg ggctgtggaa ctttcttggg actacatgca gtctgacctg 120
ggagagctgc ctgtggatgc caggttccca cccagagtgc ccaagtcctt cccattcaac 180
acctctgtgg tctacaagaa gacactcttt gtggaattca ctgaccacct gttcaacatt 240
gcaaaaccca gaccaccctg gatgggactc ctgggaccca ccattcaggc tgaggtgtat 300
gacactgtgg tcatcaccct caagaacatg gcatccccacc ctgtgtctct gcatgctgtg 360
ggagtctcat actggaaagc ctctgaaggg gctgagtatg atgaccagac atcccagaga 420
gagaaagagg atgacaaggt gttccctggg ggatctcaca cctatgtgtg gcaagtcctc 480
aaggagaatg gacccatggc atctgaccca ctctgcctga catactccta cctttctcat 540
gtggacctgg tcaaggacct caactctgga ctgattgggg cactgctggt gtgcagggaa 600
ggatccctgg ccaaggagaa aacccagaca ctgcacaagt tcattctcct gtttgctgtc 660
tttgatgagg gcaagtcttg gcactctgaa acaaagaact ccctgatgca agacagggat 720
gctgcctctg ccagggcatg gcccaagatg cacactgtga atggctatgt gaacagatca 780
ctgcctggac tcattggctg ccacaggaaa tctgtctact ggcatgtgat tggcatgggg 840
acaacccctg aagtgcactc cattttcctg gagggacaca ccttcctggt caggaaccac 900
agacaagcct ctctggagat ctctcccatc accttcctca ctgcacagac actgctgatg 960
gaccttggac agttcctgct gtcctgccac atctcttccc accagcatga tggcatggaa 1020
gcctatgtca aggtggactc atgccctgag gaaccacagc tcaggatgaa gaacaatgag 1080
gaggctgagg actatgatga tgacctgact gactctgaga tggatgtggt cagatttgat 1140
gatgacaact ctccatcctt cattcagatc aggtctgtgg caaagaaaca ccccaagaca 1200
tgggtgcact acattgctgc tgaggaagag gactgggact atgcaccact ggtcctggcc 1260
cctgatgaca ggagctacaa gtctcagtac ctcaacaatg gcccacaaag aattggaaga 1320
aagtacaaga aagtcagatt catggcctac actgatgaaa ccttcaagac aagagaagcc 1380
attcagcatg agtctggcat tctgggacca ctcctgtatg gggaagtggg agacaccctg 1440
ctcatcatct tcaagaacca ggcctccagg ccctacaaca tctacccaca tggcatcact 1500
gatgtcaggc ccctgtacag caggagactg ccaaaagggg tgaaacacct caaggacttc 1560
cccattctgc ctggagagat cttcaagtac aagtggactg tcactgtgga ggatggacca 1620
acaaagtctg accccaggtg cctcaccaga tactactcct cttttgtgaa catggagaga 1680
gacctggcat ctggactgat tggaccactg ctcatctgct acaaggagtc tgtggaccag 1740
agaggcaacc agatcatgtc tgacaagaga aatgtgattc tgttctctgt ctttgatgag 1800
aacagatcat ggtacctgac tgagaacatt cagagattcc tgcccaaccc tgctggggtg 1860
caactggaag accctgagtt ccaggcaagc aacatcatgc actccatcaa tggctatgtg 1920

-continued

```
tttgactctc tccagctttc tgtctgcctg catgaggtgg cctactggta cattctttct   1980
attggggcac aaactgactt cctttctgtc ttcttctctg gatacacctt caagcacaag   2040
atggtgtatg aggacaccct gacactcttc ccattctctg ggaaaactgt gttcatgagc   2100
atggagaacc ctggactgtg gattctggga tgccacaact ctgacttcag aaacagggga   2160
atgactgcac tgctcaaagt ctcctcctgt gacaagaaca ctggggacta ctatgaggac   2220
tcttatgagg acatctctgc ctacctgctc agcaagaaca atgccattga gcccagaagc   2280
ttctctcaga atccacctgt cctgaagaga caccagagag agatcaccag gacaaccctc   2340
cagtctgacc aggaagagat tgactatgat gacaccattt ctgtggagat gaagaaggag   2400
gactttgaca tctatgatga ggacgagaac cagtctccaa gatcattcca gaagaagaca   2460
agacactact tcattgctgc tgtggaaaga ctgtgggact atggcatgtc ttcctctccc   2520
catgtcctca ggaacagggc acagtctggc tctgtgccac agttcaagaa agtggtcttc   2580
caggagttca ctgatggctc attcacccag cccctgtaca gaggggaact gaatgagcac   2640
ctgggactcc tgggaccata catcagggct gaggtggaag acaacatcat ggtgacattc   2700
agaaaccagg cctccaggcc ctacagcttc tactcttccc tcatcagcta tgaggaagac   2760
cagagacaag gggctgagcc aagaaagaac tttgtgaaac ccaatgaaac caagacctac   2820
ttctggaaag tccagcacca catggcaccc accaaggatg agtttgactg caaggcctgg   2880
gcatacttct ctgatgtgga cctggagaaa gatgtgcact ctggcctgat tggcccactc   2940
ctggtctgcc acaccaacac cctgaaccct gcacatggaa ggcaagtgac tgtgcaggag   3000
tttgccctct tcttcaccat ctttgatgaa accaagtcat ggtacttcac tgagaacatg   3060
gagagaaact gcagagcacc atgcaacatt cagatggaag accccacctt caaggagaac   3120
tacaggttcc atgccatcaa tggctacatc atggacaccc tgcctgggct tgtcatggca   3180
caggaccaga gaatcagatg gtacctgctt tctatgggat ccaatgagaa cattcactcc   3240
atccacttct ctgggcatgt cttcactgtg agaaagaagg aggaatacaa gatggccctg   3300
tacaacctct accctggggt ctttgagact gtggagatgc tgccctccaa agctggcatc   3360
tggagggtgg aatgcctcat tggggagcac ctgcatgctg gcatgtcaac cctgttcctg   3420
gtctacagca acaagtgcca gacacccctg ggaatggcct ctggccacat cagggacttc   3480
cagatcactg cctctggcca gtatggccag tgggcaccca aactggccag gctccactac   3540
tctggctcca tcaatgcatg gtcaaccaag gagccattct cttggatcaa ggtggacctg   3600
ctggcaccca tgatcattca tggcatcaag acacaggggg caagacagaa attctcctct   3660
ctgtacatct cacagttcat catcatgtac tctctggatg gcaagaagtg gcagacatac   3720
agaggcaact ccactggcac cctcatggtc ttctttggca atgtggacag ctctggcatc   3780
aagcacaaca tcttcaaccc tcccatcatt gccagataca tcaggctgca ccccacccac   3840
tactcaatca gatcaaccct caggatggaa ctgatgggat gtgacctgaa ctcctgctca   3900
atgcccctgg gaatggagag caaggccatt tctgatgccc agatcactgc atcctcttac   3960
ttcaccaaca tgtttgccac ctggtcacca tcaaaagcca ggctgcacct ccagggaaga   4020
agcaatgcct ggagacccca ggtcaacaac ccaaaggaat ggctgcaagt ggacttccag   4080
aagacaatga aagtcactgg ggtgacaacc caggggggtca agtctctgct cacctcaatg   4140
tatgtgaagg agttcctgat ctcttcctca caggatggcc accagtggac actcttcttc   4200
cagaatggca aagtcaaggt gttccagggc aaccaggact ctttcacacc tgtggtgaac   4260
```

```
tcactggacc cccccctcct gacaagatac ctgagaattc acccccagtc ttgggtccac   4320

cagattgccc tgagaatgga agtcctggga tgtgaggcac aagacctgta ctga         4374


<210> SEQ ID NO 50
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(45)

<400> SEQUENCE: 50

gtg agc aac aat gtg agc aac aat gcc acc aat aat gct acc aac           45
Val Ser Asn Asn Val Ser Asn Asn Ala Thr Asn Asn Ala Thr Asn
1               5                   10                  15


<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Val Ser Asn Asn Val Ser Asn Asn Ala Thr Asn Asn Ala Thr Asn
1               5                   10                  15


<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(33)

<400> SEQUENCE: 52

gtg agc aac aat gcc acc aac aat gtg agc aac                           33
Val Ser Asn Asn Ala Thr Asn Asn Val Ser Asn
1               5                   10


<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Val Ser Asn Asn Ala Thr Asn Asn Val Ser Asn
1               5                   10


<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(21)
```

<400> SEQUENCE: 54 gtg agc aat aat gcc acc aac 21
Val Ser Asn Asn Ala Thr Asn
1 5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Val Ser Asn Asn Ala Thr Asn
1 5

<210> SEQ ID NO 56
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(12)

<400> SEQUENCE: 56 gtg agc aat aat 12
Val Ser Asn Asn
1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Val Ser Asn Asn
1

<210> SEQ ID NO 58
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(9)

<400> SEQUENCE: 58 agg agc ctg 9
Arg Ser Leu
1

<210> SEQ ID NO 59
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Arg Ser Leu
1

<210> SEQ ID NO 60
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: CDS
<222> LOCATION: (1)..(51)

<400> SEQUENCE: 60

```
gcc act aat gtg tct aac aac tct gct acc tct gct gac tct gct gtg       48
Ala Thr Asn Val Ser Asn Asn Ser Ala Thr Ser Ala Asp Ser Ala Val
1               5                   10                  15

agc                                                                   51
Ser
```

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

```
Ala Thr Asn Val Ser Asn Asn Ser Ala Thr Ser Ala Asp Ser Ala Val
1               5                   10                  15

Ser
```

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: CDS
<222> LOCATION: (1)..(27)

<400> SEQUENCE: 62

```
gcc acc aac tat gtg aac agg agc ctg                                   27
Ala Thr Asn Tyr Val Asn Arg Ser Leu
1               5
```

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

```
Ala Thr Asn Tyr Val Asn Arg Ser Leu
1               5
```

<210> SEQ ID NO 64
<211> LENGTH: 63
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: CDS
<222> LOCATION: (1)..(63)

<400> SEQUENCE: 64

```
gcc acc aac tat gtg aac agg agc ctg tct gcc acc tct gct gac tct       48
Ala Thr Asn Tyr Val Asn Arg Ser Leu Ser Ala Thr Ser Ala Asp Ser
1               5                   10                  15

gct gtg agc cag aat                                                   63
Ala Val Ser Gln Asn
            20
```

<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

```
Ala Thr Asn Tyr Val Asn Arg Ser Leu Ser Ala Thr Ser Ala Asp Ser
1               5                   10                  15

Ala Val Ser Gln Asn
            20
```

<210> SEQ ID NO 66
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: CDS
<222> LOCATION: (1)..(42)

<400> SEQUENCE: 66

```
gtg agc aac aat gtg agc aat gct gtg tct gct gtg tct gct               42
Val Ser Asn Asn Val Ser Asn Ala Val Ser Ala Val Ser Ala
1               5                   10
```

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

```
Val Ser Asn Asn Val Ser Asn Ala Val Ser Ala Val Ser Ala
1               5                   10
```

<210> SEQ ID NO 68
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: CDS
<222> LOCATION: (1)..(48)

<400> SEQUENCE: 68 atc act gtg gcc tct gcc acc tct aac atc act gtg gcc tct gct gac 48
Ile Thr Val Ala Ser Ala Thr Ser Asn Ile Thr Val Ala Ser Ala Asp
1 5 10 15

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Ile Thr Val Ala Ser Ala Thr Ser Asn Ile Thr Val Ala Ser Ala Asp
1 5 10 15

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: CDS
<222> LOCATION: (1)..(30)

<400> SEQUENCE: 70 atc act gtg acc aac atc act gtg act gcc 30
Ile Thr Val Thr Asn Ile Thr Val Thr Ala
1 5 10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 71

Ile Thr Val Thr Asn Ile Thr Val Thr Ala
1 5 10

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: CDS
<222> LOCATION: (1)..(30)

<400> SEQUENCE: 72 cag act gtg acc aac atc act gtg act gcc 30
Gln Thr Val Thr Asn Ile Thr Val Thr Ala
1 5 10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 73

Gln Thr Val Thr Asn Ile Thr Val Thr Ala
1 5 10

<210> SEQ ID NO 74
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(51)

<400> SEQUENCE: 74 gcc act aat gtg tct aac aac agc aac acc agc aat gac agc aat gtg 48
Ala Thr Asn Val Ser Asn Asn Ser Asn Thr Ser Asn Asp Ser Asn Val
1 5 10 15 tct 51
Ser

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Ala Thr Asn Val Ser Asn Asn Ser Asn Thr Ser Asn Asp Ser Asn Val
1 5 10 15

Ser

<210> SEQ ID NO 76
<211> LENGTH: 405
<212> TYPE: PRT
<213> ORGANISM: Homo sapiens

<400> SEQUENCE: 76

Met Pro Leu Leu Leu Tyr Thr Cys Leu Leu Trp Leu Pro Thr Ser Gly
1 5 10 15

Leu Trp Thr Val Gln Ala Met Asp Pro Asn Ala Ala Tyr Val Asn Met
20 25 30

Ser Asn His His Arg Gly Leu Ala Ser Ala Asn Val Asp Phe Ala Phe
35 40 45

Ser Leu Tyr Lys His Leu Val Ala Leu Ser Pro Lys Lys Asn Ile Phe
50 55 60

Ile Ser Pro Val Ser Ile Ser Met Ala Leu Ala Met Leu Ser Leu Gly
65 70 75 80

Thr Cys Gly His Thr Arg Ala Gln Leu Leu Gln Gly Leu Gly Phe Asn
85 90 95

Leu Thr Glu Arg Ser Glu Thr Glu Ile His Gln Gly Phe Gln His Leu
100 105 110

His Gln Leu Phe Ala Lys Ser Asp Thr Ser Leu Glu Met Thr Met Gly
115 120 125

Asn Ala Leu Phe Leu Asp Gly Ser Leu Glu Leu Leu Glu Ser Phe Ser
130 135 140

Ala Asp Ile Lys His Tyr Tyr Glu Ser Glu Val Leu Ala Met Asn Phe
145 150 155 160

-continued

```
Gln Asp Trp Ala Thr Ala Ser Arg Gln Ile Asn Ser Tyr Val Lys Asn
                165                 170                 175

Lys Thr Gln Gly Lys Ile Val Asp Leu Phe Ser Gly Leu Asp Ser Pro
            180                 185                 190

Ala Ile Leu Val Leu Val Asn Tyr Ile Phe Phe Lys Gly Thr Trp Thr
        195                 200                 205

Gln Pro Phe Asp Leu Ala Ser Thr Arg Glu Glu Asn Phe Tyr Val Asp
    210                 215                 220

Glu Thr Thr Val Val Lys Val Pro Met Met Leu Gln Ser Ser Thr Ile
225                 230                 235                 240

Ser Tyr Leu His Asp Ser Glu Leu Pro Cys Gln Leu Val Gln Met Asn
                245                 250                 255

Tyr Val Gly Asn Gly Thr Val Phe Phe Ile Leu Pro Asp Lys Gly Lys
            260                 265                 270

Met Asn Thr Val Ile Ala Ala Leu Ser Arg Asp Thr Ile Asn Arg Trp
        275                 280                 285

Ser Ala Gly Leu Thr Ser Ser Gln Val Asp Leu Tyr Ile Pro Lys Val
    290                 295                 300

Thr Ile Ser Gly Val Tyr Asp Leu Gly Asp Val Leu Glu Glu Met Gly
305                 310                 315                 320

Ile Ala Asp Leu Phe Thr Asn Gln Ala Asn Phe Ser Arg Ile Thr Gln
                325                 330                 335

Asp Ala Gln Leu Lys Ser Ser Lys Val Val His Lys Ala Val Leu Gln
            340                 345                 350

Leu Asn Glu Glu Gly Val Asp Thr Ala Gly Ser Thr Gly Val Thr Leu
        355                 360                 365

Asn Leu Thr Ser Lys Pro Ile Ile Leu Arg Phe Asn Gln Pro Phe Ile
    370                 375                 380

Ile Met Ile Phe Asp His Phe Thr Trp Ser Ser Leu Phe Leu Ala Arg
385                 390                 395                 400

Val Met Asn Pro Val
                405


<210> SEQ ID NO 77
<211> LENGTH: 4
<212> TYPE: PRT
<213> ORGANISM: Homo sapiens

<400> SEQUENCE: 77

Asn Met Ser Asn
1


<210> SEQ ID NO 78
<211> LENGTH: 4
<212> TYPE: PRT
<213> ORGANISM: Homo sapiens

<400> SEQUENCE: 78

Asn Leu Thr Glu
1


<210> SEQ ID NO 79
<211> LENGTH: 4
<212> TYPE: PRT
<213> ORGANISM: Homo sapiens

<400> SEQUENCE: 79
```

Asn Lys Thr Gln
1

<210> SEQ ID NO 80
<211> LENGTH: 4
<212> TYPE: PRT
<213> ORGANISM: Homo sapiens

<400> SEQUENCE: 80

Asn Gly Thr Val
1

<210> SEQ ID NO 81
<211> LENGTH: 4
<212> TYPE: PRT
<213> ORGANISM: Homo sapiens

<400> SEQUENCE: 81

Asn Phe Ser Arg
1

<210> SEQ ID NO 82
<211> LENGTH: 4
<212> TYPE: PRT
<213> ORGANISM: Homo sapiens

<400> SEQUENCE: 82

Asn Leu Thr Ser
1

<210> SEQ ID NO 83
<211> LENGTH: 41
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 83

```
Leu Ser Lys Asn Asn Ala Ile Glu Pro Arg Ser Phe Ser Gln Asn Ala
1               5                   10                  15

Thr Asn Val Ser Asn Asn Ser Asn Thr Ser Asn Asp Ser Asn Val Ser
            20                  25                  30

Pro Pro Val Leu Lys Arg His Gln Arg
        35                  40
```

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Asn Ala Thr Asn
1

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Asn Val Ser Asn
1

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asn Asn Ser Asn
1

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asn Thr Ser Asn
1

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asn Asp Ser Asn
1

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asn Val Ser Pro
1

<210> SEQ ID NO 90
<211> LENGTH: 4377
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
atgcagattg agctgtccac ctgcttcttt ctgtgcctgc tgagattctg cttctctgcc 60
accaggagat actacctggg ggctgtggaa ctttcttggg actacatgca gtctgacctg 120
ggagagctgc ctgtggatgc caggttccca cccagagtgc ccaagtcctt cccattcaac 180
acctctgtgg tctacaagaa gacactcttt gtggaattca ctgaccacct gttcaacatt 240

```
gcaaaaccca gaccaccctg gatgggactc ctgggaccca ccattcaggc tgaggtgtat    300
gacactgtgg tcatcaccct caagaacatg gcatcccacc ctgtgtctct gcatgctgtg    360
ggagtctcat actggaaagc ctctgaaggg gctgagtatg atgaccagac atcccagaga    420
gagaaagagg atgacaaggt gttccctggg ggatctcaca cctatgtgtg gcaagtcctc    480
aaggagaatg gacccatggc atctgaccca ctctgcctga catactccta cctttctcat    540
gtggacctgg tcaaggacct caactctgga ctgattgggg cactgctggt gtgcagggaa    600
ggatccctgg ccaaggagaa aacccagaca ctgcacaagt tcattctcct gtttgctgtc    660
tttgatgagg gcaagtcttg gcactctgaa acaaagaact ccctgatgca agacagggat    720
gctgcctctg ccagggcatg gcccaagatg cacactgtga atggctatgt gaacagatca    780
ctgcctggac tcattggctg ccacaggaaa tctgtctact ggcatgtgat tggcatgggg    840
acaacccctg aagtgcactc cattttcctg gagggacaca ccttcctggt caggaaccac    900
agacaagcct ctctggagat ctctcccatc accttcctca ctgcacagac actgctgatg    960
gaccttggac agttcctgct gtcctgccac atctcttccc accagcatga tggcatggaa   1020
gcctatgtca aggtggactc atgccctgag gaaccacagc tcaggatgaa gaacaatgag   1080
gaggctgagg actatgatga tgacctgact gactctgaga tggatgtggt cagatttgat   1140
gatgacaact ctccatcctt cattcagatc aggtctgtgg caaagaaaca ccccaagaca   1200
tgggtgcact acattgctgc tgaggaagag gactgggact atgcaccact ggtcctggcc   1260
cctgatgaca ggagctacaa gtctcagtac ctcaacaatg gcccacaaag aattggaaga   1320
aagtacaaga aagtcagatt catggcctac actgatgaaa ccttcaagac aagagaagcc   1380
attcagcatg agtctggcat tctgggacca ctcctgtatg gggaagtggg agacaccctg   1440
ctcatcatct tcaagaacca ggcctccagg ccctacaaca tctacccaca tggcatcact   1500
gatgtcaggc ccctgtacag caggagactg ccaaaagggg tgaaacacct caaggacttc   1560
cccattctgc ctggagagat cttcaagtac aagtggactg tcactgtgga ggatggacca   1620
acaaagtctg accccaggtg cctcaccaga tactactcct cttttgtgaa catggagaga   1680
gacctggcat ctggactgat tggaccactg ctcatctgct acaaggagtc tgtggaccag   1740
agaggcaacc agatcatgtc tgacaagaga aatgtgattc tgttctctgt ctttgatgag   1800
aacagatcat ggtacctgac tgagaacatt cagagattcc tgcccaaccc tgctggggtg   1860
caactggaag accctgagtt ccaggcaagc aacatcatgc actccatcaa tggctatgtg   1920
tttgactctc tccagctttc tgtctgcctg catgaggtgg cctactggta cattctttct   1980
attggggcac aaactgactt cctttctgtc ttcttctctg gatacacctt caagcacaag   2040
atggtgtatg aggacaccct gacactcttc ccattctctg ggaaaactgt gttcatgagc   2100
atggagaacc ctggactgtg gattctggga tgccacaact ctgacttcag aaacagggga   2160
atgactgcac tgctcaaagt ctcctcctgt gacaagaaca ctggggacta ctatgaggac   2220
tcttatgagg acatctctgc ctacctgctc agcaagaaca ataccaccta cgtgaaccgc   2280
tccctgtctc agaatccacc tgtcctgaag agacaccaga gagagatcac caggacaacc   2340
ctccagtctg accaggaaga gattgactat gatgacacca tttctgtgga gatgaagaag   2400
gaggactttg acatctatga tgaggacgag aaccagtctc caagatcatt ccagaagaag   2460
acaagacact acttcattgc tgctgtggaa agactgtggg actatggcat gtcttcctct   2520
ccccatgtcc tcaggaacag ggcacagtct ggctctgtgc cacagttcaa gaaagtggtc   2580
```

```
ttccaggagt tcactgatgg ctcattcacc cagcccctgt acagagggga actgaatgag   2640

cacctgggac tcctgggacc atacatcagg gctgaggtgg aagacaacat catggtgaca   2700

ttcagaaacc aggcctccag gccctacagc ttctactctt ccctcatcag ctatgaggaa   2760

gaccagagac aaggggctga gccaagaaag aactttgtga aacccaatga aaccaagacc   2820

tacttctgga aagtccagca ccacatggca cccaccaagg atgagtttga ctgcaaggcc   2880

tgggcatact tctctgatgt ggacctggag aaagatgtgc actctggcct gattggccca   2940

ctcctggtct gccacaccaa caccctgaac cctgcacatg gaaggcaagt gactgtgcag   3000

gagtttgccc tcttcttcac catctttgat gaaaccaagt catggtactt cactgagaac   3060

atggagagaa actgcagagc accatgcaac attcagatgg aagaccccac cttcaaggag   3120

aactacaggt tccatgccat caatggctac atcatggaca ccctgcctgg gcttgtcatg   3180

gcacaggacc agagaatcag atggtacctg ctttctatgg gatccaatga gaacattcac   3240

tccatccact tctctgggca tgtcttcact gtgagaaaga aggaggaata caagatggcc   3300

ctgtacaacc tctaccctgg ggtctttgag actgtggaga tgctgccctc caaagctggc   3360

atctggaggg tggaatgcct cattggggag cacctgcatg ctggcatgtc aaccctgttc   3420

ctggtctaca gcaacaagtg ccagacaccc ctgggaatgg cctctggcca catcagggac   3480

ttccagatca ctgcctctgg ccagtatggc cagtgggcac ccaaactggc caggctccac   3540

tactctggct ccatcaatgc atggtcaacc aaggagccat tctcttggat caaggtggac   3600

ctgctggcac ccatgatcat tcatggcatc aagacacagg gggcaagaca gaaattctcc   3660

tctctgtaca tctcacagtt catcatcatg tactctctgg atggcaagaa gtggcagaca   3720

tacagaggca actccactgg caccctcatg gtcttctttg gcaatgtgga cagctctggc   3780

atcaagcaca acatcttcaa ccctcccatc attgccagat acatcaggct gcaccccacc   3840

cactactcaa tcagatcaac cctcaggatg gaactgatgg gatgtgacct gaactcctgc   3900

tcaatgcccc tgggaatgga gagcaaggcc atttctgatg cccagatcac tgcatcctct   3960

tacttcacca acatgtttgc cacctggtca ccatcaaaag ccaggctgca cctccaggga   4020

agaagcaatg cctggagacc ccaggtcaac aacccaaagg aatggctgca agtggacttc   4080

cagaagacaa tgaaagtcac tggggtgaca acccaggggg tcaagtctct gctcacctca   4140

atgtatgtga aggagttcct gatctcttcc tcacaggatg gccaccagtg gacactcttc   4200

ttccagaatg gcaaagtcaa ggtgttccag ggcaaccagg actctttcac acctgtggtg   4260

aactcactgg acccccccct cctgacaaga tacctgagaa ttcaccccca gtcttgggtc   4320

caccagattg ccctgagaat ggaagtcctg ggatgtgagg cacaagacct gtactga      4377
```

<210> SEQ ID NO 91
<211> LENGTH: 4377
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91

```
atgcagattg agctgtccac ctgcttcttt ctgtgcctgc tgagattctg cttctctgcc     60

accaggagat actacctggg ggctgtggaa ctttcttggg actacatgca gtctgacctg    120

ggagagctgc ctgtggatgc caggttccca cccagagtgc ccaagtcctt cccattcaac    180

acctctgtgg tctacaagaa gacactcttt gtggaattca ctgaccacct gttcaacatt    240
```

-continued

```
gcaaaaccca gaccaccctg gatgggactc ctgggaccca ccattcaggc tgaggtgtat    300
gacactgtgg tcgtcaccct caagaacatg gcatcccacc ctgtgtctct gcatgctgtg    360
ggagtctcat actggaaatc ctctgaaggg gctgagtatg atgaccagac atcccagaga    420
gagaaagagg atgacaaggt gttccctggg aagtctcaca cctatgtgtg gcaagtcctc    480
aaggagaatg gacccactgc atctgaccca ccctgcctga catactccta cctttctcat    540
gtggacctgg tcaaggacct caactctgga ctgattgggg cactgctggt gtgcagggaa    600
ggatccctgg ccaaggagaa aacccagaca ctgcacaagt tcattctcct gtttgctgtc    660
tttgatgagg gcaagtcttg gcactctgaa acaaagaact ccctgatgca agacagggat    720
gctgcctctg ccagggcatg gcccaagatg cacactgtga atggctatgt gaacagatca    780
ctgcctggac tcattggctg ccacaggaaa tctgtctact ggcatgtgat tggcatgggg    840
acaacccctg aagtgcactc cattttcctg gagggacaca ccttcctggt caggaaccac    900
agacaagcct ctctggagat ctctcccatc accttcctca ctgcacagac actgctgatg    960
gaccttggac agttcctgct gttctgccac atctcttccc accagcatga tggcatggaa   1020
gcctatgtca aggtggactc atgccctgag gaaccacagc tcaggatgaa gaacaatgag   1080
gaggctgagg actatgatga tgacctgact gactctgaga tggatgtggt cagatttgat   1140
gatgacaact ctccatcctt cattcagatc aggtctgtgg caaagaaaca ccccaagaca   1200
tgggtgcact acattgctgc tgaggaagag gactgggact atgcaccact ggtcctggcc   1260
cctgatgaca ggagctacaa gtctcagtac ctcaacaatg gcccacaaag aattggaaga   1320
aagtacaaga aagtcagatt catggcctac actgatgaaa ccttcaagac aagagaagcc   1380
attcagcatg agtctggcat tctgggacca ctcctgtatg gggaagtggg agacaccctg   1440
ctcatcatct tcaagaacca ggcctccagg ccctacaaca tctacccaca tggcatcact   1500
gatgtcaggc ccctgtacag caggagactg ccaaaagggg tgaaacacct caaggacttc   1560
cccattctgc ctggagagat cttcaagtac aagtggactg tcactgtgga ggatggacca   1620
acaaagtctg accccaggtg cctcaccaga tactactcct cttttgtgaa catggagaga   1680
gacctggcat ctggactgat tggaccactg ctcatctgct acaaggagtc tgtggaccag   1740
agaggcaacc agatcatgtc tgacaagaga aatgtgattc tgttctctgt ctttgatgag   1800
aacagatcat ggtacctgac tgagaacatt cagagattcc tgcccaaccc tgctggggtg   1860
caactggaag accctgagtt ccaggcaagc aacatcatgc actccatcaa tggctatgtg   1920
tttgactctc tccagctttc tgtctgcctg catgaggtgg cctactggta cattctttct   1980
attggggcac aaactgactt cctttctgtc ttcttctctg gatacacctt caagcacaag   2040
atggtgtatg aggacaccct gacactcttc ccattctctg ggaaactgt gttcatgagc    2100
atggagaacc ctggactgtg gattctggga tgccacaact ctgacttcag aaacagggga   2160
atgactgcac tgctcaaagt ctcctcctgt gacaagaaca ctggggacta ctatgaggac   2220
tcttatgagg acatctctgc ctacctgctc agcaagaaca ataccaccta cgtgaaccgc   2280
tccctgtctc agaatccacc tgtcctgaag agacaccaga gagagatcac caggacaacc   2340
ctccagtctg accaggaaga gattgactat gatgacacca tttctgtgga gatgaagaag   2400
gaggactttg acatctatga tgaggacgag aaccagtctc caagatcatt ccagaagaag   2460
acaagacact acttcattgc tgctgtggaa agactgtggg actatggcat gtcttcctct   2520
ccccatgtcc tcaggaacag ggcacagtct ggctctgtgc cacagttcaa gaaagtggtc   2580
ttccaggagt tcactgatgg ctcattcacc cagcccctgt acagagggga actgaatgag   2640
```

cacctgggac tcctgggacc atacatcagg gctgaggtgg aagacaacat catggtgaca 2700
ttcagaaacc aggcctccag gccctacagc ttctactctt ccctcatcag ctatgaggaa 2760
gaccagagac aaggggctga gccaagaaag aactttgtga aacccaatga aaccaagacc 2820
tacttctgga aagtccagca ccacatggca cccaccaagg atgagtttga ctgcaaggcc 2880
tgggcatact tctctgatgt ggacctggag aaagatgtgc actctggcct gattggccca 2940
ctcctggtct gccacaccaa caccctgaac cctgcacatg gaaggcaagt gactgtgcag 3000
gagtttgccc tcttcttcac catctttgat gaaaccaagt catggtactt cactgagaac 3060
atggagagaa actgcagagc accatgcaac attcagatgg aagaccccac cttcaaggag 3120
aactacaggt tccatgccat caatggctac atcatggaca ccctgcctgg gcttgtcatg 3180
gcacaggacc agagaatcag atggtacctg ctttctatgg gatccaatga gaacattcac 3240
tccatccact tctctgggca tgtcttcact gtgagaaaga aggaggaata caagatggcc 3300
ctgtacaacc tctaccctgg ggtctttgag actgtggaga tgctgccctc caaagctggc 3360
atctggaggg tggaatgcct cattggggag cacctgcatg ctggcatgtc aaccctgttc 3420
ctggtctaca gcaacaagtg ccagacaccc ctgggaatgg cctctggcca catcagggac 3480
ttccagatca ctgcctctgg ccagtatggc cagtgggcac ccaaactggc caggctccac 3540
tactctggct ccatcaatgc atggtcaacc aaggagccat tctcttggat caaggtggac 3600
ctgctggcac ccatgatcat tcatggcatc aagacacagg gggcaagaca gaaattctcc 3660
tctctgtaca tctcacagtt catcatcatg tactctctgg atggcaagaa gtggcagaca 3720
tacagaggca actccactgg caccctcatg gtcttctttg gcaatgtgga cagctctggc 3780
atcaagcaca acatcttcaa ccctcccatc attgccagat acatcaggct gcaccccacc 3840
cactactcaa tcagatcaac cctcaggatg gaactgatgg gatgtgacct gaactcctgc 3900
tcaatgcccc tgggaatgga gagcaaggcc atttctgatg cccagatcac tgcatcctct 3960
tacttcacca acatgtttgc cacctggtca ccatcaaaag ccaggctgca cctccaggga 4020
agaagcaatg cctggagacc ccaggtcaac aacccaaagg aatggctgca agtggacttc 4080
cagaagacaa tgaaagtcac tggggtgaca acccaggggg tcaagtctct gctcacctca 4140
atgtatgtga aggagttcct gatctcttcc tcacaggatg gccaccagtg gacactcttc 4200
ttccagaatg gcaaagtcaa ggtgttccag ggcaaccagg actctttcac acctgtggtg 4260
aactcactgg acccccccct cctgacaaga tacctgagaa ttcaccccca gtcttgggtc 4320
caccagattg ccctgagaat ggaagtcctg ggatgtgagg cacaagacct gtactga 4377

<210> SEQ ID NO 92
<211> LENGTH: 4377
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 92
atgcagattg agctgtccac ctgcttcttt ctgtgcctgc tgagattctg cttctctgcc 60
accaggagat actacctggg ggctgtggaa ctttcttggg actacatgca gtctgacctg 120
ggagagctgc ctgtggatgc caggttccca cccagagtgc ccaagtcctt cccattcaac 180
acctctgtgg tctacaagaa gacactcttt gtggaattca ctgaccacct gttcaacatt 240
gcaaaaccca gaccaccctg gatgggactc ctgggaccca ccattcaggc tgaggtgtat 300

-continued

```
gacactgtgg tcatcaccct caagaacatg gcatcccacc ctgtgtctct gcatgctgtg    360
ggagtctcat actggaaagc ctctgaaggg gctgagtatg atgaccagac atcccagaga    420
gagaaagagg atgacaaggt gttccctggg ggatctcaca cctatgtgtg gcaagtcctc    480
aaggagaatg gacccatggc atctgaccca ctctgcctga catactccta cctttctcat    540
gtggacctgg tcaaggacct caactctgga ctgattgggg cactgctggt gtgcagggaa    600
ggatccctgg ccaaggagaa aacccagaca ctgcacaagt tcattctcct gtttgctgtc    660
tttgatgagg gcaagtcttg gcactctgaa acaaagaact ccctgatgca agacagggat    720
gctgcctctg ccagggcatg gcccaagatg cacactgtga atggctatgt gaacagatca    780
ctgcctggac tcattggctg ccacaggaaa tctgtctact ggcatgtgat tggcatgggg    840
acaacccctg aagtgcactc cattttcctg gagggacaca ccttcctggt caggaaccac    900
agacaagcct ctctggagat ctctcccatc accttcctca ctgcacagac actgctgatg    960
gaccttggac agttcctgct gttctgccac atctcttccc accagcatga tggcatggaa   1020
gcctatgtca aggtggactc atgccctgag gaaccacagc tcaggatgaa gaacaatgag   1080
gaggctgagg actatgatga tgacctgact gactctgaga tggatgtggt cagatttgat   1140
gatgacaact ctccatcctt cattcagatc aggtctgtgg caaagaaaca ccccaagaca   1200
tgggtgcact acattgctgc tgaggaagag gactgggact atgcaccact ggtcctggcc   1260
cctgatgaca ggagctacaa gtctcagtac ctcaacaatg gcccacaaag aattggaaga   1320
aagtacaaga aagtcagatt catggcctac actgatgaaa ccttcaagac aagagaagcc   1380
attcagcatg agtctggcat tctgggacca ctcctgtatg gggaagtggg agacaccctg   1440
ctcatcatct tcaagaacca ggcctccagg ccctacaaca tctacccaca tggcatcact   1500
gatgtcaggc ccctgtacag caggagactg ccaaaagggg tgaaacacct caaggacttc   1560
cccattctgc ctggagagat cttcaagtac aagtggactg tcactgtgga ggatggacca   1620
acaaagtctg accccaggtg cctcaccaga tactactcct cttttgtgaa catggagaga   1680
gacctggcat ctggactgat tggaccactg ctcatctgct acaaggagtc tgtggaccag   1740
agaggcaacc agatcatgtc tgacaagaga aatgtgattc tgttctctgt ctttgatgag   1800
aacagatcat ggtacctgac tgagaacatt cagagattcc tgcccaaccc tgctggggtg   1860
caactggaag accctgagtt ccaggcaagc aacatcatgc actccatcaa tggctatgtg   1920
tttgactctc tccagctttc tgtctgcctg catgaggtgg cctactggta cattctttct   1980
attggggcac aaactgactt cctttctgtc ttcttctctg gatacacctt caagcacaag   2040
atggtgtatg aggacaccct gacactcttc ccattctctg ggaaactgt gttcatgagc   2100
atggagaacc ctggactgtg gattctggga tgccacaact ctgacttcag aaacagggga   2160
atgactgcac tgctcaaagt ctcctcctgt gacaagaaca ctggggacta ctatgaggac   2220
tcttatgagg acatctctgc ctacctgctc agcaagaaca ataccaccta cgtgaaccgc   2280
tccctgtctc agaatccacc tgtcctgaag agacaccaga gagagatcac caggacaacc   2340
ctccagtctg accaggaaga gattgactat gatgacacca tttctgtgga gatgaagaag   2400
gaggactttg acatctatga tgaggacgag aaccagtctc caagatcatt ccagaagaag   2460
acaagacact acttcattgc tgctgtggaa agactgtggg actatggcat gtcttcctct   2520
ccccatgtcc tcaggaacag ggcacagtct ggctctgtgc cacagttcaa gaaagtggtc   2580
ttccaggagt tcactgatgg ctcattcacc cagcccctgt acagagggga actgaatgag   2640
```

-continued

```
cacctgggac tcctgggacc atacatcagg gctgaggtgg aagacaacat catggtgaca   2700
ttcagaaacc aggcctccag gccctacagc ttctactctt ccctcatcag ctatgaggaa   2760
gaccagagac aaggggctga gccaagaaag aactttgtga aacccaatga aaccaagacc   2820
tacttctgga aagtccagca ccacatggca cccaccaagg atgagtttga ctgcaaggcc   2880
tgggcatact tctctgatgt ggacctggag aaagatgtgc actctggcct gattggccca   2940
ctcctggtct gccacaccaa caccctgaac cctgcacatg gaaggcaagt gactgtgcag   3000
gagtttgccc tcttcttcac catctttgat gaaaccaagt catggtactt cactgagaac   3060
atggagagaa actgcagagc accatgcaac attcagatgg aagaccccac cttcaaggag   3120
aactacaggt tccatgccat caatggctac atcatggaca ccctgcctgg gcttgtcatg   3180
gcacaggacc agagaatcag atggtacctg ctttctatgg gatccaatga gaacattcac   3240
tccatccact tctctgggca tgtcttcact gtgagaaaga aggaggaata caagatggcc   3300
ctgtacaacc tctaccctgg ggtctttgag actgtggaga tgctgccctc caaagctggc   3360
atctggaggg tggaatgcct cattggggag cacctgcatg ctggcatgtc aaccctgttc   3420
ctggtctaca gcaacaagtg ccagacaccc ctgggaatgg cctctggcca catcagggac   3480
ttccagatca ctgcctctgg ccagtatggc cagtgggcac ccaaactggc caggctccac   3540
tactctggct ccatcaatgc atggtcaacc aaggagccat tctcttggat caaggtggac   3600
ctgctggcac ccatgatcat tcatggcatc aagacacagg gggcaagaca gaaattctcc   3660
tctctgtaca tctcacagtt catcatcatg tactctctgg atggcaagaa gtggcagaca   3720
tacagaggca actccactgg caccctcatg gtcttctttg gcaatgtgga cagctctggc   3780
atcaagcaca acatcttcaa ccctcccatc attgccagat acatcaggct gcaccccacc   3840
cactactcaa tcagatcaac cctcaggatg gaactgatgg gatgtgacct gaactcctgc   3900
tcaatgcccc tgggaatgga gagcaaggcc atttctgatg cccagatcac tgcatcctct   3960
tacttcacca acatgtttgc cacctggtca ccatcaaaag ccaggctgca cctccaggga   4020
agaagcaatg cctggagacc ccaggtcaac aacccaaagg aatggctgca agtggacttc   4080
cagaagacaa tgaaagtcac tggggtgaca acccaggggg tcaagtctct gctcacctca   4140
atgtatgtga aggagttcct gatctcttcc tcacaggatg gccaccagtg gacactcttc   4200
ttccagaatg gcaaagtcaa ggtgttccag ggcaaccagg actctttcac acctgtggtg   4260
aactcactgg acccccccct cctgacaaga tacctgagaa ttcacccccca gtcttgggtc   4320
caccagattg ccctgagaat ggaagtcctg ggatgtgagg cacaagacct gtactga      4377
```

<210> SEQ ID NO 93
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93

```
atgcagattg agctgtccac ctgcttcttt ctgtgcctgc tgagattctg cttctctgcc     60
accaggagat actacctggg ggctgtggaa ctttcttggg actacatgca gtctgacctg    120
ggagagctgc ctgtggatgc caggttccca cccagagtgc ccaagtcctt cccattcaac    180
acctctgtgg tctacaagaa gacactcttt gtggaattca ctgaccacct gttcaacatt    240
gcaaaaccca gaccaccctg gatgggactc ctgggaccca ccattcaggc tgaggtgtat    300
```

-continued

```
gacactgtgg tcgtcaccct caagaacatg gcatcccacc ctgtgtctct gcatgctgtg    360
ggagtctcat actggaaatc ctctgaaggg gctgagtatg atgaccagac atcccagaga    420
gagaaagagg atgacaaggt gttccctggg aagtctcaca cctatgtgtg gcaagtcctc    480
aaggagaatg gacccactgc atctgaccca ccctgcctga catactccta cctttctcat    540
gtggacctgg tcaaggacct caactctgga ctgattgggg cactgctggt gtgcagggaa    600
ggatccctgg ccaaggagaa aacccagaca ctgcacaagt tcattctcct gtttgctgtc    660
tttgatgagg gcaagtcttg gcactctgaa acaaagaact ccctgatgca agacagggat    720
gctgcctctg ccagggcatg gcccaagatg cacactgtga atggctatgt gaacagatca    780
ctgcctggac tcattggctg ccacaggaaa tctgtctact ggcatgtgat tggcatgggg    840
acaacccctg aagtgcactc cattttcctg gagggacaca ccttcctggt caggaaccac    900
agacaagcct ctctggagat ctctcccatc accttcctca ctgcacagac actgctgatg    960
gaccttggac agttcctgct gttctgccac atctcttccc accagcatga tggcatggaa   1020
gcctatgtca aggtggactc atgccctgag gaaccacagc tcaggatgaa gaacaatgag   1080
gaggctgagg actatgatga tgacctgact gactctgaga tggatgtggt cagatttgat   1140
gatgacaact ctccatcctt cattcagatc aggtctgtgg caaagaaaca ccccaagaca   1200
tgggtgcact acattgctgc tgaggaagag gactgggact atgcaccact ggtcctggcc   1260
cctgatgaca ggagctacaa gtctcagtac ctcaacaatg gcccacaaag aattggaaga   1320
aagtacaaga aagtcagatt catggcctac actgatgaaa ccttcaagac aagagaagcc   1380
attcagcatg agtctggcat tctgggacca ctcctgtatg ggaagtggg agacaccctg   1440
ctcatcatct tcaagaacca ggcctccagg ccctacaaca tctacccaca tggcatcact   1500
gatgtcaggc ccctgtacag caggagactg ccaaaagggg tgaaacacct caaggacttc   1560
cccattctgc ctggagagat cttcaagtac aagtggactg tcactgtgga ggatggacca   1620
acaaagtctg accccaggtg cctcaccaga tactactcct cttttgtgaa catggagaga   1680
gacctggcat ctggactgat tggaccactg ctcatctgct acaaggagtc tgtggaccag   1740
agaggcaacc agatcatgtc tgacaagaga aatgtgattc tgttctctgt ctttgatgag   1800
aacagatcat ggtacctgac tgagaacatt cagagattcc tgcccaaccc tgctggggtg   1860
caactggaag accctgagtt ccaggcaagc aacatcatgc actccatcaa tggctatgtg   1920
tttgactctc tccagctttc tgtctgcctg catgaggtgg cctactggta cattctttct   1980
attggggcac aaactgactt cctttctgtc ttcttctctg gatacacctt caagcacaag   2040
atggtgtatg aggacaccct gacactcttc ccattctctg gggaaactgt gttcatgagc   2100
atggagaacc ctggactgtg gattctggga tgccacaact ctgacttcag aaacagggga   2160
atgactgcac tgctcaaagt ctcctcctgt gacaagaaca ctggggacta ctatgaggac   2220
tcttatgagg acatctctgc ctacctgctc agcaagaaca atgccattga gcccagaagc   2280
ttctctcaga atccacctgt cctgaagaga caccagagag agatcaccag gacaaccctc   2340
cagtctgacc aggaagagat tgactatgat gacaccattt ctgtggagat gaagaaggag   2400
gactttgaca tctatgatga ggacgagaac cagtctccaa gatcattcca gaagaagaca   2460
agacactact tcattgctgc tgtggaaaga ctgtgggact atggcatgtc ttcctctccc   2520
catgtcctca ggaacagggc acagtctggc tctgtgccac agttcaagaa agtggtcttc   2580
caggagttca ctgatggctc attcacccag cccctgtaca gaggggaact gaatgagcac   2640
ctgggactcc tgggaccata catcagggct gaggtggaag acaacatcat ggtgacattc   2700
```

agaaaccagg cctccaggcc ctacagcttc tactcttccc tcatcagcta tgaggaagac 2760
cagagacaag ggctgagcc aagaaagaac tttgtgaaac ccaatgaaac caagacctac 2820
ttctggaaag tccagcacca catggcaccc accaaggatg agtttgactg caaggcctgg 2880
gcatacttct ctgatgtgga cctggagaaa gatgtgcact ctggcctgat tggcccactc 2940
ctggtctgcc acaccaacac cctgaaccct gcacatggaa ggcaagtgac tgtgcaggag 3000
tttgccctct tcttcaccat ctttgatgaa accaagtcat ggtacttcac tgagaacatg 3060
gagagaaact gcagagcacc atgcaacatt cagatggaag accccacctt caaggagaac 3120
tacaggttcc atgccatcaa tggctacatc atggacaccc tgcctgggct tgtcatggca 3180
caggaccaga gaatcagatg gtacctgctt tctatgggat ccaatgagaa cattcactcc 3240
atccacttct ctgggcatgt cttcactgtg agaaagaagg aggaatacaa gatggccctg 3300
tacaacctct accctggggt ctttgagact gtggagatgc tgccctccaa agctggcatc 3360
tggagggtgg aatgcctcat tggggagcac ctgcatgctg gcatgtcaac cctgttcctg 3420
gtctacagca acaagtgcca gacacccctg ggaatggcct ctggccacat cagggacttc 3480
cagatcactg cctctggcca gtatggccag tgggcaccca aactggccag gctccactac 3540
tctggctcca tcaatgcatg gtcaaccaag gagccattct cttggatcaa ggtggacctg 3600
ctggcaccca tgatcattca tggcatcaag acacaggggg caagacagaa attctcctct 3660
ctgtacatct cacagttcat catcatgtac tctctggatg gcaagaagtg gcagacatac 3720
agaggcaact ccactggcac cctcatggtc ttctttggca atgtggacag ctctggcatc 3780
aagcacaaca tcttcaaccc tcccatcatt gccagataca tcaggctgca ccccacccac 3840
tactcaatca gatcaaccct caggatggaa ctgatgggat gtgacctgaa ctcctgctca 3900
atgcccctgg gaatggagag caaggccatt tctgatgccc agatcactgc atcctcttac 3960
ttcaccaaca tgtttgccac ctggtcacca tcaaaagcca ggctgcacct ccagggaaga 4020
agcaatgcct ggagacccca ggtcaacaac ccaaaggaat ggctgcaagt ggacttccag 4080
aagacaatga aagtcactgg ggtgacaacc caggggggtca agtctctgct cacctcaatg 4140
tatgtgaagg agttcctgat ctcttcctca caggatggcc accagtggac actcttcttc 4200
cagaatggca aagtcaaggt gttccagggc aaccaggact ctttcacacc tgtggtgaac 4260
tcactggacc cccccctcct gacaagatac ctgagaattc acccccagtc ttgggtccac 4320
cagattgccc tgagaatgga agtcctggga tgtgaggcac aagacctgta ctga 4374

<210> SEQ ID NO 94
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 94
atgcagattg agctgagcac ctgcttcttc ctgtgcctgc tgaggttctg cttctctgcc 60
accaggagat actacctggg ggctgtggag ctttcttggg actacatgca gtctgacctg 120
ggggagctgc ctgtggatgc caggttccca cccagagtgc ccaaatcctt cccattcaac 180
acctctgtgg tctacaagaa gaccctcttt gtggagttca ctgaccacct gttcaacatt 240
gccaaaccca ggccaccctg gatgggactc ctgggaccca ccattcaggc tgaggtgtat 300
gacactgtgg tcgtcaccct caagaacatg gcctcccacc ctgtgagcct gcatgctgtg 360

```
ggggtcagct actggaagtc ctctgagggg gctgagtatg atgaccagac ctcccagagg    420
gagaaggagg atgacaaagt gttccctggg aagagccaca cctatgtgtg gcaggtcctc    480
aaggagaatg gccccactgc ctctgaccca ccctgcctga cctactccta cctttctcat    540
gtggacctgg tcaaggacct caactctgga ctgattgggg ccctgctggt gtgcagggag    600
ggctccctgg ccaaagagaa gacccagacc ctgcacaagt tcattctcct gtttgctgtc    660
tttgatgagg gcaagagctg gcactctgaa accaagaact ccctgatgca ggacagggat    720
gctgcctctg ccagggcctg gcccaagatg cacactgtga atggctatgt gaacaggagc    780
ctgcctggac tcattggctg ccacaggaaa tctgtctact ggcatgtgat tggcatgggg    840
acaacccctg aggtgcactc cattttcctg gagggccaca ccttcctggt caggaaccac    900
agacaggcca gcctggagat cagccccatc accttcctca ctgcccagac cctgctgatg    960
gacctcggac agttcctgct gttctgccac atcagctccc accagcatga tggcatggag   1020
gcctatgtca aggtggacag ctgccctgag gagccacagc tcaggatgaa gaacaatgag   1080
gaggctgagg actatgatga tgacctgact gactctgaga tggatgtggt ccgctttgat   1140
gatgacaaca gcccatcctt cattcagatc aggtctgtgg ccaagaaaca ccccaagacc   1200
tgggtgcact acattgctgc tgaggaggag gactgggact atgcccccact ggtcctggcc   1260
cctgatgaca ggagctacaa gagccagtac ctcaacaatg gcccacagag gattggacgc   1320
aagtacaaga aagtcaggtt catggcctac actgatgaaa ccttcaagac cagggaggcc   1380
attcagcatg agtctggcat cctgggccca ctcctgtatg ggaggtggg ggacaccctg   1440
ctcatcatct tcaagaacca ggcctccagg ccctacaaca tctacccaca tggcatcact   1500
gatgtcaggc ccctgtacag ccgcaggctg ccaaaggggg tgaaacacct caaggacttc   1560
cccattctgc ctggggagat cttcaagtac aagtggactg tcactgtgga ggatggacca   1620
accaaatctg accccaggtg cctcaccaga tactactcca gctttgtgaa catggagagg   1680
gacctggcct ctggcctgat tggcccactg ctcatctgct acaaggagtc tgtggaccag   1740
aggggaaacc agatcatgtc tgacaagagg aatgtgattc tgttctctgt ctttgatgag   1800
aacaggagct ggtacctgac tgagaacatt cagcgcttcc tgcccaaccc tgctggggtg   1860
cagctggagg accctgagtt ccaggccagc aacatcatgc actccatcaa tggctatgtg   1920
tttgacagcc tccagctttc tgtctgcctg catgaggtgg cctactggta cattctttct   1980
attggggccc agactgactt cctttctgtc ttcttctctg gctacacctt caaacacaag   2040
atggtgtatg aggacaccct gaccctcttc ccattctctg gggagactgt gttcatgagc   2100
atggagaacc ctggcctgtg gattctggga tgccacaact ctgacttccg caacaggggc   2160
atgactgccc tgctcaaagt ctcctcctgt gacaagaaca ctggggacta ctatgaggac   2220
agctatgagg acatctctgc ctacctgctc agcaagaaca atgccattga gcccaggagc   2280
ttcagccaga atccacctgt cctgaaacgc caccagaggg agatcaccag gaccaccctc   2340
cagtctgacc aggaggagat tgactatgat gacaccattt ctgtggagat gaagaaagag   2400
gactttgaca tctatgacga ggacgagaac cagagcccaa ggagcttcca gaagaagacc   2460
aggcactact tcattgctgc tgtggagcgc ctgtgggact atggcatgag ctccagcccc   2520
catgtcctca ggaacagggc ccagtctggc tctgtgccac agttcaagaa agtggtcttc   2580
caagagttca ctgatggcag cttcacccag cccctgtaca gaggggagct gaatgagcac   2640
ctgggactcc tgggcccata catcagggct gaggtggagg acaacatcat ggtgaccttc   2700
```

cgcaaccagg cctccaggcc ctacagcttc tacagctccc tcatcagcta tgaggaggac 2760
cagaggcagg gggctgagcc acgcaagaac tttgtgaaac ccaatgaaac caagacctac 2820
ttctggaaag tccagcacca catggccccc accaaggatg agtttgactg caaggcctgg 2880
gcctacttct ctgatgtgga cctggagaag gatgtgcact ctggcctgat tggcccactc 2940
ctggtctgcc acaccaacac cctgaaccct gcccatggaa ggcaagtgac tgtgcaggag 3000
tttgccctct tcttcaccat ctttgatgaa accaagagct ggtacttcac tgagaacatg 3060
gagcgcaact gcagggcccc atgcaacatt cagatggagg accccacctt caaagagaac 3120
taccgcttcc atgccatcaa tggctacatc atggacaccc tgcctgggct tgtcatggcc 3180
caggaccaga ggatcaggtg gtacctgctt tctatgggct ccaatgagaa cattcactcc 3240
atccacttct ctgggcatgt cttcactgtg cgcaagaagg aggagtacaa gatggccctg 3300
tacaacctct accctggggt ctttgagact gtggagatgc tgccctccaa agctggcatc 3360
tggagggtgg agtgcctcat tggggagcac ctgcatgctg gcatgagcac cctgttcctg 3420
gtctacagca acaagtgcca gacccccctg ggaatggcct ctggccacat caggacttc 3480 cagatcactg cctctggcca gtatggccag tgggccccca agctggccag gctccactac 3540
tctggatcca tcaatgcctg gagcaccaag gagccattca gctggatcaa agtggacctg 3600
ctggccccca tgatcatcca tggcatcaag acccaggggg ccaggcagaa gttctccagc 3660
ctgtacatca gccagttcat catcatgtac agcctggatg gcaagaaatg gcagacctac 3720
agaggcaact ccactggaac actcatggtc ttctttggca atgtggacag ctctggcatc 3780
aagcacaaca tcttcaaccc cccaatcatc gccagataca tcaggctgca ccccacccac 3840
tacagcatcc gcagcaccct caggatggag ctgatgggct gtgacctgaa ctcctgcagc 3900
atgcccctgg gcatggagag caaggccatt tctgatgccc agatcactgc ctccagctac 3960
ttcaccaaca tgtttgccac ctggagccca agcaaggcca ggctgcacct ccagggaagg 4020
agcaatgcct ggaggcccca ggtcaacaac ccaaaggagt ggctgcaggt ggacttccag 4080
aagaccatga aggtcactgg ggtgaccacc cagggggtca agagcctgct caccagcatg 4140
tatgtgaagg agttcctgat cagctccagc caggatggcc accagtggac cctcttcttc 4200
cagaatggca aggtcaaggt gttccagggc aaccaggaca gcttcacccc tgtggtgaac 4260
agcctggacc ccccctcct gaccagatac ctgaggattc acccccagag ctgggtccac 4320
cagattgccc tgaggatgga ggtcctggga tgtgaggccc aggacctgta ctga 4374

<210> SEQ ID NO 95
<211> LENGTH: 4377
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95
atgcagattg agctgagcac ctgcttcttc ctgtgcctgc tgaggttctg cttctctgcc 60
accaggagat actacctggg ggctgtggag ctttcttggg actacatgca gtctgacctg 120
ggggagctgc ctgtggatgc caggttccca cccagagtgc ccaaatcctt cccattcaac 180
acctctgtgg tctacaagaa gaccctcttt gtggagttca ctgaccacct gttcaacatt 240
gccaaaccca ggccaccctg gatgggactc ctgggaccca ccattcaggc tgaggtgtat 300
gacactgtgg tcatcaccct caagaacatg gcctcccacc ctgtgagcct gcatgctgtg 360

-continued

```
ggggtcagct actggaaggc ctctgagggg gctgagtatg atgaccagac ctcccagagg    420
gagaaggagg atgacaaagt gttccctggg ggcagccaca cctatgtgtg gcaggtcctc    480
aaggagaatg gccccatggc ctctgaccca ctctgcctga cctactccta cctttctcat    540
gtggacctgg tcaaggacct caactctgga ctgattgggg ccctgctggt gtgcagggag    600
ggctccctgg ccaaagagaa gacccagacc ctgcacaagt tcattctcct gtttgctgtc    660
tttgatgagg gcaagagctg gcactctgaa accaagaact ccctgatgca ggacagggat    720
gctgcctctg ccagggcctg gcccaagatg cacactgtga atggctatgt gaacaggagc    780
ctgcctggac tcattggctg ccacaggaaa tctgtctact ggcatgtgat tggcatgggg    840
acaacccctg aggtgcactc cattttcctg gagggccaca ccttcctggt caggaaccac    900
agacaggcca gcctggagat cagccccatc accttcctca ctgcccagac cctgctgatg    960
gacctcggac agttcctgct gttctgccac atcagctccc accagcatga tggcatggag   1020
gcctatgtca aggtggacag ctgccctgag gagccacagc tcaggatgaa gaacaatgag   1080
gaggctgagg actatgatga tgacctgact gactctgaga tggatgtggt ccgctttgat   1140
gatgacaaca gcccatcctt cattcagatc aggtctgtgg ccaagaaaca ccccaagacc   1200
tgggtgcact acattgctgc tgaggaggag gactgggact atgccccact ggtcctggcc   1260
cctgatgaca ggagctacaa gagccagtac ctcaacaatg gcccacagag gattggacgc   1320
aagtacaaga aagtcaggtt catggcctac actgatgaaa ccttcaagac cagggaggcc   1380
attcagcatg agtctggcat cctgggccca ctcctgtatg gggaggtggg ggacaccctg   1440
ctcatcatct tcaagaacca ggcctccagg ccctacaaca tctacccaca tggcatcact   1500
gatgtcaggc ccctgtacag ccgcaggctg ccaaaggggg tgaaacacct caaggacttc   1560
cccattctgc ctggggagat cttcaagtac aagtggactg tcactgtgga ggatggacca   1620
accaaatctg accccaggtg cctcaccaga tactactcca gctttgtgaa catggagagg   1680
gacctggcct ctggcctgat tggcccactg ctcatctgct acaaggagtc tgtggaccag   1740
aggggaaacc agatcatgtc tgacaagagg aatgtgattc tgttctctgt ctttgatgag   1800
aacaggagct ggtacctgac tgagaacatt cagcgcttcc tgcccaaccc tgctggggtg   1860
cagctggagg accctgagtt ccaggccagc aacatcatgc actccatcaa tggctatgtg   1920
tttgacagcc tccagctttc tgtctgcctg catgaggtgg cctactggta cattctttct   1980
attggggccc agactgactt cctttctgtc ttcttctctg gctacacctt caaacacaag   2040
atggtgtatg aggacaccct gaccctcttc ccattctctg ggagactgt gttcatgagc    2100
atggagaacc ctggcctgtg gattctggga tgccacaact ctgacttccg caacaggggc   2160
atgactgccc tgctcaaagt ctcctcctgt gacaagaaca ctggggacta ctatgaggac   2220
agctatgagg acatctctgc ctacctgctc agcaagaaca ataccaccta cgtgaaccgc   2280
tccctgagcc agaatccacc tgtcctgaaa cgccaccaga gggagatcac caggaccacc   2340
ctccagtctg accaggagga gattgactat gatgacacca tttctgtgga gatgaagaaa   2400
gaggactttg acatctatga cgaggacgag aaccagagcc caaggagctt ccagaagaag   2460
accaggcact acttcattgc tgctgtggag cgcctgtggg actatggcat gagctccagc   2520
ccccatgtcc tcaggaacag ggcccagtct ggctctgtgc cacagttcaa gaaagtggtc   2580
ttccaagagt tcactgatgg cagcttcacc cagcccctgt acagagggga gctgaatgag   2640
cacctgggac tcctgggccc atacatcagg gctgaggtgg aggacaacat catggtgacc   2700
ttccgcaacc aggcctccag gccctacagc ttctacagct ccctcatcag ctatgaggag   2760
```

```
gaccagaggc agggggctga gccacgcaag aactttgtga aacccaatga aaccaagacc   2820
tacttctgga aagtccagca ccacatggcc cccaccaagg atgagtttga ctgcaaggcc   2880
tgggcctact tctctgatgt ggacctggag aaggatgtgc actctggcct gattggccca   2940
ctcctggtct gccacaccaa caccctgaac cctgcccatg gaaggcaagt gactgtgcag   3000
gagtttgccc tcttcttcac catctttgat gaaaccaaga gctggtactt cactgagaac   3060
atggagcgca actgcagggc cccatgcaac attcagatgg aggaccccac cttcaaagag   3120
aactaccgct tccatgccat caatggctac atcatggaca ccctgcctgg gcttgtcatg   3180
gcccaggacc agaggatcag gtggtacctg ctttctatgg gctccaatga gaacattcac   3240
tccatccact tctctgggca tgtcttcact gtgcgcaaga aggaggagta caagatggcc   3300
ctgtacaacc tctaccctgg ggtctttgag actgtggaga tgctgccctc caaagctggc   3360
atctggaggg tggagtgcct cattggggag cacctgcatg ctggcatgag caccctgttc   3420
ctggtctaca gcaacaagtg ccagaccccc ctgggaatgg cctctggcca catcagggac   3480
ttccagatca ctgcctctgg ccagtatggc cagtgggccc ccaagctggc caggctccac   3540
tactctggat ccatcaatgc ctggagcacc aaggagccat tcagctggat caaagtggac   3600
ctgctggccc ccatgatcat ccatggcatc aagacccagg gggccaggca gaagttctcc   3660
agcctgtaca tcagccagtt catcatcatg tacagcctgg atggcaagaa atggcagacc   3720
tacagaggca actccactgg aacactcatg gtcttctttg gcaatgtgga cagctctggc   3780
atcaagcaca acatcttcaa ccccccaatc atcgccagat acatcaggct gcaccccacc   3840
cactacagca tccgcagcac cctcaggatg gagctgatgg gctgtgacct gaactcctgc   3900
agcatgcccc tgggcatgga gagcaaggcc atttctgatg cccagatcac tgcctccagc   3960
tacttcacca acatgtttgc cacctggagc ccaagcaagg ccaggctgca cctccaggga   4020
aggagcaatg cctggaggcc ccaggtcaac aacccaaagg agtggctgca ggtggacttc   4080
cagaagacca tgaaggtcac tggggtgacc acccaggggg tcaagagcct gctcaccagc   4140
atgtatgtga aggagttcct gatcagctcc agccaggatg gccaccagtg gaccctcttc   4200
ttccagaatg gcaaggtcaa ggtgttccag ggcaaccagg acagcttcac ccctgtggtg   4260
aacagcctgg accccccct cctgaccaga tacctgagga ttcaccccca gagctgggtc   4320
caccagattg ccctgaggat ggaggtcctg ggatgtgagg cccaggacct gtactga      4377
```

<210> SEQ ID NO 96
<211> LENGTH: 4377
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 96

```
atgcagattg agctgagcac ctgcttcttc ctgtgcctgc tgaggttctg cttctctgcc     60
accaggagat actacctggg ggctgtggag ctttcttggg actacatgca gtctgacctg    120
ggggagctgc ctgtggatgc caggttccca cccagagtgc ccaaatcctt cccattcaac    180
acctctgtgg tctacaagaa gaccctcttt gtggagttca ctgaccacct gttcaacatt    240
gccaaaccca ggccaccctg gatgggactc ctgggaccca ccattcaggc tgaggtgtat    300
gacactgtgg tcgtcaccct caagaacatg gcctccccacc ctgtgagcct gcatgctgtg    360
ggggtcagct actggaagtc ctctgagggg gctgagtatg atgaccagac ctcccagagg    420
```

-continued

```
gagaaggagg atgacaaagt gttccctggg aagagccaca cctatgtgtg gcaggtcctc    480
aaggagaatg gccccactgc ctctgaccca ccctgcctga cctactccta cctttctcat    540
gtggacctgg tcaaggacct caactctgga ctgattgggg ccctgctggt gtgcagggag    600
ggctccctgg ccaaagagaa gacccagacc ctgcacaagt tcattctcct gtttgctgtc    660
tttgatgagg gcaagagctg gcactctgaa accaagaact ccctgatgca ggacagggat    720
gctgcctctg ccagggcctg gcccaagatg cacactgtga atggctatgt gaacaggagc    780
ctgcctggac tcattggctg ccacaggaaa tctgtctact ggcatgtgat tggcatgggg    840
acaacccctg aggtgcactc cattttcctg gagggccaca ccttcctggt caggaaccac    900
agacaggcca gcctggagat cagccccatc accttcctca ctgcccagac cctgctgatg    960
gacctcggac agttcctgct gttctgccac atcagctccc accagcatga tggcatggag   1020
gcctatgtca aggtggacag ctgccctgag gagccacagc tcaggatgaa gaacaatgag   1080
gaggctgagg actatgatga tgacctgact gactctgaga tggatgtggt ccgctttgat   1140
gatgacaaca gcccatcctt cattcagatc aggtctgtgg ccaagaaaca ccccaagacc   1200
tgggtgcact acattgctgc tgaggaggag gactgggact atgccccact ggtcctggcc   1260
cctgatgaca ggagctacaa gagccagtac ctcaacaatg gcccacagag gattggacgc   1320
aagtacaaga aagtcaggtt catggcctac actgatgaaa ccttcaagac cagggaggcc   1380
attcagcatg agtctggcat cctgggccca ctcctgtatg gggaggtggg ggacaccctg   1440
ctcatcatct tcaagaacca ggcctccagg ccctacaaca tctacccaca tggcatcact   1500
gatgtcaggc ccctgtacag ccgcaggctg ccaaaggggg tgaaacacct caaggacttc   1560
cccattctgc ctggggagat cttcaagtac aagtggactg tcactgtgga ggatggacca   1620
accaaatctg accccaggtg cctcaccaga tactactcca gctttgtgaa catggagagg   1680
gacctggcct ctggcctgat tggcccactg ctcatctgct acaaggagtc tgtggaccag   1740
aggggaaacc agatcatgtc tgacaagagg aatgtgattc tgttctctgt ctttgatgag   1800
aacaggagct ggtacctgac tgagaacatt cagcgcttcc tgcccaaccc tgctggggtg   1860
cagctggagg accctgagtt ccaggccagc aacatcatgc actccatcaa tggctatgtg   1920
tttgacagcc tccagctttc tgtctgcctg catgaggtgg cctactggta cattctttct   1980
attggggccc agactgactt cctttctgtc ttcttctctg gctacacctt caaacacaag   2040
atggtgtatg aggacaccct gaccctcttc ccattctctg ggagactgt gttcatgagc   2100
atggagaacc ctggcctgtg gattctggga tgccacaact ctgacttccg caacaggggc   2160
atgactgccc tgctcaaagt ctcctcctgt gacaagaaca ctggggacta ctatgaggac   2220
agctatgagg acatctctgc ctacctgctc agcaagaaca ataccaccta cgtgaaccgc   2280
tccctgagcc agaatccacc tgtcctgaaa cgccaccaga gggagatcac caggaccacc   2340
ctccagtctg accaggagga gattgactat gatgacacca tttctgtgga gatgaagaaa   2400
gaggactttg acatctatga cgaggacgag aaccagagcc caaggagctt ccagaagaag   2460
accaggcact acttcattgc tgctgtggag cgcctgtggg actatggcat gagctccagc   2520
ccccatgtcc tcaggaacag ggcccagtct ggctctgtgc cacagttcaa gaaagtggtc   2580
ttccaagagt tcactgatgg cagcttcacc cagcccctgt acagagggga gctgaatgag   2640
cacctgggac tcctgggccc atacatcagg gctgaggtgg aggacaacat catggtgacc   2700
ttccgcaacc aggcctccag gccctacagc ttctacagct ccctcatcag ctatgaggag   2760
```

```
gaccagaggc agggggctga gccacgcaag aactttgtga aacccaatga aaccaagacc   2820

tacttctgga aagtccagca ccacatggcc cccaccaagg atgagtttga ctgcaaggcc   2880

tgggcctact tctctgatgt ggacctggag aaggatgtgc actctggcct gattggccca   2940

ctcctggtct gccacaccaa caccctgaac cctgcccatg gaaggcaagt gactgtgcag   3000

gagtttgccc tcttcttcac catctttgat gaaaccaaga gctggtactt cactgagaac   3060

atggagcgca actgcagggc cccatgcaac attcagatgg aggaccccac cttcaaagag   3120

aactaccgct tccatgccat caatggctac atcatggaca ccctgcctgg gcttgtcatg   3180

gcccaggacc agaggatcag gtggtacctg ctttctatgg gctccaatga gaacattcac   3240

tccatccact tctctgggca tgtcttcact gtgcgcaaga aggaggagta caagatggcc   3300

ctgtacaacc tctaccctgg ggtctttgag actgtggaga tgctgccctc caaagctggc   3360

atctggaggg tggagtgcct cattggggag cacctgcatg ctggcatgag caccctgttc   3420

ctggtctaca gcaacaagtg ccagaccccc ctgggaatgg cctctggcca catcagggac   3480

ttccagatca ctgcctctgg ccagtatggc cagtgggccc ccaagctggc caggctccac   3540

tactctggat ccatcaatgc ctggagcacc aaggagccat tcagctggat caaagtggac   3600

ctgctggccc ccatgatcat ccatggcatc aagacccagg gggccaggca gaagttctcc   3660

agcctgtaca tcagccagtt catcatcatg tacagcctgg atggcaagaa atggcagacc   3720

tacagaggca actccactgg aacactcatg gtcttctttg gcaatgtgga cagctctggc   3780

atcaagcaca acatcttcaa ccccccaatc atcgccagat acatcaggct gcaccccacc   3840

cactacagca tccgcagcac cctcaggatg gagctgatgg gctgtgacct gaactcctgc   3900

agcatgcccc tgggcatgga gagcaaggcc atttctgatg cccagatcac tgcctccagc   3960

tacttcacca acatgtttgc cacctggagc ccaagcaagg ccaggctgca cctccaggga   4020

aggagcaatg cctggaggcc ccaggtcaac aacccaaagg agtggctgca ggtggacttc   4080

cagaagacca tgaaggtcac tggggtgacc acccaggggg tcaagagcct gctcaccagc   4140

atgtatgtga aggagttcct gatcagctcc agccaggatg gccaccagtg gaccctcttc   4200

ttccagaatg gcaaggtcaa ggtgttccag ggcaaccagg acagcttcac ccctgtggtg   4260

aacagcctgg acccccccct cctgaccaga tacctgagga ttcaccccca gagctgggtc   4320

caccagattg ccctgaggat ggaggtcctg ggatgtgagg cccaggacct gtactga      4377
```

<210> SEQ ID NO 97
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 97

```
atgcagattg agctgagcac ctgcttcttc ctgtgcctgc tgaggttctg cttctctgcc     60

accaggagat actacctggg ggctgtggag ctttcttggg actacatgca gtctgacctg    120

ggggagctgc ctgtggatgc caggttccca cccagagtgc ccaaatcctt cccattcaac    180

acctctgtgg tctacaagaa gaccctcttt gtggagttca ctgaccacct gttcaacatt    240

gccaaaccca ggccaccctg gatgggactc ctgggaccca ccattcaggc tgaggtgtat    300

gacactgtgg tcatcaccct caagaacatg gcctcccacc ctgtgagcct gcatgctgtg    360

ggggtcagct actggaaggc ctctgagggg gctgagtatg atgaccagac ctcccagagg    420
```

-continued

```
gagaaggagg atgacaaagt gttccctggg ggcagccaca cctatgtgtg gcaggtcctc    480
aaggagaatg gccccatggc ctctgaccca ctctgcctga cctactccta cctttctcat    540
gtggacctgg tcaaggacct caactctgga ctgattgggg ccctgctggt gtgcagggag    600
ggctccctgg ccaaagagaa gacccagacc ctgcacaagt tcattctcct gtttgctgtc    660
tttgatgagg gcaagagctg gcactctgaa accaagaact ccctgatgca ggacagggat    720
gctgcctctg ccagggcctg gcccaagatg cacactgtga atggctatgt gaacaggagc    780
ctgcctggac tcattggctg ccacaggaaa tctgtctact ggcatgtgat tggcatgggg    840
acaaccccctg aggtgcactc cattttcctg gagggccaca ccttcctggt caggaaccac    900
agacaggcca gcctggagat cagccccatc accttcctca ctgcccagac cctgctgatg    960
gacctcggac agttcctgct gtcctgccac atcagctccc accagcatga tggcatggag   1020
gcctatgtca aggtggacag ctgccctgag gagccacagc tcaggatgaa gaacaatgag   1080
gaggctgagg actatgatga tgacctgact gactctgaga tggatgtggt ccgctttgat   1140
gatgacaaca gcccatcctt cattcagatc aggtctgtgg ccaagaaaca ccccaagacc   1200
tgggtgcact acattgctgc tgaggaggag gactgggact atgccccact ggtcctggcc   1260
cctgatgaca ggagctacaa gagccagtac ctcaacaatg gcccacagag gattggacgc   1320
aagtacaaga aagtcaggtt catggcctac actgatgaaa ccttcaagac cagggaggcc   1380
attcagcatg agtctggcat cctgggccca ctcctgtatg gggaggtggg ggacaccctg   1440
ctcatcatct tcaagaacca ggcctccagg ccctacaaca tctacccaca tggcatcact   1500
gatgtcaggc ccctgtacag ccgcaggctg ccaaaggggg tgaaacacct caaggacttc   1560
cccattctgc ctggggagat cttcaagtac aagtggactg tcactgtgga ggatggacca   1620
accaaatctg accccaggtg cctcaccaga tactactcca gctttgtgaa catggagagg   1680
gacctggcct ctggcctgat tggcccactg ctcatctgct acaaggagtc tgtggaccag   1740
aggggaaacc agatcatgtc tgacaagagg aatgtgattc tgttctctgt ctttgatgag   1800
aacaggagct ggtacctgac tgagaacatt cagcgcttcc tgcccaaccc tgctggggtg   1860
cagctggagg accctgagtt ccaggccagc aacatcatgc actccatcaa tggctatgtg   1920
tttgacagcc tccagctttc tgtctgcctg catgaggtgg cctactggta cattctttct   1980
attggggccc agactgactt cctttctgtc ttcttctctg gctacacctt caaacacaag   2040
atggtgtatg aggacaccct gaccctcttc ccattctctg ggagactgt gttcatgagc    2100
atggagaacc ctggcctgtg gattctggga tgccacaact ctgacttccg caacaggggc   2160
atgactgccc tgctcaaagt ctcctcctgt gacaagaaca ctggggacta ctatgaggac   2220
agctatgagg acatctctgc ctacctgctc agcaagaaca atgccattga gcccaggagc   2280
ttcagccaga atccacctgt cctgaaacgc caccagaggg agatcaccag gaccaccctc   2340
cagtctgacc aggaggagat tgactatgat gacaccattt ctgtggagat gaagaaagag   2400
gactttgaca tctatgacga ggacgagaac cagagcccaa ggagcttcca gaagaagacc   2460
aggcactact tcattgctgc tgtggagcgc ctgtgggact atggcatgag ctccagcccc   2520
catgtcctca ggaacagggc ccagtctggc tctgtgccac agttcaagaa agtggtcttc   2580
caagagttca ctgatggcag cttcacccag cccctgtaca gaggggagct gaatgagcac   2640
ctgggactcc tgggcccata catcagggct gaggtggagg acaacatcat ggtgaccttc   2700
cgcaaccagg cctccaggcc ctacagcttc tacagctccc tcatcagcta tgaggaggac   2760
cagaggcagg gggctgagcc acgcaagaac tttgtgaaac ccaatgaaac caagacctac   2820
```

ttctggaaag tccagcacca catggccccc accaaggatg agtttgactg caaggcctgg 2880
gcctacttct ctgatgtgga cctggagaag gatgtgcact ctggcctgat tggcccactc 2940
ctggtctgcc acaccaacac cctgaaccct gcccatggaa ggcaagtgac tgtgcaggag 3000
tttgccctct tcttcaccat ctttgatgaa accaagagct ggtacttcac tgagaacatg 3060
gagcgcaact gcagggcccc atgcaacatt cagatggagg accccacctt caaagagaac 3120
taccgcttcc atgccatcaa tggctacatc atggacaccc tgcctgggct tgtcatggcc 3180
caggaccaga ggatcaggtg gtacctgctt tctatgggct ccaatgagaa cattcactcc 3240
atccacttct ctgggcatgt cttcactgtg cgcaagaagg aggagtacaa gatggccctg 3300
tacaacctct accctggggt ctttgagact gtggagatgc tgccctccaa agctggcatc 3360
tggagggtgg agtgcctcat tggggagcac ctgcatgctg gcatgagcac cctgttcctg 3420
gtctacagca acaagtgcca gaccccccctg ggaatggcct ctggccacat cagggacttc 3480
cagatcactg cctctggcca gtatggccag tgggccccca agctggccag gctccactac 3540
tctggatcca tcaatgcctg gagcaccaag gagccattca gctggatcaa agtggacctg 3600
ctggccccca tgatcatcca tggcatcaag acccaggggg ccaggcagaa gttctccagc 3660
ctgtacatca gccagttcat catcatgtac agcctggatg gcaagaaatg gcagacctac 3720
agaggcaact ccactggaac actcatggtc ttctttggca atgtggacag ctctggcatc 3780
aagcacaaca tcttcaaccc cccaatcatc gccagataca tcaggctgca ccccacccac 3840
tacagcatcc gcagcaccct caggatggag ctgatgggct gtgacctgaa ctcctgcagc 3900
atgcccctgg gcatggagag caaggccatt tctgatgccc agatcactgc ctccagctac 3960
ttcaccaaca tgtttgccac ctggagccca agcaaggcca ggctgcacct ccagggaagg 4020
agcaatgcct ggaggcccca ggtcaacaac ccaaaggagt ggctgcaggt ggacttccag 4080
aagaccatga aggtcactgg ggtgaccacc caggggggtca agagcctgct caccagcatg 4140
tatgtgaagg agttcctgat cagctccagc caggatggcc accagtggac cctcttcttc 4200
cagaatggca aggtcaaggt gttccagggc aaccaggaca gcttcacccc tgtggtgaac 4260
agcctggacc cccccctcct gaccagatac ctgaggattc acccccagag ctgggtccac 4320
cagattgccc tgaggatgga ggtcctggga tgtgaggccc aggacctgta ctga 4374

<210> SEQ ID NO 98
<211> LENGTH: 4377
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98
atgcagattg agctgagcac ctgcttcttc ctgtgcctgc tgaggttctg cttctctgcc 60
accaggagat actacctggg ggctgtggag ctttcttggg actacatgca gtctgacctg 120
ggggagctgc ctgtggatgc caggttccca cccagagtgc ccaaatcctt cccattcaac 180
acctctgtgg tctacaagaa gaccctcttt gtggagttca ctgaccacct gttcaacatt 240
gccaaaccca ggccaccctg gatgggactc ctgggaccca ccattcaggc tgaggtgtat 300
gacactgtgg tcatcaccct caagaacatg gcctcccacc ctgtgagcct gcatgctgtg 360
ggggtcagct actggaaggc ctctgagggg gctgagtatg atgaccagac ctcccagagg 420
gagaaggagg atgacaaagt gttccctggg ggcagccaca cctatgtgtg gcaggtcctc 480

```
aaggagaatg gccccatggc ctctgaccca ctctgcctga cctactccta cctttctcat    540
gtggacctgg tcaaggacct caactctgga ctgattgggg ccctgctggt gtgcagggag    600
ggctccctgg ccaaagagaa gacccagacc ctgcacaagt tcattctcct gtttgctgtc    660
tttgatgagg gcaagagctg gcactctgaa accaagaact ccctgatgca ggacagggat    720
gctgcctctg ccagggcctg gcccaagatg cacactgtga atggctatgt gaacaggagc    780
ctgcctggac tcattggctg ccacaggaaa tctgtctact ggcatgtgat tggcatgggg    840
acaacccctg aggtgcactc cattttcctg gagggccaca ccttcctggt caggaaccac    900
agacaggcca gcctggagat cagccccatc accttcctca ctgcccagac cctgctgatg    960
gacctcggac agttcctgct gtcctgccac atcagctccc accagcatga tggcatggag   1020
gcctatgtca aggtggacag ctgccctgag gagccacagc tcaggatgaa gaacaatgag   1080
gaggctgagg actatgatga tgacctgact gactctgaga tggatgtggt ccgctttgat   1140
gatgacaaca gcccatcctt cattcagatc aggtctgtgg ccaagaaaca ccccaagacc   1200
tgggtgcact acattgctgc tgaggaggag gactgggact atgcccccact ggtcctggcc  1260
cctgatgaca ggagctacaa gagccagtac ctcaacaatg gcccacagag gattggacgc   1320
aagtacaaga aagtcaggtt catggcctac actgatgaaa ccttcaagac cagggaggcc   1380
attcagcatg agtctggcat cctgggccca ctcctgtatg gggaggtggg ggacaccctg   1440
ctcatcatct tcaagaacca ggcctccagg ccctacaaca tctacccaca tggcatcact   1500
gatgtcaggc ccctgtacag ccgcaggctg ccaaaggggg tgaaacacct caaggacttc   1560
cccattctgc ctggggagat cttcaagtac aagtggactg tcactgtgga ggatggacca   1620
accaaatctg accccaggtg cctcaccaga tactactcca gctttgtgaa catggagagg   1680
gacctggcct ctggcctgat tggcccactg ctcatctgct acaaggagtc tgtggaccag   1740
aggggaaacc agatcatgtc tgacaagagg aatgtgattc tgttctctgt ctttgatgag   1800
aacaggagct ggtacctgac tgagaacatt cagcgcttcc tgcccaaccc tgctggggtg   1860
cagctggagg accctgagtt ccaggccagc aacatcatgc actccatcaa tggctatgtg   1920
tttgacagcc tccagctttc tgtctgcctg catgaggtgg cctactggta cattctttct   1980
attggggccc agactgactt cctttctgtc ttcttctctg gctacacctt caaacacaag   2040
atggtgtatg aggacaccct gaccctcttc ccattctctg ggagactgt gttcatgagc    2100
atggagaacc ctggcctgtg gattctggga tgccacaact ctgacttccg caacaggggc   2160
atgactgccc tgctcaaagt ctcctcctgt gacaagaaca ctggggacta ctatgaggac   2220
agctatgagg acatctctgc ctacctgctc agcaagaaca ataccaccta cgtgaaccgc   2280
tccctgagcc agaatccacc tgtcctgaaa cgccaccaga gggagatcac caggaccacc   2340
ctccagtctg accaggagga gattgactat gatgacacca tttctgtgga gatgaagaaa   2400
gaggactttg acatctatga cgaggacgag aaccagagcc caaggagctt ccagaagaag   2460
accaggcact acttcattgc tgctgtggag cgcctgtggg actatggcat gagctccagc   2520
ccccatgtcc tcaggaacag ggcccagtct ggctctgtgc cacagttcaa gaaagtggtc   2580
ttccaagagt tcactgatgg cagcttcacc cagcccctgt acagagggga gctgaatgag   2640
cacctgggac tcctgggccc atacatcagg gctgaggtgg aggacaacat catggtgacc   2700
ttccgcaacc aggcctccag gccctacagc ttctacagct ccctcatcag ctatgaggag   2760
gaccagaggc agggggctga gccacgcaag aactttgtga aacccaatga aaccaagacc   2820
```

tacttctgga aagtccagca ccacatggcc cccaccaagg atgagtttga ctgcaaggcc 2880
tgggcctact tctctgatgt ggacctggag aaggatgtgc actctggcct gattggccca 2940
ctcctggtct gccacaccaa caccctgaac cctgcccatg gaaggcaagt gactgtgcag 3000
gagtttgccc tcttcttcac catctttgat gaaaccaaga gctggtactt cactgagaac 3060
atggagcgca actgcagggc cccatgcaac attcagatgg aggaccccac cttcaaagag 3120
aactaccgct tccatgccat caatggctac atcatggaca ccctgcctgg gcttgtcatg 3180
gcccaggacc agaggatcag gtggtacctg ctttctatgg gctccaatga gaacattcac 3240
tccatccact tctctgggca tgtcttcact gtgcgcaaga aggaggagta caagatggcc 3300
ctgtacaacc tctaccctgg ggtctttgag actgtggaga tgctgccctc caaagctggc 3360
atctggaggg tggagtgcct cattggggag cacctgcatg ctggcatgag caccctgttc 3420
ctggtctaca gcaacaagtg ccagaccccc ctgggaatgg cctctggcca catcagggac 3480
ttccagatca ctgcctctgg ccagtatggc cagtgggccc ccaagctggc caggctccac 3540
tactctggat ccatcaatgc ctggagcacc aaggagccat tcagctggat caaagtggac 3600
ctgctggccc ccatgatcat ccatggcatc aagacccagg gggccaggca gaagttctcc 3660
agcctgtaca tcagccagtt catcatcatg tacagcctgg atggcaagaa atggcagacc 3720
tacagaggca actccactgg aacactcatg gtcttctttg gcaatgtgga cagctctggc 3780
atcaagcaca acatcttcaa ccccccaatc atcgccagat acatcaggct gcaccccacc 3840
cactacagca tccgcagcac cctcaggatg gagctgatgg gctgtgacct gaactcctgc 3900
agcatgcccc tgggcatgga gagcaaggcc atttctgatg cccagatcac tgcctccagc 3960
tacttcacca acatgtttgc cacctggagc ccaagcaagg ccaggctgca cctccaggga 4020
aggagcaatg cctggaggcc ccaggtcaac aacccaaagg agtggctgca ggtggacttc 4080
cagaagacca tgaaggtcac tggggtgacc acccaggggg tcaagagcct gctcaccagc 4140
atgtatgtga aggagttcct gatcagctcc agccaggatg gccaccagtg gaccctcttc 4200
ttccagaatg gcaaggtcaa ggtgttccag ggcaaccagg acagcttcac ccctgtggtg 4260
aacagcctgg acccccccct cctgaccaga tacctgagga ttcaccccca gagctgggtc 4320
caccagattg ccctgaggat ggaggtcctg ggatgtgagg cccaggacct gtactga 4377

<210> SEQ ID NO 99
<211> LENGTH: 4377
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 99
atgcagattg agctgagcac ctgcttcttc ctgtgcctgc tgaggttctg cttctctgcc 60
accaggagat actacctggg cgccgtggag ctgagctggg actacatgca gtctgacctg 120
ggcgagctgc ctgtggacgc caggttcccc cccagagtgc ccaagagctt ccccttcaac 180
acctcagtgg tgtacaagaa gaccctgttc gtggagttca ccgaccacct gttcaacatc 240
gccaagccca ggccccctg gatgggcctg ctgggcccca ccatccaggc cgaggtgtac 300
gacaccgtgg tgatcaccct gaagaacatg gccagccacc ccgtgagcct gcacgccgtg 360
ggcgtgagct actggaaggc ctctgagggc gccgagtatg acgaccagac cagccagagg 420
gagaaggagg acgacaaggt gttccccggc ggcagccaca cctacgtgtg gcaggtgctg 480

-continued

```
aaggagaacg gccccatggc cagcgacccc ctgtgcctga cctacagcta cctgagccac     540
gtggacctgg tgaaggacct gaactctggc ctgatcggcg ccctgctggt gtgcagggag     600
ggcagcctgg ccaaggagaa gacccagacc ctgcacaagt tcatcctgct gttcgccgtg     660
ttcgatgagg gcaagagctg gcacagcgag accaagaaca gcctgatgca ggacagggat     720
gccgcctctg ccagggcctg gcccaagatg cacaccgtga acggctacgt gaacaggagc     780
ctgcccggcc tgatcggctg ccacaggaag tctgtgtact ggcacgtgat cggcatgggc     840
accacccccg aggtgcacag catcttcctg gagggccaca ccttcctggt gaggaaccac     900
aggcaggcca gcctggagat cagccccatc accttcctga ccgcccagac cctgctgatg     960
gacctgggcc agttcctgct gtcctgccac atcagcagcc accagcacga cggcatggag    1020
gcctacgtga aggtggacag ctgccccgag gagccccagc tgaggatgaa gaacaacgag    1080
gaggccgagg actatgatga tgacctgacc gactctgaga tggacgtggt gaggtttgat    1140
gatgacaaca gccccagctt catccagatc aggtctgtgg ccaagaagca ccccaagacc    1200
tgggtgcact acatcgccgc cgaggaggag gactgggact acgcccccct ggtgctggcc    1260
cccgacgaca ggagctacaa gagccagtac ctgaacaacg gcccccagag gatcggcagg    1320
aagtacaaga aggtcagatt catggcctac accgacgaga ccttcaagac cagggaggcc    1380
atccagcacg agtctggcat cctgggcccc ctgctgtacg gcgaggtggg cgacaccctg    1440
ctgatcatct tcaagaacca ggccagcagg ccctacaaca tctaccccca cggcatcacc    1500
gatgtgaggc ccctgtacag caggaggctg cccaagggcg tgaagcacct gaaggacttc    1560
cccatcctgc ccggcgagat cttcaagtac aagtggaccg tgaccgtgga ggatggcccc    1620
accaagtctg accccaggtg cctgaccagg tactacagca gcttcgtgaa catggagagg    1680
gacctggcct ctggcctgat cggccccctg ctgatctgct acaaggagag cgtggaccag    1740
aggggcaacc agatcatgtc tgacaagagg aacgtgatcc tgttctctgt gttcgatgag    1800
aacaggagct ggtatctgac cgagaacatc cagaggttcc tgcccaaccc cgccggcgtg    1860
cagctggagg accccgagtt ccaggccagc aacatcatgc acagcatcaa cggctacgtg    1920
ttcgacagcc tgcagctgtc tgtgtgcctg cacgaggtgg cctactggta catcctgagc    1980
atcggcgccc agaccgactt cctgtctgtg ttcttctctg gctacacctt caagcacaag    2040
atggtgtacg aggacaccct gaccctgttc cccttcagcg gcgagaccgt gttcatgagc    2100
atggagaacc ccggcctgtg gatcctgggc tgccacaaca gcgacttcag gaacaggggc    2160
atgaccgccc tgctgaaagt cagcagctgc gacaagaaca ccggcgacta ctacgaggac    2220
agctacgagg acatcagcgc ctacctgctg agcaagaaca acaccaccta cgtgaaccgc    2280
tccctgagcc agaacccccc cgtgctgaag aggcaccaga gggagatcac caggaccacc    2340
ctgcagagcg accaggagga gatcgactat gatgacacca tcagcgtgga gatgaagaag    2400
gaggacttcg acatctacga cgaggacgag aaccagagcc ccaggagctt ccagaagaag    2460
accaggcact acttcatcgc cgccgtggag aggctgtggg actatggcat gagcagcagc    2520
ccccacgtgc tgaggaacag ggcccagagc ggcagcgtgc cccagttcaa gaaggtggtg    2580
ttccaggagt tcaccgacgg cagcttcacc cagcccctgt acagaggcga gctgaacgag    2640
cacctgggcc tgctgggccc ctacatcagg gccgaggtgg aggacaacat catggtgacc    2700
ttcaggaacc aggccagcag gccctacagc ttctacagca gcctgatcag ctacgaggag    2760
gaccagaggc agggcgccga gcccaggaag aacttcgtga agcccaacga gaccaagacc    2820
tacttctgga aggtgcagca ccacatggcc cccaccaagg acgagttcga ctgcaaggcc    2880
```

tgggcctact tctctgatgt ggacctggag aaggacgtgc acagcggcct gatcggcccc 2940
ctgctggtgt gccacaccaa caccctgaac cccgcccacg gcaggcaggt gaccgtgcag 3000
gagttcgccc tgttcttcac catcttcgac gagaccaaga gctggtactt caccgagaac 3060
atggagagga actgcagggc cccctgcaac atccagatgg aggaccccac cttcaaggag 3120
aactacaggt tccacgccat caacggctac atcatggaca ccctgcccgg cctggtgatg 3180
gcccaggacc agaggatcag gtggtatctg ctgagcatgg gcagcaacga gaacatccac 3240
agcatccact tcagcggcca cgtgttcacc gtgaggaaga aggaggagta caagatggcc 3300
ctgtacaacc tgtaccccgg cgtgttcgag accgtggaga tgctgcccag caaggccggc 3360
atctggaggg tggagtgcct gatcggcgag cacctgcacg ccggcatgag caccctgttc 3420
ctggtgtaca gcaacaagtg ccagaccccc ctgggcatgg ccagcggcca catcagggac 3480
ttccagatca ccgcctctgg ccagtacggc cagtgggccc ccaagctggc caggctgcac 3540
tacagcggca gcatcaacgc ctggagcacc aaggagccct tcagctggat caaggtggac 3600
ctgctggccc ccatgatcat ccacggcatc aagacccagg gcgccaggca gaagttcagc 3660
agcctgtaca tcagccagtt catcatcatg tacagcctgg acggcaagaa gtggcagacc 3720
tacaggggca acagcaccgg caccctgatg gtgttcttcg gcaacgtgga cagcagcggc 3780
atcaagcaca acatcttcaa cccccccatc atcgccaggt acatcaggct gcaccccacc 3840
cactacagca tcaggagcac cctgcggatg gaactgatgg gctgcgacct gaacagctgc 3900
agcatgcccc tgggcatgga gagcaaggcc atctctgacg cccagatcac cgccagcagc 3960
tacttcacca acatgttcgc cacctggagc cccagcaagg ccaggctgca cctgcagggc 4020
aggagcaacg cctggaggcc ccaggtgaac aaccccaagg agtggctgca ggtggacttc 4080
cagaagacca tgaaggtgac cggcgtgacc acccagggcg tgaagagcct gctgaccagc 4140
atgtacgtga aggagttcct gatcagcagc agccaggacg gccaccagtg gaccctgttc 4200
ttccagaacg gcaaagtgaa ggtgttccag ggcaaccagg acagcttcac ccccgtggtg 4260
aacagcctgg acccccccct gctgaccagg tatctgagga tccaccccca gagctgggtg 4320
caccagatcg ccctgagaat ggaagtgctg ggatgcgagg cccaggacct gtactga 4377

<210> SEQ ID NO 100
<211> LENGTH: 4377
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 100
atgcagattg agctgagcac ctgcttcttc ctgtgcctgc tgaggttctg cttctctgcc 60
accaggagat actacctggg cgccgtggag ctgagctggg actacatgca gtctgacctg 120
ggcgagctgc ctgtggacgc caggttcccc cccagagtgc ccaagagctt ccccttcaac 180
acctcagtgg tgtacaagaa gaccctgttc gtggagttca ccgaccacct gttcaacatc 240
gccaagccca ggccccccctg gatgggcctg ctgggcccca ccatccaggc cgaggtgtac 300
gacaccgtgg tgatcaccct gaagaacatg gccagccacc ccgtgagcct gcacgccgtg 360
ggcgtgagct actggaaggc ctctgagggc gccgagtatg acgaccagac cagccagagg 420
gagaaggagg acgacaaggt gttccccggc ggcagccaca cctacgtgtg gcaggtgctg 480
aaggagaacg gccccatggc cagcgacccc ctgtgcctga cctacagcta cctgagccac 540

```
gtggacctgg tgaaggacct gaactctggc ctgatcggcg ccctgctggt gtgcagggag    600
ggcagcctgg ccaaggagaa gacccagacc ctgcacaagt tcatcctgct gttcgccgtg    660
ttcgatgagg gcaagagctg gcacagcgag accaagaaca gcctgatgca ggacagggat    720
gccgcctctg ccagggcctg gcccaagatg cacaccgtga acggctacgt gaacaggagc    780
ctgcccggcc tgatcggctg ccacaggaag tctgtgtact ggcacgtgat cggcatgggc    840
accacccccg aggtgcacag catcttcctg gagggccaca ccttcctggt gaggaaccac    900
aggcaggcca gcctggagat cagccccatc accttcctga ccgcccagac cctgctgatg    960
gacctgggcc agttcctgct gttctgccac atcagcagcc accagcacga cggcatggag   1020
gcctacgtga aggtggacag ctgccccgag gagccccagc tgaggatgaa gaacaacgag   1080
gaggccgagg actatgatga tgacctgacc gactctgaga tggacgtggt gaggtttgat   1140
gatgacaaca gccccagctt catccagatc aggtctgtgg ccaagaagca ccccaagacc   1200
tgggtgcact acatcgccgc cgaggaggag gactgggact acgccccccct ggtgctggcc  1260
cccgacgaca ggagctacaa gagccagtac ctgaacaacg gcccccagag gatcggcagg   1320
aagtacaaga aggtcagatt catggcctac accgacgaga ccttcaagac cagggaggcc   1380
atccagcacg agtctggcat cctgggcccc ctgctgtacg gcgaggtggg cgacaccctg   1440
ctgatcatct tcaagaacca ggccagcagg ccctacaaca tctaccccca cggcatcacc   1500
gatgtgaggc ccctgtacag caggaggctg cccaagggcg tgaagcacct gaaggacttc   1560
cccatcctgc ccggcgagat cttcaagtac aagtggaccg tgaccgtgga ggatggcccc   1620
accaagtctg accccaggtg cctgaccagg tactacagca gcttcgtgaa catggagagg   1680
gacctggcct ctggcctgat cggccccctg ctgatctgct acaaggagag cgtggaccag   1740
aggggcaacc agatcatgtc tgacaagagg aacgtgatcc tgttctctgt gttcgatgag   1800
aacaggagct ggtatctgac cgagaacatc cagaggttcc tgcccaaccc cgccggcgtg   1860
cagctggagg accccgagtt ccaggccagc aacatcatgc acagcatcaa cggctacgtg   1920
ttcgacagcc tgcagctgtc tgtgtgcctg cacgaggtgg cctactggta catcctgagc   1980
atcggcgccc agaccgactt cctgtctgtg ttcttctctg gctacacctt caagcacaag   2040
atggtgtacg aggacaccct gaccctgttc cccttcagcg gcgagaccgt gttcatgagc   2100
atggagaacc ccggcctgtg gatcctgggc tgccacaaca gcgacttcag gaacaggggc   2160
atgaccgccc tgctgaaagt cagcagctgc gacaagaaca ccggcgacta ctacgaggac   2220
agctacgagg acatcagcgc ctacctgctg agcaagaaca acaccaccta cgtgaaccgc   2280
tccctgagcc agaacccccc cgtgctgaag aggcaccaga gggagatcac caggaccacc   2340
ctgcagagcg accaggagga gatcgactat gatgacacca tcagcgtgga gatgaagaag   2400
gaggacttcg acatctacga cgaggacgag aaccagagcc ccaggagctt ccagaagaag   2460
accaggcact acttcatcgc cgccgtggag aggctgtggg actatggcat gagcagcagc   2520
ccccacgtgc tgaggaacag ggcccagagc ggcagcgtgc cccagttcaa gaaggtggtg   2580
ttccaggagt tcaccgacgg cagcttcacc cagcccctgt acagaggcga gctgaacgag   2640
cacctgggcc tgctgggccc ctacatcagg gccgaggtgg aggacaacat catggtgacc   2700
ttcaggaacc aggccagcag gccctacagc ttctacagca gcctgatcag ctacgaggag   2760
gaccagaggc agggcgccga gcccaggaag aacttcgtga agcccaacga gaccaagacc   2820
tacttctgga aggtgcagca ccacatggcc cccaccaagg acgagttcga ctgcaaggcc   2880
```

```
tgggcctact tctctgatgt ggacctggag aaggacgtgc acagcggcct gatcggcccc   2940

ctgctggtgt gccacaccaa caccctgaac cccgcccacg gcaggcaggt gaccgtgcag   3000

gagttcgccc tgttcttcac catcttcgac gagaccaaga gctggtactt caccgagaac   3060

atggagagga actgcagggc cccctgcaac atccagatgg aggaccccac cttcaaggag   3120

aactacaggt tccacgccat caacggctac atcatggaca ccctgcccgg cctggtgatg   3180

gcccaggacc agaggatcag gtggtatctg ctgagcatgg gcagcaacga gaacatccac   3240

agcatccact tcagcggcca cgtgttcacc gtgaggaaga aggaggagta caagatggcc   3300

ctgtacaacc tgtaccccgg cgtgttcgag accgtggaga tgctgcccag caaggccggc   3360

atctggaggg tggagtgcct gatcggcgag cacctgcacg ccggcatgag caccctgttc   3420

ctggtgtaca gcaacaagtg ccagaccccc ctgggcatgg ccagcggcca catcagggac   3480

ttccagatca ccgcctctgg ccagtacggc cagtgggccc ccaagctggc caggctgcac   3540

tacagcggca gcatcaacgc ctggagcacc aaggagccct tcagctggat caaggtggac   3600

ctgctggccc ccatgatcat ccacggcatc aagacccagg gcgccaggca gaagttcagc   3660

agcctgtaca tcagccagtt catcatcatg tacagcctgg acggcaagaa gtggcagacc   3720

tacaggggca acagcaccgg caccctgatg gtgttcttcg gcaacgtgga cagcagcggc   3780

atcaagcaca acatcttcaa cccccccatc atcgccaggt acatcaggct gcaccccacc   3840

cactacagca tcaggagcac cctgcggatg gaactgatgg gctgcgacct gaacagctgc   3900

agcatgcccc tgggcatgga gagcaaggcc atctctgacg cccagatcac cgccagcagc   3960

tacttcacca acatgttcgc cacctggagc cccagcaagg ccaggctgca cctgcagggc   4020

aggagcaacg cctggaggcc ccaggtgaac aaccccaagg agtggctgca ggtggacttc   4080

cagaagacca tgaaggtgac cggcgtgacc acccagggcg tgaagagcct gctgaccagc   4140

atgtacgtga aggagttcct gatcagcagc agccaggacg gccaccagtg gaccctgttc   4200

ttccagaacg gcaaagtgaa ggtgttccag ggcaaccagg acagcttcac ccccgtggtg   4260

aacagcctgg acccccccct gctgaccagg tatctgagga tccaccccca gagctgggtg   4320

caccagatcg ccctgagaat ggaagtgctg ggatgcgagg cccaggacct gtactga      4377
```

```
<210> SEQ ID NO 101
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
```

```
atgcagattg agctgagcac ctgcttcttc ctgtgcctgc tgaggttctg cttctctgcc     60

accaggagat actacctggg cgccgtggag ctgagctggg actacatgca gtctgacctg    120

ggcgagctgc ctgtggacgc caggttcccc cccagagtgc ccaagagctt ccccttcaac    180

acctcagtgg tgtacaagaa gaccctgttc gtggagttca ccgaccacct gttcaacatc    240

gccaagccca ggccccccctg gatgggcctg ctgggcccca ccatccaggc cgaggtgtac    300

gacaccgtgg tggtcaccct gaagaacatg gccagccacc ccgtgagcct gcacgccgtg    360

ggcgtgagct actggaagtc ctctgagggc gccgagtatg acgaccagac cagccagagg    420

gagaaggagg acgacaaggt gttccccggc aagagccaca cctacgtgtg gcaggtgctg    480

aaggagaacg gccccactgc cagcgacccc ccctgcctga cctacagcta cctgagccac    540
```

gtggacctgg tgaaggacct gaactctggc ctgatcggcg ccctgctggt gtgcagggag 600
ggcagcctgg ccaaggagaa gacccagacc ctgcacaagt tcatcctgct gttcgccgtg 660
ttcgatgagg gcaagagctg gcacagcgag accaagaaca gcctgatgca ggacagggat 720
gccgcctctg ccagggcctg gcccaagatg cacaccgtga acggctacgt gaacaggagc 780
ctgcccggcc tgatcggctg ccacaggaag tctgtgtact ggcacgtgat cggcatgggc 840
accacccccg aggtgcacag catcttcctg gagggccaca ccttcctggt gaggaaccac 900
aggcaggcca gcctggagat cagccccatc accttcctga ccgcccagac cctgctgatg 960
gacctgggcc agttcctgct gttctgccac atcagcagcc accagcacga cggcatggag 1020
gcctacgtga aggtggacag ctgccccgag gagccccagc tgaggatgaa gaacaacgag 1080
gaggccgagg actatgatga tgacctgacc gactctgaga tggacgtggt gaggtttgat 1140
gatgacaaca gccccagctt catccagatc aggtctgtgg ccaagaagca ccccaagacc 1200
tgggtgcact acatcgccgc cgaggaggag gactgggact acgcccccct ggtgctggcc 1260
cccgacgaca ggagctacaa gagccagtac ctgaacaacg gcccccagag gatcggcagg 1320
aagtacaaga aggtcagatt catggcctac accgacgaga ccttcaagac cagggaggcc 1380
atccagcacg agtctggcat cctgggcccc ctgctgtacg gcgaggtggg cgacaccctg 1440
ctgatcatct tcaagaacca ggccagcagg ccctacaaca tctaccccca cggcatcacc 1500
gatgtgaggc ccctgtacag caggaggctg cccaagggcg tgaagcacct gaaggacttc 1560
cccatcctgc ccggcgagat cttcaagtac aagtggaccg tgaccgtgga ggatggcccc 1620
accaagtctg accccaggtg cctgaccagg tactacagca gcttcgtgaa catggagagg 1680
gacctggcct ctggcctgat cggcccccctg ctgatctgct acaaggagag cgtggaccag 1740
aggggcaacc agatcatgtc tgacaagagg aacgtgatcc tgttctctgt gttcgatgag 1800
aacaggagct ggtatctgac cgagaacatc cagaggttcc tgcccaaccc cgccggcgtg 1860
cagctggagg accccgagtt ccaggccagc aacatcatgc acagcatcaa cggctacgtg 1920
ttcgacagcc tgcagctgtc tgtgtgcctg cacgaggtgg cctactggta catcctgagc 1980
atcggcgccc agaccgactt cctgtctgtg ttcttctctg gctacacctt caagcacaag 2040
atggtgtacg aggacaccct gaccctgttc cccttcagcg gcgagaccgt gttcatgagc 2100
atggagaacc ccggcctgtg gatcctgggc tgccacaaca gcgacttcag gaacaggggc 2160
atgaccgccc tgctgaaagt cagcagctgc gacaagaaca ccggcgacta ctacgaggac 2220
agctacgagg acatcagcgc ctacctgctg agcaagaaca acgccatcga gcccaggagc 2280
ttcagccaga accccccccgt gctgaagagg caccagaggg agatcaccag gaccaccctg 2340
cagagcgacc aggaggagat cgactatgat gacaccatca gcgtggagat gaagaaggag 2400
gacttcgaca tctacgacga ggacgagaac cagagcccca ggagcttcca gaagaagacc 2460
aggcactact tcatcgccgc cgtggagagg ctgtgggact atggcatgag cagcagcccc 2520
cacgtgctga ggaacagggc ccagagcggc agcgtgcccc agttcaagaa ggtggtgttc 2580
caggagttca ccgacggcag cttcacccag cccctgtaca gaggcgagct gaacgagcac 2640
ctgggcctgc tgggccccta catcagggcc gaggtggagg acaacatcat ggtgaccttc 2700
aggaaccagg ccagcaggcc ctacagcttc tacagcagcc tgatcagcta cgaggaggac 2760
cagaggcagg gcgccgagcc caggaagaac ttcgtgaagc ccaacgagac caagacctac 2820
ttctggaagg tgcagcacca catggccccc accaaggacg agttcgactg caaggcctgg 2880
gcctacttct ctgatgtgga cctggagaag gacgtgcaca gcggcctgat cggcccccctg 2940

-continued

```
ctggtgtgcc acaccaacac cctgaacccc gcccacggca ggcaggtgac cgtgcaggag   3000

ttcgccctgt tcttcaccat cttcgacgag accaagagct ggtacttcac cgagaacatg   3060

gagaggaact gcagggcccc ctgcaacatc cagatggagg accccacctt caaggagaac   3120

tacaggttcc acgccatcaa cggctacatc atggacaccc tgcccggcct ggtgatggcc   3180

caggaccaga ggatcaggtg gtatctgctg agcatgggca gcaacgagaa catccacagc   3240

atccacttca gcggccacgt gttcaccgtg aggaagaagg aggagtacaa gatggccctg   3300

tacaacctgt accccggcgt gttcgagacc gtggagatgc tgcccagcaa ggccggcatc   3360

tggagggtgg agtgcctgat cggcgagcac ctgcacgccg gcatgagcac cctgttcctg   3420

gtgtacagca acaagtgcca gacccccctg ggcatggcca gcggccacat cagggacttc   3480

cagatcaccg cctctggcca gtacggccag tgggccccca agctggccag gctgcactac   3540

agcggcagca tcaacgcctg gagcaccaag gagcccttca gctggatcaa ggtggacctg   3600

ctggccccca tgatcatcca cggcatcaag acccagggcg ccaggcagaa gttcagcagc   3660

ctgtacatca gccagttcat catcatgtac agcctggacg gcaagaagtg gcagacctac   3720

aggggcaaca gcaccggcac cctgatggtg ttcttcggca acgtggacag cagcggcatc   3780

aagcacaaca tcttcaaccc ccccatcatc gccaggtaca tcaggctgca ccccacccac   3840

tacagcatca ggagcaccct gcggatggaa ctgatgggct gcgacctgaa cagctgcagc   3900

atgcccctgg gcatggagag caaggccatc tctgacgccc agatcaccgc cagcagctac   3960

ttcaccaaca tgttcgccac ctggagcccc agcaaggcca ggctgcacct gcagggcagg   4020

agcaacgcct ggaggcccca ggtgaacaac cccaaggagt ggctgcaggt ggacttccag   4080

aagaccatga aggtgaccgg cgtgaccacc cagggcgtga agagcctgct gaccagcatg   4140

tacgtgaagg agttcctgat cagcagcagc caggacggcc accagtggac cctgttcttc   4200

cagaacggca aagtgaaggt gttccagggc aaccaggaca gcttcacccc cgtggtgaac   4260

agcctggacc ccccccctgct gaccaggtat ctgaggatcc acccccagag ctgggtgcac   4320

cagatcgccc tgagaatgga agtgctggga tgcgaggccc aggacctgta ctga         4374
```

<210> SEQ ID NO 102
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

```
atgcagattg agctgagcac ctgcttcttc ctgtgcctgc tgaggttctg cttctctgcc     60

accaggagat actacctggg cgccgtggag ctgagctggg actacatgca gtctgacctg    120

ggcgagctgc ctgtggacgc caggttcccc cccagagtgc ccaagagctt ccccttcaac    180

acctcagtgg tgtacaagaa gaccctgttc gtggagttca ccgaccacct gttcaacatc    240

gccaagccca ggccccccctg gatgggcctg ctgggcccca ccatccaggc cgaggtgtac    300

gacaccgtgg tgatcaccct gaagaacatg gccagccacc ccgtgagcct gcacgccgtg    360

ggcgtgagct actggaaggc ctctgagggc gccgagtatg acgaccagac cagccagagg    420

gagaaggagg acgacaaggt gttccccggc ggcagccaca cctacgtgtg gcaggtgctg    480

aaggagaacg gccccatggc cagcgacccc ctgtgcctga cctacagcta cctgagccac    540

gtggacctgg tgaaggacct gaactctggc ctgatcggcg ccctgctggt gtgcagggag    600
```

-continued

```
ggcagcctgg ccaaggagaa gacccagacc ctgcacaagt tcatcctgct gttcgccgtg    660
ttcgatgagg gcaagagctg gcacagcgag accaagaaca gcctgatgca ggacagggat    720
gccgcctctg ccagggcctg gcccaagatg cacaccgtga acggctacgt gaacaggagc    780
ctgcccggcc tgatcggctg ccacaggaag tctgtgtact ggcacgtgat cggcatgggc    840
accacccccg aggtgcacag catcttcctg gagggccaca ccttcctggt gaggaaccac    900
aggcaggcca gcctggagat cagccccatc accttcctga ccgcccagac cctgctgatg    960
gacctgggcc agttcctgct gtcctgccac atcagcagcc accagcacga cggcatggag   1020
gcctacgtga aggtggacag ctgccccgag gagccccagc tgaggatgaa gaacaacgag   1080
gaggccgagg actatgatga tgacctgacc gactctgaga tggacgtggt gaggtttgat   1140
gatgacaaca gccccagctt catccagatc aggtctgtgg ccaagaagca ccccaagacc   1200
tgggtgcact acatcgccgc cgaggaggag gactgggact acgcccccct ggtgctggcc   1260
cccgacgaca ggagctacaa gagccagtac ctgaacaacg gcccccagag gatcggcagg   1320
aagtacaaga aggtcagatt catggcctac accgacgaga ccttcaagac cagggaggcc   1380
atccagcacg agtctggcat cctgggcccc ctgctgtacg gcgaggtggg cgacaccctg   1440
ctgatcatct tcaagaacca ggccagcagg ccctacaaca tctaccccca cggcatcacc   1500
gatgtgaggc ccctgtacag caggaggctg cccaagggcg tgaagcacct gaaggacttc   1560
cccatcctgc ccggcgagat cttcaagtac aagtggaccg tgaccgtgga ggatggcccc   1620
accaagtctg accccaggtg cctgaccagg tactacagca gcttcgtgaa catggagagg   1680
gacctggcct ctggcctgat cggcccccctg ctgatctgct acaaggagag cgtggaccag   1740
aggggcaacc agatcatgtc tgacaagagg aacgtgatcc tgttctctgt gttcgatgag   1800
aacaggagct ggtatctgac cgagaacatc cagaggttcc tgcccaaccc cgccggcgtg   1860
cagctggagg accccgagtt ccaggccagc aacatcatgc acagcatcaa cggctacgtg   1920
ttcgacagcc tgcagctgtc tgtgtgcctg cacgaggtgg cctactggta catcctgagc   1980
atcggcgccc agaccgactt cctgtctgtg ttcttctctg gctacacctt caagcacaag   2040
atggtgtacg aggacaccct gaccctgttc cccttcagcg gcgagaccgt gttcatgagc   2100
atggagaacc ccggcctgtg gatcctgggc tgccacaaca gcgacttcag gaacaggggc   2160
atgaccgccc tgctgaaagt cagcagctgc gacaagaaca ccggcgacta ctacgaggac   2220
agctacgagg acatcagcgc ctacctgctg agcaagaaca acgccatcga gcccaggagc   2280
ttcagccaga acccccccgt gctgaagagg caccagaggg agatcaccag gaccaccctg   2340
cagagcgacc aggaggagat cgactatgat gacaccatca gcgtggagat gaagaaggag   2400
gacttcgaca tctacgacga ggacgagaac cagagcccca ggagcttcca gaagaagacc   2460
aggcactact tcatcgccgc cgtggagagg ctgtgggact atggcatgag cagcagcccc   2520
cacgtgctga ggaacagggc ccagagcggc agcgtgcccc agttcaagaa ggtggtgttc   2580
caggagttca ccgacggcag cttcacccag cccctgtaca gaggcgagct gaacgagcac   2640
ctgggcctgc tgggccccta catcagggcc gaggtggagg acaacatcat ggtgaccttc   2700
aggaaccagg ccagcaggcc ctacagcttc tacagcagcc tgatcagcta cgaggaggac   2760
cagaggcagg gcgccgagcc caggaagaac ttcgtgaagc ccaacgagac caagacctac   2820
ttctggaagg tgcagcacca catggccccc accaaggacg agttcgactg caaggcctgg   2880
gcctacttct ctgatgtgga cctggagaag gacgtgcaca gcggcctgat cggcccccctg   2940
```

```
ctggtgtgcc acaccaacac cctgaacccc gcccacggca ggcaggtgac cgtgcaggag   3000

ttcgccctgt tcttcaccat cttcgacgag accaagagct ggtacttcac cgagaacatg   3060

gagaggaact gcagggcccc ctgcaacatc cagatggagg accccacctt caaggagaac   3120

tacaggttcc acgccatcaa cggctacatc atggacaccc tgcccggcct ggtgatggcc   3180

caggaccaga ggatcaggtg gtatctgctg agcatgggca gcaacgagaa catccacagc   3240

atccacttca gcggccacgt gttcaccgtg aggaagaagg aggagtacaa gatggccctg   3300

tacaacctgt accccggcgt gttcgagacc gtggagatgc tgcccagcaa ggccggcatc   3360

tggagggtgg agtgcctgat cggcgagcac ctgcacgccg gcatgagcac cctgttcctg   3420

gtgtacagca acaagtgcca gaccccccctg ggcatggcca gcggccacat cagggacttc   3480

cagatcaccg cctctggcca gtacggccag tgggccccca agctggccag gctgcactac   3540

agcggcagca tcaacgcctg gagcaccaag gagcccttca gctggatcaa ggtggacctg   3600

ctggccccca tgatcatcca cggcatcaag acccagggcg ccaggcagaa gttcagcagc   3660

ctgtacatca gccagttcat catcatgtac agcctggacg gcaagaagtg gcagacctac   3720

aggggcaaca gcaccggcac cctgatggtg ttcttcggca acgtggacag cagcggcatc   3780

aagcacaaca tcttcaaccc ccccatcatc gccaggtaca tcaggctgca ccccacccac   3840

tacagcatca ggagcaccct gcggatggaa ctgatgggct gcgacctgaa cagctgcagc   3900

atgcccctgg gcatggagag caaggccatc tctgacgccc agatcaccgc cagcagctac   3960

ttcaccaaca tgttcgccac ctggagcccc agcaaggcca ggctgcacct gcagggcagg   4020

agcaacgcct ggaggcccca ggtgaacaac cccaaggagt ggctgcaggt ggacttccag   4080

aagaccatga aggtgaccgg cgtgaccacc cagggcgtga agagcctgct gaccagcatg   4140

tacgtgaagg agttcctgat cagcagcagc caggacggcc accagtggac cctgttcttc   4200

cagaacggca aagtgaaggt gttccagggc aaccaggaca gcttcacccc cgtggtgaac   4260

agcctggacc cccccctgct gaccaggtat ctgaggatcc acccccagag ctgggtgcac   4320

cagatcgccc tgagaatgga agtgctggga tgcgaggccc aggacctgta ctga         4374
```

<210> SEQ ID NO 103
<211> LENGTH: 4377
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 103

```
atgcagattg agctgagcac ctgcttcttc ctgtgcctgc tgaggttctg cttctctgcc     60

accaggagat actacctggg cgccgtggag ctgagctggg actacatgca gtctgacctg    120

ggcgagctgc ctgtggacgc caggttcccc cccagagtgc ccaagagctt ccccttcaac    180

acctcagtgg tgtacaagaa gaccctgttc gtggagttca ccgaccacct gttcaacatc    240

gccaagccca ggccccccctg gatgggcctg ctgggcccca ccatccaggc cgaggtgtac    300

gacaccgtgg tggtcaccct gaagaacatg gccagccacc ccgtgagcct gcacgccgtg    360

ggcgtgagct actggaagtc ctctgagggc gccgagtatg acgaccagac cagccagagg    420

gagaaggagg acgacaaggt gttccccggc aagagccaca cctacgtgtg gcaggtgctg    480

aaggagaacg gccccactgc cagcgacccc ccctgcctga cctacagcta cctgagccac    540

gtggacctgg tgaaggacct gaactctggc ctgatcggcg ccctgctggt gtgcagggag    600
```

-continued

```
ggcagcctgg ccaaggagaa gacccagacc ctgcacaagt tcatcctgct gttcgccgtg    660
ttcgatgagg gcaagagctg gcacagcgag accaagaaca gcctgatgca ggacagggat    720
gccgcctctg ccagggcctg gcccaagatg cacaccgtga acggctacgt gaacaggagc    780
ctgcccggcc tgatcggctg ccacaggaag tctgtgtact ggcacgtgat cggcatgggc    840
accacccccg aggtgcacag catcttcctg gagggccaca ccttcctggt gaggaaccac    900
aggcaggcca gcctggagat cagccccatc accttcctga ccgcccagac cctgctgatg    960
gacctgggcc agttcctgct gttctgccac atcagcagcc accagcacga cggcatggag   1020
gcctacgtga aggtggacag ctgccccgag gagccccagc tgaggatgaa gaacaacgag   1080
gaggccgagg actatgatga tgacctgacc gactctgaga tggacgtggt gaggtttgat   1140
gatgacaaca gccccagctt catccagatc aggtctgtgg ccaagaagca ccccaagacc   1200
tgggtgcact acatcgccgc cgaggaggag gactgggact acgccccct ggtgctggcc   1260
cccgacgaca ggagctacaa gagccagtac ctgaacaacg gcccccagag gatcggcagg   1320
aagtacaaga aggtcagatt catggcctac accgacgaga ccttcaagac cagggaggcc   1380
atccagcacg agtctggcat cctgggcccc ctgctgtacg gcgaggtggg cgacaccctg   1440
ctgatcatct tcaagaacca ggccagcagg ccctacaaca tctaccccca cggcatcacc   1500
gatgtgaggc ccctgtacag caggaggctg cccaagggcg tgaagcacct gaaggacttc   1560
cccatcctgc ccggcgagat cttcaagtac aagtggaccg tgaccgtgga ggatggcccc   1620
accaagtctg accccaggtg cctgaccagg tactacagca gcttcgtgaa catggagagg   1680
gacctggcct ctggcctgat cggcccctg ctgatctgct acaaggagag cgtggaccag   1740
aggggcaacc agatcatgtc tgacaagagg aacgtgatcc tgttctctgt gttcgatgag   1800
aacaggagct ggtatctgac cgagaacatc cagaggttcc tgcccaaccc cgccggcgtg   1860
cagctggagg accccgagtt ccaggccagc aacatcatgc acagcatcaa cggctacgtg   1920
ttcgacagcc tgcagctgtc tgtgtgcctg cacgaggtgg cctactggta catcctgagc   1980
atcggcgccc agaccgactt cctgtctgtg ttcttctctg gctacacctt caagcacaag   2040
atggtgtacg aggacaccct gaccctgttc cccttcagcg gcgagaccgt gttcatgagc   2100
atggagaacc ccggcctgtg gatcctgggc tgccacaaca gcgacttcag gaacaggggc   2160
atgaccgccc tgctgaaagt cagcagctgc gacaagaaca ccggcgacta ctacgaggac   2220
agctacgagg acatcagcgc ctacctgctg agcaagaaca acaccaccta cgtgaaccgc   2280
tccctgagcc agaacccccc cgtgctgaag aggcaccaga gggagatcac caggaccacc   2340
ctgcagagcg accaggagga gatcgactat gatgacacca tcagcgtgga gatgaagaag   2400
gaggacttcg acatctacga cgaggacgag aaccagagcc ccaggagctt ccagaagaag   2460
accaggcact acttcatcgc cgccgtggag aggctgtggg actatggcat gagcagcagc   2520
ccccacgtgc tgaggaacag ggcccagagc ggcagcgtgc cccagttcaa gaaggtggtg   2580
ttccaggagt tcaccgacgg cagcttcacc cagcccctgt acagaggcga gctgaacgag   2640
cacctgggcc tgctgggccc ctacatcagg gccgaggtgg aggacaacat catggtgacc   2700
ttcaggaacc aggccagcag gccctacagc ttctacagca gcctgatcag ctacgaggag   2760
gaccagaggc agggcgccga gcccaggaag aacttcgtga agcccaacga gaccaagacc   2820
tacttctgga aggtgcagca ccacatggcc cccaccaagg acgagttcga ctgcaaggcc   2880
tgggcctact tctctgatgt ggacctggag aaggacgtgc acagcggcct gatcggcccc   2940
ctgctggtgt gccacaccaa caccctgaac cccgcccacg gcaggcaggt gaccgtgcag   3000
```

gagttcgccc tgttcttcac catcttcgac gagaccaaga gctggtactt caccgagaac 3060
atggagagga actgcagggc cccctgcaac atccagatgg aggaccccac cttcaaggag 3120
aactacaggt tccacgccat caacggctac atcatggaca ccctgcccgg cctggtgatg 3180
gcccaggacc agaggatcag gtggtatctg ctgagcatgg gcagcaacga gaacatccac 3240
agcatccact tcagcggcca cgtgttcacc gtgaggaaga aggaggagta caagatggcc 3300
ctgtacaacc tgtaccccgg cgtgttcgag accgtggaga tgctgcccag caaggccggc 3360
atctggaggg tggagtgcct gatcggcgag cacctgcacg ccggcatgag caccctgttc 3420
ctggtgtaca gcaacaagtg ccagaccccc ctgggcatgg ccagcggcca catcagggac 3480
ttccagatca ccgcctctgg ccagtacggc cagtgggccc ccaagctggc caggctgcac 3540
tacagcggca gcatcaacgc ctggagcacc aaggagccct tcagctggat caaggtggac 3600
ctgctggccc ccatgatcat ccacggcatc aagacccagg gcgccaggca gaagttcagc 3660
agcctgtaca tcagccagtt catcatcatg tacagcctgg acggcaagaa gtggcagacc 3720
tacaggggca acagcaccgg caccctgatg gtgttcttcg gcaacgtgga cagcagcggc 3780
atcaagcaca acatcttcaa ccccccccatc atcgccaggt acatcaggct gcaccccacc 3840
cactacagca tcaggagcac cctgcggatg gaactgatgg gctgcgacct gaacagctgc 3900
agcatgcccc tgggcatgga gagcaaggcc atctctgacg cccagatcac cgccagcagc 3960
tacttcacca acatgttcgc cacctggagc cccagcaagg ccaggctgca cctgcagggc 4020
aggagcaacg cctggaggcc ccaggtgaac aaccccaagg agtggctgca ggtggacttc 4080
cagaagacca tgaaggtgac cggcgtgacc acccagggcg tgaagagcct gctgaccagc 4140
atgtacgtga aggagttcct gatcagcagc agccaggacg gccaccagtg gaccctgttc 4200
ttccagaacg gcaaagtgaa ggtgttccag ggcaaccagg acagcttcac ccccgtggtg 4260
aacagcctgg acccccccct gctgaccagg tatctgagga tccaccccca gagctgggtg 4320
caccagatcg ccctgagaat ggaagtgctg ggatgcgagg cccaggacct gtactga 4377

<210> SEQ ID NO 104
<211> LENGTH: 1458
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

Met Gln Ile Glu Leu Ser Thr Cys Phe Phe Leu Cys Leu Leu Arg Phe
1 5 10 15

Cys Phe Ser Ala Thr Arg Arg Tyr Tyr Leu Gly Ala Val Glu Leu Ser
20 25 30

Trp Asp Tyr Met Gln Ser Asp Leu Gly Glu Leu Pro Val Asp Ala Arg
35 40 45

Phe Pro Pro Arg Val Pro Lys Ser Phe Pro Phe Asn Thr Ser Val Val
50 55 60

Tyr Lys Lys Thr Leu Phe Val Glu Phe Thr Asp His Leu Phe Asn Ile
65 70 75 80

Ala Lys Pro Arg Pro Pro Trp Met Gly Leu Leu Gly Pro Thr Ile Gln
85 90 95

Ala Glu Val Tyr Asp Thr Val Val Val Thr Leu Lys Asn Met Ala Ser
100 105 110

```
His Pro Val Ser Leu His Ala Val Gly Val Ser Tyr Trp Lys Ser Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Lys Ser His Thr Tyr Val Trp Gln Val Leu
145                 150                 155                 160

Lys Glu Asn Gly Pro Thr Ala Ser Asp Pro Pro Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
```

-continued

```
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Thr Thr Tyr Val Asn Arg Ser Leu Ser Gln Asn Pro Pro Val
        755                 760                 765

Leu Lys Arg His Gln Arg Glu Ile Thr Arg Thr Thr Leu Gln Ser Asp
    770                 775                 780

Gln Glu Glu Ile Asp Tyr Asp Asp Thr Ile Ser Val Glu Met Lys Lys
785                 790                 795                 800

Glu Asp Phe Asp Ile Tyr Asp Glu Asp Glu Asn Gln Ser Pro Arg Ser
                805                 810                 815

Phe Gln Lys Lys Thr Arg His Tyr Phe Ile Ala Ala Val Glu Arg Leu
            820                 825                 830

Trp Asp Tyr Gly Met Ser Ser Ser Pro His Val Leu Arg Asn Arg Ala
        835                 840                 845

Gln Ser Gly Ser Val Pro Gln Phe Lys Lys Val Val Phe Gln Glu Phe
    850                 855                 860

Thr Asp Gly Ser Phe Thr Gln Pro Leu Tyr Arg Gly Glu Leu Asn Glu
865                 870                 875                 880

His Leu Gly Leu Leu Gly Pro Tyr Ile Arg Ala Glu Val Glu Asp Asn
                885                 890                 895

Ile Met Val Thr Phe Arg Asn Gln Ala Ser Arg Pro Tyr Ser Phe Tyr
            900                 905                 910

Ser Ser Leu Ile Ser Tyr Glu Glu Asp Gln Arg Gln Gly Ala Glu Pro
        915                 920                 925

Arg Lys Asn Phe Val Lys Pro Asn Glu Thr Lys Thr Tyr Phe Trp Lys
    930                 935                 940

Val Gln His His Met Ala Pro Thr Lys Asp Glu Phe Asp Cys Lys Ala
945                 950                 955                 960
```

```
Trp Ala Tyr Phe Ser Asp Val Asp Leu Glu Lys Asp Val His Ser Gly
                965                 970                 975

Leu Ile Gly Pro Leu Leu Val Cys His Thr Asn Thr Leu Asn Pro Ala
            980                 985                 990

His Gly Arg Gln Val Thr Val Gln  Glu Phe Ala Leu Phe  Phe Thr Ile
        995                 1000                 1005

Phe Asp  Glu Thr Lys Ser Trp  Tyr Phe Thr Glu Asn  Met Glu Arg
    1010                 1015                 1020

Asn Cys  Arg Ala Pro Cys Asn  Ile Gln Met Glu Asp  Pro Thr Phe
    1025                 1030                 1035

Lys Glu  Asn Tyr Arg Phe His  Ala Ile Asn Gly Tyr  Ile Met Asp
    1040                 1045                 1050

Thr Leu  Pro Gly Leu Val Met  Ala Gln Asp Gln Arg  Ile Arg Trp
    1055                 1060                 1065

Tyr Leu  Leu Ser Met Gly Ser  Asn Glu Asn Ile His  Ser Ile His
    1070                 1075                 1080

Phe Ser  Gly His Val Phe Thr  Val Arg Lys Lys Glu  Glu Tyr Lys
    1085                 1090                 1095

Met Ala  Leu Tyr Asn Leu Tyr  Pro Gly Val Phe Glu  Thr Val Glu
    1100                 1105                 1110

Met Leu  Pro Ser Lys Ala Gly  Ile Trp Arg Val Glu  Cys Leu Ile
    1115                 1120                 1125

Gly Glu  His Leu His Ala Gly  Met Ser Thr Leu Phe  Leu Val Tyr
    1130                 1135                 1140

Ser Asn  Lys Cys Gln Thr Pro  Leu Gly Met Ala Ser  Gly His Ile
    1145                 1150                 1155

Arg Asp  Phe Gln Ile Thr Ala  Ser Gly Gln Tyr Gly  Gln Trp Ala
    1160                 1165                 1170

Pro Lys  Leu Ala Arg Leu His  Tyr Ser Gly Ser Ile  Asn Ala Trp
    1175                 1180                 1185

Ser Thr  Lys Glu Pro Phe Ser  Trp Ile Lys Val Asp  Leu Leu Ala
    1190                 1195                 1200

Pro Met  Ile Ile His Gly Ile  Lys Thr Gln Gly Ala  Arg Gln Lys
    1205                 1210                 1215

Phe Ser  Ser Leu Tyr Ile Ser  Gln Phe Ile Ile Met  Tyr Ser Leu
    1220                 1225                 1230

Asp Gly  Lys Lys Trp Gln Thr  Tyr Arg Gly Asn Ser  Thr Gly Thr
    1235                 1240                 1245

Leu Met  Val Phe Phe Gly Asn  Val Asp Ser Ser Gly  Ile Lys His
    1250                 1255                 1260

Asn Ile  Phe Asn Pro Pro Ile  Ile Ala Arg Tyr Ile  Arg Leu His
    1265                 1270                 1275

Pro Thr  His Tyr Ser Ile Arg  Ser Thr Leu Arg Met  Glu Leu Met
    1280                 1285                 1290

Gly Cys  Asp Leu Asn Ser Cys  Ser Met Pro Leu Gly  Met Glu Ser
    1295                 1300                 1305

Lys Ala  Ile Ser Asp Ala Gln  Ile Thr Ala Ser Ser  Tyr Phe Thr
    1310                 1315                 1320

Asn Met  Phe Ala Thr Trp Ser  Pro Ser Lys Ala Arg  Leu His Leu
    1325                 1330                 1335

Gln Gly  Arg Ser Asn Ala Trp  Arg Pro Gln Val Asn  Asn Pro Lys
    1340                 1345                 1350
```

Glu Trp Leu Gln Val Asp Phe Gln Lys Thr Met Lys Val Thr Gly
1355 1360 1365

Val Thr Thr Gln Gly Val Lys Ser Leu Leu Thr Ser Met Tyr Val
1370 1375 1380

Lys Glu Phe Leu Ile Ser Ser Ser Gln Asp Gly His Gln Trp Thr
1385 1390 1395

Leu Phe Phe Gln Asn Gly Lys Val Lys Val Phe Gln Gly Asn Gln
1400 1405 1410

Asp Ser Phe Thr Pro Val Val Asn Ser Leu Asp Pro Pro Leu Leu
1415 1420 1425

Thr Arg Tyr Leu Arg Ile His Pro Gln Ser Trp Val His Gln Ile
1430 1435 1440

Ala Leu Arg Met Glu Val Leu Gly Cys Glu Ala Gln Asp Leu Tyr
1445 1450 1455

<210> SEQ ID NO 105
<211> LENGTH: 1458
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

Met Gln Ile Glu Leu Ser Thr Cys Phe Phe Leu Cys Leu Leu Arg Phe
1 5 10 15

Cys Phe Ser Ala Thr Arg Arg Tyr Tyr Leu Gly Ala Val Glu Leu Ser
20 25 30

Trp Asp Tyr Met Gln Ser Asp Leu Gly Glu Leu Pro Val Asp Ala Arg
35 40 45

Phe Pro Pro Arg Val Pro Lys Ser Phe Pro Phe Asn Thr Ser Val Val
50 55 60

Tyr Lys Lys Thr Leu Phe Val Glu Phe Thr Asp His Leu Phe Asn Ile
65 70 75 80

Ala Lys Pro Arg Pro Pro Trp Met Gly Leu Leu Gly Pro Thr Ile Gln
85 90 95

Ala Glu Val Tyr Asp Thr Val Val Ile Thr Leu Lys Asn Met Ala Ser
100 105 110

His Pro Val Ser Leu His Ala Val Gly Val Ser Tyr Trp Lys Ala Ser
115 120 125

Glu Gly Ala Glu Tyr Asp Asp Gln Thr Ser Gln Arg Glu Lys Glu Asp
130 135 140

Asp Lys Val Phe Pro Gly Gly Ser His Thr Tyr Val Trp Gln Val Leu
145 150 155 160

Lys Glu Asn Gly Pro Met Ala Ser Asp Pro Leu Cys Leu Thr Tyr Ser
165 170 175

Tyr Leu Ser His Val Asp Leu Val Lys Asp Leu Asn Ser Gly Leu Ile
180 185 190

Gly Ala Leu Leu Val Cys Arg Glu Gly Ser Leu Ala Lys Glu Lys Thr
195 200 205

Gln Thr Leu His Lys Phe Ile Leu Leu Phe Ala Val Phe Asp Glu Gly
210 215 220

Lys Ser Trp His Ser Glu Thr Lys Asn Ser Leu Met Gln Asp Arg Asp
225 230 235 240

Ala Ala Ser Ala Arg Ala Trp Pro Lys Met His Thr Val Asn Gly Tyr
245 250 255

```
Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670
```

-continued

```
Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Thr Thr Tyr Val Asn Arg Ser Leu Ser Gln Asn Pro Pro Val
        755                 760                 765

Leu Lys Arg His Gln Arg Glu Ile Thr Arg Thr Thr Leu Gln Ser Asp
    770                 775                 780

Gln Glu Glu Ile Asp Tyr Asp Asp Thr Ile Ser Val Glu Met Lys Lys
785                 790                 795                 800

Glu Asp Phe Asp Ile Tyr Asp Glu Asp Glu Asn Gln Ser Pro Arg Ser
                805                 810                 815

Phe Gln Lys Lys Thr Arg His Tyr Phe Ile Ala Ala Val Glu Arg Leu
            820                 825                 830

Trp Asp Tyr Gly Met Ser Ser Ser Pro His Val Leu Arg Asn Arg Ala
        835                 840                 845

Gln Ser Gly Ser Val Pro Gln Phe Lys Lys Val Val Phe Gln Glu Phe
    850                 855                 860

Thr Asp Gly Ser Phe Thr Gln Pro Leu Tyr Arg Gly Glu Leu Asn Glu
865                 870                 875                 880

His Leu Gly Leu Leu Gly Pro Tyr Ile Arg Ala Glu Val Glu Asp Asn
                885                 890                 895

Ile Met Val Thr Phe Arg Asn Gln Ala Ser Arg Pro Tyr Ser Phe Tyr
            900                 905                 910

Ser Ser Leu Ile Ser Tyr Glu Glu Asp Gln Arg Gln Gly Ala Glu Pro
        915                 920                 925

Arg Lys Asn Phe Val Lys Pro Asn Glu Thr Lys Thr Tyr Phe Trp Lys
    930                 935                 940

Val Gln His His Met Ala Pro Thr Lys Asp Glu Phe Asp Cys Lys Ala
945                 950                 955                 960

Trp Ala Tyr Phe Ser Asp Val Asp Leu Glu Lys Asp Val His Ser Gly
                965                 970                 975

Leu Ile Gly Pro Leu Leu Val Cys His Thr Asn Thr Leu Asn Pro Ala
            980                 985                 990

His Gly Arg Gln Val Thr Val Gln  Glu Phe Ala Leu Phe  Phe Thr Ile
        995                 1000                1005

Phe Asp  Glu Thr Lys Ser Trp  Tyr Phe Thr Glu Asn  Met Glu Arg
    1010                 1015                 1020

Asn Cys  Arg Ala Pro Cys Asn  Ile Gln Met Glu Asp  Pro Thr Phe
    1025                 1030                 1035

Lys Glu  Asn Tyr Arg Phe His  Ala Ile Asn Gly Tyr  Ile Met Asp
    1040                 1045                 1050

Thr Leu  Pro Gly Leu Val Met  Ala Gln Asp Gln Arg  Ile Arg Trp
    1055                 1060                 1065

Tyr Leu  Leu Ser Met Gly Ser  Asn Glu Asn Ile His  Ser Ile His
    1070                 1075                 1080

Phe Ser  Gly His Val Phe Thr  Val Arg Lys Lys Glu  Glu Tyr Lys
```

```
    1085                1090                1095

Met Ala  Leu Tyr Asn Leu Tyr  Pro Gly Val Phe Glu  Thr Val Glu
    1100                1105                1110

Met Leu  Pro Ser Lys Ala Gly  Ile Trp Arg Val Glu  Cys Leu Ile
    1115                1120                1125

Gly Glu  His Leu His Ala Gly  Met Ser Thr Leu Phe  Leu Val Tyr
    1130                1135                1140

Ser Asn  Lys Cys Gln Thr Pro  Leu Gly Met Ala Ser  Gly His Ile
    1145                1150                1155

Arg Asp  Phe Gln Ile Thr Ala  Ser Gly Gln Tyr Gly  Gln Trp Ala
    1160                1165                1170

Pro Lys  Leu Ala Arg Leu His  Tyr Ser Gly Ser Ile  Asn Ala Trp
    1175                1180                1185

Ser Thr  Lys Glu Pro Phe Ser  Trp Ile Lys Val Asp  Leu Leu Ala
    1190                1195                1200

Pro Met  Ile Ile His Gly Ile  Lys Thr Gln Gly Ala  Arg Gln Lys
    1205                1210                1215

Phe Ser  Ser Leu Tyr Ile Ser  Gln Phe Ile Ile Met  Tyr Ser Leu
    1220                1225                1230

Asp Gly  Lys Lys Trp Gln Thr  Tyr Arg Gly Asn Ser  Thr Gly Thr
    1235                1240                1245

Leu Met  Val Phe Phe Gly Asn  Val Asp Ser Ser Gly  Ile Lys His
    1250                1255                1260

Asn Ile  Phe Asn Pro Pro Ile  Ile Ala Arg Tyr Ile  Arg Leu His
    1265                1270                1275

Pro Thr  His Tyr Ser Ile Arg  Ser Thr Leu Arg Met  Glu Leu Met
    1280                1285                1290

Gly Cys  Asp Leu Asn Ser Cys  Ser Met Pro Leu Gly  Met Glu Ser
    1295                1300                1305

Lys Ala  Ile Ser Asp Ala Gln  Ile Thr Ala Ser Ser  Tyr Phe Thr
    1310                1315                1320

Asn Met  Phe Ala Thr Trp Ser  Pro Ser Lys Ala Arg  Leu His Leu
    1325                1330                1335

Gln Gly  Arg Ser Asn Ala Trp  Arg Pro Gln Val Asn  Asn Pro Lys
    1340                1345                1350

Glu Trp  Leu Gln Val Asp Phe  Gln Lys Thr Met Lys  Val Thr Gly
    1355                1360                1365

Val Thr  Thr Gln Gly Val Lys  Ser Leu Leu Thr Ser  Met Tyr Val
    1370                1375                1380

Lys Glu  Phe Leu Ile Ser Ser  Ser Gln Asp Gly His  Gln Trp Thr
    1385                1390                1395

Leu Phe  Phe Gln Asn Gly Lys  Val Lys Val Phe Gln  Gly Asn Gln
    1400                1405                1410

Asp Ser  Phe Thr Pro Val Val  Asn Ser Leu Asp Pro  Pro Leu Leu
    1415                1420                1425

Thr Arg  Tyr Leu Arg Ile His  Pro Gln Ser Trp Val  His Gln Ile
    1430                1435                1440

Ala Leu  Arg Met Glu Val Leu  Gly Cys Glu Ala Gln  Asp Leu Tyr
    1445                1450                1455
```

<210> SEQ ID NO 106
<211> LENGTH: 1457
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 106

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Val Thr Leu Lys Asn Met Ala Ser
            100                 105                 110

His Pro Val Ser Leu His Ala Val Gly Val Ser Tyr Trp Lys Ser Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Lys Ser His Thr Tyr Val Trp Gln Val Leu
145                 150                 155                 160

Lys Glu Asn Gly Pro Thr Ala Ser Asp Pro Pro Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Ser Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
```

-continued 385 390 395 400

Trp Val His Tyr Ile Ala Ala Glu Glu Glu Asp Trp Asp Tyr Ala Pro
405 410 415

Leu Val Leu Ala Pro Asp Asp Arg Ser Tyr Lys Ser Gln Tyr Leu Asn
420 425 430

Asn Gly Pro Gln Arg Ile Gly Arg Lys Tyr Lys Lys Val Arg Phe Met
435 440 445

Ala Tyr Thr Asp Glu Thr Phe Lys Thr Arg Glu Ala Ile Gln His Glu
450 455 460

Ser Gly Ile Leu Gly Pro Leu Leu Tyr Gly Glu Val Gly Asp Thr Leu
465 470 475 480

Leu Ile Ile Phe Lys Asn Gln Ala Ser Arg Pro Tyr Asn Ile Tyr Pro
485 490 495

His Gly Ile Thr Asp Val Arg Pro Leu Tyr Ser Arg Arg Leu Pro Lys
500 505 510

Gly Val Lys His Leu Lys Asp Phe Pro Ile Leu Pro Gly Glu Ile Phe
515 520 525

Lys Tyr Lys Trp Thr Val Thr Val Glu Asp Gly Pro Thr Lys Ser Asp
530 535 540

Pro Arg Cys Leu Thr Arg Tyr Tyr Ser Ser Phe Val Asn Met Glu Arg
545 550 555 560

Asp Leu Ala Ser Gly Leu Ile Gly Pro Leu Leu Ile Cys Tyr Lys Glu
565 570 575

Ser Val Asp Gln Arg Gly Asn Gln Ile Met Ser Asp Lys Arg Asn Val
580 585 590

Ile Leu Phe Ser Val Phe Asp Glu Asn Arg Ser Trp Tyr Leu Thr Glu
595 600 605

Asn Ile Gln Arg Phe Leu Pro Asn Pro Ala Gly Val Gln Leu Glu Asp
610 615 620

Pro Glu Phe Gln Ala Ser Asn Ile Met His Ser Ile Asn Gly Tyr Val
625 630 635 640

Phe Asp Ser Leu Gln Leu Ser Val Cys Leu His Glu Val Ala Tyr Trp
645 650 655

Tyr Ile Leu Ser Ile Gly Ala Gln Thr Asp Phe Leu Ser Val Phe Phe
660 665 670

Ser Gly Tyr Thr Phe Lys His Lys Met Val Tyr Glu Asp Thr Leu Thr
675 680 685

Leu Phe Pro Phe Ser Gly Glu Thr Val Phe Met Ser Met Glu Asn Pro
690 695 700

Gly Leu Trp Ile Leu Gly Cys His Asn Ser Asp Phe Arg Asn Arg Gly
705 710 715 720

Met Thr Ala Leu Leu Lys Val Ser Ser Cys Asp Lys Asn Thr Gly Asp
725 730 735

Tyr Tyr Glu Asp Ser Tyr Glu Asp Ile Ser Ala Tyr Leu Leu Ser Lys
740 745 750

Asn Asn Ala Ile Glu Pro Arg Ser Phe Ser Gln Asn Pro Pro Val Leu
755 760 765

Lys Arg His Gln Arg Glu Ile Thr Arg Thr Thr Leu Gln Ser Asp Gln
770 775 780

Glu Glu Ile Asp Tyr Asp Asp Thr Ile Ser Val Glu Met Lys Lys Glu
785 790 795 800

Asp Phe Asp Ile Tyr Asp Glu Asp Glu Asn Gln Ser Pro Arg Ser Phe
805 810 815

```
Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                 1005

Asp Glu  Thr Lys Ser Trp Tyr  Phe Thr Glu Asn Met  Glu Arg Asn
    1010                 1015                 1020

Cys Arg  Ala Pro Cys Asn Ile  Gln Met Glu Asp Pro  Thr Phe Lys
    1025                 1030                 1035

Glu Asn  Tyr Arg Phe His Ala  Ile Asn Gly Tyr Ile  Met Asp Thr
    1040                 1045                 1050

Leu Pro  Gly Leu Val Met Ala  Gln Asp Gln Arg Ile  Arg Trp Tyr
    1055                 1060                 1065

Leu Leu  Ser Met Gly Ser Asn  Glu Asn Ile His Ser  Ile His Phe
    1070                 1075                 1080

Ser Gly  His Val Phe Thr Val  Arg Lys Lys Glu Glu  Tyr Lys Met
    1085                 1090                 1095

Ala Leu  Tyr Asn Leu Tyr Pro  Gly Val Phe Glu Thr  Val Glu Met
    1100                 1105                 1110

Leu Pro  Ser Lys Ala Gly Ile  Trp Arg Val Glu Cys  Leu Ile Gly
    1115                 1120                 1125

Glu His  Leu His Ala Gly Met  Ser Thr Leu Phe Leu  Val Tyr Ser
    1130                 1135                 1140

Asn Lys  Cys Gln Thr Pro Leu  Gly Met Ala Ser Gly  His Ile Arg
    1145                 1150                 1155

Asp Phe  Gln Ile Thr Ala Ser  Gly Gln Tyr Gly Gln  Trp Ala Pro
    1160                 1165                 1170

Lys Leu  Ala Arg Leu His Tyr  Ser Gly Ser Ile Asn  Ala Trp Ser
    1175                 1180                 1185

Thr Lys  Glu Pro Phe Ser Trp  Ile Lys Val Asp Leu  Leu Ala Pro
    1190                 1195                 1200

Met Ile  Ile His Gly Ile Lys  Thr Gln Gly Ala Arg  Gln Lys Phe
    1205                 1210                 1215
```

-continued

Ser Ser Leu Tyr Ile Ser Gln Phe Ile Ile Met Tyr Ser Leu Asp
1220 1225 1230

Gly Lys Lys Trp Gln Thr Tyr Arg Gly Asn Ser Thr Gly Thr Leu
1235 1240 1245

Met Val Phe Phe Gly Asn Val Asp Ser Ser Gly Ile Lys His Asn
1250 1255 1260

Ile Phe Asn Pro Pro Ile Ile Ala Arg Tyr Ile Arg Leu His Pro
1265 1270 1275

Thr His Tyr Ser Ile Arg Ser Thr Leu Arg Met Glu Leu Met Gly
1280 1285 1290

Cys Asp Leu Asn Ser Cys Ser Met Pro Leu Gly Met Glu Ser Lys
1295 1300 1305

Ala Ile Ser Asp Ala Gln Ile Thr Ala Ser Ser Tyr Phe Thr Asn
1310 1315 1320

Met Phe Ala Thr Trp Ser Pro Ser Lys Ala Arg Leu His Leu Gln
1325 1330 1335

Gly Arg Ser Asn Ala Trp Arg Pro Gln Val Asn Asn Pro Lys Glu
1340 1345 1350

Trp Leu Gln Val Asp Phe Gln Lys Thr Met Lys Val Thr Gly Val
1355 1360 1365

Thr Thr Gln Gly Val Lys Ser Leu Leu Thr Ser Met Tyr Val Lys
1370 1375 1380

Glu Phe Leu Ile Ser Ser Ser Gln Asp Gly His Gln Trp Thr Leu
1385 1390 1395

Phe Phe Gln Asn Gly Lys Val Lys Val Phe Gln Gly Asn Gln Asp
1400 1405 1410

Ser Phe Thr Pro Val Val Asn Ser Leu Asp Pro Pro Leu Leu Thr
1415 1420 1425

Arg Tyr Leu Arg Ile His Pro Gln Ser Trp Val His Gln Ile Ala
1430 1435 1440

Leu Arg Met Glu Val Leu Gly Cys Glu Ala Gln Asp Leu Tyr
1445 1450 1455

<210> SEQ ID NO 107
<211> LENGTH: 1457
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 107

Met Gln Ile Glu Leu Ser Thr Cys Phe Phe Leu Cys Leu Leu Arg Phe
1 5 10 15

Cys Phe Ser Ala Thr Arg Arg Tyr Tyr Leu Gly Ala Val Glu Leu Ser
20 25 30

Trp Asp Tyr Met Gln Ser Asp Leu Gly Glu Leu Pro Val Asp Ala Arg
35 40 45

Phe Pro Pro Arg Val Pro Lys Ser Phe Pro Phe Asn Thr Ser Val Val
50 55 60

Tyr Lys Lys Thr Leu Phe Val Glu Phe Thr Asp His Leu Phe Asn Ile
65 70 75 80

Ala Lys Pro Arg Pro Pro Trp Met Gly Leu Leu Gly Pro Thr Ile Gln
85 90 95

Ala Glu Val Tyr Asp Thr Val Val Val Thr Leu Lys Asn Met Ala Ser
100 105 110

-continued

```
His Pro Val Ser Leu His Ala Val Gly Val Ser Tyr Trp Lys Ser Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Lys Ser His Thr Tyr Val Trp Gln Val Leu
145                 150                 155                 160

Lys Glu Asn Gly Pro Thr Ala Ser Asp Pro Pro Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Ser Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525
```

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp

-continued

```
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                 1015                1020

Cys Arg  Ala Pro Cys Asn Ile  Gln Met Glu Asp Pro  Thr Phe Lys
    1025                 1030                1035

Glu Asn  Tyr Arg Phe His Ala  Ile Asn Gly Tyr Ile  Met Asp Thr
    1040                 1045                1050

Leu Pro  Gly Leu Val Met Ala  Gln Asp Gln Arg Ile  Arg Trp Tyr
    1055                 1060                1065

Leu Leu  Ser Met Gly Ser Asn  Glu Asn Ile His Ser  Ile His Phe
    1070                 1075                1080

Ser Gly  His Val Phe Thr Val  Arg Lys Lys Glu Glu  Tyr Lys Met
    1085                 1090                1095

Ala Leu  Tyr Asn Leu Tyr Pro  Gly Val Phe Glu Thr  Val Glu Met
    1100                 1105                1110

Leu Pro  Ser Lys Ala Gly Ile  Trp Arg Val Glu Cys  Leu Ile Gly
    1115                 1120                1125

Glu His  Leu His Ala Gly Met  Ser Thr Leu Phe Leu  Val Tyr Ser
    1130                 1135                1140

Asn Lys  Cys Gln Thr Pro Leu  Gly Met Ala Ser Gly  His Ile Arg
    1145                 1150                1155

Asp Phe  Gln Ile Thr Ala Ser  Gly Gln Tyr Gly Gln  Trp Ala Pro
    1160                 1165                1170

Lys Leu  Ala Arg Leu His Tyr  Ser Gly Ser Ile Asn  Ala Trp Ser
    1175                 1180                1185

Thr Lys  Glu Pro Phe Ser Trp  Ile Lys Val Asp Leu  Leu Ala Pro
    1190                 1195                1200

Met Ile  Ile His Gly Ile Lys  Thr Gln Gly Ala Arg  Gln Lys Phe
    1205                 1210                1215

Ser Ser  Leu Tyr Ile Ser Gln  Phe Ile Ile Met Tyr  Ser Leu Asp
    1220                 1225                1230

Gly Lys  Lys Trp Gln Thr Tyr  Arg Gly Asn Ser Thr  Gly Thr Leu
    1235                 1240                1245

Met Val  Phe Phe Gly Asn Val  Asp Ser Ser Gly Ile  Lys His Asn
    1250                 1255                1260

Ile Phe  Asn Pro Pro Ile Ile  Ala Arg Tyr Ile Arg  Leu His Pro
    1265                 1270                1275

Thr His  Tyr Ser Ile Arg Ser  Thr Leu Arg Met Glu  Leu Met Gly
    1280                 1285                1290

Cys Asp  Leu Asn Ser Cys Ser  Met Pro Leu Gly Met  Glu Ser Lys
    1295                 1300                1305

Ala Ile  Ser Asp Ala Gln Ile  Thr Ala Ser Ser Tyr  Phe Thr Asn
    1310                 1315                1320

Met Phe  Ala Thr Trp Ser Pro  Ser Lys Ala Arg Leu  His Leu Gln
    1325                 1330                1335

Gly Arg  Ser Asn Ala Trp Arg  Pro Gln Val Asn Asn  Pro Lys Glu
    1340                 1345                1350
```

```
Trp Leu  Gln Val Asp Phe Gln  Lys Thr Met Lys Val  Thr Gly Val
    1355                 1360                 1365

Thr Thr  Gln Gly Val Lys Ser  Leu Leu Thr Ser Met  Tyr Val Lys
    1370                 1375                 1380

Glu Phe  Leu Ile Ser Ser Ser  Gln Asp Gly His Gln  Trp Thr Leu
    1385                 1390                 1395

Phe Phe  Gln Asn Gly Lys Val  Lys Val Phe Gln Gly  Asn Gln Asp
    1400                 1405                 1410

Ser Phe  Thr Pro Val Val Asn  Ser Leu Asp Pro Pro  Leu Leu Thr
    1415                 1420                 1425

Arg Tyr  Leu Arg Ile His Pro  Gln Ser Trp Val His  Gln Ile Ala
    1430                 1435                 1440

Leu Arg  Met Glu Val Leu Gly  Cys Glu Ala Gln Asp  Leu Tyr
    1445                 1450                 1455


<210> SEQ ID NO 108
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108

atgcagattg agctgtccac ctgcttcttt ctgtgcctgc tgagattctg cttctctgcc     60

accaggagat actacctggg ggctgtggaa ctttcttggg actacatgca gtctgacctg    120

ggagagctgc ctgtggatgc caggttccca cccagagtgc ccaagtcctt cccattcaac    180

acctctgtgg tctacaagaa gacactcttt gtggaattca ctgaccacct gttcaacatt    240

gcaaaaccca gaccaccctg gatgggactc ctgggaccca ccattcaggc tgaggtgtat    300

gacactgtgg tcgtcaccct caagaacatg gcatcccacc ctgtgtctct gcatgctgtg    360

ggagtctcat actggaaatc ctctgaaggg gctgagtatg atgaccagac atcccagaga    420

gagaaagagg atgacaaggt gttccctggg aagtctcaca cctatgtgtg gcaagtcctc    480

aaggagaatg gacccactgc atctgaccca ccctgcctga catactccta cctttctcat    540

gtggacctgg tcaaggacct caactctgga ctgattgggg cactgctggt gtgcagggaa    600

ggatccctgg ccaaggagaa aacccagaca ctgcacaagt tcattctcct gtttgctgtc    660

tttgatgagg gcaagtcttg gcactctgaa acaaagaact ccctgatgca agacagggat    720

gctgcctctg ccagggcatg gcccaagatg cacactgtga atggctatgt gaacagatca    780

ctgcctggac tcattggctg ccacaggaaa tctgtctact ggcatgtgat tggcatgggg    840

acaacccctg aagtgcactc cattttcctg gagggacaca ccttcctggt caggaaccac    900

agacaagcct ctctggagat ctctcccatc accttcctca ctgcacagac actgctgatg    960

gaccttggac agttcctgct gtcctgccac atctcttccc accagcatga tggcatggaa   1020

gcctatgtca aggtggactc atgccctgag gaaccacagc tcaggatgaa gaacaatgag   1080

gaggctgagg actatgatga tgacctgact gactctgaga tggatgtggt cagatttgat   1140

gatgacaact ctccatcctt cattcagatc aggtctgtgg caaagaaaca ccccaagaca   1200

tgggtgcact acattgctgc tgaggaagag gactgggact atgcaccact ggtcctggcc   1260

cctgatgaca ggagctacaa gtctcagtac ctcaacaatg gcccacaaag aattggaaga   1320

aagtacaaga aagtcagatt catggcctac actgatgaaa ccttcaagac aagagaagcc   1380
```

-continued

```
attcagcatg agtctggcat tctgggacca ctcctgtatg gggaagtggg agacaccctg   1440
ctcatcatct tcaagaacca ggcctccagg ccctacaaca tctacccaca tggcatcact   1500
gatgtcaggc ccctgtacag caggagactg ccaaaagggg tgaaacacct caaggacttc   1560
cccattctgc ctggagagat cttcaagtac aagtggactg tcactgtgga ggatggacca   1620
acaaagtctg accccaggtg cctcaccaga tactactcct cttttgtgaa catggagaga   1680
gacctggcat ctggactgat tggaccactg ctcatctgct acaaggagtc tgtggaccag   1740
agaggcaacc agatcatgtc tgacaagaga aatgtgattc tgttctctgt ctttgatgag   1800
aacagatcat ggtacctgac tgagaacatt cagagattcc tgcccaaccc tgctggggtg   1860
caactggaag accctgagtt ccaggcaagc aacatcatgc actccatcaa tggctatgtg   1920
tttgactctc tccagctttc tgtctgcctg catgaggtgg cctactggta cattctttct   1980
attggggcac aaactgactt cctttctgtc ttcttctctg gatacacctt caagcacaag   2040
atggtgtatg aggacaccct gacactcttc ccattctctg ggaaactgt gttcatgagc   2100
atggagaacc ctggactgtg gattctggga tgccacaact ctgacttcag aaacagggga   2160
atgactgcac tgctcaaagt ctcctcctgt gacaagaaca ctggggacta ctatgaggac   2220
tcttatgagg acatctctgc ctacctgctc agcaagaaca atgccattga gcccagaagc   2280
ttctctcaga atccacctgt cctgaagaga caccagagag agatcaccag gacaaccctc   2340
cagtctgacc aggaagagat tgactatgat gacaccattt ctgtggagat gaagaaggag   2400
gactttgaca tctatgatga ggacgagaac cagtctccaa gatcattcca gaagaagaca   2460
agacactact tcattgctgc tgtggaaaga ctgtgggact atggcatgtc ttcctctccc   2520
catgtcctca ggaacagggc acagtctggc tctgtgccac agttcaagaa agtggtcttc   2580
caggagttca ctgatggctc attcacccag cccctgtaca gaggggaact gaatgagcac   2640
ctgggactcc tgggaccata catcagggct gaggtggaag acaacatcat ggtgacattc   2700
agaaaccagg cctccaggcc ctacagcttc tactcttccc tcatcagcta tgaggaagac   2760
cagagacaag gggctgagcc aagaaagaac tttgtgaaac ccaatgaaac caagacctac   2820
ttctggaaag tccagcacca catggcaccc accaaggatg agtttgactg caaggcctgg   2880
gcatacttct ctgatgtgga cctggagaaa gatgtgcact ctggcctgat tggcccactc   2940
ctggtctgcc acaccaacac cctgaaccct gcacatggaa ggcaagtgac tgtgcaggag   3000
tttgccctct tcttcaccat ctttgatgaa accaagtcat ggtacttcac tgagaacatg   3060
gagagaaact gcagagcacc atgcaacatt cagatggaag accccacctt caaggagaac   3120
tacaggttcc atgccatcaa tggctacatc atggacaccc tgcctgggct tgtcatggca   3180
caggaccaga gaatcagatg gtacctgctt tctatgggat ccaatgagaa cattcactcc   3240
atccacttct ctgggcatgt cttcactgtg agaaagaagg aggaatacaa gatggccctg   3300
tacaacctct accctggggt ctttgagact gtggagatgc tgccctccaa agctggcatc   3360
tggagggtgg aatgcctcat tggggagcac ctgcatgctg gcatgtcaac cctgttcctg   3420
gtctacagca acaagtgcca gacacccctg ggaatggcct ctggccacat cagggacttc   3480
cagatcactg cctctggcca gtatggccag tgggcaccca aactggccag gctccactac   3540
tctggctcca tcaatgcatg gtcaaccaag gagccattct cttggatcaa ggtggacctg   3600
ctggcaccca tgatcattca tggcatcaag acacaggggg caagacagaa attctcctct   3660
ctgtacatct cacagttcat catcatgtac tctctggatg gcaagaagtg gcagacatac   3720
agaggcaact ccactggcac cctcatggtc ttctttggca atgtggacag ctctggcatc   3780
```

```
aagcacaaca tcttcaaccc tcccatcatt gccagataca tcaggctgca ccccacccac   3840

tactcaatca gatcaaccct caggatggaa ctgatgggat gtgacctgaa ctcctgctca   3900

atgcccctgg gaatggagag caaggccatt tctgatgccc agatcactgc atcctcttac   3960

ttcaccaaca tgtttgccac ctggtcacca tcaaaagcca ggctgcacct ccagggaaga   4020

agcaatgcct ggagacccca ggtcaacaac ccaaaggaat ggctgcaagt ggacttccag   4080

aagacaatga aagtcactgg ggtgacaacc caggggggtca agtctctgct cacctcaatg   4140

tatgtgaagg agttcctgat ctcttcctca caggatggcc accagtggac actcttcttc   4200

cagaatggca aagtcaaggt gttccagggc aaccaggact ctttcacacc tgtggtgaac   4260

tcactggacc cccccctcct gacaagatac ctgagaattc acccccagtc ttgggtccac   4320

cagattgccc tgagaatgga agtcctggga tgtgaggcac aagacctgta ctga         4374
```

<210> SEQ ID NO 109
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109

```
atgcagattg agctgagcac ctgcttcttc ctgtgcctgc tgaggttctg cttctctgcc     60

accaggagat actacctggg ggctgtggag ctttcttggg actacatgca gtctgacctg    120

ggggagctgc ctgtggatgc caggttccca cccagagtgc ccaaatcctt cccattcaac    180

acctctgtgg tctacaagaa gaccctcttt gtggagttca ctgaccacct gttcaacatt    240

gccaaaccca ggccaccctg gatgggactc ctgggaccca ccattcaggc tgaggtgtat    300

gacactgtgg tcgtcaccct caagaacatg gcctcccacc ctgtgagcct gcatgctgtg    360

ggggtcagct actggaagtc ctctgagggg gctgagtatg atgaccagac ctcccagagg    420

gagaaggagg atgacaaagt gttccctggg aagagccaca cctatgtgtg gcaggtcctc    480

aaggagaatg gccccactgc ctctgaccca ccctgcctga cctactccta cctttctcat    540

gtggacctgg tcaaggacct caactctgga ctgattgggg ccctgctggt gtgcagggag    600

ggctccctgg ccaaagagaa gacccagacc ctgcacaagt tcattctcct gtttgctgtc    660

tttgatgagg gcaagagctg gcactctgaa accaagaact ccctgatgca ggacagggat    720

gctgcctctg ccagggcctg gcccaagatg cacactgtga atggctatgt gaacaggagc    780

ctgcctggac tcattggctg ccacaggaaa tctgtctact ggcatgtgat tggcatgggg    840

acaacccctg aggtgcactc cattttcctg gagggccaca ccttcctggt caggaaccac    900

agacaggcca gcctggagat cagccccatc accttcctca ctgcccagac cctgctgatg    960

gacctcggac agttcctgct gtcctgccac atcagctccc accagcatga tggcatggag   1020

gcctatgtca aggtggacag ctgccctgag gagccacagc tcaggatgaa gaacaatgag   1080

gaggctgagg actatgatga tgacctgact gactctgaga tggatgtggt ccgctttgat   1140

gatgacaaca gcccatcctt cattcagatc aggtctgtgg ccaagaaaca ccccaagacc   1200

tgggtgcact acattgctgc tgaggaggag gactgggact atgcccccact ggtcctggcc   1260

cctgatgaca ggagctacaa gagccagtac ctcaacaatg gcccacagag gattggacgc   1320

aagtacaaga aagtcaggtt catggcctac actgatgaaa ccttcaagac cagggaggcc   1380

attcagcatg agtctggcat cctgggccca ctcctgtatg ggaggtgggg ggacaccctg   1440
```

ctcatcatct tcaagaacca ggcctccagg ccctacaaca tctacccaca tggcatcact 1500
gatgtcaggc ccctgtacag ccgcaggctg ccaaaggggg tgaaacacct caaggacttc 1560
cccattctgc ctggggagat cttcaagtac aagtggactg tcactgtgga ggatggacca 1620
accaaatctg accccaggtg cctcaccaga tactactcca gctttgtgaa catggagagg 1680
gacctggcct ctggcctgat tggcccactg ctcatctgct acaaggagtc tgtggaccag 1740
aggggaaacc agatcatgtc tgacaagagg aatgtgattc tgttctctgt ctttgatgag 1800
aacaggagct ggtacctgac tgagaacatt cagcgcttcc tgcccaaccc tgctggggtg 1860
cagctggagg accctgagtt ccaggccagc aacatcatgc actccatcaa tggctatgtg 1920
tttgacagcc tccagctttc tgtctgcctg catgaggtgg cctactggta cattctttct 1980
attggggccc agactgactt cctttctgtc ttcttctctg gctacacctt caaacacaag 2040
atggtgtatg aggacaccct gaccctcttc ccattctctg ggagactgt gttcatgagc 2100
atggagaacc ctggcctgtg gattctggga tgccacaact ctgacttccg caacaggggc 2160
atgactgccc tgctcaaagt ctcctcctgt gacaagaaca ctggggacta ctatgaggac 2220
agctatgagg acatctctgc ctacctgctc agcaagaaca atgccattga gcccaggagc 2280
ttcagccaga atccacctgt cctgaaacgc caccagaggg agatcaccag gaccaccctc 2340
cagtctgacc aggaggagat tgactatgat gacaccattt ctgtggagat gaagaaagag 2400
gactttgaca tctatgacga ggacgagaac cagagcccaa ggagcttcca gaagaagacc 2460
aggcactact tcattgctgc tgtggagcgc ctgtgggact atggcatgag ctccagcccc 2520
catgtcctca ggaacagggc ccagtctggc tctgtgccac agttcaagaa agtggtcttc 2580
caagagttca ctgatggcag cttcacccag cccctgtaca gaggggagct gaatgagcac 2640
ctgggactcc tgggcccata catcagggct gaggtggagg acaacatcat ggtgaccttc 2700
cgcaaccagg cctccaggcc ctacagcttc tacagctccc tcatcagcta tgaggaggac 2760
cagaggcagg gggctgagcc acgcaagaac tttgtgaaac ccaatgaaac caagacctac 2820
ttctggaaag tccagcacca catggccccc accaaggatg agtttgactg caaggcctgg 2880
gcctacttct ctgatgtgga cctggagaag gatgtgcact ctggcctgat tggcccactc 2940
ctggtctgcc acaccaacac cctgaaccct gcccatggaa ggcaagtgac tgtgcaggag 3000
tttgccctct tcttcaccat ctttgatgaa accaagagct ggtacttcac tgagaacatg 3060
gagcgcaact gcagggcccc atgcaacatt cagatggagg accccacctt caaagagaac 3120
taccgcttcc atgccatcaa tggctacatc atggacaccc tgcctgggct tgtcatggcc 3180
caggaccaga ggatcaggtg gtacctgctt tctatgggct ccaatgagaa cattcactcc 3240
atccacttct ctgggcatgt cttcactgtg cgcaagaagg aggagtacaa gatggccctg 3300
tacaacctct accctggggt ctttgagact gtggagatgc tgccctccaa agctggcatc 3360
tggagggtgg agtgcctcat tggggagcac ctgcatgctg gcatgagcac cctgttcctg 3420
gtctacagca acaagtgcca gaccccccctg ggaatggcct ctggccacat cagggacttc 3480
cagatcactg cctctggcca gtatggccag tgggccccca agctggccag gctccactac 3540
tctggatcca tcaatgcctg gagcaccaag gagccattca gctggatcaa agtggacctg 3600
ctggccccca tgatcatcca tggcatcaag acccaggggg ccaggcagaa gttctccagc 3660
ctgtacatca gccagttcat catcatgtac agcctggatg gcaagaaatg gcagacctac 3720
agaggcaact ccactggaac actcatggtc ttctttggca atgtggacag ctctggcatc 3780

-continued

| | |
|---|---|
| aagcacaaca tcttcaaccc cccaatcatc gccagataca tcaggctgca ccccacccac | 3840 |
| tacagcatcc gcagcaccct caggatggag ctgatgggct gtgacctgaa ctcctgcagc | 3900 |
| atgcccctgg gcatggagag caaggccatt tctgatgccc agatcactgc ctccagctac | 3960 |
| ttcaccaaca tgtttgccac ctggagccca agcaaggcca ggctgcacct ccagggaagg | 4020 |
| agcaatgcct ggaggcccca ggtcaacaac ccaaaggagt ggctgcaggt ggacttccag | 4080 |
| aagaccatga aggtcactgg ggtgaccacc cagggggtca agagcctgct caccagcatg | 4140 |
| tatgtgaagg agttcctgat cagctccagc caggatggcc accagtggac cctcttcttc | 4200 |
| cagaatggca aggtcaaggt gttccagggc aaccaggaca gcttcacccc tgtggtgaac | 4260 |
| agcctggacc ccccctcct gaccagatac ctgaggattc acccccagag ctgggtccac | 4320 |
| cagattgccc tgaggatgga ggtcctggga tgtgaggccc aggacctgta ctga | 4374 |

VIRAL VECTORS ENCODING RECOMBINANT FVIII VARIANTS WITH INCREASED EXPRESSION FOR GENE THERAPY OF HEMOPHILIA A

CROSS REFERENCE TO RELATED APPLICATIONS

This application is a Continuation of U.S. application Ser. No. 15/349,930, filed Nov. 11, 2016, which claims priority to U.S. Provisional Patent Application No. 62/255,317, filed Nov. 13, 2015, the content of which are hereby incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Nov. 9, 2016, is named 008073_5107_US02_Sequence_Listing.txt and is 345 KB bytes in size.

BACKGROUND OF THE DISCLOSURE

Blood coagulation proceeds through a complex and dynamic biological pathway of interdependent biochemical reactions, referred to as the coagulation cascade. Coagulation Factor VIII (FVIII) is a key component in the cascade. Factor VIII is recruited to bleeding sites, and forms a Xase complex with activated Factor IX (FIXa) and Factor X (FX). The Xase complex activates FX, which in turn activates prothrombin to thrombin, which then activates other components in the coagulation cascade to generate a stable clot (reviewed in Saenko et al., *Trends Cardiovasc. Med.,* 9:185-192 (1999); Lenting et al., *Blood,* 92:3983-3996 (1998)).

Hemophilia A is a congenital X-linked bleeding disorder characterized by a deficiency in Factor VIII activity. Diminished Factor VIII activity inhibits a positive feedback loop in the coagulation cascade. This causes incomplete coagulation, which manifests as bleeding episodes with increased duration, extensive bruising, spontaneous oral and nasal bleeding, joint stiffness and chronic pain, and possibly internal bleeding and anemia in severe cases (Zhang et al., *Clinic. Rev. Allerg. Immunol.,* 37:114-124 (2009)).

Conventionally, hemophilia A is treated by Factor VIII replacement therapy, which consists of administering Factor VIII protein (e.g., plasma-derived or recombinantly-produced Factor VIII) to an individual with hemophilia A. Factor VIII is administered prophylactically to prevent or reduce frequency of bleeding episodes, in response to an acute bleeding episode, and/or perioperatively to manage bleeding during surgery. However, there are several undesirable features of Factor VIII replacement therapy.

First, Factor VIII replacement therapy is used to treat or manage hemophilia A, but does not cure the underlying Factor VIII deficiency. Because of this, individuals with hemophilia A require Factor VIII replacement therapy for the duration of their lives. Continuous treatment is expensive and requires the individual to maintain strict compliance, as missing only a few prophylactic doses can have serious consequences for individuals with severe hemophilia A.

Second, because Factor VIII has a relatively short half-life in vivo, conventional prophylactic Factor VIII replacement therapy requires administration every second or third day. This places a burden on the individual to maintain compliance throughout their life. While third generation "long-acting" Factor VIII drugs may reduce the frequency of administration, prophylactic Factor FVIII replacement therapy with these drugs still requires monthly, weekly, or more frequent administration in perpetuity. For example, prophylactic treatment with ELOCTATE™ [Antihemophilic Factor (Recombinant), Fc Fusion Protein] requires administration every three to five days (ELOCTATE™ Prescribing Information, Biogen Idec Inc., (2015)). Moreover, the long-term effects of chemically modified biologics (e.g., pegylated polypeptides) are not yet fully understood.

Third, between 15% and 30% of all individuals receiving Factor VIII replacement therapy form anti-Factor VIII inhibitor antibodies, rendering the therapy inefficient. Factor VIII bypass therapy (e.g., administration of plasma-derived or recombinantly-produced prothrombin complex concentrates) can be used to treat hemophilia in individuals that form inhibitor antibodies. However, Factor VIII bypass therapy is less effective than Factor VIII replacement therapy (Mannucci P. M., J Thromb Haemost., 1(7):1349-55 (2003)) and may be associated with an increased risk of cardiovascular complication (Luu and Ewenstein, Haemophilia, 10 Suppl. 2:10-16 (2004)).

Somatic gene therapy holds great promise for the treatment of hemophilia A because it would remedy the underlying under-expression functional Factor VIII activity (e.g., due to missense or nonsense mutations), rather than provide a one-time dose of Factor VIII activity to the individual. Because of this difference in the mechanism of action, as compared to Factor VIII replacement therapy, one-time administration of a Factor VIII gene therapy vector may provide an individual with Factor VIII for several years, reducing the cost of treatment and eliminating the need for continued patient compliance.

Coagulation Factor IX (FIX) gene therapy has been used effectively to treat individuals with hemophilia B, a related blood coagulation condition characterized by diminished Factor IX activity (Manno C. S., et al., Nat Med., 12(3): 342-47 (2006)). However, Factor VIII gene therapy presents several unique challenges. For example, the full-length, wild-type Factor VIII polypeptide (2351 amino acids; UniProt accession number P00451) is five times larger than the full-length, wild-type Factor IX polypeptide (461 amino acids; UniProt accession number P00740). As such, the coding sequence of wild-type Factor VIII is 7053 base pairs, which is too large to be packaged in conventional AAV gene therapy vectors. Further, reported recombinant expression of B-domain deleted variants of Factor VIII (BDD-FVIII) has been poor. As such, several groups have attempted to alter the codon usage of BDD-FVIII constructs, with limited success.

BRIEF SUMMARY OF DISCLOSURE

Accordingly, there is a need for Factor VIII variants whose coding sequences are more efficiently packaged into, and delivered via, gene therapy vectors. There is also a need for synthetic, codon-altered nucleic acids which express Factor VIII more efficiently. Such Factor VIII variants and codon-altered nucleic acids allow for improved treatment of Factor VIII deficiencies (e.g., hemophilia A). The above deficiencies and other problems associated with the treatment of Factor VIII deficiencies (e.g., hemophilia A) are reduced or eliminated by the disclosed codon-altered Factor VIII variants.

In accordance with some embodiments, the present disclosure provides nucleic acids encoding Factor VIII variants that have high sequence identity to the disclosed codon-altered sequences of the Factor VIII heavy chain (e.g., CS01-HC-NA, CS04-HC-NA, or CS23-HC-NA) and light chain (CS01-LC-NA, CS04-LC-NA, or CS23-LC-NA). In some embodiments, these nucleic acids further include a sequence encoding a linker sequence that replaces the native Factor VIII B-domain (e.g., a linker sequences comprising a furin cleavage site), between the sequences coding for the Factor VIII heavy and light chains.

In one aspect, the disclosure provides a polynucleotide including a nucleotide sequence encoding a Factor VIII polypeptide. The Factor VIII polypeptide includes a light chain, a heavy chain, and a polypeptide linker joining the C-terminus of the heavy chain to the N-terminus of the light chain. The heavy chain of the Factor VIII polypeptide is encoded by a first nucleotide sequence having at least 95% identity to CS04-HC-NA (SEQ ID NO: 3). The light chain of the Factor FVIII polypeptide is encoded by a second nucleotide sequence having at least 95% identity to CS04-LC-NA (SEQ ID NO: 4). The polypeptide linker comprises a furin cleavage site.

In one embodiment of the polynucleotides described above, the polypeptide linker is encoded by a third nucleotide sequence having at least 95% identity to BDLO04 (SEQ ID NO: 6).

In one aspect, the disclosure provides a polynucleotide including a nucleotide sequence encoding a Factor VIII polypeptide. The Factor VIII polypeptide includes a light chain, a heavy chain, and a polypeptide linker joining the C-terminus of the heavy chain to the N-terminus of the light chain. The heavy chain of the Factor VIII polypeptide is encoded by a first nucleotide sequence having at least 95% identity to CS01-HC-NA (SEQ ID NO: 24). The light chain of the Factor FVIII polypeptide is encoded by a second nucleotide sequence having at least 95% identity to CS01-LC-NA (SEQ ID NO: 25). The polypeptide linker comprises a furin cleavage site.

In one embodiment of the polynucleotides described above, the polypeptide linker is encoded by a third nucleotide sequence having at least 95% identity to BDLO01 (SEQ ID NO: 5).

In one aspect, the disclosure provides a polynucleotide including a nucleotide sequence encoding a Factor VIII polypeptide. The Factor VIII polypeptide includes a light chain, a heavy chain, and a polypeptide linker joining the C-terminus of the heavy chain to the N-terminus of the light chain. The heavy chain of the Factor VIII polypeptide is encoded by a first nucleotide sequence having at least 95% identity to CS23-HC-NA (SEQ ID NO: 22). The light chain of the Factor FVIII polypeptide is encoded by a second nucleotide sequence having at least 95% identity to CS23-LC-NA (SEQ ID NO: 23). The polypeptide linker comprises a furin cleavage site.

In one embodiment of the polynucleotides described above, the polypeptide linker is encoded by a third nucleotide sequence having at least 95% identity to BDLO23 (SEQ ID NO: 7).

In one embodiment of the polynucleotides described above, the first nucleotide sequence encoding the heavy chain of the Factor VIII polypeptide has at least 96% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 96% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide has at least 97% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 97% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide has at least 98% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 98% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide has at least 99% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 99% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide has at least 99.5% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 99.5% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide has at least 99.9% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 99.9% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide is CS04-HC-NA (SEQ ID NO: 3), and the second nucleotide sequence encoding the light chain of the Factor FVIII polypeptide is CS04-LC-NA (SEQ ID NO: 4).

In one embodiment of the polynucleotides described above, the first nucleotide sequence encoding the heavy chain of the Factor VIII polypeptide is CS01-HC-NA (SEQ ID NO: 24), and the second nucleotide sequence encoding the light chain of the Factor FVIII polypeptide is CS01-LC-NA (SEQ ID NO: 25).

In one embodiment of the polynucleotides described above, the first nucleotide sequence encoding the heavy chain of the Factor VIII polypeptide is CS23-HC-NA (SEQ ID NO: 22), and the second nucleotide sequence encoding the light chain of the Factor FVIII polypeptide is CS23-LC-NA (SEQ ID NO: 23).

In one aspect, the disclosure provides a polynucleotide comprising a nucleotide sequence having at least 95% identity to CS04-FL-NA, wherein the polynucleotide encodes a Factor VIII polypeptide.

In one aspect, the disclosure provides a polynucleotide comprising a nucleotide sequence having at least 95% identity to CS01-FL-NA, wherein the polynucleotide encodes a Factor VIII polypeptide.

In one aspect, the disclosure provides a polynucleotide comprising a nucleotide sequence having at least 95% identity to CS23-FL-NA, wherein the polynucleotide encodes a Factor VIII polypeptide.

In one embodiment of the polynucleotides described above, the nucleotide sequence has at least 96% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence has at least 97% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence has at least 98% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence has at least 99% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence has at least 99.5% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence has at least 99.9% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence is CS04-FL-NA (SEQ ID NO: 1).

In one embodiment of the polynucleotides described above, the nucleotide sequence is CS01-FL-NA (SEQ ID NO: 13).

In one embodiment of the polynucleotides described above, the nucleotide sequence is CS23-FL-NA (SEQ ID NO: 20).

In one embodiment of the polynucleotides described above, the polynucleotide encodes a Factor VIII polypeptide comprising an amino acid sequence having at least 95% identity to CS04-FL-AA (SEQ ID NO: 2).

In one embodiment of the polynucleotides described above, the polynucleotide encodes a Factor VIII polypeptide comprising an amino acid sequence having at least 96% identity to CS04-FL-AA (SEQ ID NO: 2).

In one embodiment of the polynucleotides described above, the polynucleotide encodes a Factor VIII polypeptide comprising an amino acid sequence having at least 97% identity to CS04-FL-AA (SEQ ID NO: 2).

In one embodiment of the polynucleotides described above, the polynucleotide encodes a Factor VIII polypeptide comprising an amino acid sequence having at least 98% identity to CS04-FL-AA (SEQ ID NO: 2).

In one embodiment of the polynucleotides described above, the polynucleotide encodes a Factor VIII polypeptide comprising an amino acid sequence having at least 99% identity to CS04-FL-AA (SEQ ID NO: 2).

In one embodiment of the polynucleotides described above, the polynucleotide encodes a Factor VIII polypeptide comprising an amino acid sequence having at least 99.5% identity to CS04-FL-AA (SEQ ID NO: 2).

In one embodiment of the polynucleotides described above, the polynucleotide encodes a Factor VIII polypeptide comprising an amino acid sequence having at least 99.9% identity to CS04-FL-AA (SEQ ID NO: 2).

In one embodiment of the polynucleotides described above, the polynucleotide encodes a Factor VIII polypeptide comprising the amino acid sequence of CS04-FL-AA (SEQ ID NO: 2).

In one aspect, the disclosure provides a polynucleotide comprising a nucleotide sequence having at least 95% identity to CS04-SC1-NA (SEQ ID NO: 9), wherein the polynucleotide encodes a single-chain Factor VIII polypeptide.

In one aspect, the disclosure provides a polynucleotide comprising a nucleotide sequence having at least 95% identity to CS04-SC2-NA (SEQ ID NO: 11), wherein the polynucleotide encodes a single-chain Factor VIII polypeptide.

In one aspect, the disclosure provides a polynucleotide comprising a nucleotide sequence having at least 95% identity to CS01-SC1-NA (SEQ ID NO: 26), wherein the polynucleotide encodes a single-chain Factor VIII polypeptide.

In one aspect, the disclosure provides a polynucleotide comprising a nucleotide sequence having at least 95% identity to CS01-SC2-NA (SEQ ID NO: 27), wherein the polynucleotide encodes a single-chain Factor VIII polypeptide.

In one aspect, the disclosure provides a polynucleotide comprising a nucleotide sequence having at least 95% identity to CS23-SC1-NA (SEQ ID NO: 28), wherein the polynucleotide encodes a single-chain Factor VIII polypeptide.

In one aspect, the disclosure provides a polynucleotide comprising a nucleotide sequence having at least 95% identity to CS23-SC2-NA (SEQ ID NO: 29), wherein the polynucleotide encodes a single-chain Factor VIII polypeptide.

In one embodiment of the polynucleotides described above, the nucleotide sequence has at least 96% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence has at least 97% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence has at least 98% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence has at least 99% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence has at least 99.5% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence has at least 99.9% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence is CS04-SC1-NA (SEQ ID NO: 9).

In one embodiment of the polynucleotides described above, the nucleotide sequence is CS04-SC2-NA (SEQ ID NO: 11).

In one embodiment of the polynucleotides described above, the nucleotide sequence is CS01-SC1-NA (SEQ ID NO: 26).

In one embodiment of the polynucleotides described above, the nucleotide sequence is CS01-SC2-NA (SEQ ID NO: 27).

In one embodiment of the polynucleotides described above, the nucleotide sequence is CS23-SC1-NA (SEQ ID NO: 28).

In one embodiment of the polynucleotides described above, the nucleotide sequence is CS23-SC2-NA (SEQ ID NO: 29).

In one embodiment of the polynucleotides described above, the nucleotide sequence has at least 95% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01m1-FL-NA, CS01m2-FL-NA, CS01m3-FL-NA, CS01m4-FL-NA, CS01m12-FL-NA, CS01m13-FL-NA, CS01m23-FL-NA, CS01m24-FL-NA, CS01m34-FL-NA, CS01m123-FL-NA, CS01m234-FL-NA, CS04m1-FL-NA, CS04m2-FL-NA, CS04m3-FL-NA, CS04m4-FL-NA, CS04m12-FL-NA, CS04m13-FL-NA, CS04m23-FL-NA, CS04m24-FL-NA, CS04m34-FL-NA, CS04m123-FL-NA, CS04m234-FL-NA, CS23m1-FL-NA, CS23m2-FL-NA, CS23m3-FL-NA, CS23m4-FL-NA, CS23m12-FL-NA, CS23m13-FL-NA, CS23m23-FL-NA, CS23m24-FL-NA, CS23m34-FL-NA, CS23m123-FL-NA, CS23m234-FL-NA, CS01-SC1-NA, CS04-SC1-NA, CS23-SC1-NA, CS01m1-SC1-NA, CS01m2-SC1-NA, CS01m3-SC1-NA, CS01m4-SC1-NA, CS01m12-SC1-NA, CS01m13-SC1-NA, CS01m23-SC1-NA, CS01m24-SC1-NA, CS01m34-SC1-NA, CS01m123-SC1-NA, CS01m234-SC1-NA, CS04m1-SC1-NA, CS04m2-SC1-NA, CS04m3-SC1-NA, CS04m4-SC1-NA, CS04m12-SC1-NA, CS04m13-SC1-NA, CS04m23-SC1-NA, CS04m24-SC1-NA, CS04m34-SC1-NA, CS04m123-SC1-NA, CS04m234-SC1-NA, CS23m1-SC1-NA, CS23m2-SC1-NA, CS23m3-SC1-NA, CS23m4-SC1-NA, CS23m12-SC1-NA, CS23m13-SC1-NA, CS23m23-SC1-NA, CS23m24-SC1-NA, CS23m34-SC1-NA, CS23m123-SC1-NA, CS23m234-SC1-NA, CS01-SC2-NA, CS04-SC2-NA, CS23-SC2-NA, CS01m1-SC2-NA, CS01m2-SC2-NA, CS01m3-SC2-NA, CS01m4-SC2-NA, CS01m12-SC2-NA, CS01m13-SC2-NA, CS01m23-SC2-NA, CS01m24-SC2-NA, CS01m34-SC2-NA, CS01m123-SC2-NA, CS01m234-SC2-NA, CS04m1-SC2-NA, CS04m2-SC2-NA, CS04m3-SC2-NA, CS04m4-SC2-NA, CS04m12-SC2-NA, CS04m13-SC2-NA, CS04m23-SC2-NA, CS04m24-SC2-NA, CS04m34-SC2-NA, CS04m123-SC2-NA, CS04m234-SC2-NA, CS23m1-SC2-NA, CS23m2-SC2-NA, CS23m3-SC2-NA, CS23m4-SC2-NA, CS23m12-SC2-NA, CS23m13-SC2-NA, CS23m23-SC2-NA, CS23m24-SC2-NA, CS23m34-SC2-NA, CS23m123-SC2-NA, and CS23m234-SC2-NA.

In one embodiment of the polynucleotides described above, the nucleotide sequence has at least 96% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01m1-FL-NA, CS01m2-FL-NA, CS01m3-FL-NA, CS01m4-FL-NA, CS01m12-FL-NA, CS01m13-FL-NA, CS01m23-FL-NA, CS01m24-FL-NA, CS01m34-FL-NA, CS01m123-FL-NA, CS01m234-FL-NA, CS04m1-FL-NA, CS04m2-FL-NA, CS04m3-FL-NA, CS04m4-FL-NA, CS04m12-FL-NA, CS04m13-FL-NA, CS04m23-FL-NA, CS04m24-FL-NA, CS04m34-FL-NA, CS04m123-FL-NA, CS04m234-FL-NA, CS23m1-FL-NA, CS23m2-FL-NA, CS23m3-FL-NA, CS23m4-FL-NA, CS23m12-FL-NA, CS23m13-FL-NA, CS23m23-FL-NA, CS23m24-FL-NA, CS23m34-FL-NA, CS23m123-FL-NA, CS23m234-FL-NA, CS01-SC1-NA, CS04-SC1-NA, CS23-SC1-NA, CS01m1-SC1-NA, CS01m2-SC1-NA, CS01m3-SC1-NA, CS01m4-SC1-NA, CS01m12-SC1-NA, CS01m13-SC1-NA, CS01m23-SC1-NA, CS01m24-SC1-NA, CS01m34-SC1-NA, CS01m123-SC1-NA, CS01m234-SC1-NA, CS04m1-SC1-NA, CS04m2-SC1-NA, CS04m3-SC1-NA, CS04m4-SC1-NA, CS04m12-SC1-NA, CS04m13-SC1-NA, CS04m23-SC1-NA, CS04m24-SC1-NA, CS04m34-SC1-NA, CS04m123-SC1-NA, CS04m234-SC1-NA, CS23m1-SC1-NA, CS23m2-SC1-NA, CS23m3-SC1-NA, CS23m4-SC1-NA, CS23m12-SC1-NA, CS23m13-SC1-NA, CS23m23-SC1-NA, CS23m24-SC1-NA, CS23m34-SC1-NA, CS23m123-SC1-NA, CS23m234-SC1-NA, CS01-SC2-NA, CS04-SC2-NA, CS23-SC2-NA, CS01m1-SC2-NA, CS01m2-SC2-NA, CS01m3-SC2-NA, CS01m4-SC2-NA, CS01m12-SC2-NA, CS01m13-SC2-NA, CS01m23-SC2-NA, CS01m24-SC2-NA, CS01m34-SC2-NA, CS01m123-SC2-NA, CS01m234-SC2-NA, CS04m1-SC2-NA, CS04m2-SC2-NA, CS04m3-SC2-NA, CS04m4-SC2-NA, CS04m12-SC2-NA, CS04m13-SC2-NA, CS04m23-SC2-NA, CS04m24-SC2-NA, CS04m34-SC2-NA, CS04m123-SC2-NA, CS04m234-SC2-NA, CS23m1-SC2-NA, CS23m2-SC2-NA, CS23m3-SC2-NA, CS23m4-SC2-NA, CS23m12-SC2-NA, CS23m13-SC2-NA, CS23m23-SC2-NA, CS23m24-SC2-NA, CS23m34-SC2-NA, CS23m123-SC2-NA, and CS23m234-SC2-NA.

In one embodiment of the polynucleotides described above, the nucleotide sequence has at least 97% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01m1-FL-NA, CS01m2-FL-NA, CS01m3-FL-NA, CS01m4-FL-NA, CS01m12-FL-NA, CS01m13-FL-NA, CS01m23-FL-NA, CS01m24-FL-NA, CS01m34-FL-NA, CS01m123-FL-NA, CS01m234-FL-NA, CS04m1-FL-NA, CS04m2-FL-NA, CS04m3-FL-NA, CS04m4-FL-NA, CS04m12-FL-NA, CS04m13-FL-NA, CS04m23-FL-NA, CS04m24-FL-NA, CS04m34-FL-NA, CS04m123-FL-NA, CS04m234-FL-NA, CS23m1-FL-NA, CS23m2-FL-NA, CS23m3-FL-NA, CS23m4-FL-NA, CS23m12-FL-NA, CS23m13-FL-NA, CS23m23-FL-NA, CS23m24-FL-NA, CS23m34-FL-NA, CS23m123-FL-NA, CS23m234-FL-NA, CS01-SC1-NA, CS04-SC1-NA, CS23-SC1-NA, CS01m1-SC1-NA, CS01m2-SC1-NA, CS01m3-SC1-NA, CS01m4-SC1-NA, CS01m12-SC1-NA, CS01m13-SC1-NA, CS01m23-SC1-NA, CS01m24-SC1-NA, CS01m34-SC1-NA, CS01m123-SC1-NA, CS01m234-SC1-NA, CS04m1-SC1-NA, CS04m2-SC1-NA, CS04m3-SC1-NA, CS04m4-SC1-NA, CS04m12-SC1-NA, CS04m13-SC1-NA, CS04m23-SC1-NA, CS04m24-SC1-NA, CS04m34-SC1-NA, CS04m123-SC1-NA, CS04m234-SC1-NA, CS23m1-SC1-NA, CS23m2-SC1-NA, CS23m3-SC1-NA, CS23m4-SC1-NA, CS23m12-SC1-NA, CS23m13-SC1-NA, CS23m23-SC1-NA, CS23m24-SC1-NA, CS23m34-SC1-NA, CS23m123-SC1-NA, CS23m234-SC1-NA, CS01-SC2-NA, CS04-SC2-NA, CS23-SC2-NA, CS01m1-SC2-NA, CS01m2-SC2-NA, CS01m3-SC2-NA, CS01m4-SC2-NA, CS01m12-SC2-NA, CS01m13-SC2-NA, CS01m23-SC2-NA, CS01m24-SC2-NA, CS01m34-SC2-NA, CS01m123-SC2-NA, CS01m234-SC2-NA, CS04m1-SC2-NA, CS04m2-SC2-NA, CS04m3-SC2-NA, CS04m4-SC2-NA, CS04m12-SC2-NA, CS04m13-SC2-NA, CS04m23-SC2-NA, CS04m24-SC2-NA, CS04m34-SC2-NA, CS04m123-SC2-NA, CS04m234-SC2-NA, CS23m1-SC2-NA, CS23m2-SC2-NA, CS23m3-SC2-NA, CS23m4-SC2-NA, CS23m12-SC2-NA, CS23m13-SC2-NA, CS23m23-SC2-NA, CS23m24-SC2-NA, CS23m34-SC2-NA, CS23m123-SC2-NA, and CS23m234-SC2-NA.

In one embodiment of the polynucleotides described above, the nucleotide sequence has at least 98% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01m1-FL-NA, CS01m2-FL-NA, CS01m3-FL-NA, CS01m4-FL-NA, CS01m12-FL-NA, CS01m13-FL-NA, CS01m23-FL-NA, CS01m24-FL-NA, CS01m34-FL-NA, CS01m123-FL-NA, CS01m234-FL-NA, CS04m1-FL-NA, CS04m2-FL-NA, CS04m3-FL-NA, CS04m4-FL-NA, CS04m12-FL-NA, CS04m13-FL-NA, CS04m23-FL-NA, CS04m24-FL-NA, CS04m34-FL-NA, CS04m123-FL-NA, CS04m234-FL-NA, CS23m1-FL-NA, CS23m2-FL-NA, CS23m3-FL-NA, CS23m4-FL-NA, CS23m12-FL-NA, CS23m13-FL-NA, CS23m23-FL-NA, CS23m24-FL-NA, CS23m34-FL-NA, CS23m123-FL-NA, CS23m234-FL-NA, CS01-SC1-NA, CS04-SC1-NA, CS23-SC1-NA, CS01m1-SC1-NA, CS01m2-SC1-NA, CS01m3-SC1-NA, CS01m4-SC1-NA, CS01m12-SC1-NA, CS01m13-SC1-NA, CS01m23-SC1-NA, CS01m24-SC1-NA, CS01m34-SC1-NA, CS01m123-SC1-NA, CS01m234-SC1-NA, CS04m1-SC1-NA, CS04m2-SC1-NA, CS04m3-SC1-NA, CS04m4-SC1-NA, CS04m12-SC1-NA, CS04m13-SC1-NA, CS04m23-SC1-NA, CS04m24-SC1-NA, CS04m34-SC1-NA, CS04m123-SC1-NA, CS04m234-SC1-NA, CS23m1-SC1-NA, CS23m2-SC1-NA, CS23m3-SC1-NA, CS23m4-SC1-NA, CS23m12-SC1-NA, CS23m13-SC1-NA, CS23m23-SC1-NA, CS23m24-SC1-NA, CS23m34-SC1-NA, CS23m123-SC1-NA, CS23m234-SC1-NA, CS01-SC2-NA, CS04-SC2-NA, CS23-SC2-NA, CS01m1-SC2-NA, CS01m2-SC2-NA, CS01m3-SC2-NA, CS01m4-SC2-NA, CS01m12-SC2-NA, CS01m13-SC2-NA, CS01m23-SC2-NA, CS01m24-SC2-NA, CS01m34-SC2-NA, CS01m123-SC2-NA, CS01m234-SC2-NA, CS04m1-SC2-NA, CS04m2-SC2-NA, CS04m3-SC2-NA, CS04m4-SC2-NA, CS04m12-SC2-NA, CS04m13-SC2-NA, CS04m23-SC2-NA, CS04m24-SC2-NA, CS04m34-SC2-NA, CS04m123-SC2-NA, CS04m234-SC2-NA, CS23m1-SC2-NA, CS23m2-SC2-NA, CS23m3-SC2-NA, CS23m4-SC2-NA, CS23m12-SC2-NA, CS23m13-SC2-NA, CS23m23-SC2-NA, CS23m24-SC2-NA, CS23m34-SC2-NA, CS23m123-SC2-NA, and CS23m234-SC2-NA.

In one embodiment of the polynucleotides described above, the nucleotide sequence has at least 99% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01m1-FL-NA, CS01m2-FL-NA, CS01m3-FL-NA, CS01m4-FL-NA, CS01m12-FL-NA, CS01m13-FL-NA, CS01m23-FL-NA, CS01m24-FL-NA, CS01m34-FL-NA, CS01m123-FL-NA, CS01m234-FL-NA, CS04m1-FL-NA, CS04m2-FL-NA, CS04m3-FL-NA, CS04m4-FL-NA, CS04m12-FL-NA, CS04m13-FL-NA, CS04m23-FL-NA, CS04m24-FL-NA, CS04m34-FL-NA, CS04m123-FL-NA, CS04m234-FL-NA, CS23m1-FL-NA, CS23m2-FL-NA, CS23m3-FL-NA, CS23m4-FL-NA, CS23m12-FL-NA, CS23m13-FL-NA, CS23m23-FL-NA, CS23m24-FL-NA, CS23m34-FL-NA, CS23m123-FL-NA, CS23m234-FL-NA, CS01-SC1-NA, CS04-SC1-NA, CS23-SC1-NA, CS01m1-SC1-NA, CS01m2-SC1-NA, CS01m3-SC1-NA, CS01m4-SC1-NA, CS01m12-SC1-NA, CS01m13-SC1-NA, CS01m23-SC1-NA, CS01m24-SC1-NA, CS01m34-SC1-NA, CS01m123-SC1-NA, CS01m234-SC1-NA, CS04m1-SC1-NA, CS04m2-SC1-NA, CS04m3-SC1-NA, CS04m4-SC1-NA, CS04m12-SC1-NA, CS04m13-SC1-NA, CS04m23-SC1-NA, CS04m24-SC1-NA, CS04m34-SC1-NA, CS04m123-SC1-NA, CS04m234-SC1-NA, CS23m1-SC1-NA, CS23m2-SC1-NA, CS23m3-SC1-NA, CS23m4-SC1-NA, CS23m12-SC1-NA, CS23m13-SC1-NA, CS23m23-SC1-NA, CS23m24-SC1-NA, CS23m34-SC1-NA, CS23m123-SC1-NA, CS23m234-SC1-NA, CS01-SC2-NA, CS04-SC2-NA, CS23-SC2-NA, CS01m1-SC2-NA, CS01m2-SC2-NA, CS01m3-SC2-NA, CS01m4-SC2-NA, CS01m12-SC2-NA, CS01m13-SC2-NA, CS01m23-SC2-NA, CS01m24-SC2-NA, CS01m34-SC2-NA, CS01m123-SC2-NA, CS01m234-SC2-NA, CS04m1-SC2-NA, CS04m2-SC2-NA, CS04m3-SC2-NA, CS04m4-SC2-NA, CS04m12-SC2-NA, CS04m13-SC2-NA, CS04m23-SC2-NA, CS04m24-SC2-NA, CS04m34-SC2-NA, CS04m123-SC2-NA, CS04m234-SC2-NA, CS23m1-SC2-NA, CS23m2-SC2-NA, CS23m3-SC2-NA, CS23m4-SC2-NA, CS23m12-SC2-NA, CS23m13-SC2-NA, CS23m23-SC2-NA, CS23m24-SC2-NA, CS23m34-SC2-NA, CS23m123-SC2-NA, and CS23m234-SC2-NA.

In one embodiment of the polynucleotides described above, the nucleotide sequence has at least 99.5% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01m1-FL-NA, CS01m2-FL-NA, CS01m3-FL-NA, CS01m4-FL-NA, CS01m12-FL-NA, CS01m13-FL-NA, CS01m23-FL-NA, CS01m24-FL-NA, CS01m34-FL-NA, CS01m123-FL-NA, CS01m234-FL-NA, CS04m1-FL-NA, CS04m2-FL-NA, CS04m3-FL-NA, CS04m4-FL-NA, CS04m12-FL-NA, CS04m13-FL-NA, CS04m23-FL-NA, CS04m24-FL-NA, CS04m34-FL-NA, CS04m123-FL-NA, CS04m234-FL-NA, CS23m1-FL-NA, CS23m2-FL-NA, CS23m3-FL-NA, CS23m4-FL-NA, CS23m12-FL-NA, CS23m13-FL-NA, CS23m23-FL-NA, CS23m24-FL-NA, CS23m34-FL-NA, CS23m123-FL-NA, CS23m234-FL-NA, CS01-SC1-NA, CS04-SC1-NA, CS23-SC1-NA, CS01m1-SC1-NA, CS01m2-SC1-NA, CS01m3-SC1-NA, CS01m4-SC1-NA, CS01m12-SC1-NA, CS01m13-SC1-NA, CS01m23-SC1-NA, CS01m24-SC1-NA, CS01m34-SC1-NA, CS01m123-SC1-NA, CS01m234-SC1-NA, CS04m1-SC1-NA, CS04m2-SC1-NA, CS04m3-SC1-NA, CS04m4-SC1-NA, CS04m12-SC1-NA, CS04m13-SC1-NA, CS04m23-SC1-NA, CS04m24-SC1-NA, CS04m34-SC1-NA, CS04m123-SC1-NA, CS04m234-SC1-NA, CS23m1-SC1-NA, CS23m2-SC1-NA, CS23m3-SC1-NA, CS23m4-SC1-NA, CS23m12-SC1-NA, CS23m13-SC1-NA, CS23m23-SC1-NA, CS23m24-SC1-NA, CS23m34-SC1-NA, CS23m123-SC1-NA, CS23m234-SC1-NA, CS01-SC2-NA, CS04-SC2-NA, CS23-SC2-NA, CS01m1-SC2-NA, CS01m2-SC2-NA, CS01m3-SC2-NA, CS01m4-SC2-NA, CS01m12-SC2-NA, CS01m13-SC2-NA, CS01m23-SC2-NA, CS01m24-SC2-NA, CS01m34-SC2-NA, CS01m123-SC2-NA, CS01m234-SC2-NA, CS04m1-SC2-NA, CS04m2-SC2-NA, CS04m3-SC2-NA, CS04m4-SC2-NA, CS04m12-SC2-NA, CS04m13-SC2-NA, CS04m23-SC2-NA, CS04m24-SC2-NA, CS04m34-SC2-NA, CS04m123-SC2-NA, CS04m234-SC2-NA, CS23m1-SC2-NA, CS23m2-SC2-NA, CS23m3-SC2-NA, CS23m4-SC2-NA, CS23m12-SC2-NA, CS23m13-SC2-NA, CS23m23-SC2-NA, CS23m24-SC2-NA, CS23m34-SC2-NA, CS23m123-SC2-NA, and CS23m234-SC2-NA.

In one embodiment of the polynucleotides described above, the nucleotide sequence has at least 99.5% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01m1-FL-NA, CS01m2-FL-NA, CS01m3-FL-NA, CS01m4-FL-NA, CS01m12-FL-NA, CS01m13-FL-NA, CS01m23-FL-NA, CS01m24-FL-NA, CS01m34-FL-NA, CS01m123-FL-NA, CS01m234-FL-NA, CS04m1-FL-NA, CS04m2-FL-NA, CS04m3-FL-NA, CS04m4-FL-NA, CS04m12-FL-NA, CS04m13-FL-NA, CS04m23-FL-NA, CS04m24-FL-NA, CS04m34-FL-NA, CS04m123-FL-NA, CS04m234-FL-NA, CS23m1-FL-NA, CS23m2-FL-NA, CS23m3-FL-NA, CS23m4-FL-NA, CS23m12-FL-NA, CS23m13-FL-NA, CS23m23-FL-NA, CS23m24-FL-NA, CS23m34-FL-NA, CS23m123-FL-NA, CS23m234-FL-NA, CS01-SC1-NA, CS04-SC1-NA, CS23-SC1-NA, CS01m1-SC1-NA, CS01m2-SC1-NA, CS01m3-SC1-NA, CS01m4-SC1-NA, CS01m12-SC1-NA, CS01m13-SC1-NA, CS01m23-SC1-NA, CS01m24-SC1-NA, CS01m34-SC1-NA, CS01m123-SC1-NA, CS01m234-SC1-NA, CS04m1-SC1-NA, CS04m2-SC1-NA, CS04m3-SC1-NA, CS04m4-SC1-NA, CS04m12-SC1-NA, CS04m13-SC1-NA, CS04m23-SC1-NA, CS04m24-SC1-NA, CS04m34-SC1-NA, CS04m123-SC1-NA, CS04m234-SC1-NA, CS23m1-SC1-NA, CS23m2-SC1-NA, CS23m3-SC1-NA, CS23m4-SC1-NA, CS23m12-SC1-NA, CS23m13-SC1-NA, CS23m23-SC1-NA, CS23m24-SC1-NA, CS23m34-SC1-NA, CS23m123-SC1-NA, CS23m234-SC1-NA, CS01-SC2-NA, CS04-SC2-NA, CS23-SC2-NA, CS01m1-SC2-NA, CS01m2-SC2-NA, CS01m3-SC2-NA, CS01m4-SC2-NA, CS01m12-SC2-NA, CS01m13-SC2-NA, CS01m23-SC2-NA, CS01m24-SC2-NA, CS01m34-SC2-NA, CS01m123-SC2-NA, CS01m234-SC2-NA, CS04m1-SC2-NA, CS04m2-SC2-NA, CS04m3-SC2-NA, CS04m4-SC2-NA, CS04m12-SC2-NA, CS04m13-SC2-NA, CS04m23-SC2-NA, CS04m24-SC2-NA, CS04m34-SC2-NA, CS04m123-SC2-NA, CS04m234-SC2-NA, CS23m1-SC2-NA, CS23m2-SC2-NA, CS23m3-SC2-NA, CS23m4-SC2-NA, CS23m12-SC2-NA, CS23m13-SC2-NA, CS23m23-SC2-NA, CS23m24-SC2-NA, CS23m34-SC2-NA, CS23m123-SC2-NA, and CS23m234-SC2-NA.

In one embodiment of the polynucleotides described above, the nucleotide sequence is selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01m1-FL-NA, CS01m2-FL-NA, CS01m3-FL-NA, CS01m4-FL-NA, CS01m12-FL-NA, CS01m13-FL-NA, CS01m23-FL-NA, CS01m24-FL-NA, CS01m34-FL-NA, CS01m123-FL-NA, CS01m234-FL-NA, CS04m1-FL-NA, CS04m2-FL-NA, CS04m3-FL-NA, CS04m4-FL-NA, CS04m12-FL-NA, CS04m13-FL-NA, CS04m23-FL-NA, CS04m24-FL-NA, CS04m34-FL-NA, CS04m123-FL-NA, CS04m234-FL-NA, CS23m1-FL-NA, CS23m2-FL-NA, CS23m3-FL-NA, CS23m4-FL-NA, CS23m12-FL-NA, CS23m13-FL-NA, CS23m23-FL-NA, CS23m24-FL-NA, CS23m34-FL-NA, CS23m123-FL-NA, CS23m234-FL-NA, CS01-SC1-NA, CS04-SC1-NA, CS23-SC1-NA, CS01m1-SC1-NA, CS01m2-SC1-NA, CS01m3-SC1-NA, CS01m4-SC1-NA, CS01m12-SC1-NA, CS01m13-SC1-NA, CS01m23-SC1-NA, CS01m24-SC1-NA, CS01m34-SC1-NA, CS01m123-SC1-NA, CS01m234-SC1-NA, CS04m1-SC1-NA, CS04m2-SC1-NA, CS04m3-SC1-NA, CS04m4-SC1-NA, CS04m12-SC1-NA, CS04m13-SC1-NA, CS04m23-SC1-NA, CS04m24-SC1-NA, CS04m34-SC1-NA, CS04m123-SC1-NA, CS04m234-SC1-NA, CS23m1-SC1-NA, CS23m2-SC1-NA, CS23m3-SC1-NA, CS23m4-SC1-NA, CS23m12-SC1-NA, CS23m13-SC1-NA, CS23m23-SC1-NA, CS23m24-SC1-NA, CS23m34-SC1-NA, CS23m123-SC1-NA, CS23m234-SC1-NA, CS01-SC2-NA, CS04-SC2-NA, CS23-SC2-NA, CS01m1-SC2-NA, CS01m2-SC2-NA, CS01m3-SC2-NA, CS01m4-SC2-NA, CS01m12-SC2-NA, CS01m13-SC2-NA, CS01m23-SC2-NA, CS01m24-SC2-NA, CS01m34-SC2-NA, CS01m123-SC2-NA, CS01m234-SC2-NA, CS04m1-SC2-NA, CS04m2-SC2-NA, CS04m3-SC2-NA, CS04m4-SC2-NA, CS04m12-SC2-NA, CS04m13-SC2-NA, CS04m23-SC2-NA, CS04m24-SC2-NA, CS04m34-SC2-NA, CS04m123-SC2-NA, CS04m234-SC2-NA, CS23m1-SC2-NA, CS23m2-SC2-NA, CS23m3-SC2-NA, CS23m4-SC2-NA, CS23m12-SC2-NA, CS23m13-SC2-NA, CS23m23-SC2-NA, CS23m24-SC2-NA, CS23m34-SC2-NA, CS23m123-SC2-NA, and CS23m234-SC2-NA.

In one embodiment of the polynucleotides described above, the encoded Factor VIII polypeptide comprises a glycosylation polypeptide positioned between two consecutive amino acids.

In one embodiment of the polynucleotides described above, the encoded polypeptide linker includes a glycosylation peptide with an amino acid sequence having at least 92% identity to a glycosylation peptide selected from the group consisting of NG1-AA, NG4-AA, NG5-AA, NG6-AA, NG7-AA, NG9-AA, NG10-AA, NG16-AA, NG17-AA, NG18-AA, NG19-AA, NG20-AA, NG21-AA and NGV-AA.

In one embodiment of the polynucleotides described above, the encoded polypeptide linker comprises a glycosylation peptide with an amino acid sequence selected from the group consisting of NG1-AA, NG4-AA, NG5-AA, NG6-AA, NG7-AA, NG9-AA, NG10-AA, NG16-AA, NG17-AA, NG18-AA, NG19-AA, NG20-AA, NG21-AA and NGV-AA.

In one embodiment of the polynucleotides described above, the glycosylation peptide is encoded by a polynucleotide with a nucleotide sequence having at least 95% identity to a sequence selected from the group consisting of NG1-NA, NG4-NA, NG5-NA, NG6-NA, NG7-NA, NG9-NA, NG10-NA, NG16-NA, NG17-NA, NG18-NA, NG19-NA, NG20-NA, NG21-NA and NGV-NA.

In one embodiment of the polynucleotides described above, the glycosylation peptide is encoded by a polynucleotide with a nucleotide sequence selected from one of NG1-NA, NG4-NA, NG5-NA, NG6-NA, NG7-NA, NG9-NA, NG10-NA, NG16-NA, NG17-NA, NG18-NA, NG19-NA, NG20-NA, NG21-NA and NGV-NA.

In one embodiment of the polynucleotides described above, the polypeptide linker is encoded by a third nucleotide sequence having at least 95% identity to a sequence selected from the group consisting of BDLNG1-NA, BDLNG3-NA, BDLNGS-NA, BDLNG6-NA, BDLNG9-NA, BDLNG10-NA, BDLNG16-NA, BDLNG17-NA, BDLNG18-NA, BDLNG19-NA, BDLNG20-NA and BDLNG21-NA.

In one embodiment of the polynucleotides described above, the encoded Factor VIII polypeptide includes an F328S (SPI, F309S SPE) amino acid substitution, relative to FVIII-FL-AA (SEQ ID NO: 19).

In one embodiment of the polynucleotides described above, the encoded Factor VIII polypeptide includes I105V, A127S, G151K, M166T, and L171P (SPI; I86V, A108S, G132K, M147T, and L152P, SPE, respectively) amino acid substitutions, relative to FVIII-FL-AA (SEQ ID NO: 19).

In one embodiment of the polynucleotides described above, the encoded Factor VIII polypeptide includes a) a deletion of amino acids AIEPR755-759, relative to FVIII-FL-AA (SEQ ID NO: 19), and b) an insertion of amino acids TTYVNRSL (SEQ ID NO: 33) after N754, relative to FVIII-FL-AA (SEQ ID NO: 19). In some embodiments (e.g., where the encoded FVIII molecule includes a portion of the N-terminal region of the wild-type B-domain), the encoded Factor VIII polypeptide also includes a deletion of amino acids SF760-761, relative to FVIII-FL-AA (SEQ ID NO: 19).

In one embodiment of the polynucleotides described above, the encoded Factor VIII polypeptide includes a) an F328S (SPI; F309S SPE) amino acid substitution, relative to FVIII-FL-AA (SEQ ID NO: 19), and b) C1918G and C1922G (SPI; C1899G and C1903 SPE, respectively) amino acid substitutions, relative to FVIII-FL-AA (SEQ ID NO: 19).

In one embodiment of the polynucleotides described above, the encoded Factor VIII polypeptide includes a) an F328S (SPI; F309S SPE) amino acid substitution, relative to FVIII-FL-AA (SEQ ID NO: 19), and b) I105V, A127S, G151K, M166T, and L171P (SPI; I86V, A108S, G132K, M147T, and L152P, SPE, respectively) amino acid substitutions, relative to FVIII-FL-AA (SEQ ID NO: 19).

In one embodiment of the polynucleotides described above, the encoded Factor VIII polypeptide includes a) an F328S amino acid substitution, relative to FVIII-FL-AA (SEQ ID NO: 19), b) a deletion of amino acids AIEPR755-759, relative to FVIII-FL-AA (SEQ ID NO: 19), and c) an insertion of amino acids TTYVNRSL (SEQ ID NO: 33) after N754, relative to FVIII-FL-AA (SEQ ID NO: 19). In some embodiments (e.g., where the encoded FVIII molecule includes a portion of the N-terminal region of the wild-type B-domain), the encoded Factor VIII polypeptide also includes a deletion of amino acids SF760-761, relative to FVIII-FL-AA (SEQ ID NO: 19).

In one embodiment of the polynucleotides described above, the encoded Factor VIII polypeptide includes a) I105V, A127S, G151K, M166T, and L171P amino acid substitutions, relative to FVIII-FL-AA (SEQ ID NO: 19), b) a deletion of amino acids AIEPR755-759, relative to FVIII-FL-AA (SEQ ID NO: 19), and c) an insertion of amino acids TTYVNRSL (SEQ ID NO: 33) after N754, relative to FVIII-FL-AA (SEQ ID NO: 19). In some embodiments (e.g., where the encoded FVIII molecule includes a portion of the N-terminal region of the wild-type B-domain), the encoded Factor VIII polypeptide also includes a deletion of amino acids SF760-761, relative to FVIII-FL-AA (SEQ ID NO: 19).

In one embodiment of the polynucleotides described above, the encoded Factor VIII polypeptide includes a) an F328S amino acid substitution, relative to FVIII-FL-AA (SEQ ID NO: 19), b) C1918G and C1922G amino acid substitutions, relative to FVIII-FL-AA (SEQ ID NO: 19), and c) I105V, A127S, G151K, M166T, and L171P amino acid substitutions, relative to FVIII-FL-AA (SEQ ID NO: 19).

In one embodiment of the polynucleotides described above, the encoded Factor VIII polypeptide includes a) an F328S amino acid substitution, relative to FVIII-FL-AA (SEQ ID NO: 19), b) C1918G and C1922G amino acid substitutions, relative to FVIII-FL-AA (SEQ ID NO: 19), c) a deletion of amino acids AIEPR755-759, relative to FVIII-FL-AA (SEQ ID NO: 19), and d) an insertion of amino acids TTYVNRSL (SEQ ID NO: 33) after N754, relative to FVIII-FL-AA (SEQ ID NO: 19). In some embodiments (e.g., where the encoded FVIII molecule includes a portion of the N-terminal region of the wild-type B-domain), the encoded Factor VIII polypeptide also includes a deletion of amino acids SF760-761, relative to FVIII-FL-AA (SEQ ID NO: 19).

In one embodiment of the polynucleotides described above, the encoded Factor VIII polypeptide includes a) I105V, A127S, G151K, M166T, and L171P amino acid substitutions, relative to FVIII-FL-AA (SEQ ID NO: 19), b) an F328S amino acid substitution, relative to FVIII-FL-AA (SEQ ID NO: 19), c) C1918G and C1922G amino acid substitutions, relative to FVIII-FL-AA (SEQ ID NO: 19), d) a deletion of amino acids AIEPR755-759, relative to FVIII-FL-AA (SEQ ID NO: 19), and e) an insertion of amino acids TTYVNRSL (SEQ ID NO: 33) after N754, relative to FVIII-FL-AA (SEQ ID NO: 19). In some embodiments (e.g., where the encoded FVIII molecule includes a portion of the N-terminal region of the wild-type B-domain), the encoded Factor VIII polypeptide also includes a deletion of amino acids SF760-761, relative to FVIII-FL-AA (SEQ ID NO: 19).

In one embodiment of the polynucleotides described above, the polynucleotide also includes a promoter element operably linked to the polynucleotide encoding the Factor VIII polypeptide.

In one embodiment of the polynucleotides described above, the polynucleotide also includes an enhancer element operably linked to the polynucleotide encoding the Factor VIII polypeptide.

In one embodiment of the polynucleotides described above, the polynucleotide also includes a polyadenylation element operably linked to the polynucleotide encoding the Factor VIII polypeptide.

In one embodiment of the polynucleotides described above, the polynucleotide also includes an intron operatively linked to the nucleotide sequence encoding the Factor VIII polypeptide.

In one embodiment of the polynucleotides described above, the intron is positioned between a promoter element and the translation initiation site (e.g., the first coding ATG) of the nucleotide sequence encoding a Factor VIII polypeptide.

In another aspect, the disclosure provides a mammalian gene therapy vector including a polynucleotide as described above.

In one embodiment of the mammalian gene therapy vector described above, the mammalian gene therapy vector is an adeno-associated virus (AAV) vector.

In one embodiment of the mammalian gene therapy vector described above, the AAV vector is an AAV-8 vector.

In another aspect, the disclosure provides a method for treating hemophilia A including administering, to a patient in need thereof, a mammalian gene therapy vector as described above.

In another aspect, the disclosure provides a mammalian gene therapy vector as described above for treating hemophilia A.

In another aspect, the disclosure provides the use of a mammalian gene therapy vector as described above for the manufacture of a medicament for treating hemophilia A.

In another aspect, the disclosure provides a Factor VIII polypeptide including a light chain, a heavy chain, and a polypeptide linker joining the C-terminus of the heavy chain to the N-terminus of the light chain. The heavy chain of the Factor VIII polypeptide has a sequence at least 95% identical to the sequence CS01-HC-AAm23. The light chain of the Factor VIII polypeptide has a sequence at least 95% identical to the sequence CS01-LC-AAm23. The polypeptide linker of the Factor VIII polypeptide includes a furin cleavage site. The Factor VIII polypeptide includes i) I105V, A127S, G151K, M166T, and L171P amino acid substitutions, ii) a deletion of amino acids AIEPR755-759, relative to FVIII-FL-AA (SEQ ID NO: 19), and iii) an insertion of amino acids TTYVNRSL (SEQ ID NO: 33) after N754, relative to FVIII-FL-AA (SEQ ID NO: 19).

In another aspect, the disclosure provides a Factor VIII polypeptide including a light chain, a heavy chain, and a polypeptide linker joining the C-terminus of the heavy chain to the N-terminus of the light chain. The heavy chain of the Factor VIII polypeptide has a sequence at least 95% identical to the sequence CS01-HC-AAm123. The light chain of the Factor VIII polypeptide has a sequence at least 95% identical to the sequence CS01-LC-AAm123. The polypeptide linker of the Factor VIII polypeptide includes a furin cleavage site. The Factor VIII polypeptide includes i) I105V, A127S, G151K, M166T, and L171P amino acid substitutions, ii) a deletion of amino acids AIEPR755-759, relative to FVIII-FL-AA (SEQ ID NO: 19), iii) an insertion of amino acids TTYVNRSL (SEQ ID NO: 33) after N754, relative to FVIII-FL-AA (SEQ ID NO: 19), and iv) an F328S amino acid substitution.

In another aspect, the disclosure provides a Factor VIII polypeptide including a light chain, a heavy chain, and a polypeptide linker joining the C-terminus of the heavy chain to the N-terminus of the light chain. The heavy chain of the Factor VIII polypeptide has a sequence at least 95% identical to the sequence CS01-HC-AAm234. The light chain of the Factor VIII polypeptide has a sequence at least 95% identical to the sequence CS01-LC-AAm234. The polypeptide linker of the Factor VIII polypeptide includes a furin cleavage site. The Factor VIII polypeptide includes i) I105V, A127S, G151K, M166T, and L171P amino acid substitutions, ii) a deletion of amino acids AIEPR755-759, relative to FVIII-FL-AA (SEQ ID NO: 19), iii) an insertion of amino acids TTYVNRSL (SEQ ID NO: 33) after N754, relative to FVIII-FL-AA (SEQ ID NO: 19), and iv) F328S/C1918G/C1922G amino acid substitutions.

In one embodiment of the Factor VIII polypeptides described, the heavy chain of the Factor VIII polypeptide has a sequence at least 96% identical to the respective heavy chain sequence (e.g., CS01-HC-AAm23, CS01-HC-AAm123, or CS01-HC-AAm234), and the light chain of the Factor FVIII polypeptide has a sequence at least 96% identical to the respective light chain sequence (e.g., CS01-LC-AAm23, CS01-LC-AAm123, or CS01-LC-AAm234).

In one embodiment of the Factor VIII polypeptides described, the heavy chain of the Factor VIII polypeptide has a sequence at least 97% identical to the respective heavy chain sequence (e.g., CS01-HC-AAm23, CS01-HC-AAm123, or CS01-HC-AAm234), and the light chain of the Factor FVIII polypeptide has a sequence at least 97% identical to the respective light chain sequence (e.g., CS01-LC-AAm23, CS01-LC-AAm123, or CS01-LC-AAm234).

In one embodiment of the Factor VIII polypeptides described, the heavy chain of the Factor VIII polypeptide has a sequence at least 98% identical to the respective heavy chain sequence (e.g., CS01-HC-AAm23, CS01-HC-AAm123, or CS01-HC-AAm234), and the light chain of the Factor FVIII polypeptide has a sequence at least 98% identical to the respective light chain sequence (e.g., CS01-LC-AAm23, CS01-LC-AAm123, or CS01-LC-AAm234).

In one embodiment of the Factor VIII polypeptides described, the heavy chain of the Factor VIII polypeptide has a sequence at least 99% identical to the respective heavy chain sequence (e.g., CS01-HC-AAm23, CS01-HC-AAm123, or CS01-HC-AAm234), and the light chain of the Factor FVIII polypeptide has a sequence at least 99% identical to the respective light chain sequence (e.g., CS01-LC-AAm23, CS01-LC-AAm123, or CS01-LC-AAm234).

In one embodiment of the Factor VIII polypeptides described, the heavy chain of the Factor VIII polypeptide has a sequence at least 99.5% identical to the respective heavy chain sequence (e.g., CS01-HC-AAm23, CS01-HC-AAm123, or CS01-HC-AAm234), and the light chain of the Factor FVIII polypeptide has a sequence at least 99.5% identical to the respective light chain sequence (e.g., CS01-LC-AAm23, CS01-LC-AAm123, or CS01-LC-AAm234).

In one embodiment of the Factor VIII polypeptides described, the heavy chain of the Factor VIII polypeptide has a sequence identical to the respective heavy chain sequence (e.g., CS01-HC-AAm23, CS01-HC-AAm123, or CS01-HC-AAm234), and the light chain of the Factor FVIII polypeptide has a sequence identical to the respective light chain sequence (e.g., CS01-LC-AAm23, CS01-LC-AAm123, or CS01-LC-AAm234).

In one embodiment of the Factor VIII polypeptides described above, the polypeptide linker has at least 95% identity to BDL-SQ-AA (SEQ ID NO: 30).

In one embodiment of the Factor VIII polypeptides described above, the polypeptide linker has the amino acid sequence of BDL-SQ-AA (SEQ ID NO: 30).

In one embodiment of the Factor VIII polypeptides described above, the polypeptide linker includes a glycosylation peptide with an amino acid sequence having at least 92% identity to a glycosylation peptide selected from the group consisting of NG1-AA, NG4-AA, NG5-AA, NG6-

AA, NG7-AA, NG9-AA, NG10-AA, NG16-AA, NG17-AA, NG18-AA, NG19-AA, NG20-AA, NG21-AA and NGV-AA.

In one embodiment of the Factor VIII polypeptides described above, the polypeptide linker includes a glycosylation peptide selected from the group consisting of NG1-AA, NG4-AA, NG5-AA, NG6-AA, NG7-AA, NG9-AA, NG10-AA, NG16-AA, NG17-AA, NG18-AA, NG19-AA, NG20-AA, NG21-AA and NGV-AA.

In one embodiment of the Factor VIII polypeptides described above, the polypeptide linker has an amino acid sequence having at least 95% identity to a sequence selected from the group consisting of BDLNG1-AA, BDLNG3-AA, BDLNGS-AA, BDLNG6-AA, BDLNG9-AA, BDLNG10-AA, BDLNG16-AA, BDLNG17-AA, BDLNG18-AA, BDLNG19-AA, BDLNG20-AA and BDLNG21-AA.

In one embodiment of the Factor VIII polypeptides described above, the polypeptide linker has an amino acid sequence selected from the group consisting of BDLNG1-AA, BDLNG3-AA, BDLNGS-AA, BDLNG6-AA, BDLNG9-AA, BDLNG10-NA, BDLNG16-AA, BDLNG17-AA, BDLNG18-AA, BDLNG19-AA, BDLNG20-AA and BDLNG21-AA.

In another aspect, the disclosure provides a Factor VIII polypeptide having an amino acid sequence with at least 95% identity to CS40-FL-AAm23 (SEQ ID NO: 104). The Factor VIII polypeptide includes i) I105V, A127S, G151K, M166T, and L171P amino acid substitutions, ii) a deletion of amino acids AIEPR755-759, relative to FVIII-FL-AA (SEQ ID NO: 19), and iii) an insertion of amino acids TTYVNRSL (SEQ ID NO: 33) after N754, relative to FVIII-FL-AA (SEQ ID NO: 19).

In another aspect, the disclosure provides a Factor VIII polypeptide having an amino acid sequence with at least 95% identity to CS40-FL-AAm123. The Factor VIII polypeptide includes i) I105V, A127S, G151K, M166T, and L171P amino acid substitutions, ii) a deletion of amino acids AIEPR755-759, relative to FVIII-FL-AA (SEQ ID NO: 19), iii) an insertion of amino acids TTYVNRSL (SEQ ID NO: 33) after N754, relative to FVIII-FL-AA (SEQ ID NO: 19), and iv) an F328S amino acid substitution.

In another aspect, the disclosure provides a Factor VIII polypeptide having an amino acid sequence with at least 95% identity to CS40-FL-AAm234. The Factor VIII polypeptide includes i) I105V, A127S, G151K, M166T, and L171P amino acid substitutions, ii) a deletion of amino acids AIEPR755-759, relative to FVIII-FL-AA (SEQ ID NO: 19), iii) an insertion of amino acids TTYVNRSL (SEQ ID NO: 33) after N754, relative to FVIII-FL-AA (SEQ ID NO: 19), and iv) F328S/C1918G/C1922G amino acid substitutions.

In one embodiment of the Factor VIII polypeptides described, the Factor VIII polypeptide has a sequence at least 96% identical to the respective full-length sequence (e.g., CS40-FL-AAm23 (SEQ ID NO: 104), CS40-FL-AAm123, or CS40-FL-AAm234).

In one embodiment of the Factor VIII polypeptides described, the Factor VIII polypeptide has a sequence at least 97% identical to the respective full-length sequence (e.g., CS40-FL-AAm23 (SEQ ID NO: 104), CS40-FL-AAm123, or CS40-FL-AAm234).

In one embodiment of the Factor VIII polypeptides described, the Factor VIII polypeptide has a sequence at least 98% identical to the respective full-length sequence (e.g., CS40-FL-AAm23 (SEQ ID NO: 104), CS40-FL-AAm123, or CS40-FL-AAm234).

In one embodiment of the Factor VIII polypeptides described, the Factor VIII polypeptide has a sequence at least 99% identical to the respective full-length sequence (e.g., CS40-FL-AAm23 (SEQ ID NO: 104), CS40-FL-AAm123, or CS40-FL-AAm234).

In one embodiment of the Factor VIII polypeptides described, the Factor VIII polypeptide has a sequence at least 99.5% identical to the respective full-length sequence (e.g., CS40-FL-AAm23 (SEQ ID NO: 104), CS40-FL-AAm123, or CS40-FL-AAm234).

In one embodiment of the Factor VIII polypeptides described, the Factor VIII polypeptide has a sequence identical to the respective full-length sequence (e.g., CS40-FL-AAm23 (SEQ ID NO: 104), CS40-FL-AAm123, or CS40-FL-AAm234).

BRIEF DESCRIPTION OF DRAWINGS

FIGS. 2A and 2B show the CS04 codon-altered nucleotide sequence (SEQ ID NO: 1) encoding a Factor VIII variant in accordance with some embodiments ("CS04-FL-NA" for full-length coding sequence).

FIG. 3 shows the Factor VIII variant amino acid sequence (SEQ ID NO: 2) encoded by the CS04 codon-altered nucleotide sequence in accordance with some embodiments ("CS04-FL-AA" for full-length amino acid sequence).

FIG. 4 shows the portion of the CS04 codon-altered nucleotide sequence (SEQ ID NO: 3) encoding the heavy chain of a Factor VIII variant in accordance with some embodiments ("CS04-HC-NA").

FIG. 5 shows the portion of the CS04 codon-altered nucleotide sequence (SEQ ID NO: 4) encoding the light chain of a Factor VIII variant in accordance with some embodiments ("CS04-LC-NA").

FIG. 6 shows exemplary coding sequences (SEQ ID NOS 5-7 and 36-48, respectively, in order of appearance) for B-domain substituted linkers in accordance with some embodiments. BDLO01 (SEQ ID NO: 5), BDLO04 (SEQ ID NO: 6), and BDLO23 (SEQ ID NO: 7) are the respective portions of the CS01, CS04, and CS23 codon-altered nucleotide sequences that encode a B-domain substituted linker, respectively.

FIGS. 7A, 7B, and 7C show an AAV vector sequence (SEQ ID NO: 8) containing an CS04 codon-altered nucleotide sequence in accordance with some embodiments ("CS04-AV-NA").

FIGS. 8A and 8B show the CS01m1 codon-altered nucleotide sequence (SEQ ID NO: 49) encoding a Factor VIII variant with an F328S amino acid substitution in accordance with some embodiments ("CS01m1-FL-NA").

FIGS. 9A and 9B show the CS04Δ(760-1667) (SPI; CS04Δ(741-1648), SPE) codon-altered nucleotide sequence (SEQ ID NO: 9) encoding a single-chain Factor VIII variant in accordance with some embodiments ("CS04-SC1-NA").

FIG. 10 shows the Factor VIII variant amino acid sequence (SEQ ID NO: 10) encoded by the CS01Δ(760-1667) (SPI; CS01Δ(741-1648), SPE), CS04Δ(760-1667) (SPI; CS04Δ(741-1648), SPE), and CS23Δ(760-1667) (SPI; CS23Δ(741-1648), SPE) codon-altered nucleotide sequences in accordance with some embodiments ("CS01-SC1-AA," "CS04-SC1-AA," and "CS23-SC1-AA," respectively).

FIGS. 11A and 11B show the CS04Δ(772-1667) (SPI; CS04Δ(753-1648), SPE) codon-altered nucleotide sequence (SEQ ID NO: 11) encoding a single-chain Factor VIII variant in accordance with some embodiments ("CS04-SC2-NA").

FIG. 12 shows the Factor VIII variant amino acid sequence (SEQ ID NO: 12) encoded by the CS01Δ(772-1667) (SPI; CS01Δ(753-1648), SPE), CS04Δ(772-1667) (SPI; CS04Δ(753-1648), SPE), and CS23Δ(772-1667) (SPI; CS23Δ(753-1648), SPE) codon-altered nucleotide sequence in accordance with some embodiments ("CS01-SC2-AA," "CS04-SC2-AA," and "CS23-SC2-AA," respectively).

FIGS. 13A and 13B show amino acid and nucleotide sequences for exemplary glycosylation peptides that are inserted into the B-domain substituted linker in accordance with some embodiments. "NG1" or NG1-AA" is the code for the amino acid sequence, shown in the top line. "NG1-NA" is the code for the nucleic acid sequence, shown in the bottom line for each set. FIGS. 13A and 13B disclose the amino acid sequences as SEQ ID NOS 51, 53, 55, 57, 59, 61, 63, 65, 67, 69, 71, 73, and 75, and the nucleotide sequences as SEQ ID NOS 50, 52, 54, 56, 58, 60, 62, 64, 66, 68, 70, 72, and 74, all respectively, in order of appearance.

FIG. 14 shows the results of in silico prediction of in vivo N-glycosylation of the wild-type Factor VIII B-domain. Figure discloses SEQ ID NOS 76 and 76-82, respectively, in order of appearance.

FIG. 15 shows the results of in silico prediction of in vivo N-glycosylation of the V3 peptide linker. Figure discloses SEQ ID NOS 83 and 83-89, respectively, in order of appearance.

FIGS. 16A and 16B show the CS01 codon-altered nucleotide sequence (SEQ ID NO: 13) encoding a Factor VIII variant in accordance with some embodiments ("CS01-FL-NA").

FIGS. 17A and 17B show the CS08 codon-altered nucleotide sequence (SEQ ID NO: 14) encoding a Factor VIII variant in accordance with some embodiments ("CS08-FL-NA").

FIGS. 18A and 18B show the CS10 codon-altered nucleotide sequence (SEQ ID NO: 15) encoding a Factor VIII variant in accordance with some embodiments ("CS10-FL-NA").

FIGS. 19A and 19B show the CS11 codon-altered nucleotide sequence (SEQ ID NO: 16) encoding a Factor VIII variant in accordance with some embodiments ("CS11-FL-NA").

FIGS. 20A and 20B show the CS40 wild-type ReFacto coding sequence (SEQ ID NO: 17), in accordance with some embodiments ("CS40-FL-NA").

FIGS. 21A and 21B show the CH25 codon-altered nucleotide sequence (SEQ ID NO: 18) encoding a Factor VIII variant in accordance with some embodiments ("CH25-FL-NA").

FIG. 22 shows a wild-type human Factor VIII amino acid sequence (SEQ ID NO: 19), in accordance with some embodiments ("FVIII-FL-AA").

FIGS. 26A and 26B show the CS23 codon-altered nucleotide sequence (SEQ ID NO: 20) encoding a Factor VIII variant in accordance with some embodiments ("CS23-FL-NA").

FIG. 27 shows the Factor VIII variant amino acid sequence (SEQ ID NO: 21) encoded by the CS23 codon-altered nucleotide sequence in accordance with some embodiments ("CS23-FL-AA").

FIG. 28 shows the portion of the CS23 codon-altered nucleotide sequence (SEQ ID NO: 22) encoding the heavy chain of a Factor VIII variant in accordance with some embodiments ("CS23-HC-NA").

FIG. 29 shows the portion of the CS23 codon-altered nucleotide sequence (SEQ ID NO: 23) encoding the light chain of a Factor VIII variant in accordance with some embodiments ("CS23-LC-NA").

FIGS. 30A and 30B show the CS01m13 codon-altered nucleotide sequence (SEQ ID NO: 90) encoding a Factor VIII variant with m1 (F328S) and m3 amino acid substitutions in accordance with some embodiments ("CS01-FL-NA-m13").

FIGS. 31A and 31B show the CS01m23 codon-altered nucleotide sequence (SEQ ID NO: 91) encoding a Factor VIII variant with the m2 and m3 mutation sets in accordance with some embodiments ("CS01-FL-NA-m23").

FIGS. 32A and 32B show the CS01m3 codon-altered nucleotide sequence (SEQ ID NO: 92) encoding a Factor VIII variant with m3 amino acid substitutions in accordance with some embodiments ("CS01-FL-NA-m3").

FIGS. 33A and 33B show the CS01m2 codon-altered nucleotide sequence (SEQ ID NO: 93) encoding a Factor VIII variant with the m2 mutation set (I105V/A127S/G151K/M166T/L171P (SPI)) amino acid substitutions in accordance with some embodiments ("CS01-FL-NA-m2").

FIGS. 34A and 34B show the CS04m2 codon-altered nucleotide sequence (SEQ ID NO: 94) encoding a Factor VIII variant with the m2 mutants (I105V/A127S/G151K/M166T/L171P (SPI)) amino acid substitutions in accordance with some embodiments ("CS01-FL-NA-m2").

FIGS. 35A and 35B show the CS04m3 codon-altered nucleotide sequence (SEQ ID NO: 95) encoding a Factor VIII variant with m3 amino acid substitutions in accordance with some embodiments ("CS04-FL-NA-m3").

FIGS. 36A and 36B show the CS04m23 codon-altered nucleotide sequence (SEQ ID NO: 96) encoding a Factor VIII variant with the m2 mutant set (I105V/A127S/G151K/M166T/L171P (SPI)) and m3 amino acid substitutions in accordance with some embodiments ("CS04-FL-NA-m23").

FIGS. 37A and 37B show the CS04m1 codon-altered nucleotide sequence (SEQ ID NO: 97) encoding a Factor VIII variant with an m1 (F328S) amino acid substitution in accordance with some embodiments ("CS04-FL-NA-m1").

FIGS. 38A and 38B show the CS04m13 codon-altered nucleotide sequence (SEQ ID NO: 98) encoding a Factor VIII variant with m1 and m3 amino acid substitutions in accordance with some embodiments ("CS04-FL-NA-m13")

FIGS. 39A and 39B show the CS23m13 codon-altered nucleotide sequence (SEQ ID NO: 99) encoding a Factor VIII variant with m1 and m3 amino acid substitutions in accordance with some embodiments ("CS23m13-FL-NA")

FIGS. 40A and 40B show the CS23m3 codon-altered nucleotide sequence (SEQ ID NO: 100) encoding a Factor VIII variant with m3 amino acid substitutions in accordance with some embodiments ("CS23-FL-NA-m3")

FIGS. 41A and 41B show the CS23m2 codon-altered nucleotide sequence (SEQ ID NO: 101) encoding a Factor VIII variant with the m2 mutant set (I105V/A127S/G151K/M166T/L171P amino acid substitutions) in accordance with some embodiments ("CS23-FL-NA-m2").

FIGS. 42A and 42B show the CS23m1 codon-altered nucleotide sequence (SEQ ID NO: 102) encoding a Factor VIII variant with an m1 (F328S) amino acid substitution in accordance with some embodiments ("CS23-FL-NA-m1").

FIGS. 43A and 43B show the CS23m23 codon-altered nucleotide sequence (SEQ ID NO: 103) encoding a Factor VIII variant with the m2 mutant set (I105V/A127S/G151K/M166T/L171P) and m3 amino acid substitutions in accordance with some embodiments ("CS23-FL-NA-m23").

FIG. 47 shows the portion of the CS01 codon-altered nucleotide sequence (SEQ ID NO: 24) encoding the heavy chain of a Factor VIII variant in accordance with some embodiments ("CS01-HC-NA").

FIG. 48 shows the portion of the CS01 codon-altered nucleotide sequence (SEQ ID NO: 25) encoding the light chain of a Factor VIII variant in accordance with some embodiments ("CS01-LC-NA").

FIGS. 49A and 49B show the CS01Δ(760-1667) (SPI; CS01Δ(741-1648), SPE) codon-altered nucleotide sequence (SEQ ID NO: 26) encoding a single-chain Factor VIII variant in accordance with some embodiments ("CS01-SC1-NA").

FIGS. 50A and 50B show the CS01Δ(772-1667) (SPI; CS01Δ(753-1648), SPE) codon-altered nucleotide sequence (SEQ ID NO: 27) encoding a single-chain Factor VIII variant in accordance with some embodiments ("CS01-SC2-NA").

FIGS. 51A and 51B show the CS23Δ(760-1667) (SPI; CS23Δ(741-1648), SPE) codon-altered nucleotide sequence (SEQ ID NO: 28) encoding a single-chain Factor VIII variant in accordance with some embodiments ("CS23-SC1-NA").

FIGS. 52A and 52B show the CS23Δ(772-1667) (SPI; CS23Δ(753-1648), SPE) codon-altered nucleotide sequence (SEQ ID NO: 29) encoding a single-chain Factor VIII variant in accordance with some embodiments ("CS23-SC2-NA").

FIG. 53 shows the Factor VIII variant amino acid sequence (SEQ ID NO: 104) encoded by the CS01m23 codon-altered nucleotide sequence in accordance with some embodiments ("CS01m23-FL-AA").

FIG. 54 shows the Factor VIII variant amino acid sequence (SEQ ID NO: 105) encoded by the CS04m3 codon-altered nucleotide sequence in accordance with some embodiments ("CS01m23-FL-AA").

FIG. 55 shows the Factor VIII variant amino acid sequence (SEQ ID NO: 106) encoded by the CS01m12 codon-altered nucleotide sequence in accordance with some embodiments ("CS01m12-FL-AA").

FIG. 56 shows the Factor VIII variant amino acid sequence (SEQ ID NO: 107) encoded by the CS04m12 codon-altered nucleotide sequence in accordance with some embodiments ("CS04m12-FL-AA").

FIGS. 57A and 57B show the CS01m12 codon-altered nucleotide sequence (SEQ ID NO: 108) encoding a Factor VIII variant with m1 (F328S) and m2 amino acid substitutions in accordance with some embodiments ("CS01-FL-NAm12").

FIGS. 58A and 58B show the CS04m12 codon-altered nucleotide sequence (SEQ ID NO: 109) encoding a Factor VIII variant with m1 (F328S) and m2 amino acid substitutions in accordance with some embodiments ("CS04-FL-NAm12").

DETAILED DESCRIPTION OF DISCLOSURE

I. Introduction

Figure 1:
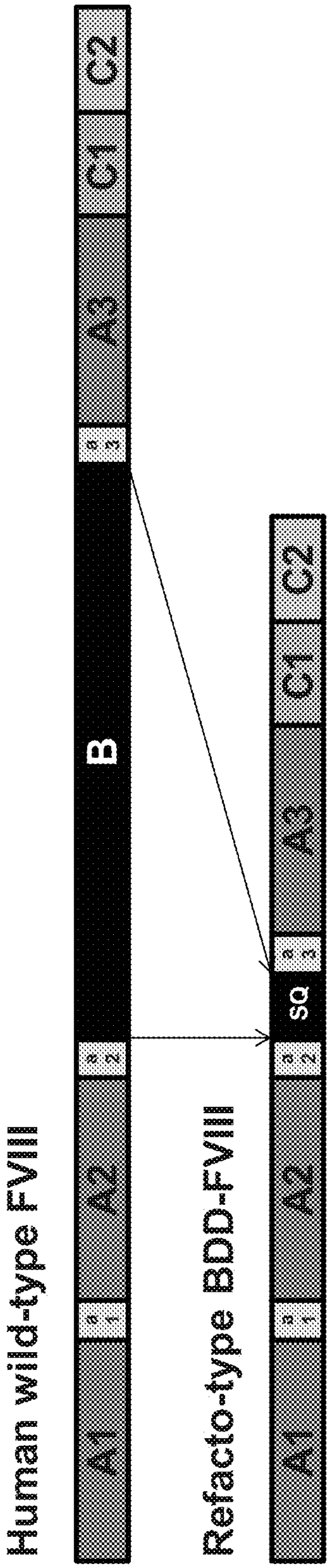
FIG. 1 shows schematic illustrations of the wild-type and ReFacto-type human Factor VIII protein constructs.

AAV-based gene therapy holds great promise for the treatment of hemophiliacs. For hemophilia B, first clinical data are encouraging in that FIX levels of about 10% can be maintained in at least some patients for more than 1 year. For hemophilia A however, achieving therapeutic expression levels of 5-10% with AAV vectors remains challenging for various reasons. First, the Factor VIII coding sequence is too large for conventional AAV-based vectors. Second, engineered B-domain deleted or truncated Factor VIII constructs suffer from poor expression in vivo, even when codon-optimized. Third, these B-domain deleted or truncated Factor VIII variant constructs have short half-lives in vivo, exacerbating the effects of poor expression. Fourth, even when expressed, FVIII is not efficiently secreted from cells, as are other coagulation factors, such as Factor IX.

Moreover, these challenges cannot be addressed by simply administering higher doses of the gene therapy construct. According to current knowledge, the vector dose of an AAV-based gene therapy vector should be increased above $2\times10^{12}$ vg/kg bodyweight. This is because at such high doses a T cell immune response is triggered, which destroys transduced cells and, as a consequence, transgene expression is reduced or even eliminated. Therefore, strategies to improve the expression of FVIII are needed to make FVIII gene therapy a viable therapeutic option for hemophilia A patients.

The present disclosure relates to the discovery of codon-altered Factor VIII variant coding sequences that solve these and other problems associated with Factor VIII gene therapy. For example, the polynucleotides disclosed herein provide markedly improved expression in mammalian cells, and display improved virion packaging due to stabilized packing interactions. In some implementations, these advantages are realized by using coding sequences for the heavy and light chains of Factor VIII with high sequence identity to the codon altered CS01, CS04, and CS23 constructs (e.g., with high sequence identity to one of the CS01-HC, CS04-HC, and CS23-HC heavy chain coding sequences and high sequence identity to one of the CS01-LC, CS04-LC, and CS23-LC light chain coding sequences).

In some implementations, the Factor VIII molecules encoded by the polynucleotides described herein have been shortened by truncating, deleting, or replacing the wild-type B-domain. As such, the polynucleotides are better suited for expressing Factor VIII via conventional gene therapy vectors, which inefficiently express larger polypeptides, such as the wild-type Factor VIII.

Advantageously, it is shown herein that the CS01, CS04, and CS23 codon-altered Factor VIII variant coding sequences provide superior expression of a B-domain deleted Factor VIII construct in vivo. For example, it is demonstrated in Example 2 and Example 4 that intravenous administration of AAV-based gene therapy vectors having the CS01 (SEQ ID NO: 13), CS04 (SEQ ID NO: 1), and CS23 (SEQ ID NO: 20) coding sequence provide 18-fold, 74-fold, and 30-fold increases in Factor VIII expression, relative to the corresponding CS40 construct encoded with the wild-type polynucleotide sequence (SEQ ID NO: 17), in Factor VIII knock-out mice (Table 4 and Table 7).

Further, it also shown herein that the CS01 and CS04 codon-altered Factor VIII variant coding sequences provide superior virion packaging and virus production. For example, it is demonstrated in Example 1 that AAV vector constructs containing the CS01 and CS04 constructs provided 5 to 7-fold greater viral yield, relative to the corresponding CS40 construct encoded with the wild-type polynucleotide sequence, when isolated from the same amount of cell pellet.

Advantageously, Applicants also found that the improved Factor VIII activity generated from the CS01, CS04, and CS23 codon altered sequences could be further enhanced by introducing mutations into the underlying Factor VIII polypeptide sequence. For example, as demonstrated in Example 4, the F328S, X5, and X1 mutations, alone and in combination with one another, further increased FVIII activity when expressed in vivo in the CS01 or CS04 codon altered background 2 to 7-fold, relative to the wild type, codon altered constructs (Table 7). More strikingly, these codon altered sequences, encoding the mutant Factor VIII mutants, provided up to 246-fold greater increase as compared to the corresponding CS40 construct encoded with the wild-type polynucleotide sequence (Table 7).

II. Definitions

As used herein, the following terms have the meanings ascribed to them unless specified otherwise.

As used herein, the terms "Factor VIII" and "FVIII" are used interchangeably, and refer to any protein with Factor VIII activity (e.g., active FVIII, often referred to as FVIIIa) or protein precursor (e.g., pro-protein or pre-pro-protein) of a protein with Factor VIII activity, particularly Factor IXa cofactor activity. In an exemplary embodiment, a Factor VIII polypeptide refers to a polypeptide that has sequences with high sequence identity (e.g., at least 70%, 75%, 80%, 85%, 90%, 95%, 99%, or more) to the heavy and light chains of a wild type Factor VIII polypeptide. In some embodiments, the B-domain of a Factor VIII polypeptide is deleted, truncated, or replaced with a linker polypeptide to reduce the size of the polynucleotide encoding the Factor VIII polypeptide. In an exemplary embodiment, amino acids 20-1457 of SEQ ID NO: 2 constitute a Factor VIII polypeptide.

Non-limiting examples of wild type Factor VIII polypeptides include human pre-pro-Factor VIII (e.g., GenBank accession nos. AAA52485, CAA25619, AAA58466, AAA52484, AAA52420, AAV85964, BAF82636, BAG36452, CAI41660, CAI41666, CAI41672, CAI43241, CA003404, EAW72645, AAH22513, AAH64380, AAH98389, AAI11968, AAI11970, or AAB61261), corresponding pro-Factor VIII, and natural variants thereof; porcine pre-pro-Factor VIII (e.g., UniProt accession nos. F1RZ36 or K7GSZ5), corresponding pro-Factor VIII, and natural variants thereof; mouse pre-pro-Factor VIII (e.g., GenBank accession nos. AAA37385, CAM15581, CAM26492, or EDL29229), corresponding pro-Factor VIII, and natural variants thereof; rat pre-pro-Factor VIII (e.g., GenBank accession no. AAQ21580), corresponding pro-Factor VIII, and natural variants thereof; rat pre-pro-Factor VIII; and other mammalian Factor VIII homologues (e.g., monkey, ape, hamster, guinea pig, etc.).

As used herein, a Factor VIII polypeptide includes natural variants and artificial constructs with Factor IX cofactor activity. As used in the present disclosure, Factor VIII encompasses any natural variants, alternative sequences, isoforms, or mutant proteins that retain some basal Factor IX cofactor activity (e.g., at least 5%, 10%, 25%, 50%, 75%, or more of the corresponding wild type activity). Examples of Factor VIII amino acid variations (relative to FVIII-FL-AA (SEQ ID NO: 19)) found in the human population include, without limitation, S19R, R22T, Y24C, Y25C, L26P/R, E30V, W33G, Y35C/H, G41C, R48C/K, K67E/N, L69P, E72K, D75E/V/Y, P83R, G89D/V, G92A/V, A97P, E98K, V99D, D101G/H/V, V104D, K108T, M110V, A111T/V, H113R/Y, L117F/R, G121S, E129V, G130R, E132D, Y133C, D135G/Y, T137A/I, S138R, E141K, D145H, V147D, Y155H, V159A, N163K, G164D/V, P165S, C172W, S176P, S179P, V181E/M, K185T, D186G/N/Y, S189L, L191F, G193R, L195P, C198G, S202N/R, F214V, L217H, A219D/T, V220G, D222V, E223K, G224W, T252I, V253F, N254I, G255V, L261P, P262L, G263S, G266F, C267Y, W274C, H275L, G278R, G280D, E284K, V285G, E291G/K, T294I, F295L, V297A, N299I, R301C/H/L, A303E/P, 1307S, S308L, F312S, T314A/I, A315V, G323E, L326P, L327P/V, C329F, I331V, M339T, E340K, V345A/L, C348R/S/Y, Y365C, R391C/H/P, S392L/P, A394S, W401G, I405F/S, E409G, W412G/R, K427I, L431F/S, R437P/W, I438F, G439D/S/V, Y442C, K444R, Y450D/N, T454I, F455C, G466E, P470L/R/T, G474E/R/V, E475K, G477V, D478N, T479R, F484C, A488G, R490G, Y492C/H, Y492H, I494T, P496R, G498R, R503H, G513S/V, I522Y, K529E, W532G, P540T, T541S, D544N, R546W, R550C/G/H, S553P, S554C/G, V556D, R560T, D561G/H/Y, I567T, P569R, S577F, V578A, D579A/H, N583S, Q584H/K/R, I585R/T, M586V, D588G/Y, L594Q, S596P, N601D/K, R602G, S603I/R, W604C, Y605H/S, N609I, R612C, N631K/S, M633I, S635N, N637D/I/S, Y639C, L644V, L650F, V653A/M, L659P, A663V, Q664P, F677L, M681I, V682F, Y683C/N, T686R, F698L, M699T/V, M701I, G705V, G710W, N713I, R717L/W, G720D/S, M721I/L, A723T, L725Q, V727F, E739K, Y742C, R795G, P947R, V1012L, E1057K, H1066Y, D1260E, K1289Q, Q1336K, N1460K, L1481P, A1610S, I1698T, Y1699C/F, E1701K, Q1705H, R1708C/H, T1714S, R1715G, A1720V, E1723K, D1727V, Y1728C, R1740G, K1751Q, F1762L, R1768H, G1769R, L1771P, L1775F/V, L1777P, G1779E/R, P1780L, I1782R, D1788H, M1791T, A1798P, S1799H, R1800C/G/H, P1801A, Y1802C, S1803Y, F1804S, L1808F, M1842I, P1844S, T1845P, E1848G, A1853T/V, S1858C, K1864E, D1865N/Y, H1867P/R, G1869D/V, G1872E, P1873R, L1875P, V1876L, C1877R/Y, L1882P, R1888I, E1894G, 11901F, E1904D/K, S1907C/R, W1908L, Y1909C, A1939T/V, N1941D/S, G1942A, M1945V, L1951F, R1960L/Q, L1963P, S1965I, M19661/V, G1967D, S1968R, N1971T, H1973L, G1979V, H1980P/Y, F1982I, R1985Q, L1994P, Y1998C, G2000A, T2004R, M2007I, G2013R, W2015C, R2016P/W, E2018G, G2022D, G2028R, S2030N, V2035A, Y2036C, N2038S, 2040Y, G2045E/V, 12051S, I2056N, A2058P, W2065R, P2067L, A2070V, S2082N, S2088F, D2093G/Y, H2101D, T2105N, Q2106E/P/R, G2107S, R2109C, 12117F/S, Q2119R, F2120C/L, Y2124C, R2135P, S2138Y, T2141N, M2143V, F2145C, N2148S, N2157D, P2162L, R2169C/H, P2172L/Q/R, T2173A/I, H2174D, R2178C/H/L, R2182C/H/P, M2183R/V, L2185S/W, S2192I, C2193G, P2196R, G2198V, E2200D, 12204T, 12209N, A2211P, A2220P, P2224L, R2228G/L/P/Q, L2229F, V2242M, W2248C/S, V2251A/E, M2257V, T2264A, Q2265R, F2279C/I, I2281T, D2286G, W2290L, G2304V, D2307A, P2319L/S, R2323C/G/H/L, R2326G/L/P/Q, Q2330P, W2332R, I2336F, R2339T, G2344C/D/S, and C2345S/Y. Factor VIII proteins also include polypeptides containing post-translational modifications.

Generally, polynucleotides encoding Factor VIII encode for an inactive single-chain polypeptide (e.g., a pre-pro-protein) that undergoes post-translational processing to form an active Factor VIII protein (e.g., FVIIIa). For example, referring to FIG. 1, the wild type human Factor VIII pre-pro-protein is first cleaved to release the encoded signal peptide (not shown), forming a first single-chain pro-protein (shown as "human wild-type FVIII). The pro-protein is then cleaved between the B and A3 domains to form a first polypeptide that includes the Factor VIII heavy chain (e.g., the A1 and A2 domains) and B-domain, and a second polypeptide that includes the Factor VIII light chain (e.g., including the A3, C1, and C3 domains). The first polypeptide is further cleaved to remove the B-domain, and also to separate the A1 and A2 domains, which remain associated with the Factor VIII light chain in the mature Factor VIIIa protein. For review of the Factor VIII maturation process, see Graw et al., Nat Rev Genet., 6(6):488-501 (2005), the content of which is incorporated herein by reference in its entirety for all purposes.

However, in some embodiments, the Factor VIII polypeptide is a single-chain Factor VIII polypeptide. Single-chain Factor VIII polypeptides are engineered to remove natural cleavage sites, and optionally remove, truncate, or replace the B-domain of Factor VIII. As such, they are not matured by cleavage (other than cleavage of an optional signal and/or leader peptide), and are active as a single chain. Non-limiting examples of single-chain Factor VIII polypeptides are described in Zollner et al. (Thromb Res, 134(1):125-31 (2014)) and Donath et al. (Biochem J., 312 (1):49-55 (1995)), the disclosures of which are hereby incorporated by reference in their entireties for all purposes.

As used herein, the terms "Factor VIII heavy chain," or simply "heavy chain," refers to the aggregate of the A1 and A2 domains of a Factor VIII polypeptide. In an exemplary embodiment, amino acids 20-759 of CS04-FL-AA (SEQ ID NO: 2) constitute a Factor VIII heavy chain.

As used herein, the term "Factor VIII light chain," or simply "light chain," refers to the aggregate of the A3, C1, and C2 domains of a Factor VIII polypeptide. In an exemplary embodiment, amino acids 774-1457 CS04-FL-AA (SEQ ID NO: 2) constitute a Factor VIII light chain. In some embodiments, a Factor VIII light chain excludes the acidic a3 peptide, which is released during maturation in vivo.

Generally, Factor VIII heavy and light chains are expressed as a single polypeptide chain, e.g., along with an optional B-domain or B-domain substituted linker. However, in some embodiments, a Factor VIII heavy chain and Factor VIII light chain are expressed as separate polypeptide chains (e.g., co-expressed), and reconstituted to form a Factor VIII protein (e.g., in vivo or in vitro).

As used herein, the terms "B-domain substituted linker" and "Factor VIII linker" are used interchangeably, and refer to truncated versions of a wild type Factor VIII B-domain (e.g., amino acids 760-1667 of FVIII-FL-AA (SEQ ID NO: 19)) or peptides engineered to replace the B-domain of a Factor VIII polypeptide. As used herein, a Factor VIII linker is positioned between the C-terminus of a Factor VIII heavy chain and the N-terminus of a Factor VIII light chain in a Factor VIII variant polypeptide in accordance with some embodiments. Non-limiting examples of B-domain substituted linkers are disclosed in U.S. Pat. Nos. 4,868,112, 5,112,950, 5,171,844, 5,543,502, 5,595,886, 5,610,278, 5,789,203, 5,972,885, 6,048,720, 6,060,447, 6,114,148, 6,228,620, 6,316,226, 6,346,513, 6,458,563, 6,924,365, 7,041,635, and 7,943,374; U.S. Patent Application Publication Nos. 2013/024960, 2015/0071883, and 2015/0158930; and PCT Publication Nos. WO 2014/064277 and WO 2014/127215, the disclosures of which are hereby incorporated by reference, in their entireties, for all purposes.

Unless otherwise specified herein, the numbering of Factor VIII amino acids refers to the corresponding amino acid in the full-length, wild-type human Factor VIII sequence (FVIII-FL-AA), presented as SEQ ID NO: 19 in FIG. 22. As such, when referring to an amino acid substitution in a Factor VIII variant protein disclosed herein, the recited amino acid number refers to the analogous (e.g., structurally or functionally equivalent) and/or homologous (e.g., evolutionarily conserved in the primary amino acid sequence) amino acid in the full-length, wild-type Factor VIII sequence. For example, a T2105N amino acid substitution refers to a T to N substitution at position 2105 of the full-length, wild-type human Factor VIII sequence (FVIII-FL-AA; SEQ ID NO: 19), a T to N substitution at position 1211 of the Factor VIII variant protein encoded by CS04 (CS04-FL-AA; SEQ ID NO: 2), and a T to N substitution at position 1212 of the Factor VIII variant encoded by CS04m3 (CS04m3-FL-AA; SEQ ID NO: 105).

As described herein, the Factor VIII amino acid numbering system is dependent on whether the Factor VIII signal peptide (e.g., amino acids 1-19 of the full-length, wild-type human Factor VIII sequence) is included. Where the signal peptide is included, the numbering is referred to as "signal peptide inclusive" or "SPI". Where the signal peptide is not included, the numbering is referred to as "signal peptide exclusive" or "SPE." For example, F328S is SPI numbering for the same amino acid as F309S, in SPE numbering. Unless otherwise indicated, all amino acid numbering refers to the corresponding amino acid in the full-length, wild-type human Factor VIII sequence (FVIII-FL-AA), presented as SEQ ID NO: 19 in FIG. 22.

As described herein, the codon-altered polynucleotides provide increased expression of transgenic Factor VIII in vivo (e.g., when administered as part of a gene therapy vector), as compared to the level of Factor VIII expression provided by a natively-coded Factor VIII construct (e.g., a polynucleotide encoding the same Factor VIII construct using the wild-type human codons). As used herein, the term "increased expression" refers to an increased level of transgenic Factor VIII activity in the blood of an animal administered the codon-altered polynucleotide encoding Factor VIII, as compared to the level of transgenic Factor VIII activity in the blood of an animal administered a natively-coded Factor VIII construct. The activity levels can be measured using any Factor VIII activity known in the art. An exemplary assay for determining Factor VIII activity is the Technochrome FVIII assay (Technoclone, Vienna, Austria).

In some embodiments, increased expression refers to at least 25% greater transgenic Factor VIII activity in the blood of an animal administered the codon-altered Factor VIII polynucleotide, as compared to the level of transgenic Factor VIII activity in the blood of an animal administered a natively coded Factor VIII polynucleotide. In some embodiments, increased expression refers to at least 50% greater, at least 75% greater, at least 100% greater, at least 3-fold greater, at least 4-fold greater, at least 5-fold greater, at least 6-fold greater, at least 7-fold greater, at least 8-fold greater, at least 9-fold greater, at least 10-fold greater, at least 15-fold greater, at least 20-fold greater, at least 25-fold greater, at least 30-fold greater, at least 40-fold greater, at least 50-fold greater, at least 60-fold greater, at least 70-fold greater, at least 80-fold greater, at least 90-fold greater, at least 100-fold greater, at least 125-fold greater, at least 150-fold greater, at least 175-fold greater, at least 200-fold greater, at least 225-fold greater, or at least 250-fold greater transgenic Factor VIII activity in the blood of an animal administered the codon-altered Factor VIII polynucleotide, as compared to the level of transgenic Factor VIII activity in the blood of an animal administered a natively coded Factor VIII polynucleotide.

As described herein, the codon-altered polynucleotides provide increased vector production, as compared to the level of vector production provided by a natively-coded Factor VIII construct (e.g., a polynucleotide encoding the same Factor VIII construct using the wild-type human codons). As used herein, the term "increased virus production" refers to an increased vector yield in cell culture (e.g., titer per liter culture) inoculated with the codon-altered polynucleotide encoding Factor VIII, as compared to the vector yield in cell culture inoculated with a natively-coded Factor VIII construct. The vector yields can be measured using any vector titer assay known in the art. An exemplary assay for determining vector yield (e.g., of an AAV vector) is qPCR targeting the AAV2 inverted terminal repeats (Aurnhammer, Human Gene Therapy Methods: Part B 23:18-28 (2012)).

In some embodiments, increased virus production refers to at least 25% greater codon-altered vector yield, as compared to the yield of a natively-coded Factor VIII construct in the same type of culture. In some embodiments, increased vector production refers to at least 50% greater, at least 75% greater, at least 100% greater, at least 3-fold greater, at least 4-fold greater, at least 5-fold greater, at least 6-fold greater, at least 7-fold greater, at least 8-fold greater, at least 9-fold greater, at least 10-fold greater, at least 15-fold greater, or at least 20-fold greater codon-altered vector yield, as compared to the yield of a natively-coded Factor VIII construct in the same type of culture.

As used herein, the term "hemophilia" refers to a group of disease states broadly characterized by reduced blood clotting or coagulation. Hemophilia may refer to Type A, Type B, or Type C hemophilia, or to the composite of all three diseases types. Type A hemophilia (hemophilia A) is caused by a reduction or loss of factor VIII (FVIII) activity and is the most prominent of the hemophilia subtypes. Type B hemophilia (hemophilia B) results from the loss or reduction of factor IX (FIX) clotting function. Type C hemophilia (hemophilia C) is a consequence of the loss or reduction in factor XI (FXI) clotting activity. Hemophilia A and B are X-linked diseases, while hemophilia C is autosomal. Conventional treatments for hemophilia include both prophylactic and on-demand administration of clotting factors, such as FVIII, FIX, including Bebulin®-VH, and FXI, as well as FEIBA-VH, desmopressin, and plasma infusions.

As used herein, the term "FVIII gene therapy" includes any therapeutic approach of providing a nucleic acid encoding Factor VIII to a patient to relieve, diminish, or prevent the reoccurrence of one or more symptoms (e.g., clinical factors) associated with hemophilia. The term encompasses administering any compound, drug, procedure, or regimen comprising a nucleic acid encoding a Factor VIII molecule, including any modified form of Factor VIII (e.g., Factor VIII variant), for maintaining or improving the health of an individual with hemophilia. One skilled in the art will appreciate that either the course of FVIII therapy or the dose of a FVIII therapeutic agent can be changed, e.g., based upon the results obtained in accordance with the present disclosure.

As used herein, the term "bypass therapy" includes any therapeutic approach of providing non-Factor VIII hemostatic agents, compounds or coagulation factors to a patient to relieve, diminish, or prevent the reoccurrence of one or more symptoms (e.g., clinical factors) associated with hemophilia. Non-Factor VIII compounds and coagulation factors include, but are not limited to, Factor VIII Inhibitor Bypass Activity (FEIBA), recombinant activated factor VII (FVIIa), prothrombin complex concentrates, and activated prothrombin complex concentrates. These non-Factor VIII compounds and coagulation factors may be recombinant or plasma-derived. One skilled in the art will appreciate that either the course of bypass therapy or the dose of bypass therapy can be changed, e.g., based upon the results obtained in accordance with the present disclosure.

As used herein, a "combination therapy" including administration of a nucleic acid encoding a Factor VIII molecule and a conventional hemophilia A therapeutic agent includes any therapeutic approach of providing both a nucleic acid encoding a Factor VIII molecule and a Factor VIII molecule and/or non-Factor VIII hemostatic agent (e.g., bypass therapeutic agent) to a patient to relieve, diminish, or prevent the reoccurrence of one or more symptoms (e.g., clinical factors) associated with hemophilia. The term encompasses administering any compound, drug, procedure, or regimen including a nucleic acid encoding a Factor VIII molecule, including any modified form of factor VIII, which is useful for maintaining or improving the health of an individual with hemophilia and includes any of the therapeutic agents described herein.

The terms "therapeutically effective amount or dose" or "therapeutically sufficient amount or dose" or "effective or sufficient amount or dose" refer to a dose that produces therapeutic effects for which it is administered. For example, a therapeutically effective amount of a drug useful for treating hemophilia can be the amount that is capable of preventing or relieving one or more symptoms associated with hemophilia. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

As used herein, the term "gene" refers to the segment of a DNA molecule that codes for a polypeptide chain (e.g., the coding region). In some embodiments, a gene is positioned by regions immediately preceding, following, and/or intervening the coding region that are involved in producing the polypeptide chain (e.g., regulatory elements such as a promoter, enhancer, polyadenylation sequence, 5'-untranslated region, 3'-untranslated region, or intron).

As used herein, the term "regulatory elements" refers to nucleotide sequences, such as promoters, enhancers, terminators, polyadenylation sequences, introns, etc, that provide for the expression of a coding sequence in a cell.

As used herein, the term "promoter element" refers to a nucleotide sequence that assists with controlling expression of a coding sequence. Generally, promoter elements are located 5' of the translation start site of a gene. However, in certain embodiments, a promoter element may be located within an intron sequence, or 3' of the coding sequence. In some embodiments, a promoter useful for a gene therapy vector is derived from the native gene of the target protein (e.g., a Factor VIII promoter). In some embodiments, a promoter useful for a gene therapy vector is specific for expression in a particular cell or tissue of the target organism (e.g., a liver-specific promoter). In yet other embodiments, one of a plurality of well characterized promoter elements is used in a gene therapy vector described herein. Non-limiting examples of well-characterized promoter elements include the CMV early promoter, the β-actin promoter, and the methyl CpG binding protein 2 (MeCP2) promoter. In some embodiments, the promoter is a constitutive promoter, which drives substantially constant expression of the target protein. In other embodiments, the promoter is an inducible promoter, which drives expression of the target protein in response to a particular stimulus (e.g., exposure to a particular treatment or agent). For a review of designing promoters for AAV-mediated gene therapy, see Gray et al. (Human Gene Therapy 22:1143-53 (2011)), the contents of which are expressly incorporated by reference in their entirety for all purposes.

As used herein, the term "vector" refers to any vehicle used to transfer a nucleic acid (e.g., encoding a Factor VIII gene therapy construct) into a host cell. In some embodiments, a vector includes a replicon, which functions to replicate the vehicle, along with the target nucleic acid. Non-limiting examples of vectors useful for gene therapy include plasmids, phages, cosmids, artificial chromosomes, and viruses, which function as autonomous units of replication in vivo. In some embodiments, a vector is a viral vehicle for introducing a target nucleic acid (e.g., a codon-altered polynucleotide encoding a Factor VIII variant). Many modified eukaryotic viruses useful for gene therapy are known in the art. For example, adeno-associated viruses (AAVs) are particularly well suited for use in human gene therapy because humans are a natural host for the virus, the native viruses are not known to contribute to any diseases, and the viruses illicit a mild immune response.

As used herein, the term "CpG island" refers to a region within a polynucleotide having a statistically elevated density of CpG dinucleotides. As used herein, a region of a polynucleotide (e.g., a polynucleotide encoding a codon-altered Factor VIII protein) is a CpG island if, over a 200-base pair window: (i) the region has GC content of greater than 50%, and (ii) the ratio of observed CpG dinucleotides per expected CpG dinucleotides is at least 0.6, as defined by the relationship:

$$\frac{N[CpG]*N[\text{length of window}]}{N[C]*N[G]} \geq 0.6.$$

For additional information on methods for identifying CpG islands, see Gardiner-Garden M. et al., J Mol Biol., 196(2): 261-82 (1987), the content of which is expressly incorporated herein by reference, in its entirety, for all purposes.

As used herein, the term "nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

The term "amino acid" refers to naturally occurring and non-natural amino acids, including amino acid analogs and amino acid mimetics that function in a manner similar to the naturally occurring amino acids. Naturally occurring amino acids include those encoded by the genetic code, as well as those amino acids that are later modified, e.g., hydroxyproline, y-carboxyglutamate, and O-phosphoserine. Naturally occurring amino acids can include, e.g., D- and L-amino acids. The amino acids used herein can also include non-natural amino acids. Amino acid analogs refer to compounds that have the same basic chemical structure as a naturally occurring amino acid, i.e., any carbon that is bound to a hydrogen, a carboxyl group, an amino group, and an R group, e.g., homoserine, norleucine, methionine sulfoxide, or methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The nucleotide sequences that encode the mutant Factor VIII constructs herein may be identical to the coding sequence provided herein or may be a different coding sequence, which sequence, as a result of the redundancy or degeneracy of the genetic code, encodes the same polypeptides as the coding sequences provided herein. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each variation of a nucleic acid which encodes a same polypeptide is implicit in each described sequence with respect to the expression product, but not with respect to actual gene therapy constructs.

As to amino acid sequences, one of ordinary skill in the art will recognize that individual substitutions, deletions or additions to a nucleic acid or peptide sequence that alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

Conservative amino acid substitutions providing functionally similar amino acids are well known in the art. Dependent on the functionality of the particular amino acid, e.g., catalytic, structural, or sterically important amino acids, different groupings of amino acid may be considered conservative substitutions for each other. Table 1 provides groupings of amino acids that are considered conservative substitutions based on the charge and polarity of the amino acid, the hydrophobicity of the amino acid, the surface exposure/structural nature of the amino acid, and the secondary structure propensity of the amino acid.

TABLE 1

Groupings of conservative amino acid substitutions based on the functionality of the residue in the protein.

| Important Feature | Conservative Groupings |
|---|---|
| Charge/Polarity | 1. H, R, and K |
| | 2. D and E |
| | 3. C, T, S, G, N, Q, and Y |
| | 4. A, P, M, L, I, V, F, and W |
| Hydrophobicity | 1. D, E, N, Q, R, and K |
| | 2. C, S, T, P, G, H, and Y |
| | 3. A, M, I, L, V, F, and W |
| Structural/Surface Exposure | 1. D, E, N, Q, H, R, and K |
| | 2. C, S, T, P, A, G, W, and Y |
| | 3. M, I, L, V, and F |
| Secondary Structure Propensity | 1. A, E, Q, H, K, M, L, and R |
| | 2. C, T, I, V, F, Y, and W |
| | 3. S, G, P, D, and N |
| Evolutionary Conservation | 1. D and E |
| | 2. H, K, and R |
| | 3. N and Q |
| | 4. S and T |
| | 5. L, I, and V |
| | 6. F, Y, and W |
| | 7. A and G |
| | 8. M and C |

The terms “identical” or percent “identity,” in the context of two or more nucleic acids or peptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection.

As is known in the art, a number of different programs may be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387-395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, “Current Methods in Sequence Comparison and Analysis,” Macromolecule Sequencing and Synthesis, Selected Methods and Applications, pp 127-149 (1988), Alan R. Liss, Inc, all of which are incorporated by reference.

An example of a useful algorithm is PILEUP. PILEUP creates a multiple sequence alignment from a group of related sequences using progressive, pair wise alignments. It may also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989), both incorporated by reference. Useful PILEUP parameters including a default gap weight of 3.00, a default gap length weight of 0.10, and weighted end gaps.

Another example of a useful algorithm is the BLAST algorithm, described in: Altschul et al., J. Mol. Biol. 215, 403-410, (1990); Altschul et al., Nucleic Acids Res. 25:3389-3402 (1997); and Karlin et al., Proc. Natl. Acad. Sci. U.S.A. 90:5873-5787 (1993), both incorporated by reference. A particularly useful BLAST program is the WU-BLAST-2 program which was obtained from Altschul et al., Methods in Enzymology, 266:460-480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST, as reported by Altschul et al., Nucl. Acids Res., 25:3389-3402, incorporated by reference. Gapped BLAST uses BLOSUM-62 substitution scores; threshold T parameter set to 9; the two-hit method to trigger ungapped extensions; charges gap lengths of k a cost of 10+k; Xu set to 16, and Xg set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the “longer” sequence in the aligned region. The “longer” sequence is the one having the most actual residues in the aligned region (gaps introduced by WU-Blast-2 to maximize the alignment score are ignored). In a similar manner, “percent (%) nucleic acid sequence identity” with respect to the coding sequence of the polypeptides identified is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequence of FIG. 2 (SEQ ID NO:1), it is understood that in one embodiment, the percentage of sequence identity will be determined based on the number of identical amino acids or nucleotides in relation to the total number of amino acids or nucleotides. Thus, for example, sequence identity of sequences shorter than that shown in FIG. 2 (SEQ ID NO:1), as discussed below, will be determined using the number of nucleotides in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity may be calculated, for example, by dividing the number of matching identical residues by the total number of residues of the "shorter" sequence in the aligned region and multiplying by 100. The "longer" sequence is the one having the most actual residues in the aligned region.

The term "allelic variants" refers to polymorphic forms of a gene at a particular genetic locus, as well as cDNAs derived from mRNA transcripts of the genes, and the polypeptides encoded by them. The term "preferred mammalian codon" refers a subset of codons from among the set of codons encoding an amino acid that are most frequently used in proteins expressed in mammalian cells as chosen from the following list: Gly (GGC, GGG); Glu (GAG); Asp (GAC); Val (GTG, GTC); Ala (GCC, GCT); Ser (AGC, TCC); Lys (AAG); Asn (AAC); Met (ATG); Ile (ATC); Thr (ACC); Trp (TGG); Cys (TGC); Tyr (TAT, TAC); Leu (CTG); Phe (TTC); Arg (CGC, AGG, AGA); Gln (CAG); His (CAC); and Pro (CCC).

As used herein, the term codon-altered refers to a polynucleotide sequence encoding a polypeptide (e.g., a Factor VIII variant protein), where at least one codon of the native polynucleotide encoding the polypeptide has been changed to improve a property of the polynucleotide sequence. In some embodiments, the improved property promotes increased transcription of mRNA coding for the polypeptide, increased stability of the mRNA (e.g., improved mRNA half-life), increased translation of the polypeptide, and/or increased packaging of the polynucleotide within the vector. Non-limiting examples of alterations that can be used to achieve the improved properties include changing the usage and/or distribution of codons for particular amino acids, adjusting global and/or local GC content, removing AT-rich sequences, removing repeated sequence elements, adjusting global and/or local CpG dinucleotide content, removing cryptic regulatory elements (e.g., TATA box and CCAAT box elements), removing of intron/exon splice sites, improving regulatory sequences (e.g., introduction of a Kozak consensus sequence), and removing sequence elements capable of forming secondary structure (e.g., stem-loops) in the transcribed mRNA.

As discussed herein, there are various nomenclatures to refer to components of the disclosure herein. "CS-number" (e.g. "CS04", "CS01", "CS23", etc.) refer to codon altered polynucleotides encoding FVIII polypeptides and/or the encoded polypeptides, including variants. For example, CS01-FL refers to the Full Length codon altered CS01 polynucleotide sequence or amino acid sequence (sometimes referred to herein as "CS01-FL-AA" for the Amino Acid sequence and "CS01-FL-NA" for the Nucleic Acid sequence) encoded by the CS01 polynucleotide sequence. Similarly, "CS01-LC" refers to either the codon altered nucleic acid sequence ("CS01-LC-NA") encoding the light chain of a FVIII polypeptide or the amino acid sequence (also sometimes referred to herein as "CS01-LC-AA") of the FVIII light chain encoded by the CS01 polynucleotide sequence. Likewise, CS01-HC, CS01-HC-AA and CS01-HC-NA are the same for the FVIII heavy chain. As will be appreciated by those in the art, for constructs such as CS01, CS04, CS23, etc., that are only codon-altered (e.g. they do not contain additional amino acid substitutions as compared to Refacto), the amino acid sequences will be identical, as the amino acid sequences are not altered by the codon optimization. Thus, sequence constructs of the disclosure include, but are not limited to, CS01-FL-NA, CS01-FL-AA, CS01-LC-NA, CS01-LC-AA, CS01-HC-AA, CS01-HC-NA, CS04-FL-NA, CS04-FL-AA, CS04-LC-NA, CS04-LC-AA, CS04-HC-AA, CS04-HC-NA, CS23-FL-NA, CS23-FL-AA, CS23-LC-NA, CS23-LC-AA, CS23-HC-AA and CS23-HC-NA.

This nomenclature also applies to glycosylation peptides as shown in FIG. 13, such that "NGA1-AA" refers to the amino acid sequence and NGA1-NA refers to the nucleic acid sequence.

The disclosure also includes additional new Factor VIII variants, as described below, with the appropriate nomenclature.

III. Codon-Altered Factor VIII Variants

In some embodiments, the present disclosure provides codon-altered polynucleotides encoding Factor VIII variants. These codon-altered polynucleotides provide markedly improved expression of Factor VIII when administered in an AAV-based gene therapy construct. The codon-altered polynucleotides also demonstrate improved AAV-virion packaging, as compared to conventionally codon-optimized constructs. As demonstrated in Example 2 and Example 4, Applicants have achieve these advantages through the discovery of three codon-altered polynucleotides (CS01-FL-NA, CS04-FL-NA, and CS23-FL-NA) encoding a Factor VIII polypeptide with human wild-type Factor VIII heavy and light chains, and a short, 14 amino acid, B-domain substituted linker (the "SQ" linker) containing a furin cleavage site to facilitate maturation of an active FVIIIa protein in vivo. As further demonstrated in Example 4, incorporation of various combinations of the F328S, X5, and X1 amino acid mutations into the encoded Factor VIII molecule further increased the in vivo expression of Factor VIII activity.

In one embodiment, a codon-altered polynucleotide provided herein has nucleotide sequences with high sequence identity to at least the sequences within CS01, CS04, or CS23 (SEQ ID NOS 13, 1, and 20, respectively) encoding the Factor VIII heavy chain and Factor VIII light chains. As known in the art, the B-domain of Factor VIII is dispensable for activity in vivo. Thus, in some embodiments, the codon-altered polynucleotides provided herein completely lack a Factor VIII B-domain. In some embodiments, the native Factor VIII B-domain is replaced with a short amino acid linker containing a furin cleavage site, e.g., the "SQ" linker consisting of amino acids 760-773 of the CS01, CS04, or CS23 (SEQ ID NOS 2, 2, and 21, respectively) constructs. The "SQ" linker is also referred to as BDLO04, (–AA for the amino acid sequence and –NA for the nucleotide sequence shown in FIG. 6).

In one embodiment, the Factor VIII heavy and light chains encoded by the codon-altered polynucleotide are human Factor VIII heavy and light chains, respectively. In other embodiments, the Factor VIII heavy and light chains encoded by the codon-altered polynucleotide are heavy and light chain sequences from another mammal (e.g., porcine Factor VIII). In yet other embodiments, the Factor VIII heavy and light chains are chimeric heavy and light chains (e.g., a combination of human and a second mammalian sequence). In yet other embodiments, the Factor VIII heavy and light chains are humanized version of the heavy and light chains from another mammal, e.g., heavy and light chain sequences from another mammal in which human residues are substituted at select positions to reduce the immunogenicity of the resulting peptide when administered to a human.

The GC content of human genes varies widely, from less than 25% to greater than 90%. However, in general, human genes with higher GC contents are expressed at higher levels. For example, Kudla et al. (PLoS Biol., 4(6):80 (2006)) demonstrate that increasing a gene's GC content increases expression of the encoded polypeptide, primarily by increasing transcription and effecting a higher steady state level of the mRNA transcript. Generally, the desired GC content of a codon-optimized gene construct is equal or greater than 60%. However, native AAV genomes have GC contents of around 56%.

Accordingly, in some embodiments, the codon-altered polynucleotides provided herein have a CG content that more closely matches the GC content of native AAV virions (e.g., around 56% GC), which is lower than the preferred CG contents of polynucleotides that are conventionally codon-optimized for expression in mammalian cells (e.g., at or above 60% GC). As outlined in Example 1, CS04-FL-NA (SEQ ID NO: 1), which has a GC content of about 56%, has improved virion packaging as compared to similarly codon-altered coding sequences with higher GC content.

Thus, in some embodiments, the overall GC content of a codon-altered polynucleotide encoding a Factor VIII polypeptide is less than 60%. In some embodiments, the overall GC content of a codon-altered polynucleotide encoding a Factor VIII polypeptide is less than 59%. In some embodiments, the overall GC content of a codon-altered polynucleotide encoding a Factor VIII polypeptide is less than 58%. In some embodiments, the overall GC content of a codon-altered polynucleotide encoding a Factor VIII polypeptide is less than 57%. In some embodiments, the overall GC content of a codon-altered polynucleotide encoding a Factor VIII polypeptide is no more than 56%.

In some embodiments, the overall GC content of a codon-altered polynucleotide encoding a Factor VIII polypeptide is from 54% to 59%. In some embodiments, the overall GC content of a codon-altered polynucleotide encoding a Factor VIII polypeptide is from 55% to 59%. In some embodiments, the overall GC content of a codon-altered polynucleotide encoding a Factor VIII polypeptide is from 56% to 59%. In some embodiments, the overall GC content of a codon-altered polynucleotide encoding a Factor VIII polypeptide is from 54% to 58%. In some embodiments, the overall GC content of a codon-altered polynucleotide encoding a Factor VIII polypeptide is from 55% to 58%. In some embodiments, the overall GC content of a codon-altered polynucleotide encoding a Factor VIII polypeptide is from 56% to 58%. In some embodiments, the overall GC content of a codon-altered polynucleotide encoding a Factor VIII polypeptide is from 54% to 57%. In some embodiments, the overall GC content of a codon-altered polynucleotide encoding a Factor VIII polypeptide is from 55% to 57%. In some embodiments, the overall GC content of a codon-altered polynucleotide encoding a Factor VIII polypeptide is from 56% to 57%. In some embodiments, the overall GC content of a codon-altered polynucleotide encoding a Factor VIII polypeptide is from 54% to 56%. In some embodiments, the overall GC content of a codon-altered polynucleotide encoding a Factor VIII polypeptide is from 55% to 56%.

In some embodiments, the overall GC content of a codon-altered polynucleotide encoding a Factor VIII polypeptide is 56±0.5%. In some embodiments, the overall GC content of a codon-altered polynucleotide encoding a Factor VIII polypeptide is 56±0.4%. In some embodiments, the overall GC content of a codon-altered polynucleotide encoding a Factor VIII polypeptide is 56±0.3%. In some embodiments, the overall GC content of a codon-altered polynucleotide encoding a Factor VIII polypeptide is 56±0.2%. In some embodiments, the overall GC content of a codon-altered polynucleotide encoding a Factor VIII polypeptide is 56±0.1%. In some embodiments, the overall GC content of a codon-altered polynucleotide encoding a Factor VIII polypeptide is 56%.

A. Factor VIII Amino Acid Substitutions

To further increase the efficiency of AAV-vector based expression of the Factor VIII constructs described herein, amino acid substitutions know to improve secretion, increase specific activity, and/or enhanced the stability of Factor VIII are further incorporated, in some implementations. A number of potential variants were identified that increase the plasma levels of FVIII activity at a given vector dose. These variants include those with a more efficient signal peptide, amino acid substitutions that prevent BiP interactions, amino acid substitutions resembling more efficiently secreted Factor VIII orthologs (e.g., porcine Factor VIII), single-chain Factor VIII variants, and amino acid substitutions that stabilize Factor VIII and/or reduce subunit dissociation.

Mutation of residues A108, R121, and L2302 (SPE), located at the interface between the A1 and C2 domains, increases the stability of Factor VIII. For example, the A108I amino acid substitution introduces a hydrophobic residue that better fills the inter-domain space, stabilizing the interaction. Likewise, an R121C/L2302C (SPE) double amino acid substitution introduces a disulfide bond spanning the A1-C2 domains, further stabilizing the interaction. Taken together, all three amino acid substitutions increase the thermal stability of Factor VIII by 3 to 4-fold. For review, see Wakabayashi et al., J Biol Chem. 286(29):25748-55 (2011) and Wakabayashi et al., Thromb Haemost. 10(3): 492-95 (2012). Accordingly, in some embodiments, the encoded Factor VIII polypeptide includes A108I and/or R121C/L2302C amino acid substitutions.

Mutation of E113 (SPE), located within the calcium binding domain of Factor VIII, increases the specific FVIII clotting activity. For example, E113A appears to increase FXase formation through increased FVIII affinity for Factor IXa. Specifically, the E113A amino acid substitution increases specific FVIII clotting activity two-fold and increases affinity for Factor IXa by four-fold (Biochemistry, 41:8485 (2002); J. Biol. Chem., 279:12677 (2004); and Biochemistry, 44:10298 (2005)). Accordingly, in some embodiments, the encoded Factor VIII polypeptides include an E113A amino acid substitution.

Substitution of one or more amino acid residues surrounding the Factor VIII APC cleavage site (residues 331-341 (SPE)) reduce Factor VIIIa inactivation by activated protein C, without affecting FVIII activity. For example PQL333-335VDQ (SPE) amino acid substitutions reduce Factor VIII inactivation by 16-fold. Likewise, MKN336-339GNQ amino acid substitutions reduce Factor VIII inactivation by 9-fold. When combined, the two triple amino acid substitutions (e.g., PQLRMKN333-339VDQRGNQ) (SEQ ID NOS 34 and 35, respectively) reduce Factor VIII inactivation by 100-fold (J. Biol. Chem., 282:20264 (2007). Accordingly, in some embodiments, the encoded Factor VIII polypeptide include PQL333-335VDQ and/or MKN337-339GNQ (SPE) amino acid substitutions.

Mutations within the A2 domain interface also increase Factor VIII stability. Specifically, mutating charged residues in the A1-A2 and A2-A3 domain interfaces increases stability and retention of the A2 subunit in Factor VIIIa. For example, mutation of D519, E665, and E1984 to V or A yields up to 2-fold increased stability in Factor VIII and up to 5-fold stability in Factor VIIIa. Specifically, D519A/E665V amino acid substitutions provide a 3-fold increase in stability; D519V/E665V amino acid substitutions provide a 2-fold increase in stability, an 8-fold decrease in A2 dissociation, and a 2-4-fold increase in thrombin generation potential; D519V/E1984A amino acid substitutions provide a 2-fold increase in stability; and D519V/E665V/E1984A amino acid substitution provide a 2-fold increase in stability (Blood 112:2761-69 (2008); J. Thromb. Haemost., 7:438-44 (2009)). Accordingly, in some embodiments, the encoded Factor VIII polypeptides include one or more of D519A/V, E665A/V, and E1984A/V amino acid substitutions.

Of particular relevance to the present disclosure are a number of specific mutations that can be included separately or in combinations with other variants described herein. These variants are coded as sets herein as follows: "m1" refers to a single amino acid change, "m2" is a set of 5 amino acid variants, "m3" is a combination of a deletion of 7 amino acids and an insertion of six amino acids that span the junction between the polypeptide linker and the heavy chain, "m4" is a combination of the m1 single mutation and the m5 double mutation, and "m5" is a set of two cysteine ablations. These mutations are described below. These can be included in any particular construct alone or in combination with other variants, and they are coded accordingly. For example, "m23" is a combination of the m2 and m3 variants onto a particular scaffold, as outlined herein; thus "CS01m23-FL-NA" or "CS01-FL-NAm23" refers to the CS01 codon-altered polynucleotide sequence with the nucleotides encoding the m2 and m3 mutations included, and "CS01m23-FL-AA" or "CS01-FL-AAm23" refers to the amino acid sequence. As CS01 is codon-altered but does not change the amino acid sequence of Refacto, these can be thought of on the amino acid level as mutations as compared to the Refacto amino acid sequence of CS01-FL-AA (SEQ ID NO: 2).

In many embodiments, the polypeptides of the disclosure are made with the "m1" variant included. Mutations within an 11 amino acid hydrophobic β-sheet in the A1 domain, which interacts with BiP, increase secretion of Factor VIII. For example, an F328S (SPI, F309S SPE) amino acid substitution within the pocket increased Factor VIII secretion 3-fold. The F328S variant is referred to herein as the "m1" mutation and is within the heavy chain. Again, as described herein, the number of the variants can be done inclusive of the signal peptide, "Signal Peptide Inclusive", or "SPI", or starting from the processed final protein sequence, "Signal Peptide Exclusive", or "SPE". Thus, using SPI numbering, the mutation F328S is the same as the F309 SPE mutant. Generally the specification uses the SPI numbering, but as will be appreciated by those in the art, either numbering system results in the same mutation(s).

Accordingly, included in the present disclosure are polypeptides that include the m1 mutation, including CS01-FL-AAm1, CS01-HC-AAm1, CS04-FL-AAm1, CS04-HC-AAm1 CS23-FL-AAm1, CS23-HC-AAm1, CS40-FL-AAm1 and CS40-HC-AAm1 (all of which encode the same corresponding protein sequences).

In addition, included in the present disclosure are not only polypeptide sequences that include the m1 mutation, but also those codon-altered polynucleotide sequences that encode proteins with the m1 mutation, such as CS01-FL-NAm1, CS01-HC-NAm1, CS04-FL-NAm1, CS04-HC-NAm1, CS23-FL-NAm1, CS23-HC-NA-m1, CS40-FL-NAm1 and CS40-HC-NAm1.

In many embodiments, the polypeptides of the disclosure are made with the "m2" variant set included, which is the I105V/A127S/G151K/M166T/L171P mutations (SPI numbering; (SPE numbering is V86I/S108A/K132G/T147M/P152L, respectively). The m2 mutation set is based on the fact that substitution of porcine amino acids 82-176 for the corresponding human amino acids in a B-domain deleted gene therapy construct increased Factor VIII activity when expressed in HEK293 cells (W. Xiao, communication). Id. Back-mutation of single porcine amino acids into the human BDD-FVIII construct identified five amino acids within the A1 domain that contribute to this phenomenon: I105V, A127S, G151K, M166T, and L171P (SPI). Introduction of the combination of these mutations into the human construct recapitulated the improved activity of the larger porcine substitution. Id. Accordingly, in some embodiments, the encoded Factor VIII polypeptides include one or more amino acid substitutions selected from I105V, A127S, G151K, M166T, and L171P, with the entire 5 amino acid set, m2, finding particular use in many embodiments. As for the m1 mutation, the m2 variants are in the heavy chain, and thus the present disclosure includes polypeptides that include the m2 mutation, including CS01-FL-AAm2, CS01-HC-AAm2, CS04-FL-AAm2, CS04-HC-AAm2, CS23-FL-AAm2, CS23-HC-AAm2, CS40-FL-AAm2 and CS40-HC-AAm2 (all of which encode the same corresponding protein sequences).

In addition, included in the present disclosure are not only polypeptide sequences that include the m2 mutation, but also those codon-altered polynucleotide sequences that encode proteins with the m2 mutation, such as CS01-FL-NAm2, CS01-HC-NAm2, CS04-FL-NAm2, CS04-HC-NAm2, CS23-FL-NAm2, CS23-HC-NA-m2, CS40-FL-NAm2 and CS40-HC-NAm2.

In additional embodiments, the polypeptides and polynucleotides of the disclosure include m3 mutations. m3 is the substitution of seven amino acids for six across the HC-B domain interface that introduces an additional glycosylation site introduced close to the interface. Accordingly, in some embodiments, m3 is the deletion of amino acids AIEPRSF755-761 and the insertion of amino acids TTYVNRSL (SEQ ID NO: 33) after N754, relative to FVIII-FL-AA (SEQ ID NO: 19) (e.g., AIEPRSF755-761TTYVNRSL) ("TTYVNRSL" disclosed as SEQ ID NO: 33). Residues AIEPR755-759, relative to SEQ ID NO: 19, fall within the end of the heavy chain, while residues 5760 and F761 fall within the B-domain. In some embodiments, where the FVIII B-domain is deleted, truncated, or replaced, residues 5760 and F761 may not be present in the underlying amino acid sequence being mutated. Accordingly, in some embodiments, m3 is the deletion of amino acids AIEPR755-759 and the insertion of amino acids TTYVNRSL (SEQ ID NO: 33) after N754, relative to FVIII-FL-AA (SEQ ID NO: 19) (e.g., AIEPR755-759TTYVNRSL ("TTYVNRSL" disclosed as SEQ ID NO: 33)

The m3 variants are in the junction between the heavy chain and the B domain, and thus the present disclosure includes polypeptides that include the m3 mutation, including CS01-FL-AAm3, CS01-HC-AAm3, CS04-FL-AAm3, CS04-HC-AAm3, CS23-FL-AAm3, CS23-HC-AAm3, CS40-FL-AAm3 and CS40-HC-AAm3 (all of which encode the same corresponding protein sequences).

In addition, included in the present disclosure are not only polypeptide sequences that include the m3 mutation, but also those codon-altered polynucleotide sequences that encode proteins with the m3 mutations, such as CS01-FL-NAm3, CS01-HC-NAm3, CS04-FL-NAm3, CS04-HC-NAm3, CS23-FL-NAm3, CS23-HC-NA-m3, CS40-FL-NAm3 and CS40-HC-NAm3.

In additional embodiments, the polypeptides and polynucleotides of the disclosure include m4 mutations. Elimination of the C1899-C1903 disulfide bond in Factor VIII also increased secretion. Moreover, the increases in Factor VIII secretion are additive for the combination of F328S (SPI, F309S SPE) and C1918G/C1922G amino acid substitutions (Miao et al., Blood, 103:3412-19 (2004); Selvaraj et al., J. Thromb. Haemost., 10:107-15 (2012)). Accordingly, in some embodiments, the encoded Factor VIII polypeptides include m4 mutations, which is the F328S (SPI, F309S SPE) and C1918G/C1922G (SPI) amino acid substitutions. As the F328S variant is in the heavy chain and the two cysteine variants are in the light chain, polypeptide sequences that include m4 mutations are CS01-FL-AAm4, CS01-HC-AAm4, CS01-LC-AAm4, CS04-FL-AAm4, CS04-HC-AAm4, CS04-LC-AAm4, CS23-FL-AAm4, CS23-HC-AAm4 and CS23-LC-AAm4.

In addition, included in the present disclosure are not only polypeptide sequences that include the m4 mutation, but also those codon-altered polynucleotide sequences that encode proteins with the m4 mutations, such as CS01-FL-NAm4, CS01-HC-NAm4, CS01-LC-NAm4, CS04-FL-NAm4, CS04-HC-NAm4, CS04-LC-NAm4, CS23-FL-NAm4, CS23-HC-NAm4, CS23-LC-NAm4, CS40-FL-NA-m4, CS40-HC-NA-m4 and CS40-LC-NA-m4.

In additional embodiments, the polypeptides and polynucleotides of the disclosure include m5 mutations. As above, elimination of the C1899-C1903 disulfide bond in Factor VIII also increased secretion. C1918G/C1922G (SPI) amino acid substitutions, contained within the light chain, referred to herein as the m5 mutation set.

The m5 variants are in the light chain, and thus the present disclosure includes polypeptides that include the m5 mutation, including CS01-FL-AAm5, CS01-LC-AAm5, CS04-FL-AAm5, CS04-LC-AAm5, CS23-FL-AAm5, CS23-LC-AAm5, CS40-FL-AAm5 and CS40-LC-AAm5 (all of which encode the same corresponding protein sequences).

In addition, included in the present disclosure are not only polypeptide sequences that include the m5 mutation, but also those codon-altered polynucleotide sequences that encode proteins with the m5 mutations, such as CS01-FL-NAm5, CS01-LC-NAm5, CS04-FL-NAm5, CS04-LC-NAm5, CS23-FL-NA-m5, CS23-LC-NA-m5, CS40-FL-NA-m5 and CS40-LC-NA-m5.

In addition to specific constructs (both amino acid and nucleic acid) that include m1, m2, m3, m4 and m5 individually, combinations of mutation sets can be made as outlined herein. As noted herein, these are noted as "m12", which is the combination of m1 and m2 sets, or "m123" which is the combination of m1, m2 and m3 sets. Thus, included in the disclosure are dual combinations including m12, m13, m14, m15, m23, m24, m25, m34, m35 and m45. Also included are triple combinations, m123, m124, m125, m234, m235 and m345. Further included are quad combinations, m1234, m1235, m1345 and the m12345 combination.

Of particular interest in some embodiments are the following mutation sets: m1, m2, m3 and m4, m23, m123, and m234.

B. Factor VIII B-Domain Substituted Linkers

In some embodiments, the linkage between the FVIII heavy chain and the light chain (e.g., the B-domain in wild-type Factor VIII) is further altered. Due to size constraints of AAV packaging capacity, B-domain deleted, truncated, and or linker substituted variants should improve the efficacy of the FVIII gene therapy construct. The most conventionally used B-domain substituted linker is that of SQ FVIII, which retains only 14 amino acids of the B domain as linker sequence. Another variant of porcine VIII ("OBI-1," described in U.S. Pat. No. 6,458,563) is well expressed in CHO cells, and has a slightly longer linker of 24 amino acids. In some embodiments, the Factor VIII constructs encoded by the codon-altered polynucleotides described herein include an SQ-type B-domain linker sequence. In other embodiments, the Factor VIII constructs encoded by the codon-altered polynucleotides described herein include an OBI-1-type B-domain linker sequence.

In some embodiments, the encoded Factor VIII polypeptides described herein include an SQ-type B-domain linker, including amino acids 760-762/1657-1667 of the wild-type human Factor VIII B-domain (FVIII-FL-AA; SEQ ID NO: 19) (Sandberg et al. Thromb. Haemost. 85:93 (2001)). In some embodiments, the SQ-type B-domain linker has one amino acid substitution relative to the corresponding wild-type sequence. In some embodiments, the SQ-type B-domain linker has two amino acid substitutions relative to the corresponding wild-type sequence. In some embodiments, a glycosylation peptide is inserted into the SQ-type B-domain linker. In some embodiments, the glycosylation peptide is selected from those shown in FIG. 13 (SEQ ID NOS 51, 53, 55, 57, 59, 61, 63, 65, 67, 69, 71, 73, and 75, respectively, in order of appearance).

In some embodiments, the encoded Factor VIII polypeptides described herein include a Greengene-type B-domain linker, including amino acids 760/1582-1667 of the wild-type human Factor VIII B-domain (FVIII-FL-AA; SEQ ID NO: 19) (Oh et al., Biotechnol. Prog., 17:1999 (2001)). In some embodiments, the Greengene-type B-domain linker has one amino acid substitution relative to the corresponding wild-type sequence. In some embodiments, the Greengene-type B-domain linker has two amino acid substitutions relative to the corresponding wild-type sequence. In some embodiments, a glycosylation peptide is inserted into the Greengene-type B-domain linker. In some embodiments, the glycosylation peptide is selected from those shown in FIG. 13 (SEQ ID NOS 51, 53, 55, 57, 59, 61, 63, 65, 67, 69, 71, 73, and 75, respectively, in order of appearance).

In some embodiments, the encoded Factor VIII polypeptides described herein include an extended SQ-type B-domain linker (SFSQNPPVLKRHQR; BDL-SQ-AA; SEQ ID NO: 30), including amino acids 760-769/1657-1667 of the wild-type human Factor VIII B-domain (FVIII-FL-AA; SEQ ID NO: 19) (Thim et al., Haemophilia, 16:349 (2010)). In some embodiments, the extended SQ-type B-domain linker has one amino acid substitution relative to the corresponding wild-type sequence. In some embodiments, the extended SQ-type B-domain linker has two amino acid substitutions relative to the corresponding wild-type sequence. In some embodiments, a glycosylation peptide is inserted into the extended SQ-type B-domain linker. In some embodiments, the glycosylation peptide is selected from those shown in FIG. 13 (SEQ ID NOS 51, 53, 55, 57, 59, 61, 63, 65, 67, 69, 71, 73, and 75, respectively, in order of appearance).

In some embodiments, the encoded Factor VIII polypeptides described herein include a porcine OBI-1-type B-domain linker, including the amino acids SFAQNSRPPSASAPKPPVLRRHQR (SEQ ID NO: 31) from the wild-type porcine Factor VIII B-domain (Toschi et al., Curr. Opin. Mol. Ther. 12:517 (2010)). In some embodiments, the porcine OBI-1-type B-domain linker has one amino acid substitution relative to the corresponding wild-type sequence. In some embodiments, the porcine OBI-1-type B-domain linker has two amino acid substitutions relative to the corresponding wild-type sequence. In some embodiments, a glycosylation peptide is inserted into the porcine OBI-1-type B-domain linker. In some embodiments, the glycosylation peptide is selected from those shown in FIG. 13 (SEQ ID NOS 51, 53, 55, 57, 59, 61, 63, 65, 67, 69, 71, 73, and 75, respectively, in order of appearance).

In some embodiments, the encoded Factor VIII polypeptides described herein include a human OBI-1-type B-domain linker, including amino acids 760-772/1655-1667 of the wild-type human Factor VIII B-domain (FVIII-FL-AA; SEQ ID NO: 19). In some embodiments, the human OBI-1-type B-domain linker has one amino acid substitution relative to the corresponding wild-type sequence. In some embodiments, the human OBI-1-type B-domain linker has two amino acid substitutions relative to the corresponding wild-type sequence. In some embodiments, a glycosylation peptide is inserted into the human OBI-1-type B-domain linker. In some embodiments, the glycosylation peptide is selected from those shown in FIG. 13 (SEQ ID NOS 51, 53, 55, 57, 59, 61, 63, 65, 67, 69, 71, 73, and 75, respectively, in order of appearance).

In some embodiments, the encoded Factor VIII polypeptides described herein include an 08-type B-domain linker, including the amino acids SFSQNSRHQAYRYRRG (SEQ ID NO: 32) from the wild-type porcine Factor VIII B-domain (Toschi et al., Curr. Opin. Mol. Ther. 12:517 (2010)). In some embodiments, the porcine OBI-1-type B-domain linker has one amino acid substitution relative to the corresponding wild-type sequence. In some embodiments, the porcine OBI-1-type B-domain linker has two amino acid substitutions relative to the corresponding wild-type sequence. In some embodiments, a glycosylation peptide is inserted into the porcine OBI-1-type B-domain linker. In some embodiments, the glycosylation peptide is selected from those shown in FIG. 13 (SEQ ID NOS 51, 53, 55, 57, 59, 61, 63, 65, 67, 69, 71, 73, and 75, respectively, in order of appearance).

Removal of the B-domain from Factor VIII constructs does not appear to affect the activity of the activated enzyme (e.g., FVIIIa), presumably because the B-domain is removed during activation. However, the B-domain of Factor VIII contains several residues that are post-translationally modified, e.g., by N- or O-linked glycosylation. In silico analysis (Prediction of N-glycosylation sites in human proteins, R. Gupta, E. Jung and S. Brunak, in preparation (2004)) of the wild-type Factor VIII B-domain predicts that at least four of these sites are glycosylated in vivo (FIG. 14). It is thought that these modifications within the B-domain contribute to the post-translational regulation and/or half-life of Factor VIII in vivo.

While the Factor VIII B-domain is absent in mature Factor VIIIa protein, glycosylation within the B-domain of the precursor Factor VIII molecule may increase the circulating half-life of the protein prior to activation. Thus, in some embodiments, the polypeptide linker of the encoded Factor VIII constructs described herein includes one or more glycosylation sequences, to allow for glycosylation in vivo. In some embodiments, the polypeptide linker includes at least one consensus glycosylation sequence (e.g., an N- or O-linked glycosylation consensus sequence). In some embodiments, the polypeptide linker includes at least two consensus glycosylation sequences. In some embodiments, the polypeptide linker includes at least three consensus glycosylation sequences. In some embodiments, the polypeptide linker includes at least four consensus glycosylation sequences. In some embodiments, the polypeptide linker includes at least five consensus glycosylation sequences. In some embodiments, the polypeptide linker includes at least 6, 7, 8, 9, 10, or more consensus glycosylation sequences.

In some embodiments, the polypeptide linker contains at least one N-linked glycosylation sequence N-X-S/T, where X is any amino acid other than P, S, or T. In some embodiments, the polypeptide linker contains at least two N-linked glycosylation sequences N-X-S/T, where X is any amino acid other than P, S, or T. In some embodiments, the polypeptide linker contains at least three N-linked glycosylation sequences N-X-S/T, where X is any amino acid other than P, S, or T. In some embodiments, the polypeptide linker contains at least four N-linked glycosylation sequences N-X-S/T, where X is any amino acid other than P, S, or T. In some embodiments, the polypeptide linker contains at least five N-linked glycosylation sequences N-X-S/T, where X is any amino acid other than P, S, or T. In some embodiments, the polypeptide linker contains at least 6, 7, 8, 9, 10, or more N-linked glycosylation sequences N-X-S/T, where X is any amino acid other than P, S, or T.

In some embodiments, the polypeptide linker includes a glycosylation peptide with high sequence identity to any one of SEQ ID NOS 51, 53, 55, 57, 59, 61, 63, 65, 67, 69, 71, 73, and 75, respectively, in order of appearance, as shown in FIGS. 13A-13B. In some embodiments, the glycosylation polypeptide has at least 92% identity to any one of SEQ ID NOS 51, 53, 55, 57, 59, 61, 63, 65, 67, 69, 71, 73, and 75, respectively, in order of appearance, as shown in FIGS. 13A-13B. In some embodiments, the glycosylation peptide has no more than two amino acid substitutions relative to any one of SEQ ID NOS 51, 53, 55, 57, 59, 61, 63, 65, 67, 69, 71, 73, and 75, respectively, in order of appearance, as shown in FIGS. 13A-13B. In some embodiments, the glycosylation peptide has no more than one amino acid substitution relative to any of SEQ ID NOS 51, 53, 55, 57, 59, 61, 63, 65, 67, 69, 71, 73, and 75, respectively, in order of appearance, as shown in FIGS. 13A-13B. In some embodiments, the glycosylation peptide has an amino acid sequence selected from any of SEQ ID NOS 51, 53, 55, 57, 59, 61, 63, 65, 67, 69, 71, 73, and 75, respectively, in order of appearance, as shown in FIGS. 13A-13B.

In some embodiments, the glycosylation peptide has at least 92% identity to any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 90% identity to a corresponding nucleotide sequence selected from SEQ ID NOS 50, 52, 54, 56, 58, 60, 62, 64, 66, 68, 70, 72, and 74, respectively, as shown in FIGS. 13A-13B. In some embodiments, the glycosylation peptide has at least 92% identity to any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 95% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B. In some embodiments, the glycosylation peptide has at least 92% identity to any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 98% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B.

In some embodiments, the glycosylation peptide has no more than two amino acid substitutions relative to any one of SEQ ID NOS 51, 53, 55, 57, 59, 61, 63, 65, 67, 69, 71, 73, and 75, respectively, in order of appearance, as shown in FIGS. 13A-13B, and is encoded by a polynucleotide sequence having at least 90% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B. In some embodiments, the glycosylation peptide has no more than two amino acid substitutions relative to any one of SEQ ID NOS 51, 53, 55, 57, 59, 61, 63, 65, 67, 69, 71, 73, and 75, respectively, in order of appearance, as shown in FIGS. 13A-13B, and is encoded by a polynucleotide sequence having at least 95% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B. In some embodiments, the glycosylation peptide has no more than two amino acid substitutions relative to any one of SEQ ID NOS 51, 53, 55, 57, 59, 61, 63, 65, 67, 69, 71, 73, and 75, respectively, in order of appearance, as shown in FIGS. 13A-13B, and is encoded by a polynucleotide sequence having at least 98% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B.

In some embodiments, the glycosylation peptide has no more than one amino acid substitution relative to any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 90% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B. In some embodiments, the glycosylation peptide has no more than one amino acid substitution relative to any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 95% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B. In some embodiments, the glycosylation peptide has no more than one amino acid substitution relative to any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 98% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B.

In some embodiments, the glycosylation peptide has a sequence selected from any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 90% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B. In some embodiments, the glycosylation peptide has a sequence selected from any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 95% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B. In some embodiments, the glycosylation peptide has a sequence selected from any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 98% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B.

In some embodiments, the Factor VIII polypeptide encoded by a codon-altered polynucleotide described herein has a B-domain substituted linker in which a glycosylation peptide is inserted into the SQ linker sequence (amino acids 760-773 of CS04-FL-AA; SEQ ID NO: 2). In a specific embodiment, the glycosylation peptide is selected from selected from any one of SEQ ID NOS 51, 53, 55, 57, 59, 61, 63, 65, 67, 69, 71, 73, and 75, respectively, in order of appearance, as shown in FIGS. 13A-13B, a glycosylation peptide having at least 92% identity to any one of SEQ ID NOS 51, 53, 55, 57, 59, 61, 63, 65, 67, 69, 71, 73, and 75, respectively, in order of appearance, as shown in FIGS. 13A-13B, a glycosylation peptide having no more than two amino acid substitutions relative to any one of SEQ ID NOS 51, 53, 55, 57, 59, 61, 63, 65, 67, 69, 71, 73, and 75, respectively, in order of appearance, as shown in FIGS. 13A-13B, and a glycosylation peptide having no more than one amino acid substitution relative to any one of SEQ ID NOS 51, 53, 55, 57, 59, 61, 63, 65, 67, 69, 71, 73, and 75, respectively, in order of appearance, as shown in FIGS. 13A-13B. In some embodiments, the glycosylation peptide is inserted in the SQ peptide between residues N768 and P769 (relative to CS04-FL-AA; SEQ ID NO: 2).

In some embodiments, the polypeptide linker of the Factor VIII construct is encoded by a third nucleotide sequence having high sequence identity to any one of those shown in FIG. 6 (SEQ ID NOS 5-7 and 36-48, respectively, in order of appearance). In some embodiments, the third nucleotide sequence has at least 95% identity to any one of those shown in FIG. 13 (SEQ ID NOS 50, 52, 54, 56, 58, 60, 62, 64, 66, 68, 70, 72, and 74, respectively, in order of appearance). In some embodiments, the third nucleotide sequence has at least 96% identity to any one of those shown in FIG. 13 (SEQ ID NOS 50, 52, 54, 56, 58, 60, 62, 64, 66, 68, 70, 72, and 74, respectively, in order of appearance). In some embodiments, the third nucleotide sequence has at least 97% identity to any one of those shown in FIG. 13 (SEQ ID NOS 50, 52, 54, 56, 58, 60, 62, 64, 66, 68, 70, 72, and 74, respectively, in order of appearance). In some embodiments, the third nucleotide sequence has at least 98% identity to any one of those shown in FIG. 13 (SEQ ID NOS 50, 52, 54, 56, 58, 60, 62, 64, 66, 68, 70, 72, and 74, respectively, in order of appearance). In some embodiments, the third nucleotide sequence has at least 99% identity to any one of those shown in FIG. 13 (SEQ ID NOS 50, 52, 54, 56, 58, 60, 62, 64, 66, 68, 70, 72, and 74, respectively, in order of appearance). In some embodiments, the third nucleotide sequence has at least 99.5% identity to any one of those shown in FIG. 13 (SEQ ID NOS 50, 52, 54, 56, 58, 60, 62, 64, 66, 68, 70, 72, and 74, respectively, in order of appearance). In some embodiments, the third nucleotide sequence has at least 99.9% identity to any one of those shown in FIG. 13 (SEQ ID NOS 50, 52, 54, 56, 58, 60, 62, 64, 66, 68, 70, 72, and 74, respectively, in order of appearance). In some embodiments, the third nucleotide sequence is identical to any one of those shown in FIG. 13 (SEQ ID NOS 50, 52, 54, 56, 58, 60, 62, 64, 66, 68, 70, 72, and 74, respectively, in order of appearance).

C. Codon-Altered Polynucleotides Encoding a Factor VIII Variant with a Cleavable Linker CS04 Codon Altered Polynucleotides In one embodiment, the codon-altered polynucleotides provided herein include a nucleotide sequence encoding a Factor VIII variant polypeptide with a linker that is cleavable in vivo. The Factor VIII polypeptide includes a Factor VIII light chain, a Factor VIII heavy chain, and a polypeptide linker joining the C-terminus of the heavy chain to the N-terminus of the light chain. The heavy chain of the Factor VIII polypeptide is encoded by a first nucleotide sequence having high sequence identity to CS04-HC-NA (SEQ ID NO: 3), which is the portion of CS04-FL-NA (SEQ ID NO: 1) encoding for a Factor VIII heavy chain. The light chain of the Factor VIII polypeptide is encoded by a second nucleotide sequence with high sequence identity to CS04-LC-NA (SEQ ID NO: 4), which is the portion of CS04-FL-NA (SEQ ID NO: 1) encoding for a Factor VIII light chain. The polypeptide linker includes a furin cleavage site, which allows for maturation in vivo (e.g., after expression in vivo or administration of the precursor polypeptide).

In some embodiments, the first and second nucleotide sequences have at least 95% sequence identity to CS04-HC-NA and CS04-LC-NA (SEQ ID NOS 3 and 4), respectively. In some embodiments, the first and second nucleotide sequences have at least 96% sequence identity to CS04-HC-NA and CS04-LC-NA (SEQ ID NOS 3 and 4), respectively. In some embodiments, the first and second nucleotide sequences have at least 97% sequence identity to CS04-HC-NA and CS04-LC-NA (SEQ ID NOS 3 and 4), respectively. In some embodiments, the first and second nucleotide sequences have at least 98% sequence identity to CS04-HC-NA and CS04-LC-NA (SEQ ID NOS 3 and 4), respectively. In some embodiments, the first and second nucleotide sequences have at least 99% sequence identity to CS04-HC-NA and CS04-LC-NA (SEQ ID NOS 3 and 4), respectively. In some embodiments, the first and second nucleotide sequences have at least 99.5% sequence identity to CS04-HC-NA and CS04-LC-NA (SEQ ID NOS 3 and 4), respectively. In some embodiments, the first and second nucleotide sequences have at least 99.9% sequence identity to CS04-HC-NA and CS04-LC-NA (SEQ ID NOS 3 and 4), respectively. In some embodiments, the first and second nucleotide sequences are identical to CS04-HC-NA and CS04-LC-NA (SEQ ID NOS 3 and 4), respectively.

In some embodiments, the polypeptide linker of the Factor VIII construct is encoded by a third nucleotide sequence having high sequence identity to BDLO04 (SEQ ID NO: 6), which encodes the 14-amino acid linker corresponding to amino acids 760-773 of CS04-FL-AA (SEQ ID NO: 2). In some embodiments, the third nucleotide sequence has at least 95% identity to BDLO04 (SEQ ID NO: 6). In some embodiments, the third nucleotide sequence has at least 96% identity to BDLO04 (SEQ ID NO: 6). In some embodiments, the third nucleotide sequence has at least 97% identity to BDLO04 (SEQ ID NO: 6). In some embodiments, the third nucleotide sequence has at least 98% identity to BDLO04 (SEQ ID NO: 6). In some embodiments, the third nucleotide sequence is identical to BDLO04 (SEQ ID NO: 6).

In some embodiments, the codon-altered polynucleotide has a nucleotide sequence with high sequence identity to CS04-FL-NA (SEQ ID NO: 1). In some embodiments, the nucleotide sequence has at least 95% identity to CS04-FL-NA (SEQ ID NO: 1). In some embodiments, the nucleotide sequence has at least 96% identity to CS04-FL-NA (SEQ ID NO: 1). In some embodiments, the nucleotide sequence has at least 97% identity to CS04-FL-NA (SEQ ID NO: 1). In some embodiments, the nucleotide sequence has at least 98% identity to CS04-FL-NA (SEQ ID NO: 1). In some embodiments, the nucleotide sequence has at least 99% identity to CS04-FL-NA (SEQ ID NO: 1). In some embodiments, the nucleotide sequence has at least 99.5% identity to CS04-FL-NA (SEQ ID NO: 1). In some embodiments, the nucleotide sequence has at least 99.9% identity to CS04-FL-NA (SEQ ID NO: 1). In some embodiments, the nucleotide sequence is identical to CS04-FL-NA (SEQ ID NO: 1).

In some embodiments, the Factor VIII variant encoded by the codon-altered polynucleotide has an amino acid sequence with high sequence identity to CS04-FL-AA (SEQ ID NO: 2). In some embodiments, the amino acid sequence has at least 97% identity to CS04-FL-AA (SEQ ID NO: 2). In some embodiments, the amino acid sequence has at least 98% identity to CS04-FL-AA (SEQ ID NO: 2). In some embodiments, the amino acid sequence has at least 99% identity to CS04-FL-AA (SEQ ID NO: 2). In some embodiments, the amino acid sequence has at least 99.5% identity to CS04-FL-AA (SEQ ID NO: 2). In some embodiments, the amino acid sequence has at least 99.9% identity to CS04-FL-AA (SEQ ID NO: 2). In some embodiments, the amino acid sequence is identical to CS04-FL-AA (SEQ ID NO: 2).

In some embodiments, the Factor VIII variant encoded by the CS04 polynucleotide, having high sequence homology to CS04-FL-AA (e.g., at least 95%, 96%, 97%, 98%, 99%, 99.5%, or 99.9% identity), comprises one or more amino acid substitutions selected from m1, m2, m3, m4, and m5.

In one embodiment, the Factor VIII variant encoded by the CS04 polynucleotide comprises an m1 amino acid substitution. In one embodiment, the Factor VIII variant encoded by the CS04 polynucleotide comprises an m2 amino acid substitution. In one embodiment, the Factor VIII variant encoded by the CS04 polynucleotide comprises an m3 amino acid substitution. In one embodiment, the Factor VIII variant encoded by the CS04 polynucleotide comprises an m4 amino acid substitution. In one embodiment, the Factor VIII variant encoded by the CS04 polynucleotide comprises an m5 amino acid substitution.

In one embodiment, the Factor VIII variant encoded by the CS04 polynucleotide comprises m12 amino acid substitutions. In one embodiment, the Factor VIII variant encoded by the CS04 polynucleotide comprises m13 amino acid substitutions. In one embodiment, the Factor VIII variant encoded by the CS04 polynucleotide comprises m23 amino acid substitutions. In one embodiment, the Factor VIII variant encoded by the CS04 polynucleotide comprises m24 amino acid substitutions. In one embodiment, the Factor VIII variant encoded by the CS04 polynucleotide comprises m25 amino acid substitutions. In one embodiment, the Factor VIII variant encoded by the CS04 polynucleotide comprises m34 amino acid substitutions. In one embodiment, the Factor VIII variant encoded by the CS04 polynucleotide comprises m35 amino acid substitutions.

In one embodiment, the Factor VIII variant encoded by the CS04 polynucleotide comprises m123 amino acid substitutions. In one embodiment, the Factor VIII variant encoded by the CS04 polynucleotide comprises m234 amino acid substitutions. In one embodiment, the Factor VIII variant encoded by the CS04 polynucleotide comprises m125 amino acid substitutions.

CS01 Codon Altered Polynucleotides

In one embodiment, the codon-altered polynucleotides provided herein include a nucleotide sequence encoding a Factor VIII variant polypeptide with a linker that is cleavable in vivo. The Factor VIII polypeptide includes a Factor VIII light chain, a Factor VIII heavy chain, and a polypeptide linker joining the C-terminus of the heavy chain to the N-terminus of the light chain. The heavy chain of the Factor VIII polypeptide is encoded by a first nucleotide sequence having high sequence identity to CS01-HC-NA (SEQ ID NO: 24), which is the portion of CS01-FL-NA (SEQ ID NO: 13) encoding for a Factor VIII heavy chain. The light chain of the Factor VIII polypeptide is encoded by a second nucleotide sequence with high sequence identity to CS01-LC-NA (SEQ ID NO: 25), which is the portion of CS01-FL-NA (SEQ ID NO: 13) encoding for a Factor VIII light chain. The polypeptide linker includes a furin cleavage site, which allows for maturation in vivo (e.g., after expression in vivo or administration of the precursor polypeptide).

In some embodiments, the first and second nucleotide sequences have at least 95% sequence identity to CS01-HC-NA and CS01-LC-NA (SEQ ID NOS 24 and 25), respectively. In some embodiments, the first and second nucleotide sequences have at least 96% sequence identity to CS01-HC-NA and CS01-LC-NA (SEQ ID NOS 24 and 25), respectively. In some embodiments, the first and second nucleotide sequences have at least 97% sequence identity to CS01-HC-NA and CS01-LC-NA (SEQ ID NOS 24 and 25), respectively. In some embodiments, the first and second nucleotide sequences have at least 98% sequence identity to CS01-HC-NA and CS01-LC-NA (SEQ ID NOS 24 and 25), respectively. In some embodiments, the first and second nucleotide sequences have at least 99% sequence identity to CS01-HC-NA and CS01-LC-NA (SEQ ID NOS 24 and 25), respectively. In some embodiments, the first and second nucleotide sequences have at least 99.5% sequence identity to CS01-HC-NA and CS01-LC-NA (SEQ ID NOS 24 and 25), respectively. In some embodiments, the first and second nucleotide sequences have at least 99.9% sequence identity to CS01-HC-NA and CS01-LC-NA (SEQ ID NOS 24 and 25), respectively. In some embodiments, the first and second nucleotide sequences are identical to CS01-HC-NA and CS01-LC-NA (SEQ ID NOS 24 and 25), respectively.

In some embodiments, the polypeptide linker of the Factor VIII construct is encoded by a third nucleotide sequence having high sequence identity to BDLO04 (SEQ ID NO: 6), which encodes the 14-amino acid linker corresponding to amino acids 760-773 of CS01-FL-AA (SEQ ID NO: 2). In some embodiments, the third nucleotide sequence has at least 95% identity to BDLO04 (SEQ ID NO: 6). In some embodiments, the third nucleotide sequence has at least 96% identity to BDLO04 (SEQ ID NO: 6). In some embodiments, the third nucleotide sequence has at least 97% identity to BDLO04 (SEQ ID NO: 6). In some embodiments, the third nucleotide sequence has at least 98% identity to BDLO04 (SEQ ID NO: 6). In some embodiments, the third nucleotide sequence is identical to BDLO04 (SEQ ID NO: 6).

In some embodiments, the codon-altered polynucleotide has a nucleotide sequence with high sequence identity to CS01-FL-NA (SEQ ID NO: 13). In some embodiments, the nucleotide sequence has at least 95% identity to CS01-FL-NA (SEQ ID NO: 13). In some embodiments, the nucleotide sequence has at least 96% identity to CS01-FL-NA (SEQ ID NO: 13). In some embodiments, the nucleotide sequence has at least 97% identity to CS01-FL-NA (SEQ ID NO: 13). In some embodiments, the nucleotide sequence has at least 98% identity to CS01-FL-NA (SEQ ID NO: 13). In some embodiments, the nucleotide sequence has at least 99% identity to CS01-FL-NA (SEQ ID NO: 13). In some embodiments, the nucleotide sequence has at least 99.5% identity to CS01-FL-NA (SEQ ID NO: 13). In some embodiments, the nucleotide sequence has at least 99.9% identity to CS01-FL-NA (SEQ ID NO: 13). In some embodiments, the nucleotide sequence is identical to CS01-FL-NA (SEQ ID NO: 13).

In some embodiments, the Factor VIII variant encoded by the codon-altered polynucleotide has an amino acid sequence with high sequence identity to CS01-FL-AA (SEQ ID NO: 2). In some embodiments, the amino acid sequence has at least 97% identity to CS01-FL-AA (SEQ ID NO: 2). In some embodiments, the amino acid sequence has at least 98% identity to CS01-FL-AA (SEQ ID NO: 2). In some embodiments, the amino acid sequence has at least 99% identity to CS01-FL-AA (SEQ ID NO: 2). In some embodiments, the amino acid sequence has at least 99.5% identity to CS01-FL-AA (SEQ ID NO: 2). In some embodiments, the amino acid sequence has at least 99.9% identity to CS01-FL-AA (SEQ ID NO: 2). In some embodiments, the amino acid sequence is identical to CS01-FL-AA (SEQ ID NO: 2).

In some embodiments, the Factor VIII variant encoded by the CS01 polynucleotide, having high sequence homology to CS01-FL-AA (e.g., at least 95%, 96%, 97%, 98%, 99%, 99.5%, or 99.9% identity), comprises one or more amino acid substitutions selected from m1, m2, m3, m4, and m5.

In one embodiment, the Factor VIII variant encoded by the CS01 polynucleotide comprises an m1 amino acid substitution. In one embodiment, the Factor VIII variant encoded by the CS01 polynucleotide comprises an m2 amino acid substitution. In one embodiment, the Factor VIII variant encoded by the CS01 polynucleotide comprises an m3 amino acid substitution. In one embodiment, the Factor VIII variant encoded by the CS01 polynucleotide comprises an m4 amino acid substitution. In one embodiment, the Factor VIII variant encoded by the CS01 polynucleotide comprises an m5 amino acid substitution.

In one embodiment, the Factor VIII variant encoded by the CS01 polynucleotide comprises m12 amino acid substitutions. In one embodiment, the Factor VIII variant encoded by the CS01 polynucleotide comprises m13 amino acid substitutions. In one embodiment, the Factor VIII variant encoded by the CS01 polynucleotide comprises m23 amino acid substitutions. In one embodiment, the Factor VIII variant encoded by the CS01 polynucleotide comprises m24 amino acid substitutions. In one embodiment, the Factor VIII variant encoded by the CS01 polynucleotide comprises m25 amino acid substitutions. In one embodiment, the Factor VIII variant encoded by the CS01 polynucleotide comprises m34 amino acid substitutions. In one embodiment, the Factor VIII variant encoded by the CS01 polynucleotide comprises m35 amino acid substitutions.

In one embodiment, the Factor VIII variant encoded by the CS01 polynucleotide comprises m123 amino acid substitutions. In one embodiment, the Factor VIII variant encoded by the CS01 polynucleotide comprises m234 amino acid substitutions. In one embodiment, the Factor VIII variant encoded by the CS01 polynucleotide comprises m125 amino acid substitutions.

CS23 Codon Altered Polynucleotides

In one embodiment, the codon-altered polynucleotides provided herein include a nucleotide sequence encoding a Factor VIII variant polypeptide with a linker that is cleavable in vivo. The Factor VIII polypeptide includes a Factor VIII light chain, a Factor VIII heavy chain, and a polypeptide linker joining the C-terminus of the heavy chain to the N-terminus of the light chain. The heavy chain of the Factor VIII polypeptide is encoded by a first nucleotide sequence having high sequence identity to CS23-HC-NA (SEQ ID NO: 22), which is the portion of CS23-FL-NA (SEQ ID NO: 20) encoding for a Factor VIII heavy chain. The light chain of the Factor VIII polypeptide is encoded by a second nucleotide sequence with high sequence identity to CS23-LC-NA (SEQ ID NO: 23), which is the portion of CS23-FL-NA (SEQ ID NO: 20) encoding for a Factor VIII light chain. The polypeptide linker includes a furin cleavage site, which allows for maturation in vivo (e.g., after expression in vivo or administration of the precursor polypeptide).

In some embodiments, the first and second nucleotide sequences have at least 95% sequence identity to CS23-HC-NA and CS23-LC-NA (SEQ ID NOS 22 and 23), respectively. In some embodiments, the first and second nucleotide sequences have at least 96% sequence identity to CS23-HC-NA and CS23-LC-NA (SEQ ID NOS 22 and 23), respectively. In some embodiments, the first and second nucleotide sequences have at least 97% sequence identity to CS23-HC-NA and CS23-LC-NA (SEQ ID NOS 22 and 23), respectively. In some embodiments, the first and second nucleotide sequences have at least 98% sequence identity to CS23-HC-NA and CS23-LC-NA (SEQ ID NOS 22 and 23), respectively. In some embodiments, the first and second nucleotide sequences have at least 99% sequence identity to CS23-HC-NA and CS23-LC-NA (SEQ ID NOS 22 and 23), respectively. In some embodiments, the first and second nucleotide sequences have at least 99.5% sequence identity to CS23-HC-NA and CS23-LC-NA (SEQ ID NOS 22 and 23), respectively. In some embodiments, the first and second nucleotide sequences have at least 99.9% sequence identity to CS23-HC-NA and CS23-LC-NA (SEQ ID NOS 22 and 23), respectively. In some embodiments, the first and second nucleotide sequences are identical to CS23-HC-NA and CS23-LC-NA (SEQ ID NOS 22 and 23), respectively.

In some embodiments, the polypeptide linker of the Factor VIII construct is encoded by a third nucleotide sequence having high sequence identity to BDLO04 (SEQ ID NO: 6), which encodes the 14-amino acid linker corresponding to amino acids 760-773 of CS23-FL-AA (SEQ ID NO: 21). In some embodiments, the third nucleotide sequence has at least 95% identity to BDLO04 (SEQ ID NO: 6). In some embodiments, the third nucleotide sequence has at least 96% identity to BDLO04 (SEQ ID NO: 6). In some embodiments, the third nucleotide sequence has at least 97% identity to BDLO04 (SEQ ID NO: 6). In some embodiments, the third nucleotide sequence has at least 98% identity to BDLO04 (SEQ ID NO: 6). In some embodiments, the third nucleotide sequence is identical to BDLO04 (SEQ ID NO: 6).

In some embodiments, the codon-altered polynucleotide has a nucleotide sequence with high sequence identity to CS23-FL-NA (SEQ ID NO: 20). In some embodiments, the nucleotide sequence has at least 95% identity to CS23-FL-NA (SEQ ID NO: 20). In some embodiments, the nucleotide sequence has at least 96% identity to CS23-FL-NA (SEQ ID NO: 20). In some embodiments, the nucleotide sequence has at least 97% identity to CS23-FL-NA (SEQ ID NO: 20). In some embodiments, the nucleotide sequence has at least 98% identity to CS23-FL-NA (SEQ ID NO: 20). In some embodiments, the nucleotide sequence has at least 99% identity to CS23-FL-NA (SEQ ID NO: 20). In some embodiments, the nucleotide sequence has at least 99.5% identity to CS23-FL-NA (SEQ ID NO: 20). In some embodiments, the nucleotide sequence has at least 99.9% identity to CS23-FL-NA (SEQ ID NO: 20). In some embodiments, the nucleotide sequence is identical to CS23-FL-NA (SEQ ID NO: 20).

In some embodiments, the Factor VIII variant encoded by the codon-altered polynucleotide has an amino acid sequence with high sequence identity to CS23-FL-AA (SEQ ID NO: 21). In some embodiments, the amino acid sequence has at least 97% identity to CS23-FL-AA (SEQ ID NO: 21). In some embodiments, the amino acid sequence has at least 98% identity to CS23-FL-AA (SEQ ID NO: 21). In some embodiments, the amino acid sequence has at least 99% identity to CS23-FL-AA (SEQ ID NO: 21). In some embodiments, the amino acid sequence has at least 99.5% identity to CS23-FL-AA (SEQ ID NO: 21). In some embodiments, the amino acid sequence has at least 99.9% identity to CS23-FL-AA (SEQ ID NO: 21). In some embodiments, the amino acid sequence is identical to CS23-FL-AA (SEQ ID NO: 21).

In some embodiments, the Factor VIII variant encoded by the CS23 polynucleotide, having high sequence homology to CS23-FL-AA (e.g., at least 95%, 96%, 97%, 98%, 99%, 99.5%, or 99.9% identity), comprises one or more amino acid substitutions selected from m1, m2, m3, m4, and m5.

In one embodiment, the Factor VIII variant encoded by the CS23 polynucleotide comprises an m1 amino acid substitution. In one embodiment, the Factor VIII variant encoded by the CS23 polynucleotide comprises an m2 amino acid substitution. In one embodiment, the Factor VIII variant encoded by the CS23 polynucleotide comprises an m3 amino acid substitution. In one embodiment, the Factor VIII variant encoded by the CS23 polynucleotide comprises an m4 amino acid substitution. In one embodiment, the Factor VIII variant encoded by the CS23 polynucleotide comprises an m5 amino acid substitution.

In one embodiment, the Factor VIII variant encoded by the CS23 polynucleotide comprises m12 amino acid substitutions. In one embodiment, the Factor VIII variant encoded by the CS23 polynucleotide comprises m13 amino acid substitutions. In one embodiment, the Factor VIII variant encoded by the CS23 polynucleotide comprises m23 amino acid substitutions. In one embodiment, the Factor VIII variant encoded by the CS23 polynucleotide comprises m24 amino acid substitutions. In one embodiment, the Factor VIII variant encoded by the CS23 polynucleotide comprises m25 amino acid substitutions. In one embodiment, the Factor VIII variant encoded by the CS23 polynucleotide comprises m34 amino acid substitutions. In one embodiment, the Factor VIII variant encoded by the CS23 polynucleotide comprises m35 amino acid substitutions.

In one embodiment, the Factor VIII variant encoded by the CS23 polynucleotide comprises m123 amino acid substitutions. In one embodiment, the Factor VIII variant encoded by the CS23 polynucleotide comprises m234 amino acid substitutions. In one embodiment, the Factor VIII variant encoded by the CS23 polynucleotide comprises m125 amino acid substitutions.

D. Codon-Altered Polynucleotides Encoding a Single-Chain Factor VIII Protein

Factor VIII constructs in which the furin cleavage site located at the C-terminal end of the B-domain is removed retain activity as a single chain polypeptide, despite that normal maturation of the Factor VIII molecule cannot occur (Leyte et al. (1991)). Similarly, a B-domain deleted Factor VIII construct with an attenuated furin site (containing an R1664H amino acid substitution) is more biologically active than the corresponding Factor VIII construct with a wild-type furin cleavage site (Siner et al. (2013)). Accordingly, in some embodiments, the codon-altered polynucleotides provided herein include a nucleotide sequence encoding a single-chain Factor VIII variant polypeptide. The single-chain Factor VIII polypeptide includes a Factor VIII light chain, a Factor VIII heavy chain, and a polypeptide linker joining the C-terminus of the heavy chain to the N-terminus of the light chain. The polypeptide linker does not include a furin cleavage site.

Single-Chain CS04 Codon Altered Polynucleotides

In one embodiment, the codon-altered polynucleotides provided herein include a nucleotide sequence encoding a single-chain Factor VIII variant polypeptide. The Factor VIII polypeptide includes a Factor VIII light chain, a Factor VIII heavy chain, and an optional polypeptide linker joining the C-terminus of the heavy chain to the N-terminus of the light chain. The heavy chain of the Factor VIII polypeptide is encoded by a first nucleotide sequence having high sequence identity to CS04-HC-NA (SEQ ID NO: 3), which is the portion of CS04-FL-NA (SEQ ID NO: 1) encoding for a Factor VIII heavy chain. The light chain of the Factor VIII polypeptide is encoded by a second nucleotide sequence with high sequence identity to CS04-LC-NA (SEQ ID NO: 4), which is the portion of CS04-FL-NA (SEQ ID NO: 1) encoding for a Factor VIII light chain. The optional polypeptide linker does not include a furin cleavage site.

In some embodiments, the first and second nucleotide sequences have at least 95% sequence identity to CS04-HC-NA and CS04-LC-NA (SEQ ID NOS 3 and 4), respectively. In some embodiments, the first and second nucleotide sequences have at least 96% sequence identity to CS04-HC-NA and CS04-LC-NA (SEQ ID NOS 3 and 4), respectively. In some embodiments, the first and second nucleotide sequences have at least 97% sequence identity to CS04-HC-NA and CS04-LC-NA (SEQ ID NOS 3 and 4), respectively. In some embodiments, the first and second nucleotide sequences have at least 98% sequence identity to CS04-HC-NA and CS04-LC-NA (SEQ ID NOS 3 and 4), respectively. In some embodiments, the first and second nucleotide sequences have at least 99% sequence identity to CS04-HC-NA and CS04-LC-NA (SEQ ID NOS 3 and 4), respectively. In some embodiments, the first and second nucleotide sequences have at least 99.5% sequence identity to CS04-HC-NA and CS04-LC-NA (SEQ ID NOS 3 and 4), respectively. In some embodiments, the first and second nucleotide sequences have at least 99.9% sequence identity to CS04-HC-NA and CS04-LC-NA (SEQ ID NOS 3 and 4), respectively. In some embodiments, the first and second nucleotide sequences are identical to CS04-HC-NA and CS04-LC-NA (SEQ ID NOS 3 and 4), respectively.

In some embodiments, the codon-altered polynucleotide has a nucleotide sequence with high sequence identity to CS04-SC1-NA (SEQ ID NO: 9). In some embodiments, the nucleotide sequence has at least 95% identity to CS04-SC1-NA (SEQ ID NO: 9). In some embodiments, the nucleotide sequence has at least 96% identity to CS04-SC1-NA (SEQ ID NO: 9). In some embodiments, the nucleotide sequence has at least 97% identity to CS04-SC1-NA (SEQ ID NO: 9). In some embodiments, the nucleotide sequence has at least 98% identity to CS04-SC1-NA (SEQ ID NO: 9). In some embodiments, the nucleotide sequence has at least 99% identity to CS04-SC1-NA (SEQ ID NO: 9). In some embodiments, the nucleotide sequence has at least 99.5% identity to CS04-SC1-NA (SEQ ID NO: 9). In some embodiments, the nucleotide sequence has at least 99.9% identity to CS04-SC1-NA (SEQ ID NO: 9). In some embodiments, the nucleotide sequence is identical to CS04-SC1-NA (SEQ ID NO: 9).

In some embodiments, the codon-altered polynucleotide has a nucleotide sequence with high sequence identity to CS04-SC2-NA (SEQ ID NO: 11). In some embodiments, the nucleotide sequence has at least 95% identity to CS04-SC2-NA (SEQ ID NO: 11). In some embodiments, the nucleotide sequence has at least 96% identity to CS04-SC2-NA (SEQ ID NO: 11). In some embodiments, the nucleotide sequence has at least 97% identity to CS04-SC2-NA (SEQ ID NO: 11). In some embodiments, the nucleotide sequence has at least 98% identity to CS04-SC2-NA (SEQ ID NO: 11). In some embodiments, the nucleotide sequence has at least 99% identity to CS04-SC2-NA (SEQ ID NO: 11). In some embodiments, the nucleotide sequence has at least 99.5% identity to CS04-SC2-NA (SEQ ID NO: 11). In some embodiments, the nucleotide sequence has at least 99.9% identity to CS04-SC2-NA (SEQ ID NO: 11). In some embodiments, the nucleotide sequence is identical to CS04-SC2-NA (SEQ ID NO: 11).

In some embodiments, the single-chain Factor VIII variant encoded by the codon-altered polynucleotide has an amino acid sequence with high sequence identity to CS04-SC1-AA (SEQ ID NO: 10; human Factor VIIIΔ(760-1667) (SPI; HsFVIIIΔ(741-1648), SPE)). In some embodiments, the Factor VIII variant encoded by the codon-altered polynucleotide has an amino acid sequence with high sequence identity to CS04-SC1-AA (SEQ ID NO: 10). In some embodiments, the amino acid sequence has at least 97% identity to CS04-SC1-AA (SEQ ID NO: 10). In some embodiments, the amino acid sequence has at least 98% identity to CS04-SC1-AA (SEQ ID NO: 10). In some embodiments, the amino acid sequence has at least 99% identity to CS04-SC1-AA (SEQ ID NO: 10). In some embodiments, the amino acid sequence has at least 99.5% identity to CS04-SC1-AA (SEQ ID NO: 10). In some embodiments, the amino acid sequence has at least 99.9% identity to CS04-SC1-AA (SEQ ID NO: 10). In some embodiments, the amino acid sequence is identical to CS04-SC1-AA (SEQ ID NO: 10).

In some embodiments, the Factor VIII variant encoded by the CS04-SC1 polynucleotide, having high sequence homology to CS04-SC1-AA (e.g., at least 95%, 96%, 97%, 98%, 99%, 99.5%, or 99.9% identity), comprises one or more amino acid substitutions selected from m1, m2, m3, m4, and m5.

In some embodiments, the single-chain Factor VIII variant encoded by the codon-altered polynucleotide has an amino acid sequence with high sequence identity to CS04-SC2-AA (SEQ ID NO: 12; human Factor VIIIΔ(772-1667) (SPI; HsFVIIIΔ(753-1648), SPE)). In some embodiments, the Factor VIII variant encoded by the codon-altered polynucleotide has an amino acid sequence with high sequence identity to CS04-SC2-AA (SEQ ID NO: 12). In some embodiments, the amino acid sequence has at least 97% identity to CS04-SC2-AA (SEQ ID NO: 12). In some embodiments, the amino acid sequence has at least 98% identity to CS04-SC2-AA (SEQ ID NO: 12). In some embodiments, the amino acid sequence has at least 99% identity to CS04-SC2-AA (SEQ ID NO: 12). In some embodiments, the amino acid sequence has at least 99.5% identity to CS04-SC2-AA (SEQ ID NO: 12). In some embodiments, the amino acid sequence has at least 99.9% identity to CS04-SC2-AA (SEQ ID NO: 12). In some embodiments, the amino acid sequence is identical to CS04-SC2-AA (SEQ ID NO: 12).

In some embodiments, the single-chain Factor VIII variant encoded by the CS04-SC2 polynucleotide, having high sequence homology to CS04-SC2-AA (e.g., at least 95%, 96%, 97%, 98%, 99%, 99.5%, or 99.9% identity), comprises one or more amino acid substitutions selected from m1, m2, m3, m4, and m5.

In one embodiment, the single-chain Factor VIII variant encoded by the CS04 polynucleotide comprises an m1 amino acid substitution. In one embodiment, the Factor VIII variant encoded by the CS04 polynucleotide comprises an m2 amino acid substitution. In one embodiment, the Factor VIII variant encoded by the CS04 polynucleotide comprises an m3 amino acid substitution. In one embodiment, the Factor VIII variant encoded by the CS04 polynucleotide comprises an m4 amino acid substitution. In one embodiment, the Factor VIII variant encoded by the CS04 polynucleotide comprises an m5 amino acid substitution.

In one embodiment, the single-chain Factor VIII variant encoded by the CS04 polynucleotide comprises m12 amino acid substitutions. In one embodiment, the Factor VIII variant encoded by the CS04 polynucleotide comprises m13 amino acid substitutions. In one embodiment, the Factor VIII variant encoded by the CS04 polynucleotide comprises m23 amino acid substitutions. In one embodiment, the Factor VIII variant encoded by the CS04 polynucleotide comprises m24 amino acid substitutions. In one embodiment, the Factor VIII variant encoded by the CS04 polynucleotide comprises m25 amino acid substitutions. In one embodiment, the Factor VIII variant encoded by the CS04 polynucleotide comprises m34 amino acid substitutions. In one embodiment, the Factor VIII variant encoded by the CS04 polynucleotide comprises m35 amino acid substitutions.

In one embodiment, the single-chain Factor VIII variant encoded by the CS04 polynucleotide comprises m123 amino acid substitutions. In one embodiment, the Factor VIII variant encoded by the CS04 polynucleotide comprises m234 amino acid substitutions. In one embodiment, the Factor VIII variant encoded by the CS04 polynucleotide comprises m125 amino acid substitutions.

Single-Chain CS01 Codon Altered Polynucleotides

In one embodiment, the codon-altered polynucleotides provided herein include a nucleotide sequence encoding a single-chain Factor VIII variant polypeptide. The Factor VIII polypeptide includes a Factor VIII light chain, a Factor VIII heavy chain, and an optional polypeptide linker joining the C-terminus of the heavy chain to the N-terminus of the light chain. The heavy chain of the Factor VIII polypeptide is encoded by a first nucleotide sequence having high sequence identity to CS01-HC-NA (SEQ ID NO: 24), which is the portion of CS01-FL-NA (SEQ ID NO: 13) encoding for a Factor VIII heavy chain. The light chain of the Factor VIII polypeptide is encoded by a second nucleotide sequence with high sequence identity to CS01-LC-NA (SEQ ID NO: 25), which is the portion of CS01-FL-NA (SEQ ID NO: 13) encoding for a Factor VIII light chain. The optional polypeptide linker does not include a furin cleavage site.

In some embodiments, the first and second nucleotide sequences have at least 95% sequence identity to CS01-HC-NA and CS01-LC-NA (SEQ ID NOS 24 and 25), respectively. In some embodiments, the first and second nucleotide sequences have at least 96% sequence identity to CS01-HC-NA and CS01-LC-NA (SEQ ID NOS 24 and 25), respectively. In some embodiments, the first and second nucleotide sequences have at least 97% sequence identity to CS01-HC-NA and CS01-LC-NA (SEQ ID NOS 24 and 25), respectively. In some embodiments, the first and second nucleotide sequences have at least 98% sequence identity to CS01-HC-NA and CS01-LC-NA (SEQ ID NOS 24 and 25), respectively. In some embodiments, the first and second nucleotide sequences have at least 99% sequence identity to CS01-HC-NA and CS01-LC-NA (SEQ ID NOS 24 and 25), respectively. In some embodiments, the first and second nucleotide sequences have at least 99.5% sequence identity to CS01-HC-NA and CS01-LC-NA (SEQ ID NOS 24 and 25), respectively. In some embodiments, the first and second nucleotide sequences have at least 99.9% sequence identity to CS01-HC-NA and CS01-LC-NA (SEQ ID NOS 24 and 25), respectively. In some embodiments, the first and second nucleotide sequences are identical to CS01-HC-NA and CS01-LC-NA (SEQ ID NOS 24 and 25), respectively.

In some embodiments, the codon-altered polynucleotide has a nucleotide sequence with high sequence identity to CS01-SC1-NA (SEQ ID NO: 26). In some embodiments, the nucleotide sequence has at least 95% identity to CS01-SC1-NA (SEQ ID NO: 26). In some embodiments, the nucleotide sequence has at least 96% identity to CS01-SC1-NA (SEQ ID NO: 26). In some embodiments, the nucleotide sequence has at least 97% identity to CS01-SC1-NA (SEQ ID NO: 26). In some embodiments, the nucleotide sequence has at least 98% identity to CS01-SC1-NA (SEQ ID NO: 26). In some embodiments, the nucleotide sequence has at least 99% identity to CS01-SC1-NA (SEQ ID NO: 26). In some embodiments, the nucleotide sequence has at least 99.5% identity to CS01-SC1-NA (SEQ ID NO: 26). In some embodiments, the nucleotide sequence has at least 99.9% identity to CS01-SC1-NA (SEQ ID NO: 26). In some embodiments, the nucleotide sequence is identical to CS01-SC1-NA (SEQ ID NO: 26).

In some embodiments, the codon-altered polynucleotide has a nucleotide sequence with high sequence identity to CS01-SC2-NA (SEQ ID NO: 27). In some embodiments, the nucleotide sequence has at least 95% identity to CS01-SC2-NA (SEQ ID NO: 27). In some embodiments, the nucleotide sequence has at least 96% identity to CS01-SC2-NA (SEQ ID NO: 27). In some embodiments, the nucleotide sequence has at least 97% identity to CS01-SC2-NA (SEQ ID NO: 27). In some embodiments, the nucleotide sequence has at least 98% identity to CS01-SC2-NA (SEQ ID NO: 27). In some embodiments, the nucleotide sequence has at least 99% identity to CS01-SC2-NA (SEQ ID NO: 27). In some embodiments, the nucleotide sequence has at least 99.5% identity to CS01-SC2-NA (SEQ ID NO: 27). In some embodiments, the nucleotide sequence has at least 99.9% identity to CS01-SC2-NA (SEQ ID NO: 27). In some embodiments, the nucleotide sequence is identical to CS01-SC2-NA (SEQ ID NO: 27).

In some embodiments, the single-chain Factor VIII variant encoded by the codon-altered polynucleotide has an amino acid sequence with high sequence identity to CS01-SC1-AA (SEQ ID NO: 10; human Factor VIIIΔ(760-1667) (SPI; HsFVIIIΔ(741-1648), SPE)). In some embodiments, the Factor VIII variant encoded by the codon-altered polynucleotide has an amino acid sequence with high sequence identity to CS01-SC1-AA (SEQ ID NO: 10). In some embodiments, the amino acid sequence has at least 97% identity to CS01-SC1-AA (SEQ ID NO: 10). In some embodiments, the amino acid sequence has at least 98% identity to CS01-SC1-AA (SEQ ID NO: 10). In some embodiments, the amino acid sequence has at least 99% identity to CS01-SC1-AA (SEQ ID NO: 10). In some embodiments, the amino acid sequence has at least 99.5% identity to CS01-SC1-AA (SEQ ID NO: 10). In some embodiments, the amino acid sequence has at least 99.9% identity to CS01-SC1-AA (SEQ ID NO: 10). In some embodiments, the amino acid sequence is identical to CS01-SC1-AA (SEQ ID NO: 10).

In some embodiments, the Factor VIII variant encoded by the CS01-SC1 polynucleotide, having high sequence homology to CS01-SC1-AA (e.g., at least 95%, 96%, 97%, 98%, 99%, 99.5%, or 99.9% identity), comprises one or more amino acid substitutions selected from m1, m2, m3, m4, and m5.

In some embodiments, the single-chain Factor VIII variant encoded by the codon-altered polynucleotide has an amino acid sequence with high sequence identity to CS01-SC2-AA (SEQ ID NO: 12; human Factor VIIIΔ(772-1667) (SPI; HsFVIIIΔ(753-1648), SPE)). In some embodiments, the Factor VIII variant encoded by the codon-altered polynucleotide has an amino acid sequence with high sequence identity to CS01-SC2-AA (SEQ ID NO: 12). In some embodiments, the amino acid sequence has at least 97% identity to CS01-SC2-AA (SEQ ID NO: 12). In some embodiments, the amino acid sequence has at least 98% identity to CS01-SC2-AA (SEQ ID NO: 12). In some embodiments, the amino acid sequence has at least 99% identity to CS01-SC2-AA (SEQ ID NO: 12). In some embodiments, the amino acid sequence has at least 99.5% identity to CS01-SC2-AA (SEQ ID NO: 12). In some embodiments, the amino acid sequence has at least 99.9% identity to CS01-SC2-AA (SEQ ID NO: 12). In some embodiments, the amino acid sequence is identical to CS01-SC2-AA (SEQ ID NO: 12).

In some embodiments, the single-chain Factor VIII variant encoded by the CS01-SC2 polynucleotide, having high sequence homology to CS01-SC2-AA (e.g., at least 95%, 96%, 97%, 98%, 99%, 99.5%, or 99.9% identity), comprises one or more amino acid substitutions selected from m1, m2, m3, m4, and m5.

In one embodiment, the single-chain Factor VIII variant encoded by the CS01 polynucleotide comprises an m1 amino acid substitution. In one embodiment, the Factor VIII variant encoded by the CS01 polynucleotide comprises an m2 amino acid substitution. In one embodiment, the Factor VIII variant encoded by the CS01 polynucleotide comprises an m3 amino acid substitution. In one embodiment, the Factor VIII variant encoded by the CS01 polynucleotide comprises an m4 amino acid substitution. In one embodiment, the Factor VIII variant encoded by the CS01 polynucleotide comprises an m5 amino acid substitution.

In one embodiment, the single-chain Factor VIII variant encoded by the CS01 polynucleotide comprises m12 amino acid substitutions. In one embodiment, the Factor VIII variant encoded by the CS01 polynucleotide comprises m13 amino acid substitutions. In one embodiment, the Factor VIII variant encoded by the CS01 polynucleotide comprises m23 amino acid substitutions. In one embodiment, the Factor VIII variant encoded by the CS01 polynucleotide comprises m24 amino acid substitutions. In one embodiment, the Factor VIII variant encoded by the CS01 polynucleotide comprises m25 amino acid substitutions. In one embodiment, the Factor VIII variant encoded by the CS01 polynucleotide comprises m34 amino acid substitutions. In one embodiment, the Factor VIII variant encoded by the CS01 polynucleotide comprises m35 amino acid substitutions.

In one embodiment, the single-chain Factor VIII variant encoded by the CS01 polynucleotide comprises m123 amino acid substitutions. In one embodiment, the Factor VIII variant encoded by the CS01 polynucleotide comprises m234 amino acid substitutions. In one embodiment, the Factor VIII variant encoded by the CS01 polynucleotide comprises m125 amino acid substitutions.

Single-Chain CS23 Codon Altered Polynucleotides

In one embodiment, the codon-altered polynucleotides provided herein include a nucleotide sequence encoding a single-chain Factor VIII variant polypeptide. The Factor VIII polypeptide includes a Factor VIII light chain, a Factor VIII heavy chain, and an optional polypeptide linker joining the C-terminus of the heavy chain to the N-terminus of the light chain. The heavy chain of the Factor VIII polypeptide is encoded by a first nucleotide sequence having high sequence identity to CS23-HC-NA (SEQ ID NO: 22), which is the portion of CS23-FL-NA (SEQ ID NO: 20) encoding for a Factor VIII heavy chain. The light chain of the Factor VIII polypeptide is encoded by a second nucleotide sequence with high sequence identity to CS23-LC-NA (SEQ ID NO: 23), which is the portion of CS23-FL-NA (SEQ ID NO: 20) encoding for a Factor VIII light chain. The optional polypeptide linker does not include a furin cleavage site.

In some embodiments, the first and second nucleotide sequences have at least 95% sequence identity to CS23-HC-NA and CS23-LC-NA (SEQ ID NOS 22 and 23), respectively. In some embodiments, the first and second nucleotide sequences have at least 96% sequence identity to CS23-HC-NA and CS23-LC-NA (SEQ ID NOS 22 and 23), respectively. In some embodiments, the first and second nucleotide sequences have at least 97% sequence identity to CS23-HC-NA and CS23-LC-NA (SEQ ID NOS 22 and 23), respectively. In some embodiments, the first and second nucleotide sequences have at least 98% sequence identity to CS23-HC-NA and CS23-LC-NA (SEQ ID NOS 22 and 23), respectively. In some embodiments, the first and second nucleotide sequences have at least 99% sequence identity to CS23-HC-NA and CS23-LC-NA (SEQ ID NOS 22 and 23), respectively. In some embodiments, the first and second nucleotide sequences have at least 99.5% sequence identity to CS23-HC-NA and CS23-LC-NA (SEQ ID NOS 22 and 23), respectively. In some embodiments, the first and second nucleotide sequences have at least 99.9% sequence identity to CS23-HC-NA and CS23-LC-NA (SEQ ID NOS 22 and 23), respectively. In some embodiments, the first and second nucleotide sequences are identical to CS23-HC-NA and CS23-LC-NA (SEQ ID NOS 22 and 23), respectively.

In some embodiments, the codon-altered polynucleotide has a nucleotide sequence with high sequence identity to CS23-SC1-NA (SEQ ID NO: 28). In some embodiments, the nucleotide sequence has at least 95% identity to CS23-SC1-NA (SEQ ID NO: 28). In some embodiments, the nucleotide sequence has at least 96% identity to CS23-SC1-NA (SEQ ID NO: 28). In some embodiments, the nucleotide sequence has at least 97% identity to CS23-SC1-NA (SEQ ID NO: 28). In some embodiments, the nucleotide sequence has at least 98% identity to CS23-SC1-NA (SEQ ID NO: 28). In some embodiments, the nucleotide sequence has at least 99% identity to CS23-SC1-NA (SEQ ID NO: 28). In some embodiments, the nucleotide sequence has at least 99.5% identity to CS23-SC1-NA (SEQ ID NO: 28). In some embodiments, the nucleotide sequence has at least 99.9% identity to CS23-SC1-NA (SEQ ID NO: 28). In some embodiments, the nucleotide sequence is identical to CS23-SC1-NA (SEQ ID NO: 28).

In some embodiments, the codon-altered polynucleotide has a nucleotide sequence with high sequence identity to CS23-SC2-NA (SEQ ID NO: 29). In some embodiments, the nucleotide sequence has at least 95% identity to CS23-SC2-NA (SEQ ID NO: 29). In some embodiments, the nucleotide sequence has at least 96% identity to CS23-SC2-NA (SEQ ID NO: 29). In some embodiments, the nucleotide sequence has at least 97% identity to CS23-SC2-NA (SEQ ID NO: 29). In some embodiments, the nucleotide sequence has at least 98% identity to CS23-SC2-NA (SEQ ID NO: 29). In some embodiments, the nucleotide sequence has at least 99% identity to CS23-SC2-NA (SEQ ID NO: 29). In some embodiments, the nucleotide sequence has at least 99.5% identity to CS23-SC2-NA (SEQ ID NO: 29). In some embodiments, the nucleotide sequence has at least 99.9% identity to CS23-SC2-NA (SEQ ID NO: 29). In some embodiments, the nucleotide sequence is identical to CS23-SC2-NA (SEQ ID NO: 29).

In some embodiments, the single-chain Factor VIII variant encoded by the codon-altered polynucleotide has an amino acid sequence with high sequence identity to CS23-SC1-AA (SEQ ID NO: 10; human Factor VIIIΔ(760-1667) (SPI; CS04Δ(741-1648), SPE)). In some embodiments, the Factor VIII variant encoded by the codon-altered polynucleotide has an amino acid sequence with high sequence identity to CS23-SC1-AA (SEQ ID NO: 10). In some embodiments, the amino acid sequence has at least 97% identity to CS23-SC1-AA (SEQ ID NO: 10). In some embodiments, the amino acid sequence has at least 98% identity to CS23-SC1-AA (SEQ ID NO: 10). In some embodiments, the amino acid sequence has at least 99% identity to CS23-SC1-AA (SEQ ID NO: 10). In some embodiments, the amino acid sequence has at least 99.5% identity to CS23-SC1-AA (SEQ ID NO: 10). In some embodiments, the amino acid sequence has at least 99.9% identity to CS23-SC1-AA (SEQ ID NO: 10). In some embodiments, the amino acid sequence is identical to CS23-SC1-AA (SEQ ID NO: 10).

In some embodiments, the Factor VIII variant encoded by the CS23-SC1 polynucleotide, having high sequence homology to CS23-SC1-AA (e.g., at least 95%, 96%, 97%, 98%, 99%, 99.5%, or 99.9% identity), comprises one or more amino acid substitutions selected from m1, m2, m3, m4, and m5.

In some embodiments, the single-chain Factor VIII variant encoded by the codon-altered polynucleotide has an amino acid sequence with high sequence identity to CS23-SC2-AA (SEQ ID NO: 12; human Factor VIIIΔ(772-1667) (SPI; HsFVIIIΔ(753-1648), SPE)). In some embodiments, the Factor VIII variant encoded by the codon-altered polynucleotide has an amino acid sequence with high sequence identity to CS23-SC2-AA (SEQ ID NO: 12). In some embodiments, the amino acid sequence has at least 97% identity to CS23-SC2-AA (SEQ ID NO: 12). In some embodiments, the amino acid sequence has at least 98% identity to CS23-SC2-AA (SEQ ID NO: 12). In some embodiments, the amino acid sequence has at least 99% identity to CS23-SC2-AA (SEQ ID NO: 12). In some embodiments, the amino acid sequence has at least 99.5% identity to CS23-SC2-AA (SEQ ID NO: 12). In some embodiments, the amino acid sequence has at least 99.9% identity to CS23-SC2-AA (SEQ ID NO: 12). In some embodiments, the amino acid sequence is identical to CS23-SC2-AA (SEQ ID NO: 12).

In some embodiments, the single-chain Factor VIII variant encoded by the CS23-SC2 polynucleotide, having high sequence homology to CS23-SC2-AA (e.g., at least 95%, 96%, 97%, 98%, 99%, 99.5%, or 99.9% identity), comprises one or more amino acid substitutions selected from m1, m2, m3, m4, and m5.

In one embodiment, the single-chain Factor VIII variant encoded by the CS23 polynucleotide comprises an m1 amino acid substitution. In one embodiment, the Factor VIII variant encoded by the CS23 polynucleotide comprises an m2 amino acid substitution. In one embodiment, the Factor VIII variant encoded by the CS23 polynucleotide comprises an m3 amino acid substitution. In one embodiment, the Factor VIII variant encoded by the CS23 polynucleotide comprises an m4 amino acid substitution. In one embodiment, the Factor VIII variant encoded by the CS23 polynucleotide comprises an m5 amino acid substitution.

In one embodiment, the single-chain Factor VIII variant encoded by the CS23 polynucleotide comprises m12 amino acid substitutions. In one embodiment, the Factor VIII variant encoded by the CS23 polynucleotide comprises m13 amino acid substitutions. In one embodiment, the Factor VIII variant encoded by the CS23 polynucleotide comprises m23 amino acid substitutions. In one embodiment, the Factor VIII variant encoded by the CS23 polynucleotide comprises m24 amino acid substitutions. In one embodiment, the Factor VIII variant encoded by the CS23 polynucleotide comprises m25 amino acid substitutions. In one embodiment, the Factor VIII variant encoded by the CS23 polynucleotide comprises m34 amino acid substitutions. In one embodiment, the Factor VIII variant encoded by the CS23 polynucleotide comprises m35 amino acid substitutions.

In one embodiment, the single-chain Factor VIII variant encoded by the CS23 polynucleotide comprises m123 amino acid substitutions. In one embodiment, the Factor VIII variant encoded by the CS23 polynucleotide comprises m234 amino acid substitutions. In one embodiment, the Factor VIII variant encoded by the CS23 polynucleotide comprises m125 amino acid substitutions.

E. Factor VIII Expression Vectors

In some embodiments, the codon-altered polynucleotides described herein are integrated into expression vectors. Non-limiting examples of expression vectors include viral vectors (e.g., vectors suitable for gene therapy), plasmid vectors, bacteriophage vectors, cosmids, phagemids, artificial chromosomes, and the like.

Non-limiting examples of viral vectors include: retrovirus, e.g., Moloney murine leukemia virus (MMLV), Harvey murine sarcoma virus, murine mammary tumor virus, and Rous sarcoma virus; adenoviruses, adeno-associated viruses; SV40-type viruses; polyomaviruses; Epstein-Barr viruses; papilloma viruses; herpes viruses; vaccinia viruses; and polio viruses.

In some embodiments, the codon-altered polynucleotides described herein are integrated into a gene therapy vector. In some embodiments, the gene therapy vector is a retrovirus, and particularly a replication-deficient retrovirus. Protocols for the production of replication-deficient retroviruses are known in the art. For review, see Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the gene therapy vector is an adeno-associated virus (AAV) based gene therapy vector. AAV systems have been described previously and are generally well known in the art (Kelleher and Vos, *Biotechniques,*

17(6):1110-17 (1994); Cotten et al., *Proc Natl Acad Sci USA,* 89(13):6094-98 (1992); Curiel, *Nat Immun,* 13(2-3): 141-64 (1994); Muzyczka, *Curr Top Microbiol Immunol,* 158:97-129 (1992); and Asokan A, et al., *Mol. Ther.,* 20(4): 699-708 (2012), each incorporated herein by reference in their entireties for all purposes). Details concerning the generation and use of rAAV vectors are described, for example, in U.S. Pat. Nos. 5,139,941 and 4,797,368, each incorporated herein by reference in their entireties for all purposes. In a particular embodiment, the AAV vector is an AAV-8 vector.

In some embodiments, the codon-altered polynucleotides described herein are integrated into a retroviral expression vector. These systems have been described previously, and are generally well known in the art (Mann et al., *Cell,* 33:153-159, 1983; Nicolas and Rubinstein, In: Vectors: A survey of molecular cloning vectors and their uses, Rodriguez and Denhardt, eds., Stoneham: Butterworth, pp. 494-513, 1988; Temin, In: Gene Transfer, Kucherlapati (ed.), New York: Plenum Press, pp. 149-188, 1986). In a specific embodiment, the retroviral vector is a lentiviral vector (see, for example, Naldini et al., *Science,* 272(5259):263-267, 1996; Zufferey et al., *Nat Biotechnol,* 15(9):871-875, 1997; Blomer et al., *J Virol.,* 71(9):6641-6649, 1997; U.S. Pat. Nos. 6,013,516 and 5,994,136).

A wide variety of vectors can be used for the expression of a Factor VIII polypeptide from a codon-altered polypeptide in cell culture, including eukaryotic and prokaryotic expression vectors. In certain embodiments, a plasmid vector is contemplated for use in expressing a Factor VIII polypeptide in cell culture. In general, plasmid vectors containing replicon and control sequences which are derived from species compatible with the host cell are used in connection with these hosts. The vector can carry a replication site, as well as marking sequences which are capable of providing phenotypic selection in transformed cells. The plasmid will include the codon-altered polynucleotide encoding the Factor VIII polypeptide, operably linked to one or more control sequences, for example, a promoter.

Non-limiting examples of vectors for prokaryotic expression include plasmids such as pRSET, pET, pBAD, etc., wherein the promoters used in prokaryotic expression vectors include lac, trc, trp, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

IV. Examples

Example 1—Construction of a Codon Altered Factor VIII Variant Expression Sequence Two hurdles had to be overcome in order to create a Factor VIII coding sequence that is effective for gene therapy of hemophilia A. First, because of the genomic size limitations of conventional gene therapy delivery vectors (e.g., AAV virions), the encoded Factor VIII polypeptide had to be shortened considerably. Second, the coding sequence had to be altered to: (i) stabilize packaging interactions within the delivery vector, (ii) stabilize the mRNA intermediary, and (iii) improve the robustness of transcription/translation of the mRNA.

To achieve the first objective, Applicants started with a B-domain deleted Factor VIII variant construct, referred to herein as "FVIII-BDD-SQ." In this construct, the B-domain is replaced with a fourteen amino acid sequence referred to as the "SQ" sequence. Recombinant FVIII-BDD-SQ is sold under the trade name REFACTO®, and has been shown to be effective for the management of hemophilia A. However, the native coding sequence for FVIII-BDD-SQ, which includes human wild-type nucleic acid sequences for the Factor VIII heavy and light chains, is ineffectively expressed in gene therapy vectors.

To address the poor expression of the native FVIII-BDD-SQ, the codon optimization algorithm described in Fath et al. (PLoS ONE, 6:e17596 (2011)), modified as described in Ward et al. (Blood, 117:798 (2011)) and in McIntosh et al. (Blood, 121, 3335-3344 (2013)), was applied to the FVIII-BDD-SQ sequence to create first intermediate coding sequence CS04a. However, Applicants recognized that the CS04a sequence created using the modified algorithm could be improved by further modifying the sequence. Accordingly, Applicants re-introduced CpG dinucleotides, re-introduced the CGC codon for arginine, changed the leucine and serine codon distributions, re-introduced highly conserved codon pairs, and removed cryptic TATA box, CCAAT box, and splice site elements, while avoiding CpG islands and local overrepresentation of AT-rich and GC-rich stretches.

First, the modified algorithm systematically replaces codons containing CpG-dinucleotides (e.g., arginine codons) with non-CpG-dinucleotide codons, and eliminates/avoids CpG-dinucleotides created by neighboring codons. This strict avoidance of CpG dinucleotides is usually done to prevent TLR-induced immunity after intramuscular injection of DNA vaccines. However, doing so limits the codon optimization possibilities. For example, the modified algorithm excludes use of the complete set of CGX arginine codons. This is particularly disruptive in the coding of genes for expression in human cells, because CGC is the most frequently used arginine codon in highly expressed human genes. Additionally, avoiding the creation of CpGs by neighboring codons further limits the optimization possibilities (e.g., limits the number of codon pairs that may be used together).

Because TLR-induced immunity is not expected to be a problem associated with liver-directed, AAV-based gene therapy, codons including CpGs, and neighboring codons creating CpGs, were re-introduced into intermediate coding sequence CS04a, preferentially in the sequence coding for the Factor VIII light chain (e.g., at the 3' end of the FVIII-BDD-SQ coding sequence). This allowed for more frequent use of preferred human codons, particularly those for arginine. Care was taken, however, to avoid creation of CpG islands, which are regions of coding sequence having a high frequency of CpG sites. This is contrary to the teachings of Krinner et al. (Nucleic Acids Res., 42(6):3551-64 (2014)), which suggests that CpG domains downstream of transcriptional start sites promote high levels of gene expression.

Second, the modified algorithm applies certain codons exclusively, such as CTG for leucine, GTG for valine, and CAG for glutamine. However, this offends the principles of balanced codon use, for example, as proposed in Haas et al. (Current Biology, 6(3):315-24 (1996)). To account for the overuse of preferred codons by the modified algorithm, alternate leucine codons were re-introduced where allowed by the other rules applied to the codon alteration (e.g., CpG frequency and GC content).

Third, the modified algorithm replaces codon pairs without regard to how conserved they are in nature, when certain criteria (e.g., the presence of CG-dinucleotides) are met. To account for beneficial properties which may have been conserved by evolution, the most conserved codon pairs that were replaced by the algorithm and the most conserved preferred codon pairs, e.g., as described in Tats et al. (BMC Genomics 9:463 (2008)), were analyzed and adjusted where allowed by the other rules applied to the codon alteration (e.g., CpG frequency and GC content).

Fourth, serine codons used in the intermediate coding sequence were also re-engineered. Specifically, AGC, TCC, and TCT serine codons were introduced into the modified coding sequence with higher frequency, to better match overall for human codon usage (Haas et al., supra).

Fifth, TATA box, CCAAT box elements, and intron/exon splice sites were screened and removed from the modified coding sequence. When modifying the coding sequence, care was taken to avoid local overrepresentation of AT-rich or GC rich stretches.

Finally, in addition to optimizing the codon usage within the coding sequence, the structural requirements of the underlying AAV virion were considered when further refining the intermediate coding sequence CS04a. AAV vectors (e.g., the nucleic acid portion of an AAV virion) are packaged as single stranded DNA molecules into their capsids (for review, see, Daya and Berns, Clin. Microbiol Rev., 21(4):583-93 (2008)). The GC content of the vector is therefore likely to influence packaging of the genome and, thus, vector yields during production. Like many algorithms, the modified algorithm used here creates an optimized gene sequence with a GC content of at least 60% (see, Fath et al., PLoS One, 6(3):e17596 (2011) (erratum in: PLoS One, (6)3 (2011)). However, the AAV8 capsid protein is encoded by a nucleotide sequence having a lower GC content of about 56%. Thus, to better mimic the native AAV8 capsid protein coding sequence, the GC content of the intermediate coding sequence CS04a was reduced to 56%.

The resulting CS04 coding sequence, shown in FIG. 2, has an overall GC content of 56%. The CpG-dinucleotide content of the sequence is moderate. However, CpG dinucleotides are predominantly present in the downstream portion of the coding sequence, e.g., the portion coding for the Factor VIII light chain. The CS04 sequence has 79.77% nucleotide sequence identity to the corresponding coding sequences in wild-type Factor VIII (Genbank accession M14113).

For comparison purposes, several other codon-optimized, ReFacto constructs were prepared. CS01 was constructed by applying the codon-optimization algorithm of Fath et al., as modified by Ward et al., as done for CS04. However, unlike CS04, the CS01 construct does not contain any CpG islands. The CS08 ReFacto construct was codon-optimized as described in Radcliff P. M. et al., Gene Therapy, 15:289-97 (2008), the content of which is hereby expressly incorporated by reference herein, in its entirety, for all purposes. The CS10 codon-optimized ReFacto construct was obtained from Eurofins Genomics (Ebersberg, Germany). The CS11 codon-optimized ReFacto construct was obtained from Integrated DNA Technologies, Inc. (Coralville, USA). The CH25 codon-optimized ReFacto construct was obtained from ThermoFischer Scientific's GeneArt services (Regensburg, Germany). The CS40 ReFacto construct consists of the wild type Factor VIII coding sequence. The algorithm used to construct CS23 is based on the JCAT tool (www.jcat.de), an on-line tool for codon-optimizations (Grote et al., 2005; Nucl. Acids Res. W526-31). The sequence was further modified to more reflect the codon usage of the albumin superfamily (Mirsafian et al. 2014: Sc. Word Journal 2014, ID 639682). The sequence identities shared between each of the ReFacto coding sequences is shown in Table 2, below.

TABLE 2

Percent identity matrix for codon-altered Factor VIII constructs.

| | CS01 | CS04 | CS08 | CS10 | CS11 | CS40 | CH25 | C23 |
|---|---|---|---|---|---|---|---|---|
| CS01 | 100% | | | | | | | |
| CS04 | 93.0% | 100% | | | | | | |
| CS08 | 80.7% | 82.2.% | 100% | | | | | |
| CS10 | 79.1% | 79.4% | 78.4% | 100% | | | | |
| CS11 | 78.3% | 78.3% | 78.1% | 77.5% | 100% | | | |
| CS40 | 79.6% | 79.8% | 76.7% | 77.6% | 75.4% | 100% | | |
| CH25 | 81.3% | 85.1% | 85.0% | 79.9% | 79.4% | 75.8% | 100% | |
| CS23 | 84.3% | 89.2% | 85.1% | 80.3% | 79.9 | 76.5% | 93.2% | 100% |

Figure 23:
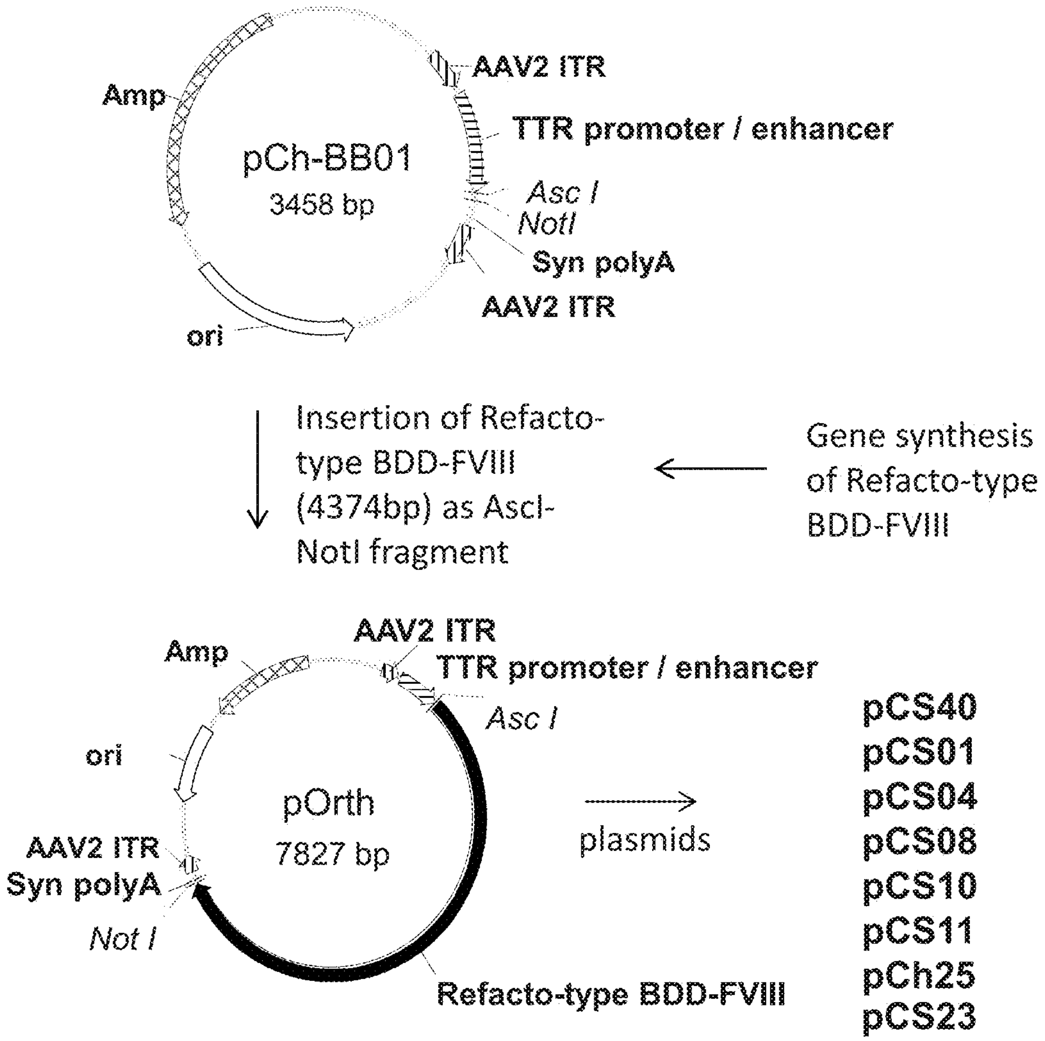
FIG. 23 illustrates the scheme for cloning the pCS40, pCS01, pCS04, pCS08, pCS10, pCS11, and pCh25 constructs, by inserting synthetic Refacto-type BDD-FVIII DNA sequences into the vector backbone pCh-BB01 via AscI and NotI restriction sites.

Plasmids of each construct were constructed by cloning different synthetic DNA fragments into the same vector backbone plasmid (pCh-BB01). DNA synthesis of the Refacto-type BDD-FVIII fragments with flanking AscI and NotI enzyme restriction sites were done by ThermoFischer Scientific (Regensburg, Germany). The vector backbone contains two flanking AAV2-derived inverted terminal repeats (ITRs) that encompass a promoter/enhancer sequence derived from the liver-specific murine transthyretin gene, AscI and NotI enzyme restriction sites for insertion of the respective Refacto-type BDD-FVIII and a synthetic polyA site. After ligation of the prepared vector backbone and inserts via the AscI and NotI sites, the resulting plasmids were amplified in milligram scale. The Refacto-type BDD-FVIII sequences of the constructs were verified by direct sequencing (Microsynth, Balgach, Switzerland). The cloning resulted in seven different plasmid constructs named pCS40, pCS01, pCS04, pCS08, pCS10, pCS11, and pCh25 (FIG. 23). The constructs have the same vector backbone and encode the same B-domain deleted FVIII protein (Refacto-type BDD-FVIII), but differ in their FVIII coding sequence.

AAV8-based vectors were prepared by the three plasmid transfection method, as described in Grieger J C, et al. (Virus Vectors Using Suspension HEK293 Cells and Continuous Harvest of Vector From the Culture Media for GMP FIX and FLT1 Clinical Vector, Mol Ther., Oct. 6, 2015 doi: 10.1038/mt.2015.187. [Epub ahead of print]), the content of which is hereby expressly incorporated by reference herein, in its entirety, for all purposes. HEK293 suspensions cells were used for plasmid transfections using the corresponding FVIII vector plasmid, the helper plasmid pXX6-80 (carrying adenoviral helper genes), and the packaging plasmid pGSK2/8 (contributing the rep2 and cap8 genes). To isolate the AAV8 constructs, the cell pellets of one liter cultures were processed using iodixanol gradients, as described in Grieger et al. (2015, Supra). The procedure resulted in vector preparations called vCS01, vCS04, vCS08, vCS10, vCS11, and vCH25. Vectors were quantified by qPCR using the universal qPCR procedure targeting the AAV2 inverted terminal repeats (Aurnhammer, Human Gene Therapy Methods: Part B 23:18-28 (2012)). A control vector plasmid carrying AAV2 inverted terminal repeats served for preparing the standard curve. The resulting vCS04 construct is presented as SEQ ID NO: 8 in FIGS. 7A-7C.

Figure 24:
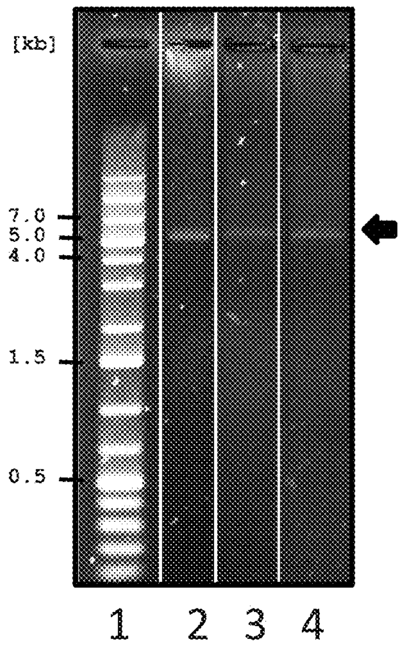
FIG. 24 shows the integrity of AAV vector genome preparations, as analyzed by agarose gel electrophoresis. Lane 1, DNA marker; lane 2, vCS40; lane 3, vCS01; lane 4, vCS04. The AAV vectors have all the same-sized genomes, migrating at approximately 5 kb (arrow, right side). The scale on the left side indicates size of the DNA fragments in kilobases (kb).

The integrity of the vector genomes was analyzed by AAV agarose gel electrophoresis. The electrophoresis was performed as described in Fagone et al., Human Gene Therapy Methods 23:1-7 (2012). Briefly, AAV vector preparations were incubated at 75° C. for 10 minutes in the presence of 0.5% SDS and then cooled down to room temperature. Approximately 1.5E10 vector genomes (vg) were loaded per lane on a 1% 1×TAE agarose gel and electrophoresed for 60 min at 7 V/cm of gel length. The gel was then stained in 2× GelRed (Biotium Cat #41003) solution and imaged by ChemiDocTMMP (Biorad). The results shown in FIG. 24 demonstrate that the vCS01, vCS04, and vCS40 viral vectors have the same-sized genome, indicated by a distinct band in the 5 kb range (FIG. 24, lanes 2-4). Despite a vector size of approx. 5.2 kb, the genome is a homogenous band confirming correct packaging of the somewhat oversized genome (relative to an AAV wild-type genome of 4.7 kb). All other vCS vector preparations show the same genomic size (data not shown).

Figure 25:
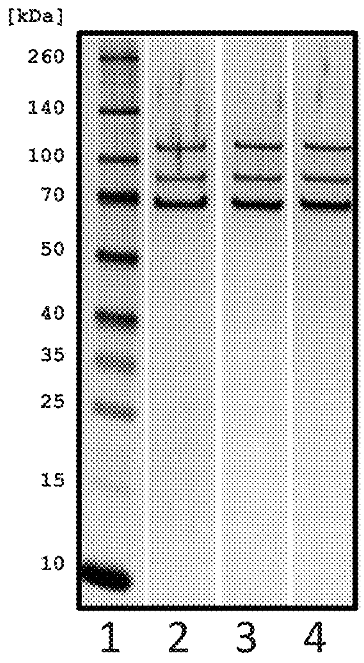
FIG. 25 shows the protein analysis of AAV vector preparations by PAGE and silver staining. Lane 1, protein marker (M); lane 2, vCS40, lane 3, vCS01; and lane 4, vCS04. The constructs all have the same AAV8 capsids consisting of VP1, VP2, and VP3 (arrows right side). The scale on the left side indicates size of the protein marker in kilodaltons (kDa).

In order to confirm the expected pattern of capsid proteins, SDS PAGE followed by silver staining was performed with the vectors vCS01, vCS04, and vCS40 (FIG. 25). As shown in the figure, the downstream purification procedure resulted in highly purified material displaying the expected protein pattern of VP1, VP2 and VP3 (FIG. 25, lanes 2-4). The same pattern was seen with all other viral preparations (not shown). The SDS-PAGE procedure of AAV preparations was done according to standard procedures. Each lane contained 1E10 vg of the respective viral construct, and were separated on a 4-12% Bis-Tris (NuPAGE® Novex, Life Technologies) gel as per manufacturer's instructions. Silver staining was performed with a SilverQuest™ kit (Novex, Life Technologies) according to the manufacturer's instructions.

Surprisingly, AAV vectors vCS01 and vCS04 had higher virion packaging, measured by higher yields in AAV virus production, as compared to the vCS40 wild-type coding construct and the other codon-optimized constructs. As shown in Table 3, the vCS01 and vCS04 vectors replicated substantially better than vCS40, providing a 5-7 fold yield increase in AAV titer.

TABLE 3

Yields per liter cell culture obtained with AAV vector constructs vCS01, vCS04, and vCD40, as purified from cell pellets.

| Construct | Vector concentration [vg/ml] ×10E12 | Yields [vg/liter] ×10E12 | Fold increase vs wt |
|---|---|---|---|
| vCS40 | 2.0 | 11.0 | — |
| vCS01 | 9.2 | 51.4 | 4.7 |
| vCS04 - Sample 1 | 17.6 | 79.2 | 7.2 |
| vCS04 - Sample 2 | 15.9 | 58.8 | 5.4 |

Example 2—In Vivo Expression of Codon Altered Factor VIII Variant Expression Sequences To test the biological potency of the codon-altered Factor VIII variant sequences, the ReFacto-type FVIII constructs described in Example 1 were administered to mice lacking Factor VIII. Briefly, the assays were performed in C57Bl/6 FVIII knock-out (ko) mice (with 6-8 animals per group) by tail vein injection of 4E12 vector genomes (vg) per kilogram body weight of mouse. Blood was drawn 14 days after injection by retroorbital puncture and plasma was prepared and frozen using standard procedures. Expression levels at day 14 were chosen because there is minimal influence of inhibitory antibodies at this time, which are seen in some animals of this mouse model at later times. FVIII activity in the mouse plasma was determined using the Technochrome FVIII assay performed, with only minor modifications, as suggested by the manufacture (Technoclone, Vienna, Austria). For the assay, the plasma samples were appropriately diluted and mixed with assay reagents, containing thrombin, activated factor IX (FIXa), phospholipids, factor X and calcium. Following FVIII activation by thrombin a complex with FIXa, phospholipids and calcium is formed. This complex activates FX to activated FX (FXa) which in turn cleaves para-nitroanilide (pNA) from the chromogenic substrate. The kinetics of pNA formation is measured at 405 nm. The rate is directly proportional to the FVIII concentration in the sample. FVIII concentrations are read from a reference curve and results are given in IU FVIII/milliliter.

The results, presented in Table 4 below, demonstrate that the codon-altered sequences designed using commercial algorithms (CS10, CS11, and CH25) provided only a modest increase in BDD-Factor VIII (3-4 fold) as compared to the wild-type BDD-Factor VIII construct (CS40). Similarly, the codon-altered BDD-Factor VIII construct prepared as described in Radcliffe et al. (CS08), only provided a 3-4 fold increase in BDD-FVIII expression. This result is consistent with the results reported in Radcliff et al. Surprisingly, the CS01, CS04, and CS23 constructs provided much higher BDD-FVIII expression in the in-vivo biopotency assays (18-, 74-, and -30-fold increases, respectively).

TABLE 4

Expression of FVIII in the plasma of FVIII-knock-out mice induced by the different AAV vector constructs.

| Construct | Codon Algorithm | Average FVIII Expression at Day 14 [IU/ml] | Standard deviation | Number of mice | Fold increase vs wt |
|---|---|---|---|---|---|
| vCS40 | Human wild-type | 0.03 | 0.03 | 12 | — |
| vCS01 | Applicants' | 0.55 | 0.28 | 22 | 18.3 |
| vCS04 | Applicants' | 2.21 | 1.20 | 55 | 73.7 |
| vCS08 | Radcliffe et al. | 0.11 | 0.01 | 6 | 3.6 |

TABLE 4-continued

Expression of FVIII in the plasma of FVIII-knock-out mice induced by the different AAV vector constructs.

| Construct | Codon Algorithm | Average FVIII Expression at Day 14 [IU/ml] | Standard deviation | Number of mice | Fold increase vs wt |
|---|---|---|---|---|---|
| vCS10 | Eurofins | 0.09 | 0.01 | 7 | 3.0 |
| vCS11 | IDT | 0.08 | 0.02 | 8 | 2.7 |
| vCH25 | GeneArt | 0.13 | 0.12 | 18 | 4.3 |
| vCS23 | Applicants' | 0.91 | 0.32 | 5 | 30.3 |

Example 3—Design of Glycosylation Peptides for the B-Domain Substituted Linker Others have shown that inclusion of a small peptide (the "V3 peptide") containing six putative N-linked glycosylation sites from the wild-type Factor VIII B-domain, into a B-domain deleted gene therapy construct, increased Factor VIII levels in the plasma of mice (McIntosh et al., Blood 121(17):3335-44 (2013)). However, in order to maintain the small size of the B-domain substituted linker, the glycosylation sites were taken out of the context of the wild-type B-domain. In silico prediction (Gupta et al., Supra) of the linker containing the V3 peptide suggests that only two of these glycosylation sites in the V3 peptide will be modified in vivo (FIG. 15).

Thus, Applicants attempted to identify alternative glycosylation peptides that would support higher levels of glycosylation in vivo, which matched wild type glycosylation more closely than the V3 peptide. Applicants designed and tested several alternative glycosylation peptides, in silico. Several of these peptides, shown in FIGS. 13A-13B, were predicted to have equal or greater glycosylation in vivo than the V3 peptide, when placed between amino acids N768 and P769 of the B-domain substituted linker in SEQ ID NO:2. The results of the in silico predictions are shown in Table 5, below. Table 5 also reports the results of expression experiments performed for several constructs encoding a ReFacto-type Factor VIII protein with a glycosylation peptide incorporated into the B-domain substituted linker, in a CS01 codon-optimized background.

TABLE 5

Prediction of N-glycosylation in B-domain substituted linker peptides and performance of AAV vector constructs in vivo.

| Sequence | Number of Predicted N-glycosylation sites | Day 28 expression [IU/ml] | SD | Number of mice [n] | Fold expression |
|---|---|---|---|---|---|
| vCS01 | 0 | 0.74 | 0.52 | 5 | 21 |
| vNG1/CS01 | 4 | n.d. | — | — | — |
| vNG4/CS01 | 3 | 1.93 | 0.57 | 6 | 55 |
| vNG5/CS01 | 2 | n.d. | — | — | — |
| vNG6/CS01 | 1 | 0.80 | 0.67 | 5 | 23 |
| vNG9/CS01 | 1 | n.d. | — | — | — |
| vNG10/CS01 | 2 | 2.66 | 0.52 | 6 | 76 |
| vNG16/CS01 | 2 | 1.59 | 0.57 | 6 | 45 |
| vNG17/CS01 | 2 | n.d. | — | — | — |
| vNG18/CS01 | 2 | n.d. | — | — | — |
| vNG19/CS01 | 2 | 0.88 | 0.25 | 5 | 25 |
| vNG20/CS01 | 2 | n.d. | — | — | — |
| vNG21/CS01 | 2 | n.d. | — | — | — |
| vCS40 | 0 | 0.035 | 0.030 | 12 | 1 |

AAV vectors containing the NG variants were constructed as described in Example 1 and tested in FVIII knock-out mice as described in Example 2. All virus vectors (except the control vector vCS40) shown in Table 5 are based on the algorithm as used in vCS01. A parallel set of constructs using the algorithm of vCS04 was also prepared (vNG/CS04 series) and is tested in the mouse model. Results were compared to the expression levels achieved with the wild-type vCS40 construct. The day 28 expression levels were chosen in this example, because expression levels of the majority of construct reached the highest levels at this time point. Three AAV vectors achieved greater than 40-fold FVIII expression levels including vNG4/CS01, vNG10/CS01 and vNG16/CS01 (Table 5). The corrresponding constructs vNG4/CS04, vNG10/CS04 and vNG16/CS04 are expected to show even higher expression because they are based on the superior vCS04 algorithm.

Surprisingly, the AAV vectors of the vNG/CS01 series had higher virion packaging, measured by higher yields in AAV virus production, as compared to the vCS40 wild-type coding construct. As shown in Table 6, the vNG/CS01-based vectors replicated substantially better than vCS40, providing an approximately 3-fold yield increase in AAV titer.

TABLE 6

Yields per liter cell culture obtained with AAV vector constructs as purified from cell pellets.

| Sequence | Vector conc. [vg/ml] $\times 10^{12}$ | Yields [vg/liter] $\times 10^{12}$ | Fold increase vs wild-type |
|---|---|---|---|
| vCS01 | 9.17 | 51.35 | 4.7 |
| vNG1/CS01 | 2.13 | 17.04 | 1.5 |
| vNG4/CS01 | 5.74 | 33.01 | 3.0 |
| vNG5/CS01 | 6.91 | 27.29 | 2.5 |
| vNG6/CS01 | 7.01 | 40.66 | 3.7 |
| vNG9/CS01 | 6.39 | 29.39 | 2.7 |
| vNG10/CS01 | 8.57 | 37.71 | 3.4 |
| vNG16/CS01 | 5.3 | 28.36 | 2.6 |
| vNG17/CS01 | 4.24 | 32.22 | 2.9 |
| vNG18/CS01 | 6.11 | 37.88 | 3.4 |
| vNG19/CS01 | 9.42 | 39.56 | 3.6 |
| vNG20/CS01 | 4.09 | 30.27 | 2.8 |
| vNG21/CS01 | n.d | — | — |
| vCS40 | 2.03 | 11 | 1.0 |

Example 4—Construction of Mutant BDD-FVIII Constructs

Numerous different mutated Refacto-type BDD-FVIII constructs, carrying amino acid mutations within the Factor VIII heavy chain and/or B-domain substituted linker, were cloned and screened. The corresponding vectors, as referred to herein as the "vCS" series of vectors, encode BDD-FVIII variants in the CS01, CS04, and CS23 codon-altered backgrounds. The method used to construct the CS01 and CS04 backgrounds is described in Example 1. The method used to construct CS23 was based on the JCAT tool (www.jcat.de), an on-line tool for codon-optimizations (Grote et al., 2005; Nucl. Acids Res. W526-31). The sequence was further modified to better reflect the codon usage of the albumin superfamily (Mirsafian et al., Sc. Word Journal, ID 639682 (2014)), the content of which is hereby expressly incorporated by reference, in its entirety, for all purposes.

Combinations of three types of mutations were included in the FVIII sequences of the vCS series of constructs. The first amino acid change introduced into the FVIII sequence is the X1 mutation (TTYVNRSL (SEQ ID NO: 33); X.

Xiao), which introduces an additional glycosylation site near the B-domain substituted linker. The X1 mutation is also referred to herein as the "m3" mutation. The second amino acid change made in the FVIII sequence includes the F328S (SPI, F309S SPE) mutation, an amino acid change known to improve secretion of FVIII (Swaaroop, J. Biol. Chem., 272:24121-24 (1997)). This mutation is also referred to herein as the "m1" mutation. The third change is the so-called X5 mutation, which is a combination of five amino acid changes in the A1 domain of the heavy chain that improves specific activity and secretion of BDD-FVIII (Cao et al., 2014; ASGCT abstract #460; details of mutations disclosed in oral presentation). The X5 mutation is also referred to herein as the "m2" mutation. Next, combinations of X1 and F328S (SPI, F309S SPE) were made, followed by combinations of X1 and X5, also referred to as "X6," and yet other combinations of X5 and F328S (SPI, F309S SPE) were made (Table 7).

Figure 44:
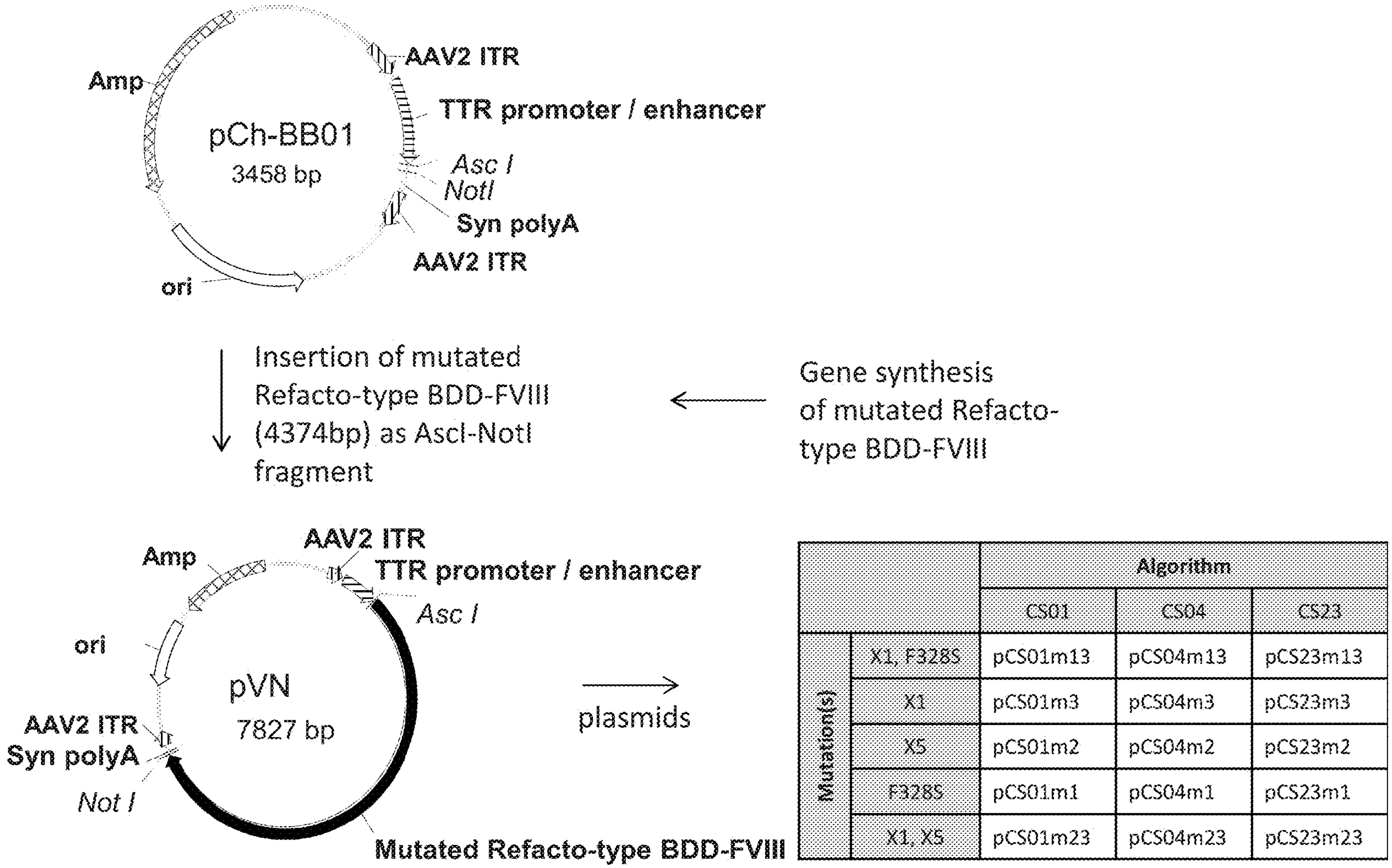
FIG. 44 depicts cloning of the pCS constructs, done by inserting synthetic Refacto-type BDD-FVIII carrying different mutations (see inserted table) into the vector backbone pCh-BB01 via AscI and NotI restriction sites.

Gene synthesis and cloning of the vector plasmids. The plasmids were constructed by cloning different synthetic DNA fragments into the same vector backbone plasmid (pCh-BB01). DNA synthesis of the Refacto-type BDD-FVIII fragments with flanking AscI and NotI enzyme restriction sites were done by ThermoFischer Scientific (Regensburg, Germany). The vector backbone contains two flanking AAV2-derived inverted terminal repeats (ITRs) that encompass a promoter/enhancer sequence derived from the liver-specific murine transthyretin gene, AscI and NotI enzyme restriction sites for insertion of the respective Refacto-type BDD-FVIII, and a synthetic polyA site. After ligation of the prepared vector backbone and insertions via the AscI and NotI sites, the resulting plasmids were amplified in milligram scale. The Refacto-type BDD-FVIII sequences of the constructs were verified by direct sequencing (Microsynth, Balgach, Switzerland). The cloning resulted in different plasmid constructs, as shown in FIG. 44.

Small scale vector preparations and quantification by quantitative PCR (qPCR). AAV8-based vectors were prepared by the three plasmid transfection method essentially as described in Grieger et al. (2015, Supra). HEK293 suspensions cells were used for plasmid transfections using the corresponding FVIII vector plasmid, the helper plasmid pXX6X80 (carrying adenoviral helper genes) and the packaging plasmid pGSK2/8 (contributing the rep2 and cap8 genes). In the downstream process the cell pellet of a one liter culture was processed using iodixanol gradients as described above. The procedure resulted in vector preparations as outlined in Table 8. Vectors were quantified by qPCR using the universal qPCR procedure targeting the AAV2 inverted terminal repeats (Aurnhammer, HUMAN GENE THERAPY METHODS: Part B 23:18-28 (2012)). An accurately quantified vector plasmid carrying AAV2 Inverted terminal repeats served for preparing the standard curve.

Figure 45:
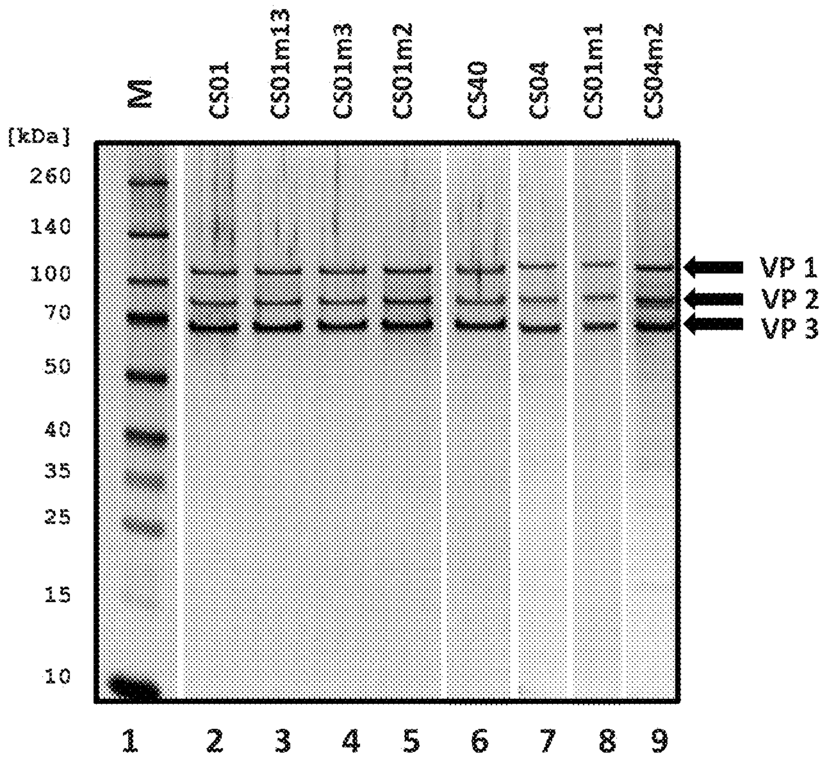
FIG. 45 depicts the protein analysis of AAV vector preparations by PAGE and silver staining. Lane 1, protein marker (M); lane 2, vCS01, lane 3, vCS17; lane 4, vCS19; lane 5, vCS20; lane 6, vCS40; lane 7, vCS04; lane 8, vCS17; lane 9, vCS24 construct. The constructs have all the same AAV8 capsids consisting of VP1, VP2 and VP3 (arrows right side). The scale on the left side indicates size of the protein marker in kilo Daltons (kDa).

AAV vector characterizations. The integrity of the vector genome was analyzed by AAV agarose gel electrophoresis. The electrophoresis was done similar as described in Fagone et al. (Human Gene Therapy Methods, 23:1-7 (2012)). AAV vector preparations were incubated at 75° C. for 10 minutes in the presence of 0.5% SDS and then cooled down to room temperature. Approximately 1.5E10 vector genomes (vg) were loaded per lane on a 1% 1×TAE agarose gel and electrophoresed for 60 min at 7 V/cm of gel length. The gel was then stained in 2× GelRed (Biotium Cat #41003) solution and imaged by ChemiDoc™ MP (Biorad). The results of a selection of vectors are shown in FIG. 45. The viral vectors vCS04 (control), vCS17, vCS20, vCS24, vCS16 and vCS40 (control) show all the same-sized genome as a distinct band in the 5 kb range (FIG. 45, lanes 2-7; arrow right side). Despite a vector size of approx. 5.2 kb, the genome is a homogenous band confirming correct packaging of the somewhat oversized genome (relative to an AAV wild-type genome of 4.7 kb).

Figure 46:
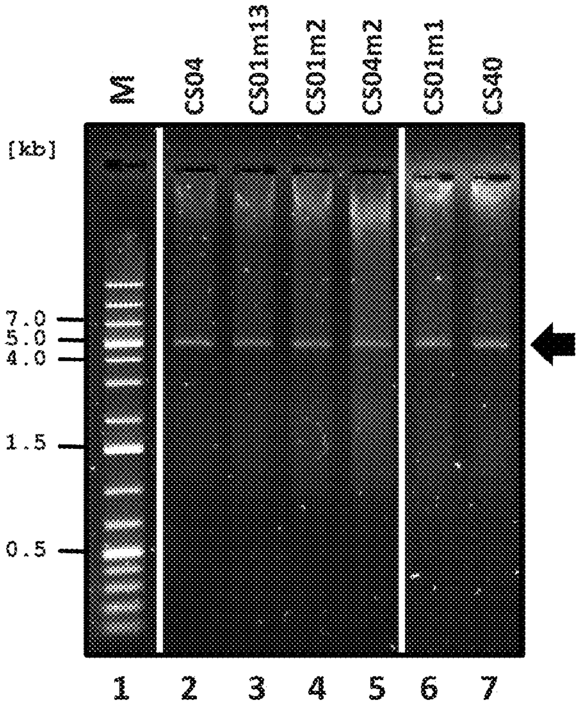
FIG. 46 depicts the integrity of AAV vector genome preparations analyzed by agarose gel electrophoresis. Lane 1, DNA marker (M); lane 2, vCS04, lane 3, vCS17; lane 4, vCS20; lane 5, vCS24; lane 6, vCS16; lane 7, vCS40 construct. Vector load is 1.5E10 vg per lane. The AAV vectors have the same-sized genomes, migrating at approximately 5 kb (arrow, right side). The scale on the left side indicates size of the DNA fragments in kilobases (kb).

In order to confirm purity of the vector and the expected pattern of capsid proteins, SDS PAGE followed by silver staining was performed with the vectors, as shown in FIG. 46. As shown in the figure, the downstream purification procedure resulted in highly purified material displaying the expected protein pattern of VP1, VP2 and VP3 (FIG. 46 lanes 2-9; arrows right hand side). The SDS-PAGE procedure of AAV preparations was done according to standard procedures. The amounts of 1E10 vg per lane were separated on a 4-12% Bis-Tris (NuPAGE® Novex, Life Technologies) gel as per manufacturer's instructions. Silver staining was performed with a SilverQuest™ kit (Novex, Life Technologies) according to the instructions of the manufacturer.

In-vivo biopotency screening of vectors. The different Refacto-type BDD-FVIII constructs were screened in mice. The assay was performed in C57Bl/6 FVIII knock-out (ko) mice (with 6-8 animals per group) by tail vein injection of 4E12 vector genomes (vg) per kilogram body weight of mouse. Blood was drawn 14 days after injection by retroorbital puncture and plasma was prepared and frozen using standard procedures. FVIII activity in mouse plasma was determined with a chromogenic assay from Technoclone with minor modifications (Technochrome FVIII, Technoclone, Vienna, Austria). In brief, the plasma sample was appropriately diluted and mixed with assay reagents, containing thrombin, activated factor IX (FIXa), phospholipids, factor X and calcium. Following FVIII activation by thrombin a complex with FIXa, phospholipids and calcium is formed. This complex activates FX to activated FX (FXa) which in turn cleaves para-nitroanilide (pNA) from the chromogenic substrate. The kinetics of pNA formation is measured at 405 nm. The rate is directly proportional to the FVIII concentration in the sample. FVIII concentrations are read from a reference curve and results are given in IU FVIII/milliliter.

The results of the mouse biopotency assay (day 14 expression data of FVIII in international units per milliliter [IU/ml] in mouse plasma and fold expression compared to the wild-type vCS40 control) are shown in Table 7. AAV vectors vCS19, vCS26 and vCS32 all contain the X1 glycosylation site in the CS01, CS04, and CS23 codon-altered backgrounds, respectively. As seen in Table 7, surprisingly high expression levels were obtained, as compared to the wild-type construct vCS40 (level defined as 1). vCS26, for instance, expressed 202-fold higher levels compared to the wild-type vCS40 vector. Another control construct for the X1-series of vectors, vCH111, that contains the X1 mutation in the Geneart codon context, showed a more modest increase in expression (12-fold).

Vectors vCS16, vCS28, and vCS34 all contain the F328S (SPI, F309S SPE) mutation enhancing secretion in the CS01, CS04, and CS23 codon-altered backgrounds, respectively. As seen in Table 7, high expression levels (45-93-fold higher than the wt vCS40 control) were obtained with vCS16 and vCS28.

Vectors vCS20, vCS24, and vCS33 contain the X5 mutation in the CS01, CS04, and CS23 codon-altered backgrounds, respectively. The best performing variant in the X5 series was vCS20, achieving levels of >3 units/ml after day 14 and a 121-fold increase over the wt vCS40 control.

Vectors vCS17, vCS29, and vCS31 contain the combination of the X1 and F328S (SPI, F309S SPE) mutations in the CS01, CS04, and CS23 codon-altered backgrounds, respectively (Table 6). The vCS17 and vCS29 constructs achieved very high expression levels in the mouse studies (115 to 246-fold increase over the vCS40 control). Remarkably, in the FVIII KO mouse model used, the majority of mice treated with the vCS17 construct did not develop neutralizing antibodies over time, evidenced by increasing levels of FVIII at later time points (e.g., day 28 and day 42; data not shown). This is an unexpected finding, because in some other constructs the expression levels began to decrease with time due to the formation of neutralizing antibodies. The CS01 background combined with the secretion-enhancing mutations F328S (SPI, F309S SPE) and X1 resulted in low immunogenicity induction.

Vectors vCS18, vCS27, and vCS35 contain the combination of the X1 and X5 mutations in the CS01, CS04, and CS23 codon-altered backgrounds, respectively. The combination of these two mutations was also very efficient. A 145-fold increase over the vCS40 control could be achieved with vCS18, for example (Table 7).

Vectors vCS48 and vCS49 contain the combination of the X5 and F328S (SPI, F309S SPE) mutations in the CS01 and CS04 codon-altered backgrounds, respectively. The combination of these two mutations was also very efficient. One of the largest increases of all mutants, a 239-fold increase over the vCS40 control, could be achieved with vCS49 confirming the special value of the combinations including the F328S (SPI, F309S SPE) mutation.

A further surprising observation was that the mutant AAV vectors grew substantially better than the vCS40 construct harboring the wild-type BDD-FVIII codons. Sequence optimization resulted in a several-fold yield increase in vector production. In some of the best expressing constructs (e.g., vCS29, vCS17, vCS20, and vCS26) the increase in yields due to codon-alteration and/or mutant sequence was approximately 3-5-fold higher, as compared to the wild-type vector (Table 8).

Expression of BDD-FVIII in the plasma of FVIII-knockout mice induced by the different AAV vector constructs is shown in Table 7. The constructs have the same vector backbone, however, encode different types of mutated FVIII, including different codon optimization backgrounds. Expression levels at day 14 were chosen because at this time point there is minimal influence of inhibitory antibodies usually seen in some animals in the mouse model at later times. N.d., not determined.

TABLE 7

In vivo biopotency data of vCS constructs.

| # | Vector | Algorithm, mutations | Day 14 expression [IU/ml] | SD | Number of mice [n] | Fold expression |
|---|---|---|---|---|---|---|
| 1 | vCS19 | CS01, X1 | 2.34 | 1.10 | 13 | 78 |
| 2 | vCS26 | CS04, X1 | 6.07 | 2.72 | 12 | 202 |
| 3 | vCS32 | CS23, X1 | n.d. | — | — | — |
| 4 | vCS16 | CS01, F328S | 1.35 | 0.88 | 6 | 45 |
| 5 | vCS28 | CS04, F328S | 2.78 | 0.92 | 7 | 93 |
| 6 | vCS34 | CS23, F328S | n.d. | — | — | — |
| 7 | vCS20 | CS01, X5 | 3.62 | 1.96 | 21 | 121 |
| 8 | vCS24 | CS04, X5 | 0.79 | 0.89 | 18 | 26 |
| 9 | vCS33 | CS23, X5 | n.d. | — | — | n.d. |
| 10 | vCS17 | CS01, X1, F328S | 3.44 | 1.92 | 20 | 115 |
| 11 | vCS29 | CS04, X1, F328S | 7.39 | 2.64 | 9 | 246 |
| 12 | vCS31 | CS23, X1, F328S | n.d. | | | n.d. |

TABLE 7-continued

In vivo biopotency data of vCS constructs.

| # | Vector | Algorithm, mutations | Day 14 expression [IU/ml] | SD | Number of mice [n] | Fold expression |
|---|---|---|---|---|---|---|
| 13 | vCS18 | CS01, X1 + X5 (X6) | 4.34 | 2.50 | 6 | 145 |
| 14 | vCS27 | CS04, X1 + X5 (X6) | 8.03 | 3.97- | 6- | 268- |
| 15 | vCS35 | CS23, X1 + X5 (X6) | n.d. | — | — | — |
| 19 | vCS48 | CS01, X5, F328S | 2.54 | 0.72 | 8 | 85 |
| 20 | vCS49 | CS04, X5, F328S | 7.17 | 1.30 | 7 | 239 |
| | controls | | | | | |
| 16 | vCS40 | Human wild-type | 0.03 | 0.03 | 12 | 1 |
| 17 | vCh25 | Geneart | 0.13 | 0.12 | 18 | 4 |
| 18 | vCh111 | Geneart + X1 | 0.37 | 0.21 | 17 | 12 |

TABLE 8

Yields per liter cell culture (packaging efficiency) obtained with the different AAV vector constructs. The vectors were purified out of the cell pellets; n.d., not determined.

| | construct | Algorithm, mutations | Vector conc. [vg/ml] $\times 10^{12}$ | Yields [vg /liter] $\times 10^{12}$ | Fold increase vs wt |
|---|---|---|---|---|---|
| 1 | vCS19 | CS01, X1 | 9.71 | 36 | 3.22 |
| 2 | vCS26 | CS04, X1 | 5.93 | 32 | 2.87 |
| 3 | vCS32 | CS23, X1 | n.d. | n.d. | n.d. |
| 4 | vCS16 | CS01, F328S | 6.51 | 29 | 2.56 |
| 5 | vCS28 | CS04, F328S | 5.85 | 32 | 2.88 |
| 6 | vCS34 | CS23, F328S | n.d. | n.d. | n.d. |
| 7 | vCS20 | CS01, X5 | 9.90 | 50 | 4.48 |
| 8 | vCS24 | CS04, X5 | 3.00 | 16 | 1.46 |
| 9 | vCS33 | CS23, X5 | n.d. | n.d. | n.d. |
| 10 | vCS17 | CS01, X1, F328S | 8.94 | 37 | 3.34 |
| 11 | vCS29 | CS04, X1, F328S | 7.42 | 53 | 4.72 |
| 12 | vCS31 | CS23, X1, F328S | n.d. | n.d. | n.d. |
| 13 | vCS18 | CS01, X1 + X5 (X6) | 21.20 | 53 | 4.75 |
| 14 | vCS27 | CS04, X1 + X5 (X6) | 4.15 | 19 | 1.67 |
| 15 | vCS35 | CS23, X1 + X5 (X6) | n.d. | n.d. | n.d. |
| 16 | vCS48 | CS01, X5, F328S | 7.14 | 42.1 | 3.77 |
| 17 | vCS49 | CS04, X5, F328S | 8.27 | 37.2 | 3.33 |
| 18 | vCS40 | Human wild-type | 2.03 | 11 | 1.00 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A polynucleotide comprising the nucleotide sequence of SEQ ID NO: 13, wherein the polynucleotide encodes a Factor VIII polypeptide.

2. The polynucleotide of claim 1, further comprising a promoter element operably linked to the polynucleotide encoding the Factor VIII polypeptide.

3. The polynucleotide of claim 2, wherein the promoter element is a liver-specific promoter sequence upstream of the nucleotide sequence encoding the Factor VIII polypeptide.

4. The polynucleotide of claim 3, further comprising an intron sequence positioned between the liver-specific promoter sequence and the nucleotide sequence encoding the Factor VIII polypeptide.

5. An adeno-associated virus (AAV) vector comprising a polynucleotide of claim 1.

6. An adeno-associated virus (AAV) particle comprising a polynucleotide of claim 1.

7. A host cell infected with an adeno-associated virus (AAV) particle comprising a polynucleotide of claim 1.

8. A method for producing an adeno-associated virus (AAV) particle comprising introducing a polynucleotide of claim 1 into a mammalian host cell, wherein the polynucleotide is competent for replication in the mammalian host cell.

9. A method for treating hemophilia A comprising administering, to a patient in need thereof, an adeno-associated virus (AAV) particle according to claim 6.

10. A method for transducing a host cell comprising contacting the host cell with an adeno-associated virus (AAV) particle according to claim 6.

* * * * *